United States Patent [19]
Katayama et al.

[11] Patent Number: 6,090,753
[45] Date of Patent: Jul. 18, 2000

[54] PYRIDAZIN-3-ONE DERIVATIVES, THEIR USE, AND INTERMEDIATES FOR THEIR PRODUCTION

[75] Inventors: Tadashi Katayama, Toyonaka; Shinichi Kawamura, Osaka; Yuzuru Sanemitsu, Kobe; Yoko Mine, Tanashi, all of Japan

[73] Assignee: Sumitomo Chemical Company Limited, Osaka-Fu, Japan

[21] Appl. No.: 09/011,269

[22] PCT Filed: Aug. 19, 1996

[86] PCT No.: PCT/JP96/02311

§ 371 Date: Jan. 30, 1998

§ 102(e) Date: Jan. 30, 1998

[87] PCT Pub. No.: WO97/07104

PCT Pub. Date: Feb. 27, 1997

[30] Foreign Application Priority Data

| Aug. 21, 1995 | [JP] | Japan | .................... 7-236098 |
| Feb. 21, 1996 | [JP] | Japan | .................... 8-060232 |
| Apr. 1, 1996 | [JP] | Japan | .................... 8-104618 |

[51] Int. Cl.$^7$ .................... A01N 43/58; C07D 237/14; C07D 403/04; C07D 405/04; C07D 413/04

[52] U.S. Cl. .................... 504/238; 504/225; 504/221; 544/114; 544/238; 544/239; 544/105; 544/58.5

[58] Field of Search .................... 544/239, 238, 544/114; 504/238, 225

[56] References Cited

U.S. PATENT DOCUMENTS

4,360,672  11/1982  Parg et al. .................... 544/241

FOREIGN PATENT DOCUMENTS

| 0029123 | 5/1981 | European Pat. Off. . |
| 1210241 | 2/1966 | Germany . |
| 2706700 | 8/1978 | Germany . |
| 4343528 | 6/1995 | Germany . |
| WO9639392 | 12/1996 | WIPO . |

*Primary Examiner*—Emily Bernhardt
*Attorney, Agent, or Firm*—Sughrue, Mion, Zinn, Macpeak & Seas, PLLC

[57] ABSTRACT

Novel pyridazin-3-one derivatives of formula [1] are provided, which are useful as active ingredients of herbicides, wherein $R^1$ is haloalkyl; $R^2$ and $R^3$ are the same or different and are hydrogen, alkyl, haloalkyl, or alkoxyalkyl; and Q is [Q-1], [Q-2], [Q-3], [Q-4], or [Q-5]. Also provided are their use and intermediates for their production.

129 Claims, No Drawings

PYRIDAZIN-3-ONE DERIVATIVES, THEIR USE, AND INTERMEDIATES FOR THEIR PRODUCTION

TECHNICAL FIELD

The present invention relates to pyridazin-3-one derivatives, their use as herbicides, and intermediates for their production.

BACKGROUND ART

EP-A-0029123 discloses a process for the preparation of substituted anilines and novel substituted anilines. In particular, it teaches that certain substituted anilines obtained by this process are useful as important starting materials for the preparation of novel substituted pyridazin-3-one derivatives having herbicidal activity in postemergence application. These pyridazin-3-one derivatives are, however, different from those of the present invention in that they have a substituted phenoxyphenyl group as an essential structural element at position 2 of the pyridazinone ring and further have quite distinct substituents on the pyridazinone ring.

DISCLOSURE OF INVENTION

The present inventors have intensively studied to find a compound having excellent herbicidal activity. As a result, they have found that pyridazin-3-one derivatives represented by formula [1] as depicted below have excellent herbicidal activity, thereby completing the present invention.

Thus the present invention provides a compound of the formula:

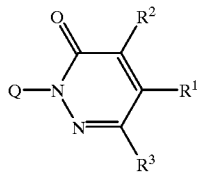

[1]

wherein $R^1$ is $C_1$–$C_3$ haloalkyl; $R^2$ and $R^3$ are the same or different and are hydrogen, $C_1$–$C_3$ alkyl, $C_1$–$C_3$ haloalkyl, or $C_1$–$C_3$ alkoxy $C_1$–$C_3$ alkyl; and Q is [Q-1], [Q-2], [Q-3], [Q-4], or [Q-5] of the formula:

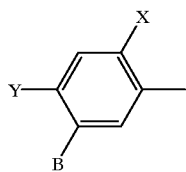

[Q-1]

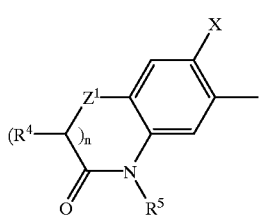

[Q-2]

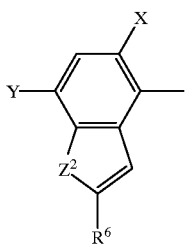

[Q-3]

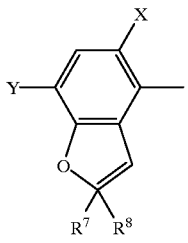

[Q-4]

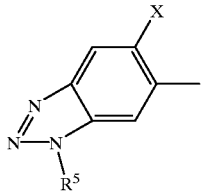

[Q-5]

wherein X is hydrogen or halogen;
Y is halogen, nitro, cyano, or trifluoromethyl;
$Z^1$ is oxygen, sulfur, or NH;
$Z^2$ is oxygen or sulfur;
n is 0 or 1;
B is hydrogen, halogen, nitro, cyano, chlorosulfonyl, $OR^{10}$, $SR^{10}$, $SO_2$—$OR^{10}$, $N(R^{11})R^{12}$, $SO_2N(R^{11})R^{12}$, $NR^{11}(COR^{13})$, $NR^{11}(SO_2R^{14})$, $N(SO_2R^{14})$—$(SO_2R^{15})$, $N(SO_2R^{14})(COR^{13})$, $NHCOOR^{13}$, $COOR^{10}$, $CON(R^{11})R^{12}$, $CSN(R^{11})R^{12}$, $COR^{16}$, $CR^{17}$=$CR^{18}COR^{16}$, $CR^{17}$=$CR^{18}COOR^{13}$, $CR^{17}$=$CR^{18}CON(R^{11})R^{12}$, $CH_2CH$—$WCOOR^{13}$, $CH_2CHWCON(R^{11})R^{12}$, $CR^{17}$=$NOR^{33}$, $CR^{17}$=$NN(R^{11})R^{12}$, $CR^{17}(Z^2$—$R^{34})_2$, $OCO_2R^{19}$, or $OCOR^{19}$;
$R^4$ is hydrogen or $C_1$–$C_3$ alkyl;
$R^5$ is hydrogen, $C_1$–$C_6$ alkyl, $C_1$–$C_6$ haloalkyl, $C_3$–$C_8$ cycloalkylalkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl, $C_3$–$C_8$ alkoxyalkoxyalkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, $CH_2CON(R^{11})R^{12}$, $CH_2COON(R^{11})R^{12}$, $CH(C_1$–$C_4$ alkyl)CON$(R^{11})R^{12}$, $CH(C_1$–$C_4$ alkyl)COON$(R^{11})R^{12}$, $C_2$–$C_8$ alkylthioalkyl, or hydroxy $C_1$–$C_6$ alkyl;
$R^6$ is $C_1$–$C_6$ alkyl, $C_1$–$C_6$ haloalkyl, formyl, cyano, carboxyl, hydroxy $C_1$–$C_6$ alkyl, $C_1$–$C_6$ alkoxy $C_1$–$C_6$ alkyl, $C_1$–$C_6$ alkoxy $C_1$–$C_6$ alkoxy $C_1$–$C_6$ alkyl, ($C_1$–$C_6$ alkyl)carbonyloxy $C_1$–$C_6$ alkyl, ($C_1$–$C_6$ haloalkyl)carbonyloxy $C_1$–$C_6$ alkyl, ($C_1$–$C_6$ alkoxy)carbonyl, or ($C_1$–$C_6$ alkyl)carbonyl;
$R^7$ is hydrogen or $C_1$–$C_6$ alkyl; and
$R^8$ is hydrogen, $C_1$–$C_6$ alkyl, $C_1$–$C_6$ haloalkyl, hydroxy $C_1$–$C_6$ alkyl, $C_2$–$C_8$ alkoxyalkyl, $C_3$–$C_{10}$ alkoxyalkoxyalkyl, $(C_1-C_5$ alkyl)carbonyloxy $C_1-C_6$ alkyl, $(C_1-C_6$ haloalkyl)carbonyloxy $C_1-C_6$ alkyl, carboxyl, carboxy $C_1-C_6$ alkyl, $(C_1-C_8$ alkoxy)carbonyl, $(C_1-C_6$ haloalkoxy)carbonyl, $(C_3-C_{10}$ cycloalkoxy)carbonyl, $(C_3-C_8$ alkenyloxy)carbonyl, $(C_3-C_8$ alkynyloxy)carbonyl, aminocarbonyl, $(C_1-C_6$ alkyl)aminocarbonyl, di$(C_1-C_6$ alkyl)aminocarbonyl, $(C_1-C_6$ alkyl)aminocarbonyloxy $C_1-C_6$ alkyl, or di$(C_1-C_6$ alkyl)aminocarbonyloxy $C_1-C_6$ alkyl;

wherein $R^{10}$ is hydrogen, $C_1-C_6$ alkyl, $C_1-C_6$ haloalkyl, $C_3-C_8$ cycloalkyl, benzyl, $C_3-C_6$ alkenyl, $C_3-C_6$ haloalkenyl, $C_3-C_6$ alkynyl, $C_3-C_6$ haloalkynyl, cyano $C_1-C_6$ alkyl, $C_2-C_8$ alkoxyalkyl, $C_2-C_8$ alkylthioalkyl, carboxy $C_1-C_6$ alkyl, $(C_1-C_8$ alkoxy)carbonyl $C_1-C_6$ alkyl, $(C_1-C_6$ haloalkoxy)carbonyl $C_1-C_6$ alkyl, $\{(C_1-C_4$ alkoxy) $C_1-C_4$ alkoxy$\}$carbonyl $C_1-C_6$ alkyl, $(C_3-C_8$ cycloalkoxy)carbonyl $C_1-C_6$ alkyl, $(C_1-C_6$ alkyl)carbonyl $C_1-C_6$ alkyl, $(C_1-C_6$ haloalkyl)carbonyl $C_1-C_6$ alkyl, $\{(C_1-C_4$ alkoxy) $C_1-C_4$ alkyl$\}$carbonyl $C_1-C_6$ alkyl, $(C_3-C_8$ cycloalkyl)carbonyl $C_1-C_6$ alkyl, $CH_2CON—(R^{11})R^{12}$, $CH_2COON(R^{11})R^{12}$, $CH(C_1-C_4$ alkyl)$CON(R^{11})R^{12}$, $CH(C_1-C_4$ alkyl)$COON(R^{11})R^{12}$, $\{(C_1-C_6$ alkoxy)carbonyl $C_1-C_6$ alkyl$\}$oxycarbonyl $C_1-C_6$ alkyl, or hydroxy $C_1-C_6$ alkyl;

$R^{11}$ and $R^{12}$ are independently hydrogen, $C_1-C_6$ alkyl, $C_1-C_6$ haloalkyl, $C_3-C_6$ alkenyl, $C_3-C_6$ alkynyl, cyano $C_1-C_6$ alkyl, $C_2-C_8$ alkoxyalkyl, $C_2-C_8$ alkylthioalkyl, carboxy $C_1-C_6$ alkyl, $(C_1-C_6$ alkoxy)carbonyl $C_1-C_6$ alkyl, $(C_3-C_8$ cycloalkoxy)carbonyl $C_1-C_6$ alkyl, $\{(C_1-C_4$ alkoxy) $C_1-C_4$ alkoxy$\}$carbonyl $C_1-C_6$ alkyl, or $R^{11}$ and $R^{12}$ are combined together to form tetramethylene, pentamethylene, or ethyleneoxyethylene;

$R^{13}$ is hydrogen, $C_1-C_6$ alkyl, $C_1-C_6$ haloalkyl, $C_3-C_8$ cycloalkyl, or $C_3-C_6$ alkenyl;

$R^{14}$ and $R^{15}$ are independently $C_1-C_6$ alkyl, $C_1-C_6$ haloalkyl, or phenyl optionally substituted with methyl or nitro;

$R^{16}$ is hydrogen, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_2-C_8$ alkoxyalkyl, or hydroxy $C_1-C_6$ alkyl;

$R^{17}$ and $R^{18}$ are independently hydrogen or $C_1-C_6$ alkyl;

$R^{19}$ is $C_1-C_6$ alkyl;

$R^{33}$ is hydrogen, $C_1-C_6$ alkyl, $C_1-C_6$ haloalkyl, $C_3-C_8$ cycloalkyl, $C_3-C_6$ alkenyl, $C_3-C_6$ haloalkenyl, $C_3-C_6$ alkynyl, $C_3-C_6$ haloalkynyl, cyano $C_1-C_6$ alkyl, or $(C_1-C_6$ alkoxy)carbonyl $C_1-C_6$ alkyl;

$R^{34}$ is $C_1-C_6$ alkyl, or two $R^{34}$'s are combined together to form $(CH_2)_2$ or $(CH_2)_3$; and W is hydrogen, chlorine, or bromine, (hereinafter referred to as the present compound(s)); and a herbicide containing it as an active ingredient.

The present invention also provides a compound of the formula:

[2]
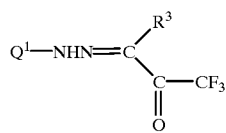

wherein $R^3$ is as defined above, and $Q^1$ is [$Q^1$-1], [Q-2], [$Q^1$-3], [Q-4], or [Q-5] of the formula:

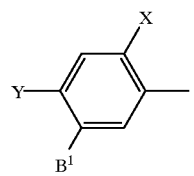
[$Q^1$-1]

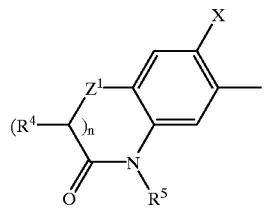
[Q-2]

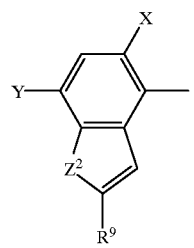
[$Q^1$-3]

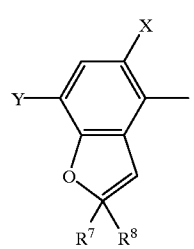
[Q-4]

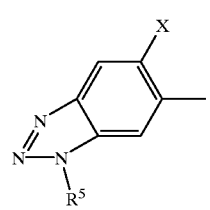
[Q-5]

wherein X, Y, $Z^1$, $Z^2$, n, $R^4$, $R^5$, $R^7$, and $R^8$ are as defined above; $B^1$ is hydrogen, halogen, nitro, cyano, $OR^{27}$, $SR^{27}$, $SO_2OR^{27}$, $NR^{11}(R^{12})$, $SO_2NR^{11}(R^{12})$, $NR^{11}(COR^{13})$, $NR^{11}(SO_2R^{14})$, $N(SO_2R^{14})(SO_2R^{15})$, $N(SO_2R^{14})(COR^3)$, $NHCOOR^{13}$ $COOR^{27}$, $CONR^{11}(R^{12})$, $CSNR^{11}(R^{12})$, $CR^{17}=CR^{18}COOR^{13}$, $CR^{17}=CR^{18}CONR^{11}—(R^{12})$, $CH_2CHWCOOR^{13}$, $CH_2CHWCONR^{11}(R^{12})$, $CR^{17}=NOR^{33}$, $CR^{17}=NNR^{11}(R^{12})$, $CR^{17}(Z^2R^{34})_2$, $OCO_2R^{19}$, or $OCOR^{19}$; $R^9$ is $C_1-C_6$ alkyl, $C_1-C_6$ cyano, carboxyl, hydroxy $C_1-C_6$ alkyl, $C_1-C_6$ alkoxy $C_1-C_6$ alkyl, $C_1-C_6$ alkoxy $C_1-C_6$ alkoxy $C_1-C_6$ alkyl, $(C_1-C_6$ alkyl)carbonyloxy $C_1-C_6$ alkyl, $(C_1-C_6$ haloalkyl)carbonyloxy $C_1-C_6$ alkyl, $(C_1-C_6$ alkoxy)carbonyl, or $(C_1-C_6$ alkyl)carbonyl; wherein $R^{19}$ is as defined above; $R^{27}$ is hydrogen, $C_1-C_6$ alkyl, $C_1-C_6$ haloalkyl, $C_3-C_8$ cycloalkyl, benzyl, $C_3-C_6$ alkenyl, $C_3-C_6$ haloalkenyl, $C_3-C_6$ alkynyl, $C_3-C_6$ haloalkynyl, cyano $C_1-C_6$ alkyl, $C_2-C_8$ alkoxyalkyl, $C_2-C_8$ alkylthioalkyl, carboxy $C_1-C_6$ alkyl, $(C_1-C_8$ alkoxy)carbonyl $C_1-C_6$ alkyl, $(C_1-C_6$ haloalkoxy)carbonyl $C_1-C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, $CH_2CON(R^{11})R^{12}$, $CH_2COON(R^{11})R^{12}$, $CH(C_1$–$C_4$ alkyl)$CON(R^{11})R^{12}$, $CH(C_1$–$C_4$ alkyl)$COON(R^{11})R^{12}$, {($C_1$–$C_6$ alkoxy) carbonyl $C_1$–$C_6$ alkyl}oxycarbonyl $C_1$–$C_6$ alkyl, or hydroxy $C_1$–$C_6$ alkyl; and $R^{11}$, $R^{12}$, $R^{13}$, $R^{14}$, $R^{15}$, $R^{17}$, $R^{18}$, $R^{19}$, $R^{33}$, $R^{34}$, and $Z^2$ are as defined above.

In the above definition of the present compounds, the respective substituents are exemplified as follows:

Examples of the $C_1$–$C_3$ haloalkyl represented by $R^1$ include trifluoromethyl and chlorodifluoromethyl.

Examples of the $C_1$–$C_3$ alkyl represented by $R^2$ and $R^3$ include methyl, ethyl, and isopropyl.

Examples of the $C_1$–$C_3$ haloalkyl represented by $R^2$ and $R^3$ include trichloromethyl, trifluoromethyl, difluoromethyl, chlorodifluoromethyl, and pentafluoroethyl.

Examples of the $C_1$–$C_3$ alkoxy $C_1$–$C_3$ alkyl represented by $R^2$ and $R^3$ include methoxymethyl.

Examples of the halogen represented by X, Y, and B include chlorine, fluorine, bromine, or iodine.

Examples of the $C_1$–$C_6$ alkyl represented by $R^{10}$ include methyl, ethyl, isopropyl, propyl, isobutyl, butyl, t-butyl, amyl, isoamyl, and t-amyl.

Examples of the $C_1$–$C_6$ haloalkyl represented by $R^{10}$ include 2-chloroethyl, 3-chloropropyl, and 2,2,2-trifluoroethyl.

Examples of the $C_3$–$C_8$ cycloalkyl represented by $R^{10}$ include cyclopropyl, cyclobutyl, cyclopentyl, and cyclohexyl.

Examples of the $C_3$–$C_6$ alkenyl represented by $R^{10}$ include allyl, 1-methyl-2-propenyl, 3-butenyl, 2-butenyl, 3-methyl-2-butenyl, and 2-methyl-3-butenyl.

Examples of the $C_3$–$C_6$ haloalkenyl represented by $R^{10}$ include 2-chloro-2-propenyl and 3,3-dichloro-2-propenyl.

Examples of the $C_3$–$C_6$ alkynyl represented by $R^{10}$ include propargyl, 1-methyl-2-propynyl, 2-butynyl, and 1,1-dimethyl-2-propynyl.

Examples of the $C_3$–$C_6$ haloalkynyl represented by $R^{10}$ include 4-bromo-2-butynyl.

Examples of the cyano $C_1$–$C_6$ alkyl represented by $R^{10}$ include cyanomethyl.

Examples of the $C_2$–$C_8$ alkoxyalkyl represented by $R^{10}$ include methoxymethyl, methoxyethyl, ethoxymethyl, and ethoxyethyl.

Examples of the $C_2$–$C_8$ alkylthioalkyl represented by $R^{10}$ include methylthiomethyl.

Examples of the carboxy $C_1$–$C_6$ alkyl represented by $R^{10}$ include carboxymethyl, 1-carboxyethyl, and 2-carboxyethyl.

Examples of the ($C_1$–$C_8$ alkoxy)carbonyl $C_1$–$C_6$ alkyl represented by $R^{10}$ include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

Examples of the ($C_1$–$C_6$ haloalkoxy)carbonyl $C_1$–$C_6$ alkyl represented by $R^{10}$ include 2-chloroethoxycarbonylmethyl.

Examples of the {($C_1$–$C_4$ alkoxy) $C_1$–$C_4$ alkoxy}carbonyl $C_1$–$C_6$ alkyl represented by $R^{10}$ include methoxymethoxycarbonylmethyl and 1-methoxymethoxycarbonylmethyl.

Examples of the ($C_3$–$C_8$ cycloalkoxy)carbonyl $C_1$–$C_6$ alkyl represented by $R^{10}$ include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, and 1-cyclohexyloxycarbonylethyl.

Examples of the ($C_1$–$C_6$ alkyl)carbonyl $C_1$–$C_6$ alkyl represented by $R^{10}$ include methylcarbonylmethyl.

Examples of the ($C_1$–$C_6$ haloalkyl)carbonyl $C_1$–$C_6$ alkyl represented by $R^{10}$ include chloromethylcarbonylmethyl.

Examples of the {($C_1$–$C_4$ alkoxy) $C_1$–$C_4$ alkyl}carbonyl $C_1$–$C_6$ alkyl represented by $R^{10}$ include 2-methoxyethylcarbonylmethyl.

Examples of the ($C_3$–$C_8$ cycloalkyl)carbonyl $C_1$–$C_6$ alkyl represented by $R^{10}$ include cyclopentylcarbonylmethyl.

Examples of the {($C_1$–$C_6$ alkoxy)carbonyl $C_1$–$C_6$ alkyl}oxycarbonyl $C_1$–$C_6$ alkyl represented by $R^{10}$ include (ethoxycarbonyl)methoxycarbonylmethyl.

Examples of the $C_1$–$C_6$ alkyl represented by $R^{11}$ and $R^{12}$ include methyl, ethyl, propyl, butyl, isopropyl, and isobutyl.

Examples of the $C_1$–$C_6$ haloalkyl represented by $R^{11}$ and $R^{12}$ include chloroethyl and bromoethyl.

Examples of the $C_3$–$C_6$ alkenyl represented by $R^{11}$ and $R^{12}$ include allyl, 1-methyl-2-propenyl, and 3-butenyl.

Examples of the $C_3$–$C_6$ alkynyl represented by $R^{11}$ and $R^{12}$ include propargyl and 1-methyl-2-propynyl.

Examples of the cyano $C_1$–$C_6$ alkyl represented by $R^{11}$ and $R^{12}$ include cyanomethyl.

Examples of the $C_2$–$C_8$ alkoxyalkyl represented by $R^{11}$ and $R^{12}$ include methoxymethyl and ethoxyethyl.

Examples of the $C_2$–$C_8$ alkylthioalkyl represented by $R^{11}$ and $R^{12}$ include methylthiomethyl and methylthioethyl.

Examples of the carboxy $C_1$–$C_6$ alkyl represented by $R^{11}$ and $R^{12}$ include carboxymethyl and 1-carboxyethyl.

Examples of the ($C_1$–$C_6$ alkoxy)carbonyl $C_1$–$C_6$ alkyl represented by $R^{11}$ and $R^{12}$ include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

Examples of the ($C_3$–$C_8$ cycloalkoxy)carbonyl $C_1$–$C_6$ alkyl represented by $R^{11}$ and $R^{12}$ include cyclopentyloxycarbonylmethyl.

Examples of the {($C_1$–$C_4$ alkoxy) $C_1$–$C_4$ alkoxy}carbonyl $C_1$–$C_6$ alkyl represented by $R^{11}$ and $R^{12}$ include methoxymethoxycarbonylmethyl and 1-methoxymethoxycarbonylethyl.

Examples of the $C_1$–$C_6$ alkyl represented by $R^{13}$ include methyl, ethyl, propyl, butyl, amyl, isopropyl, isobutyl, and isoamyl.

Examples of the $C_1$–$C_6$ haloalkyl represented by $R^{13}$ include 2,2,2-trifluoroethyl.

Examples of the $C_3$–$C_8$ cycloalkyl represented by $R^{13}$ include cyclopropyl, cyclobutyl, cyclopentyl, and cyclohexyl.

Examples of the $C_3$–$C_6$ alkenyl represented by $R^{13}$ include allyl.

Examples of the $C_1$–$C_6$ alkyl represented by $R^{14}$ and $R^{15}$ include methyl, ethyl, propyl, butyl, and isopropyl.

Examples of the $C_1$–$C_6$ haloalkyl represented by $R^{14}$ and $R^{15}$ include trifluoromethyl, 2,2,2-trifluoroethyl, 2-chloroethyl, chloromethyl, and trichloromethyl.

Examples of the phenyl optionally substituted by methyl or nitro, which is represented by $R^{14}$ and $R^{15}$, include phenyl, p-methylphenyl, 2-nitrophenyl, 3-nitrophenyl, and 4-nitrophenyl.

Examples of the $C_1$–$C_6$ alkyl represented by $R^{16}$ include methyl, ethyl, propyl, butyl, amyl, isopropyl, isobutyl, t-butyl, isoamyl, and t-amyl.

Examples of the $C_1$–$C_6$ haloalkyl represented by $R^{16}$ include chloromethyl, dichloromethyl, bromomethyl, dibromomethyl, 1-chloroethyl, 1,1-dichloroethyl, 1-bromoethyl, and 1,1-dibromoethyl.

Examples of the $C_2$–$C_6$ alkenyl represented by $R^{16}$ include vinyl, allyl, 1-propenyl, and 1-methyl-2-propenyl.

Examples of the $C_2$–$C_6$ haloalkenyl represented by $R^{16}$ include 3,3-dichloro-2-propenyl and 3,3-dibromo-2-propenyl.

Examples of the $C_2$–$C_6$ alkynyl represented by $R^{16}$ include ethynyl and 2-butynyl.

Examples of the $C_2$–$C_6$ haloalkynyl represented by $R^{16}$ include 3-bromo-2-propynyl.

Examples of the $C_2$–$C_8$ alkoxyalkyl represented by $R^{16}$ include methoxymethyl, ethoxymethyl, and isopropoxymethyl.

Examples of the hydroxy $C_1$–$C_6$ alkyl represented by $R^{16}$ include hydroxymethyl.

Examples of the $C_1$–$C_6$ alkyl represented by $R^{17}$ and $R^{18}$ include methyl.

Examples of the $C_1$–$C_6$ alkyl represented by $R^{19}$ include methyl and ethyl.

Examples of the $C_1$–$C_6$ alkyl represented by $R^{33}$ include methyl and ethyl.

Examples of the $C_1$–$C_6$ haloalkyl represented by $R^{33}$ include 2-chloroethyl.

Examples of the $C_3$–$C_8$ cycloalkyl represented by $R^{33}$ include cyclopentyl.

Examples of the $C_3$–$C_6$ alkenyl represented by $R^{33}$ include allyl.

Examples of the $C_3$–$C_6$ haloalkenyl represented by $R^{33}$ include 2-chloro-2-propenyl.

Examples of the $C_3$–$C_6$ alkynyl represented by $R^{33}$ include propargyl.

Examples of the $C_3$–$C_6$ haloalkynyl represented by $R^{33}$ include 4-chloro-2-butynyl.

Examples of the cyano $C_1$–$C_6$ alkyl represented by $R^{33}$ include 2-cyanoethyl and cyanomethyl.

Examples of the ($C_1$–$C_6$ alkoxy)carbonyl $C_1$–$C_6$ alkyl represented by $R^{33}$ include ethoxycarbonylmethyl.

Examples of the $C_1$–$C_6$ alkyl represented by $R^{34}$ include methyl and ethyl.

Examples of the $C_1$–$C_3$ alkyl represented by $R^4$ include methyl.

Examples of the $C_1$–$C_6$ alkyl represented by $R^5$ include methyl, ethyl, propyl, butyl, amyl, isopropyl, isobutyl, and isoamyl.

Examples of the $C_1$–$C_6$ haloalkyl represented by $R^5$ include 2-chloroethyl, 2-bromoethyl, 3-chlorobutyl, 3-bromobutyl, difluoromethyl, and bromodifluoromethyl.

Examples of the $C_3$–$C_8$ cycloalkylalkyl represented by $R^5$ include cyclopentylmethyl.

Examples of the $C_3$–$C_6$ alkenyl represented by $R^5$ include allyl, 1-methyl-2-propenyl, 3-butenyl, 2-butenyl, 3-methyl-2-butenyl, and 2-methyl-3-butenyl.

Examples of the $C_3$–$C_6$ haloalkenyl represented by $R^5$ include 2-chloro-2-propenyl and 3,3-dichloro-2-propenyl.

Examples of the $C_3$–$C_6$ alkynyl represented by $R^5$ include propargyl, 1-methyl-2-propynyl, 2-butynyl, and 1,1-dimethyl-2-propynyl.

Examples of the $C_3$–$C_6$ haloalkynyl represented by $R^5$ include 3-iodo-2-propynyl and 3-bromo-2-propynyl.

Examples of the cyano $C_1$–$C_6$ alkyl represented by $R^5$ include cyanomethyl.

Examples of the $C_2$–$C_8$ alkoxyalkyl represented by $R^5$ include methoxymethyl, ethoxymethyl, and 1-methoxyethyl.

Examples of the $C_3$–$C_8$ alkoxyalkoxyalkyl represented by $R^5$ include methoxyethoxymethyl.

Examples of the carboxy $C_1$–$C_6$ alkyl represented by $R^5$ include carboxymethyl, 1-carboxyethyl, and 2-carboxyethyl.

Examples of the ($C_1$–$C_6$ alkoxy)carbonyl $C_1$–$C_6$ alkyl represented by $R^5$ include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

Examples of the {($C_1$–$C_4$ alkoxy) $C_1$–$C_4$ alkoxy}carbonyl $C_1$–$C_6$ alkyl represented by $R^5$ include methoxymethoxycarbonylmethyl and 1-methoxymethoxycarbonylethyl.

Examples of the ($C_3$–$C_8$ cycloalkoxy)carbonyl $C_1$–$C_6$ alkyl represented by $R^5$ include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, and 1-cyclohexyloxycarbonylethyl.

Examples of the $C_2$–$C_8$ alkylthioalkyl represented by $R^5$ include methylthiomethyl.

Examples of the hydroxy $C_1$–$C_6$ alkyl represented by $R^5$ include hydroxymethyl, hydroxyethyl, and hydroxypropyl.

Examples of the $C_1$–$C_6$ alkyl represented by $R^6$ include methyl and ethyl.

Examples of the $C_1$–$C_6$ haloalkyl represented by $R^6$ include bromomethyl, dibromomethyl, tribromomethyl, 1-bromoethyl, chloromethyl, dichloromethyl, and trichloromethyl.

Examples of the hydroxy $C_1$–$C_6$ alkyl represented by $R^6$ include hydroxymethyl.

Examples of the $C_1$–$C_6$ alkoxy $C_1$–$C_6$ alkyl represented by $R^6$ include methoxymethyl, ethoxymethyl, propoxymethyl, and isopropoxymethyl.

Examples of the $C_1$–$C_6$ alkoxy $C_1$–$C_6$ alkoxy $C_1$–$C_6$ alkyl represented by $R^6$ include methoxymethoxymethyl, methoxyethoxymethyl, and ethoxymethoxymethyl.

Examples of the ($C_1$–$C_6$ alkyl)carbonyloxy $C_1$–$C_6$ alkyl represented by $R^6$ include acetyloxymethyl, ethylcarbonyloxymethyl, and isopropylcarbonyloxymethyl.

Examples of the ($C_1$–$C_6$ haloalkyl)carbonyloxy $C_1$–$C_6$ alkyl represented by $R^6$ include trifluoroacetyloxymethyl, chloroacetyloxymethyl, and trichloroacetyloxymethyl.

Examples of the ($C_1$–$C_6$ alkoxy)carbonyl represented by $R^6$ include methoxycarbonyl, ethoxycarbonyl, propoxycarbonyl, butoxycarbonyl, amyloxycarbonyl, isopropoxycarbonyl, isobutoxycarbonyl, and isoamyloxycarbonyl.

Examples of the ($C_1$–$C_6$ alkyl)carbonyl represented by $R^6$ include methylcarbonyl, ethylcarbonyl, and isopropylcarbonyl.

Examples of the $C_1$–$C_6$ alkyl represented by $R^7$ include methyl.

Examples of the $C_1$–$C_6$ alkyl represented by $R^8$ include methyl and ethyl.

Examples of the $C_1$–$C_6$ haloalkyl represented by $R^8$ include chloromethyl, bromomethyl, and fluoromethyl.

Examples of the $C_1$–$C_6$ hydroxyalkyl represented by $R^8$ include hydroxymethyl.

Examples of the $C_2$–$C_8$ alkoxyalkyl represented by $R^8$ include methoxymethyl, ethoxymethyl, isopropoxymethyl, butoxymethyl, and isobutoxymethyl.

Examples of the $C_3$–$C_{10}$ alkoxyalkoxyalkyl represented by $R^8$ include methoxymethoxymethyl, methoxyethoxymethyl, and ethoxymethoxymethyl.

Examples of the ($C_1$–$C_5$ alkyl)carbonyloxy $C_1$–$C_6$ alkyl represented by $R^8$ include acetyloxymethyl, ethylcarbonyloxymethyl, and isopropylcarbonyloxymethyl.

Examples of the ($C_1$–$C_6$ haloalkyl)carbonyloxy $C_1$–$C_6$ alkyl represented by $R^8$ include 2-chloroethylcarbonyloxymethyl.

Examples of the carboxy $C_1$–$C_6$ alkyl represented by $R^8$ include carboxymethyl.

Examples of the ($C_1$–$C_8$)alkoxycarbonyl represented by $R^8$ include methoxycarbonyl, ethoxycarbonyl, propoxycarbonyl, butoxycarbonyl, amyloxycarbonyl, isopropoxycarbonyl, isobutoxycarbonyl, and isoamyloxycarbonyl.

Examples of the ($C_1$–$C_6$ haloalkoxy)carbonyl represented by $R^8$ include 2-chloroethoxycarbonyl, 2-bromoethoxycarbonyl, 3-chlorobutoxycarbonyl, 1-chloro-2-propoxycarbonyl, 1,3-dichloro-2-propoxycarbonyl, 2,2-dichloroethoxycarbonyl, 2,2,2-trifluoroethoxycarbonyl, 2,2,2-trichloroethoxycarbonyl, and 2,2,2-tribromoethoxycarbonyl.

Examples of the ($C_3$–$C_{10}$ cycloalkoxy)carbonyl represented by $R^8$ include cyclobutyloxycarbonyl, cyclopentyloxycarbonyl, and cyclohexyloxycarbonyl.

Examples of the ($C_3$–$C_8$ alkenyloxy)carbonyl represented by $R^8$ include allyloxycarbonyl and 3-butenyloxycarbonyl.

Examples of the ($C_3$–$C_8$ alkynyloxy)carbonyl represented by $R^8$ include propargyloxycarbonyl, 3-butynyloxycarbonyl, and 1-methyl-2-propynyloxycarbonyl.

Examples of the ($C_1$–$C_6$ alkyl)aminocarbonyl represented by $R^8$ include methylaminocarbonyl, ethylaminocarbonyl, and propylaminocarbonyl.

Examples of the di($C_1$–$C_6$ alkyl)aminocarbonyl represented by $R^8$ include dimethylaminocarbonyl, diethylaminocarbonyl, and diisopropylaminocarbonyl.

Examples of the ($C_1$–$C_6$ alkyl)aminocarbonyloxy $C_1$–$C_6$ alkyl represented by $R^8$ include methylaminocarbonyloxymethyl, ethylaminocarbonyloxymethyl, and propylaminocarbonyloxymethyl.

Examples of the di($C_1$–$C_6$ alkyl)aminocarbonyloxy $C_1$–$C_6$ alkyl represented by $R^8$ include dimethylaminocarbonyloxyalkyl and diethylaminocarbonyloxyalkyl.

In the present compounds, preferred substituents from the viewpoint of their herbicidal activity are as follows:

$R^1$ is preferably methyl substituted with one or more fluorine atoms, such as trifluoromethyl or chlorodifluoromethyl, or ethyl substituted with one or more fluorine atoms, such as pentafluoroethyl, and more preferably trifluoromethyl;

$R^2$ is preferably $C_1$–$C_3$ alkyl such as methyl or ethyl, or hydrogen, and more preferably methyl or hydrogen;

$R^3$ is preferably $C_1$–$C_3$ alkyl such as methyl or ethyl, or hydrogen, and more preferably methyl or hydrogen; and Q is preferably [Q-1], [Q-2], [Q-3], or [Q-4].

Preferred examples of the present compounds from the viewpoint of their herbicidal activity are those which contain the above preferred substituents in combination.

When Q is [Q-1], more preferred compounds are those wherein X is hydrogen or fluorine and Y is chlorine. Among these compounds are more preferred ones wherein B is $OR^{10}$, $SR^{10}$, $N(R^{11})R^{12}$, $NR^{11}(SO_2R^{14})$, or $COOR^{10}$. Among these compounds are more preferred ones wherein $R^{10}$ is $C_1$–$C_6$ alkyl, $C_3$–$C_6$ alkynyl, ($C_1$–$C_8$ alkoxy)carbonyl $C_1$–$C_6$ alkyl, or ($C_3$–$C_8$ cycloalkoxy)carbonyl $C_1$–$C_6$ alkyl; $R^{11}$ is hydrogen; $R^{12}$ is ($C_1$–$C_6$ alkoxy)carbonyl $C_1C_6$ alkyl; and $R^{14}$ is $C_1$–$C_6$ alkyl or $C_1$–$C_6$ haloalkyl.

When Q is [Q-2], more preferred compounds are those wherein X is fluorine or hydrogen; $Z^1$ is oxygen; $R^4$ is hydrogen; and n is 1. Among these compounds are more preferred ones wherein $R^5$ is $C_3$–$C_6$ alkynyl.

Typical examples of the preferred compounds are as follows:

7-Fluoro-6-(5-trifluoromethyl-3-pyridazinon-2-yl)-4-propargyl-2H-1,4-benzoxazin-3-one;

7-Fluoro-6-(4-methyl-5-trifluoromethyl-3-pyridazinon-2-yl)-4-propargyl-2H-1,4-benzoxazin-3-one;

6-(5-Trifluoromethyl-3-pyridazinon-2-yl)-4-propargyl-2H-1,4-benzoxazin-3-one;

6-(4-Methyl-5-trifluoromethyl-3-pyridazinon-2-yl)-4-propargyl-2H-1,4-benzoxazin-3-one;

2-(4-Chloro-2-fluoro-5-isopropoxyphenyl)-4-methyl-5-trifluoromethylpyridazin-3-one;

2-(4-Chloro-2-fluoro-5-methoxyphenyl)-4-methyl-5-trifluoromethylpyridazin-3-one;

2-(4-Chloro-2-fluoro-5-ethoxyphenyl)-4-methyl-5-trifluoromethylpyridazin-3-one;

2-(4-Chloro-2-fluoro-5-propargyloxyphenyl)-4-methyl-5-trifluoromethylpyridazin-3-one;

Methyl 2-chloro-4-fluoro-5-(4-methyl-5-trifluoromethyl-3-pyridazinon-2-yl)phenoxyacetate;

Ethyl 2-chloro-4-fluoro-5-(4-methyl-5-trifluoromethyl-3-pyridazinon-2-yl)phenoxyacetate;

Propyl 2-chloro-4-fluoro-5-(4-methyl-5-trifluoromethyl-3-pyridazinon-2-yl)phenoxyacetate;

Isopropyl 2-chloro-4-fluoro-5-(4-methyl-5-trifluoromethyl-3-pyridazinon-2-yl)phenoxyacetate;

Butyl 2-chloro-4-fluoro-5-(4-methyl-5-trifluoromethyl-3-pyridazinon-2-yl)phenoxyacetate;

Pentyl 2-chloro-4-fluoro-5-(4-methyl-5-trifluoromethyl-3-pyridazinon-2-yl)phenoxyacetate;

Cyclopentyl 2-chloro-4-fluoro-5-(4-methyl-5-trifluoromethyl-3-pyridazinon-2-yl)phenoxyacetate;

Ethyl 2-{2-chloro-4-fluoro-5-(4-methyl-5-trifluoromethyl-3-pyridazinon-2-yl)phenoxy}propionate;

Methyl 2-{2-chloro-4-fluoro-5-(4-methyl-5-trifluoromethyl-3-pyridazinon-2-yl)phenoxy}propionate;

Ethyl 2-chloro-4-fluoro-5-(4-methyl-5-trifluoromethyl-3-pyridazinon-2-yl)phenylthioacetate;

Methyl 2-chloro-4-fluoro-5-(4-methyl-5-trifluoromethyl-3-pyridazinon-2-yl)phenylthioacetate;

Ethyl 2-{2-chloro-4-fluoro-5-(4-methyl-5-trifluoromethyl-3-pyridazinon-2-yl)phenylthio}propionate;

Methyl 2-{2-chloro-4-fluoro-5-(4-methyl-5-trifluoromethyl-3-pyridazinon-2-yl)phenylthio}propionate;

Methyl 2-{2-chloro-4-fluoro-5-(5-trifluoromethyl-3-pyridazinon-2-yl)phenoxy}propionate;

Ethyl 2-{2-chloro-4-fluoro-5-(5-trifluoromethyl-3-pyridazinon-2-yl)phenoxy}propionate;

Ethyl 2-chloro-4-fluoro-5-(5-trifluoromethyl-3-pyridazinon-2-yl)phenylthioacetate;

Methyl 2-chloro-4-fluoro-5-(5-trifluoromethyl-3-pyridazinon-2-yl)phenylthioacetate;

Ethyl 2-{2-chloro-4-fluoro-5-(5-trifluoromethyl-3-pyridazinon-2-yl)phenylthio}propionate;

Methyl 2-{2-chloro-4-fluoro-5-(5-trifluoromethyl-3-pyridazinon-2-yl)phenylthio}propionate;

Isopropyl 2-{2-chloro-4-fluoro-5-(5-trifluoromethyl-3-pyridazinon-2-yl)phenylthio}propionate;

Ethyl 2-{2-chloro-4-fluoro-5-(4-methyl-5-trifluoromethyl-3-pyridazinon-2-yl)phenylamino}propionate;

Ethyl 2-{2-chloro-4-fluoro-5-(5-trifluoromethyl-3-pyridazinon-2-yl)phenylamino}propionate;

N-{2-chloro-4-fluoro-5-(4-methyl-5-trifluoromethyl-3-pyridazinon-2-yl)phenyl}methanesulfonamide;

N-{2-chloro-4-fluoro-5-(4-methyl-5-trifluoromethyl-3-pyridazinon-2-yl)phenyl}chloromethanesulfonamide;

N-{2-chloro-5-(4-methyl-5-trifluoromethyl-3-pyridazinon-2-yl)phenyl}methanesulfonamide;

Methyl 2-chloro-4-fluoro-5-(4-methyl-5-trifluoromethyl-3-pyridazinon-2-yl)benzoate;

Ethyl 2-chloro-4-fluoro-5-(4-methyl-5-trifluoromethyl-3-pyridazinon-2-yl)benzoate;

Ethyl 2-chloro-5-(4-methyl-5-trifluoromethyl-3-pyridazinon-2-yl)benzoate;

Isopropyl 2-chloro-5-(4-methyl-5-trifluoromethyl-3-pyridazinon-2-yl)benzoate; and 2-(4—Chloro-2-fluoro-5-propargyloxyphenyl)-6-methyl-5-trifluoromethylpyridazin-3-one.

Among these compounds, more preferred ones from the viewpoint of their herbicidal activity are as follows:

7-Fluoro-6-(5-trifluoro methyl-3-pyridazinon-2-yl)-4-proparygyl-2H-1,4-benzoxazin-3-one;

7-Fluoro-6-(4-methyl-5-trifluoromethyl-3-pyridazinon-2-yl)-4-propargyl- 2H-1,4-benzoxazin-3-one;

6-(4-Methyl-5-trifluoromethyl-3-pyridazinon-2-yl)-4-propargyl-2H-1,4-benzoxazin-3-one, Ethyl 2-{2-chloro-4-fluoro-5-(5-trifluoromethyl-3-pyrizazinon-2-yl)phenoxy}propionate; and Ethyl 2-{2-chloro-4-fluoro-5-(5-trifluoromethyl-3-pyridazinon-2-yl)phenylthio}propionate.

In addition, more preferred ones from the viewpoint of their selectivity between crop plants and undesired weeds are as follows:

2-(4—Chloro-2-fluoro-5-propargyloxyphenyl)-4-methyl-5-trifluoromethylpyrizazin-3-one;

Ethyl 2-chloro-4-fluoro-5-(4-methyl-5-trifluoromethyl-3-pyridazinon-2-yl)phenoxyacetate;

N-{2-chloro-4-fluoro-5-(4-nethyl-5-trifluoromethyl-3-pyridazinon-2-yl)phenyl}methanesulfonamide; and Ethyl 2-chloro-4-fluoro-5-(4-methyl-5-trifluoromethyl-3-pyridazinon-2-yl)benzoate.

The present compounds can be produced, for example, according to the production processes described below.

(Production Process 1)

This is the production process in which among the present compounds, a compound of the formula:

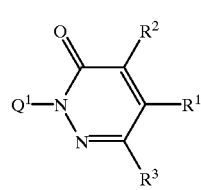

[3]

wherein $R^1$, $R^2$, $R^3$, and $Q^1$ are as defined above, is produced by reacting a hydrazone derivative of the formula:

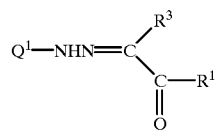

[4]

wherein $R^1$, $R^3$, and $Q^1$ are as defined above, with a compound of the formula:

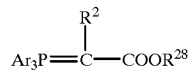

[5]

wherein $R^2$ is as defined above; $R^{28}$ is $C_1$–$C_6$ alkyl such as methyl or ethyl; and Ar is an optionally substituted phenyl such as phenyl.

The reaction is usually effected in a solvent. The reaction temperature is usually in the range of –20° to 150° C., preferably 0° to 100° C. The reaction time is usually in the range of a moment to 72 hours. The amounts of the reagents to be used in the reaction, although the proportion of 1 mole of compound [5] to 1 mole of compound [4] is ideal, can be freely changed depending upon the reaction conditions.

Examples of the solvent which can be used include aliphatic hydrocarbons such as hexane, heptane, ligroin, cyclohexane, and petroleum ether; aromatic hydrocarbons such as benzene, toluene, and xylene; ethers such as diethyl ether, diisopropyl ether, dioxane, tetrahydrofuran (THF), and ethylene glycol dimethyl ether; nitro compounds such as nitromethane and nitrobenzene; acid amides such as formamide, N,N-dimethylformamide, and acetamide; tertiary amines such as pyridine, triethylamnine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; water; and mixtures thereof.

After completion of the reaction, the reaction solvent is distilled out from the reaction mixture and the residue is subjected to chromatography, or the reaction mixture is subjected to ordinary post-treatments such as extraction with an organic solvent and concentration, followed by, if necessary, subsequent purification by a technique such as chromatography or recrystallization. Thus the desired compound of the present invention can be isolated.

The above reaction is effected through a compound of the formula:

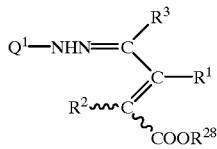

[6]

wherein $R^1$, $R^2$, $R^3$, $R^{28}$, and $Q^1$ are as defined above.

This production process can also be conducted by isolating compound [6] and effecting intramolecular cyclization of compound [6]. The cyclization can usually be effected in a solvent. The reaction temperature is usually in the range of −20° to 150° C., preferably 50° to 150° C. The reaction time is usually in the range of a moment to 72 hours.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, dichloroethane, chlorobenzene, and dichlorobenzene; ethers such as diethyl ether, diisopropyl ether, dioxane, tetrahydrofuran, and ethylene glycol dimethyl ether; ketones such as acetone, methyl ethyl ketone, methyl isobutyl ketone, isophorone, and cyclohexanone; esters such as ethyl formate, ethyl acetate, butyl acetate, and diethyl carbonate; nitro compounds such as nitromethane and nitrobenzene; nitriles such as acetonitrile and isobutyronitrile; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; fatty acids such as formic acid, acetic acid, and propionic acid; alcohols such as methanol, ethanol, ethylene glycol, and isopropanol; water; and mixtures thereof.

As the reaction catalyst, acids such as sulfuric acid or bases such as sodium methylate can be used.

(Production Process 2)

This is the production process according to the following scheme:

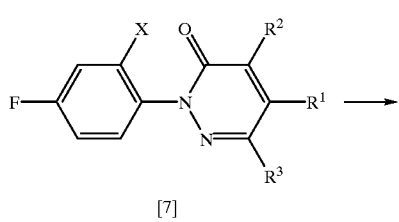

[7]

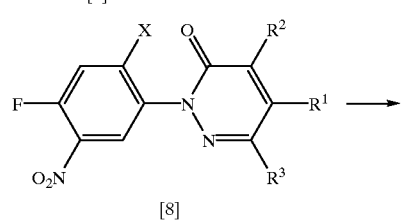

[8]

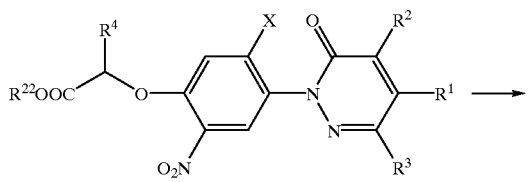

[9]

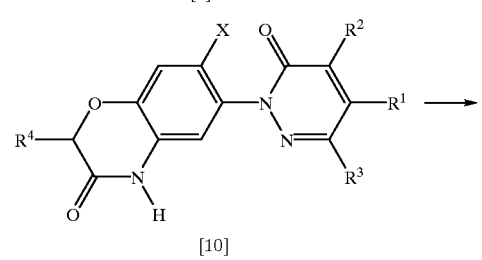

[10]

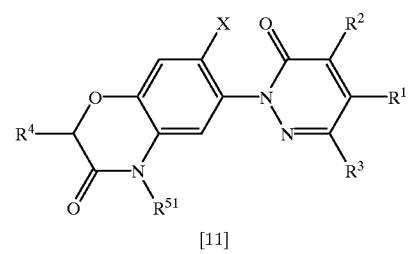

[11]

wherein $R^{51}$ is a substituent other than hydrogen, which is included in the definition of $R^5$; $R^1$, $R^2$, $R^3$, $R^4$, and X are as defined above; $R^{22}$ is $C_1$–$C_6$ alkyl; and D is chlorine, bromine, iodine, methanesulfonyloxy, trifluoromethanesulfonyloxy, or p-toluenesulfonyloxy.

Process for Producing Compound [8] from Compound [7]

Compound [8] can be produced by reacting compound [7] with a nitrating agent in a solvent.

Nitrating agent: nitric acid or the like

Amount of nitrating agent: 1 to 10 moles per mole of compound [7]

Solvent: sulfuric acid

Temperature: −10° C. to room temperature

Time: a moment to 24 hours

Process for Producing Compound [9] from Compound [8]

Compound [9] can be produced by reacting compound [8] with a compound of the formula:

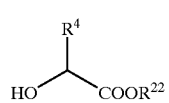

[12]

wherein $R^4$ and $R^{22}$ are as defined above, in the presence of potassium fluoride in a solvent.

Amount of compound [12]: 1 to 50 moles per mole of compound [8]

Amount of potassium fluoride: 1 to 50 moles per mole of compound [8]

Solvent: 1,4-dioxane or the like

Temperature: room temperature to refluxing temperature under heating

Time: a moment to 96 hours

Process for Producing Compound [10] from Compound [9]

Compound [10] can be produced by reducing compound [9] with iron powder or the like in the presence of an acid in a solvent.

Amount of iron powder: 3 moles to an excess per mole of compound [9]

Acid: acetic acid or the like

Amount of acid: 1 to 10 moles

Solvent: water, ethyl acetate, or the like

Temperature: room temperature to refluxing temperature under heating

Time: a moment to 24 hours

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, tetrahydrofuran, and ethylene glycol dimethyl ether; nitro compounds such as nitrobenzene; acid amides such as formamide, N,N-dimethylformamide, and acetamide; tertiary amines such as pyridine, triethylamine, diisopropylethylamine, N,N-dimethylamine, N,N-diethylaniline, and N-methylmorpholine; and mixtures thereof.

After completion of the reaction, the reaction mixture is poured into water, if necessary, and subjected to ordinary post-treatments such as extraction with an organic solvent and concentration, followed by, if necessary, subsequent purification by a technique such as column chromatography or recrystallization. Thus the present compound [11] can be obtained.

The above compound [9] can also be produced according to the following scheme:

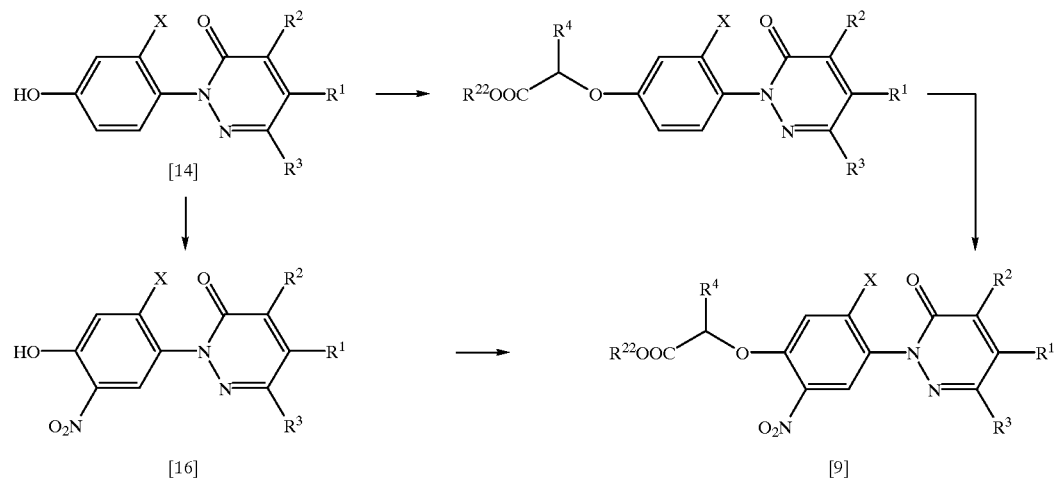

wherein $R^1$, $R^2$, $R^3$ $R^4$, $R^{22}$, and X are as defined above.

Process for Producing Compound [15] from Compound [14]

Compound [15] can be produced by reacting compound [14] with a compound of the formula:

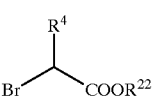 [17]

wherein $R^4$ and $R^{22}$ are as defined above, in the presence of a base in a solvent.

Amount of compound [17]: 1 to 2 moles per mole of compound [14]

Base: sodium hydride, sodium carbonate, or the like

Amount of base: 1 to 2 moles per mole of compound [14]

Process for Producing Compound [11] from Compound [10]

Compound [11] can be produced by reacting compound [10] with a compound of the formula:

$R^{51}$—D  [13]

wherein $R^{51}$ and D are as defined above.

The reaction is usually effected in the presence of a base in a solvent. The reaction temperature is usually in the range of −20° to 150° C., preferably 0° to 50° C. The reaction time is usually in the range of a moment to 48 hours. The amounts of the reagents to be used in the reaction are usually 1 to 3 moles of compound [13] and usually 1 to 2 moles of the base, per mole of compound [10].

Examples of the base which can be used include inorganic bases such as sodium hydride, potassium hydride, sodium hydroxide, potassium hydroxide, potassium carbonate, and sodium carbonate; and organic bases such as triethylamine, diisopropylethylamine, pyridine, 4-dimethylaminopyridine, N,N-dimethylaniline, and N,N-diethylaniline.

Solvent: 1,4-dioxane, N,N-dimethylformamide, or the like

Temperature: 0° to 100° C.

Time: a moment to 24 hours

Process for Producing Compound [9] from Compound [15]

Compound [9] can be produced by reacting compound [15] with a nitrating agent in a solvent.

Nitrating agent: nitric acid or the like

Amount of nitrating agent: 1 to 10 moles per mole of compound [15]

Solvent: sulfuric acid, acetic acid, or the like

Temperature: −10° C. to room temperature

Time: a moment to 24 hours

Process for Producing Compound [16] from Compound [14]

Compound [16] can be produced by reacting compound [14] with a nitrating agent in a solvent.

Nitrating agent: nitric acid or the like

Amount of nitrating agent: 1 to 10 moles per mole of compound [14]

Solvent: sulfuric acid, acetic acid, or the like

Temperature: −10° C. to room temperature

Time: a moment to 24 hours

Process for Producing Compound [9] from Compound [16]

Compound [9] can be produced by reacting compound [16] with compound [17] in the presence of a base in a solvent.

Amount of compound [17]: 1 to 2 moles per mole of compound [16]

Base: sodium hydride, potassium carbonate, or the like

Amount of base: 1 to 2 moles per mole of compound [16]

Solvent: 1,4-dioxane, N,N-dimethylformamide, or the like

Temperature: 0° to 100° C.

Time: a moment to 24 hours (Production Process 3)

This is the production process according to the following scheme:

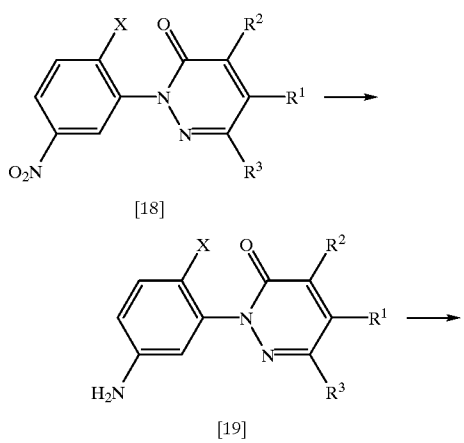

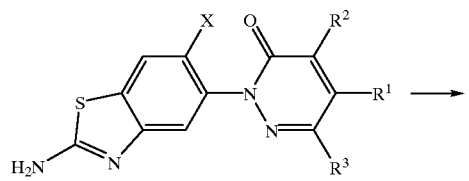

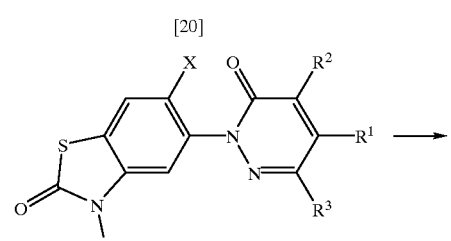

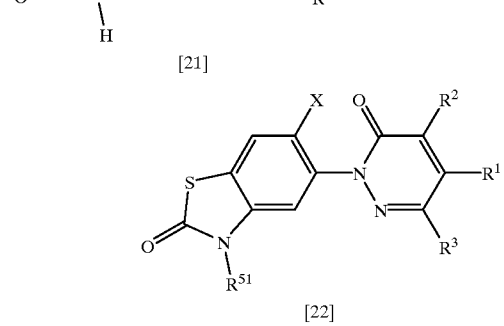

wherein X, $R^1$, $R^2$, $R^3$, $R^{51}$, and D are as defined above.

Process for Producing Compound [19] from Compound [18]

Compound [19] can be produced by reducing compound [18] with iron powder or the like in the presence of an acid in a solvent.

Amount of iron powder: 3 moles to an excess per mole of compound [18]

Acid: acetic acid or the like

Amount of acid: 1 to 10 moles per mole of compound [18]

Solvent: water, ethyl acetate, or the like

Temperature: room temperature to refluxing temperature under heating

Time: a moment to 24 hours

Process for Producing Compound [21] from Compound [20]

Compound [20] can be produced by reacting compound [19] with sodium thiocyanate, potassium thiocyanate, or the like in a solvent, and then reacting it with bromine or chlorine in a solvent.

Amount of sodium thiocyanate, potassium thiocyanate, or the like: 1 to 10 moles per mole of compound [19]

Amount of bromine or chlorine: 1 to 10 moles per mole of compound [19]

Solvent: aqueous hydrochloric acid, aqueous acetic acid, aqueous sulfuric acid, or the like Temperature: 0° to 50° C.

Time: a moment to 150 hours

Process for Producing Compound [219 from Compound [20]

Compound [21] can be produced by 1) reacting compound [20] with sodium nitrite, potassium nitrite, or the like in a solvent, and then 2) heating it in an acidic solution.

<Reaction 1>
 Amount of sodium nitrite, potassium nitrite, or the like: 1 to 2 moles per mole of compound [20]
 Solvent: aqueous hydrochloric acid or aqueous sulfuric acid
 Temperature: −10° to 10° C.
 Time: a moment to 5 hours
<Reaction 2>
 Acidic solution: aqueous hydrochloric acid, aqueous sulfuric acid, or the like
 Temperature: 70° C. to refluxing temperature under heating
 Time: a moment to 24 hours

Process for Producing Compound [22] from Compound [21]

Compound [22] can be produced by reacting compound [21] with compound [13] in the presence of a base in a solvent.
 Amount of compound [13]: 1 to 3 moles per mole of compound [21]
 Base: sodium hydride, potassium carbonate, or the like
 Amount of base: 1 to 2 moles per mole of compound [21]
 Solvent: 1,4-dioxane, N,N-dimethylformamide, or the like
 Temperature: 0 to 100° C.
 Time: a moment to 48 hours (Production Process 4)

This is the production process according to the following scheme:

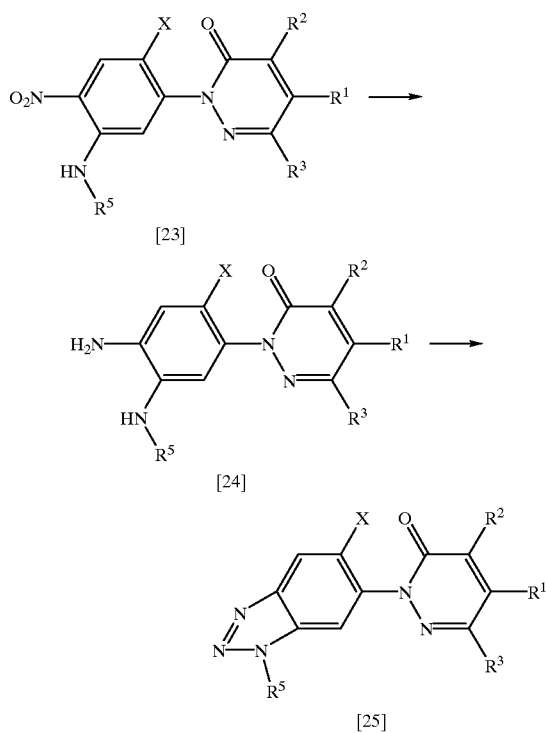

wherein X, $R^1$, $R^2$, $R^3$, and $R^5$ are as defined above.

Process for Producing Compound [24] from Compound [23]

Compound [24] can be produced by reducing compound [23] with iron powder or the like in the presence of an acid in a solvent.

Amount of iron powder: 3 moles to an excess per mole of compound [23]
 Acid: acetic acid or the like
 Amount of acid: 1 to 10 moles per mole of compound [23]
 Solvent: water, ethyl acetate, or the like
 Temperature: room temperature to refluxing temperature under heating
 Time: a moment to 24 hours

Process for Producing Compound [25] from Compound [24]

Compound [25] can be produced by 1) reacting compound [24] with a nitrite salt in a solvent to form a diazonium salt, and then 2) raising the temperature to cause the cyclization of the diazonium salt in a solvent.

<Reaction 1>
 Nitrite salt: sodium nitrite, potassium nitrite, or the like
 Amount of nitrite salt: 1 to 2 moles per mole of compound [24]
 Solvent: aqueous hydrochloric acid, aqueous sulfuric acid, or the like
 Temperature: −10° to 10° C.
 Time: a moment to 5 hours
<Reaction 2>
 Solvent: aqueous hydrochloric acid, aqueous sulfuric acid, or the like
 Temperature: room temperature to 80° C.
 Time: a moment to 24 hours (Production Process 5)

This is the production process according to the following scheme:

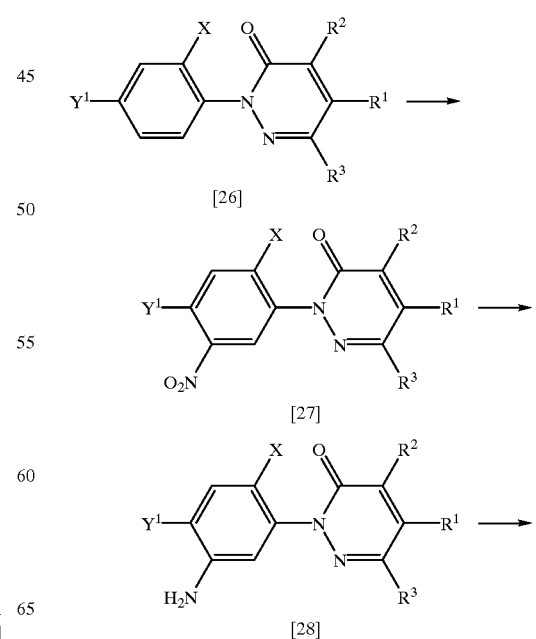

-continued

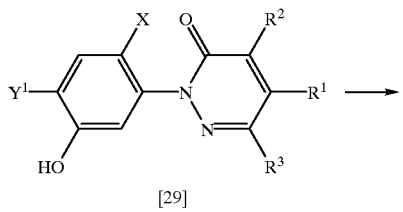

[29]

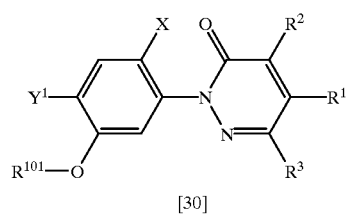

[30]

wherein $Y^1$ is a substituent other than nitro, which is included in the definition of Y;

$R^{101}$ is a substituent other than hydrogen, which is included in the definition of $R^{10}$; and X, $R^1$, $R^2$, and $R^3$ are as defined above.

Process for Producing Compound [27] from compound [26]

Compound [27] can be produced by adding nitric acid to compound [26] in a solvent (see Organic Synthesis Collective, Vol. 1, p. 372).

The reaction temperature is usually in the range of 0° to 100° C. The reaction time is usually in the range of a moment to 24 hours. The amounts of the reagents to be used in the reaction, although the proportion of 1 mole of nitric acid to 1 mole of compound [26] is ideal, can be freely changed depending upon the reaction conditions.

Examples of the solvent which can be used include acidic solvents such as sulfuric acid.

Process for Producing Compound [28] from compound [27]

Compound [28] can be produced by reducing compound [27] in a solvent (see Organic Synthesis Collective, Vol. 2, p. 471, and ibid., Vol. 5, p. 829).

For example, the production can be achieved by adding compound [27], which is neat or dissolved in a solvent such as ethyl acetate, to a mixture of acetic acid, iron powder, and water. The reaction temperature is usually in the range of 0° to 100° C. The reaction time is usually in the range of a moment to 24 hours.

After completion of the reaction, the reaction mixture is filtered to collect the crystals, which may be precipitated by the addition of water, if necessary, or the reaction mixture is subjected to ordinary post-treatments such as extraction with an organic solvent and concentration, followed by, if necessary, subsequent purification by a technique such as column chromatography or recrystallization. Thus the desired product can be isolated.

Process for Producing Compound [29] from compound [28]

Compound [29] can be produced by 1) reacting compound [28] with a nitrite salt in a solvent, and then 2) heating it in an acidic solvent.

<Reaction 1)>

Nitrite salt: sodium nitrite, potassium nitrite, or the like

Amount of nitrite salt: 1 to 2 moles per mole of compound [28]

Solvent: aqueous hydrochloric acid, aqueous sulfuric acid, or the like

Temperature: −10° to 10° C.

Time: a moment to 5 hours

<Reaction 2)>

Acidic solvent: aqueous hydrochloric acid or aqueous sulfuric acid

Temperature: 70° C. to refluxing temperature under heating

Time: a moment to 24 hours.

Process for Producing Compound [30] from Compound [29]

Compound [30] can be produced by reacting compound [29] with a compound of the formula:

$$R^{101}\text{—D} \qquad [31]$$

wherein $R^{101}$ and D are as defined above, in the presence of a base in a solvent.

The reaction is usually effected in a solvent. The reaction temperature is usually in the range of −20° to 150° C., preferably 0° to 100° C. The reaction time is usually in the range of a moment to 72 hours. The amounts of the reagents to be used in the reaction, although the proportion of 1 mole of compound [31] and 1 mole of a base to 1 mole of compound [29] is ideal, can be freely changed depending upon the reaction conditions.

Examples of the base which can be used include organic bases and inorganic bases such as potassium carbonate, sodium hydroxide, and sodium hydride.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, dichloroethane, chlorobenzene, and dichlorobenzene; ethers such as diethyl ether, diisopropyl ether, dioxane, tetrahydrofuran, and ethylene glycol dimethyl ether; ketones such as acetone, methyl ethyl ketone, methyl isobutyl ketone, isophorone, and cyclohexanone; esters such as ethyl formate, ethyl acetate, butyl acetate, and diethyl carbonate; nitro compounds such as nitromethane and nitrobenzene; nitriles such as acetonitrile and isobutyronitrile; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; and mixtures thereof.

After completion of the reaction, the reaction mixture is filtered to collect the crystals, which may be precipitated by the addition of water, if necessary, or the reaction mixture is subjected to ordinary post-treatments such as extraction with an organic solvent and concentration, followed by, if necessary, subsequent purification by a technique such as column chromatography or recrystallization. Thus the desired product can be isolated.

(Production Process 6)

This is the production process according to the following scheme:

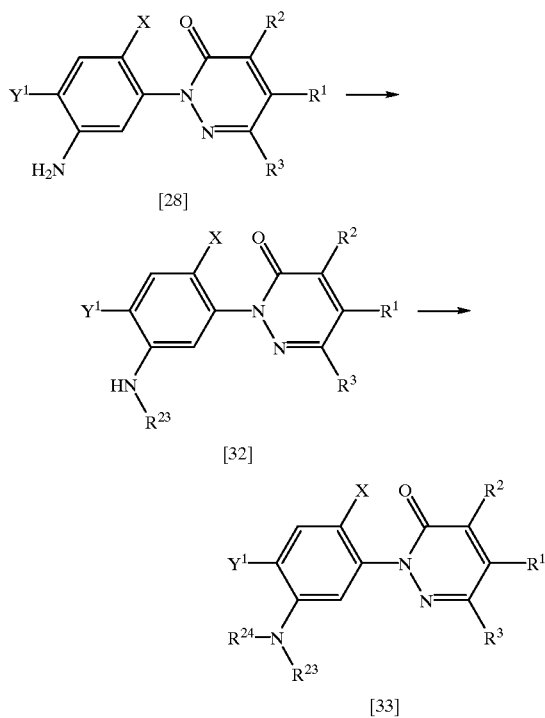

wherein $R^{23}$ and $R^{24}$ are independently a substituent other than hydrogen, which is included in the definition of $R^{11}$ and $R^{12}$; or $COR^{13}$, $SO_2R^{14}$, $SO_2R^{15}$, or $COOR^{10}$, wherein $R^{10}$, $R^{13}$, $R^{14}$, and $R^{15}$ are as defined above; X, $Y^1$, $R^1$, $R^2$, and $R^3$ are as defined above.

Process for Producing compound [32] from Compound [28]

Compound [32] can be produced by reacting compound [28] with a compound of the formula:

 $R^{20}$—D  [34]

wherein $R^{20}$ is a substituent other than hydrogen, which is included in the definition of $R^{11}$ or $R^{12}$; or $COR^{13}$, $SO_2R^{14}$, $SO_2R^{15}$ or $COOR^{10}$, wherein $R^{10}$, $R^{13}$, $R^{14}$, are as defined above; and D is as defined above; or with a compound of the formula:

 $(R^{21})_2O$  [35]

wherein $R^{21}$ is $COR^{13}$, $SO_2R^{14}$, $SO_2R^{15}$, or $COOR^{10}$, wherein $R^{10}$, $R^{13}$, $R^{14}$, and $R^{15}$ are as defined above, usually in the presence of a base and usually in a solvent.

The reaction temperature is usually in the range of −20° to 200° C., preferably 0° to 180° C. The reaction time is usually in the range of a moment to 72 hours. The amounts of the reagents to be used in the reaction, although the proportion of 1 mole of compound [34] or [35] to 1 mole of compound [28] is ideal, can be freely changed depending upon the reaction conditions.

Examples of the base which can be used include organic bases such as pyridine and triethylamine, and inorganic bases.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, dichloroethane, chlorobenzene, and dichlorobenzene; ethers such as diethyl ether, diisopropyl ether, dioxane, tetrahydrofuran, and ethylene glycol dimethyl ether; ketones such as acetone, methyl ethyl ketone, methyl isobutyl ketone, isophorone, and cyclohexanone; esters such as ethyl formate, ethyl acetate, butyl acetate, and diethyl carbonate; nitro compounds such as nitromethane and nitrobenzene; nitrites such as acetonitrile and isobutyronitrile; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; and mixtures thereof.

After completion of the reaction, the reaction mixture is filtered to collect the precipitated crystals, or the reaction mixture is subjected to ordinary post-treatments such as extraction with an organic solvent and concentration, followed by, if necessary, subsequent purification by a technique such as column chromatography or recrystallization. Thus the desired product can be isolated.

Process for Producing Compound [33] from Compound [32]

Compound [33] can be produced by reacting compound [32] with compound [34] or [35]. This production process is based on the process for producing compound [32] from compound [28].

(Production Process 7)

This is the production process according to the following scheme:

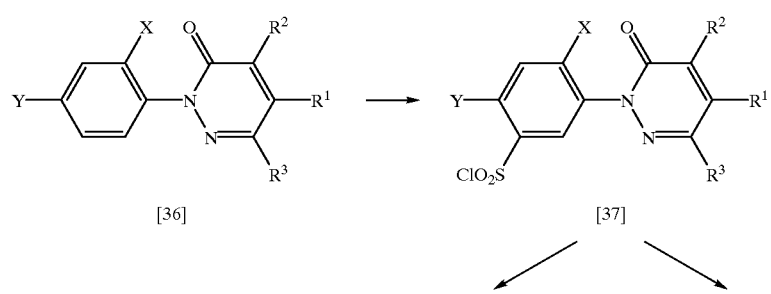

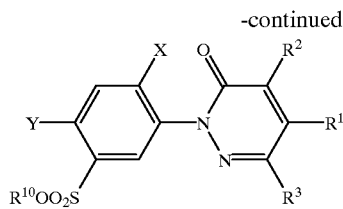

[38]

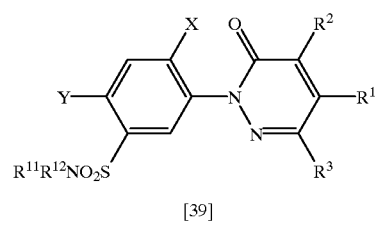

[39]

wherein X, Y, $R^1$, $R^2$, $R^3$, $R^{10}$, $R^{11}$, and $R^{12}$ are as defined above.

Process for Producing compound [37] from compound [36]

Compound [37] can be produced by reacting compound [36] with chlorosulfonic acid without any solvent or in a solvent.

Amount of chlorosulfonic acid: 1 mole to an excess per mole of compound [36]
Solvent: sulfuric acid
Temperature: 0° to 70° C.
Time: a moment to 24 hours
(see Org. Syn. Coll., Vol. 1, 8 (1941))

Process for Producing Compound [38] from Compound [37]

Compound [38] can be produced by reacting compound [37] with a compound of the formula:

$R^{10}$—OH  [40]

wherein $R^{10}$ is as defined above, in the presence of a base without any solvent or in a solvent.

Amount of compound [24]: 1 mole to an excess per mole of compound [37]
Base: organic bases such as triethylamine or inorganic bases such as potassium carbonate
Amount of base: 1 to 2 moles per mole of compound [37]
Solvent: N,N-dimethylformamide, 1,4-dioxane, or the like
Temperature: 0° to 100° C.
Time: a moment to 24 hours Process for Producing Compound [39] from Compound [37]

Compound [39] can be produced by reacting compound [37] with a compound of the formula:

$R^{11}R^{12}$NH  [41]

wherein $R^{11}$ and $R^{12}$ are as defined above, in the presence or absence of a base without any solvent or in a solvent.

Amount of compound [41]: 1 mole to an excess per mole of compound [37]
Base: organic bases such as triethylarine or inorganic bases such as potassium carbonate
Amount of base: 1 to 2 moles per mole of compound [37]
Solvent: 1,4-dioxane, N,N-dimethylformamide, or the like
Temperature: 0° to 100° C.

Time: a moment to 24 hours
(Production Process 8)

This is the production process according to the following scheme:

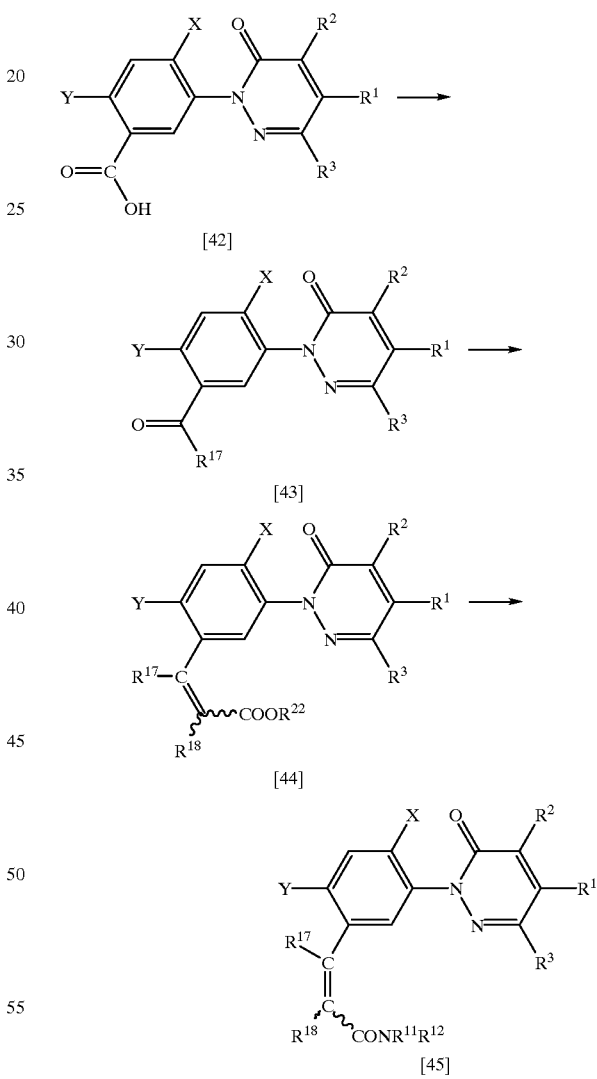

wherein X, Y, $R^1$, $R^2$, $R^3$, $R^{11}$, $R^{12}$, $R^{17}$, $R^{18}$, and $R^{22}$ are as defined above.

Process for Producing Compound [43] from Compound [42]

Compound [43] can be produced from compound [42] according to the method described in JP-A 5-294920/1993, pp. 15–16.

Process for Producing Compound [44] from Compound [43]

Compound [44] can be produced by reacting compound [43] with a compound of the formula:

   [45]

or

   [46]

wherein $R^{18}$ and $R^{22}$ are as defined above, in a solvent, and when compound [46] is used, in the presence of a base.

Amount of compound [45] or [46]: 1 to 2 moles per mole of compound [43]
Solvent: tetrahydrofuran, toluene, or the like
Base: sodium hydride or the like
Amount of base: 1 to 2 moles per mole of compound [43]
Temperature: 0° to 50° C.
Time: a moment to 24 hours Process for Producing Compound [45] from Compound [44]

Compound [45] can be produced by reacting compound [44] with compound [41].
(Production Process 9)
This is the production process according to the following scheme:

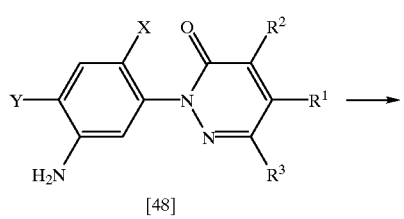

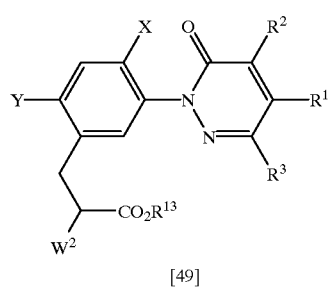

wherein $W^2$ is chlorine or bromine; and X, Y, $R^1$, $R^2$, $R^3$, and $R^{13}$ are as defined above.

The reaction conditions are described, for example, in U.S. Pat. No. 5,208,212.

The production can be achieved by converting compound [48] into a diazonium salt in a solution of hydrochloric acid, hydrobromic acid, or the like according to the ordinary method, and then reacting it with a compound of the formula:

   [50]

wherein $R^{13}$ is as defined above, in the presence of a copper salt, such as copper (II) chloride or copper (II) bromide, in a solvent such as acetonitrile.

The reaction temperature is usually in the range of −20° to 150° C., preferably 0° to 60° C. The reaction time is usually in the range of a moment to 72 hours.

After completion of the reaction, the reaction mixture is filtered to collect the crystals, which may be precipitated by the addition of water, if necessary, or the reaction mixture is subjected to ordinary post-treatments such as extraction with an organic solvent and concentration, followed by, if necessary, subsequent purification by a technique such as column chromatography or recrystallization. Thus the desired product can be isolated.
(Production Process 10)
This is the production process according to the following scheme:

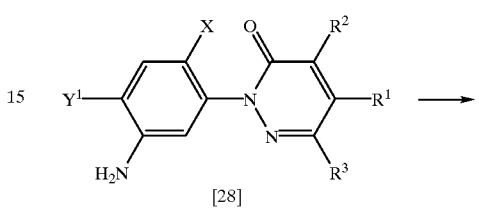

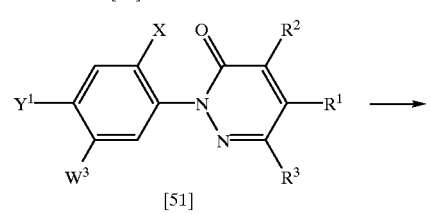

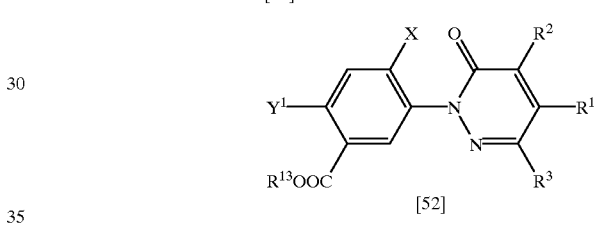

wherein $W^3$ is bromine or iodine; and X, $Y^1$, $R^1$, $R^2$, $R^3$, and $R^{13}$ are as defined above.

Process for Producing Compound [51] from compound [28]

Compound [51] can be produced by 1) making a diazonium salt from compound [28] in a solvent and then 2) reacting it with potassium iodide or copper (I) bromide in a solvent.
<Reaction 1)>
Diazotizing agent: sodium nitrite, potassium nitrite, or the like.
Amount of diazotizing agent: 1 to 2 moles per mole of compound [28]
Solvent: aqueous hydrogen bromide, aqueous sulfuric acid, or the like.
Temperature: −10° to 10° C.
Time: a moment to 5 hours
<Reaction 2)>
Amount of potassium iodide or copper (I) bromide: 1 mole to an excess per mole of compound [28]
Solvent: aqueous hydrogen bromide, aqueous sulfuric acid, or the like
Temperature: 0° to 80° C.
Time: a moment to 24 hours
(see Org. Syn. Coll., Vol. 2, 604 (1943), and ibid., Vol. 1, 136 (1941))

Process for Producing Compound [52] from Compound [51]

Compound [52] can be produced by reacting compound [51] with a compound of the formula:

$$R^{13}\text{—OH} \qquad [53]$$

wherein $R^{13}$ is as defined above, in the presence of a transition metal catalyst and a base in a solvent under an atmosphere of carbon monoxide.

Catalyst: $PdCl_2(PPh_3)_2$ or the like

Amount of catalyst: a catalytic amount to 0.5 mole per mole of compound [51]

Amount of compound [53]: 1 mole to an excess per mole of compound [51]

Base: organic bases such as diethylamine

Amount of base: 1 to 2 moles per mole of compound [51]

Solvent: N,N-dimethylformamide or the like

Pressure of carbon monoxide: 1 to 150 atm.

Temperature: 0° to 100° C.

Time: a moment to 72 hours (see Bull. Chem. Soc. Jpn., 48 (7) 2075 (1975))

(Production Process 11)

This is the production process according to the following scheme:

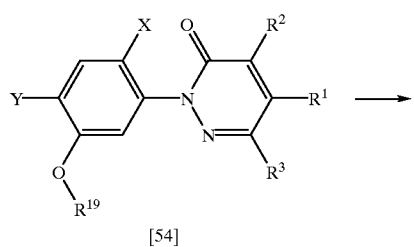

[54]

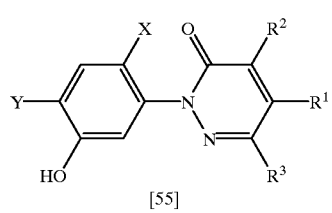

[55]

wherein X, Y, $R^1$, $R^2$, $R^3$, and $R^{19}$ are as defined above.

Compound [55] can be produced by hydrolyzing compound [54] in an acid solvent such as sulfuric acid, or in the presence of an acid such as boron tribromide in a solvent such as methylene chloride.

The reaction temperature is usually in the range of −20° to 150° C., preferably 0° to 100° C. The reaction time is usually in the range of a moment to 72 hours.

The amount of the acid to be used in the reaction, although the proportion of 1 mole of the acid to 1 mole of compound [54] is ideal, can be freely changed depending upon the reaction conditions.

After completion of the reaction, the reaction mixture is filtered to collect the crystals, which may be precipitated by the addition of water, if necessary, or the reaction mixture is subjected to ordinary post-treatments such as extraction with an organic solvent and concentration, followed by, if necessary, subsequent purification by a technique such as column chromatography or recrystallization. Thus the desired product can be isolated.

(Production Process 12)

This is the production process according to the following scheme:

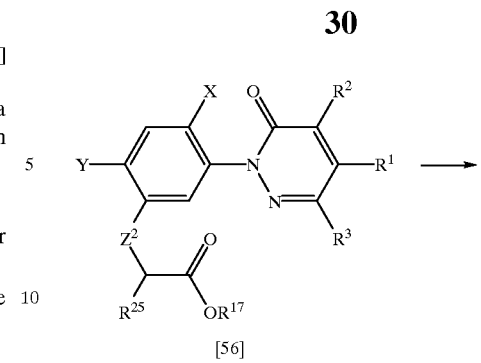

[56]

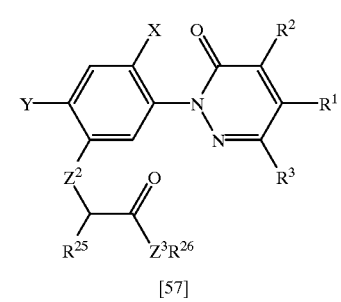

[57]

wherein X, Y, $R^1$, $R^2$, $R^3$, $Z^2$, and $R^{17}$ are as defined above; $Z^3$ is oxygen or sulfur; $R^{25}$ is hydrogen or $C_1$–$C_5$ alkyl; and $R^{26}$ is $C_1$–$C_6$ alkyl, $C_3$–$C_6$ alkenyl, or $C_3$–$C_6$ alkynyl.

Compound [57] can be produced by reacting compound [56] with a compound of the formula:

$$R^{26}Z^3H \qquad [58]$$

wherein $R^{26}$ and $Z^3$ are as defined above, in the presence or absence of a catalyst and usually in a solvent.

The amount of compound [58] to be used in the reaction, although the proportion of 1 mole of compound [58] to 1 mole of compound [56] is ideal, can be freely changed depending upon the reaction conditions.

Examples of the catalyst which can be used include p-toluenesulfonic acid. Examples of the solvent which can be used include toluene, xylene or the like, or compound [56].

The reaction temperature is usually in the range of 0° to 200° C., preferably 50° to 150° C. The reaction time is usually in the range of a moment to 72 hours.

After completion of the reaction, the reaction mixture is filtered to collect the crystals, which may be precipitated by the addition of water, if necessary, or the reaction mixture is subjected to ordinary post-treatments such as extraction with an organic solvent and concentration, followed by, if necessary, subsequent purification by a technique such as column chromatography or recrystallization. Thus the desired product can be isolated.

(Production Process 13)

This is the production process according to the following scheme:

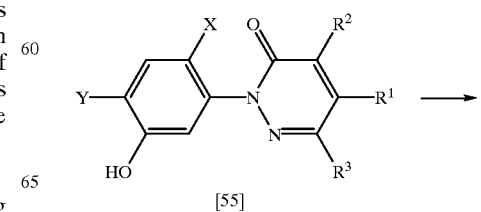

[55]

-continued

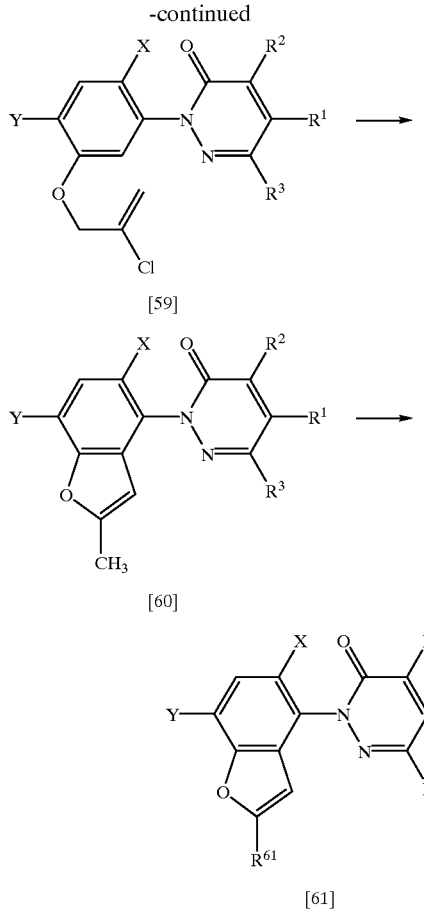

wherein $R^{61}$ is a substituent other than methyl, which is included in the definition of $R^6$;

and X, Y, $R^1$, $R^2$, and $R^3$ are as defined above.

Process for Producing Compound [59] from Compound [55]

Compound [59] can be produced by reacting compound [55] with 2,3-dichloropropene in the presence of a base in a solvent.

Amount of 2,3-dichloropropene: 1 to 3 moles per mole compound [55]
Base: inorganic bases such as potassium carbonate
Amount of base: 1 to 2 moles per mole of compound [55]
Solvent: N,N-dimethylformamide or the like
Temperature: 0° to 70° C.
Time: a moment to 24 hours Process for Producing Compound [60] from Compound [59]

Compound [60] can be produced by heating compound [59] in a solvent.

Solvent: N,N-dimethylformamide, N,N-dimethylaniline, N,N-diethylaniline, p-diisopropylbenzene, or the like
Temperature: 70° to 200° C.
Time: a moment to 24 hours Process for Producing Compound [61] from Compound [60]

Compound [61] can be produced from compound [62] according to the method in which the methyl group in position 2 on the benzofuran ring is replaced with another substituent, as described in U.S. Pat. No. 5,308,829, columns 2-11.

(Production Process 14)

This is the production process according to the following scheme:

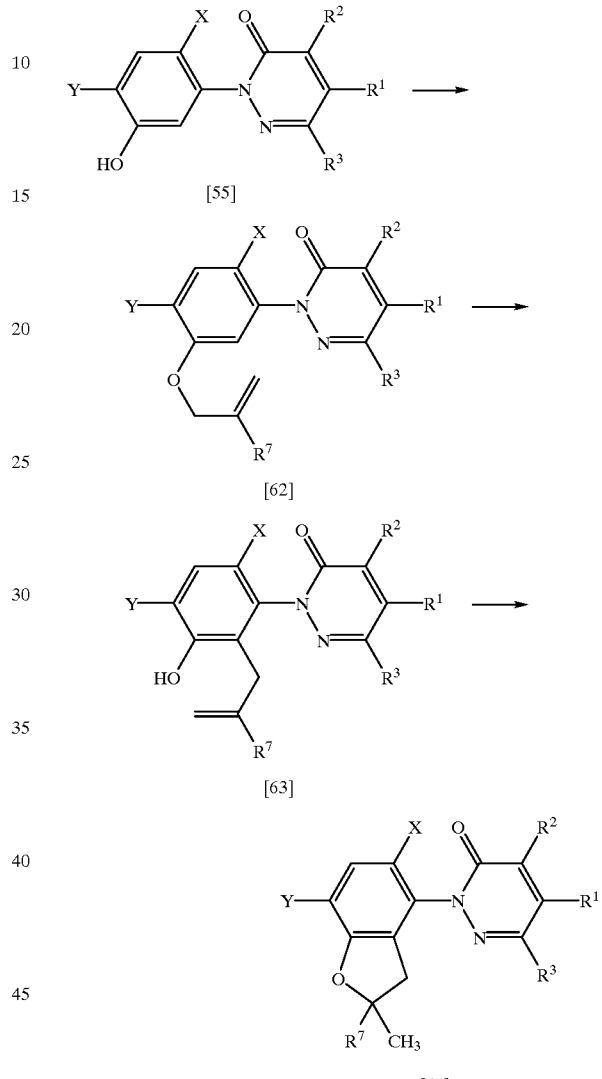

wherein X, Y, $R^1$, $R^2$, $R^3$, and $R^7$ are as defined above.

Process for Producing Compound [62] from Compound [55]

Compound [62] can be produced by reacting compound [55] with a compound of the formula:

$$CH_2=CR^7CH_2W^2 \qquad [65]$$

wherein $W^2$ and $R^7$ are as defined above, in the presence of a base in a solvent.

Amount of compound [65]: 1 to 5 moles per mole of compound [55]
Base: inorganic bases such as potassium carbonate
Amount of base: 1 to 2 moles per mole of compound [55]
Solvent: N,N-dimethylformamide, 1,4-dioxane, or the like Temperature: 0° to 70° C.
Time: a moment to 24 hours Process for Producing Compound [63] from Compound [62]

Compound [64] can be produced by heating compound [62] in a solvent.

Solvent: N,N-dimethylaniline, N,N-diethylaniline, p-diisopropylbenzene, or the like
Temperature: 100° to 200° C.
Time: a moment to 24 hours Process for Producing Compound [64] from Compound [63]

Compound [64] can be produced by heating compound [63] in the presence of an acid in a solvent.

Acid: organic acids such as p-toluenesulfonic acid; and inorganic acids such as sulfuric acid
Amount of acid: a catalytic amount to 1 mole per mole of compound [63]
Solvent: toluene, xylene, or the like
Temperature: 100° to 250° C.
Time: a moment to 24 hours (Production Process 15)

This is the production process according to the following scheme:

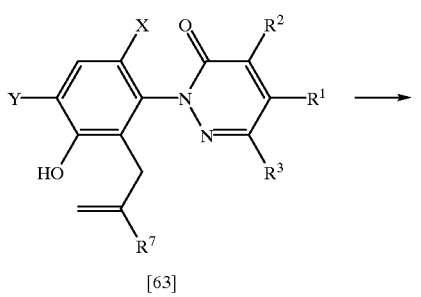

[63]

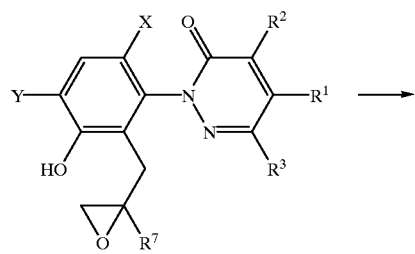

[66]

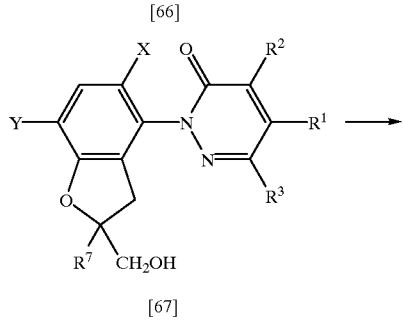

[67]

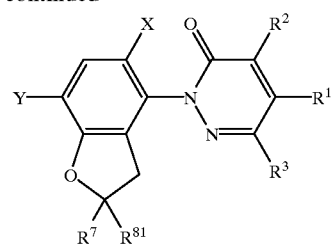

[68]

wherein $R^{81}$ is a substituent other than methyl and hydroxymethyl, which is included in the definition of $R^8$; and X, Y, $R^1$, $R^2$, $R^3$, and $R^7$ are as defined above.

Process for Producing Compound [66] from Compound [63]

Compound [66] can be produced by reacting compound [63] with a peracid in a solvent.

Peracid: m-chloroperbenzoic acid or peracetic acid
Amount of peracid: 1 mole to an excess per mole of compound [63]
Solvent: halogenated hydrocarbons such as dichloromethane; and organic acids such as acetic acid
Temperature: −20° C. to room temperature
Time: a moment to 24 hours Process for Producing Compound [67] from Compound [66]

Compound [67] can be produced by reacting compound [66] in the presence of a base in a solvent.

Base: potassium carbonate or the like
Amount of base: 1 to 2 moles per mole of compound [66]
Solvent: methanol, ethanol, or the like
Temperature: 0° to 50° C.
Time: a moment to 5 hours Process for Producing Compound [68] from Compound [67]

Compound [68] can be produced from compound [67] according to the method in which the hydroxyalkyl group in position 2 on the dihydrobenzofuran ring is replaced with another substituent, as described in U.S. Pat. No. 5,411,935, columns 5–10.

(Production Process 16)

This is the production process according to the following scheme:

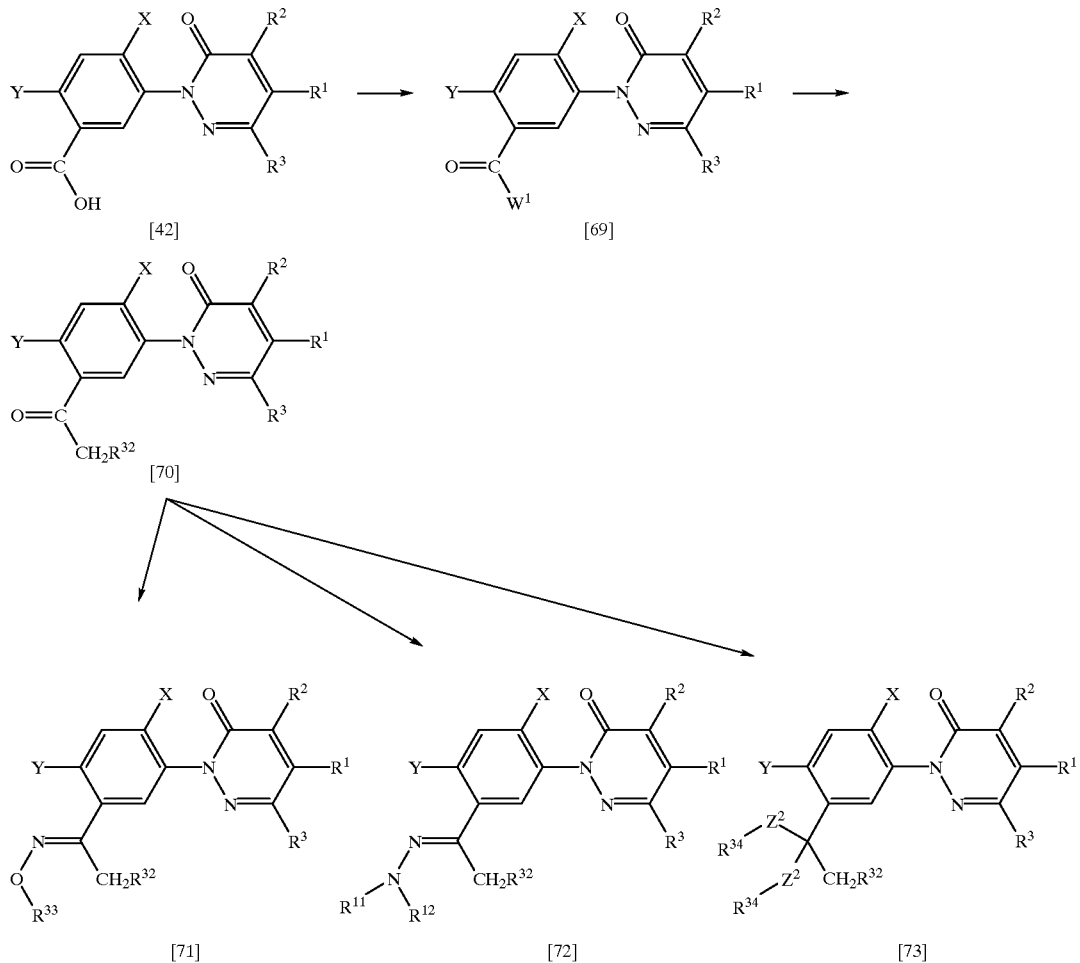

wherein $W^1$ is halogen, preferably chlorine; $R^{32}$ is hydrogen or $C_1$–$C_5$ alkyl; and X, Y, $Z^2$, $R^1$, $R^2$, $R^3$, $R^{11}$, $R^{12}$, $R^{33}$, and $R^{34}$ are as defined above.

Process for Producing Compound [69] from Compound [42]

Compound [69] can be produced by reacting compound [42] with a halogenating agent such as thionyl chloride in a solvent according to the ordinary method.

Process for Producing Compound [70] from Compound [69]

Compound [70] can be produced by reacting compound [69] with a compound of the formula:

[74]

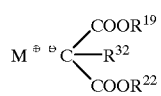

wherein $M^{\oplus}$ is an alkali metal cation, preferably lithium cation or sodium cation; and $R^{19}$, $R^{22}$, and $R^{32}$ are as defined above, to give a compound of the formula:

[75]

wherein X, Y, $R^1$, $R^2$, $R^3$, $R^{19}$, $R^{22}$, and $R^{32}$ are as defined above, and then hydrolyzing and decarboxylating compound [75].

The first reaction is usually effected in a solvent. The reaction temperature is usually in the range of –20° to 50° C., preferably room temperature. The reaction time is usually in the range of a moment to 72 hours.

Examples of the solvent which can be used include aliphatic hydrocarbons such as hexane, heptane, ligroin, cyclohexane, and petroleum ether; ethers such as diethyl ether, diisopropyl ether, dioxane, tetrahydrofuran, and ethylene glycol dimethyl ether; acid amides such as formamide, N,N-dimethylformamide, and acetamide; sulfur compounds such as dimethylsulfoxide and sulforane; and mixtures thereof.

The second reaction is effected in the presence of sulfuric acid, hydrobromic acid, or the like in a solvent such as a lower carboxylic acid, e.g., acetic acid, or without any solvent. The reaction temperature is usually in the range of 80° to 140° C., preferably 100° to 120° C. The reaction time is usually in the range of a moment to 72 hours.

Process for Producing Compound [71] from Compound [70]

Compound [71] can be produced by reacting compound [70] with a compound of the formula:

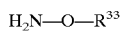  [76]

wherein $R^{33}$ is as defined above.

The reaction is effected in a lower alcohol such as methanol, ethanol or isopropanol, or in a mixed solution of such a lower alcohol and water. The reaction temperature is in the range of 0° to 80° C. The reaction time is in the range of a moment to 72 hours.

Compound [76] can be used in the form of a free base or an acid addition salt such as a hydrochloride salt or a sulfate salt.

The above reaction can also be effected with the addition of a basic catalyst such as an organic base, e.g., pyridine; an alkali metal carbonate, e.g., sodium carbonate, potassium carbonate or the like; alkali metal hydrogencarbonate; or alkaline earth metal carbonate.

Compound [71] can also be produced by reacting a compound of the formula:

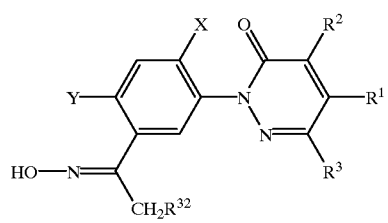  [77]

wherein X, Y, $R^1$, $R^2$, $R^3$, and $R^{32}$ are as defined above, with a compound of the formula:

  [78]

wherein $R^{33}$ and D are as defined above, in the presence of a base, usually in a solvent.

Examples of the base which can be used include alkali metal alcoholates and alkali metal hydrides such as sodium hydride.

The amounts of the reagents to be used in the reaction, although the proportion of about 1 mole of compound [78] and 1 to 2 moles of the base to 1 mole of compound [77] is ideal, can be free changed depending upon the reaction conditions.

Examples of the solvent which can be used include ethers such as diethyl ether, diisopropyl ether, dioxane, tetrahydrofuran, and ethylene glycol dimethyl ether; acid amides such as formamide, N,N-dimethylformamide, and acetamide; sulfur compounds such as dimethylsulfoxide and sulforane; alcohols such as methanol, ethanol, ethylene glycol, and isopropanol; and mixtures thereof.

The reaction temperature in the above reaction is in the range of –10° to 100° C., preferably 0° to 80° C. The reaction time is in the range of a moment to 72 hours.

Process for Producing Compound [72] from Compound [70]

Compound [72] can be produced by reacting compound [70] with a compound of the formula:

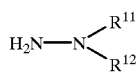  [79]

wherein $R^{11}$ and $R^{12}$ are as defined above.

The reaction is effected in a lower alcohol such as methanol, ethanol or isopropanol, or in a mixed solution of such a lower alcohol and water. The reaction temperature is in the range of 0° to 80° C. The reaction time is in the range of a moment to 72 hours.

Compound [79] can be used in the form of a free base or an acid addition salt such as a hydrochloride salt or a sulfate salt.

The above reaction can also be effected with the addition of a basic catalyst such as an organic base, e.g., pyridine; an alkali metal carbonate, e.g., sodium carbonate, potassium carbonate or the like; alkali metal hydrogencarbonate; or alkaline earth metal carbonate.

Process for Producing Compound [73] from Compound [70]

Compound [73] can be produced by reacting compound [70] with a compound of the formula:

  [80]

wherein $Z^2$ and $R^{34}$ are as defined above, usually in the presence of a catalytic amount to an excess of an acid such as p-toluenesulfonic acid, hydrochloric acid or sulfuric acid, in an organic solvent such as benzene or chloroform.

The reaction temperature is in the range of –30° C. to the boiling temperature of the reaction mixture. The reaction time is in the range of a moment to 72 hours.

(Production Process 17)

This is the production process according to the following scheme:

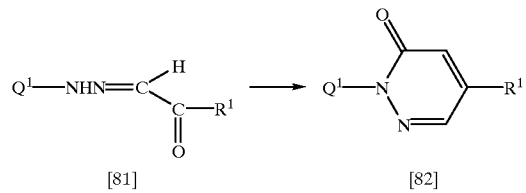

wherein $Q^1$ and $R^1$ are as defined above.

Compound [82] can be produced by reacting compound [81] with a compound of the formula:

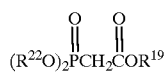  [83]

wherein $R^{19}$ and $R^{22}$ are as defined above, in a solvent.

The reaction temperature is usually in the range of 30° to 120° C., preferably 40° to 80° C. The reaction time is usually in the range of 5 to 72 hours. The amounts of the reagents to be used in the reaction, although the proportion of 1 mole of compound [83] to 1 mole of compound [81] is ideal, can be changed depending upon the reaction conditions.

Examples the solvent which can be used include tertiary amines such as triethylamine.

After completion of the reaction, the reaction solvent is distilled out from the reaction mixture and the residue is subjected to chromatography, or the reaction mixture is subjected to ordinary post-treatments such as extraction with an organic solvent and concentration, followed by, if necessary, subsequent purification by a technique such as column chromatography or recrystallization. Thus the desired compound of the present invention can be isolated.

(Production Process 18)

This is the production process according to the following scheme:

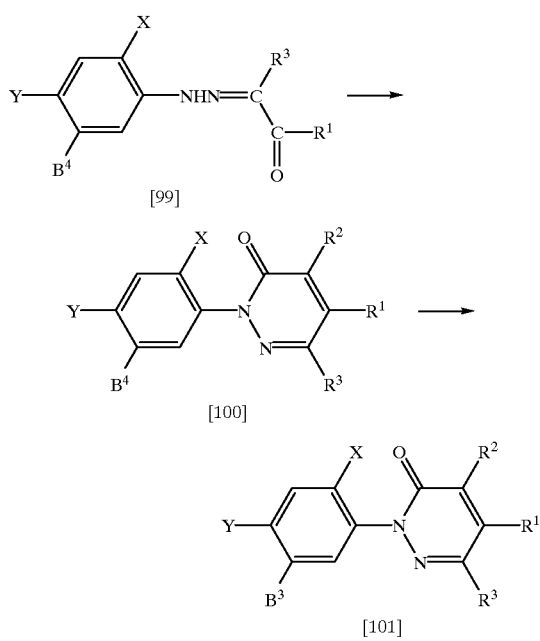

wherein $B^3$ is $OR^{35}$, $SR^{35}$, $COOR^{35}$, $COR^{16}$, or $CR^{17}=CR^{18}COR^{16}$ (wherein $R^{35}$ is ($C_1$-$C_6$ alkyl)carbonyl $C_1$-$C_6$ alkyl ($C_1$-$C_6$ haloalkyl)carbonyl $C_1$-$C_6$ alkyl, {($C_1$-$C_4$ alkoxy) $C_1$-$C_4$ alkyl}carbonyl $C_1$-$C_6$ alkyl, or ($C_3$-$C_8$ cycloalkyl)carbonyl $C_1$-$C_6$ alkyl; and $R^{16}$, $R^{17}$, and $R^{18}$ are as defined above); $B^4$ is a substituent derived from $B^3$ by protecting its ketone or aldehyde moiety with an alcohol; and X, Y, $R^1$, $R^2$, and $R^3$ are as defined above.

Process for Producing Compound [100] from Compound [99]

Compound [100] can be produced in the same manner as described in Production Process 1, except that compound [99] is used in place of compound [4].

Process for Producing Compound [101] from Compound [100]

Compound [101] can be produced by deprotecting the ketal or acetal moiety of compound [100] by the ordinary method.

Compound [99] can be produced in the same manner as described below in the production process for compound [4], except that the ketone or aldehyde moiety in the substituent $B^3$ of a compound of the formula:

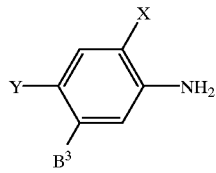

wherein X, Y, and $B^3$ are as defined above, is protected with an alcohol such as methanol to give a compound of the formula:

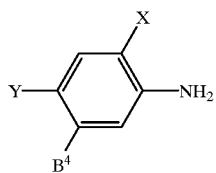

wherein X, Y, and $B^4$ are as defined above, and compound [103] is used in place of compound [91] as described below.

Compound [5], which is one of the starting compounds in the production of the present compounds by production process 1, can be obtained from commercial sources or can be produced, for example, according to the method described in Jikken Kagaku Kouza (Maruzen K.K.), 4th ed., Vol. 24, pp. 259–260.

Compound [4], which is the other starting compound used in production process 1, can be produced by reacting a compound of the formula:

wherein $R^1$ and $R^3$ are as defined above; and V is iodine, bromine, or chlorine, with water in the presence of a base to give a compound of the formula:

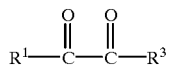

wherein $R^1$ and $R^3$ are as defined above (hereinafter referred to as reaction 1), and then reacting compound [85] with a compound of the formula:

$Q^1$—NHNH$_2$      [86]

wherein $Q^1$ is as defined above (hereinafter referred to as reaction 2).

Compound [85] can also be reacted as its hydrate or acetal derivative in water or an alcohol.

Reaction 1 is usually effected in a solvent. The reaction temperature is usually in the range of 20° to 100° C. The reaction time is usually in the range of a moment to 24 hours. The amounts of the reagents to be used in the reaction, although the proportion of 2 moles of water and 2 moles of a base to I mole of compound [84] is ideal, can be changed, if necessary.

Examples of the base which can be used include organic bases and inorganic bases such as sodium acetate and potassium acetate.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, tetrahydrofuran, and ethylene glycol dimethyl ether; esters such as ethyl formate, ethyl acetate, butyl acetate, and diethyl carbonate; nitro compounds such as nitromethane and nitrobenzene; nitriles such as acetonitrile and isobutyronitrile; acid amides such as N,N-dimethylformamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; water; and mixtures thereof.

Reaction 2 is usually effected in a solvent. The reaction temperature is usually in the range of −20° to 200° C. The reaction time is usually in the range of a moment to 72 hours. The amounts of the reagents to be used in the reaction, although the proportion of 1 mole of compound [86] to 1 mole of compound [84] used in reaction 1 is ideal, can be freely changed depending upon the reaction conditions. If necessary, the hydrochloride salt or sulfate salt of compound [86] can also be used.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, dichloroethane, chlorobenzene, and dichlorobenzene; ethers such as diethyl ether, diisopropyl ether, dioxane, tetrahydrofuran, and ethylene glycol dimethyl ether; esters such as ethyl formate, ethyl acetate, butyl acetate, and diethyl carbonate; nitro compounds such as nitromethane and nitrobenzene; nitriles such as acetonitrile and isobutyronitrile; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; fatty acids such as formic acid, acetic acid, and propionic acid; alcohols such as methanol, ethanol, ethylene glycol, and isopropanol; water; and mixtures thereof.

After completion of the reaction, the reaction mixture is filtered to collect the crystals, which may be precipitated by the addition of water, if necessary, or the reaction mixture is subjected to ordinary post-treatments such as extraction with an organic solvent and concentration, followed by, if necessary, subsequent purification by a technique such as column chromatography or recrystallization. Thus the desired product can be isolated.

Among the examples of compound [4], a compound of the formula:

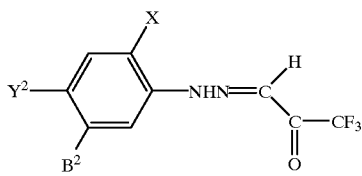

[87]

wherein X is as defined above; $Y^2$ is halogen; and $B^2$ is hydrogen, halogen, $C_1$–$C_6$ alkoxy, or $C_1$–$C_6$ alkylthio, can also be produced according to the following scheme:

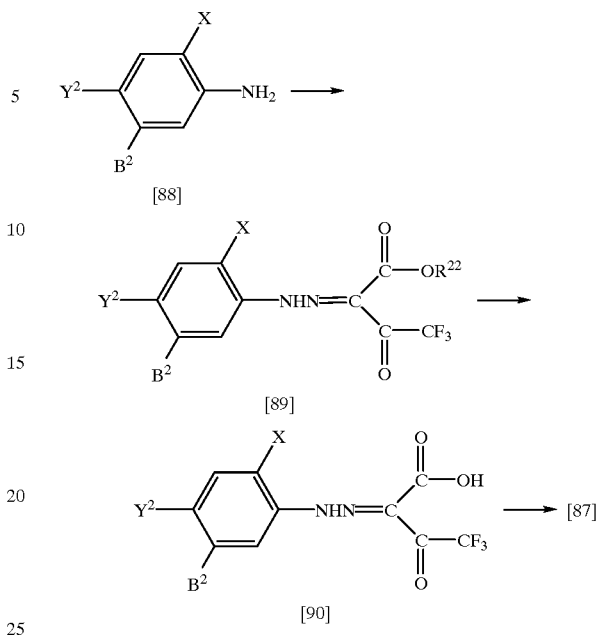

wherein X, $Y^2$, $B^2$, and $R^{22}$ are as defined above.

Process for Producing Compound [89] from Compound [88]

Compound [89] can be produced by reacting compound [88] with a nitrite salt in hydrochloric acid or sulfuric acid to convert it into a diazonium salt, and then reacting the diazonium salt with a compound of the formula:

$$CF_3CCH_2COR^{22}$$ [104]

wherein $R^{22}$ is as defined above, in the presence of a base such as sodium acetate or pyridine.

(see, e.g., Tetrahedron, Vol. 35, p. 2013 (1979))

Process for Producing Compound [90] from Compound [89]

Compound [90] can be produced by hydrolyzing compound [89] usually in the presence of a base in a solvent.

The reaction temperature is in the range of 0° to 150° C., preferably 20° to 100° C. The reaction time is in the range of 1 to 24 hours, preferably 1 to 10 hours. The amounts of the reagents to be used in the reaction, although the proportion of 1 mole of a base to 1 mole of compound [89] is ideal, can be changed, if necessary.

Examples of the base which can be used include inorganic bases such as potassium hydroxide, lithium hydroxide, barium hydroxide, and sodium hydroxide.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, tetrahydrofuran, and ethylene glycol dimethyl ether; ketones such as acetone, methyl ethyl ketone, methyl isobutyl ketone, isophorone, and cyclohexanone; nitro compounds such as nitromethane and nitrobenzene; acid amides such as N,N-dimethylformamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; water; and mixtures thereof.

Process for Producing Compound [87] from Compound [90]

Compound [87] can be produced by heating compound [90] in a solvent.

The reaction temperature is in the range of 50° to 200° C., preferably 50° to 150° C. The reaction time is in the range of a moment to 72 hours.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, dichloroethane, chlorobenzene, and dichlorobenzene; ethers such as diethyl ether, diisopropyl ether, dioxane, tetrahydrofuran, and ethylene glycol dimethyl ether; ketones such as acetone, methyl ethyl ketone, methyl isobutyl ketone, isophorone, and cyclohexanone; esters such as ethyl formate, ethyl acetate, butyl acetate, and diethyl carbonate; nitro compounds such as nitromethane and nitrobenzene; nitriles such as acetonitrile and isobutyronitrile; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; fatty acids such as formic acid, acetic acid, and propionic acid; alcohols such as methanol, ethanol, ethylene glycol, and isopropanol; water; and mixtures thereof.

The above reaction can also be effected with the use of a metal, e.g., copper, as a catalyst.

After completion of the reaction, the reaction mixture is filtered to collect the precipitated crystals, or the reaction mixture is subjected to ordinary post-treatments such as extraction with an organic solvent and concentration, followed by, if necessary, subsequent purification by a technique such as column chromatography or recrystallization. Thus the desired compound can be isolated.

Compound [86] can also be produced by the following scheme:

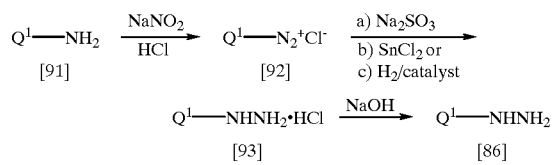

wherein $Q^1$ is as defined above.

(see Organic Synthesis Collective, Vol. 1, p.442)

Compound [91] is known in, or can be produced according to the method as described in, EP-61741-A; U.S. Pat. No. 4,670,046, U.S. Pat. No. 4,770,695, U.S. Pat. No. 4,709,049, U.S. Pat. No. 4,640,707, U.S. Pat. No. 4,720,297, U.S. Pat. No. 5,169,431; and JP-A 63-156787/1988.

Some examples of compound [91] can also be produced according to the following scheme:

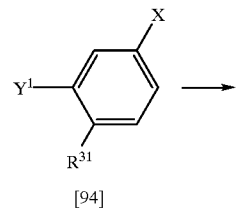

[94]

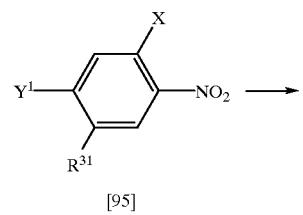

[95]

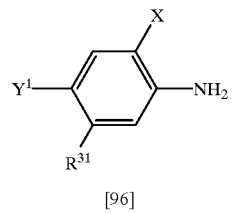

[96]

wherein $R^{31}$ is $COR^{16}$ or $COOR^{10}$.

Process for Producing Compound [95] from Compound [94]

Compound [95] can be produced by reacting compound [94] with nitric acid in a solvent.

The reaction temperature is usually in the range of 0° to 100° C. The reaction time is usually in the range of a moment to 24 hours. The amounts of the reagents to be used in the reaction, although the proportion of 1 mole of nitric acid to 1 mole of compound [94] is ideal, can be freely changed depending upon the reaction conditions.

Examples of the solvent which can be used include acidic solvents such as mixtures of nitric acid and sulfuric acid.

(see Organic Synthesis Collective, Vol. 1, p. 372)

Process for Producing Compound [96] from Compound [95]

Compound [96] can be produced by reducing compound [95] in a mixture of acetic acid, iron powder, and water.

The reaction temperature is usually in the range of 0° to 100° C. The reaction time is usually in the range of a moment to 24 hours.

After completion of the reaction, the reaction mixture is subjected to ordinary post-treatments such as extraction with an organic solvent and concentration, followed by, if necessary, subsequent purification by a technique such as column chromatography or recrystallization. Thus the desired compound can be isolated.

(see Organic Synthesis Collective, Vol. 2, p. 471, and ibid., Vol. 5, p. 829)

The present compounds have excellent herbicidal activity, and some of them exhibit excellent selectivity between crop plants and unfavorable weeds. In particular, the present compounds have herbicidal activity against various unfavorable weeds as recited below, which may cause trouble in the foliar treatment and soil treatment on upland fields.

Polygonaceae:
  wild buckwheat (*Polygonum convolvulus*), pale smartweed (*Polygonum lapathifolium*), Pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)
Portulacaceae:
  common purslane (*Portulaca oleracea*)
Caryophyllaceae:
  common chickweed (*Stellania media*)
Chenopodiaceae:
  common lambsquarters (*Chenopodium album*), kochia (*Kochia scoparia*)
Amaranthaceae:
  redroot pigweed (*Amaranthus retroflexus*), smooth pigweed (*Amaranthus hybridus*)
Crusiferae
  wild radish (*Raphatius raphanistrum*), wild mustard (*Sinapis arvensis*), shepherdspurse (*Capsella bursa-pastoris*)
Leguminosae:
  hemp sesbania (*Sesbania exaltata*), sicklepod (*Cassia obtusifolia*), Florida beggarweed (*Desmodium tortuosurm*), white clover (*Trifolium repens*)
Malvaceae:
  velvetleaf (*Abutilon theophrasti*), prickly sida (*Sida spinosa*)
Violaceae:
  field pansy (*Viola arvensis*), wild pansy (*Viola tricolor*)
Rubiaceae:
  catchweed bedstraw (cleavers) (*Galium aparine*)
Convolvulaceae:
  ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)
Labiatae:
  red deadnettle (*Lamium purpureum*), henbit (*Lamium amplexicaule*)
Solanaceae:
  jimsonweed (*Datura stramonium*), black nightshade (*Solanum nigrum*)
Scrophulariaceae:
  birdseye speedwell (*Veronica persica*), ivyleaf speedwell (*Veronica hederaefolia*)
Compositae:
  common cocklebur (*Xanthium pensylvanicum*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)
Boraginaceae:
  field forget-me-not (*Myosotis arvensis*)
Asclepiadaceae:
  common milkweed (*Asclepias syriaca*)
Euphorbiaceae:
  sun spurge (*Euphorbia helioscopia*), spotted spurge (*Euphorbia maculata*)
Gramineae:
  barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)
Commelinaceae:
  common dayflower (*Commelina communis*)
Equisetaceae:
  field horsetail (*Equisetum arvense*)
Cyperaceae:
  rice flatsedge (*Cyperus iria*), purple nutsedge (*Cyperus rotundus*), yellow nutsedge (*Cyperus esculentus*)

Furthermore, some of the present compounds have no problematic phytotoxicity on main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*) and canola (*Brassica napus*); garden crops such as flowers and ornamental plants; and vegetable crops.

The present compounds can attain effective control of unfavorable weeds in the no-tillage cultivation of soybean (*Glycine max*), corn (*Zea mays*), and wheat (*Triticum aestivum*). Furthermore, some of them exhibit no problematic phytotoxicity on crop plants.

The present compounds have herbicidal activity against various unfavorable weeds as recited below under the flooding treatment on paddy fields.
Gramineae:
  barnyardgrass (*Echinochloa oryzicola*)
Scrophulariaceae:
  common falsepimpernel (*Lindernia procumbens*)
Lythraceae:
  *Rotala indica, Ammannia multiflora*
Elatinaceae:
  *Elatine triandra*
Cyperaceae:
  smallflower umbrellaplant (*Cyperus difformis*), hardstem bulrush (*Scirpus juncoides*), needle spikerush (*Eleocharis acicularis*), *Cyperus serotinus, Eleocharis kuroguwai*
Pontederiaceae:
  *Monochoria vaginalis*
Alismataceae:
  *Sagittaria pygmaea, Sagittaria trifolia, Alisma canaliculatum*
Potamogetonaceae:
  roundleaf pondweed (*Potamogeton distinctus*)
Umbelliferae:
  *Oenanthe javanica*

Furthermore, some of the present compounds have no problematic phytotoxicity on transplanted paddy rice.

The present compounds can attain effective control of various unfavorable weeds in orchards, grasslands, lawns, forests, waterways, canals, or other non-cultivated lands.

The present compounds also have herbicidal activity against various aquatic plants such as water hyacinth (*Eichhornia crassipes*), which will grow in waterways, canals, or the like.

The present compounds have substantially the same characteristics as those of the herbicidal compounds described in the publication of International Patent Application, WO95/34659. In the case where crop plants with tolerance imparted by introducing a herbicide tolerance gene described in the publication are cultivated, the present compounds can be used at greater doses than those used when ordinary crop plants without tolerance are cultivated, and it is, therefore, possible to attain effective control of other unfavorable plants.

When the present compounds are used as active ingredients of herbicides, they are usually mixed with solid or liquid carriers or diluents, surfactants, and other auxiliary agents to give formulations such as emulsifiable concentrates, wettable powders, flowables, granules, concentrated emulsions, and water-dispersible granules.

These formulations may contain any of the present compounds as an active ingredient at an amount of 0.001% to 80% by weight, preferably 0.005% to 70% by weight, based on the total weight of the formulation.

Examples of the solid carrier or diluent may include fine powders or granules of the following materials: mineral matters such as kaolin clay, attapulgite clay, bentonite, terra alba, pyrophyllite, talc, diatomaceous earth, and calcite; organic substances such as walnut shell powder; water-soluble organic substances such as urea; inorganic salts such as ammonium sulfate; and synthetic hydrated silicon oxide. Examples of the liquid carrier or diluent may include aromatic hydrocarbons such as methylnaphthalene, phenylxylylethane, and alkylbenzenes (e.g., xylene); alcohols such as isopropanol, ethylene glycol, and 2-ethoxyethanol; esters such as phthalic acid dialkyl esters; ketones such as acetone, cyclohexanone, and isophorone; mineral oils such as machine oil; vegetable oils such as soybean oil and cotton seed oil; dimethylsulfoxide, N,N-dimethylformamide, acetonitrile, N-methylpyrrolidone, water, and the like.

Examples of the surfactant used for emulsification, dispersing, or spreading may include surfactants of the anionic type, such as alkylsulfates, alkylsulfonates, alkylarylsulfonates, dialkylsulfosuccinates, and phosphates of polyoxyethylene alkyl aryl ethers; and surfactants of the nonionic type, such as polyoxyethylene alkyl ethers, polyoxyethylene alkyl aryl ethers, polyoxyethylene polyoxypropylene block copolymers, sorbitan fatty acid esters, and polyoxyethylene sorbitan fatty acid esters.

Examples of the auxiliary agent used for formulation may include ligninsulfonates, alginates, polyvinyl alcohol, gum arabic, carboxymethyl cellulose (CMC), and isopropyl acid phosphate (PAP).

The present compounds are usually formulated as described above and then used for the pre- or post-emergence soil, foliar, or flooding treatment of unfavorable weeds. The soil treatment may include soil surface treatment and soil incorporation. The foliar treatment may include application over the plants and directed application in which a chemical is applied only to the unfavorable weeds so as to keep off the crop plants.

The present compounds can be used, if necessary, in combination with other compounds having herbicidal activity. Examples of the compounds which can be used in combination with the present compounds may include various compounds described in Catalog 1995 Edition of Farm Chemicals Handbook (Meister Publishing Company); AG CHEM NEW COMPOUND REVIEW, VOL. 13, 1995 (AG CHEM INFORMATION SERVICE); or JOSOUZAI KENKYU SOURAN (Hakuyu-sha). Typical examples of such compounds are as follows: atrazin, cyanazine, dimethametryn, metribuzin, prometryn, simazine, simetryn, chlorotoluron, diuron, dymuron, fluometuron, isoproturon, linuron, methabenzthiazuron, bromoxynil, ioxynil, ethalfluralin, pendimethalin, trifluralin, acifluorfen, acifluorfen-sodium, bifenox, chlomethoxynil, fomesafen, lactofen, oxadiazon, oxyfluorfen, carfentrazone, flumiclorac-pentyl, flumioxazine, fluthiacet-methyl, sulfentrazone, thidiazimin, difenzoquat, diquat, paraquat, 2,4-D, 2,4-DB, DCPA, MCPA, MCPB, clomeprop, clopyralid, dicamba, dithiopyr, fluroxypyr, mecoprop, naploanilide, phenothiol, quinclorac, triclopyr, acetochlor, alachlor, butachlor, diethatylethyl, metolachlor, pretilachlor, propachlor, bensulfuron-methyl, chlorsulfuron, chlorimuron-ethyl, halosulfuron-methyl, metsulfuron-methyl, nicosulfuron, primisulfuron, pyrazosulfuron-ethyl, sulfometuron-methyl, thifensulfuron-methyl, triasulfuron, tribenuron-methyl, azimsulfuron, cloransulam-methyl, cyclosulfamuron, flumeturam, flupyrsulfuron, flazasulfuron, imazosulfuron, metosulam, prosulfuron, rimsulfuron, triflusulfuron-methyl, imazamethabenz-methyl, imazapyr, imazaquin, imazethapyr, imazameth, imazamox, bispyribac-sodium, pyriminobac-methyl, pyrithiobac-sodium, alloxydimsodium, clethodim, sethoxydim, tralkoxydim, diclofop-methyl, fenoxaprop-ethyl, fenoxaprop-p-ethyl, fluazifop-butyl, fluazifop-p-butyl, haloxyfop-methyl, quizalofop-p-ethyl, cyhalofop-butyl, clodinafop-propargyl, benzofenap, clomazone, diflufenican, norflurazon, pyrazolate, pyrazoxyfen, isoxaflutole, sulcotrione, glufosinate-ammonium, glyphosate, bentazon, benthiocarb, bromobutide, butamifos, butylate, dimepiperate, dimethenamid, DSMA, EPTC, esprocarb, isoxaben, mefenacet, molinate, MSMA, piperophos, pributycarb, propanil, pyridate, triallate, cafenstrol, flupoxam, and thiafluamide.

The following will describe typical examples of such a combination, where the present compounds are designated by their compound numbers shown in Tables 1 to 5.

1. A mixture of one compound selected from the group consisting of compounds 1-495, 1-496, 1-499, 1-503 and 1-577, and one compound selected from the group consisting of atrazin, cyanazine, bromoxynil and bentazon at a weight ratio of 1:1 to 100.

2. A mixture of one compound selected from the group consisting of compounds 1-495, 1-496, 1-499, 1-503 and 1-577, and one compound selected from the group consisting of clethodim, sethoxydim, dichlofop-methyl, quizalofop-p-ethyl, lactofen, acifluorfen, acifluorfen-sodium, fomesafen, flumiclorac-pentyl and dicamba at a weight ratio of 1:0.5 to 50.

3. A mixture of one compound selected from the group consisting of compounds 1-495, 1-496, 1-499, 1-503 and 1-577, and one compound selected from the group consisting of nicosulfuron, primisulfuron, prosulfuron, chlorimuran-ethyl, thifensulfuron, rimsulfuron, halosulfuron, oxasulfuron, isoxaflutole, imazethapyr and imazamox at a weight ratio of 1:0.1 to 10.

4. A mixture of one compound selected from the group consisting of compounds 1-439, 1-482, 1-486, 1-496, 1-1076, 1-1123 and 1-1441, and one compound selected from the group consisting of isoproturon and chlorotoluron at a weight ratio of 1:1 to 100.

5. A mixture of one compound selected from the group consisting of compounds 1-439, 1-482, 1-486, 1-496, 1-1076, 1-1123 and 1-1441, and one compound selected from the group consisting of mecoprop, fluroxypyr and ioxynil at a weight ratio of 1:0.5 to 50.

6. A mixture of one compound selected from the group consisting of compounds 1-439, 1-482, 1-486, 1-496, 1-1076, 1-1123 and 1-1441, and one compound selected from the group consisting of diflufenican, metsulfuron-methyl, fenoxaprop-ethyl and clodinafop-propargyl at a weight ratio of 1:0.1 to 10.

7. A mixture of one compound selected from the group consisting of compounds 1-1 141, 1-1222 and 2-203, and one compound selected from the group consisting of glyphosate, glufosinate-ammonium and paraquat at a weight ratio of 1:1 to 100.

Moreover, the present compounds may also be used in admixture with insecticides, acaricides, nematocides, fungicides, plant growth regulators, fertilizers, soil improver, and the like.

When the present compounds are used as active ingredients of herbicides, the application amount is usually in the range of 0.01 to 10,000 g, preferably 1 to 8000 g, per hectare, although it may vary depending upon the weather conditions, formulation type, application timing, application method, soil conditions, crop plants, unfavorable weeds, and the like. In the case of emulsifiable concentrates, wettable powders, flowables, concentrated emulsions, water-dispersible granules, or the like, the formulation is usually applied at a prescribed amount after diluted with water having a volume of about 10 to 1000 liters per hectare, if necessary, with the addition of an adjuvant such as a spreading agent. In the case of granules or some types of flowables, the formulation is usually applied as such without any dilution.

Examples of the adjuvant used, if necessary, may include, in addition to the surfactants recited above, polyoxyethylene resin acids (esters), ligninsulfonates, abietates, dinaphthylmethanedisulfonates, crop oil concentrates, and vegetable oils such as soybean oil, corn oil, cotton seed oil, and sunflower oil.

The present compounds can also be used as active ingredients of harvesting aids such as defoliants and desiccating agents for cotton, and desiccating agents for potato. In these cases, the present compounds are usually formulated in the same manner as the case where they are used as active ingredients of herbicides, and used alone or in combination with other harvesting aids for foliar treatment before the harvesting of crops.

The present invention will be further illustrated by the following production examples, reference examples, formulation examples, and test examples; however, the present invention is not limited to these examples.

The following will describe production examples for the present compounds and the hydrazones of formula [2] as the intermediate compounds, where the present compounds are designated by their compound numbers shown in Tables 1 to 5.

PRODUCTION EXAMPLE 1
(Production of Compound 2-631)

To a mixed solution of 8.0 g (97.2 mmol) of sodium acetate and 50 ml of water was added under ice cooling 6.6 g (24.3 mmol) of 1,1-dibromo-3,3,3-trifluoroacetone, and the reaction was allowed to proceed at 80° C. for 30 minutes. Then, the reaction mixture was cooled to 0° C., to which 4.4 g (18.7 mmol) of 7-fluoro-6-hydrazino-4-propargyl-2H-1,4-benzoxazin-3-one was added, and the reaction mixture was stirred at room temperature for 2 hours. The precipitated crystals were collected by filtration, washed twice with 10 ml of water, and dried, which afforded 6.3 g (18.37 mmol) of 7-fluoro-6-trifluoroacetylmethylidenhydrazino-4-propargyl-2H-1,4-benzoxazin-3-one [another name: 3,3,3-trifluoro-2-oxopropanal 1-(7-fluoro-3-oxo-4-propargyl-2H-1,4-benzoxazin-6-ylhydrazone)], m.p. 190.6° C. (decomp.).

To a mixed solution of 6.0 g (17.5 mmol) of the above compound and 50 ml of toluene was added 9.1 g (26.2 mmol) of carbethoxymethylenetriphenylphosphorane, and the mixture was heated under reflux for I hour. The toluene was distilled out under reduced pressure, and the residue was subjected to silica gel column chromatography, which afforded 1.3 g (3.5 mmol) of 7-fluoro-6-[5-trifluoromethyl-3-pyridazinon-2-yl]-4-propargyl-2H-1,4-benzoxazin-3-one (compound 2-631).

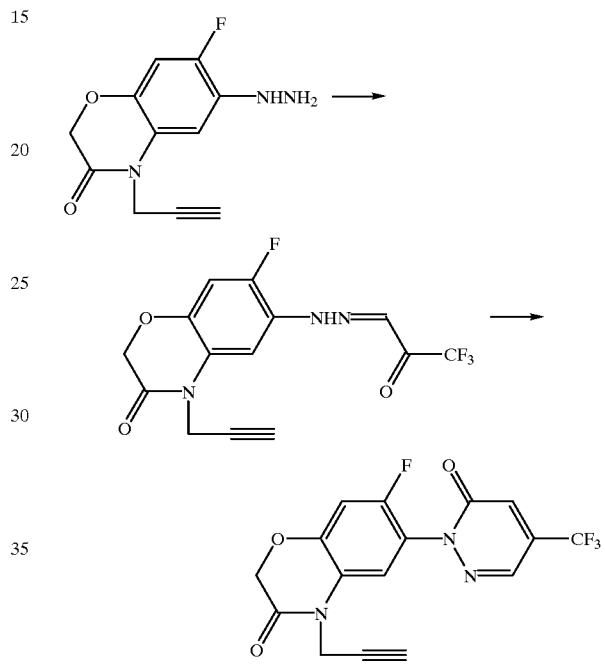

PRODUCTION EXAMPLE 2

(Production of Compound 1-476)

To a mixed solution of 5.3 g (53.5 mmol) of sodium acetate and about 100 ml of water was added under ice cooling 6.6 g (24.3 mmol) of 1,1-dibromo-3,3,3-trifluoroacetone, and the reaction was allowed to proceed at 70° C. for 20 minutes. Then, the reaction mixture was cooled to room temperature, to which a solution of 5.8 g (21.5 mmol) of 2-fluoro-4-chloro-5-isopropoxyphenylhydrazine dissolved in about 20 ml of diethyl ether was added, and the reaction mixture was stirred at room temperature for 1 hour. The ether layer was separated and concentrated. Then, about 60 ml of THF was added to the residue, to which 8.3 g (23.0 mmol) of carbethoxyethylidenetriphenylphosphorane was added, and the mixture was heated under reflux for 2 hours. The toluene was distilled out under reduced pressure, and the residue was subjected to silica gel column chromatography, which afforded 3.8 g (10.5 mmol) of 2-[2-fluoro-4-chloro-5-isopropoxyphenyl]-4-methyl-5-trifluoromethylpyridazin-3-one (compound 1-476).

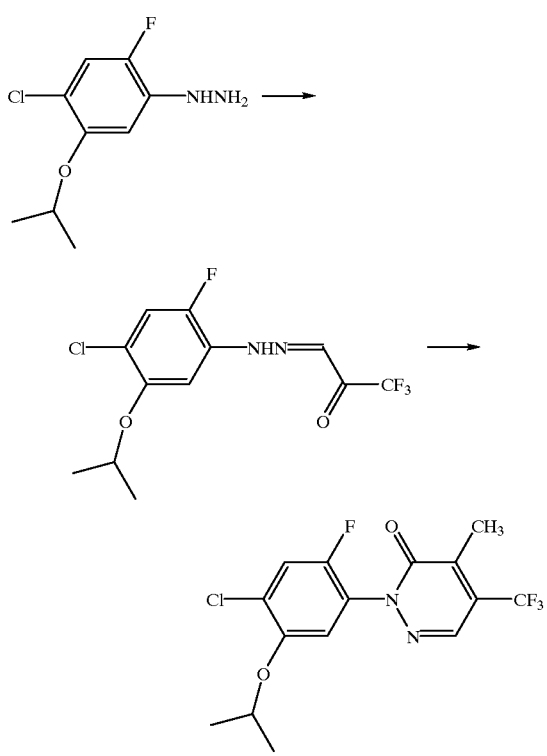

PRODUCTION EXAMPLE 3

(Production of Compound 1-391)

First, 3.5 g (9.7 mmol) of 2-[2-fluoro-4-chloro-5-isopropoxyphenyl]-4-methyl-5-trifluoromethylpyridazin-3-one (compound 1-476) was dissolved in about 10 ml of concentrated sulfuric acid under ice cooling, and the solution was warmed to room temperature. After 10 minutes, about 100 ml of water was added to the reaction mixture, and the precipitated crystals were collected by filtration, and washed twice with 20 ml of water and once with 10 ml of hexane. These crystals were recrystallized from isopropanol, which afforded 3.2 g (9.0 mmol) of 2-[2-fluoro-4-chloro-5-hydroxyphenyl]-4-methyl-5-trifluoromethylpyridazin-3-one (compound 1-391).

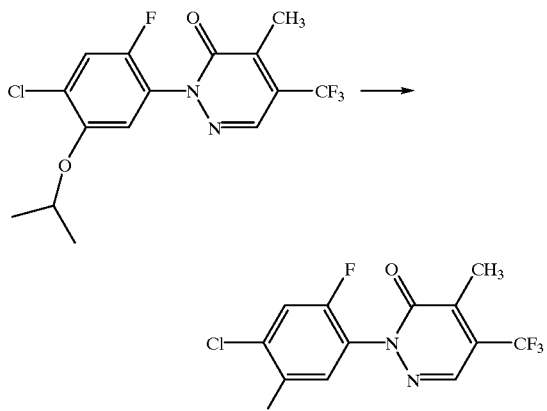

PRODUCTION EXAMPLE 4

(Production of Compound 1-486)

First, 3.2 g (10 mmol) of compound 1-391 was dissolved in about 50 ml of DMF, to which 2.0 g (13 mmol) of potassium carbonate was added at room temperature and 1.3 g (11 mmol) of propargyl bromide was then added, and the mixture was stirred at room temperature for 30 minutes, followed by the addition of 100 ml of water. The precipitated crystals were collected by filtration, washed with hexane, and recrystallized from isopropanol, which afforded 3.4 g (9 mmol) of compound 1-486.

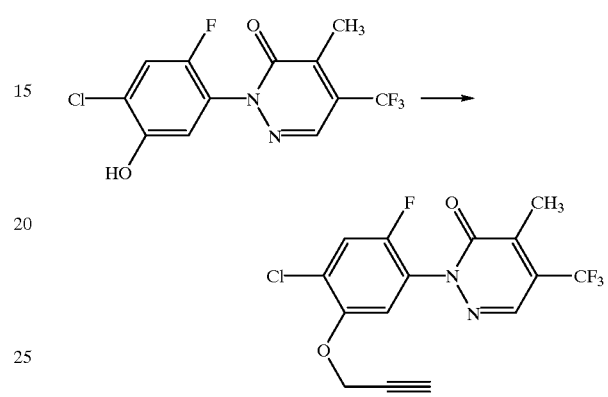

PRODUCTION EXAMPLE 5

(Production of Compound 1-496)

First, 3.2 g (10 mmol) of compound 1-391 was dissolved in about 50 ml of DMF, to which 0.44 g (11 mmol) of sodium hydride (60 wt. %, oil dispersion) was added, and the mixture was allowed to stand at room temperature for 30 minutes, followed by the addition of 1.8 g (11 mmol) of ethyl bromoacetate under ice cooling. After stirring at room temperature for 1 hour, the reaction mixture was extracted with diethyl ether. The organic layer was washed with 10% aqueous HCl, aqueous sodium bicarbonate solution and then with saturated sodium chloride solution, and dried with anhydrous magnesium sulfate. The solvent was distilled out under reduced pressure, and the residue was subjected to silica gel column chromatography, which afforded 2.4 g (5.5 mmol) of compound 1-496.

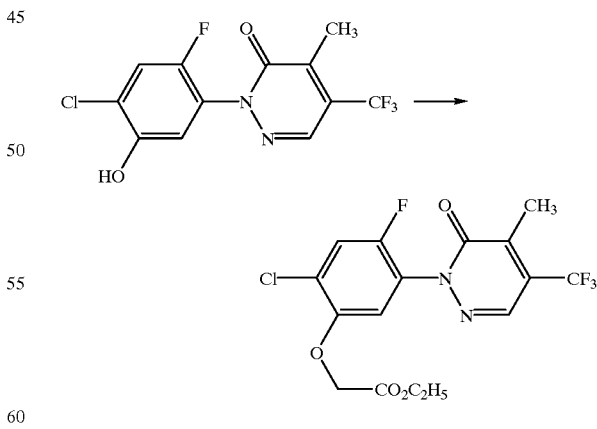

PRODUCTION EXAMPLE 6

(Production of Compound 2-251)

To a mixed solution of 5.3 g (53.5 mmol) of sodium acetate and about 50 ml of water was added under ice cooling 6.6 g (24.3 mmol) of 1,1-dibromo-3,3,3-trifluoroacetone, and the reaction was allowed to proceed at 80° C. for 1 hour. Then, the reaction mixture was cooled to 0° C., to which 4.4 g (18.7 mmol) of 7-fluoro-6-hydrazino-4-propargyl-2H-1,4-benzoxazin-3-one was added, and the reaction mixture was stirred at room temperature for 2 hours. The precipitated crystals were collected by filtration, washed twice with 10 mnl of water and once with 10 ml of hexane, and then dissolved in 50 ml of toluene without drying. To this solution was added 8.8 g (24.3 mmol) of carbethoxyethylidenetriphenylphosphorane, and the mixture was heated under reflux for 1 hour, while conducting azeotropic dehydration. The toluene was distilled out under reduced pressure, and the residue was subjected to silica gel column chromatography, which afforded 3.5 g (9.01 mmol) of compound 2-251.

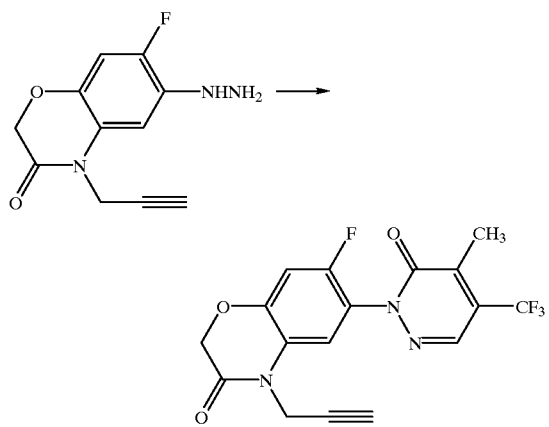

PRODUCTION EXAMPLE 7

(Production of Compound 2-328)

To a mixed solution of 5.3 g (53.5 mmol) of sodium acetate and about 50 ml of water was added under ice cooling 6.6 g (24.3 mmol) of 1,1-dibromo-3,3,3-trifluoroacetone, and the reaction was allowed to proceed at 80° C. for 1 hour. Then, the reaction mixture was cooled to 0° C., to which 4.8 g (18.7 mmol) of 6-fluoro-5-hydrazino-3-(sec-butyl)-1,3-benzothiazol-2-one was added, and the reaction mixture was stirred at room temperature for 2 hours. Then, 100 ml of ether was added to the reaction mixture, followed by stirring and phase separation, and the organic layer was concentrated. The residue was dissolved in 50 ml of THF, to which 8.8 g (24.3 mmol) of carbethoxyethylidenetriphenylphosphorane was added, and the mixture was heated under reflux for 1 hour. The THF was distilled out under reduced pressure, and the residue was subjected to silica gel column chromatography, which afforded 3.7 g (9.6 mmol) of compound 2-328.

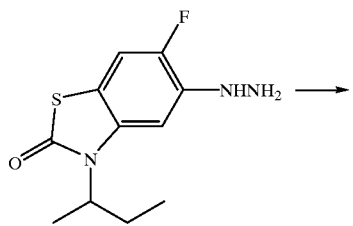

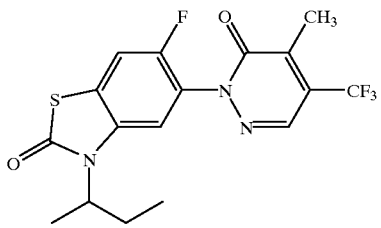

PRODUCTION EXAMPLE 8

(Production of Compound 1-347)

First, 50 ml of concentrated sulfuric acid was ice cooled, in which 7.0 g (22.8 mmol) of compound 1-341 was dissolved. Then, 1.51 g (24 mmol) of fuming nitric acid was added dropwise at 5° C. or lower, followed by maturation at 0° to 5° C. for 1 hour. The mixture was poured into 300 ml of ice-water and extracted three times with 50 ml of ether. The combined ether layer was washed with about 100 ml of water and neutralized with 100 ml of aqueous sodium bicarbonate solution, followed by phase separation. The organic layer was dried with magnesium sulfate and concentrated to half volume, and the residue was subjected to silica gel column chromatography, which afforded 6.1 g (17.4 mmol) of compound 1-347.

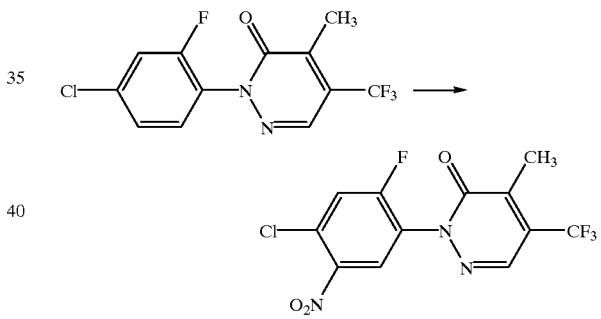

PRODUCTION EXAMPLE 9

(Production of Compound 1-353)

First, 5.0 g of iron powder, 75 ml of acetic acid, and 10 ml of water were mixed, and the mixture was warmed to about 80° C., followed by maturation for about 15 minutes. Then, 6.0 g (17.1 mmol) of compound 1-347 was dissolved in 40 ml of ethyl acetate, which was added dropwise to the above mixture at 80° C. or lower. After maturation at about 80° C. for I hour, the reaction mixture was allowed to stand for cooling to room temperature, and extracted twice with 100 ml of ethyl acetate. The combined ethyl acetate layer was washed twice with 50 ml of water and neutralized with aqueous sodium bicarbonate solution, followed by phase separation. The organic layer was dried with magnesium sulfate, and the ethyl acetate was distilled out under reduced pressure. The residue was subjected to silica gel chromatography, which afforded 5.1 g (15.9 mmol) of compound 1-353.

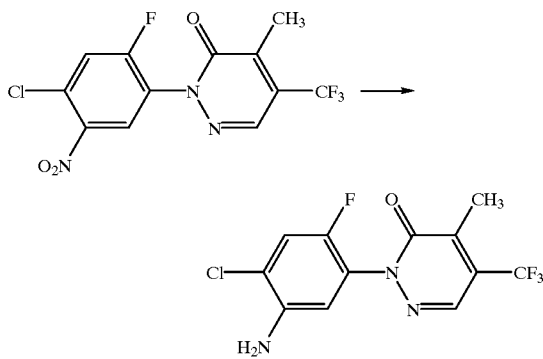

PRODUCTION EXAMPLE 10

(Production of Compound 1-420)

First, 500 mg (1.6 mmol) of compound 1-353 was mixed with 10 ml (77.3 mmol) of ethyl 2-bromopropionate, and the mixture was heated under reflux at about 160° C. for about 12 hours. After allowing to stand for cooling, the reaction mixture was subjected to silica gel column chromatography, which afforded 60 mg (0.6 mmol) of compound 1-420.

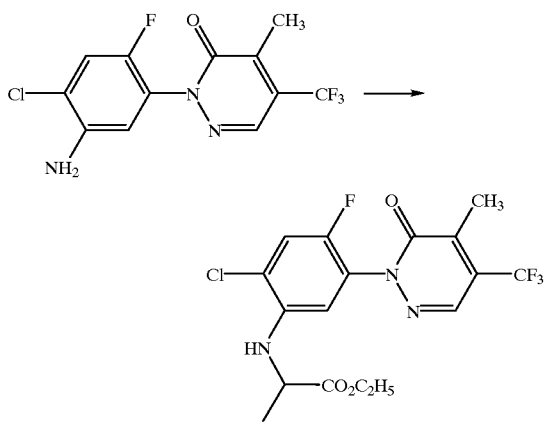

PRODUCTION EXAMPLE 11

(Production of Compound 1-1622)

First, 6 ml (55.4 mmol) of ethyl acrylate, 0.5 g (4.8 mmol) of t-butyl nitrite, and 0.6 g (4.5 mmol) of copper (II) chloride were mixed together in 5 ml of acetonitrile, followed by ice cooling. Then, 1.0 g (3.1 mmol) of compound 1-353 dissolved in 5 ml of acetonitrile was added dropwise at 5° C. or lower, followed by overnight maturation at room temperature. The reaction mixture was poured into ice-water and extracted twice with 100 ml of ethyl acetate. The combined ethyl acetate layer was washed with 50 ml of diluted hydrochloric acid and dried with magnesium sulfate. The solvent was distilled out under reduced pressure, and the residue was subjected to silica gel column chromatography, which afforded 0.51 g (1.2 mmol) of compound 1-1622.

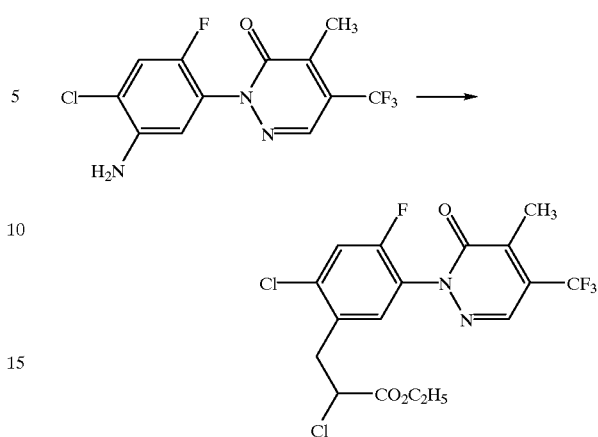

PRODUCTION EXAMPLE 12

(Production of Compound 1-1221)

To a mixed solution of 5.3 g (53.5 mmol) of sodium acetate and about 50 ml of water was added under ice cooling 6.6 g (24.3 mmol) of 1,1-dibromo-3,3,3-trifluoroacetone, and the reaction was allowed to proceed at 80° C. for 1 hour. Then, the reaction mixture was cooled to 0° C., to which 5.2 g (18.7 mmol) of methyl 2-(2-chloro-4-fluoro-5-hydrazinophenylthio)propionate was added, and the reaction mixture was stirred at room temperature for 2 hours. The precipitated crystals were collected by filtration, washed twice with 10 ml of water and once with 10 ml of hexane, and dried. The residue was dissolved in 50 ml of THF, to which 8.4 g (22.4 mmol) of carbethoxymethylenetriphenylphosphorane was added, and the solution was stirred at room temperature for 3 hours. The THF was distilled out under reduced pressure, and the residue was subjected to silica gel column chromatography, which afforded 3.8 g (9.0 mmol) of compound 1-1221.

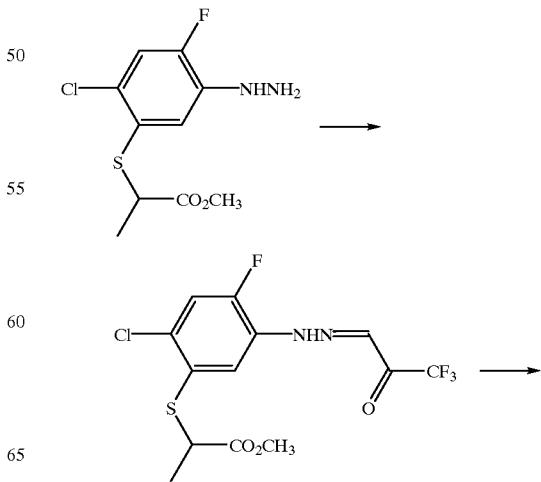

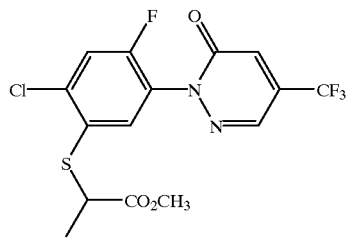

PRODUCTION EXAMPLE 13
(Production of Compound 2-821)

To a mixed solution of 8.0 g (97.2 mmol) of sodium acetate and about 50 ml of water was added under ice cooling 6.9 g (24.3 mmol) of 3,3-dibromo-1,1,1-trifluorobutanone, and the reaction was allowed to proceed at 80° C. for 30 minutes. Then, the reaction mixture was cooled to 0° C., to which 4.4 g (18.7 mmol) of 7-fluoro-6-hydrazino-4-propargyl-2H-1,4-benzoxazin-3-one was added, and the reaction mixture was stirred at room temperature for 2 hours. The precipitated crystals were collected by filtration, washed twice with 10 ml of water, and dried, which afforded 6.1 g (17.0 mmol) of 1,1,1-trifluoro-2,3-butandione 3-(7-fluoro-3-oxo-4-propargyl-2H-1,4-benzoxazin-6-ylhydrazone).

To a mixed solution of 6.1 g (17.0 mmol) of the above compound and 50 ml of THF was added 7.1 g (20.4 mmol) of carbethoxymethylenetriphenylphosphorane, and the mixture was heated under reflux for 1 hour. The THF was distilled out under reduced pressure, and the residue was subjected to silica gel column chromatography, which afforded 0.61 g (1.6 mmol) of 7-fluoro-6-(6-methyl-5-trifluoromethyl-3-pyridazinon-2-yl)-4-propargyl-2H-1,4-benzoxazin-3-one (compound 2-821).

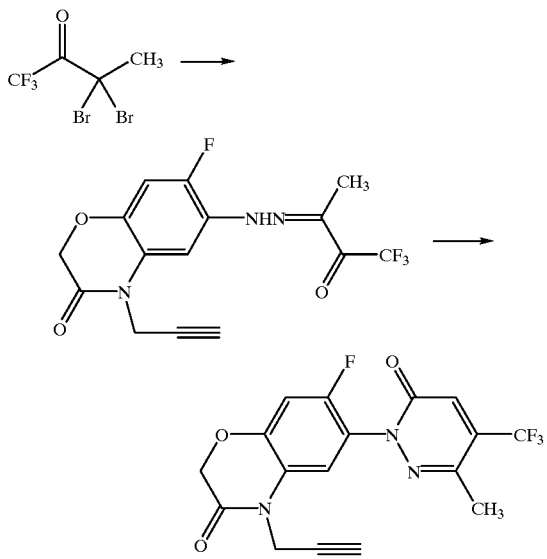

REFERENCE EXAMPLE 1

This is a production example for 3,3-dibromo-1,1,1-trifluoro-2-butanone used in Production Example 13.

First, 34.0 g of sodium acetate was dissolved in 270 ml of acetic acid, to which 25 g (0.20 mol) of 1,1,1-trifluoro-2-butanone was added, and while keeping the temperature at 15° to 20° C., 66.3 g (0.42 mol) of bromine was added dropwise over 45 minutes. The reaction mixture was stirred for 5 hours, while keeping the temperature at 15° to 20° C., and then allowed to stand at room temperature for 68 hours. The supernatant was taken and washed with 600 ml of concentrated sulfuric acid. Further washing with 307 ml of concentrated sulfuric acid and distillation under normal pressure gave 28 g (0.10 mol) of 3,3-dibromo-1,1,1-trifluoro-2-butanone.

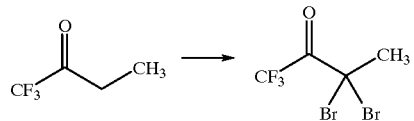

PRODUCTION EXAMPLE 14
(Production of Compound 1-1346)

To a mixed solution of 5.3 g (53.5 mmol) of sodium acetate and about 50 ml of water was added under ice cooling 6.9 g (24.3 mmol) of 3,3-dibromo-1,1,1-trifluoro-2-butanone, and the reaction was allowed to proceed at 80° C. for 1 hour. Then, the reaction mixture was cooled to 0° C., to which 3.3 g (18.7 mmol) of 2-chloro-4-fluoro-5-hydrazinophenol was added, and the reaction mixture was stirred at room temperature for 2 hours. The precipitated crystals were collected by filtration, washed twice with 10 ml of water and once with 10 ml of hexane, dried, and then dissolved in 50 ml of THF. To this solution was added 8.8 g (24.3 mmol) of carbethoxymethylenetriphenylphosphorane, and the mixture was stirred at room temperature for 3 hours. The THF was distilled out under reduced pressure, and the residue was subjected to silica gel chromatography, which afforded 0.51 g (1.6 mmol) of compound 1-1346.

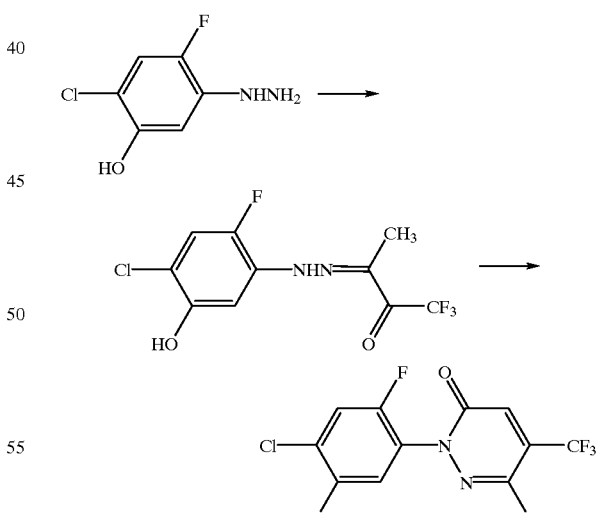

PRODUCTION EXAMPLE 15
(Production of Compound 1-1441)

First, 3.2 g (10 mmol) of compound 1-1346 was dissolved in about 50 ml of DMF, to which 2.0 g (13 mmol) of potassium carbonate was added at room temperature and 1.3 g (11 mmol) of propargyl bromide was then added, and the mixture was stirred at room temperature for 30 minutes, followed by the addition of 100 ml of water. The precipitated crystals were collected by filtration, washed with hexane, and recrystallized from isopropanol, which afforded 3.2 g (8.5 mmol) of compound 1-1441.

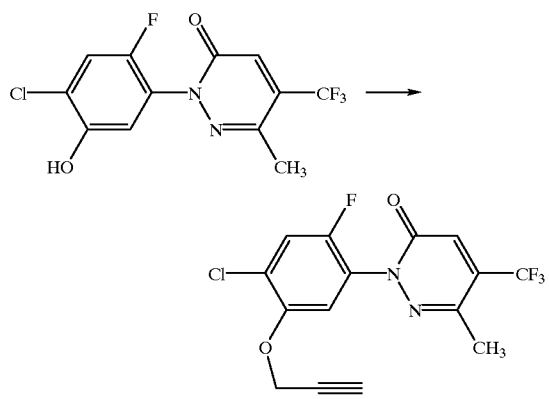

PRODUCTION EXAMPLE 16
(Production of Compound 1-499)

This example followed the procedures of Production Example 5, except that 1.8 g (1.1 mmol) of n-pentyl chloroacetate was used in place of ethyl bromoacetate. After the addition of this compound, the reaction mixture was stirred at 40° C. for 3 hours and then extracted with diethyl ether. The organic layer was washed with 10% HCl, aqueous sodium bicarbonate solution and saturated sodium chloride solution, and dried with anhydrous magnesium sulfate. The solvent was distilled out under reduced pressure, and the residue was subjected to silica gel chromatography, which afforded 3.8 g (8.0 mmol) of compound 1-499.

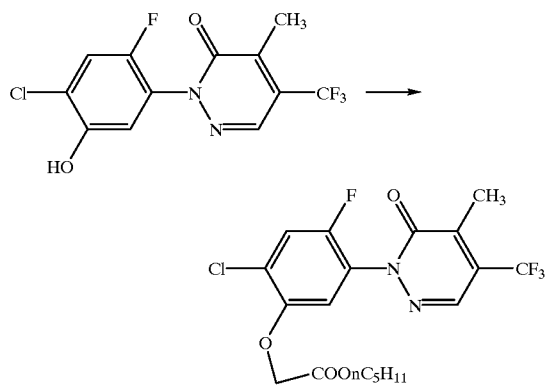

PRODUCTION EXAMPLE 17
(Production of Compound 2-203)

To a mixed solution of 5.3 g (53.5 mmol) of sodium acetate and about 50 ml of water was added under ice cooling 6.6 g (24.3 mmol) of 1,1-dibromo-3,3,3-trifluoroacetone, and the reaction was allowed to proceed at 80° C. for 1 hour. Then, the reaction mixture was cooled to 0° C., to which 4.0 g (18.7 mmol) of 6-hydrazino-4-propargyl-2H-1,4-benzoxazin-3-one was added, and the reaction mixture was stirred at room temperature for 2 hours. The precipitated crystals were collected by filtration, washed twice with 10 ml of water and once with 10 ml of hexane, and then dissolved in 50 ml of THF without drying. To this solution was added 8.8 g (24.3 mmol) of carbethoxyethylidenetriphenylphosphorane, and the mixture was heated under reflux for 3 hours. The THF was distilled out under reduced pressure, and the residue was subjected to silica gel column chromatography, which afforded 3.3 g (8.8 mmol) of compound 2-203.

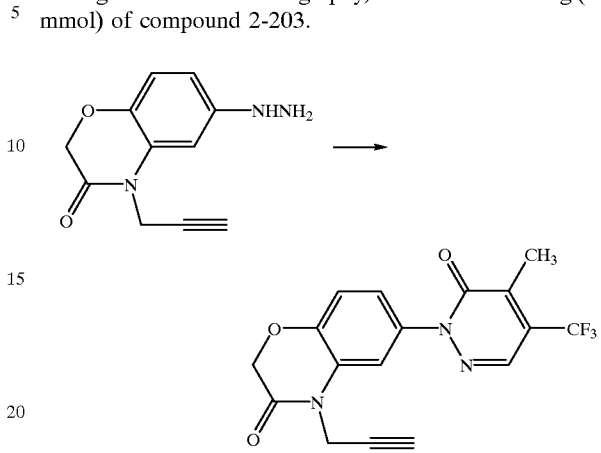

PRODUCTION EXAMPLE 18

(Production of Compound 1-1222)

To a mixed solution of 5.3 g (53.5 mmol) of sodium acetate and about 50 ml of water was added under ice cooling 6.6 g (24.3 mmol) of 1,1-dibromo-3,3,3-trifluoroacetone, and the reaction was allowed to proceed at 80° C. for 1 hour. Then, the reaction mixture was cooled to 0° C., to which 5.5 g (18.7 mmol) of ethyl 2-(2-chloro-4-fluoro-5-hydrazinophenylthio)propionate was added, and the reaction mixture was stirred at room temperature for 2 hours. The precipitated crystals were collected by filtration, washed twice with 10 ml of water and once with 10 ml of hexane, dried, and then dissolved in 50 nml of THF. To this solution was added 8.4 g (22.4 mmol) of carbethoxymethylenetriphenylphosphorane, and the mixture was stirred at room temperature for 3 hours. The THF was distilled out under reduced pressure, and the residue was subjected to silica gel column chromatography, which afforded 4.3 g (9.9 mmol) of compound 1-1222.

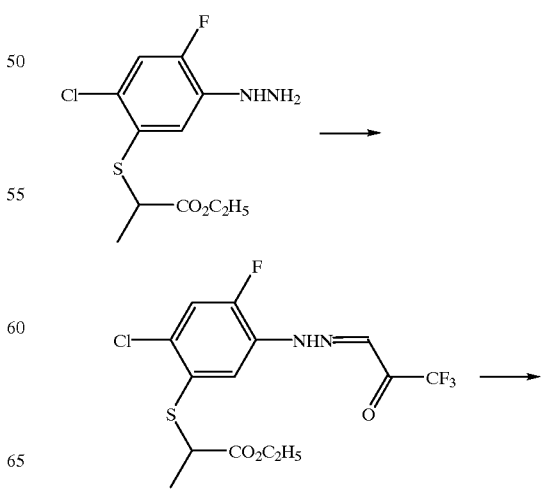

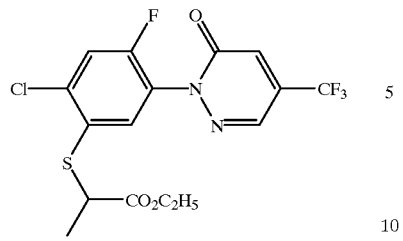

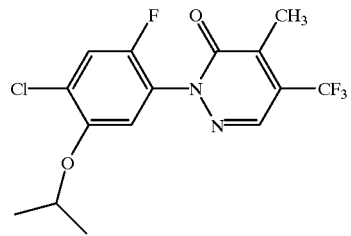

PRODUCTION EXAMPLE 19

(Production of Compound 1-476)

To a mixed solution of 5.3 g (53.5 mmol) of sodium acetate and about 100 ml of water was added under ice cooling 6.6 g (24.3 mmol) of 1,1-dibromo-3,3,3-trifluoroacetone, and the reaction was allowed to proceed at 70° C. for 20 minutes. Then, the reaction mixture was cooled to room temperature, to which a solution of 5.8 g (21.5 mmol) of 2-fluoro-4-chloro-5-isopropoxyphenylhydrazine dissolved in about 20 ml of diethyl ether was added, and the reaction mixture was stirred at room temperature for 1 hour. The ether layer was separated, washed once with 10 ml of saturated sodium chloride solution, and dried with magnesium sulfate. The diethyl ether was distilled out, which afforded 6.5 g (20.0 mmol) of 3,3,3-trifluoro-2-oxo-propanal 1-(4-chloro-2-fluoro-5-isopropoxyphenylhydrazone).

$^1$H-NMR (250 MHz, CDCl$_3$, TMS δ (ppm)) 1.39 (6H, d, J=6.0 Hz), 4.38–4.52 (1H, m), 7.15 (1H, d, J=10.5 Hz), 7.22 (1H, d, J=7.3 Hz), 7.43 (1H, q J=1.7 Hz), 9.18 (1H, br).

This compound was dissolved in 50 ml of THF. To this solution was added 8.3 g (23.0 mmol) of carbethoxyethylidenetriphenylphosphorane, and the mixture was heated under reflux for 2 hours. The THF was distilled out under reduced pressure, and the residue was subjected to silica gel column chromatography, which afforded 3.8 g (10.5 mmol) of 2-[2-fluoro-4-chloro-5-isopropoxyphenyl]-4-methyl-5-trifluoromethylpyridazin-3-one (compound 1-476).

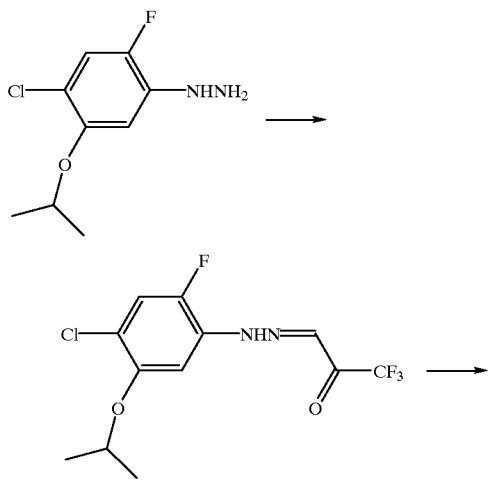

PRODUCTION EXAMPLE 20

(Production of Compound 1-642)

To a mixed aqueous solution of 5.3 g (53.5 mmol) of sodium acetate and about 100 ml of water was added under ice cooling 6.6 g (24.3 mmol) of 1,1-dibromo-3,3,3-trifluoroacetone, and the reaction was allowed to proceed at 70° C. for 20 minutes. Then, the reaction mixture was cooled to room temperature. Separately, 5.8 g (21.5 mmol) of crude ethyl 2-chloro-4-fluoro-5-hydrazinobenzoate hydrochloride was dissolved in 30 ml of water, to which 100 ml of diethyl ether was added, and while cooling, the mixture was neutralized by the addition of saturated sodium hydrogencarbonate solution, followed by washing with saturated sodium chloride solution, which afforded a solution of ethyl 2-chloro-4-fluoro-5-hydrazinobenzoate in diethyl ether. This solution was added to the above reaction mixture, followed by vigorous stirring at room temperature for 2 hours. The ether layer was separated, washed once with 10 ml of saturated sodium chloride solution, and dried with magnesium sulfate. The diethyl ether was distilled out. The residue was dissolved in 50 ml of THF, to which 8.3 g (23.0 mmol) of carbethoxyethylidenetriphenylphosphorane was added, and the mixture was heated under reflux for 2 hours. The THF was distilled out under reduced pressure, and the residue was subjected to silica gel column chromatography, which afforded 3.8 g (10.0 mmol) of compound 1-642.

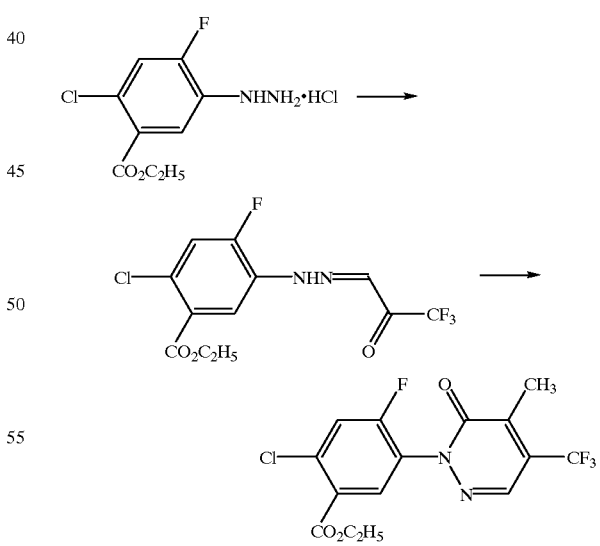

REFERENCE EXAMPLE 2

This is a production example for ethyl 2-chloro-4-fluoro-5-hydrazinobenzoate hydrochloride used in Production Example 20.

First, 50 g (0.29 mol) of 2-chloro-4-fluorobenzoic acid was dissolved in 150 ml of hydrochloric acid at room temperature, to which a mixed acid of 28 ml (0.31 mol) of fuming nitric acid and 56 ml of concentrated sulfuric acid was added dropwise at 35° to 45° C. Then, the solution was stirred at 40° C. for 1 hour and poured into 250 ml of ice-water. The precipitated crystals were collected by filtration and recrystallized from a mixed solution of hexane and ethyl acetate, which afforded 55 g (0.25 mol) of 2-chloro-4-fluoro-5-nitrobenzoic acid. Then, 55 g (0.25 mol) of 2-chloro-4-fluoro-5-nitrobenzoic acid was dissolved in 50 ml of ethyl acetate, to which 33 g (0.28 mol) of thionyl chloride was added, and the mixture was heated under reflux for 3 hours and then allowed to stand for cooling to room temperature. Then, 20 ml of ethanol and 30 g of triethylamine were added under ice cooling, and the mixture was stirred at room temperature for 2 hours. The solvent was distilled out, and the residue was purified by silica gel chromatography, which afforded 57 g (0.23 mol) of ethyl 2-chloro-4-fluoro-5-nitrobenzoate.

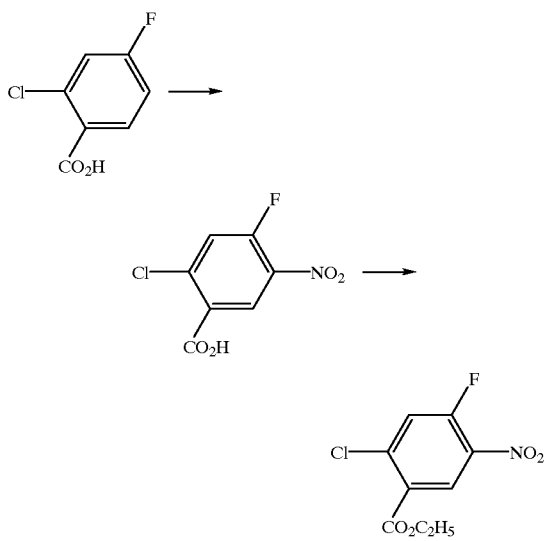

Then, 60 g of iron powder and 500 ml of 10% acetic acid were mixed, and the mixture was heated to 40° C. Separately, 50 g (0.20 mol) of ethyl 2-chloro-4-fluoro-5-nitrobenzoate was dissolved in a mixed solution of 20 ml of acetic acid and 20 ml of ethyl acetate, and added dropwise to the above iron powder-acetic acid mixed solution. Then, the reaction mixture was stirred at 50° C. for 1 hour and filtered though celite. The filtrate was extracted with 100 ml of ethyl acetate. The ethyl acetate layer was washed with aqueous sodium bicarbonate solution and saturated sodium chloride solution, and dried with magnesium sulfate. The solvent was distilled out, and the residue was purified by silica gel chromatography, which afforded to 40 g (0.18 mol) of ethyl 5-amino-2-chloro-4-fluorobenzoate.

Then, 19 g (87.4 mmol) of ethyl 5-amino-2-chloro-4-fluorobenzoate was dissolved in 120 ml of hydrochloric acid, followed by cooling to 0° C., to which a solution of 6.3 g (91.7 mmol) of sodium nitrite dissolved in 10 ml of water was added dropwise at 10° C. or lower. The mixture was stirred at 0° C. for 30 minutes and then cooled to −30° C., into which a solution of 58 g (0.31 mol) of anhydrous tin (II) chloride dissolved in 40 ml of hydrochloric acid was poured, followed by further stirring at 0° C. for 3 hours. The precipitated crystals were collected by filtration and then dried, which afforded 13.6 g (50.7 mmol) of crude ethyl 2-chloro-4-fluoro-5-hydrazinobenzoate hydrochloride.

PRODUCTION EXAMPLE 21

(Production of Compound 1-1789)

First, 5.0 g (15.5 mmol) of compound 1-391 was dissolved in about 50 ml of DMF, to which 2.8 g (20.2 mmol) of potassium carbonate was added at room temperature and then 1.5 g (17.1 mmol) of 3-bromo-2-methyl-1-propene was added, and the mixture was stirred at room temperature for 30 minutes, followed by the addition of 100 ml of water. The precipitated crystals were collected by filtration, washed with hexane, and recrystallized from isopropanol, which afforded 4.4 g (13.2 mmol) of compound 1-1789.

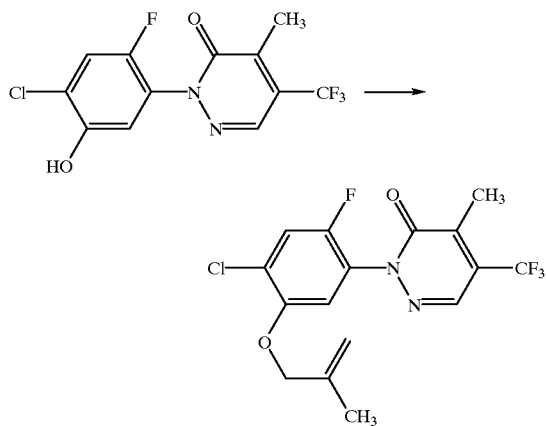

PRODUCTION EXAMPLE 22

(Production of Compound 4-451)

First, 4.0 g (12.0 mmol) of compound 1-1789 was dissolved in 20 ml of N,N-dimethylaniline, and the solution was heated at 180° C. for 3 hours. After cooling to room temperature, 100 ml of ethyl acetate was added, and the mixture was washed with 1N aqueous hydrochloric acid and saturated sodium chloride solution, and dried with magnesium sulfate. The solvent was distilled out, and the precipitated crystals were recrystallized from isopropanol, which afforded 3.4 g (10.2 mmol) of 2-[4-chloro-6-fluoro-3-hydroxy-2-(2-methyl-2-propenyl)]-4-methyl-5-trifluoromethylpyridazin-3-one, m.p. 133.2° C.

The product was dissolved in 30 ml of xylene, to which a catalytic amount of p-toluenesulfonic acid was added, and the mixture was heated under reflux for 1 hour. After cooling to room temperature, 100 ml of ethyl acetate was added, and the mixture was washed with aqueous sodium bicarbonate solution and sodium chloride solution, and dried with magnesium sulfate. The solvent was distilled out, and the residue was purified by silica gel column chromatography, which afforded 3.0 g (9.0 mmol) of compound 4-451.

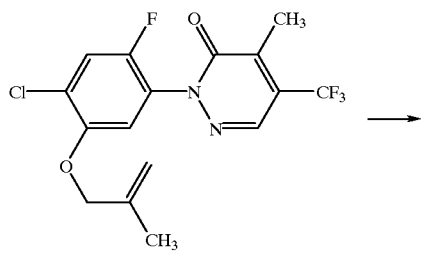

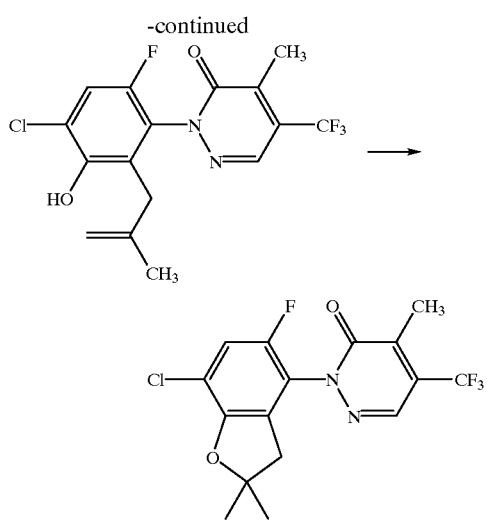

PRODUCTION EXAMPLE 23
(Production of Compound 1-483)

First, 5.0 g (15.5 mmol) of compound 1-391 was dissolved in about 20 ml of DMF, to which 2.4 g (17.1 mmol) of potassium carbonate was added at room temperature. The solution was heated to about 40° C., to which 1.7 g (17.1 mmol) of 2,3-dichloropropene was added, and after 1 hour, the mixture was allowed to stand for cooling and poured into ice-water. The precipitated crystals were collected by filtration, washed with hexane, and recrystallized from isopropanol, which afforded 5.2 g (13.1 mmol) of compound 1-483.

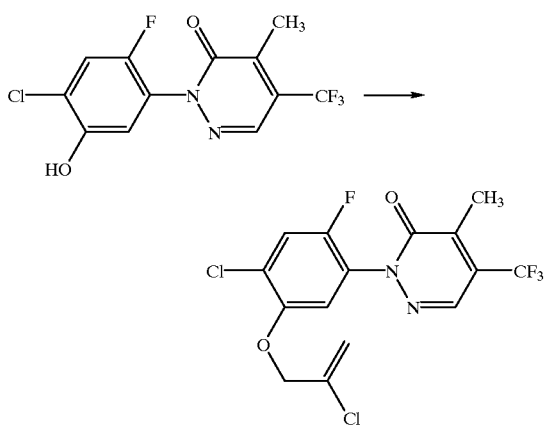

PRODUCTION EXAMPLE 24
(Production of Compound 3-139)

First, 3.0 g (7.6 mmol) of compound 1-436 was dissolved in 10 ml of N,N-dimethylaniline, and the solution was heated under reflux for 3 hours. After cooling to room temperature, 50 ml of ethyl acetate was added, and the mixture was washed with 1N aqueous hydrochloric acid and saturated sodium chloride solution, and dried with magnesium sulfate. The solvent was distilled out, and the precipitated crystals were recrystallized from isopropanol, which afforded 2.2 g (5.6 mmol) of 2-[4-chloro-6-fluoro-3-hydroxy-2-(2-chloro-2-propenyl)]-4-methyl-5-trifluoromethylpyridazin-3-one.

$^1$H-NMR (300 MHz, CDCl$_3$, TMS δ (ppm)) 2.41 (3H, q, J=1.9 Hz), 3.56 (1H, d, J=16.3 Hz), 3.72 (1H, d, J=16.3 Hz), 4.91 (1H, q, J=1.4 Hz), 5.12 (1H, d, J=1.5 Hz), 5.72 (1H, s), 7.25 (1H, d, J=8.7 Hz), 8.00 (1H, s)

The product was dissolved in 10 ml of trifluoromethanesulfonic acid cooled by ice, and the solution was stirred under ice cooling. After 30 minutes, the solution was poured into ice-water, and the precipitated crystals were collected by filtration and subjected to silica gel column chromatography, which afforded 1.9 g (5.4 mmol) of compound 3-139.

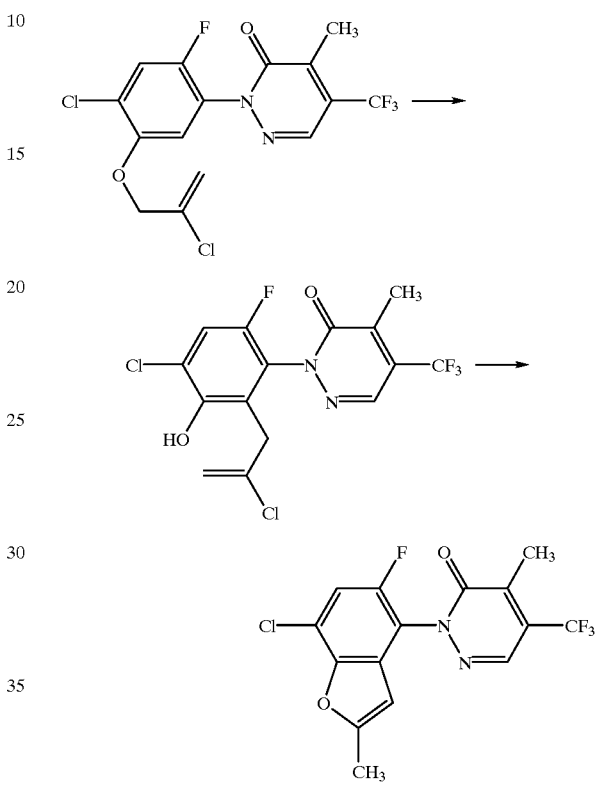

PRODUCTION EXAMPLE 25
(Production of Compound 1-1744)

This example followed the procedures of Production Example 20, except that 6.1 g (21.5 mmol) of ethyl 2,4-dichloro-5-hydrazinobenzoate hydrochloride was used in place of ethyl 2-chloro-4-fluoro-5-hydrazinobenzoate hydrochloride, which afforded 4.8 g (12.2 mmol) of compound 1-1744.

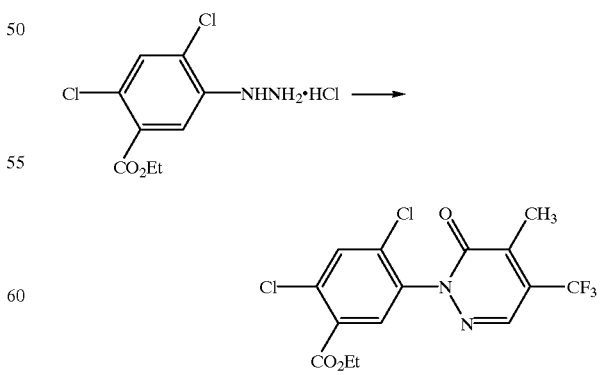

The ethyl 2,4-dichloro-5-hydrazinobenzoate hydrochloride used above was produced from 2,4-dichlorobenzoic acid by the same process as shown in Reference Example 2.

PRODUCTION EXAMPLE 26
(Production of Compound 1-1279)

To a mixed aqueous solution of 5.3 g (53.5 mmol) of sodium acetate and about 100 ml of water was added under ice cooling 6.6 g (24.3 mmol) of 1,1-dibromo-3,3,3-trifluoroacetone, and the reaction was allowed to proceed at 70° C. for 20 minutes. Then, the reaction mixture was cooled to room temperature. Separately, 5.8 g (21.5 mmol) of ethyl 2-chloro-4-fluoro-5-hydrazinobenzoate hydrochloride was dissolved in 30 ml of water, to which 100 ml of diethyl ether was added, and while cooling, the mixture was neutralized by the addition of saturated sodium hydrogen-carbonate solution, followed by washing with saturated sodium chloride solution, which afforded a solution of ethyl 2-chloro-4-fluoro-5-hydrazinobenzoate in diethyl ether. This solution was added to the above reaction mixture, followed by vigorous stirring at room temperature for 2 hours. The ether layer was separated, washed once with 10 ml of saturated sodium chloride solution, and dried with magnesium sulfate. The diethyl ether was distilled out, and a small amount of hexane was added to give 4.3 g (12.6 mmol) of ethyl 2-chloro-4-fluoro-5-(2-oxo-3,3,3-trifluoropentylidenehydrazino)benzoate. This product was dissolved in 50 ml of THF, to which 5.0 g (14.4 mmol) of carbethoxymethylenetriphenylphosphorane was added, and the mixture was heated under reflux for 2 hours. The THF was distilled out under reduced pressure, and the residue was subjected to silica gel column chromatography, which afforded 3.6 g (9.7 mmol) of compound 1-1279.

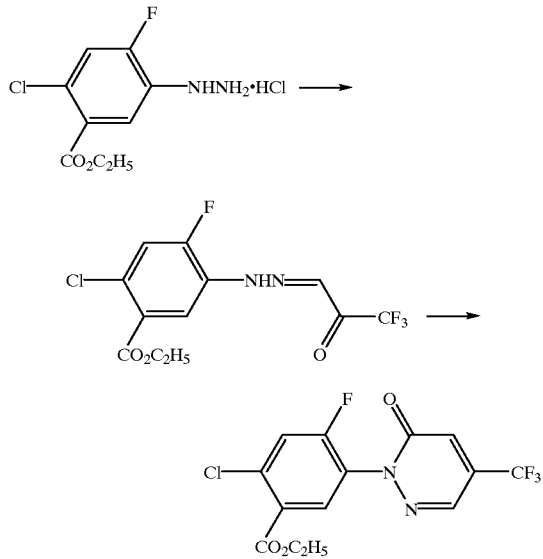

PRODUCTION EXAMPLE 27
(Production of Compound 1-1780)

First, 50 g (0.61 mol) of sodium acetate and 41 g (0.14 mol) of 1,1-dibromo-3,3,3-trifluoroacetone were mixed with 500 ml of water, and the mixture was stirred at 80° C. for 30 minutes and then cooled to 0° C. Then, 45 g (0.14 mol) of 4-bromo-2-fluoro-5-isopropoxyphenylhydrazine hydrochloride was added at 10° C. or lower, and the mixture was stirred at 10° C. or lower for 3 hours. The precipitated crystals were collected by filtration and dried, which afforded 35 g (94.3 mmol) of 3,3,3-trifluoro-2-oxopropanal 1-(4-bromo-2-fluoro-5-isopropoxyphenylhydrazone).

Then, 16 g (46.0 mmol) of carbethoxymethylenetriphenylphosphorane and 16 g (43.1 mmol) of 3,3,3-trifluoro-2-oxopropanal 1-(4-bromo-2-fluoro-5-isopropyloxyphenylhydrazone) were stirred in 100 ml of THF at room temperature for 4 hours. After completion of the reaction, the reaction mixture was concentrated, and the residue was subjected to silica gel chromatography, which afforded 9.4 g (23.8 mmol) of compound 1-1780.

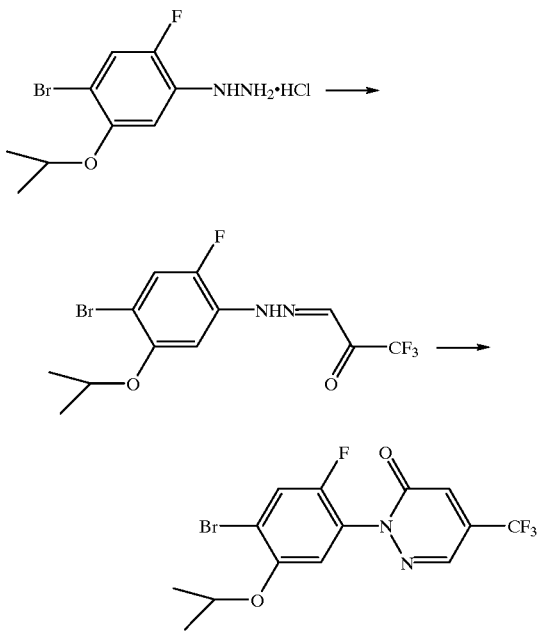

REFERENCE EXAMPLE 3

This is a production example for 4-bromo-2-fluoro-5-isopropoxyphenylhydrazine hydrochloride used in Production Example 27.

First, 93 g (0.49 mol) of 2-bromo-4-fluorophenol was suspended in 200 ml of water, into which 55 g (0.59 mol) of methyl chloroformate and a solution of 21.5 g (0.51 mol) of sodium hydroxide in 60 ml of water were poured together at 10° C. or lower, and the mixture was stirred at the same temperature for 2 hours. The precipitated crystals were collected by filtration, washed with water, and dried in a vacuum oven, which afforded 111.6 g (0.45 mol) of methyl 2-bromo-4-fluorophenoxyformate.

Then, 110 g (0.44 mol) of methyl 2-bromo-4-fluorophenoxyformate was dissolved in 250 ml of sulfuric acid, to which a mixed acid of 30 g of fuming nitric acid and 30 ml of sulfuric acid was added dropwise at 5° C. or lower, and the mixture was stirred for 2 hours. The reaction mixture was poured onto ice, and the precipitated crystals were collected by filtration, washed with water, and dried, which afforded 126 g (0.43 mol) of methyl 2-bromo-4-fluoro-5-nitrophenoxyformate.

Then, 125 g (0.43 mol) of methyl 2-bromo-4-fluoro-5-nitrophenoxyformate was suspended in 200 ml of water, to which 19 g (0.47 mol) of sodium hydroxide was added, and the mixture was stirred at 50° to 60° C. for 4 hours. After completion of the reaction, the reaction mixture was cooled to room temperature and washed with chloroform. The aqueous layer was acidified with aqueous hydrochloric acid and extracted with ethyl acetate. The ethyl acetate layer was dried and concentrated, which afforded 104 g (0.43 mol) of 2-bromo-4-fluoro-5-nitrophenol.

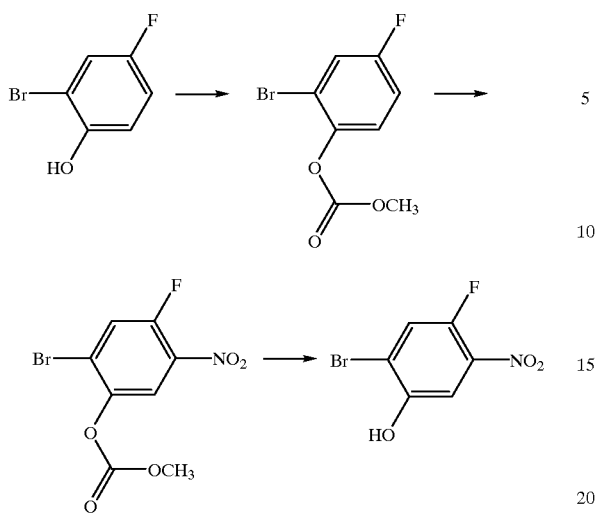

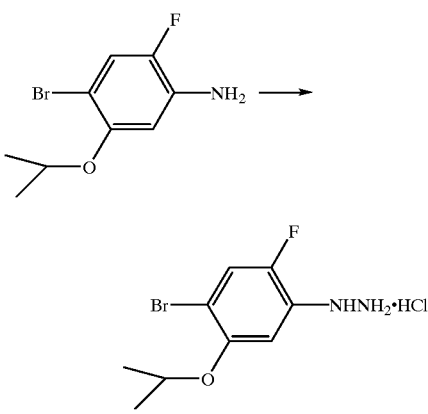

Then, 100 g (0.42 mol) of 2-bromo-4-fluoro-5-nitrophenol was dissolved in 400 ml of dimethylformamide, to which 70 g (0.50 mol) of potassium carbonate was added and after warming to 50° C., 94 g (0.55 mol) of isopropyl iodide was added dropwise, and the mixture was stirred at 45° to 50° C. for 1 hour. After completion of the reaction, the reaction mixture was poured into water and extracted with ethyl acetate. The ethyl acetate layer was washed with water and then with diluted hydrochloric acid, dried, and concentrated. The residue was subjected to column chromatography, which afforded 99.8 g (0.36 mol) of 2-bromo-4-fluoro-5-nitrophenyl isopropyl ether.

Then, 60 g (0.22 mol) of 2-bromo-4-fluoro-5-nitrophenyl isopropyl ether was dissolved in 300 ml of ethyl acetate, to which 1.0 g of 10% palladium-carbon was added, and the hydrogenation was effected under an atmosphere of hydrogen. After completion of the reaction, the palladium-carbon was removed by filtration, and the filtrate was concentrated, which afforded 52 g (0.21 mol) of 4-bromo-2-fluoro-5-isopropoxyaniline.

Then, 108 g (0.57 mol) of tin (II) chloride was dissolved in 100 ml of concentrated hydrochloric acid, followed by cooling to −30° C., to which a diazonium solution prepared from 47 g (0.19 mol) of 4-bromo-2-fluoro-5-isopropoxyaniline, 13.5 g (0.20 mol) of sodium nitrite, and 120 ml of hydrochloric acid was added dropwise at 0° C. or lower, and the mixture was stirred at room temperature for 2 hours. The precipitated crystals were collected by filtration and dried in a vacuum oven to give 45 g (0.14 mol) of the crude product, 4-bromo-2-fluoro-5-isopropoxyphenylhydrazine hydrochloride.

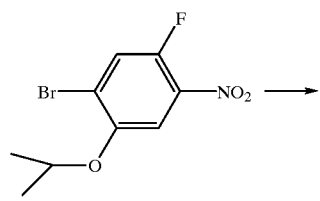

PRODUCTION EXAMPLE 28

(Production of Compound 1-1783)

First, 19 g (52.4 mmol) of carbethoxyethylidenetriphenylphosphorane and 19 g (63.2 mmol) of 3,3,3-trifluoro-2-oxopropanal 1-(4-bromo-2-fluoro-5-isopropyloxyphenylhydrazone) were heated under reflux in 100 ml of THF for 5 hours. After completion of the reaction, the reaction mixture was concentrated, and the residue was subjected to silica gel chromatography, which afforded 9.1 g (22.2 mmol) of compound 1-1783.

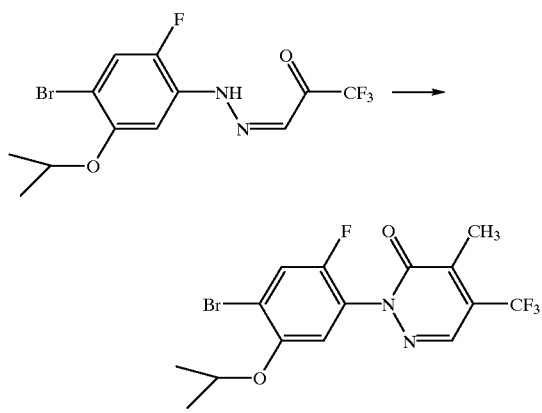

PRODUCTION EXAMPLE 29

(Production of Compound 1-1748)

This example followed the procedures of Production Example 27, except that 41 g (0.41 mol) of 2,4-dichloro-5-isopropoxyphenylhydrazine hydrochloride was used in place of 4-bromo-2-fluoro-5-isopropoxyphenylhydrazine hydrochloride, which afforded 31.3 g (91.3 mmol) of 3,3,3-trifluoro-2-oxopropanal 1-(2,4-dichloro-5-isopropoxyphenylhydrazone). Then, this compound and 40 g (0.11 mol) of carbethoxyethylidenetriphenylphosphorane were heated under reflux in 100 ml of THF for 5 hours. After completion of the reaction, the reaction mixture was concentrated, and the residue was subjected to silica gel column chromatography, which afforded 21 g (54.8 mmol) of compound 1-1748.

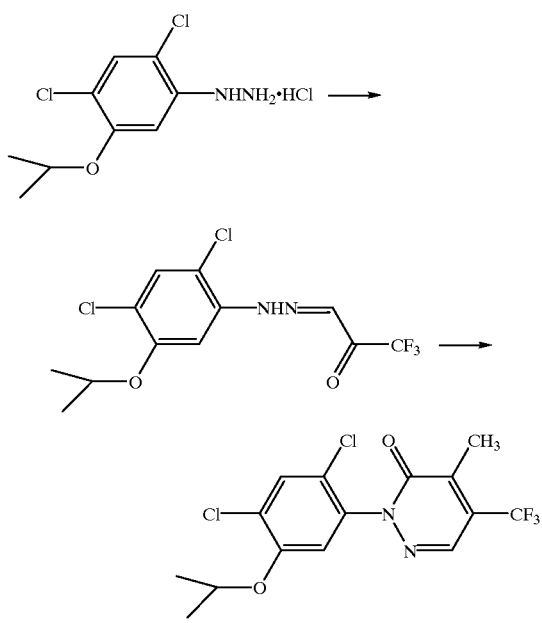

The 2,4-dichloro-5-isopropoxyphenylhydrazine hydrochloride used above was produced from 2,4-dichlorophenol by the same process as shown in Reference Example 3.

PRODUCTION EXAMPLE 30
(Production of Compound 1-1029)

First, 9 g (22.8 mmol) of 2-(4-bromo-2-fluoro-5-isopropyloxyphenyl)-5-trifluoromethylpyridazin-3-one was added to 50 ml of sulfuric acid, and the mixture was stirred for 1 hour. After completion of the reaction, the reaction mixture was poured onto ice and extracted with ethyl acetate. The ethyl acetate layer was dried and concentrated, and the residue was subjected to column chromatography (eluent, hexane:ethyl acetate=5:1), which afforded 5.9 g (16.7 mmol) of compound 1-1029.

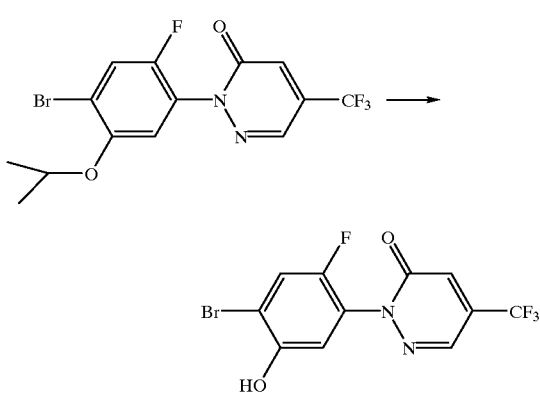

PRODUCTION EXAMPLE 31
(Production of Compound 1-392)

First, 9 g (22.0 mmol) of 2-(4-bromo-2-fluoro-5-isopropyloxyphenyl)-4-methyl-5-trifluoromethylpyridazin-3-one was added to 50 ml of sulfuric acid, and the mixture was stirred for 1 hour. After completion of the reaction, the reaction mixture was poured onto ice and extracted with ethyl acetate. The ethyl acetate layer was dried and concentrated, and the residue was subjected to column chromatography (eluent, hexane:ethyl acetate=5:1), which afforded 4.2 g (11.5 mmol) of compound 1-392.

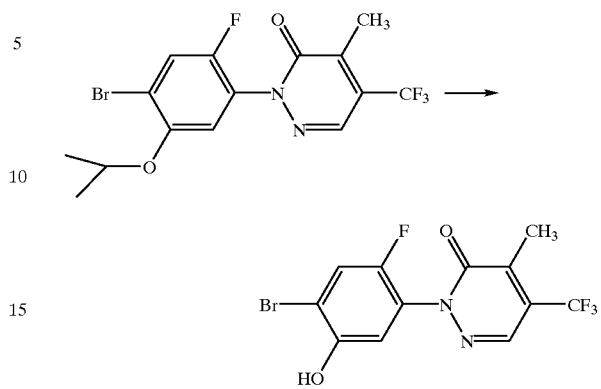

PRODUCTION EXAMPLE 32
(Production of Compound 1-1274)

First, 7.4 g (90.2 mmol) of sodium acetate and 8.0 g (28.2 mmol) of 1,1-dibromo-3,3,3-trifluoroacetone were mixed with 70 ml of water, and the mixture was stirred at 80° C. for 30 minutes and then cooled, to which 7.0 g of ethyl 2-chloro-5-hydrazinocinnamate was added at 10° C. or lower, and the mixture was stirred for 3 hours. The precipitated crystals were collected by filtration and dried, which afforded 9.6 g (27.5 mmol) of ethyl 2-chloro-5-(3,3,3-trifluoro-2-oxopropylidenehydrazino)cinnamate.

$^1$H-NMR (250 MHz, CDCl$_3$, TMS δ (ppm)) 1.36 (3H, t, J=6.9 Hz), 4.30 (2H, q, J=6.9 Hz), 6.4–6.6 (1H, m), 7.2–7.5 (3H, m), 7.65 (1H, d, J=2.5 Hz), 8.0–8.1 (1H, m)

Then, 1.0 g (2.9 mmol) of carbethoxymethylenetriphenylphosphorane and 1.0 g (2.9 mmol) of ethyl 2-chloro-5-(3,3,3-trifluoro-2-oxopropylidenehydrazino)cinnamate were stirred in 10 ml of THF at room temperature for 1 hour. After completion of the reaction, the reaction mixture was concentrated, and the residue was subjected to column chromatography (eluent, hexane:ethyl acetate=5:1), which afforded 0.43 g (11.5 mmol) of compound 1-1274.

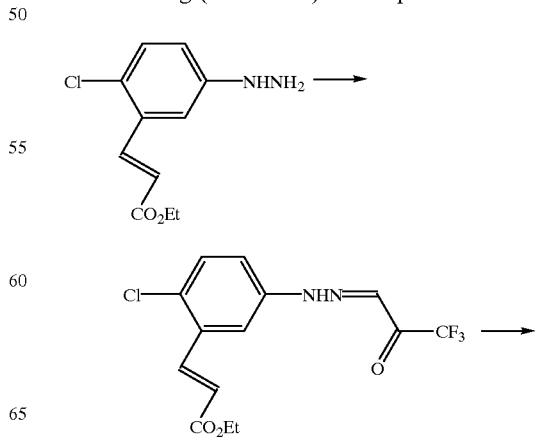

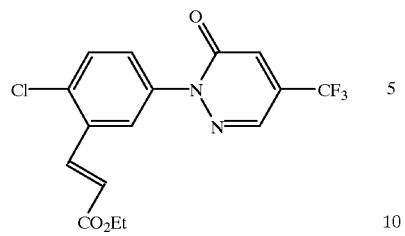

REFERENCE EXAMPLE 4

The ethyl 2-chloro-5-hydrazinocinnamate used in Production Example 32 was produced by the following process.

First, 60 g of tin (II) chloride was dissolved in 60 ml of concentrated hydrochloric acid, and the mixture was cooled to −30° C., to which a diazonium solution prepared from 19 g of ethyl 5-amino-2-chlorocinnamate and 6.3 g of sodium nitrite was added dropwise at 0° C. or lower. The reaction mixture was stirred at room temperature for 1 hour, and the precipitated crystals were collected by filtration. These crystals were added to ice-water, neutralized with 2N aqueous sodium hydroxide, and extracted with chloroform. The chloroform layer was dried and concentrated, which afforded 7.0 g of ethyl 2-chloro-5-hydrazinocinnamate.

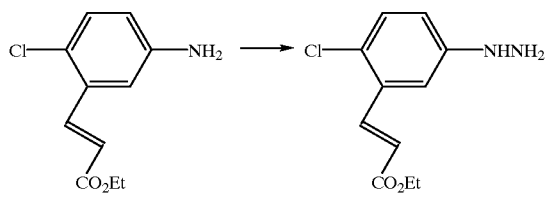

PRODUCTION EXAMPLE 33

(Production of Compound 1-637)

First, 1.1 g (2.9 mmol) of carbethoxyethylidenetriphenylphosphorane and 1.0 g (2.9 mmol) of ethyl 2-chloro-5-(3,3,3-trifluoro-2-oxopropylidenehydrazino)cinnamate were heated under reflux in 10 ml of THF for 3 hours. After completion of the reaction, the reaction mixture was concentrated, and the residue was subjected to column chromatography (eluent, hexane:ethyl acetate=5:1), which afforded 0.66 g (1.7 mmol) of compound 1-637.

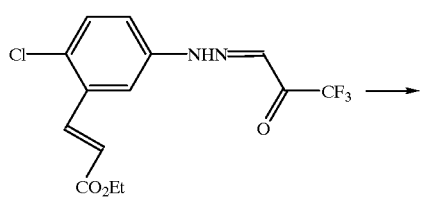

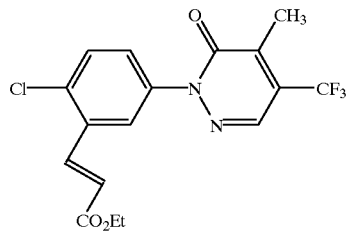

PRODUCTION EXAMPLE 34

(Production of Compound 1-367)

First, 0.5 g (1.6 mmol) of compound 1-353 was dissolved in 1.5 ml of pyridine, to which 0.2 g (1.7 mmol) of methanesulfonyl chloride was added dropwise, followed by stirring for 2 hours. The reaction mixture was poured into ice-water and extracted with ethyl acetate. The ethyl acetate layer was washed with diluted hydrochloric acid, dried, and concentrated. The residue was subjected to column chromatography (eluent, hexane:ethyl acetate=3:1), which afforded 0.42 g (1.1 mmol) of compound 1-367.

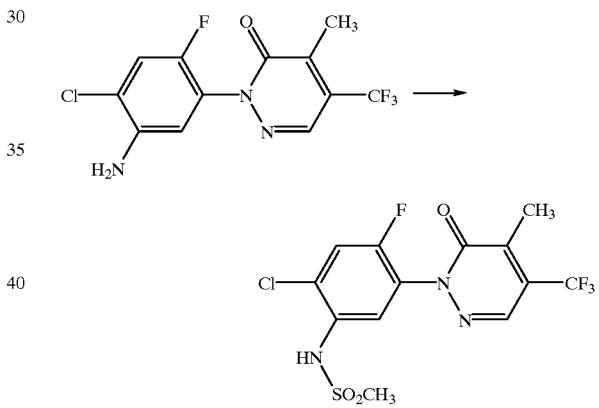

PRODUCTION EXAMPLE 35

(Production of Compound 1-369)

This example followed the procedures of Production Example 34, except that 0.23 g (1.6 mmol) of chloromethylsulfonyl chloride was used in place of methanesulfonyl chloride, which afforded 0.38 g (0.91 mmol) of compound 1-369.

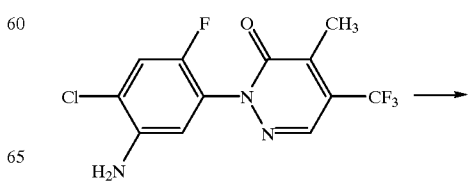

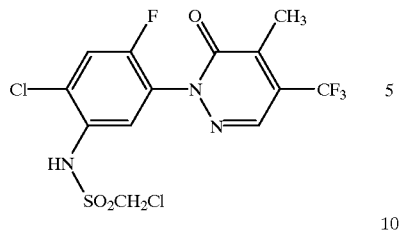

PRODUCTION EXAMPLE 36
(Production of Compound 1-391)

First, 32.3 g of 5-amino-2-chloro-4-fluorophenol was mixed with 150 ml of concentrated hydrochloric acid, and the mixture was stirred at 50° C. for 30 minutes, to which a solution of 15 g of sodium nitrite dissolved in 40 ml of water was added dropwise at 0° C. over 10 minutes. After stirring at 0° C. for 1 hour, the mixture was cooled to −50° C. Then, a solution of 132 g of tin (II) chloride dissolved in 132 g of concentrated sulfuric acid was rapidly added dropwise at −50° C., and the mixture was gradually warmed to room temperature and stirred for 1 hour. The solids formed were collected by filtration and dried at 80° C. under reduced pressure to give 75 g of the crude 2-fluoro-4-chloro-5-hydroxyphenylhydrazine hydrochloride crystals.

$^1$H-NMR (DMSO-$d_6$, TMS δ (ppm)) 3–5 (2H, br), 6.73 (1H, d), 7.22 (1H, d), 8.20 (1H, s), 9–11 (2H, br)

Then, 49.2 g of sodium acetate and 40.5 g of 1,1-dibromo-3,3,3-trifluoroacetone were dissolved in 400 ml of water, and the solution was heated at 80° to 90° C. for 40 minutes. The solution was cooled to 0° C., to which 75 g of the crude 2-fluoro-4-chloro-5-hydroxyphenylhydrazine hydrochloride crystals obtained above was added, and the mixture was stirred at room temperature for 70 minutes. The precipitated crystals were collected by filtration and dried under reduced pressure, which afforded 35.4 g of 3,3,3-trifluoro-2-oxopropanal 1-(4-chloro-2-fluoro-5-hydroxyphenylhydrazone).

$^1$H-NMR (300 MHz, CDCl$_3$, TMS δ (ppm)) 5.49 (1H, s), 7.15 (1H, d, J=10.5 Hz), 7.25 (1H, d, J=7.4 Hz), 7.38 (1H, q, J=1.8 Hz), 8.75 (1H, s)

Then, 12.9 g of 3,3,3-trifluoro-2-oxopropanal 1-(4-chloro-2-fluoro-5-hydroxyphenylhydrazone) and 22.3 g of carbethoxyethylidenetriphenylphosphorane were dissolved in 110 ml of tetrahydrofuran, and the solution was heated under reflux for 3 hours. The solvent was distilled out under reduced pressure, and the residue was subjected to silica gel chromatography, which afforded 8.8 g of 2-(2-fluoro-4-chloro-5-hydroxyphenyl)-4-methyl-5-trifluoromethylpyridazin-3-one (compound 1-391).

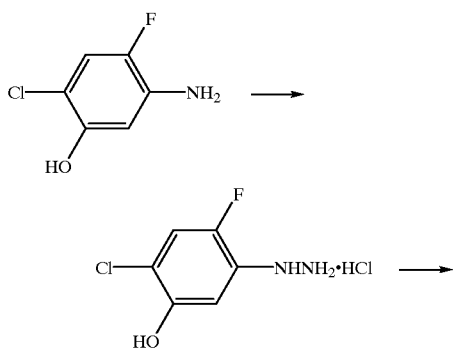

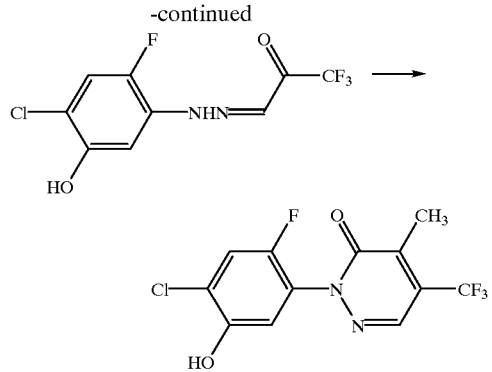

The 5-amino-2-chloro-4-fluorophenol used above can be produced by the method described in the publication of European Patent Application, EP-61741-A.

PRODUCTION EXAMPLE 37
(Production of Compound 1-332)

First, 2 g of 3,3,3-trifluoro-2-oxo-1-propanal 1-(4-chlorophenylhydrazone) and 2 g of ethyl diethylphosphonoacetate were mixed with 20 ml of triethylamine, and the reaction was allowed to proceed at 50° C. for 24 hours. The solvent was distilled out under reduced pressure, and the residue was subjected to column chromatography, which afforded 1.16 g of 2-(4-chlorophenyl)-5-trifluoromethylpyridazin-3-one (compound 1-332).

REFERENCE EXAMPLE 5

The 3,3,3-trifluoro-2-oxopropanal 1-(4-chloro-2-fluoro-5-isopropoxyphenylhydrazone) produced in Production Example 19 can also be produced by the following process.

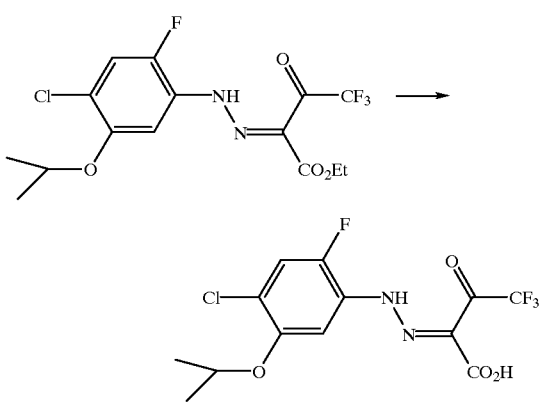

First, 20.1 g of ethyl 4,4,4-trifluoroacetoacetate and 25 g of sodium acetate were dissolved in 150 ml of water, to which a diazonium solution in hydrochloric acid prepared from 20.3 g of 4-chloro-2-fluoro-5-isopropoxyaniline, 20 ml of concentrated hydrochloric acid, 20 ml of water, and 7.35 g of sodium nitrite was added dropwise at 10° C. or lower. After stirring at room temperature for 1 hour, the precipitated crystals were collected by filtration, washed with water, and dried, which afforded 34 g of the desired product as orange crystals (yield, 85%).

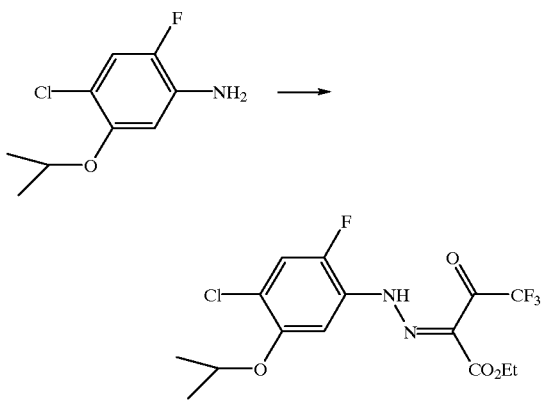

Then, 15.9 g of the ester obtained above and 1.7 g of lithium hydroxide monohydrate were added to 30 ml of 1,4-dioxane and 3 ml of water, and the mixture was heated under reflux for 6 hours. The reaction mixture was poured into ice-water, neutralized with diluted hydrochloric acid, and extracted with ethyl acetate. The ethyl acetate layer was dried and concentrated, and the precipitated crystals were washed with hexane, which afforded 11.3 g of the desired product as yellow crystals (yield, 76.3%).

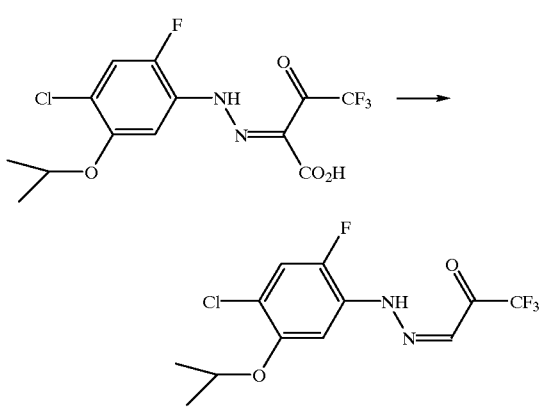

Then, 7.4 g of the carboxylic acid obtained above was dissolved in 42 ml of N,N-dimethylformamide, and the reaction solution was heated to 100° C. and kept at the same temperature for 30 minutes. Thereafter, the reaction solution was cooled to room temperature, poured into water, and extracted with ethyl acetate. The ethyl acetate layer was washed with diluted hydrochloric acid, dried with magnesium sulfate, and concentrated, which afforded 5.9 g of the desired product as orange crystals (yield, 90%).

$^1$H-NMR (250 MHz, CDCl$_3$, TMS δ (ppm)) 1.39 (6H, d, J=6.0 Hz), 4.38–4.52 (1H, m), 7.15 (1H, d, J=10.5 Hz), 7.22 (1H, d, J=7.3 Hz), 7.43 (1H, q, J=1.7 Hz), 9.18 (1H, br)

REFERENCE EXAMPLE 6

In the same manner as described in Reference Example 2, 3,3,3-trifluoro-2-oxopropanal 4-chlorophenylhydrazone was produced.

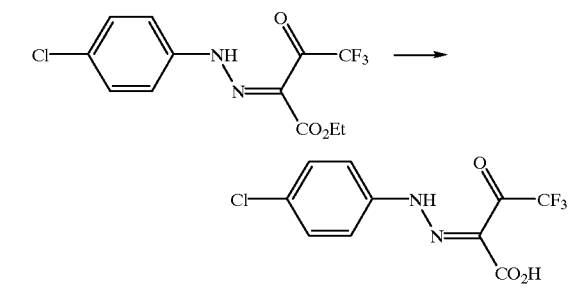

First, 5.0 g of the ester as the starting material and 0.67 g of lithium hydroxide monohydrate were added to a mixed solution of 30 ml of 1,4-dioxane and 2 ml of water, and the mixture was heated under reflux for 1.5 hours. The reaction mixture was poured into ice-water, neutralized with diluted hydrochloric acid, and extracted with ethyl acetate. The ethyl acetate layer was dried with magnesium sulfate and concentrated, and the precipitated crystals were washed with a mixed solvent of hexane and diethyl ether (hexane:diethyl ether=2:1), which afforded 3.3 g of the desired compound as yellow crystals (yield, 73%).

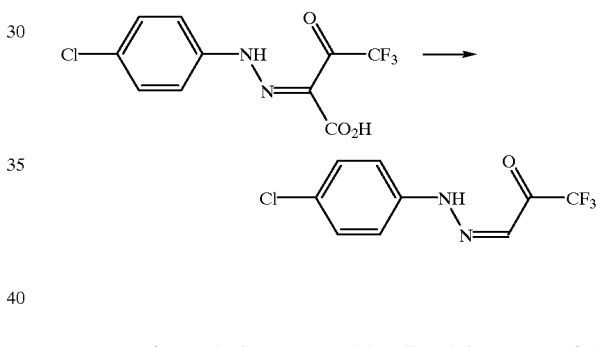

Process 1) A solution prepared by dissolving 3.3 g of the carboxylic acid obtained by the above reaction in 10 ml of dimethylsulfoxide was heated to 100° C. and kept at the same temperature for 10 minutes, followed by cooling to room temperature. Thereafter, the reaction mixture was subjected to silica gel chromatography (eluent, hexane:ethyl acetate=7:1), which afforded 2.55 g of the desired product (yield, 91%).

Process 2) A reaction mixture prepared by adding 5.0 g of the carboxylic acid obtained by the above reaction, 0.5 ml of quinoline, and 0.1 g of copper powder to 40 ml of toluene was heated to 100° C. and kept at the same temperature for 20 minutes. After completion of the reaction, the reaction mixture was cooled to room temperature and subjected to silica gel chromatography (eluent, hexane:ethyl acetate= 8:1), which afforded 3.6 g of the desired product (yield, 86%).

Some of the present compounds are shown with their compound numbers in Tables 1 to 5, where the symbol "n" refers to normal-; "i", iso-; "s", secondary-; and "c", cyclo-.

TABLE 1

Compounds of the formula:

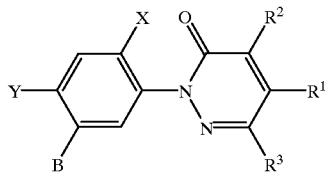

| Compound No. | X | Y | R³ | R¹ | R² | B |
|---|---|---|---|---|---|---|
| 1-1 | H | F | H | $CF_2Cl$ | H | H |
| 1-2 | H | Cl | H | $CF_2Cl$ | H | H |
| 1-3 | H | Br | H | $CF_2Cl$ | H | H |
| 1-4 | H | F | H | $CF_2Cl$ | $CH_3$ | H |
| 1-5 | H | Cl | H | $CF_2Cl$ | $CH_3$ | H |
| 1-6 | H | Br | H | $CF_2Cl$ | $CH_3$ | H |
| 1-7 | F | F | H | $CF_2Cl$ | H | H |
| 1-8 | F | Cl | H | $CF_2Cl$ | H | H |
| 1-9 | F | Br | H | $CF_2Cl$ | H | H |
| 1-10 | F | F | H | $CF_2Cl$ | $CH_3$ | H |
| 1-11 | F | Cl | H | $CF_2Cl$ | $CH_3$ | H |
| 1-12 | F | Br | H | $CF_2Cl$ | $CH_3$ | H |
| 1-13 | H | F | H | $CF_2Cl$ | $CH_3$ | $NO_2$ |
| 1-14 | H | Cl | H | $CF_2Cl$ | $CH_3$ | $NO_2$ |
| 1-15 | H | Br | H | $CF_2Cl$ | $CH_3$ | $NO_2$ |
| 1-16 | F | F | H | $CF_2Cl$ | $CH_3$ | $NO_2$ |
| 1-17 | F | Cl | H | $CF_2Cl$ | $CH_3$ | $NO_2$ |
| 1-18 | F | Br | H | $CF_2Cl$ | $CH_3$ | $NO_2$ |
| 1-19 | H | F | H | $CF_2Cl$ | $CH_3$ | $NH_2$ |
| 1-20 | H | Cl | H | $CF_2Cl$ | $CH_3$ | $NH_2$ |
| 1-21 | H | Br | H | $CF_2Cl$ | $CH_3$ | $NH_2$ |
| 1-22 | F | F | H | $CF_2Cl$ | $CH_3$ | $NH_2$ |
| 1-23 | F | Cl | H | $CF_2Cl$ | $CH_3$ | $NH_2$ |
| 1-24 | F | Br | H | $CF_2Cl$ | $CH_3$ | $NH_2$ |
| 1-25 | H | F | H | $CF_2Cl$ | $CH_3$ | OH |
| 1-26 | H | Cl | H | $CF_2Cl$ | $CH_3$ | OH |
| 1-27 | H | Br | H | $CF_2Cl$ | $CH_3$ | OH |
| 1-28 | F | F | H | $CF_2Cl$ | $CH_3$ | OH |
| 1-29 | F | Cl | H | $CF_2Cl$ | $CH_3$ | OH |
| 1-30 | F | Br | H | $CF_2Cl$ | $CH_3$ | OH |
| 1-31 | H | Cl | H | $CF_2Cl$ | $CH_3$ | $NHCH_3$ |
| 1-32 | H | Cl | H | $CF_2Cl$ | $CH_3$ | $NHC_2H_5$ |
| 1-33 | H | Cl | H | $CF_2Cl$ | $CH_3$ | $NHCH_2CH=CH_2$ |
| 1-34 | H | Cl | H | $CF_2Cl$ | $CH_3$ | $NHCH_2C\equiv CH$ |
| 1-35 | H | Cl | H | $CF_2Cl$ | $CH_3$ | $NHCH(CH_3)C\equiv CH$ |
| 1-36 | H | Cl | H | $CF_2Cl$ | $CH_3$ | $NHSO_2CH_3$ |
| 1-37 | H | Cl | H | $CF_2Cl$ | $CH_3$ | $NHSO_2C_2H_5$ |
| 1-38 | H | Cl | H | $CF_2Cl$ | $CH_3$ | $NHSO_2CH_2Cl$ |
| 1-39 | H | Cl | H | $CF_2Cl$ | $CH_3$ | $NHSO_2CF_3$ |
| 1-40 | H | Cl | H | $CF_2Cl$ | $CH_3$ | $N(CH_3)SO_2CH_3$ |
| 1-41 | H | Cl | H | $CF_2Cl$ | $CH_3$ | $N(CH_2C\equiv CH)SO_2CH_3$ |
| 1-42 | H | Cl | H | $CF_2Cl$ | $CH_3$ | $NHCOOCH_3$ |
| 1-43 | H | Cl | H | $CF_2Cl$ | $CH_3$ | $NHCOOC_2H_5$ |
| 1-44 | H | Cl | H | $CF_2Cl$ | $CH_3$ | $NHCOO^nC_3H_7$ |
| 1-45 | H | Cl | H | $CF_2Cl$ | $CH_3$ | $NHCOO^iC_3H_7$ |
| 1-46 | H | Cl | H | $CF_2Cl$ | $CH_3$ | $NHCOO^nC_4H_9$ |
| 1-47 | H | Cl | H | $CF_2Cl$ | $CH_3$ | $NHCOO^nC_5H_{11}$ |
| 1-48 | H | Cl | H | $CF_2Cl$ | $CH_3$ | $NHCH_2COOCH_3$ |
| 1-49 | H | Cl | H | $CF_2Cl$ | $CH_3$ | $NHCH_2COOC_2H_5$ |
| 1-50 | H | Cl | H | $CF_2Cl$ | $CH_3$ | $NHCH_2COO^nC_3H_7$ |
| 1-51 | H | Cl | H | $CF_2Cl$ | $CH_3$ | $NHCH_2COO^nC_4H_9$ |
| 1-52 | H | Cl | H | $CF_2Cl$ | $CH_3$ | $NHCH_2COO^nC_5H_{11}$ |
| 1-53 | H | Cl | H | $CF_2Cl$ | $CH_3$ | $NHCH_2COO^iC_3H_7$ |
| 1-54 | H | Cl | H | $CF_2Cl$ | $CH_3$ | $NHCH_2COO^cC_5H_9$ |
| 1-55 | H | Cl | H | $CF_2Cl$ | $CH_3$ | $NHCH_2COO^cC_5H_{11}$ |
| 1-56 | H | Cl | H | $CF_2Cl$ | $CH_3$ | $NHCH(CH_3)COOCH_3$ |
| 1-57 | H | Cl | H | $CF_2Cl$ | $CH_3$ | $NHCH(CH_3)COOC_2H_5$ |
| 1-58 | H | Cl | H | $CF_2Cl$ | $CH_3$ | $NHCH(CH_3)COO^nC_3H_7$ |
| 1-59 | H | Cl | H | $CF_2Cl$ | $CH_3$ | $NHCH(CH_3)COO^nC_4H_9$ |
| 1-60 | H | Cl | H | $CF_2Cl$ | $CH_3$ | $NHCH(CH_3)COO^nC_5H_{11}$ |
| 1-61 | H | Cl | H | $CF_2Cl$ | $CH_3$ | $NHCH(CH_3)COO^iC_3H_7$ |
| 1-62 | H | Cl | H | $CF_2Cl$ | $CH_3$ | $NHCH(CH_3)COO^cC_5H_9$ |
| 1-63 | H | Cl | H | $CF_2Cl$ | $CH_3$ | $NHCH(CH_3)COO^cC_6H_{11}$ |
| 1-64 | F | Cl | H | $CF_2Cl$ | $CH_3$ | $NHCH_3$ |

TABLE 1-continued

Compounds of the formula:

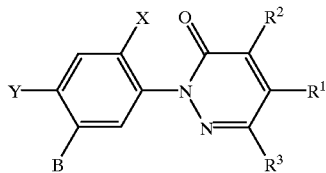

| Compound No. | X | Y | $R^3$ | $R^1$ | $R^2$ | B |
|---|---|---|---|---|---|---|
| 1-65 | F | Cl | H | $CF_2Cl$ | $CH_3$ | $NHC_2H_5$ |
| 1-66 | F | Cl | H | $CF_2Cl$ | $CH_3$ | $NHCH_2CH=CH_2$ |
| 1-67 | F | Cl | H | $CF_2Cl$ | $CH_3$ | $NHCH_2C\equiv CH$ |
| 1-68 | F | Cl | H | $CF_2Cl$ | $CH_3$ | $NHCH(CH_3)C\equiv CH$ |
| 1-69 | F | Cl | H | $CF_2Cl$ | $CH_3$ | $NHSO_2CH_3$ |
| 1-70 | F | Cl | H | $CF_2Cl$ | $CH_3$ | $NHSO_2C_2H_5$ |
| 1-71 | F | Cl | H | $CF_2Cl$ | $CH_3$ | $NHSO_2CH_2Cl$ |
| 1-72 | F | Cl | H | $CF_2Cl$ | $CH_3$ | $NHSO_2CF_3$ |
| 1-73 | F | Cl | H | $CF_2Cl$ | $CH_3$ | $N(CH_3)SO_2CH_3$ |
| 1-74 | F | Cl | H | $CF_2Cl$ | $CH_3$ | $N(CH_2C\equiv CH)SO_2CH_3$ |
| 1-75 | F | Cl | H | $CF_2Cl$ | $CH_3$ | $NHCOOCH_3$ |
| 1-76 | F | Cl | H | $CF_2Cl$ | $CH_3$ | $NHCOOC_2H_5$ |
| 1-77 | F | Cl | H | $CF_2Cl$ | $CH_3$ | $NHCOO^nC_3H_7$ |
| 1-78 | F | Cl | H | $CF_2Cl$ | $CH_3$ | $NHCOO^iC_3H_7$ |
| 1-79 | F | Cl | H | $CF_2Cl$ | $CH_3$ | $NHCOO^nC_4H_9$ |
| 1-80 | F | Cl | H | $CF_2Cl$ | $CH_3$ | $NHCOO^nC_5H_{11}$ |
| 1-81 | F | Cl | H | $CF_2Cl$ | $CH_3$ | $NHCH_2COOCH_3$ |
| 1-82 | F | Cl | H | $CF_2Cl$ | $CH_3$ | $NHCH_2COOC_2H_5$ |
| 1-83 | F | Cl | H | $CF_2Cl$ | $CH_3$ | $NHCH_2COO^nC_3H_7$ |
| 1-84 | F | Cl | H | $CF_2Cl$ | $CH_3$ | $NHCH_2COO^nC_4H_9$ |
| 1-85 | F | Cl | H | $CF_2Cl$ | $CH_3$ | $NHCH_2COO^nC_5H_{11}$ |
| 1-86 | F | Cl | H | $CF_2Cl$ | $CH_3$ | $NHCH_2COO^iC_3H_7$ |
| 1-87 | F | Cl | H | $CF_2Cl$ | $CH_3$ | $NHCH_2COO^cC_5H_9$ |
| 1-88 | F | Cl | H | $CF_2Cl$ | $CH_3$ | $NHCH_2COO^cC_5H_{11}$ |
| 1-89 | F | Cl | H | $CF_2Cl$ | $CH_3$ | $NHCH(CH_3)COOCH_3$ |
| 1-90 | F | Cl | H | $CF_2Cl$ | $CH_3$ | $NHCH(CH_3)COOC_2H_5$ |
| 1-91 | F | Cl | H | $CF_2Cl$ | $CH_3$ | $NHCH(CH_3)COO^nC_3H_7$ |
| 1-92 | F | Cl | H | $CF_2Cl$ | $CH_3$ | $NHCH(CH_3)COO^nC_4H_9$ |
| 1-93 | F | Cl | H | $CF_2Cl$ | $CH_3$ | $NHCH(CH_3)COO^nC_5H_{11}$ |
| 1-94 | F | Cl | H | $CF_2Cl$ | $CH_3$ | $NHCH(CH_3)COO^iC_3H_7$ |
| 1-95 | F | Cl | H | $CF_2Cl$ | $CH_3$ | $NHCH(CH_3)COO^cC_5H_9$ |
| 1-96 | F | Cl | H | $CF_2Cl$ | $CH_3$ | $NHCH(CH_3)COO^cC_6H_{11}$ |
| 1-97 | H | Cl | H | $CF_2Cl$ | $CH_3$ | $OCH_3$ |
| 1-98 | H | Cl | H | $CF_2Cl$ | $CH_3$ | $OC_2H_5$ |
| 1-99 | H | Cl | H | $CF_2Cl$ | $CH_3$ | $O^iC_3H_7$ |
| 1-100 | H | Cl | H | $CF_2Cl$ | $CH_3$ | $O^nC_3H_7$ |
| 1-101 | H | Cl | H | $CF_2Cl$ | $CH_3$ | $OCH_2CH_2Cl$ |
| 1-102 | H | Cl | H | $CF_2Cl$ | $CH_3$ | $OCF_2CF_2H$ |
| 1-103 | H | Cl | H | $CF_2Cl$ | $CH_3$ | $O^cC_5H_9$ |
| 1-104 | H | Cl | H | $CF_2Cl$ | $CH_3$ | $O^cC_6H_{11}$ |
| 1-105 | H | Cl | H | $CF_2Cl$ | $CH_3$ | $OCH_2CH=CH_2$ |
| 1-106 | H | Cl | H | $CF_2Cl$ | $CH_3$ | $OCH_2CCl=CH_2$ |
| 1-107 | H | Cl | H | $CF_2Cl$ | $CH_3$ | $OCH_2CCl=CHCl$ |
| 1-108 | H | Cl | H | $CF_2Cl$ | $CH_3$ | $OCH(CH_3)CH=CH_2$ |
| 1-109 | H | Cl | H | $CF_2Cl$ | $CH_3$ | $OCH_2C\equiv CH$ |
| 1-110 | H | Cl | H | $CF_2Cl$ | $CH_3$ | $OCH(CH_3)C\equiv CH$ |
| 1-111 | H | Cl | H | $CF_2Cl$ | $CH_3$ | $OCH_2C\equiv CBr$ |
| 1-112 | H | Cl | H | $CF_2Cl$ | $CH_3$ | $OCH_2C\equiv CCl$ |
| 1-113 | H | Cl | H | $CF_2Cl$ | $CH_3$ | $OCH_2C\equiv CCH_2Cl$ |
| 1-114 | H | Cl | H | $CF_2Cl$ | $CH_3$ | $OCH_2CN$ |
| 1-115 | H | Cl | H | $CF_2Cl$ | $CH_3$ | $OCH_2OCH_3$ |
| 1-116 | H | Cl | H | $CF_2Cl$ | $CH_3$ | $OCH_2OC_2H_5$ |
| 1-117 | H | Cl | H | $CF_2Cl$ | $CH_3$ | $OCH_2SCH_3$ |
| 1-118 | H | Cl | H | $CF_2Cl$ | $CH_3$ | $OCH_2COOCH_3$ |
| 1-119 | H | Cl | H | $CF_2Cl$ | $CH_3$ | $OCH_2COOC_2H_5$ |
| 1-120 | H | Cl | H | $CF_2Cl$ | $CH_3$ | $OCH_2COO^nC_3H_7$ |
| 1-121 | H | Cl | H | $CF_2Cl$ | $CH_3$ | $OCH_2COO^nC_4H_9$ |
| 1-122 | H | Cl | H | $CF_2Cl$ | $CH_3$ | $OCH_2COO^nC_5H_{11}$ |
| 1-123 | H | Cl | H | $CF_2Cl$ | $CH_3$ | $OCH_2COO^iC_3H_7$ |
| 1-124 | H | Cl | H | $CF_2Cl$ | $CH_3$ | $OCH_2COO^cC_5H_9$ |
| 1-125 | H | Cl | H | $CF_2Cl$ | $CH_3$ | $OCH_2COO^cC_6H_{11}$ |
| 1-126 | H | Cl | H | $CF_2Cl$ | $CH_3$ | $OCH(CH_3)COOCH_3$ |
| 1-127 | H | Cl | H | $CF_2Cl$ | $CH_3$ | $OCH(CH_3)COOC_2H_5$ |
| 1-128 | H | Cl | H | $CF_2Cl$ | $CH_3$ | $OCH(CH_3)COO^nC_3H_7$ |

TABLE 1-continued

Compounds of the formula:

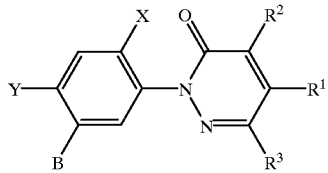

| Compound No. | X | Y | $R^3$ | $R^1$ | $R^2$ | B |
|---|---|---|---|---|---|---|
| 1-129 | H | Cl | H | $CF_2Cl$ | $CH_3$ | $OCH(CH_3)COO^nC_4H_9$ |
| 1-130 | H | Cl | H | $CF_2Cl$ | $CH_3$ | $OCH(CH_3)COO^nC_5H_{11}$ |
| 1-131 | H | Cl | H | $CF_2Cl$ | $CH_3$ | $OCH(CH_3)COO^iC_3H_7$ |
| 1-132 | H | Cl | H | $CF_2Cl$ | $CH_3$ | $OCH(CH_3)COO^cC_5H_9$ |
| 1-133 | H | Cl | H | $CF_2Cl$ | $CH_3$ | $OCH(CH_3)COO^cC_6H_{11}$ |
| 1-134 | H | Cl | H | $CF_2Cl$ | $CH_3$ | $OCH_2CON(CH_3)_2$ |
| 1-135 | H | Cl | H | $CF_2Cl$ | $CH_3$ | $OCH_2CON(C_2H_5)_2$ |
| 1-136 | H | Cl | H | $CF_2Cl$ | $CH_3$ | $OCH_2CON(CH_3)C_2H_5$ |
| 1-137 | H | Cl | H | $CF_2Cl$ | $CH_3$ | $OCH(CH_3)CON(CH_3)_2$ |
| 1-138 | H | Cl | H | $CF_2Cl$ | $CH_3$ | $OCH(CH_3)CON(C_2H_5)_2$ |
| 1-139 | H | Cl | H | $CF_2Cl$ | $CH_3$ | $OCH(CH_3)CON(CH_3)C_2H_5$ |
| 1-140 | H | Cl | H | $CF_2Cl$ | $CH_3$ | $OCH_2COON(CH_3)_2$ |
| 1-141 | H | Cl | H | $CF_2Cl$ | $CH_3$ | $OCH_2COON(C_2H_5)_2$ |
| 1-142 | H | Cl | H | $CF_2Cl$ | $CH_3$ | $OCH(CH_3)COON(CH_3)_2$ |
| 1-143 | H | Cl | H | $CF_2Cl$ | $CH_3$ | $OCH(CH_3)COON(C_2H_5)_2$ |
| 1-144 | F | Cl | H | $CF_2Cl$ | $CH_3$ | $OCH_3$ |
| 1-145 | F | Cl | H | $CF_2Cl$ | $CH_3$ | $OC_2H_5$ |
| 1-146 | F | Cl | H | $CF_2Cl$ | $CH_3$ | $O^iC_3H_7$ |
| 1-147 | F | Cl | H | $CF_2Cl$ | $CH_3$ | $O^nC_3H_7$ |
| 1-148 | F | Cl | H | $CF_2Cl$ | $CH_3$ | $OCH_2CH_2Cl$ |
| 1-149 | F | Cl | H | $CF_2Cl$ | $CH_3$ | $OCF_2CF_2H$ |
| 1-150 | F | Cl | H | $CF_2Cl$ | $CH_3$ | $O^cC_5H_9$ |
| 1-151 | F | Cl | H | $CF_2Cl$ | $CH_3$ | $O^cC_6H_{11}$ |
| 1-152 | F | Cl | H | $CF_2Cl$ | $CH_3$ | $OCH_2CH=CH_2$ |
| 1-153 | F | Cl | H | $CF_2Cl$ | $CH_3$ | $OCH_2CCl=CH_2$ |
| 1-154 | F | Cl | H | $CF_2Cl$ | $CH_3$ | $OCH_2CCl=CHCl$ |
| 1-155 | F | Cl | H | $CF_2Cl$ | $CH_3$ | $OCH(CH_3)CH=CH_2$ |
| 1-156 | F | Cl | H | $CF_2Cl$ | $CH_3$ | $OCH_2C\equiv CH$ |
| 1-157 | F | Cl | H | $CF_2Cl$ | $CH_3$ | $OCH(CH_3)C\equiv CH$ |
| 1-158 | F | Cl | H | $CF_2Cl$ | $CH_3$ | $OCH_2C\equiv CBr$ |
| 1-159 | F | Cl | H | $CF_2Cl$ | $CH_3$ | $OCH_2C\equiv CCl$ |
| 1-160 | F | Cl | H | $CF_2Cl$ | $CH_3$ | $OCH_2C\equiv CCH_2Cl$ |
| 1-161 | F | Cl | H | $CF_2Cl$ | $CH_3$ | $OCH_2CN$ |
| 1-162 | F | Cl | H | $CF_2Cl$ | $CH_3$ | $OCH_2OCH_3$ |
| 1-163 | F | Cl | H | $CF_2Cl$ | $CH_3$ | $OCH_2OC_2H_5$ |
| 1-164 | F | Cl | H | $CF_2Cl$ | $CH_3$ | $OCH_2SCH_3$ |
| 1-165 | F | Cl | H | $CF_2Cl$ | $CH_3$ | $OCH_2COOCH_3$ |
| 1-166 | F | Cl | H | $CF_2Cl$ | $CH_3$ | $OCH_2COOC_2H_5$ |
| 1-167 | F | Cl | H | $CF_2Cl$ | $CH_3$ | $OCH_2COO^nC_3H_7$ |
| 1-168 | F | Cl | H | $CF_2Cl$ | $CH_3$ | $OCH_2COO^nC_4H_9$ |
| 1-169 | F | Cl | H | $CF_2Cl$ | $CH_3$ | $OCH_2COO^nC_5H_{11}$ |
| 1-170 | F | Cl | H | $CF_2Cl$ | $CH_3$ | $OCH_2COO^iC_3H_7$ |
| 1-171 | F | Cl | H | $CF_2Cl$ | $CH_3$ | $OCH_2COO^cC_5H_9$ |
| 1-172 | F | Cl | H | $CF_2Cl$ | $CH_3$ | $OCH_2COO^cC_6H_{11}$ |
| 1-173 | F | Cl | H | $CF_2Cl$ | $CH_3$ | $OCH(CH_3)COOCH_3$ |
| 1-174 | F | Cl | H | $CF_2Cl$ | $CH_3$ | $OCH(CH_3)COOC_2H_5$ |
| 1-175 | F | Cl | H | $CF_2Cl$ | $CH_3$ | $OCH(CH_3)COO^nC_3H_7$ |
| 1-176 | F | Cl | H | $CF_2Cl$ | $CH_3$ | $OCH(CH_3)COO^nC_4H_9$ |
| 1-177 | F | Cl | H | $CF_2Cl$ | $CH_3$ | $OCH(CH_3)COO^nC_5H_{11}$ |
| 1-178 | F | Cl | H | $CF_2Cl$ | $CH_3$ | $OCH(CH_3)COO^iC_3H_7$ |
| 1-179 | F | Cl | H | $CF_2Cl$ | $CH_3$ | $OCH(CH_3)COO^cC_5H_9$ |
| 1-180 | F | Cl | H | $CF_2Cl$ | $CH_3$ | $OCH(CH_3)COO^cC_6H_{11}$ |
| 1-181 | F | Cl | H | $CF_2Cl$ | $CH_3$ | $OCH_2CON(CH_3)_2$ |
| 1-182 | F | Cl | H | $CF_2Cl$ | $CH_3$ | $OCH_2CON(C_2H_5)_2$ |
| 1-183 | F | Cl | H | $CF_2Cl$ | $CH_3$ | $OCH_2CON(CH_3)C_2H_5$ |
| 1-184 | F | Cl | H | $CF_2Cl$ | $CH_3$ | $OCH(CH_3)CON(CH_3)_2$ |
| 1-185 | F | Cl | H | $CF_2Cl$ | $CH_3$ | $OCH(CH_3)CON(C_2H_5)_2$ |
| 1-186 | F | Cl | H | $CF_2Cl$ | $CH_3$ | $OCH(CH_3)CON(CH_3)C_2H_5$ |
| 1-187 | F | Cl | H | $CF_2Cl$ | $CH_3$ | $OCH_2COON(CH_3)_2$ |
| 1-188 | F | Cl | H | $CF_2Cl$ | $CH_3$ | $OCH_2COON(C_2H_5)_2$ |
| 1-189 | F | Cl | H | $CF_2Cl$ | $CH_3$ | $OCH(CH_3)COON(CH_3)_2$ |
| 1-190 | F | Cl | H | $CF_2Cl$ | $CH_3$ | $OCH(CH_3)COON(C_2H_5)_2$ |
| 1-191 | H | F | H | $CF_2Cl$ | $CH_3$ | SH |
| 1-192 | H | Cl | H | $CF_2Cl$ | $CH_3$ | SH |

TABLE 1-continued

Compounds of the formula:

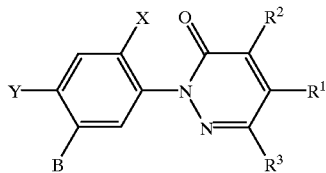

| Compound No. | X | Y | $R^3$ | $R^1$ | $R^2$ | B |
|---|---|---|---|---|---|---|
| 1-193 | H | Br | H | $CF_2Cl$ | $CH_3$ | SH |
| 1-194 | F | F | H | $CF_2Cl$ | $CH_3$ | SH |
| 1-195 | F | Cl | H | $CF_2Cl$ | $CH_3$ | SH |
| 1-196 | F | Br | H | $CF_2Cl$ | $CH_3$ | SH |
| 1-197 | H | Cl | H | $CF_2Cl$ | $CH_3$ | $SCH_3$ |
| 1-198 | H | Cl | H | $CF_2Cl$ | $CH_3$ | $SC_2H_5$ |
| 1-199 | H | Cl | H | $CF_2Cl$ | $CH_3$ | $S^iC_3H_7$ |
| 1-200 | H | Cl | H | $CF_2Cl$ | $CH_3$ | $SCH_2CH_2Cl$ |
| 1-201 | H | Cl | H | $CF_2Cl$ | $CH_3$ | $S^cC_5H_9$ |
| 1-202 | H | Cl | H | $CF_2Cl$ | $CH_3$ | $S^cC_6H_{11}$ |
| 1-203 | H | Cl | H | $CF_2Cl$ | $CH_3$ | $SCH_2CH=CH_2$ |
| 1-204 | H | Cl | H | $CF_2Cl$ | $CH_3$ | $SCH_2CCl=CH_2$ |
| 1-205 | H | Cl | H | $CF_2Cl$ | $CH_3$ | $SCH_2CCl=CHCl$ |
| 1-206 | H | Cl | H | $CF_2Cl$ | $CH_3$ | $SCH(CH_3)CH=CH_2$ |
| 1-207 | H | Cl | H | $CF_2Cl$ | $CH_3$ | $SCH_2C\equiv CH$ |
| 1-208 | H | Cl | H | $CF_2Cl$ | $CH_3$ | $SCH(CH_3)C\equiv CH$ |
| 1-209 | H | Cl | H | $CF_2Cl$ | $CH_3$ | $SCH_2COOCH_3$ |
| 1-210 | H | Cl | H | $CF_2Cl$ | $CH_3$ | $SCH_2COOC_2H_5$ |
| 1-211 | H | Cl | H | $CF_2Cl$ | $CH_3$ | $SCH_2COO^nC_3H_7$ |
| 1-212 | H | Cl | H | $CF_2Cl$ | $CH_3$ | $SCH_2COO^nC_4H_9$ |
| 1-213 | H | Cl | H | $CF_2Cl$ | $CH_3$ | $SCH_2COO^nC_5H_{11}$ |
| 1-214 | H | Cl | H | $CF_2Cl$ | $CH_3$ | $SCH_2COO^iC_3H_7$ |
| 1-215 | H | Cl | H | $CF_2Cl$ | $CH_3$ | $SCH_2COO^cC_5H_9$ |
| 1-216 | H | Cl | H | $CF_2Cl$ | $CH_3$ | $SCH_2COO^cC_6H_{11}$ |
| 1-217 | H | Cl | H | $CF_2Cl$ | $CH_3$ | $SCH(CH_3)COOCH_3$ |
| 1-218 | H | Cl | H | $CF_2Cl$ | $CH_3$ | $SCH(CH_3)COOC_2H_5$ |
| 1-219 | H | Cl | H | $CF_2Cl$ | $CH_3$ | $SCH(CH_3)COO^nC_3H_7$ |
| 1-220 | H | Cl | H | $CF_2Cl$ | $CH_3$ | $SCH(CH_3)COO^nC_4H_9$ |
| 1-221 | H | Cl | H | $CF_2Cl$ | $CH_3$ | $SCH(CH_3)COO^nC_5H_{11}$ |
| 1-222 | H | Cl | H | $CF_2Cl$ | $CH_3$ | $SCH(CH_3)COO^iC_3H_7$ |
| 1-223 | H | Cl | H | $CF_2Cl$ | $CH_3$ | $SCH(CH_3)COO^cC_5H_9$ |
| 1-224 | H | Cl | H | $CF_2Cl$ | $CH_3$ | $SCH(CH_3)COO^cC_6H_{11}$ |
| 1-225 | H | Cl | H | $CF_2Cl$ | $CH_3$ | $SCH_2CON(CH_3)_2$ |
| 1-226 | H | Cl | H | $CF_2Cl$ | $CH_3$ | $SCH_2CON(C_2H_5)_2$ |
| 1-227 | H | Cl | H | $CF_2Cl$ | $CH_3$ | $SCH_2CON$(tetramethylene) |
| 1-228 | H | Cl | H | $CF_2Cl$ | $CH_3$ | $SCH_2CON$(pentamethylene) |
| 1-229 | H | Cl | H | $CF_2Cl$ | $CH_3$ | $SCH_2CON$ (ethyleneoxyethylene) |
| 1-230 | H | Cl | H | $CF_2Cl$ | $CH_3$ | $SCH(CH_3)CON(CH_3)_2$ |
| 1-231 | H | Cl | H | $CF_2Cl$ | $CH_3$ | $SCH(CH_3)CON(C_2H_5)_2$ |
| 1-232 | H | Cl | H | $CF_2Cl$ | $CH_3$ | $SCH(CH_3)CON$ (tetramethylene) |
| 1-233 | H | Cl | H | $CF_2Cl$ | $CH_3$ | $SCH(CH_3)CON$ (pentamethylene) |
| 1-234 | F | Cl | H | $CF_2Cl$ | $CH_3$ | $SCH_3$ |
| 1-235 | F | Cl | H | $CF_2Cl$ | $CH_3$ | $SC_2H_5$ |
| 1-236 | F | Cl | H | $CF_2Cl$ | $CH_3$ | $S^iC_3H_7$ |
| 1-237 | F | Cl | H | $CF_2Cl$ | $CH_3$ | $SCH_2CH_2Cl$ |
| 1-238 | F | Cl | H | $CF_2Cl$ | $CH_3$ | $S^cC_5H_9$ |
| 1-239 | F | Cl | H | $CF_2Cl$ | $CH_3$ | $S^cC_6H_{11}$ |
| 1-240 | F | Cl | H | $CF_2Cl$ | $CH_3$ | $SCH_2CH=CH_2$ |
| 1-241 | F | Cl | H | $CF_2Cl$ | $CH_3$ | $SCH_2CCl=CH_2$ |
| 1-242 | F | Cl | H | $CF_2Cl$ | $CH_3$ | $SCH_2CCl=CHCl$ |
| 1-243 | F | Cl | H | $CF_2Cl$ | $CH_3$ | $SCH(CH_3)CH=CH_2$ |
| 1-244 | F | Cl | H | $CF_2Cl$ | $CH_3$ | $SCH_2C\equiv CH$ |
| 1-245 | F | Cl | H | $CF_2Cl$ | $CH_3$ | $SCH(CH_3)C\equiv CH$ |
| 1-246 | F | Cl | H | $CF_2Cl$ | $CH_3$ | $SCH_2COOCH_3$ |
| 1-247 | F | Cl | H | $CF_2Cl$ | $CH_3$ | $SCH_2COOC_2H_5$ |
| 1-248 | F | Cl | H | $CF_2Cl$ | $CH_3$ | $SCH_2COO^nC_3H_7$ |
| 1-249 | F | Cl | H | $CF_2Cl$ | $CH_3$ | $SCH_2COO^nC_4H_9$ |
| 1-250 | F | Cl | H | $CF_2Cl$ | $CH_3$ | $SCH_2COO^nC_5H_{11}$ |
| 1-251 | F | Cl | H | $CF_2Cl$ | $CH_3$ | $SCH_2COO^iC_3H_7$ |
| 1-252 | F | Cl | H | $CF_2Cl$ | $CH_3$ | $SCH_2COO^cC_5H_9$ |
| 1-253 | F | Cl | H | $CF_2Cl$ | $CH_3$ | $SCH_2COO^cC_6H_{11}$ |

TABLE 1-continued

Compounds of the formula:

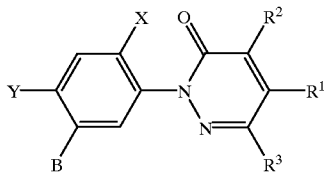

| Compound No. | X | Y | $R^3$ | $R^1$ | $R^2$ | B |
|---|---|---|---|---|---|---|
| 1-254 | F | Cl | H | $CF_2Cl$ | $CH_3$ | $SCH(CH_3)COOCH_3$ |
| 1-255 | F | Cl | H | $CF_2Cl$ | $CH_3$ | $SCH(CH_3)COOC_2H_5$ |
| 1-256 | F | Cl | H | $CF_2Cl$ | $CH_3$ | $SCH(CH_3)COO^nC_3H_7$ |
| 1-257 | F | Cl | H | $CF_2Cl$ | $CH_3$ | $SCH(CH_3)COO^nC_4H_9$ |
| 1-258 | F | Cl | H | $CF_2Cl$ | $CH_3$ | $SCH(CH_3)COO^nC_5H_{11}$ |
| 1-259 | F | Cl | H | $CF_2Cl$ | $CH_3$ | $SCH(CH_3)COO^iC_3H_7$ |
| 1-260 | F | Cl | H | $CF_2Cl$ | $CH_3$ | $SCH(CH_3)COO^cC_5H_9$ |
| 1-261 | F | Cl | H | $CF_2Cl$ | $CH_3$ | $SCH(CH_3)COO^cC_6H_{11}$ |
| 1-262 | F | Cl | H | $CF_2Cl$ | $CH_3$ | $SCH_2CON(CH_3)_2$ |
| 1-263 | F | Cl | H | $CF_2Cl$ | $CH_3$ | $SCH_2CON(C_2H_5)_2$ |
| 1-264 | F | Cl | H | $CF_2Cl$ | $CH_3$ | $SCH_2CON(tetramethylene)$ |
| 1-265 | F | Cl | H | $CF_2Cl$ | $CH_3$ | $SCH_2CON(pentamethylene)$ |
| 1-266 | F | Cl | H | $CF_2Cl$ | $CH_3$ | $SCH_2CON(ethyleneoxyethylene)$ |
| 1-267 | F | Cl | H | $CF_2Cl$ | $CH_3$ | $SCH(CH_3)CON(CH_3)_2$ |
| 1-268 | F | Cl | H | $CF_2Cl$ | $CH_3$ | $SCH(CH_3)CON(C_2H_5)_2$ |
| 1-269 | F | Cl | H | $CF_2Cl$ | $CH_3$ | $SCH(CH_3)CON(tetramethylene)$ |
| 1-270 | F | Cl | H | $CF_2Cl$ | $CH_3$ | $SCH(CH_3)CON(pentamethylene)$ |
| 1-271 | H | F | H | $CF_2Cl$ | $CH_3$ | $SO_2Cl$ |
| 1-272 | H | Cl | H | $CF_2Cl$ | $CH_3$ | $SO_2Cl$ |
| 1-273 | H | Br | H | $CF_2Cl$ | $CH_3$ | $SO_2Cl$ |
| 1-274 | F | F | H | $CF_2Cl$ | $CH_3$ | $SO_2Cl$ |
| 1-275 | F | Cl | H | $CF_2Cl$ | $CH_3$ | $SO_2Cl$ |
| 1-276 | F | Br | H | $CF_2Cl$ | $CH_3$ | $SO_2Cl$ |
| 1-277 | H | Cl | H | $CF_2Cl$ | $CH_3$ | $SO_2OCH_3$ |
| 1-278 | H | Cl | H | $CF_2Cl$ | $CH_3$ | $SO_2OC_2H_5$ |
| 1-279 | H | Cl | H | $CF_2Cl$ | $CH_3$ | $SO_2O^iC_3H_7$ |
| 1-280 | H | Cl | H | $CF_2Cl$ | $CH_3$ | $SO_2OCH_2CH=CH_2$ |
| 1-281 | F | Cl | H | $CF_2Cl$ | $CH_3$ | $SO_2OCH_3$ |
| 1-282 | F | Cl | H | $CF_2Cl$ | $CH_3$ | $SO_2OC_2H_5$ |
| 1-283 | F | Cl | H | $CF_2Cl$ | $CH_3$ | $SO_2O^iC_3H_7$ |
| 1-284 | F | Cl | H | $CF_2Cl$ | $CH_3$ | $SO_2OCH_2CH=CH_2$ |
| 1-285 | H | Cl | H | $CF_2Cl$ | $CH_3$ | $SO_2N(CH_3)_2$ |
| 1-286 | H | Cl | H | $CF_2Cl$ | $CH_3$ | $SO_2N(C_2H_5)_2$ |
| 1-287 | F | Cl | H | $CF_2Cl$ | $CH_3$ | $SO_2N(CH_3)_2$ |
| 1-288 | F | Cl | H | $CF_2Cl$ | $CH_3$ | $SO_2N(C_2H_5)_2$ |
| 1-289 | H | Cl | H | $CF_2Cl$ | $CH_3$ | $COOH$ |
| 1-290 | H | Cl | H | $CF_2Cl$ | $CH_3$ | $COOCH_3$ |
| 1-291 | H | Cl | H | $CF_2Cl$ | $CH_3$ | $COOC_2H_5$ |
| 1-292 | H | Cl | H | $CF_2Cl$ | $CH_3$ | $COO^nC_3H_7$ |
| 1-293 | H | Cl | H | $CF_2Cl$ | $CH_3$ | $COO^nC_4H_9$ |
| 1-294 | H | Cl | H | $CF_2Cl$ | $CH_3$ | $COO^nC_5H_{11}$ |
| 1-295 | H | Cl | H | $CF_2Cl$ | $CH_3$ | $COO^iC_3H_7$ |
| 1-296 | H | Cl | H | $CF_2Cl$ | $CH_3$ | $COOCH_2CH_2Cl$ |
| 1-297 | H | Cl | H | $CF_2Cl$ | $CH_3$ | $COOCH_2CH_2Br$ |
| 1-298 | H | Cl | H | $CF_2Cl$ | $CH_3$ | $CON(CH_3)_2$ |
| 1-299 | H | Cl | H | $CF_2Cl$ | $CH_3$ | $CONHCH_3$ |
| 1-300 | H | Cl | H | $CF_2Cl$ | $CH_3$ | $CON(C_2H_5)_2$ |
| 1-301 | H | Cl | H | $CF_2Cl$ | $CH_3$ | $CONHC_2H_5$ |
| 1-302 | H | Cl | H | $CF_2Cl$ | $CH_3$ | $COCH_3$ |
| 1-303 | H | Cl | H | $CF_2Cl$ | $CH_3$ | $COC_2H_5$ |
| 1-304 | H | Cl | H | $CF_2Cl$ | $CH_3$ | $COCH_2Cl$ |
| 1-305 | H | Cl | H | $CF_2Cl$ | $CH_3$ | $CHO$ |
| 1-306 | H | Cl | H | $CF_2Cl$ | $CH_3$ | $CH=CHCOOCH_3$ |
| 1-307 | H | Cl | H | $CF_2Cl$ | $CH_3$ | $CH=CHCOOC_2H_5$ |
| 1-308 | H | Cl | H | $CF_2Cl$ | $CH_3$ | $CH_2CH_2COOCH_3$ |
| 1-309 | H | Cl | H | $CF_2Cl$ | $CH_3$ | $CH_2CH_2COOC_2H_5$ |
| 1-310 | F | Cl | H | $CF_2Cl$ | $CH_3$ | $COOH$ |
| 1-311 | F | Cl | H | $CF_2Cl$ | $CH_3$ | $COOCH_3$ |
| 1-312 | F | Cl | H | $CF_2Cl$ | $CH_3$ | $COOC_2H_5$ |
| 1-313 | F | Cl | H | $CF_2Cl$ | $CH_3$ | $COO^nC_3H_7$ |
| 1-314 | F | Cl | H | $CF_2Cl$ | $CH_3$ | $COO^nC_4H_9$ |

TABLE 1-continued

Compounds of the formula:

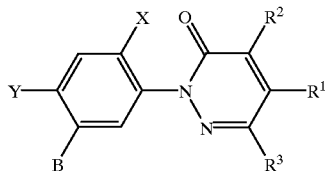

| Compound No. | X | Y | R³ | R¹ | R² | B |
|---|---|---|---|---|---|---|
| 1-315 | F | Cl | H | $CF_2Cl$ | $CH_3$ | $COO^nC_5H_{11}$ |
| 1-316 | F | Cl | H | $CF_2Cl$ | $CH_3$ | $COO^iC_3H_7$ |
| 1-317 | F | Cl | H | $CF_2Cl$ | $CH_3$ | $COOCH_2CH_2Cl$ |
| 1-318 | F | Cl | H | $CF_2Cl$ | $CH_3$ | $COOCH_2CH_2Br$ |
| 1-319 | F | Cl | H | $CF_2Cl$ | $CH_3$ | $CON(CH_3)_2$ |
| 1-320 | F | Cl | H | $CF_2Cl$ | $CH_3$ | $CONHCH_3$ |
| 1-321 | F | Cl | H | $CF_2Cl$ | $CH_3$ | $CON(C_2H_5)_2$ |
| 1-322 | F | Cl | H | $CF_2Cl$ | $CH_3$ | $CONHC_2H_5$ |
| 1-323 | F | Cl | H | $CF_2Cl$ | $CH_3$ | $COCH_3$ |
| 1-324 | F | Cl | H | $CF_2Cl$ | $CH_3$ | $COC_2H_5$ |
| 1-325 | F | Cl | H | $CF_2Cl$ | $CH_3$ | $COCH_2Cl$ |
| 1-326 | F | Cl | H | $CF_2Cl$ | $CH_3$ | $CHO$ |
| 1-327 | F | Cl | H | $CF_2Cl$ | $CH_3$ | $CH{=}CHCOOCH_3$ |
| 1-328 | F | Cl | H | $CF_2Cl$ | $CH_3$ | $CH{=}CHCOOC_2H_5$ |
| 1-329 | F | Cl | H | $CF_2Cl$ | $CH_3$ | $CH_2CH_2COOCH_3$ |
| 1-330 | F | Cl | H | $CF_2Cl$ | $CH_3$ | $CH_2CH_2COOC_2H_5$ |
| 1-331 | H | F | H | $CF_3$ | H | H |
| 1-332 | H | Cl | H | $CF_3$ | H | H |
| 1-333 | H | Br | H | $CF_3$ | H | H |
| 1-334 | H | F | H | $CF_3$ | $CH_3$ | H |
| 1-335 | H | Cl | H | $CF_3$ | $CH_3$ | H |
| 1-336 | H | Br | H | $CF_3$ | $CH_3$ | H |
| 1-337 | F | F | H | $CF_3$ | H | H |
| 1-338 | F | Cl | H | $CF_3$ | H | H |
| 1-339 | F | Br | H | $CF_3$ | H | H |
| 1-340 | F | F | H | $CF_3$ | $CH_3$ | H |
| 1-341 | F | Cl | H | $CF_3$ | $CH_3$ | H |
| 1-342 | F | Br | H | $CF_3$ | $CH_3$ | H |
| 1-343 | H | F | H | $CF_3$ | $CH_3$ | $NO_2$ |
| 1-344 | H | Cl | H | $CF_3$ | $CH_3$ | $NO_2$ |
| 1-345 | H | Br | H | $CF_3$ | $CH_3$ | $NO_2$ |
| 1-346 | F | F | H | $CF_3$ | $CH_3$ | $NO_2$ |
| 1-347 | F | Cl | H | $CF_3$ | $CH_3$ | $NO_2$ |
| 1-348 | F | Br | H | $CF_3$ | $CH_3$ | $NO_2$ |
| 1-349 | H | F | H | $CF_3$ | $CH_3$ | $NH_2$ |
| 1-350 | H | Cl | H | $CF_3$ | $CH_3$ | $NH_2$ |
| 1-351 | H | Br | H | $CF_3$ | $CH_3$ | $NH_2$ |
| 1-352 | F | F | H | $CF_3$ | $CH_3$ | $NH_2$ |
| 1-353 | F | Cl | H | $CF_3$ | $CH_3$ | $NH_2$ |
| 1-354 | H | Cl | H | $CF_3$ | $CH_3$ | $NHCH(CH_3)COOCH_3$ |
| 1-355 | H | Cl | H | $CF_3$ | $CH_3$ | $NHCH(CH_3)COOC_2H_5$ |
| 1-356 | H | Cl | H | $CF_3$ | $CH_3$ | $NHCH(CH_3)COO^nC_3H_7$ |
| 1-357 | H | Cl | H | $CF_3$ | $CH_3$ | $NHCH(CH_3)COO^nC_4H_9$ |
| 1-358 | H | Cl | H | $CF_3$ | $CH_3$ | $NHCH(CH_3)COO^nC_5H_{11}$ |
| 1-359 | H | Cl | H | $CF_3$ | $CH_3$ | $NHCH(CH_3)COO^iC_3H_7$ |
| 1-360 | H | Cl | H | $CF_3$ | $CH_3$ | $NHCH(CH_3)COO^cC_4H_9$ |
| 1-361 | H | Cl | H | $CF_3$ | $CH_3$ | $NHCH(CH_3)COO^cC_6H_{11}$ |
| 1-362 | F | Cl | H | $CF_3$ | $CH_3$ | $NHCH_3$ |
| 1-363 | F | Cl | H | $CF_3$ | $CH_3$ | $NHC_2H_5$ |
| 1-364 | F | Cl | H | $CF_3$ | $CH_3$ | $NHCH_2CH{=}CH_2$ |
| 1-365 | F | Cl | H | $CF_3$ | $CH_3$ | $NHCH_2C{\equiv}CH$ |
| 1-366 | F | Cl | H | $CF_3$ | $CH_3$ | $NHCH(CH_3)C{\equiv}CH$ |
| 1-367 | F | Cl | H | $CF_3$ | $CH_3$ | $NHSO_2CH_3$ |
| 1-368 | F | Cl | H | $CF_3$ | $CH_3$ | $NHSO_2C_2H_5$ |
| 1-369 | F | Cl | H | $CF_3$ | $CH_3$ | $NHSO_2CH_2Cl$ |
| 1-370 | F | Cl | H | $CF_3$ | $CH_3$ | $NHSO_2CF_3$ |
| 1-371 | F | Cl | H | $CF_3$ | $CH_3$ | $N(CH_3)SO_2CH_3$ |
| 1-372 | F | Cl | H | $CF_3$ | $CH_3$ | $N(CH_2C{\equiv}CH)SO_2CH_3$ |
| 1-373 | F | Cl | H | $CF_3$ | $CH_3$ | $NHCOOCH_3$ |
| 1-374 | F | Cl | H | $CF_3$ | $CH_3$ | $NHCOOC_2H_5$ |
| 1-375 | F | Cl | H | $CF_3$ | $CH_3$ | $NHCOO^nC_3H_7$ |
| 1-376 | F | Cl | H | $CF_3$ | $CH_3$ | $NHCOO^iC_3H_7$ |
| 1-377 | F | Cl | H | $CF_3$ | $CH_3$ | $NHCOO^nC_4H_9$ |
| 1-378 | F | Cl | H | $CF_3$ | $CH_3$ | $NHCOO^nC_5H_{11}$ |

TABLE 1-continued

Compounds of the formula:

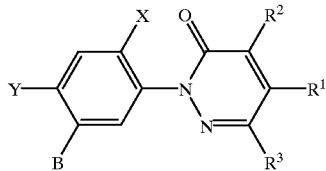

| Compound No. | X | Y | $R^3$ | $R^1$ | $R^2$ | B |
|---|---|---|---|---|---|---|
| 1-379 | F | Cl | H | $CF_3$ | $CH_3$ | $NHCH_2COOCH_3$ |
| 1-380 | F | Cl | H | $CF_3$ | $CH_3$ | $NHCH_2COOC_2H_5$ |
| 1-381 | F | Cl | H | $CF_3$ | $CH_3$ | $NHCH_2COO^nC_3H_7$ |
| 1-382 | F | Cl | H | $CF_3$ | $CH_3$ | $NHCH_2COO^nC_4H_9$ |
| 1-383 | F | Cl | H | $CF_3$ | $CH_3$ | $NHCH_2COO^nC_5H_{11}$ |
| 1-384 | F | Cl | H | $CF_3$ | $CH_3$ | $NHCH_2COO^iC_3H_7$ |
| 1-385 | F | Cl | H | $CF_3$ | $CH_3$ | $NHCH_2COO^cC_5H_9$ |
| 1-386 | F | Br | H | $CF_3$ | $CH_3$ | $NH_2$ |
| 1-387 | H | F | H | $CF_3$ | $CH_3$ | OH |
| 1-388 | H | Cl | H | $CF_3$ | $CH_3$ | OH |
| 1-389 | H | Br | H | $CF_3$ | $CH_3$ | OH |
| 1-390 | F | F | H | $CF_3$ | $CH_3$ | OH |
| 1-391 | F | Cl | H | $CF_3$ | $CH_3$ | OH |
| 1-392 | F | Br | H | $CF_3$ | $CH_3$ | OH |
| 1-393 | H | Cl | H | $CF_3$ | $CH_3$ | $NHCH_3$ |
| 1-394 | H | Cl | H | $CF_3$ | $CH_3$ | $NHC_2H_5$ |
| 1-395 | H | Cl | H | $CF_3$ | $CH_3$ | $NHCH_2CH=CH_2$ |
| 1-396 | H | Cl | H | $CF_3$ | $CH_3$ | $NHCH_2C\equiv CH$ |
| 1-397 | H | Cl | H | $CF_3$ | $CH_3$ | $NHCH(CH_3)C\equiv CH$ |
| 1-398 | H | Cl | H | $CF_3$ | $CH_3$ | $NHSO_2CH_3$ |
| 1-399 | H | Cl | H | $CF_3$ | $CH_3$ | $NHSO_2C_2H_5$ |
| 1-400 | H | Cl | H | $CF_3$ | $CH_3$ | $NHSO_2CH_2Cl$ |
| 1-401 | H | Cl | H | $CF_3$ | $CH_3$ | $NHSO_2CF_3$ |
| 1-402 | H | Cl | H | $CF_3$ | $CH_3$ | $N(CH_3)SO_2CH_3$ |
| 1-403 | H | Cl | H | $CF_3$ | $CH_3$ | $N(CH_2C\equiv CH)SO_2CH_3$ |
| 1-404 | H | Cl | H | $CF_3$ | $CH_3$ | $NHCOOCH_3$ |
| 1-405 | H | Cl | H | $CF_3$ | $CH_3$ | $NHCOOC_2H_5$ |
| 1-406 | H | Cl | H | $CF_3$ | $CH_3$ | $NHCOO^nC_3H_7$ |
| 1-407 | H | Cl | H | $CF_3$ | $CH_3$ | $NHCOO^iC_3H_7$ |
| 1-408 | H | Cl | H | $CF_3$ | $CH_3$ | $NHCOO^nC_4H_9$ |
| 1-409 | H | Cl | H | $CF_3$ | $CH_3$ | $NHCOO^nC_5H_{11}$ |
| 1-410 | H | Cl | H | $CF_3$ | $CH_3$ | $NHCH_2COOCH_3$ |
| 1-411 | H | Cl | H | $CF_3$ | $CH_3$ | $NHCH_2COOC_2H_5$ |
| 1-412 | H | Cl | H | $CF_3$ | $CH_3$ | $NHCH_2COO^nC_3H_7$ |
| 1-413 | H | Cl | H | $CF_3$ | $CH_3$ | $NHCH_2COO^nC_4H_9$ |
| 1-414 | H | Cl | H | $CF_3$ | $CH_3$ | $NHCH_2COO^nC_5H_{11}$ |
| 1-415 | H | Cl | H | $CF_3$ | $CH_3$ | $NHCH_2COO^iC_3H_7$ |
| 1-416 | H | Cl | H | $CF_3$ | $CH_3$ | $NHCH_2COO^cC_5H_9$ |
| 1-417 | H | Cl | H | $CF_3$ | $CH_3$ | $NHCH_2COO^cC_5H_{11}$ |
| 1-418 | F | Cl | H | $CF_3$ | $CH_3$ | $NHCH_2COO^cC_6H_{11}$ |
| 1-419 | F | Cl | H | $CF_3$ | $CH_3$ | $NHCH(CH_3)COOCH_3$ |
| 1-420 | F | Cl | H | $CF_3$ | $CH_3$ | $NHCH(CH_3)COOC_2H_5$ |
| 1-421 | F | Cl | H | $CF_3$ | $CH_3$ | $NHCH(CH_3)COO^nC_3H_7$ |
| 1-422 | F | Cl | H | $CF_3$ | $CH_3$ | $NHCH(CH_3)COO^nC_4H_9$ |
| 1-423 | F | Cl | H | $CF_3$ | $CH_3$ | $NHCH(CH_3)COO^nC_5H_{11}$ |
| 1-424 | F | Cl | H | $CF_3$ | $CH_3$ | $NHCH(CH_3)COO^iC_3H_7$ |
| 1-425 | F | Cl | H | $CF_3$ | $CH_3$ | $NHCH(CH_3)COO^cC_5H_9$ |
| 1-426 | F | Cl | H | $CF_3$ | $CH_3$ | $NHCH(CH_3)COO^cC_6H_{11}$ |
| 1-427 | H | Cl | H | $CF_3$ | $CH_3$ | $OCH_3$ |
| 1-428 | H | Cl | H | $CF_3$ | $CH_3$ | $OC_2H_5$ |
| 1-429 | H | Cl | H | $CF_3$ | $CH_3$ | $O^iC_3H_7$ |
| 1-430 | H | Cl | H | $CF_3$ | $CH_3$ | $O^nC_3H_7$ |
| 1-431 | H | Cl | H | $CF_3$ | $CH_3$ | $OCH_2CH_2Cl$ |
| 1-432 | H | Cl | H | $CF_3$ | $CH_3$ | $OCF_2CF_2H$ |
| 1-433 | H | Cl | H | $CF_3$ | $CH_3$ | $O^cC_5H_9$ |
| 1-434 | H | Cl | H | $CF_3$ | $CH_3$ | $O^cC_6H_{11}$ |
| 1-435 | H | Cl | H | $CF_3$ | $CH_3$ | $OCH_2CH=CH_2$ |
| 1-436 | H | Cl | H | $CF_3$ | $CH_3$ | $OCH_2CCl=CH_2$ |
| 1-437 | H | Cl | H | $CF_3$ | $CH_3$ | $OCH_2CCl=CHCl$ |
| 1-438 | H | Cl | H | $CF_3$ | $CH_3$ | $OCH(CH_3)CH=CH_2$ |
| 1-439 | H | Cl | H | $CF_3$ | $CH_3$ | $OCH_2C\equiv CH$ |
| 1-440 | H | Cl | H | $CF_3$ | $CH_3$ | $OCH(CH_3)C\equiv CH$ |
| 1-441 | H | Cl | H | $CF_3$ | $CH_3$ | $OCH_2C\equiv CBr$ |
| 1-442 | H | Cl | H | $CF_3$ | $CH_3$ | $OCH_2C\equiv CCl$ |

TABLE 1-continued

Compounds of the formula:

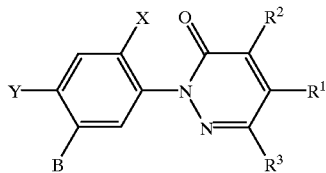

| Compound No. | X | Y | $R^3$ | $R^1$ | $R^2$ | B |
|---|---|---|---|---|---|---|
| 1-443 | H | Cl | H | $CF_3$ | $CH_3$ | $OCH_2C\equiv CCH_2Cl$ |
| 1-444 | H | Cl | H | $CF_3$ | $CH_3$ | $OCH_2CN$ |
| 1-445 | H | Cl | H | $CF_3$ | $CH_3$ | $OCH_2OCH_3$ |
| 1-446 | H | Cl | H | $CF_3$ | $CH_3$ | $OCH_2OC_2H_5$ |
| 1-447 | H | Cl | H | $CF_3$ | $CH_3$ | $OCH_2SCH_3$ |
| 1-448 | H | Cl | H | $CF_3$ | $CH_3$ | $OCH_2COOCH_3$ |
| 1-449 | H | Cl | H | $CF_3$ | $CH_3$ | $OCH_2COOC_2H_5$ |
| 1-450 | H | Cl | H | $CF_3$ | $CH_3$ | $OCH_2COO^nC_3H_7$ |
| 1-451 | H | Cl | H | $CF_3$ | $CH_3$ | $OCH_2COO^nC_4H_9$ |
| 1-452 | H | Cl | H | $CF_3$ | $CH_3$ | $OCH_2COO^nC_5H_{11}$ |
| 1-453 | H | Cl | H | $CF_3$ | $CH_3$ | $OCH_2COO^iC_3H_7$ |
| 1-454 | H | Cl | H | $CF_3$ | $CH_3$ | $OCH_2COO^cC_5H_9$ |
| 1-455 | H | Cl | H | $CF_3$ | $CH_3$ | $OCH_2COO^cC_6H_{11}$ |
| 1-456 | H | Cl | H | $CF_3$ | $CH_3$ | $OCH(CH_3)COOCH_3$ |
| 1-457 | H | Cl | H | $CF_3$ | $CH_3$ | $OCH(CH_3)COOC_2H_5$ |
| 1-458 | H | Cl | H | $CF_3$ | $CH_3$ | $OCH(CH_3)COO^nC_3H_7$ |
| 1-459 | H | Cl | H | $CF_3$ | $CH_3$ | $OCH(CH_3)COO^nC_4H_9$ |
| 1-460 | H | Cl | H | $CF_3$ | $CH_3$ | $OCH(CH_3)COO^nC_5H_{11}$ |
| 1-461 | H | Cl | H | $CF_3$ | $CH_3$ | $OCH(CH_3)COO^iC_3H_7$ |
| 1-462 | H | Cl | H | $CF_3$ | $CH_3$ | $OCH(CH_3)COO^cC_5H_9$ |
| 1-463 | H | Cl | H | $CF_3$ | $CH_3$ | $OCH(CH_3)COO^cC_6H_{11}$ |
| 1-464 | H | Cl | H | $CF_3$ | $CH_3$ | $OCH_2CON(CH_3)_2$ |
| 1-465 | H | Cl | H | $CF_3$ | $CH_3$ | $OCH_2CON(C_2H_5)_2$ |
| 1-466 | H | Cl | H | $CF_3$ | $CH_3$ | $OCH_2CON(CH_3)C_2H_5$ |
| 1-467 | H | Cl | H | $CF_3$ | $CH_3$ | $OCH(CH_3)CON(CH_3)_2$ |
| 1-468 | H | Cl | H | $CF_3$ | $CH_3$ | $OCH(CH_3)CON(C_2H_5)_2$ |
| 1-469 | H | Cl | H | $CF_3$ | $CH_3$ | $OCH(CH_3)CON(CH_3)C_2H_5$ |
| 1-470 | H | Cl | H | $CF_3$ | $CH_3$ | $OCH_2COON(CH_3)_2$ |
| 1-471 | H | Cl | H | $CF_3$ | $CH_3$ | $OCH_2COON(C_2H_5)_2$ |
| 1-472 | H | Cl | H | $CF_3$ | $CH_3$ | $OCH(CH_3)COON(CH_3)_2$ |
| 1-473 | H | Cl | H | $CF_3$ | $CH_3$ | $OCH(CH_3)COON(C_2H_5)_2$ |
| 1-474 | F | Cl | H | $CF_3$ | $CH_3$ | $OCH_3$ |
| 1-475 | F | Cl | H | $CF_3$ | $CH_3$ | $OC_2H_5$ |
| 1-476 | F | Cl | H | $CF_3$ | $CH_3$ | $O^iC_3H_7$ |
| 1-477 | F | Cl | H | $CF_3$ | $CH_3$ | $O^nC_3H_7$ |
| 1-478 | F | Cl | H | $CF_3$ | $CH_3$ | $OCH_2CH_2Cl$ |
| 1-479 | F | Cl | H | $CF_3$ | $CH_3$ | $OCF_2CF_2H$ |
| 1-480 | F | Cl | H | $CF_3$ | $CH_3$ | $O^cC_5H_9$ |
| 1-481 | F | Cl | H | $CF_3$ | $CH_3$ | $O^cC_6H_{11}$ |
| 1-482 | F | Cl | H | $CF_3$ | $CH_3$ | $OCH_2CH=CH_2$ |
| 1-483 | F | Cl | H | $CF_3$ | $CH_3$ | $OCH_2CCl=CH_2$ |
| 1-484 | F | Cl | H | $CF_3$ | $CH_3$ | $OCH_2CCl=CHCl$ |
| 1-485 | F | Cl | H | $CF_3$ | $CH_3$ | $OCH(CH_3)CH=CH_2$ |
| 1-486 | F | Cl | H | $CF_3$ | $CH_3$ | $OCH_2C\equiv CH$ |
| 1-487 | F | Cl | H | $CF_3$ | $CH_3$ | $OCH(CH_3)C\equiv CH$ |
| 1-488 | F | Cl | H | $CF_3$ | $CH_3$ | $OCH_2C\equiv CBr$ |
| 1-489 | F | Cl | H | $CF_3$ | $CH_3$ | $OCH_2C\equiv CCl$ |
| 1-490 | F | Cl | H | $CF_3$ | $CH_3$ | $OCH_2C\equiv CCH_2Cl$ |
| 1-491 | F | Cl | H | $CF_3$ | $CH_3$ | $OCH_2CN$ |
| 1-492 | F | Cl | H | $CF_3$ | $CH_3$ | $OCH_2OCH_3$ |
| 1-493 | F | Cl | H | $CF_3$ | $CH_3$ | $OCH_2OC_2H_5$ |
| 1-494 | F | Cl | H | $CF_3$ | $CH_3$ | $OCH_2SCH_3$ |
| 1-495 | F | Cl | H | $CF_3$ | $CH_3$ | $OCH_2COOCH_3$ |
| 1-496 | F | Cl | H | $CF_3$ | $CH_3$ | $OCH_2COOC_2H_5$ |
| 1-497 | F | Cl | H | $CF_3$ | $CH_3$ | $OCH_2COO^nC_3H_7$ |
| 1-498 | F | Cl | H | $CF_3$ | $CH_3$ | $OCH_2COO^nC_4H_9$ |
| 1-499 | F | Cl | H | $CF_3$ | $CH_3$ | $OCH_2COO^nC_5H_{11}$ |
| 1-500 | F | Cl | H | $CF_3$ | $CH_3$ | $OCH_2COO^iC_3H_7$ |
| 1-501 | F | Cl | H | $CF_3$ | $CH_3$ | $OCH_2COO^cC_5H_9$ |
| 1-502 | F | Cl | H | $CF_3$ | $CH_3$ | $OCH_2COO^cC_6H_{11}$ |
| 1-503 | F | Cl | H | $CF_3$ | $CH_3$ | $OCH(CH_3)COOCH_3$ |
| 1-504 | F | Cl | H | $CF_3$ | $CH_3$ | $OCH(CH_3)COOC_2H_5$ |
| 1-505 | F | Cl | H | $CF_3$ | $CH_3$ | $OCH(CH_3)COO^nC_3H_7$ |
| 1-506 | F | Cl | H | $CF_3$ | $CH_3$ | $OCH(CH_3)COO^nC_4H_9$ |

TABLE 1-continued

Compounds of the formula:

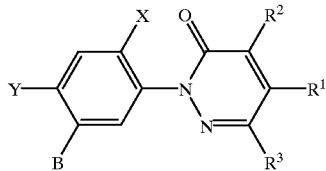

| Compound No. | X | Y | $R^3$ | $R^1$ | $R^2$ | B |
|---|---|---|---|---|---|---|
| 1-507 | F | Cl | H | $CF_3$ | $CH_3$ | $OCH(CH_3)COO^nC_5H_{11}$ |
| 1-508 | F | Cl | H | $CF_3$ | $CH_3$ | $OCH(CH_3)COO^iC_3H_7$ |
| 1-509 | F | Cl | H | $CF_3$ | $CH_3$ | $OCH(CH_3)COO^cC_5H_9$ |
| 1-510 | F | Cl | H | $CF_3$ | $CH_3$ | $OCH(CH_3)COO^cC_6H_{11}$ |
| 1-511 | F | Cl | H | $CF_3$ | $CH_3$ | $OCH_2CON(CH_3)_2$ |
| 1-512 | F | Cl | H | $CF_3$ | $CH_3$ | $OCH_2CON(C_2H_5)_2$ |
| 1-513 | F | Cl | H | $CF_3$ | $CH_3$ | $OCH_2CON(CH_3)C_2H_5$ |
| 1-514 | F | Cl | H | $CF_3$ | $CH_3$ | $OCH(CH_3)CON(CH_3)_2$ |
| 1-515 | F | Cl | H | $CF_3$ | $CH_3$ | $OCH(CH_3)CON(C_2H_5)_2$ |
| 1-516 | F | Cl | H | $CF_3$ | $CH_3$ | $OCH(CH_3)CON(CH_3)C_2H_5$ |
| 1-517 | F | Cl | H | $CF_3$ | $CH_3$ | $OCH_2COON(CH_3)_2$ |
| 1-518 | F | Cl | H | $CF_3$ | $CH_3$ | $OCH_2COON(C_2H_5)_2$ |
| 1-519 | F | Cl | H | $CF_3$ | $CH_3$ | $OCH(CH_3)COON(CH_3)_2$ |
| 1-520 | F | Cl | H | $CF_3$ | $CH_3$ | $OCH(CH_3)COON(C_2H_5)_2$ |
| 1-521 | H | F | H | $CF_3$ | $CH_3$ | SH |
| 1-522 | F | Cl | H | $CF_3$ | $CH_3$ | SH |
| 1-523 | H | Br | H | $CF_3$ | $CH_3$ | SH |
| 1-524 | F | F | H | $CF_3$ | $CH_3$ | SH |
| 1-525 | F | Cl | H | $CF_3$ | $CH_3$ | SH |
| 1-526 | F | Br | H | $CF_3$ | $CH_3$ | SH |
| 1-527 | H | Cl | H | $CF_3$ | $CH_3$ | $SCH_3$ |
| 1-528 | H | Cl | H | $CF_3$ | $CH_3$ | $SC_2H_5$ |
| 1-529 | H | Cl | H | $CF_3$ | $CH_3$ | $S^iC_3H_7$ |
| 1-530 | H | Cl | H | $CF_3$ | $CH_3$ | $SCH_2CH_2Cl$ |
| 1-531 | H | Cl | H | $CF_3$ | $CH_3$ | $S^cC_5H_9$ |
| 1-532 | H | Cl | H | $CF_3$ | $CH_3$ | $S^cC_6H_{11}$ |
| 1-533 | H | Cl | H | $CF_3$ | $CH_3$ | $SCH_2CH=CH_2$ |
| 1-534 | H | Cl | H | $CF_3$ | $CH_3$ | $SCH_2CCl=CH_2$ |
| 1-535 | H | Cl | H | $CF_3$ | $CH_3$ | $SCH_2CCl=CHCl$ |
| 1-536 | H | Cl | H | $CF_3$ | $CH_3$ | $SCH(CH_3)CH=CH_2$ |
| 1-537 | H | Cl | H | $CF_3$ | $CH_3$ | $SCH_2C\equiv CH$ |
| 1-538 | H | Cl | H | $CF_3$ | $CH_3$ | $SCH(CH_3)C\equiv CH$ |
| 1-539 | H | Cl | H | $CF_3$ | $CH_3$ | $SCH_2COOCH_3$ |
| 1-540 | H | Cl | H | $CF_3$ | $CH_3$ | $SCH_2COOC_2H_5$ |
| 1-541 | H | Cl | H | $CF_3$ | $CH_3$ | $SCH_2COO^nC_3H_7$ |
| 1-542 | H | Cl | H | $CF_3$ | $CH_3$ | $SCH_2COO^nC_4H_9$ |
| 1-543 | H | Cl | H | $CF_3$ | $CH_3$ | $SCH_2COO^nC_5H_{11}$ |
| 1-544 | H | Cl | H | $CF_3$ | $CH_3$ | $SCH_2COO^iC_3H_7$ |
| 1-545 | H | Cl | H | $CF_3$ | $CH_3$ | $SCH_2COO^cC_5H_9$ |
| 1-546 | H | Cl | H | $CF_3$ | $CH_3$ | $SCH_2COO^cC_6H_{11}$ |
| 1-547 | H | Cl | H | $CF_3$ | $CH_3$ | $SCH(CH_3)COOCH_3$ |
| 1-548 | H | Cl | H | $CF_3$ | $CH_3$ | $SCH(CH_3)COOC_2H_5$ |
| 1-549 | H | Cl | H | $CF_3$ | $CH_3$ | $SCH(CH_3)COO^nC_3H_7$ |
| 1-550 | H | Cl | H | $CF_3$ | $CH_3$ | $SCH(CH_3)COO^nC_4H_9$ |
| 1-551 | H | Cl | H | $CF_3$ | $CH_3$ | $SCH(CH_3)COO^nC_5H_{11}$ |
| 1-552 | H | Cl | H | $CF_3$ | $CH_3$ | $SCH(CH_3)COO^iC_3H_7$ |
| 1-553 | H | Cl | H | $CF_3$ | $CH_3$ | $SCH(CH_3)COO^cC_5H_9$ |
| 1-554 | H | Cl | H | $CF_3$ | $CH_3$ | $SCH(CH_3)COO^cC_6H_{11}$ |
| 1-555 | H | Cl | H | $CF_3$ | $CH_3$ | $SCH_2CON(CH_3)_2$ |
| 1-556 | H | Cl | H | $CF_3$ | $CH_3$ | $SCH_2CON(C_2H_5)_2$ |
| 1-557 | H | Cl | H | $CF_3$ | $CH_3$ | $SCH_2CON(tetramethylene)$ |
| 1-558 | H | Cl | H | $CF_3$ | $CH_3$ | $SCH_2CON(pentamethylene)$ |
| 1-559 | H | Cl | H | $CF_3$ | $CH_3$ | $SCH_2CON$ (ethyleneoxyethylene) |
| 1-560 | H | Cl | H | $CF_3$ | $CH_3$ | $SCH(CH_3)CON(CH_3)_2$ |
| 1-561 | H | Cl | H | $CF_3$ | $CH_3$ | $SCH(CH_3)CON(C_2H_5)_2$ |
| 1-562 | H | Cl | H | $CF_3$ | $CH_3$ | $SCH(CH_3)CON$ (tetramethylene) |
| 1-563 | H | Cl | H | $CF_3$ | $CH_3$ | $SCH(CH_3)CON$ (pentamethylene) |
| 1-564 | F | Cl | H | $CF_3$ | $CH_3$ | $SCH_3$ |
| 1-565 | F | Cl | H | $CF_3$ | $CH_3$ | $SC_2H_5$ |
| 1-566 | F | Cl | H | $CF_3$ | $CH_3$ | $S^iC_3H_7$ |
| 1-567 | F | Cl | H | $CF_3$ | $CH_3$ | $SCH_2CH_2Cl$ |

TABLE 1-continued

Compounds of the formula:

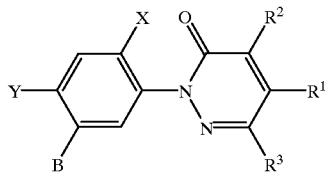

| Compound No. | X | Y | $R^3$ | $R^1$ | $R^2$ | B |
|---|---|---|---|---|---|---|
| 1-568 | F | Cl | H | $CF_3$ | $CH_3$ | $S^cC_5H_9$ |
| 1-569 | F | Cl | H | $CF_3$ | $CH_3$ | $S^cC_6H_{11}$ |
| 1-570 | F | Cl | H | $CF_3$ | $CH_3$ | $SCH_2CH=CH_2$ |
| 1-571 | F | Cl | H | $CF_3$ | $CH_3$ | $SCH_2CCl=CH_2$ |
| 1-572 | F | Cl | H | $CF_3$ | $CH_3$ | $SCH_2CCl=CHCl$ |
| 1-573 | F | Cl | H | $CF_3$ | $CH_3$ | $SCH(CH_3)CH=CH_2$ |
| 1-574 | F | Cl | H | $CF_3$ | $CH_3$ | $SCH_2C\equiv CH$ |
| 1-575 | F | Cl | H | $CF_3$ | $CH_3$ | $SCH(CH_3)C\equiv CH$ |
| 1-576 | F | Cl | H | $CF_3$ | $CH_3$ | $SCH_2COOCH_3$ |
| 1-577 | F | Cl | H | $CF_3$ | $CH_3$ | $SCH_2COOC_2H_5$ |
| 1-578 | F | Cl | H | $CF_3$ | $CH_3$ | $SCH_2COO^nC_3H_7$ |
| 1-579 | F | Cl | H | $CF_3$ | $CH_3$ | $SCH_2COO^nC_4H_9$ |
| 1-580 | F | Cl | H | $CF_3$ | $CH_3$ | $SCH_2COO^nC_5H_{11}$ |
| 1-581 | F | Cl | H | $CF_3$ | $CH_3$ | $SCH_2COO^iC_3H_7$ |
| 1-582 | F | Cl | H | $CF_3$ | $CH_3$ | $SCH_2COO^cC_5H_9$ |
| 1-583 | F | Cl | H | $CF_3$ | $CH_3$ | $SCH_2COO^cC_6H_{11}$ |
| 1-584 | F | Cl | H | $CF_3$ | $CH_3$ | $SCH(CH_3)COOCH_3$ |
| 1-585 | F | Cl | H | $CF_3$ | $CH_3$ | $SCH(CH_3)COOC_2H_5$ |
| 1-586 | F | Cl | H | $CF_3$ | $CH_3$ | $SCH(CH_3)COO^nC_3H_7$ |
| 1-587 | F | Cl | H | $CF_3$ | $CH_3$ | $SCH(CH_3)COO^nC_4H_9$ |
| 1-588 | F | Cl | H | $CF_3$ | $CH_3$ | $SCH(CH_3)COO^nC_5H_{11}$ |
| 1-589 | F | Cl | H | $CF_3$ | $CH_3$ | $SCH(CH_3)COO^iC_3H_7$ |
| 1-590 | F | Cl | H | $CF_3$ | $CH_3$ | $SCH(CH_3)COO^cC_5H_9$ |
| 1-591 | F | Cl | H | $CF_3$ | $CH_3$ | $SCH(CH_3)COO^cC_6H_{11}$ |
| 1-592 | F | Cl | H | $CF_3$ | $CH_3$ | $SCH_2CON(CH_3)_2$ |
| 1-593 | F | Cl | H | $CF_3$ | $CH_3$ | $SCH_2CON(C_2H_5)_2$ |
| 1-594 | F | Cl | H | $CF_3$ | $CH_3$ | $SCH_2CON$(tetramethylene) |
| 1-595 | F | Cl | H | $CF_3$ | $CH_3$ | $SCH_2CON$(pentamethylene) |
| 1-596 | F | Cl | H | $CF_3$ | $CH_3$ | $SCH_2CON$ (ethyleneoxyethylene) |
| 1-597 | F | Cl | H | $CF_3$ | $CH_3$ | $SCH(CH_3)CON(CH_3)_2$ |
| 1-598 | F | Cl | H | $CF_3$ | $CH_3$ | $SCH(CH_3)CON(C_2H_5)_2$ |
| 1-599 | F | Cl | H | $CF_3$ | $CH_3$ | $SCH(CH_3)CON$ (tetramethylene) |
| 1-600 | F | Cl | H | $CF_3$ | $CH_3$ | $SCH(CH_3)CON$ (pentamethylene) |
| 1-601 | H | F | H | $CF_3$ | $CH_3$ | $SO_2Cl$ |
| 1-602 | F | Cl | H | $CF_3$ | $CH_3$ | $SO_2Cl$ |
| 1-603 | H | Br | H | $CF_3$ | $CH_3$ | $SO_2Cl$ |
| 1-604 | F | F | H | $CF_3$ | $CH_3$ | $SO_2Cl$ |
| 1-605 | F | Cl | H | $CF_3$ | $CH_3$ | $SO_2Cl$ |
| 1-606 | F | Br | H | $CF_3$ | $CH_3$ | $SO_2Cl$ |
| 1-607 | F | Cl | H | $CF_3$ | $CH_3$ | $SO_2OCH_3$ |
| 1-608 | F | Cl | H | $CF_3$ | $CH_3$ | $SO_2OC_2H_5$ |
| 1-609 | F | Cl | H | $CF_3$ | $CH_3$ | $SO_2O^iC_3H_7$ |
| 1-610 | F | Cl | H | $CF_3$ | $CH_3$ | $SO_2OCH_2CH=CH_2$ |
| 1-611 | F | Cl | H | $CF_3$ | $CH_3$ | $SO_2OCH_3$ |
| 1-612 | F | Cl | H | $CF_3$ | $CH_3$ | $SO_2OC_2H_5$ |
| 1-613 | F | Cl | H | $CF_3$ | $CH_3$ | $SO_2O^iC_3H_7$ |
| 1-614 | F | Cl | H | $CF_3$ | $CH_3$ | $SO_2OCH_2CH=CH_2$ |
| 1-615 | F | Cl | H | $CF_3$ | $CH_3$ | $SO_2N(CH_3)_2$ |
| 1-616 | F | Cl | H | $CF_3$ | $CH_3$ | $SO_2N(C_2H_5)_2$ |
| 1-617 | F | Cl | H | $CF_3$ | $CH_3$ | $SO_2N(CH_3)_2$ |
| 1-618 | F | Cl | H | $CF_3$ | $CH_3$ | $SO_2N(C_2H_5)_2$ |
| 1-619 | H | Cl | H | $CF_3$ | $CH_3$ | $COOH$ |
| 1-620 | H | Cl | H | $CF_3$ | $CH_3$ | $COOCH_3$ |
| 1-621 | H | Cl | H | $CF_3$ | $CH_3$ | $COOC_2H_5$ |
| 1-622 | H | Cl | H | $CF_3$ | $CH_3$ | $COO^nC_3H_7$ |
| 1-623 | H | Cl | H | $CF_3$ | $CH_3$ | $COO^nC_4H_9$ |
| 1-624 | H | Cl | H | $CF_3$ | $CH_3$ | $COO^nC_5H_{11}$ |
| 1-625 | H | Cl | H | $CF_3$ | $CH_3$ | $COO^iC_3H_7$ |
| 1-626 | H | Cl | H | $CF_3$ | $CH_3$ | $COOCH_2CH_2Cl$ |
| 1-627 | H | Cl | H | $CF_3$ | $CH_3$ | $COOCH_2CH_2Br$ |
| 1-628 | H | Cl | H | $CF_3$ | $CH_3$ | $CON(CH_3)_2$ |

TABLE 1-continued

Compounds of the formula:

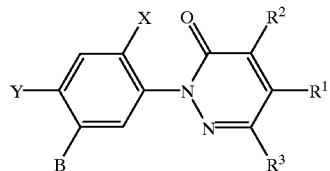

| Compound No. | X | Y | R³ | R¹ | R² | B |
|---|---|---|---|---|---|---|
| 1-629 | H | Cl | H | $CF_3$ | $CH_3$ | $CONHCH_3$ |
| 1-630 | H | Cl | H | $CF_3$ | $CH_3$ | $CON(C_2H_5)_2$ |
| 1-631 | H | Cl | H | $CF_3$ | $CH_3$ | $CONHC_2H_5$ |
| 1-632 | H | Cl | H | $CF_3$ | $CH_3$ | $COCH_3$ |
| 1-633 | H | Cl | H | $CF_3$ | $CH_3$ | $COC_2H_5$ |
| 1-634 | H | Cl | H | $CF_3$ | $CH_3$ | $COCH_2Cl$ |
| 1-635 | H | Cl | H | $CF_3$ | $CH_3$ | CHO |
| 1-636 | H | Cl | H | $CF_3$ | $CH_3$ | $CH=CHCOOCH_3$ |
| 1-637 | H | Cl | H | $CF_3$ | $CH_3$ | $CH=CHCOOC_2H_5$ |
| 1-638 | H | Cl | H | $CF_3$ | $CH_3$ | $CH_2CH_2COOCH_3$ |
| 1-639 | H | Cl | H | $CF_3$ | $CH_3$ | $CH_2CH_2COOC_2H_5$ |
| 1-640 | F | Cl | H | $CF_3$ | $CH_3$ | COOH |
| 1-641 | F | Cl | H | $CF_3$ | $CH_3$ | $COOCH_3$ |
| 1-642 | F | Cl | H | $CF_3$ | $CH_3$ | $COOC_2H_5$ |
| 1-643 | F | Cl | H | $CF_3$ | $CH_3$ | $COO^nC_3H_7$ |
| 1-644 | F | Cl | H | $CF_3$ | $CH_3$ | $COO^nC_4H_9$ |
| 1-645 | F | Cl | H | $CF_3$ | $CH_3$ | $COO^nC_5H_{11}$ |
| 1-646 | F | Cl | H | $CF_3$ | $CH_3$ | $COO^iC_3H_7$ |
| 1-647 | F | Cl | H | $CF_3$ | $CH_3$ | $COOCH_2CH_2Cl$ |
| 1-648 | F | Cl | H | $CF_3$ | $CH_3$ | $COOCH_2CH_2Br$ |
| 1-649 | F | Cl | H | $CF_3$ | $CH_3$ | $CON(CH_3)_2$ |
| 1-650 | F | Cl | H | $CF_3$ | $CH_3$ | $CONHCH_3$ |
| 1-651 | F | Cl | H | $CF_3$ | $CH_3$ | $CON(C_2H_5)_2$ |
| 1-652 | F | Cl | H | $CF_3$ | $CH_3$ | $CONHC_2H_5$ |
| 1-653 | F | Cl | H | $CF_3$ | $CH_3$ | $COCH_3$ |
| 1-654 | F | Cl | H | $CF_3$ | $CH_3$ | $COC_2H_5$ |
| 1-655 | F | Cl | H | $CF_3$ | $CH_3$ | $COCH_2Cl$ |
| 1-656 | F | Cl | H | $CF_3$ | $CH_3$ | CHO |
| 1-657 | F | Cl | H | $CF_3$ | $CH_3$ | $CH=CHCOOCH_3$ |
| 1-658 | F | Cl | H | $CF_3$ | $CH_3$ | $CH=CHCOOC_2H_5$ |
| 1-659 | F | Cl | H | $CF_3$ | $CH_3$ | $CH_2CH_2COOCH_3$ |
| 1-660 | F | Cl | H | $CF_3$ | $CH_3$ | $CH_2CH_2COOC_2H_5$ |
| 1-661 | Cl | Cl | H | $CF_2Cl$ | H | H |
| 1-662 | H | F | H | $CF_2Cl$ | H | $NO_2$ |
| 1-663 | H | Cl | H | $CF_2Cl$ | H | $NO_2$ |
| 1-664 | H | Br | H | $CF_2Cl$ | H | $NO_2$ |
| 1-665 | F | F | H | $CF_2Cl$ | H | $NO_2$ |
| 1-666 | F | Cl | H | $CF_2Cl$ | H | $NO_2$ |
| 1-667 | F | Br | H | $CF_2Cl$ | H | $NO_2$ |
| 1-668 | H | F | H | $CF_2Cl$ | H | $NH_2$ |
| 1-669 | H | Cl | H | $CF_2Cl$ | H | $NH_2$ |
| 1-670 | H | Br | H | $CF_2Cl$ | H | $NH_2$ |
| 1-671 | F | F | H | $CF_2Cl$ | H | $NH_2$ |
| 1-672 | F | Cl | H | $CF_2Cl$ | H | $NH_2$ |
| 1-673 | F | Br | H | $CF_2Cl$ | H | $NH_2$ |
| 1-674 | H | F | H | $CF_2Cl$ | H | OH |
| 1-675 | H | Cl | H | $CF_2Cl$ | H | OH |
| 1-676 | H | Br | H | $CF_2Cl$ | H | OH |
| 1-677 | F | F | H | $CF_2Cl$ | H | OH |
| 1-678 | F | Cl | H | $CF_2Cl$ | H | OH |
| 1-679 | F | Br | H | $CF_2Cl$ | H | OH |
| 1-680 | H | Cl | H | $CF_2Cl$ | H | $NHCH_3$ |
| 1-681 | H | Cl | H | $CF_2Cl$ | H | $NHC_2H_5$ |
| 1-682 | H | Cl | H | $CF_2Cl$ | H | $NHCH_2CH=CH_2$ |
| 1-683 | H | Cl | H | $CF_2Cl$ | H | $NHCH_2C\equiv CH$ |
| 1-684 | H | Cl | H | $CF_2Cl$ | H | $NHCH(CH_3)C\equiv CH$ |
| 1-685 | H | Cl | H | $CF_2Cl$ | H | $NHSO_2CH_3$ |
| 1-686 | H | Cl | H | $CF_2Cl$ | H | $NHSO_2C_2H_5$ |
| 1-687 | H | Cl | H | $CF_2Cl$ | H | $NHSO_2CH_2Cl$ |
| 1-688 | H | Cl | H | $CF_2Cl$ | H | $NHSO_2CF_3$ |
| 1-689 | H | Cl | H | $CF_2Cl$ | H | $N(CH_3)SO_2CH_3$ |
| 1-690 | H | Cl | H | $CF_2Cl$ | H | $N(CH_2C\equiv CH)SO_2CH_3$ |
| 1-691 | H | Cl | H | $CF_2Cl$ | H | $NHCOOCH_3$ |
| 1-692 | H | Cl | H | $CF_2Cl$ | H | $NHCOOC_2H_5$ |

TABLE 1-continued

Compounds of the formula:

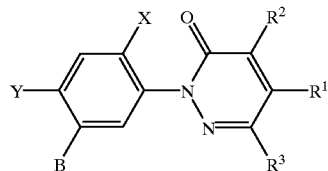

| Compound No. | X | Y | $R^3$ | $R^1$ | $R^2$ | B |
|---|---|---|---|---|---|---|
| 1-693 | H | Cl | H | $CF_2Cl$ | H | $NHCOO^nC_3H_7$ |
| 1-694 | H | Cl | H | $CF_2Cl$ | H | $NHCOO^iC_3H_7$ |
| 1-695 | H | Cl | H | $CF_2Cl$ | H | $NHCOO^nC_4H_9$ |
| 1-696 | H | Cl | H | $CF_2Cl$ | H | $NHCOO^nC_5H_{11}$ |
| 1-697 | H | Cl | H | $CF_2Cl$ | H | $NHCH_2COOCH_3$ |
| 1-698 | H | Cl | H | $CF_2Cl$ | H | $NHCH_2COOC_2H_5$ |
| 1-699 | H | Cl | H | $CF_2Cl$ | H | $NHCH_2COO^nC_3H_7$ |
| 1-700 | H | Cl | H | $CF_2Cl$ | H | $NHCH_2COO^nC_4H_9$ |
| 1-701 | H | Cl | H | $CF_2Cl$ | H | $NHCH_2COO^nC_5H_{11}$ |
| 1-702 | H | Cl | H | $CF_2Cl$ | H | $NHCH_2COO^iC_3H_7$ |
| 1-703 | H | Cl | H | $CF_2Cl$ | H | $NHCH_2COO^cC_5H_9$ |
| 1-704 | H | Cl | H | $CF_2Cl$ | H | $NHCH_2COO^cC_5H_{11}$ |
| 1-705 | H | Cl | H | $CF_2Cl$ | H | $NHCH(CH_3)COOCH_3$ |
| 1-706 | H | Cl | H | $CF_2Cl$ | H | $NHCH(CH_3)COOC_2H_5$ |
| 1-707 | H | Cl | H | $CF_2Cl$ | H | $NHCH(CH_3)COO^nC_3H_7$ |
| 1-708 | H | Cl | H | $CF_2Cl$ | H | $NHCH(CH_3)COO^nC_4H_9$ |
| 1-709 | H | Cl | H | $CF_2Cl$ | H | $NHCH(CH_3)COO^nC_5H_{11}$ |
| 1-710 | H | Cl | H | $CF_2Cl$ | H | $NHCH(CH_3)COO^iC_3H_7$ |
| 1-711 | H | Cl | H | $CF_2Cl$ | H | $NHCH(CH_3)COO^cC_5H_9$ |
| 1-712 | H | Cl | H | $CF_2Cl$ | H | $NHCH(CH_3)COO^cC_6H_{11}$ |
| 1-713 | F | Cl | H | $CF_2Cl$ | H | $NHCH_3$ |
| 1-714 | F | Cl | H | $CF_2Cl$ | H | $NHC_2H_5$ |
| 1-715 | F | Cl | H | $CF_2Cl$ | H | $NHCH_2CH{=}CH_2$ |
| 1-716 | F | Cl | H | $CF_2Cl$ | H | $NHCH_2C{\equiv}CH$ |
| 1-717 | F | Cl | H | $CF_2Cl$ | H | $NHCH(CH_3)C{\equiv}CH$ |
| 1-718 | F | Cl | H | $CF_2Cl$ | H | $NHSO_2CH_3$ |
| 1-719 | F | Cl | H | $CF_2Cl$ | H | $NHSO_2C_2H_5$ |
| 1-720 | F | Cl | H | $CF_2Cl$ | H | $NHSO_2CH_2Cl$ |
| 1-721 | F | Cl | H | $CF_2Cl$ | H | $NHSO_2CF_3$ |
| 1-722 | F | Cl | H | $CF_2Cl$ | H | $N(CH_3)SO_2CH_3$ |
| 1-723 | F | Cl | H | $CF_2Cl$ | H | $N(CH_2C{\equiv}CH)SO_2CH_3$ |
| 1-724 | F | Cl | H | $CF_2Cl$ | H | $NHCOOCH_3$ |
| 1-725 | F | Cl | H | $CF_2Cl$ | H | $NHCOOC_2H_5$ |
| 1-726 | F | Cl | H | $CF_2Cl$ | H | $NHCOO^nC_3H_7$ |
| 1-727 | F | Cl | H | $CF_2Cl$ | H | $NHCOO^iC_3H_7$ |
| 1-728 | F | Cl | H | $CF_2Cl$ | H | $NHCOO^nC_4H_9$ |
| 1-729 | F | Cl | H | $CF_2Cl$ | H | $NHCOO^nC_5H_{11}$ |
| 1-730 | F | Cl | H | $CF_2Cl$ | H | $NHCH_2COOCH_3$ |
| 1-731 | F | Cl | H | $CF_2Cl$ | H | $NHCH_2COOC_2H_5$ |
| 1-732 | F | Cl | H | $CF_2Cl$ | H | $NHCH_2COO^nC_3H_7$ |
| 1-733 | F | Cl | H | $CF_2Cl$ | H | $NHCH_2COO^nC_4H_9$ |
| 1-734 | F | Cl | H | $CF_2Cl$ | H | $NHCH_2COO^nC_5H_{11}$ |
| 1-735 | F | Cl | H | $CF_2Cl$ | H | $NHCH_2COO^iC_3H_7$ |
| 1-736 | F | Cl | H | $CF_2Cl$ | H | $NHCH_2COO^cC_5H_9$ |
| 1-737 | F | Cl | H | $CF_2Cl$ | H | $NHCH_2COO^cC_5H_{11}$ |
| 1-738 | F | Cl | H | $CF_2Cl$ | H | $NHCH(CH_3)COOCH_3$ |
| 1-739 | F | Cl | H | $CF_2Cl$ | H | $NHCH(CH_3)COOC_2H_5$ |
| 1-740 | F | Cl | H | $CF_2Cl$ | H | $NHCH(CH_3)COO^nC_3H_7$ |
| 1-741 | F | Cl | H | $CF_2Cl$ | H | $NHCH(CH_3)COO^nC_4H_9$ |
| 1-742 | F | Cl | H | $CF_2Cl$ | H | $NHCH(CH_3)COO^nC_5H_{11}$ |
| 1-743 | F | Cl | H | $CF_2Cl$ | H | $NHCH(CH_3)COO^iC_3H_7$ |
| 1-744 | F | Cl | H | $CF_2Cl$ | H | $NHCH(CH_3)COO^cC_5H_9$ |
| 1-745 | F | Cl | H | $CF_2Cl$ | H | $NHCH(CH_3)COO^cC_6H_{11}$ |
| 1-746 | H | Cl | H | $CF_2Cl$ | H | $OCH_3$ |
| 1-747 | H | Cl | H | $CF_2Cl$ | H | $OC_2H_5$ |
| 1-748 | H | Cl | H | $CF_2Cl$ | H | $O^iC_3H_7$ |
| 1-749 | H | Cl | H | $CF_2Cl$ | H | $O^nC_3H_7$ |
| 1-750 | H | Cl | H | $CF_2Cl$ | H | $OCH_2CH_2Cl$ |
| 1-751 | H | Cl | H | $CF_2Cl$ | H | $OCF_2CF_2H$ |
| 1-752 | H | Cl | H | $CF_2Cl$ | H | $O^cC_5H_9$ |
| 1-753 | H | Cl | H | $CF_2Cl$ | H | $O^cC_6H_{11}$ |
| 1-754 | H | Cl | H | $CF_2Cl$ | H | $OCH_2CH{=}CH_2$ |
| 1-755 | H | Cl | H | $CF_2Cl$ | H | $OCH_2CCl{=}CH_2$ |
| 1-756 | H | Cl | H | $CF_2Cl$ | H | $OCH_2CCl{=}CHCl$ |

TABLE 1-continued

Compounds of the formula:

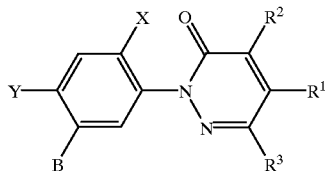

| Compound No. | X | Y | R³ | R¹ | R² | B |
|---|---|---|---|---|---|---|
| 1-757 | H | Cl | H | $CF_2Cl$ | H | $OCH(CH_3)CH=CH_2$ |
| 1-758 | H | Cl | H | $CF_2Cl$ | H | $OCH_2C\equiv CH$ |
| 1-759 | H | Cl | H | $CF_2Cl$ | H | $OCH(CH_3)C\equiv CH$ |
| 1-760 | H | Cl | H | $CF_2Cl$ | H | $OCH_2C\equiv CBr$ |
| 1-761 | H | Cl | H | $CF_2Cl$ | H | $OCH_2C\equiv CCl$ |
| 1-762 | H | Cl | H | $CF_2Cl$ | H | $OCH_2C\equiv CCH_2Cl$ |
| 1-763 | H | Cl | H | $CF_2Cl$ | H | $OCH_2CN$ |
| 1-764 | H | Cl | H | $CF_2Cl$ | H | $OCH_2OCH_3$ |
| 1-765 | H | Cl | H | $CF_2Cl$ | H | $OCH_2OC_2H_5$ |
| 1-766 | H | Cl | H | $CF_2Cl$ | H | $OCH_2SCH_3$ |
| 1-767 | H | Cl | H | $CF_2Cl$ | H | $OCH_2COOCH_3$ |
| 1-768 | H | Cl | H | $CF_2Cl$ | H | $OCH_2COOC_2H_5$ |
| 1-769 | H | Cl | H | $CF_2Cl$ | H | $OCH_2COO^nC_3H_7$ |
| 1-770 | H | Cl | H | $CF_2Cl$ | H | $OCH_2COO^nC_4H_9$ |
| 1-771 | H | Cl | H | $CF_2Cl$ | H | $OCH_2COO^nC_5H_{11}$ |
| 1-772 | H | Cl | H | $CF_2Cl$ | H | $OCH_2COO^iC_3H_7$ |
| 1-773 | H | Cl | H | $CF_2Cl$ | H | $OCH_2COO^cC_5H_9$ |
| 1-774 | H | Cl | H | $CF_2Cl$ | H | $OCH_2COO^cC_6H_{11}$ |
| 1-775 | H | Cl | H | $CF_2Cl$ | H | $OCH(CH_3)COOCH_3$ |
| 1-776 | H | Cl | H | $CF_2Cl$ | H | $OCH(CH_3)COOC_2H_5$ |
| 1-777 | H | Cl | H | $CF_2Cl$ | H | $OCH(CH_3)COO^nC_3H_7$ |
| 1-778 | H | Cl | H | $CF_2Cl$ | H | $OCH(CH_3)COO^nC_4H_9$ |
| 1-779 | H | Cl | H | $CF_2Cl$ | H | $OCH(CH_3)COO^nC_5H_{11}$ |
| 1-780 | H | Cl | H | $CF_2Cl$ | H | $OCH(CH_3)COO^iC_3H_7$ |
| 1-781 | H | Cl | H | $CF_2Cl$ | H | $OCH(CH_3)COO^cC_5H_9$ |
| 1-782 | H | Cl | H | $CF_2Cl$ | H | $OCH(CH_3)COO^cC_6H_{11}$ |
| 1-783 | H | Cl | H | $CF_2Cl$ | H | $OCH_2CON(CH_3)_2$ |
| 1-784 | H | Cl | H | $CF_2Cl$ | H | $OCH_2CON(C_2H_5)_2$ |
| 1-785 | H | Cl | H | $CF_2Cl$ | H | $OCH_2CON(CH_3)C_2H_5$ |
| 1-786 | H | Cl | H | $CF_2Cl$ | H | $OCH(CH_3)CON(CH_3)_2$ |
| 1-787 | H | Cl | H | $CF_2Cl$ | H | $OCH(CH_3)CON(C_2H_5)_2$ |
| 1-788 | H | Cl | H | $CF_2Cl$ | H | $OCH(CH_3)CON(CH_3)C_2H_5$ |
| 1-789 | H | Cl | H | $CF_2Cl$ | H | $OCH_2COON(CH_3)_2$ |
| 1-790 | H | Cl | H | $CF_2Cl$ | H | $OCH_2COON(C_2H_5)_2$ |
| 1-791 | H | Cl | H | $CF_2Cl$ | H | $OCH(CH_3)COON(CH_3)_2$ |
| 1-792 | H | Cl | H | $CF_2Cl$ | H | $OCH(CH_3)COON(C_2H_5)_2$ |
| 1-793 | F | Cl | H | $CF_2Cl$ | H | $OCH_3$ |
| 1-794 | F | Cl | H | $CF_2Cl$ | H | $OC_2H_5$ |
| 1-795 | F | Cl | H | $CF_2Cl$ | H | $O^iC_3H_7$ |
| 1-796 | F | Cl | H | $CF_2Cl$ | H | $O^nC_3H_7$ |
| 1-797 | F | Cl | H | $CF_2Cl$ | H | $OCH_2CH_2Cl$ |
| 1-798 | F | Cl | H | $CF_2Cl$ | H | $OCF_2CF_2H$ |
| 1-799 | F | Cl | H | $CF_2Cl$ | H | $O^cC_5H_9$ |
| 1-800 | F | Cl | H | $CF_2Cl$ | H | $O^cC_6H_{11}$ |
| 1-801 | F | Cl | H | $CF_2Cl$ | H | $OCH_2CH=CH_2$ |
| 1-802 | F | Cl | H | $CF_2Cl$ | H | $OCH_2CCl=CH_2$ |
| 1-803 | F | Cl | H | $CF_2Cl$ | H | $OCH_2CCl=CHCl$ |
| 1-804 | F | Cl | H | $CF_2Cl$ | H | $OCH(CH_3)CH=CH_2$ |
| 1-805 | F | Cl | H | $CF_2Cl$ | H | $OCH_2C\equiv CH$ |
| 1-806 | F | Cl | H | $CF_2Cl$ | H | $OCH(CH_3)C\equiv CH$ |
| 1-807 | F | Cl | H | $CF_2Cl$ | H | $OCH_2C\equiv CBr$ |
| 1-808 | F | Cl | H | $CF_2Cl$ | H | $OCH_2C\equiv CCl$ |
| 1-809 | F | Cl | H | $CF_2Cl$ | H | $OCH_2C\equiv CCH_2Cl$ |
| 1-810 | F | Cl | H | $CF_2Cl$ | H | $OCH_2CN$ |
| 1-811 | F | Cl | H | $CF_2Cl$ | H | $OCH_2OCH_3$ |
| 1-812 | F | Cl | H | $CF_2Cl$ | H | $OCH_2OC_2H_5$ |
| 1-813 | F | Cl | H | $CF_2Cl$ | H | $OCH_2SCH_3$ |
| 1-814 | F | Cl | H | $CF_2Cl$ | H | $OCH_2COOCH_3$ |
| 1-815 | F | Cl | H | $CF_2Cl$ | H | $OCH_2COOC_2H_5$ |
| 1-816 | F | Cl | H | $CF_2Cl$ | H | $OCH_2COO^nC_3H_7$ |
| 1-817 | F | Cl | H | $CF_2Cl$ | H | $OCH_2COO^nC_4H_9$ |
| 1-818 | F | Cl | H | $CF_2Cl$ | H | $OCH_2COO^nC_5H_{11}$ |
| 1-819 | F | Cl | H | $CF_2Cl$ | H | $OCH_2COO^iC_3H_7$ |
| 1-820 | F | Cl | H | $CF_2Cl$ | H | $OCH_2COO^cC_5H_9$ |

TABLE 1-continued

Compounds of the formula:

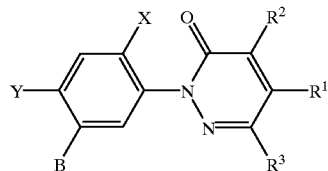

| Compound No. | X | Y | $R^3$ | $R^1$ | $R^2$ | B |
|---|---|---|---|---|---|---|
| 1-821 | F | Cl | H | $CF_2Cl$ | H | $OCH_2COO^cC_6H_{11}$ |
| 1-822 | F | Cl | H | $CF_2Cl$ | H | $OCH(CH_3)COOCH_3$ |
| 1-823 | F | Cl | H | $CF_2Cl$ | H | $OCH(CH_3)COOC_2H_5$ |
| 1-824 | F | Cl | H | $CF_2Cl$ | H | $OCH(CH_3)COO^nC_3H_7$ |
| 1-825 | F | Cl | H | $CF_2Cl$ | H | $OCH(CH_3)COO^nC_4H_9$ |
| 1-826 | F | Cl | H | $CF_2Cl$ | H | $OCH(CH_3)COO^nC_5H_{11}$ |
| 1-827 | F | Cl | H | $CF_2Cl$ | H | $OCH(CH_3)COO^iC_3H_7$ |
| 1-828 | F | Cl | H | $CF_2Cl$ | H | $OCH(CH_3)COO^cC_5H_9$ |
| 1-829 | F | Cl | H | $CF_2Cl$ | H | $OCH(CH_3)COO^cC_6H_{11}$ |
| 1-830 | F | Cl | H | $CF_2Cl$ | H | $OCH_2CON(CH_3)_2$ |
| 1-831 | F | Cl | H | $CF_2Cl$ | H | $OCH_2CON(C_2H_5)_2$ |
| 1-832 | F | Cl | H | $CF_2Cl$ | H | $OCH_2CON(CH_3)C_2H_5$ |
| 1-833 | F | Cl | H | $CF_2Cl$ | H | $OCH(CH_3)CON(CH_3)_2$ |
| 1-834 | F | Cl | H | $CF_2Cl$ | H | $OCH(CH_3)CON(C_2H_5)_2$ |
| 1-835 | F | Cl | H | $CF_2Cl$ | H | $OCH(CH_3)CON(CH_3)C_2H_5$ |
| 1-836 | F | Cl | H | $CF_2Cl$ | H | $OCH_2COON(CH_3)_2$ |
| 1-837 | F | Cl | H | $CF_2Cl$ | H | $OCH_2COON(C_2H_5)_2$ |
| 1-838 | F | Cl | H | $CF_2Cl$ | H | $OCH(CH_3)COON(CH_3)_2$ |
| 1-839 | F | Cl | H | $CF_2Cl$ | H | $OCH(CH_3)COON(C_2H_5)_2$ |
| 1-840 | H | F | H | $CF_2Cl$ | H | SH |
| 1-841 | H | Cl | H | $CF_2Cl$ | H | SH |
| 1-842 | H | Br | H | $CF_2Cl$ | H | SH |
| 1-843 | F | F | H | $CF_2Cl$ | H | SH |
| 1-844 | F | Cl | H | $CF_2Cl$ | H | SH |
| 1-845 | F | Br | H | $CF_2Cl$ | H | SH |
| 1-846 | H | Cl | H | $CF_2Cl$ | H | $SCH_3$ |
| 1-847 | H | Cl | H | $CF_2Cl$ | H | $SC_2H_5$ |
| 1-848 | H | Cl | H | $CF_2Cl$ | H | $S^iC_3H_7$ |
| 1-849 | H | Cl | H | $CF_2Cl$ | H | $SCH_2CH_2Cl$ |
| 1-850 | H | Cl | H | $CF_2Cl$ | H | $S^cC_5H_9$ |
| 1-851 | H | Cl | H | $CF_2Cl$ | H | $S^cC_6H_{11}$ |
| 1-852 | H | Cl | H | $CF_2Cl$ | H | $SCH_2CH=CH_2$ |
| 1-853 | H | Cl | H | $CF_2Cl$ | H | $SCH_2CCl=CH_2$ |
| 1-854 | H | Cl | H | $CF_2Cl$ | H | $SCH_2CCl=CHCl$ |
| 1-855 | H | Cl | H | $CF_2Cl$ | H | $SCH(CH_3)CH=CH_2$ |
| 1-856 | H | Cl | H | $CF_2Cl$ | H | $SCH_2C\equiv CH$ |
| 1-857 | H | Cl | H | $CF_2Cl$ | H | $SCH(CH_3)C\equiv CH$ |
| 1-858 | H | Cl | H | $CF_2Cl$ | H | $SCH_2COOCH_3$ |
| 1-859 | H | Cl | H | $CF_2Cl$ | H | $SCH_2COOC_2H_5$ |
| 1-860 | H | Cl | H | $CF_2Cl$ | H | $SCH_2COO^nC_3H_7$ |
| 1-861 | H | Cl | H | $CF_2Cl$ | H | $SCH_2COO^nC_4H_9$ |
| 1-862 | H | Cl | H | $CF_2Cl$ | H | $SCH_2COO^nC_5H_{11}$ |
| 1-863 | H | Cl | H | $CF_2Cl$ | H | $SCH_2COO^iC_3H_7$ |
| 1-864 | H | Cl | H | $CF_2Cl$ | H | $SCH_2COO^cC_5H_9$ |
| 1-865 | H | Cl | H | $CF_2Cl$ | H | $SCH_2COO^cC_6H_{11}$ |
| 1-866 | H | Cl | H | $CF_2Cl$ | H | $SCH(CH_3)COOCH_3$ |
| 1-867 | H | Cl | H | $CF_2Cl$ | H | $SCH(CH_3)COOC_2H_5$ |
| 1-868 | H | Cl | H | $CF_2Cl$ | H | $SCH(CH_3)COO^nC_3H_7$ |
| 1-869 | H | Cl | H | $CF_2Cl$ | H | $SCH(CH_3)COO^nC_4H_9$ |
| 1-870 | H | Cl | H | $CF_2Cl$ | H | $SCH(CH_3)COO^nC_5H_{11}$ |
| 1-871 | H | Cl | H | $CF_2Cl$ | H | $SCH(CH_3)COO^iC_3H_7$ |
| 1-872 | H | Cl | H | $CF_2Cl$ | H | $SCH(CH_3)COO^cC_5H_9$ |
| 1-873 | H | Cl | H | $CF_2Cl$ | H | $SCH(CH_3)COO^cC_6H_{11}$ |
| 1-874 | H | Cl | H | $CF_2Cl$ | H | $SCH_2CON(CH_3)_2$ |
| 1-875 | H | Cl | H | $CF_2Cl$ | H | $SCH_2CON(C_2H_5)_2$ |
| 1-876 | H | Cl | H | $CF_2Cl$ | H | $SCH_2CON$(tetramethylene) |
| 1-877 | H | Cl | H | $CF_2Cl$ | H | $SCH_2CON$(pentamethylene) |
| 1-878 | H | Cl | H | $CF_2Cl$ | H | $SCH_2CON$ (ethyleneoxyethylene) |
| 1-879 | H | Cl | H | $CF_2Cl$ | H | $SCH(CH_3)CON(CH_3)_2$ |
| 1-880 | H | Cl | H | $CF_2Cl$ | H | $SCH(CH_3)CON(C_2H_5)_2$ |
| 1-881 | H | Cl | H | $CF_2Cl$ | H | $SCH(CH_3)CON$ (tetramethylene) |
| 1-882 | H | Cl | H | $CF_2Cl$ | H | $SCH(CH_3)CON$ |

TABLE 1-continued

Compounds of the formula:

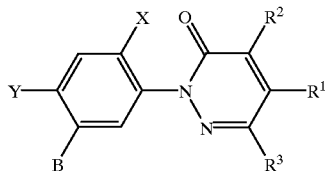

| Compound No. | X | Y | $R^3$ | $R^1$ | $R^2$ | B |
|---|---|---|---|---|---|---|
| | | | | | | (pentamethylene) |
| 1-883 | F | Cl | H | $CF_2Cl$ | H | $SCH_3$ |
| 1-884 | F | Cl | H | $CF_2Cl$ | H | $SC_2H_5$ |
| 1-885 | F | Cl | H | $CF_2Cl$ | H | $S^iC_3H_7$ |
| 1-886 | F | Cl | H | $CF_2Cl$ | H | $SCH_2CH_2Cl$ |
| 1-887 | F | Cl | H | $CF_2Cl$ | H | $S^cC_5H_9$ |
| 1-888 | F | Cl | H | $CF_2Cl$ | H | $S^cC_6H_{11}$ |
| 1-889 | F | Cl | H | $CF_2Cl$ | H | $SCH_2CH=CH_2$ |
| 1-890 | F | Cl | H | $CF_2Cl$ | H | $SCH_2CCl=CH_2$ |
| 1-891 | F | Cl | H | $CF_2Cl$ | H | $SCH_2CCl=CHCl$ |
| 1-892 | F | Cl | H | $CF_2Cl$ | H | $SCH(CH_3)CH=CH_2$ |
| 1-893 | F | Cl | H | $CF_2Cl$ | H | $SCH_2C\equiv CH$ |
| 1-894 | F | Cl | H | $CF_2Cl$ | H | $SCH(CH_3)C\equiv CH$ |
| 1-895 | F | Cl | H | $CF_2Cl$ | H | $SCH_2COOCH_3$ |
| 1-896 | F | Cl | H | $CF_2Cl$ | H | $SCH_2COOC_2H_5$ |
| 1-897 | F | Cl | H | $CF_2Cl$ | H | $SCH_2COO^nC_3H_7$ |
| 1-898 | F | Cl | H | $CF_2Cl$ | H | $SCH_2COO^nC_4H_9$ |
| 1-899 | F | Cl | H | $CF_2Cl$ | H | $SCH_2COO^nC_5H_{11}$ |
| 1-900 | F | Cl | H | $CF_2Cl$ | H | $SCH_2COO^iC_3H_7$ |
| 1-901 | F | Cl | H | $CF_2Cl$ | H | $SCH_2COO^cC_5H_9$ |
| 1-902 | F | Cl | H | $CF_2Cl$ | H | $SCH_2COO^cC_6H_{11}$ |
| 1-903 | F | Cl | H | $CF_2Cl$ | H | $SCH(CH_3)COOCH_3$ |
| 1-904 | F | Cl | H | $CF_2Cl$ | H | $SCH(CH_3)COOC_2H_5$ |
| 1-905 | F | Cl | H | $CF_2Cl$ | H | $SCH(CH_3)COO^nC_3H_7$ |
| 1-906 | F | Cl | H | $CF_2Cl$ | H | $SCH(CH_3)COO^nC_4H_9$ |
| 1-907 | F | Cl | H | $CF_2Cl$ | H | $SCH(CH_3)COO^nC_5H_{11}$ |
| 1-908 | F | Cl | H | $CF_2Cl$ | H | $SCH(CH_3)COO^iC_3H_7$ |
| 1-909 | F | Cl | H | $CF_2Cl$ | H | $SCH(CH_3)COO^cC_5H_9$ |
| 1-910 | F | Cl | H | $CF_2Cl$ | H | $SCH(CH_3)COO^cC_6H_{11}$ |
| 1-911 | F | Cl | H | $CF_2Cl$ | H | $SCH_2CON(CH_3)_2$ |
| 1-912 | F | Cl | H | $CF_2Cl$ | H | $SCH_2CON(C_2H_5)_2$ |
| 1-913 | F | Cl | H | $CF_2Cl$ | H | $SCH_2CON$(tetramethylene) |
| 1-914 | F | Cl | H | $CF_2Cl$ | H | $SCH_2CON$(pentamethylene) |
| 1-915 | F | Cl | H | $CF_2Cl$ | H | $SCH_2CON$ (ethyleneoxyethylene) |
| 1-916 | F | Cl | H | $CF_2Cl$ | H | $SCH(CH_3)CON(CH_3)_2$ |
| 1-917 | F | Cl | H | $CF_2Cl$ | H | $SCH(CH_3)CON(C_2H_5)_2$ |
| 1-918 | F | Cl | H | $CF_2Cl$ | H | $SCH(CH_3)CON$ (tetramethylene) |
| 1-919 | F | Cl | H | $CF_2Cl$ | H | $SCH(CH_3)CON$ (pentamethylene) |
| 1-920 | H | F | H | $CF_2Cl$ | H | $SO_2Cl$ |
| 1-921 | H | Cl | H | $CF_2Cl$ | H | $SO_2Cl$ |
| 1-922 | H | Br | H | $CF_2Cl$ | H | $SO_2Cl$ |
| 1-923 | F | F | H | $CF_2Cl$ | H | $SO_2Cl$ |
| 1-924 | F | Cl | H | $CF_2Cl$ | H | $SO_2Cl$ |
| 1-925 | F | Br | H | $CF_2Cl$ | H | $SO_2Cl$ |
| 1-926 | H | Cl | H | $CF_2Cl$ | H | $SO_2OCH_3$ |
| 1-927 | H | Cl | H | $CF_2Cl$ | H | $SO_2OC_2H_5$ |
| 1-928 | H | Cl | H | $CF_2Cl$ | H | $SO_2O^iC_3H_7$ |
| 1-929 | H | Cl | H | $CF_2Cl$ | H | $SO_2OCH_2CH=CH_2$ |
| 1-930 | F | Cl | H | $CF_2Cl$ | H | $SO_2OCH_3$ |
| 1-931 | F | Cl | H | $CF_2Cl$ | H | $SO_2OC_2H_5$ |
| 1-932 | F | Cl | H | $CF_2Cl$ | H | $SO_2O^iC_3H_7$ |
| 1-933 | F | Cl | H | $CF_2Cl$ | H | $SO_2OCH_2CH=CH_2$ |
| 1-934 | H | Cl | H | $CF_2Cl$ | H | $SO_2N(CH_3)_2$ |
| 1-935 | H | Cl | H | $CF_2Cl$ | H | $SO_2N(C_2H_5)_2$ |
| 1-936 | F | Cl | H | $CF_2Cl$ | H | $SO_2N(CH_3)_2$ |
| 1-937 | F | Cl | H | $CF_2Cl$ | H | $SO_2N(C_2H_5)_2$ |
| 1-938 | H | Cl | H | $CF_2Cl$ | H | $COOH$ |
| 1-939 | H | Cl | H | $CF_2Cl$ | H | $COOCH_3$ |
| 1-940 | H | Cl | H | $CF_2Cl$ | H | $COOC_2H_5$ |
| 1-941 | H | Cl | H | $CF_2Cl$ | H | $COO^nC_3H_7$ |
| 1-942 | H | Cl | H | $CF_2Cl$ | H | $COO^nC_4H_9$ |

TABLE 1-continued

Compounds of the formula:

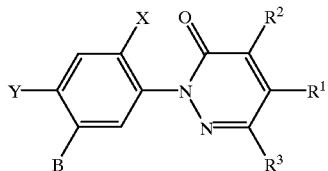

| Compound No. | X | Y | R³ | R¹ | R² | B |
|---|---|---|---|---|---|---|
| 1-943 | H | Cl | H | $CF_2Cl$ | H | $COO^nC_5H_{11}$ |
| 1-944 | H | Cl | H | $CF_2Cl$ | H | $COO^iC_3H_7$ |
| 1-945 | H | Cl | H | $CF_2Cl$ | H | $COOCH_2CH_2Cl$ |
| 1-946 | H | Cl | H | $CF_2Cl$ | H | $COOCH_2CH_2Br$ |
| 1-947 | H | Cl | H | $CF_2Cl$ | H | $CON(CH_3)_2$ |
| 1-948 | H | Cl | H | $CF_2Cl$ | H | $CONHCH_3$ |
| 1-949 | H | Cl | H | $CF_2Cl$ | H | $CON(C_2H_5)_2$ |
| 1-950 | H | Cl | H | $CF_2Cl$ | H | $CONHC_2H_5$ |
| 1-951 | H | Cl | H | $CF_2Cl$ | H | $COCH_3$ |
| 1-952 | H | Cl | H | $CF_2Cl$ | H | $COC_2H_5$ |
| 1-953 | H | Cl | H | $CF_2Cl$ | H | $COCH_2Cl$ |
| 1-954 | H | Cl | H | $CF_2Cl$ | H | CHO |
| 1-955 | H | Cl | H | $CF_2Cl$ | H | $CH=CHCOOCH_3$ |
| 1-956 | H | Cl | H | $CF_2Cl$ | H | $CH=CHCOOC_2H_5$ |
| 1-957 | H | Cl | H | $CF_2Cl$ | H | $CH_2CH_2COOCH_3$ |
| 1-958 | H | Cl | H | $CF_2Cl$ | H | $CH_2CH_2COOC_2H_5$ |
| 1-959 | F | Cl | H | $CF_2Cl$ | H | COOH |
| 1-960 | F | Cl | H | $CF_2Cl$ | H | $COOCH_3$ |
| 1-961 | F | Cl | H | $CF_2Cl$ | H | $COOC_2H_5$ |
| 1-962 | F | Cl | H | $CF_2Cl$ | H | $COO^nC_3H_7$ |
| 1-963 | F | Cl | H | $CF_2Cl$ | H | $COO^nC_4H_9$ |
| 1-964 | F | Cl | H | $CF_2Cl$ | H | $COO^nC_5H_{11}$ |
| 1-965 | F | Cl | H | $CF_2Cl$ | H | $COO^iC_3H_7$ |
| 1-966 | F | Cl | H | $CF_2Cl$ | H | $COOCH_2CH_2Cl$ |
| 1-967 | F | Cl | H | $CF_2Cl$ | H | $COOCH_2CH_2Br$ |
| 1-968 | F | Cl | H | $CF_2Cl$ | H | $CON(CH_3)_2$ |
| 1-969 | F | Cl | H | $CF_2Cl$ | H | $CONHCH_3$ |
| 1-970 | F | Cl | H | $CF_2Cl$ | H | $CON(C_2H_5)_2$ |
| 1-971 | F | Cl | H | $CF_2Cl$ | H | $CONHC_2H_5$ |
| 1-972 | F | Cl | H | $CF_2Cl$ | H | $COCH_3$ |
| 1-973 | F | Cl | H | $CF_2Cl$ | H | $COC_2H_5$ |
| 1-974 | F | Cl | H | $CF_2Cl$ | H | $COCH_2Cl$ |
| 1-975 | F | Cl | H | $CF_2Cl$ | H | CHO |
| 1-976 | F | Cl | H | $CF_2Cl$ | H | $CH=CHCOOCH_3$ |
| 1-977 | F | Cl | H | $CF_2Cl$ | H | $CH=CHCOOC_2H_5$ |
| 1-978 | F | Cl | H | $CF_2Cl$ | H | $CH_2CH_2COOCH_3$ |
| 1-979 | F | Cl | H | $CF_2Cl$ | H | $CH_2CH_2COOC_2H_5$ |
| 1-980 | H | F | H | $CF_3$ | H | $NO_2$ |
| 1-981 | H | Cl | H | $CF_3$ | H | $NO_2$ |
| 1-982 | H | Br | H | $CF_3$ | H | $NO_2$ |
| 1-983 | F | F | H | $CF_3$ | H | $NO_2$ |
| 1-984 | F | Cl | H | $CF_3$ | H | $NO_2$ |
| 1-985 | F | Br | H | $CF_3$ | H | $NO_2$ |
| 1-986 | H | F | H | $CF_3$ | H | $NH_2$ |
| 1-987 | H | Cl | H | $CF_3$ | H | $NH_2$ |
| 1-988 | H | Br | H | $CF_3$ | H | $NH_2$ |
| 1-989 | F | F | H | $CF_3$ | H | $NH_2$ |
| 1-990 | F | Cl | H | $CF_3$ | H | $NH_2$ |
| 1-991 | H | Cl | H | $CF_3$ | H | $NHCH(CH_3)COOCH_3$ |
| 1-992 | H | Cl | H | $CF_3$ | H | $NHCH(CH_3)COOC_2H_5$ |
| 1-993 | H | Cl | H | $CF_3$ | H | $NHCH(CH_3)COO^nC_3H_7$ |
| 1-994 | H | Cl | H | $CF_3$ | H | $NHCH(CH_3)COO^nC_4H_9$ |
| 1-995 | H | Cl | H | $CF_3$ | H | $NHCH(CH_3)COO^nC_5H_{11}$ |
| 1-996 | H | Cl | H | $CF_3$ | H | $NHCH(CH_3)COO^iC_3H_7$ |
| 1-997 | H | Cl | H | $CF_3$ | H | $NHCH(CH_3)COO^cC_4H_9$ |
| 1-998 | H | Cl | H | $CF_3$ | H | $NHCH(CH_3)COO^cC_6H_{11}$ |
| 1-999 | F | Cl | H | $CF_3$ | H | $NHCH_3$ |
| 1-1000 | F | Cl | H | $CF_3$ | H | $NHC_2H_5$ |
| 1-1001 | F | Cl | H | $CF_3$ | H | $NHCH_2CH=CH_2$ |
| 1-1002 | F | Cl | H | $CF_3$ | H | $NHCH_2C\equiv CH$ |
| 1-1003 | F | Cl | H | $CF_3$ | H | $NHCH(CH_3)C\equiv CH$ |
| 1-1004 | F | Cl | H | $CF_3$ | H | $NHSO_2CH_3$ |
| 1-1005 | F | Cl | H | $CF_3$ | H | $NHSO_2C_2H_5$ |
| 1-1006 | F | Cl | H | $CF_3$ | H | $NHSO_2CH_2Cl$ |

TABLE 1-continued

Compounds of the formula:

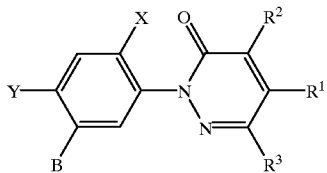

| Compound No. | X | Y | $R^3$ | $R^1$ | $R^2$ | B |
|---|---|---|---|---|---|---|
| 1-1007 | F | Cl | H | $CF_3$ | H | $NHSO_2CF_3$ |
| 1-1008 | F | Cl | H | $CF_3$ | H | $N(CH_3)SO_2CH_3$ |
| 1-1009 | F | Cl | H | $CF_3$ | H | $N(CH_2C\equiv CH)SO_2CH_3$ |
| 1-1010 | F | Cl | H | $CF_3$ | H | $NHCOOCH_3$ |
| 1-1011 | F | Cl | H | $CF_3$ | H | $NHCOOC_2H_5$ |
| 1-1012 | F | Cl | H | $CF_3$ | H | $NHCOO^nC_3H_7$ |
| 1-1013 | F | Cl | H | $CF_3$ | H | $NHCOO^iC_3H_7$ |
| 1-1014 | F | Cl | H | $CF_3$ | H | $NHCOO^nC_4H_9$ |
| 1-1015 | F | Cl | H | $CF_3$ | H | $NHCOO^nC_5H_{11}$ |
| 1-1016 | F | Cl | H | $CF_3$ | H | $NHCH_2COOCH_3$ |
| 1-1017 | F | Cl | H | $CF_3$ | H | $NHCH_2COOC_2H_5$ |
| 1-1018 | F | Cl | H | $CF_3$ | H | $NHCH_2COO^nC_3H_7$ |
| 1-1019 | F | Cl | H | $CF_3$ | H | $NHCH_2COO^nC_4H_9$ |
| 1-1020 | F | Cl | H | $CF_3$ | H | $NHCH_2COO^nC_5H_{11}$ |
| 1-1021 | F | Cl | H | $CF_3$ | H | $NHCH_2COO^iC_3H_7$ |
| 1-1022 | F | Cl | H | $CF_3$ | H | $NHCH_2COO^cC_5H_9$ |
| 1-1023 | F | Br | H | $CF_3$ | H | $NH_2$ |
| 1-1024 | H | F | H | $CF_3$ | H | OH |
| 1-1025 | H | Cl | H | $CF_3$ | H | OH |
| 1-1026 | H | Br | H | $CF_3$ | H | OH |
| 1-1027 | F | F | H | $CF_3$ | H | OH |
| 1-1028 | F | Cl | H | $CF_3$ | H | OH |
| 1-1029 | F | Br | H | $CF_3$ | H | OH |
| 1-1030 | H | Cl | H | $CF_3$ | H | $NHCH_3$ |
| 1-1031 | H | Cl | H | $CF_3$ | H | $NHC_2H_5$ |
| 1-1032 | H | Cl | H | $CF_3$ | H | $NHCH_2CH=CH_2$ |
| 1-1033 | H | Cl | H | $CF_3$ | H | $NHCH_2C\equiv CH$ |
| 1-1034 | H | Cl | H | $CF_3$ | H | $NHCH(CH_3)C\equiv CH$ |
| 1-1035 | H | Cl | H | $CF_3$ | H | $NHSO_2CH_3$ |
| 1-1036 | H | Cl | H | $CF_3$ | H | $NHSO_2C_2H_5$ |
| 1-1037 | H | Cl | H | $CF_3$ | H | $NHSO_2CH_2Cl$ |
| 1-1038 | H | Cl | H | $CF_3$ | H | $NHSO_2CF_3$ |
| 1-1039 | H | Cl | H | $CF_3$ | H | $N(CH_3)SO_2CH_3$ |
| 1-1040 | H | Cl | H | $CF_3$ | H | $N(CH_2C\equiv CH)SO_2CH_3$ |
| 1-1041 | H | Cl | H | $CF_3$ | H | $NHCOOCH_3$ |
| 1-1042 | H | Cl | H | $CF_3$ | H | $NHCOOC_2H_5$ |
| 1-1043 | H | Cl | H | $CF_3$ | H | $NHCOO^nC_3H_7$ |
| 1-1044 | H | Cl | H | $CF_3$ | H | $NHCOO^iC_3H_7$ |
| 1-1045 | H | Cl | H | $CF_3$ | H | $NHCOO^nC_4H_9$ |
| 1-1046 | H | Cl | H | $CF_3$ | H | $NHCOO^nC_5H_{11}$ |
| 1-1047 | H | Cl | H | $CF_3$ | H | $NHCH_2COOCH_3$ |
| 1-1048 | H | Cl | H | $CF_3$ | H | $NHCH_2COOC_2H_5$ |
| 1-1049 | H | Cl | H | $CF_3$ | H | $NHCH_2COO^nC_3H_7$ |
| 1-1050 | H | Cl | H | $CF_3$ | H | $NHCH_2COO^nC_4H_9$ |
| 1-1051 | H | Cl | H | $CF_3$ | H | $NHCH_2COO^nC_5H_{11}$ |
| 1-1052 | H | Cl | H | $CF_3$ | H | $NHCH_2COO^iC_3H_7$ |
| 1-1053 | H | Cl | H | $CF_3$ | H | $NHCH_2COO^cC_5H_9$ |
| 1-1054 | H | Cl | H | $CF_3$ | H | $NHCH_2COO^cC_5H_{11}$ |
| 1-1055 | F | Cl | H | $CF_3$ | H | $NHCH_2COO^cC_6H_{11}$ |
| 1-1056 | F | Cl | H | $CF_3$ | H | $NHCH(CH_3)COOCH_3$ |
| 1-1057 | F | Cl | H | $CF_3$ | H | $NHCH(CH_3)COOC_2H_5$ |
| 1-1058 | F | Cl | H | $CF_3$ | H | $NHCH(CH_3)COO^nC_3H_7$ |
| 1-1059 | F | Cl | H | $CF_3$ | H | $NHCH(CH_3)COO^nC_4H_9$ |
| 1-1060 | F | Cl | H | $CF_3$ | H | $NHCH(CH_3)COO^nC_5H_{11}$ |
| 1-1061 | F | Cl | H | $CF_3$ | H | $NHCH(CH_3)COO^iC_3H_7$ |
| 1-1062 | F | Cl | H | $CF_3$ | H | $NHCH(CH_3)COO^cC_5H_9$ |
| 1-1063 | F | Cl | H | $CF_3$ | H | $NHCH(CH_3)COO^cC_6H_{11}$ |
| 1-1064 | H | Cl | H | $CF_3$ | H | $OCH_3$ |
| 1-1065 | H | Cl | H | $CF_3$ | H | $OC_2H_5$ |
| 1-1066 | H | Cl | H | $CF_3$ | H | $O^iC_3H_7$ |
| 1-1067 | H | Cl | H | $CF_3$ | H | $O^nC_3H_7$ |
| 1-1068 | H | Cl | H | $CF_3$ | H | $OCH_2CH_2Cl$ |
| 1-1069 | H | Cl | H | $CF_3$ | H | $OCF_2CF_2H$ |
| 1-1070 | H | Cl | H | $CF_3$ | H | $O^cC_5H_9$ |

TABLE 1-continued

Compounds of the formula:

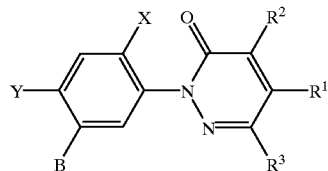

| Compound No. | X | Y | $R^3$ | $R^1$ | $R^2$ | B |
|---|---|---|---|---|---|---|
| 1-1071 | H | Cl | H | $CF_3$ | H | $O^cC_6H_{11}$ |
| 1-1072 | H | Cl | H | $CF_3$ | H | $OCH_2CH=CH_2$ |
| 1-1073 | H | Cl | H | $CF_3$ | H | $OCH_2CCl=CH_2$ |
| 1-1074 | H | Cl | H | $CF_3$ | H | $OCH_2CCl=CHCl$ |
| 1-1075 | H | Cl | H | $CF_3$ | H | $OCH(CH_3)CH=CH_2$ |
| 1-1076 | H | Cl | H | $CF_3$ | H | $OCH_2C\equiv CH$ |
| 1-1077 | H | Cl | H | $CF_3$ | H | $OCH(CH_3)C\equiv CH$ |
| 1-1078 | H | Cl | H | $CF_3$ | H | $OCH_2C\equiv CBr$ |
| 1-1079 | H | Cl | H | $CF_3$ | H | $OCH_2C\equiv CCl$ |
| 1-1080 | H | Cl | H | $CF_3$ | H | $OCH_2C\equiv CCH_2Cl$ |
| 1-1081 | H | Cl | H | $CF_3$ | H | $OCH_2CN$ |
| 1-1082 | H | Cl | H | $CF_3$ | H | $OCH_2OCH_3$ |
| 1-1083 | H | Cl | H | $CF_3$ | H | $OCH_2OC_2H_5$ |
| 1-1084 | H | Cl | H | $CF_3$ | H | $OCH_2SCH_3$ |
| 1-1085 | H | Cl | H | $CF_3$ | H | $OCH_2COOCH_3$ |
| 1-1086 | H | Cl | H | $CF_3$ | H | $OCH_2COOC_2H_5$ |
| 1-1087 | H | Cl | H | $CF_3$ | H | $OCH_2COO^nC_3H_7$ |
| 1-1088 | H | Cl | H | $CF_3$ | H | $OCH_2COO^nC_4H_9$ |
| 1-1089 | H | Cl | H | $CF_3$ | H | $OCH_2COO^nC_5H_{11}$ |
| 1-1090 | H | Cl | H | $CF_3$ | H | $OCH_2COO^iC_3H_7$ |
| 1-1091 | H | Cl | H | $CF_3$ | H | $OCH_2COO^cC_5H_9$ |
| 1-1092 | H | Cl | H | $CF_3$ | H | $OCH_2COO^cC_6H_{11}$ |
| 1-1093 | H | Cl | H | $CF_3$ | H | $OCH(CH_3)COOCH_3$ |
| 1-1094 | H | Cl | H | $CF_3$ | H | $OCH(CH_3)COOC_2H_5$ |
| 1-1095 | H | Cl | H | $CF_3$ | H | $OCH(CH_3)COO^nC_3H_7$ |
| 1-1096 | H | Cl | H | $CF_3$ | H | $OCH(CH_3)COO^nC_4H_9$ |
| 1-1097 | H | Cl | H | $CF_3$ | H | $OCH(CH_3)COO^nC_5H_{11}$ |
| 1-1098 | H | Cl | H | $CF_3$ | H | $OCH(CH_3)COO^iC_3H_7$ |
| 1-1099 | H | Cl | H | $CF_3$ | H | $OCH(CH_3)COO^cC_5H_9$ |
| 1-1100 | H | Cl | H | $CF_3$ | H | $OCH(CH_3)COO^cC_6H_{11}$ |
| 1-1101 | H | Cl | H | $CF_3$ | H | $OCH_2CON(CH_3)_2$ |
| 1-1102 | H | Cl | H | $CF_3$ | H | $OCH_2CON(C_2H_5)_2$ |
| 1-1103 | H | Cl | H | $CF_3$ | H | $OCH_2CON(CH_3)C_2H_5$ |
| 1-1104 | H | Cl | H | $CF_3$ | H | $OCH(CH_3)CON(CH_3)_2$ |
| 1-1105 | H | Cl | H | $CF_3$ | H | $OCH(CH_3)CON(C_2H_5)_2$ |
| 1-1106 | H | Cl | H | $CF_3$ | H | $OCH(CH_3)CON(CH_3)C_2H_5$ |
| 1-1107 | H | Cl | H | $CF_3$ | H | $OCH_2COON(CH_3)_2$ |
| 1-1108 | H | Cl | H | $CF_3$ | H | $OCH_2COON(C_2H_5)_2$ |
| 1-1109 | H | Cl | H | $CF_3$ | H | $OCH(CH_3)COON(CH_3)_2$ |
| 1-1110 | H | Cl | H | $CF_3$ | H | $OCH(CH_3)COON(C_2H_5)_2$ |
| 1-1111 | F | Cl | H | $CF_3$ | H | $OCH_3$ |
| 1-1112 | F | Cl | H | $CF_3$ | H | $OC_2H_5$ |
| 1-1113 | F | Cl | H | $CF_3$ | H | $O^iC_3H_7$ |
| 1-1114 | F | Cl | H | $CF_3$ | H | $O^nC_3H_7$ |
| 1-1115 | F | Cl | H | $CF_3$ | H | $OCH_2CH_2Cl$ |
| 1-1116 | F | Cl | H | $CF_3$ | H | $OCF_2CF_2H$ |
| 1-1117 | F | Cl | H | $CF_3$ | H | $O^cC_5H_9$ |
| 1-1118 | F | Cl | H | $CF_3$ | H | $O^cC_6H_{11}$ |
| 1-1119 | F | Cl | H | $CF_3$ | H | $OCH_2CH=CH_2$ |
| 1-1120 | F | Cl | H | $CF_3$ | H | $OCH_2CCl=CH_2$ |
| 1-1121 | F | Cl | H | $CF_3$ | H | $OCH_2CCl=CHCl$ |
| 1-1122 | F | Cl | H | $CF_3$ | H | $OCH(CH_3)CH=CH_2$ |
| 1-1123 | F | Cl | H | $CF_3$ | H | $OCH_2C\equiv CH$ |
| 1-1124 | F | Cl | H | $CF_3$ | H | $OCH(CH_3)C\equiv CH$ |
| 1-1125 | F | Cl | H | $CF_3$ | H | $OCH_2C\equiv CBr$ |
| 1-1126 | F | Cl | H | $CF_3$ | H | $OCH_2C\equiv CCl$ |
| 1-1127 | F | Cl | H | $CF_3$ | H | $OCH_2C\equiv CCH_2Cl$ |
| 1-1128 | F | Cl | H | $CF_3$ | H | $OCH_2CN$ |
| 1-1129 | F | Cl | H | $CF_3$ | H | $OCH_2OCH_3$ |
| 1-1130 | F | Cl | H | $CF_3$ | H | $OCH_2OC_2H_5$ |
| 1-1131 | F | Cl | H | $CF_3$ | H | $OCH_2SCH_3$ |
| 1-1132 | F | Cl | H | $CF_3$ | H | $OCH_2COOCH_3$ |
| 1-1133 | F | Cl | H | $CF_3$ | H | $OCH_2COOC_2H_5$ |
| 1-1134 | F | Cl | H | $CF_3$ | H | $OCH_2COO^nC_3H_7$ |

TABLE 1-continued

Compounds of the formula:

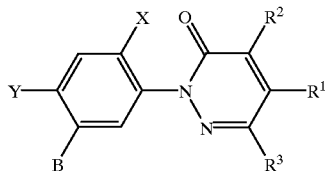

| Compound No. | X | Y | $R^3$ | $R^1$ | $R^2$ | B |
|---|---|---|---|---|---|---|
| 1-1135 | F | Cl | H | $CF_3$ | H | $OCH_2COO^nC_4H_9$ |
| 1-1136 | F | Cl | H | $CF_3$ | H | $OCH_2COO^nC_5H_{11}$ |
| 1-1137 | F | Cl | H | $CF_3$ | H | $OCH_2COO^iC_3H_7$ |
| 1-1138 | F | Cl | H | $CF_3$ | H | $OCH_2COO^cC_5H_9$ |
| 1-1139 | F | Cl | H | $CF_3$ | H | $OCH_2COO^cC_6H_{11}$ |
| 1-1140 | F | Cl | H | $CF_3$ | H | $OCH(CH_3)COOCH_3$ |
| 1-1141 | F | Cl | H | $CF_3$ | H | $OCH(CH_3)COOC_2H_5$ |
| 1-1142 | F | Cl | H | $CF_3$ | H | $OCH(CH_3)COO^nC_3H_7$ |
| 1-1143 | F | Cl | H | $CF_3$ | H | $OCH(CH_3)COO^nC_4H_9$ |
| 1-1144 | F | Cl | H | $CF_3$ | H | $OCH(CH_3)COO^nC_5H_{11}$ |
| 1-1145 | F | Cl | H | $CF_3$ | H | $OCH(CH_3)COO^iC_3H_7$ |
| 1-1146 | F | Cl | H | $CF_3$ | H | $OCH(CH_3)COO^cC_5H_9$ |
| 1-1147 | F | Cl | H | $CF_3$ | H | $OCH(CH_3)COO^cC_6H_{11}$ |
| 1-1148 | F | Cl | H | $CF_3$ | H | $OCH_2CON(CH_3)_2$ |
| 1-1149 | F | Cl | H | $CF_3$ | H | $OCH_2CON(C_2H_5)_2$ |
| 1-1150 | F | Cl | H | $CF_3$ | H | $OCH_2CON(CH_3)C_2H_5$ |
| 1-1151 | F | Cl | H | $CF_3$ | H | $OCH(CH_3)CON(CH_3)_2$ |
| 1-1152 | F | Cl | H | $CF_3$ | H | $OCH(CH_3)CON(C_2H_5)_2$ |
| 1-1153 | F | Cl | H | $CF_3$ | H | $OCH(CH_3)CON(CH_3)C_2H_5$ |
| 1-1154 | F | Cl | H | $CF_3$ | H | $OCH_2COON(CH_3)_2$ |
| 1-1155 | F | Cl | H | $CF_3$ | H | $OCH_2COON(C_2H_5)_2$ |
| 1-1156 | F | Cl | H | $CF_3$ | H | $OCH(CH_3)COON(CH_3)_2$ |
| 1-1157 | F | Cl | H | $CF_3$ | H | $OCH(CH_3)COON(C_2H_5)_2$ |
| 1-1158 | H | F | H | $CF_3$ | H | SH |
| 1-1159 | F | Cl | H | $CF_3$ | H | SH |
| 1-1160 | H | Br | H | $CF_3$ | H | SH |
| 1-1161 | F | F | H | $CF_3$ | H | SH |
| 1-1162 | F | Cl | H | $CF_3$ | H | SH |
| 1-1163 | F | Br | H | $CF_3$ | H | SH |
| 1-1164 | H | Cl | H | $CF_3$ | H | $SCH_3$ |
| 1-1165 | H | Cl | H | $CF_3$ | H | $SC_2H_5$ |
| 1-1166 | H | Cl | H | $CF_3$ | H | $S^iC_3H_7$ |
| 1-1167 | H | Cl | H | $CF_3$ | H | $SCH_2CH_2Cl$ |
| 1-1168 | H | Cl | H | $CF_3$ | H | $S^cC_5H_9$ |
| 1-1169 | H | Cl | H | $CF_3$ | H | $S^cC_6H_{11}$ |
| 1-1170 | H | Cl | H | $CF_3$ | H | $SCH_2CH=CH_2$ |
| 1-1171 | H | Cl | H | $CF_3$ | H | $SCH_2CCl=CH_2$ |
| 1-1172 | H | Cl | H | $CF_3$ | H | $SCH_2CCl=CHCl$ |
| 1-1173 | H | Cl | H | $CF_3$ | H | $SCH(CH_3)CH=CH_2$ |
| 1-1174 | H | Cl | H | $CF_3$ | H | $SCH_2C\equiv CH$ |
| 1-1175 | H | Cl | H | $CF_3$ | H | $SCH(CH_3)C\equiv CH$ |
| 1-1176 | H | Cl | H | $CF_3$ | H | $SCH_2COOCH_3$ |
| 1-1177 | H | Cl | H | $CF_3$ | H | $SCH_2COOC_2H_5$ |
| 1-1178 | H | Cl | H | $CF_3$ | H | $SCH_2COO^nC_3H_7$ |
| 1-1179 | H | Cl | H | $CF_3$ | H | $SCH_2COO^nC_4H_9$ |
| 1-1180 | H | Cl | H | $CF_3$ | H | $SCH_2COO^nC_5H_{11}$ |
| 1-1181 | H | Cl | H | $CF_3$ | H | $SCH_2COO^iC_3H_7$ |
| 1-1182 | H | Cl | H | $CF_3$ | H | $SCH_2COO^cC_5H_9$ |
| 1-1183 | H | Cl | H | $CF_3$ | H | $SCH_2COO^cC_6H_{11}$ |
| 1-1184 | H | Cl | H | $CF_3$ | H | $SCH(CH_3)COOCH_3$ |
| 1-1185 | H | Cl | H | $CF_3$ | H | $SCH(CH_3)COOC_2H_5$ |
| 1-1186 | H | Cl | H | $CF_3$ | H | $SCH(CH_3)COO^nC_3H_7$ |
| 1-1187 | H | Cl | H | $CF_3$ | H | $SCH(CH_3)COO^nC_4H_9$ |
| 1-1188 | H | Cl | H | $CF_3$ | H | $SCH(CH_3)COO^nC_5H_{11}$ |
| 1-1189 | H | Cl | H | $CF_3$ | H | $SCH(CH_3)COO^iC_3H_7$ |
| 1-1190 | H | Cl | H | $CF_3$ | H | $SCH(CH_3)COO^cC_5H_9$ |
| 1-1191 | H | Cl | H | $CF_3$ | H | $SCH(CH_3)COO^cC_6H_{11}$ |
| 1-1192 | H | Cl | H | $CF_3$ | H | $SCH_2CON(CH_3)_2$ |
| 1-1193 | H | Cl | H | $CF_3$ | H | $SCH_2CON(C_2H_5)_2$ |
| 1-1194 | H | Cl | H | $CF_3$ | H | $SCH_2CON(tetramethylene)$ |
| 1-1195 | H | Cl | H | $CF_3$ | H | $SCH_2CON(pentamethylene)$ |
| 1-1196 | H | Cl | H | $CF_3$ | H | $SCH_2CON(ethyleneoxyethylene)$ |
| 1-1197 | H | Cl | H | $CF_3$ | H | $SCH(CH_3)CON(CH_3)_2$ |

TABLE 1-continued

Compounds of the formula:

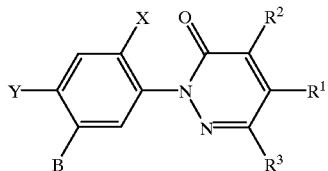

| Compound No. | X | Y | $R^3$ | $R^1$ | $R^2$ | B |
|---|---|---|---|---|---|---|
| 1-1198 | H | Cl | H | $CF_3$ | H | $SCH(CH_3)CON(C_2H_5)_2$ |
| 1-1199 | H | Cl | H | $CF_3$ | H | $SCH(CH_3)CON$ (tetramethylene) |
| 1-1200 | H | Cl | H | $CF_3$ | H | $SCH(CH_3)CON$ (pentamethylene) |
| 1-1201 | F | Cl | H | $CF_3$ | H | $SCH_3$ |
| 1-1202 | F | Cl | H | $CF_3$ | H | $SC_2H_5$ |
| 1-1203 | F | Cl | H | $CF_3$ | H | $S^iC_3H_7$ |
| 1-1204 | F | Cl | H | $CF_3$ | H | $SCH_2CH_2Cl$ |
| 1-1205 | F | Cl | H | $CF_3$ | H | $S^cC_5H_9$ |
| 1-1206 | F | Cl | H | $CF_3$ | H | $S^cC_6H_{11}$ |
| 1-1207 | F | Cl | H | $CF_3$ | H | $SCH_2CH=CH_2$ |
| 1-1208 | F | Cl | H | $CF_3$ | H | $SCH_2CCl=CH_2$ |
| 1-1209 | F | Cl | H | $CF_3$ | H | $SCH_2CCl=CHCl$ |
| 1-1210 | F | Cl | H | $CF_3$ | H | $SCH(CH_3)CH=CH_2$ |
| 1-1211 | F | Cl | H | $CF_3$ | H | $SCH_2C\equiv CH$ |
| 1-1212 | F | Cl | H | $CF_3$ | H | $SCH(CH_3)C\equiv CH$ |
| 1-1213 | F | Cl | H | $CF_3$ | H | $SCH_2COOCH_3$ |
| 1-1214 | F | Cl | H | $CF_3$ | H | $SCH_2COOC_2H_5$ |
| 1-1215 | F | Cl | H | $CF_3$ | H | $SCH_2COO^nC_3H_7$ |
| 1-1216 | F | Cl | H | $CF_3$ | H | $SCH_2COO^nC_4H_9$ |
| 1-1217 | F | Cl | H | $CF_3$ | H | $SCH_2COO^nC_5H_{11}$ |
| 1-1218 | F | Cl | H | $CF_3$ | H | $SCH_2COO^iC_3H_7$ |
| 1-1219 | F | Cl | H | $CF_3$ | H | $SCH_2COO^cC_5H_9$ |
| 1-1220 | F | Cl | H | $CF_3$ | H | $SCH_2COO^cC_6H_{11}$ |
| 1-1221 | F | Cl | H | $CF_3$ | H | $SCH(CH_3)COOCH_3$ |
| 1-1222 | F | Cl | H | $CF_3$ | H | $SCH(CH_3)COOC_2H_5$ |
| 1-1223 | F | Cl | H | $CF_3$ | H | $SCH(CH_3)COO^nC_3H_7$ |
| 1-1224 | F | Cl | H | $CF_3$ | H | $SCH(CH_3)COO^nC_4H_9$ |
| 1-1225 | F | Cl | H | $CF_3$ | H | $SCH(CH_3)COO^nC_5H_{11}$ |
| 1-1226 | F | Cl | H | $CF_3$ | H | $SCH(CH_3)COO^iC_3H_7$ |
| 1-1227 | F | Cl | H | $CF_3$ | H | $SCH(CH_3)COO^cC_5H_9$ |
| 1-1228 | F | Cl | H | $CF_3$ | H | $SCH(CH_3)COO^cC_6H_{11}$ |
| 1-1229 | F | Cl | H | $CF_3$ | H | $SCH_2CON(CH_3)_2$ |
| 1-1230 | F | Cl | H | $CF_3$ | H | $SCH_2CON(C_2H_5)_2$ |
| 1-1231 | F | Cl | H | $CF_3$ | H | $SCH_2CON(tetramethylene)$ |
| 1-1232 | F | Cl | H | $CF_3$ | H | $SCH_2CON(pentamethylene)$ |
| 1-1233 | F | Cl | H | $CF_3$ | H | $SCH_2CON$ (ethyleneoxyethylene) |
| 1-1234 | F | Cl | H | $CF_3$ | H | $SCH(CH_3)CON(CH_3)_2$ |
| 1-1235 | F | Cl | H | $CF_3$ | H | $SCH(CH_3)CON(C_2H_5)_2$ |
| 1-1236 | F | Cl | H | $CF_3$ | H | $SCH(CH_3)CON$ (tetramethylene) |
| 1-1237 | F | Cl | H | $CF_3$ | $CH_3$ | $SCH(CH_3)CON$ (pentamethylene) |
| 1-1238 | H | F | H | $CF_3$ | H | $SO_2Cl$ |
| 1-1239 | H | Cl | H | $CF_3$ | H | $SO_2Cl$ |
| 1-1240 | H | Br | H | $CF_3$ | H | $SO_2Cl$ |
| 1-1241 | F | F | H | $CF_3$ | H | $SO_2Cl$ |
| 1-1242 | F | Cl | H | $CF_3$ | H | $SO_2Cl$ |
| 1-1243 | F | Br | H | $CF_3$ | H | $SO_2Cl$ |
| 1-1244 | H | Cl | H | $CF_3$ | H | $SO_2OCH_3$ |
| 1-1245 | H | Cl | H | $CF_3$ | H | $SO_2OC_2H_5$ |
| 1-1246 | H | Cl | H | $CF_3$ | H | $SO_2O^iC_3H_7$ |
| 1-1247 | H | Cl | H | $CF_3$ | H | $SO_2OCH_2CH=CH_2$ |
| 1-1248 | F | Cl | H | $CF_3$ | H | $SO_2OCH_3$ |
| 1-1249 | F | Cl | H | $CF_3$ | H | $SO_2OC_2H_5$ |
| 1-1250 | F | Cl | H | $CF_3$ | H | $SO_2O^iC_3H_7$ |
| 1-1251 | F | Cl | H | $CF_3$ | H | $SO_2OCH_2CH=CH_2$ |
| 1-1252 | H | Cl | H | $CF_3$ | H | $SO_2N(CH_3)_2$ |
| 1-1253 | H | Cl | H | $CF_3$ | H | $SO_2N(C_2H_5)_2$ |
| 1-1254 | F | Cl | H | $CF_3$ | H | $SO_2N(CH_3)_2$ |
| 1-1255 | F | Cl | H | $CF_3$ | H | $SO_2N(C_2H_5)_2$ |
| 1-1256 | H | Cl | H | $CF_3$ | H | COOH |

TABLE 1-continued

Compounds of the formula:

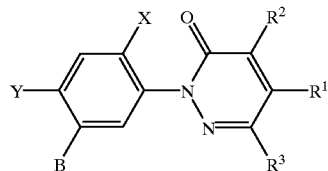

| Compound No. | X | Y | $R^3$ | $R^1$ | $R^2$ | B |
|---|---|---|---|---|---|---|
| 1-1257 | H | Cl | H | $CF_3$ | H | $COOCH_3$ |
| 1-1258 | H | Cl | H | $CF_3$ | H | $COOC_2H_5$ |
| 1-1259 | H | Cl | H | $CF_3$ | H | $COO^nC_3H_7$ |
| 1-1260 | H | Cl | H | $CF_3$ | H | $COO^nC_4H_9$ |
| 1-1261 | H | Cl | H | $CF_3$ | H | $COO^nC_5H_{11}$ |
| 1-1262 | H | Cl | H | $CF_3$ | H | $COO^iC_3H_7$ |
| 1-1263 | H | Cl | H | $CF_3$ | H | $COOCH_2CH_2Cl$ |
| 1-1264 | H | Cl | H | $CF_3$ | H | $COOCH_2CH_2Br$ |
| 1-1265 | H | Cl | H | $CF_3$ | H | $CON(CH_3)_2$ |
| 1-1266 | H | Cl | H | $CF_3$ | H | $CONHCH_3$ |
| 1-1267 | H | Cl | H | $CF_3$ | H | $CON(C_2H_5)_2$ |
| 1-1268 | H | Cl | H | $CF_3$ | H | $CONHC_2H_5$ |
| 1-1269 | H | Cl | H | $CF_3$ | H | $COCH_3$ |
| 1-1270 | H | Cl | H | $CF_3$ | H | $COC_2H_5$ |
| 1-1271 | H | Cl | H | $CF_3$ | H | $COCH_2Cl$ |
| 1-1272 | H | Cl | H | $CF_3$ | H | CHO |
| 1-1273 | H | Cl | H | $CF_3$ | H | $CH=CHCOOCH_3$ |
| 1-1274 | H | Cl | H | $CF_3$ | H | $CH=CHCOOC_2H_5$ |
| 1-1275 | H | Cl | H | $CF_3$ | H | $CH_2CH_2COOCH_3$ |
| 1-1276 | H | Cl | H | $CF_3$ | H | $CH_2CH_2COOC_2H_5$ |
| 1-1277 | F | Cl | H | $CF_3$ | H | COOH |
| 1-1278 | F | Cl | H | $CF_3$ | H | $COOCH_3$ |
| 1-1279 | F | Cl | H | $CF_3$ | H | $COOC_2H_5$ |
| 1-1280 | F | Cl | H | $CF_3$ | H | $COO^nC_3H_7$ |
| 1-1281 | F | Cl | H | $CF_3$ | H | $COO^nC_4H_9$ |
| 1-1282 | F | Cl | H | $CF_3$ | H | $COO^nC_5H_{11}$ |
| 1-1283 | F | Cl | H | $CF_3$ | H | $COO^iC_3H_7$ |
| 1-1284 | F | Cl | H | $CF_3$ | H | $COOCH_2CH_2Cl$ |
| 1-1285 | F | Cl | H | $CF_3$ | H | $COOCH_2CH_2Br$ |
| 1-1286 | F | Cl | H | $CF_3$ | H | $CON(CH_3)_2$ |
| 1-1287 | F | Cl | H | $CF_3$ | H | $CONHCH_3$ |
| 1-1288 | F | Cl | H | $CF_3$ | H | $CON(C_2H_5)_2$ |
| 1-1289 | F | Cl | H | $CF_3$ | H | $CONHC_2H_5$ |
| 1-1290 | F | Cl | H | $CF_3$ | H | $COCH_3$ |
| 1-1291 | F | Cl | H | $CF_3$ | H | $COC_2H_5$ |
| 1-1292 | F | Cl | H | $CF_3$ | H | $COCH_2Cl$ |
| 1-1293 | F | Cl | H | $CF_3$ | H | CHO |
| 1-1294 | F | Cl | H | $CF_3$ | H | $CH=CHCOOCH_3$ |
| 1-1295 | F | Cl | H | $CF_3$ | H | $CH=CHCOOC_2H_5$ |
| 1-1296 | F | Cl | H | $CF_3$ | H | $CH_2CH_2COOCH_3$ |
| 1-1297 | F | Cl | H | $CF_3$ | H | $CH_2CH_2COOC_2H_5$ |
| 1-1298 | H | F | $CH_3$ | $CF_3$ | H | $NO_2$ |
| 1-1299 | H | Cl | $CH_3$ | $CF_3$ | H | $NO_2$ |
| 1-1300 | H | Br | $CH_3$ | $CF_3$ | H | $NO_2$ |
| 1-1301 | F | F | $CH_3$ | $CF_3$ | H | $NO_2$ |
| 1-1302 | F | Cl | $CH_3$ | $CF_3$ | H | $NO_2$ |
| 1-1303 | F | Br | $CH_3$ | $CF_3$ | H | $NO_2$ |
| 1-1304 | H | F | $CH_3$ | $CF_3$ | H | $NH_2$ |
| 1-1305 | H | Cl | $CH_3$ | $CF_3$ | H | $NH_2$ |
| 1-1306 | H | Br | $CH_3$ | $CF_3$ | H | $NH_2$ |
| 1-1307 | F | F | $CH_3$ | $CF_3$ | H | $NH_2$ |
| 1-1308 | F | Cl | $CH_3$ | $CF_3$ | H | $NH_2$ |
| 1-1309 | H | Cl | $CH_3$ | $CF_3$ | H | $NHCH(CH_3)COOCH_3$ |
| 1-1310 | H | Cl | $CH_3$ | $CF_3$ | H | $NHCH(CH_3)COOC_2H_5$ |
| 1-1311 | H | Cl | $CH_3$ | $CF_3$ | H | $NHCH(CH_3)COO^nC_3H_7$ |
| 1-1312 | H | Cl | $CH_3$ | $CF_3$ | H | $NHCH(CH_3)COO^nC_4H_9$ |
| 1-1313 | H | Cl | $CH_3$ | $CF_3$ | H | $NHCH(CH_3)COO^nC_5H_{11}$ |
| 1-1314 | H | Cl | $CH_3$ | $CF_3$ | H | $NHCH(CH_3)COO^iC_3H_7$ |
| 1-1315 | H | Cl | $CH_3$ | $CF_3$ | H | $NHCH(CH_3)COO^cC_5H_9$ |
| 1-1316 | H | Cl | $CH_3$ | $CF_3$ | H | $NHCH(CH_3)COO^cC_6H_{11}$ |
| 1-1317 | F | Cl | $CH_3$ | $CF_3$ | H | $NHCH_3$ |
| 1-1318 | F | Cl | $CH_3$ | $CF_3$ | H | $NHC_2H_5$ |
| 1-1319 | F | Cl | $CH_3$ | $CF_3$ | H | $NHCH_2CH=CH_2$ |
| 1-1320 | F | Cl | $CH_3$ | $CF_3$ | H | $NHCH_2C\equiv CH$ |

TABLE 1-continued

Compounds of the formula:

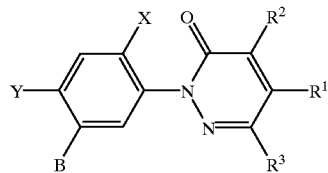

| Compound No. | X | Y | $R^3$ | $R^1$ | $R^2$ | B |
|---|---|---|---|---|---|---|
| 1-1321 | F | Cl | $CH_3$ | $CF_3$ | H | $NHCH(CH_3)C{\equiv}CH$ |
| 1-1322 | F | Cl | $CH_3$ | $CF_3$ | H | $NHSO_2CH_3$ |
| 1-1323 | F | Cl | $CH_3$ | $CF_3$ | H | $NHSO_2C_2H_5$ |
| 1-1324 | F | Cl | $CH_3$ | $CF_3$ | H | $NHSO_2CH_2Cl$ |
| 1-1325 | F | Cl | $CH_3$ | $CF_3$ | H | $NHSO_2CF_3$ |
| 1-1326 | F | Cl | $CH_3$ | $CF_3$ | H | $N(CH_3)SO_2CH_3$ |
| 1-1327 | F | Cl | $CH_3$ | $CF_3$ | H | $N(CH_2C{\equiv}CH)SO_2CH_3$ |
| 1-1328 | F | Cl | $CH_3$ | $CF_3$ | H | $NHCOOCH_3$ |
| 1-1329 | F | Cl | $CH_3$ | $CF_3$ | H | $NHCOOC_2H_5$ |
| 1-1330 | F | Cl | $CH_3$ | $CF_3$ | H | $NHCOO^nC_3H_7$ |
| 1-1331 | F | Cl | $CH_3$ | $CF_3$ | H | $NHCOO^iC_3H_7$ |
| 1-1332 | F | Cl | $CH_3$ | $CF_3$ | H | $NHCOO^nC_4H_9$ |
| 1-1333 | F | Cl | $CH_3$ | $CF_3$ | H | $NHCOO^nC_5H_{11}$ |
| 1-1334 | F | Cl | $CH_3$ | $CF_3$ | H | $NHCH_2COOCH_3$ |
| 1-1335 | F | Cl | $CH_3$ | $CF_3$ | H | $NHCH_2COOC_2H_5$ |
| 1-1336 | F | Cl | $CH_3$ | $CF_3$ | H | $NHCH_2COO^nC_3H_7$ |
| 1-1337 | F | Cl | $CH_3$ | $CF_3$ | H | $NHCH_2COO^nC_4H_9$ |
| 1-1338 | F | Cl | $CH_3$ | $CF_3$ | H | $NHCH_2COO^nC_5H_{11}$ |
| 1-1339 | F | Cl | $CH_3$ | $CF_3$ | H | $NHCH_2COO^iC_3H_7$ |
| 1-1340 | F | Cl | $CH_3$ | $CF_3$ | H | $NHCH_2COO^cC_5H_9$ |
| 1-1341 | F | Br | $CH_3$ | $CF_3$ | H | $NH_2$ |
| 1-1342 | H | F | $CH_3$ | $CF_3$ | H | OH |
| 1-1343 | F | Cl | $CH_3$ | $CF_3$ | H | OH |
| 1-1344 | H | Br | $CH_3$ | $CF_3$ | H | OH |
| 1-1345 | F | F | $CH_3$ | $CF_3$ | H | OH |
| 1-1346 | F | Cl | $CH_3$ | $CF_3$ | H | OH |
| 1-1347 | F | Br | $CH_3$ | $CF_3$ | H | OH |
| 1-1348 | H | Cl | $CH_3$ | $CF_3$ | H | $NHCH_3$ |
| 1-1349 | H | Cl | $CH_3$ | $CF_3$ | H | $NHC_2H_5$ |
| 1-1350 | H | Cl | $CH_3$ | $CF_3$ | H | $NHCH_2CH{=}CH_2$ |
| 1-1351 | H | Cl | $CH_3$ | $CF_3$ | H | $NHCH_2C{\equiv}CH$ |
| 1-1352 | H | Cl | $CH_3$ | $CF_3$ | H | $NHCH(CH_3)C{\equiv}CH$ |
| 1-1353 | H | Cl | $CH_3$ | $CF_3$ | H | $NHSO_2CH_3$ |
| 1-1354 | H | Cl | $CH_3$ | $CF_3$ | H | $NHSO_2C_2H_5$ |
| 1-1355 | H | Cl | $CH_3$ | $CF_3$ | H | $NHSO_2CH_2Cl$ |
| 1-1356 | H | Cl | $CH_3$ | $CF_3$ | H | $NHSO_2CF_3$ |
| 1-1357 | H | Cl | $CH_3$ | $CF_3$ | H | $N(CH_3)SO_2CH_3$ |
| 1-1358 | H | Cl | $CH_3$ | $CF_3$ | H | $N(CH_2C{\equiv}CH)SO_2CH_3$ |
| 1-1359 | H | Cl | $CH_3$ | $CF_3$ | H | $NHCOOCH_3$ |
| 1-1360 | H | Cl | $CH_3$ | $CF_3$ | H | $NHCOOC_2H_5$ |
| 1-1361 | H | Cl | $CH_3$ | $CF_3$ | H | $NHCOO^nC_3H_7$ |
| 1-1362 | H | Cl | $CH_3$ | $CF_3$ | H | $NHCOO^iC_3H_7$ |
| 1-1363 | H | Cl | $CH_3$ | $CF_3$ | H | $NHCOO^nC_4H_9$ |
| 1-1364 | H | Cl | $CH_3$ | $CF_3$ | H | $NHCOO^nC_5H_{11}$ |
| 1-1365 | H | Cl | $CH_3$ | $CF_3$ | H | $NHCH_2COOCH_3$ |
| 1-1366 | H | Cl | $CH_3$ | $CF_3$ | H | $NHCH_2COOC_2H_5$ |
| 1-1367 | H | Cl | $CH_3$ | $CF_3$ | H | $NHCH_2COO^nC_3H_7$ |
| 1-1368 | H | Cl | $CH_3$ | $CF_3$ | H | $NHCH_2COO^nC_4H_9$ |
| 1-1369 | H | Cl | $CH_3$ | $CF_3$ | H | $NHCH_2COO^nC_5H_{11}$ |
| 1-1370 | H | Cl | $CH_3$ | $CF_3$ | H | $NHCH_2COO^iC_3H_7$ |
| 1-1371 | H | Cl | $CH_3$ | $CF_3$ | H | $NHCH_2COO^cC_5H_9$ |
| 1-1372 | H | Cl | $CH_3$ | $CF_3$ | H | $NHCH_2COO^cC_5H_{11}$ |
| 1-1373 | F | Cl | $CH_3$ | $CF_3$ | H | $NHCH_2COO^cC_6H_{11}$ |
| 1-1374 | F | Cl | $CH_3$ | $CF_3$ | H | $NHCH(CH_3)COOCH_3$ |
| 1-1375 | F | Cl | $CH_3$ | $CF_3$ | H | $NHCH(CH_3)COOC_2H_5$ |
| 1-1376 | F | Cl | $CH_3$ | $CF_3$ | H | $NHCH(CH_3)COO^nC_3H_7$ |
| 1-1377 | F | Cl | $CH_3$ | $CF_3$ | H | $NHCH(CH_3)COO^nC_4H_9$ |
| 1-1378 | F | Cl | $CH_3$ | $CF_3$ | H | $NHCH(CH_3)COO^nC_5H_{11}$ |
| 1-1379 | F | Cl | $CH_3$ | $CF_3$ | H | $NHCH(CH_3)COO^iC_3H_7$ |
| 1-1380 | F | Cl | $CH_3$ | $CF_3$ | H | $NHCH(CH_3)COO^cC_5H_9$ |
| 1-1381 | F | Cl | $CH_3$ | $CF_3$ | H | $NHCH(CH_3)COO^cC_6H_{11}$ |
| 1-1382 | H | Cl | $CH_3$ | $CF_3$ | H | $OCH_3$ |
| 1-1383 | H | Cl | $CH_3$ | $CF_3$ | H | $OC_2H_5$ |
| 1-1384 | H | Cl | $CH_3$ | $CF_3$ | H | $O^iC_3H_7$ |

TABLE 1-continued

Compounds of the formula:

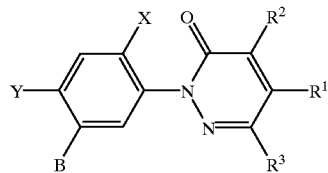

| Compound No. | X | Y | $R^3$ | $R^1$ | $R^2$ | B |
|---|---|---|---|---|---|---|
| 1-1385 | H | Cl | $CH_3$ | $CF_3$ | H | $O^nC_3H_7$ |
| 1-1386 | H | Cl | $CH_3$ | $CF_3$ | H | $OCH_2CH_2Cl$ |
| 1-1387 | H | Cl | $CH_3$ | $CF_3$ | H | $OCF_2CF_2H$ |
| 1-1388 | H | Cl | $CH_3$ | $CF_3$ | H | $O^cC_5H_9$ |
| 1-1389 | H | Cl | $CH_3$ | $CF_3$ | H | $O^cC_6H_{11}$ |
| 1-1390 | H | Cl | $CH_3$ | $CF_3$ | H | $OCH_2CH=CH_2$ |
| 1-1391 | H | Cl | $CH_3$ | $CF_3$ | H | $OCH_2CCl=CH_2$ |
| 1-1392 | H | Cl | $CH_3$ | $CF_3$ | H | $OCH_2CCl=CHCl$ |
| 1-1393 | H | Cl | $CH_3$ | $CF_3$ | H | $OCH(CH_3)CH=CH_2$ |
| 1-1394 | H | Cl | $CH_3$ | $CF_3$ | H | $OCH_2C\equiv CH$ |
| 1-1395 | H | Cl | $CH_3$ | $CF_3$ | H | $OCH(CH_3)C\equiv CH$ |
| 1-1396 | H | Cl | $CH_3$ | $CF_3$ | H | $OCH_2C\equiv CBr$ |
| 1-1397 | H | Cl | $CH_3$ | $CF_3$ | H | $OCH_2C\equiv CCl$ |
| 1-1398 | H | Cl | $CH_3$ | $CF_3$ | H | $OCH_2C\equiv CCH_2Cl$ |
| 1-1399 | H | Cl | $CH_3$ | $CF_3$ | H | $OCH_2CN$ |
| 1-1400 | H | Cl | $CH_3$ | $CF_3$ | H | $OCH_2OCH_3$ |
| 1-1401 | H | Cl | $CH_3$ | $CF_3$ | H | $OCH_2OC_2H_5$ |
| 1-1402 | H | Cl | $CH_3$ | $CF_3$ | H | $OCH_2SCH_3$ |
| 1-1403 | H | Cl | $CH_3$ | $CF_3$ | H | $OCH_2COOCH_3$ |
| 1-1404 | H | Cl | $CH_3$ | $CF_3$ | H | $OCH_2COOC_2H_5$ |
| 1-1405 | H | Cl | $CH_3$ | $CF_3$ | H | $OCH_2COO^nC_3H_7$ |
| 1-1406 | H | Cl | $CH_3$ | $CF_3$ | H | $OCH_2COO^nC_4H_9$ |
| 1-1407 | H | Cl | $CH_3$ | $CF_3$ | H | $OCH_2COO^nC_5H_{11}$ |
| 1-1408 | H | Cl | $CH_3$ | $CF_3$ | H | $OCH_2COO^iC_3H_7$ |
| 1-1409 | H | Cl | $CH_3$ | $CF_3$ | H | $OCH_2COO^cC_5H_9$ |
| 1-1410 | H | Cl | $CH_3$ | $CF_3$ | H | $OCH_2COO^cC_6H_{11}$ |
| 1-1411 | H | Cl | $CH_3$ | $CF_3$ | H | $OCH(CH_3)COOCH_3$ |
| 1-1412 | H | Cl | $CH_3$ | $CF_3$ | H | $OCH(CH_3)COOC_2H_5$ |
| 1-1413 | H | Cl | $CH_3$ | $CF_3$ | H | $OCH(CH_3)COO^nC_3H_7$ |
| 1-1414 | H | Cl | $CH_3$ | $CF_3$ | H | $OCH(CH_3)COO^nC_4H_9$ |
| 1-1415 | H | Cl | $CH_3$ | $CF_3$ | H | $OCH(CH_3)COO^nC_5H_{11}$ |
| 1-1416 | H | Cl | $CH_3$ | $CF_3$ | H | $OCH(CH_3)COO^iC_3H_7$ |
| 1-1417 | H | Cl | $CH_3$ | $CF_3$ | H | $OCH(CH_3)COO^cC_5H_9$ |
| 1-1418 | H | Cl | $CH_3$ | $CF_3$ | H | $OCH(CH_3)COO^cC_6H_{11}$ |
| 1-1419 | H | Cl | $CH_3$ | $CF_3$ | H | $OCH_2CON(CH_3)_2$ |
| 1-1420 | H | Cl | $CH_3$ | $CF_3$ | H | $OCH_2CON(C_2H_5)_2$ |
| 1-1421 | H | Cl | $CH_3$ | $CF_3$ | H | $OCH_2CON(CH_3)C_2H_5$ |
| 1-1422 | H | Cl | $CH_3$ | $CF_3$ | H | $OCH(CH_3)CON(CH_3)_2$ |
| 1-1423 | H | Cl | $CH_3$ | $CF_3$ | H | $OCH(CH_3)CON(C_2H_5)_2$ |
| 1-1424 | H | Cl | $CH_3$ | $CF_3$ | H | $OCH(CH_3)CON(CH_3)C_2H_5$ |
| 1-1425 | H | Cl | $CH_3$ | $CF_3$ | H | $OCH_2COON(CH_3)_2$ |
| 1-1426 | H | Cl | $CH_3$ | $CF_3$ | H | $OCH_2COON(C_2H_5)_2$ |
| 1-1427 | H | Cl | $CH_3$ | $CF_3$ | H | $OCH(CH_3)COON(CH_3)_2$ |
| 1-1428 | H | Cl | $CH_3$ | $CF_3$ | H | $OCH(CH_3)COON(C_2H_5)_2$ |
| 1-1429 | F | Cl | $CH_3$ | $CF_3$ | H | $OCH_3$ |
| 1-1430 | F | Cl | $CH_3$ | $CF_3$ | H | $OC_2H_5$ |
| 1-1431 | F | Cl | $CH_3$ | $CF_3$ | H | $O^iC_3H_7$ |
| 1-1432 | F | Cl | $CH_3$ | $CF_3$ | H | $O^nC_3H_7$ |
| 1-1433 | F | Cl | $CH_3$ | $CF_3$ | H | $OCH_2CH_2Cl$ |
| 1-1434 | F | Cl | $CH_3$ | $CF_3$ | H | $OCF_2CF_2H$ |
| 1-1435 | F | Cl | $CH_3$ | $CF_3$ | H | $O^cC_5H_9$ |
| 1-1436 | F | Cl | $CH_3$ | $CF_3$ | H | $O^cC_6H_{11}$ |
| 1-1437 | F | Cl | $CH_3$ | $CF_3$ | H | $OCH_2CH=CH_2$ |
| 1-1438 | F | Cl | $CH_3$ | $CF_3$ | H | $OCH_2CCl=CH_2$ |
| 1-1439 | F | Cl | $CH_3$ | $CF_3$ | H | $OCH_2CCl=CHCl$ |
| 1-1440 | F | Cl | $CH_3$ | $CF_3$ | H | $OCH(CH_3)CH=CH_2$ |
| 1-1441 | F | Cl | $CH_3$ | $CF_3$ | H | $OCH_2C\equiv CH$ |
| 1-1442 | F | Cl | $CH_3$ | $CF_3$ | H | $OCH(CH_3)C\equiv CH$ |
| 1-1443 | F | Cl | $CH_3$ | $CF_3$ | H | $OCH_2C\equiv CBr$ |
| 1-1444 | F | Cl | $CH_3$ | $CF_3$ | H | $OCH_2C\equiv CCl$ |
| 1-1445 | F | Cl | $CH_3$ | $CF_3$ | H | $OCH_2C\equiv CCH_2Cl$ |
| 1-1446 | F | Cl | $CH_3$ | $CF_3$ | H | $OCH_2CN$ |
| 1-1447 | F | Cl | $CH_3$ | $CF_3$ | H | $OCH_2OCH_3$ |
| 1-1448 | F | Cl | $CH_3$ | $CF_3$ | H | $OCH_2OC_2H_5$ |

TABLE 1-continued

Compounds of the formula:

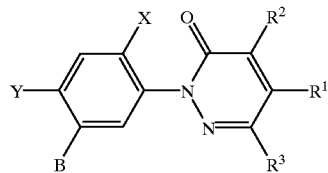

| Compound No. | X | Y | $R^3$ | $R^1$ | $R^2$ | B |
|---|---|---|---|---|---|---|
| 1-1449 | F | Cl | $CH_3$ | $CF_3$ | H | $OCH_2SCH_3$ |
| 1-1450 | F | Cl | $CH_3$ | $CF_3$ | H | $OCH_2COOCH_3$ |
| 1-1451 | F | Cl | $CH_3$ | $CF_3$ | H | $OCH_2COOC_2H_5$ |
| 1-1452 | F | Cl | $CH_3$ | $CF_3$ | H | $OCH_2COO^nC_3H_7$ |
| 1-1453 | F | Cl | $CH_3$ | $CF_3$ | H | $OCH_2COO^nC_4H_9$ |
| 1-1454 | F | Cl | $CH_3$ | $CF_3$ | H | $OCH_2COO^nC_5H_{11}$ |
| 1-1455 | F | Cl | $CH_3$ | $CF_3$ | H | $OCH_2COO^iC_3H_7$ |
| 1-1456 | F | Cl | $CH_3$ | $CF_3$ | H | $OCH_2COO^cC_5H_9$ |
| 1-1457 | F | Cl | $CH_3$ | $CF_3$ | H | $OCH_2COO^cC_6H_{11}$ |
| 1-1458 | F | Cl | $CH_3$ | $CF_3$ | H | $OCH(CH_3)COOCH_3$ |
| 1-1459 | F | Cl | $CH_3$ | $CF_3$ | H | $OCH(CH_3)COOC_2H_5$ |
| 1-1460 | F | Cl | $CH_3$ | $CF_3$ | H | $OCH(CH_3)COO^nC_3H_7$ |
| 1-1461 | F | Cl | $CH_3$ | $CF_3$ | H | $OCH(CH_3)COO^nC_4H_9$ |
| 1-1462 | F | Cl | $CH_3$ | $CF_3$ | H | $OCH(CH_3)COO^nC_5H_{11}$ |
| 1-1463 | F | Cl | $CH_3$ | $CF_3$ | H | $OCH(CH_3)COO^iC_3H_7$ |
| 1-1464 | F | Cl | $CH_3$ | $CF_3$ | H | $OCH(CH_3)COO^cC_5H_9$ |
| 1-1465 | F | Cl | $CH_3$ | $CF_3$ | H | $OCH(CH_3)COO^cC_6H_{11}$ |
| 1-1466 | F | Cl | $CH_3$ | $CF_3$ | H | $OCH_2CON(CH_3)_2$ |
| 1-1467 | F | Cl | $CH_3$ | $CF_3$ | H | $OCH_2CON(C_2H_5)_2$ |
| 1-1468 | F | Cl | $CH_3$ | $CF_3$ | H | $OCH_2CON(CH_3)C_2H_5$ |
| 1-1469 | F | Cl | $CH_3$ | $CF_3$ | H | $OCH(CH_3)CON(CH_3)_2$ |
| 1-1470 | F | Cl | $CH_3$ | $CF_3$ | H | $OCH(CH_3)CON(C_2H_5)_2$ |
| 1-1471 | F | Cl | $CH_3$ | $CF_3$ | H | $OCH(CH_3)CON(CH_3)C_2H_5$ |
| 1-1472 | F | Cl | $CH_3$ | $CF_3$ | H | $OCH_2COON(CH_3)_2$ |
| 1-1473 | F | Cl | $CH_3$ | $CF_3$ | H | $OCH_2COON(C_2H_5)_2$ |
| 1-1474 | F | Cl | $CH_3$ | $CF_3$ | H | $OCH(CH_3)COON(CH_3)_2$ |
| 1-1475 | F | Cl | $CH_3$ | $CF_3$ | H | $OCH(CH_3)COON(C_2H_5)_2$ |
| 1-1476 | H | F | $CH_3$ | $CF_3$ | H | SH |
| 1-1477 | H | Cl | $CH_3$ | $CF_3$ | H | SH |
| 1-1478 | H | Br | $CH_3$ | $CF_3$ | H | SH |
| 1-1479 | F | F | $CH_3$ | $CF_3$ | H | SH |
| 1-1480 | F | Cl | $CH_3$ | $CF_3$ | H | SH |
| 1-1481 | F | Br | $CH_3$ | $CF_3$ | H | SH |
| 1-1482 | H | Cl | $CH_3$ | $CF_3$ | H | $SCH_3$ |
| 1-1483 | H | Cl | $CH_3$ | $CF_3$ | H | $SC_2H_5$ |
| 1-1484 | H | Cl | $CH_3$ | $CF_3$ | H | $S^iC_3H_7$ |
| 1-1485 | H | Cl | $CH_3$ | $CF_3$ | H | $SCH_2CH_2Cl$ |
| 1-1486 | H | Cl | $CH_3$ | $CF_3$ | H | $S^cC_5H_9$ |
| 1-1487 | H | Cl | $CH_3$ | $CF_3$ | H | $S^cC_6H_{11}$ |
| 1-1488 | H | Cl | $CH_3$ | $CF_3$ | H | $SCH_2CH=CH_2$ |
| 1-1489 | H | Cl | $CH_3$ | $CF_3$ | H | $SCH_2CCl=CH_2$ |
| 1-1490 | H | Cl | $CH_3$ | $CF_3$ | H | $SCH_2CCl=CHCl$ |
| 1-1491 | H | Cl | $CH_3$ | $CF_3$ | H | $SCH(CH_3)CH=CH_2$ |
| 1-1492 | H | Cl | $CH_3$ | $CF_3$ | H | $SCH_2C\equiv CH$ |
| 1-1493 | H | Cl | $CH_3$ | $CF_3$ | H | $SCH(CH_3)C\equiv CH$ |
| 1-1494 | H | Cl | $CH_3$ | $CF_3$ | H | $SCH_2COOCH_3$ |
| 1-1495 | H | Cl | $CH_3$ | $CF_3$ | H | $SCH_2COOC_2H_5$ |
| 1-1496 | H | Cl | $CH_3$ | $CF_3$ | H | $SCH_2COO^nC_3H_7$ |
| 1-1497 | H | Cl | $CH_3$ | $CF_3$ | H | $SCH_2COO^nC_4H_9$ |
| 1-1498 | H | Cl | $CH_3$ | $CF_3$ | H | $SCH_2COO^nC_5H_{11}$ |
| 1-1499 | H | Cl | $CH_3$ | $CF_3$ | H | $SCH_2COO^iC_3H_7$ |
| 1-1500 | H | Cl | $CH_3$ | $CF_3$ | H | $SCH_2COO^cC_5H_9$ |
| 1-1501 | H | Cl | $CH_3$ | $CF_3$ | H | $SCH_2COO^cC_6H_{11}$ |
| 1-1502 | H | Cl | $CH_3$ | $CF_3$ | H | $SCH(CH_3)COOCH_3$ |
| 1-1503 | H | Cl | $CH_3$ | $CF_3$ | H | $SCH(CH_3)COOC_2H_5$ |
| 1-1504 | H | Cl | $CH_3$ | $CF_3$ | H | $SCH(CH_3)COO^nC_3H_7$ |
| 1-1505 | H | Cl | $CH_3$ | $CF_3$ | H | $SCH(CH_3)COO^nC_4H_9$ |
| 1-1506 | H | Cl | $CH_3$ | $CF_3$ | H | $SCH(CH_3)COO^nC_5H_{11}$ |
| 1-1507 | H | Cl | $CH_3$ | $CF_3$ | H | $SCH(CH_3)COO^iC_3H_7$ |
| 1-1508 | H | Cl | $CH_3$ | $CF_3$ | H | $SCH(CH_3)COO^cC_5H_9$ |
| 1-1509 | H | Cl | $CH_3$ | $CF_3$ | H | $SCH(CH_3)COO^cC_6H_{11}$ |
| 1-1510 | H | Cl | $CH_3$ | $CF_3$ | H | $SCH_2CON(CH_3)_2$ |
| 1-1511 | H | Cl | $CH_3$ | $CF_3$ | H | $SCH_2CON(C_2H_5)_2$ |
| 1-1512 | H | Cl | $CH_3$ | $CF_3$ | H | $SCH_2CON(tetramethylene)$ |

TABLE 1-continued

Compounds of the formula:

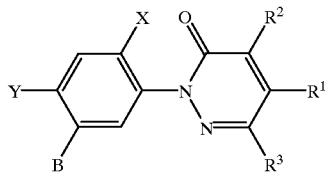

| Compound No. | X | Y | $R^3$ | $R^1$ | $R^2$ | B |
|---|---|---|---|---|---|---|
| 1-1513 | H | Cl | $CH_3$ | $CF_3$ | H | $SCH_2CON$(pentamethylene) |
| 1-1514 | H | Cl | $CH_3$ | $CF_3$ | H | $SCH_2CON$(ethyleneoxyethylene) |
| 1-1515 | H | Cl | $CH_3$ | $CF_3$ | H | $SCH(CH_3)CON(CH_3)_2$ |
| 1-1516 | H | Cl | $CH_3$ | $CF_3$ | H | $SCH(CH_3)CON(C_2H_5)_2$ |
| 1-1517 | H | Cl | $CH_3$ | $CF_3$ | H | $SCH(CH_3)CON$(tetramethylene) |
| 1-1518 | H | Cl | $CH_3$ | $CF_3$ | H | $SCH(CH_3)CON$(pentamethylene) |
| 1-1519 | F | Cl | $CH_3$ | $CF_3$ | H | $SCH_3$ |
| 1-1520 | F | Cl | $CH_3$ | $CF_3$ | H | $SC_2H_5$ |
| 1-1521 | F | Cl | $CH_3$ | $CF_3$ | H | $S^iC_3H_7$ |
| 1-1522 | F | Cl | $CH_3$ | $CF_3$ | H | $SCH_2CH_2Cl$ |
| 1-1523 | F | Cl | $CH_3$ | $CF_3$ | H | $S^cC_5H_9$ |
| 1-1524 | F | Cl | $CH_3$ | $CF_3$ | H | $S^cC_6H_{11}$ |
| 1-1525 | F | Cl | $CH_3$ | $CF_3$ | H | $SCH_2CH=CH_2$ |
| 1-1526 | F | Cl | $CH_3$ | $CF_3$ | H | $SCH_2CCl=CH_2$ |
| 1-1527 | F | Cl | $CH_3$ | $CF_3$ | H | $SCH_2CCl=CHCl$ |
| 1-1528 | F | Cl | $CH_3$ | $CF_3$ | H | $SCH(CH_3)CH=CH_2$ |
| 1-1529 | F | Cl | $CH_3$ | $CF_3$ | H | $SCH_2C\equiv CH$ |
| 1-1530 | F | Cl | $CH_3$ | $CF_3$ | H | $SCH(CH_3)C\equiv CH$ |
| 1-1531 | F | Cl | $CH_3$ | $CF_3$ | H | $SCH_2COOCH_3$ |
| 1-1532 | F | Cl | $CH_3$ | $CF_3$ | H | $SCH_2COOC_2H_5$ |
| 1-1533 | F | Cl | $CH_3$ | $CF_3$ | H | $SCH_2COO^nC_3H_7$ |
| 1-1534 | F | Cl | $CH_3$ | $CF_3$ | H | $SCH_2COO^nC_4H_9$ |
| 1-1535 | F | Cl | $CH_3$ | $CF_3$ | H | $SCH_2COO^nC_5H_{11}$ |
| 1-1536 | F | Cl | $CH_3$ | $CF_3$ | H | $SCH_2COO^iC_3H_7$ |
| 1-1537 | F | Cl | $CH_3$ | $CF_3$ | H | $SCH_2COO^cC_5H_9$ |
| 1-1538 | F | Cl | $CH_3$ | $CF_3$ | H | $SCH_2COO^cC_6H_{11}$ |
| 1-1539 | F | Cl | $CH_3$ | $CF_3$ | H | $SCH(CH_3)COOCH_3$ |
| 1-1540 | F | Cl | $CH_3$ | $CF_3$ | H | $SCH(CH_3)COOC_2H_5$ |
| 1-1541 | F | Cl | $CH_3$ | $CF_3$ | H | $SCH(CH_3)COO^nC_3H_7$ |
| 1-1542 | F | Cl | $CH_3$ | $CF_3$ | H | $SCH(CH_3)COO^nC_4H_9$ |
| 1-1543 | F | Cl | $CH_3$ | $CF_3$ | H | $SCH(CH_3)COO^nC_5H_{11}$ |
| 1-1544 | F | Cl | $CH_3$ | $CF_3$ | H | $SCH(CH_3)COO^iC_3H_7$ |
| 1-1545 | F | Cl | $CH_3$ | $CF_3$ | H | $SCH(CH_3)COO^cC_5H_9$ |
| 1-1546 | F | Cl | $CH_3$ | $CF_3$ | H | $SCH(CH_3)COO^cC_6H_{11}$ |
| 1-1547 | F | Cl | $CH_3$ | $CF_3$ | H | $SCH_2CON(CH_3)_2$ |
| 1-1548 | F | Cl | $CH_3$ | $CF_3$ | H | $SCH_2CON(C_2H_5)_2$ |
| 1-1549 | F | Cl | $CH_3$ | $CF_3$ | H | $SCH_2CON$(tetramethylene) |
| 1-1550 | F | Cl | $CH_3$ | $CF_3$ | H | $SCH_2CON$(pentamethylene) |
| 1-1551 | F | Cl | $CH_3$ | $CF_3$ | H | $SCH_2CON$(ethyleneoxyethylene) |
| 1-1552 | F | Cl | $CH_3$ | $CF_3$ | H | $SCH(CH_3)CON(CH_3)_2$ |
| 1-1553 | F | Cl | $CH_3$ | $CF_3$ | H | $SCH(CH_3)CON(C_2H_5)_2$ |
| 1-1554 | F | Cl | $CH_3$ | $CF_3$ | H | $SCH(CH_3)CON$(tetramethylene) |
| 1-1555 | F | Cl | $CH_3$ | $CF_3$ | H | $SCH(CH_3)CON$(pentamethylene) |
| 1-1556 | H | F | $CH_3$ | $CF_3$ | H | $SO_2Cl$ |
| 1-1557 | H | Cl | $CH_3$ | $CF_3$ | H | $SO_2Cl$ |
| 1-1558 | H | Br | $CH_3$ | $CF_3$ | H | $SO_2Cl$ |
| 1-1559 | F | F | $CH_3$ | $CF_3$ | H | $SO_2Cl$ |
| 1-1560 | F | Cl | $CH_3$ | $CF_3$ | H | $SO_2Cl$ |
| 1-1561 | F | Br | $CH_3$ | $CF_3$ | H | $SO_2Cl$ |
| 1-1562 | H | Cl | $CH_3$ | $CF_3$ | H | $SO_2OCH_3$ |
| 1-1563 | H | Cl | $CH_3$ | $CF_3$ | H | $SO_2OC_2H_5$ |
| 1-1564 | H | Cl | $CH_3$ | $CF_3$ | H | $SO_2O^iC_3H_7$ |
| 1-1565 | H | Cl | $CH_3$ | $CF_3$ | H | $SO_2OCH_2CH=CH_2$ |
| 1-1566 | F | Cl | $CH_3$ | $CF_3$ | H | $SO_2OCH_3$ |
| 1-1567 | F | Cl | $CH_3$ | $CF_3$ | H | $SO_2OC_2H_5$ |
| 1-1568 | F | Cl | $CH_3$ | $CF_3$ | H | $SO_2O^iC_3H_7$ |
| 1-1569 | F | Cl | $CH_3$ | $CF_3$ | H | $SO_2OCH_2CH=CH_2$ |
| 1-1570 | H | Cl | $CH_3$ | $CF_3$ | H | $SO_2N(CH_3)_2$ |

TABLE 1-continued

Compounds of the formula:

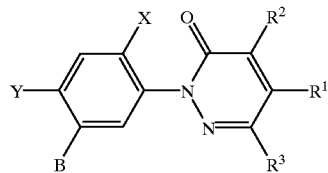

| Compound No. | X | Y | $R^3$ | $R^1$ | $R^2$ | B |
|---|---|---|---|---|---|---|
| 1-1571 | H | Cl | $CH_3$ | $CF_3$ | H | $SO_2N(C_2H_5)_2$ |
| 1-1572 | F | Cl | $CH_3$ | $CF_3$ | H | $SO_2N(CH_3)_2$ |
| 1-1573 | F | Cl | $CH_3$ | $CF_3$ | H | $SO_2N(C_2H_5)_2$ |
| 1-1574 | H | Cl | $CH_3$ | $CF_3$ | H | COOH |
| 1-1575 | H | Cl | $CH_3$ | $CF_3$ | H | $COOCH_3$ |
| 1-1576 | H | Cl | $CH_3$ | $CF_3$ | H | $COOC_2H_5$ |
| 1-1577 | H | Cl | $CH_3$ | $CF_3$ | H | $COO^nC_3H_7$ |
| 1-1578 | H | Cl | $CH_3$ | $CF_3$ | H | $COO^nC_4H_9$ |
| 1-1579 | H | Cl | $CH_3$ | $CF_3$ | H | $COO^nC_5H_{11}$ |
| 1-1580 | H | Cl | $CH_3$ | $CF_3$ | H | $COO^iC_3H_7$ |
| 1-1581 | H | Cl | $CH_3$ | $CF_3$ | H | $COOCH_2CH_2Cl$ |
| 1-1582 | H | Cl | $CH_3$ | $CF_3$ | H | $COOCH_2CH_2Br$ |
| 1-1583 | H | Cl | $CH_3$ | $CF_3$ | H | $CON(CH_3)_2$ |
| 1-1584 | H | Cl | $CH_3$ | $CF_3$ | H | $CONHCH_3$ |
| 1-1585 | H | Cl | $CH_3$ | $CF_3$ | H | $CON(C_2H_5)_2$ |
| 1-1586 | H | Cl | $CH_3$ | $CF_3$ | H | $CONHC_2H_5$ |
| 1-1587 | H | Cl | $CH_3$ | $CF_3$ | H | $COCH_3$ |
| 1-1588 | H | Cl | $CH_3$ | $CF_3$ | H | $COC_2H_5$ |
| 1-1589 | H | Cl | $CH_3$ | $CF_3$ | H | $COCH_2Cl$ |
| 1-1590 | H | Cl | $CH_3$ | $CF_3$ | H | CHO |
| 1-1591 | H | Cl | $CH_3$ | $CF_3$ | H | $CH=CHCOOCH_3$ |
| 1-1592 | H | Cl | $CH_3$ | $CF_3$ | H | $CH=CHCOOC_2H_5$ |
| 1-1593 | H | Cl | $CH_3$ | $CF_3$ | H | $CH_2CH_2COOCH_3$ |
| 1-1594 | H | Cl | $CH_3$ | $CF_3$ | H | $CH_2CH_2COOC_2H_5$ |
| 1-1595 | F | Cl | $CH_3$ | $CF_3$ | H | COOH |
| 1-1596 | F | Cl | $CH_3$ | $CF_3$ | H | $COOCH_3$ |
| 1-1597 | F | Cl | $CH_3$ | $CF_3$ | H | $COOC_2H_5$ |
| 1-1598 | F | Cl | $CH_3$ | $CF_3$ | H | $COO^nC_3H_7$ |
| 1-1599 | F | Cl | $CH_3$ | $CF_3$ | H | $COO^nC_4H_9$ |
| 1-1600 | F | Cl | $CH_3$ | $CF_3$ | H | $COO^nC_5H_{11}$ |
| 1-1601 | F | Cl | $CH_3$ | $CF_3$ | H | $COO^iC_3H_7$ |
| 1-1602 | F | Cl | $CH_3$ | $CF_3$ | H | $COOCH_2CH_2Cl$ |
| 1-1603 | F | Cl | $CH_3$ | $CF_3$ | H | $COOCH_2CH_2Br$ |
| 1-1604 | F | Cl | $CH_3$ | $CF_3$ | H | $CON(CH_3)_2$ |
| 1-1605 | F | Cl | $CH_3$ | $CF_3$ | H | $CONHCH_3$ |
| 1-1606 | F | Cl | $CH_3$ | $CF_3$ | H | $CON(C_2H_5)_2$ |
| 1-1607 | F | Cl | $CH_3$ | $CF_3$ | H | $CONHC_2H_5$ |
| 1-1608 | F | Cl | $CH_3$ | $CF_3$ | H | $COCH_3$ |
| 1-1609 | F | Cl | $CH_3$ | $CF_3$ | H | $COC_2H_5$ |
| 1-1610 | F | Cl | $CH_3$ | $CF_3$ | H | $COCH_2Cl$ |
| 1-1611 | F | Cl | $CH_3$ | $CF_3$ | H | CHO |
| 1-1612 | F | Cl | $CH_3$ | $CF_3$ | H | $CH=CHCOOCH_3$ |
| 1-1613 | F | Cl | $CH_3$ | $CF_3$ | H | $CH=CHCOOC_2H_5$ |
| 1-1614 | F | Cl | $CH_3$ | $CF_3$ | H | $CH_2CH_2COOCH_3$ |
| 1-1615 | F | Cl | $CH_3$ | $CF_3$ | H | $CH_2CH_2COOC_2H_5$ |
| 1-1616 | H | F | $CH_3$ | $CF_3$ | H | H |
| 1-1617 | H | Cl | $CH_3$ | $CF_3$ | H | H |
| 1-1618 | H | Br | $CH_3$ | $CF_3$ | H | H |
| 1-1619 | F | F | $CH_3$ | $CF_3$ | H | H |
| 1-1620 | F | Cl | $CH_3$ | $CF_3$ | H | H |
| 1-1621 | F | Br | $CH_3$ | $CF_3$ | H | H |
| 1-1622 | F | Cl | H | $CF_3$ | $CH_3$ | $CH_2CHClCO_2C_2H_5$ |
| 1-1623 | F | Cl | H | $CF_3$ | H | $CH_2CHClCO_2C_2H_5$ |
| 1-1624 | F | Cl | H | $CF_3$ | $CH_3$ | $CH_2CHClCO_2CH_3$ |
| 1-1625 | F | Cl | H | $CF_3$ | H | $CH_2CHClCO_2CH_3$ |
| 1-1626 | F | Cl | H | $CF_3$ | H | $OCH_2CO_2H$ |
| 1-1627 | F | Cl | H | $CF_3$ | $CH_3$ | $OCH_2CO_2H$ |
| 1-1628 | F | Cl | $CH_3$ | $CF_3$ | H | $OCH_2CO_2H$ |
| 1-1629 | F | Cl | H | $CF_3$ | H | $OCH(CH_3)CO_2H$ |
| 1-1630 | F | Cl | H | $CF_3$ | $CH_3$ | $OCH(CH_3)CO_2H$ |
| 1-1631 | F | Cl | $CH_3$ | $CF_3$ | H | $OCH(CH_3)CO_2H$ |
| 1-1632 | H | Cl | H | $CF_3$ | H | $OCH_2CO_2H$ |
| 1-1633 | H | Cl | H | $CF_3$ | $CH_3$ | $OCH_2CO_2H$ |
| 1-1634 | H | Cl | $CH_3$ | $CF_3$ | H | $OCH_2CO_2H$ |

TABLE 1-continued

Compounds of the formula:

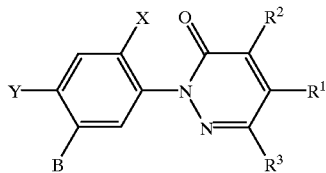

| Compound No. | X | Y | $R^3$ | $R^1$ | $R^2$ | B |
|---|---|---|---|---|---|---|
| 1-1635 | H | Cl | H | $CF_3$ | H | $OCH(CH_3)CO_2H$ |
| 1-1636 | H | Cl | H | $CF_3$ | $CH_3$ | $OCH(CH_3)CO_2H$ |
| 1-1637 | H | Cl | $CH_3$ | $CF_3$ | H | $OCH(CH_3)CO_2H$ |
| 1-1638 | F | Cl | H | $CF_3$ | H | $SCH_2CO_2H$ |
| 1-1639 | F | Cl | H | $CF_3$ | $CH_3$ | $SCH_2CO_2H$ |
| 1-1640 | F | Cl | $CH_3$ | $CF_3$ | H | $SCH_2CO_2H$ |
| 1-1641 | F | Cl | H | $CF_3$ | H | $SCH(CH_3)CO_2H$ |
| 1-1642 | F | Cl | H | $CF_3$ | $CH_3$ | $SCH(CH_3)CO_2H$ |
| 1-1643 | F | Cl | $CH_3$ | $CF_3$ | H | $SCH(CH_3)CO_2H$ |
| 1-1644 | H | Cl | H | $CF_3$ | H | $SCH_2CO_2H$ |
| 1-1645 | H | Cl | H | $CF_3$ | $CH_3$ | $SCH_2CO_2H$ |
| 1-1646 | H | Cl | $CH_3$ | $CF_3$ | H | $SCH_2CO_2H$ |
| 1-1647 | H | Cl | H | $CF_3$ | H | $SCH(CH_3)CO_2H$ |
| 1-1648 | H | Cl | H | $CF_3$ | $CH_3$ | $SCH(CH_3)CO_2H$ |
| 1-1649 | H | Cl | $CH_3$ | $CF_3$ | H | $SCH(CH_3)CO_2H$ |
| 1-1650 | F | Cl | H | $CF_3$ | $CH_3$ | $OCH(C_2H_5))CO_2CH_3$ |
| 1-1651 | Cl | Cl | H | $CF_3$ | H | $OCH_2CO_2CH_3$ |
| 1-1652 | Cl | Cl | H | $CF_3$ | H | $OCH_2CO_2C_2H_5$ |
| 1-1653 | Cl | Cl | H | $CF_3$ | H | $OCH_2CO_2{}^iC_3H_7$ |
| 1-1654 | Cl | Cl | H | $CF_3$ | $CH_3$ | $OCH_2CO_2CH_3$ |
| 1-1655 | Cl | Cl | H | $CF_3$ | $CH_3$ | $OCH_2CO_2C_2H_5$ |
| 1-1656 | Cl | Cl | H | $CF_3$ | $CH_3$ | $OCH_2CO_2{}^iC_3H_7$ |
| 1-1657 | Cl | Cl | $CH_3$ | $CF_3$ | H | $OCH_2CO_2CH_3$ |
| 1-1658 | Cl | Cl | $CH_3$ | $CF_3$ | H | $OCH_2CO_2C_2H_5$ |
| 1-1659 | Cl | Cl | $CH_3$ | $CF_3$ | H | $OCH_2CO_2{}^iC_3H_7$ |
| 1-1660 | Cl | Cl | H | $CF_3$ | H | $OCH_2C{\equiv}CH$ |
| 1-1661 | Cl | Cl | H | $CF_3$ | H | $OCH(CH_3)C{\equiv}CH$ |
| 1-1662 | Cl | Cl | H | $CF_3$ | H | $OCH(CH_3)CO_2C_2H_5$ |
| 1-1663 | Cl | Cl | H | $CF_3$ | $CH_3$ | $OCH_2C{\equiv}CH$ |
| 1-1664 | Cl | Cl | H | $CF_3$ | $CH_3$ | $OCH(CH_3)C{\equiv}CH$ |
| 1-1665 | Cl | Cl | H | $CF_3$ | $CH_3$ | $OCH(CH_3)CO_2C_2H_5$ |
| 1-1666 | Cl | Cl | $CH_3$ | $CF_3$ | H | $OCH_2C{\equiv}CH$ |
| 1-1667 | Cl | Cl | $CH_3$ | $CF_3$ | H | $OCH(CH_3)C{\equiv}CH$ |
| 1-1668 | Cl | Cl | $CH_3$ | $CF_3$ | H | $OCH(CH_3)CO_2C_2H_5$ |
| 1-1669 | F | Br | H | $CF_3$ | H | $OCH_2CO_2CH_3$ |
| 1-1670 | F | Br | H | $CF_3$ | H | $OCH_2CO_2C_2H_5$ |
| 1-1671 | F | Br | H | $CF_3$ | H | $OCH_2CO_2{}^iC_3H_7$ |
| 1-1672 | F | Br | H | $CF_3$ | $CH_3$ | $OCH_2CO_2CH_3$ |
| 1-1673 | F | Br | H | $CF_3$ | $CH_3$ | $OCH_2CO_2C_2H_5$ |
| 1-1674 | F | Br | H | $CF_3$ | $CH_3$ | $OCH_2CO_2{}^iC_3H_7$ |
| 1-1675 | F | Br | $CH_3$ | $CF_3$ | H | $OCH_2CO_2CH_3$ |
| 1-1676 | F | Br | $CH_3$ | $CF_3$ | H | $OCH_2CO_2C_2H_5$ |
| 1-1677 | F | Br | $CH_3$ | $CF_3$ | H | $OCH_2CO_2C_3H_7$ |
| 1-1678 | F | Br | H | $CF_3$ | H | $OCH_2C{\equiv}CH$ |
| 1-1679 | F | Br | H | $CF_3$ | H | $OCH(CH_3)C{\equiv}CH$ |
| 1-1680 | F | Br | H | $CF_3$ | H | $OCH(CH_3)CO_2C_2H_5$ |
| 1-1681 | F | Br | H | $CF_3$ | $CH_3$ | $OCH_2C{\equiv}CH$ |
| 1-1682 | F | Br | H | $CF_3$ | $CH_3$ | $OCH(CH_3)C{\equiv}CH$ |
| 1-1683 | F | Br | H | $CF_3$ | $CH_3$ | $OCH(CH_3)CO_2C_2H_5$ |
| 1-1684 | F | Br | $CH_3$ | $CF_3$ | H | $OCH_2C{\equiv}CH$ |
| 1-1685 | F | Br | $CH_3$ | $CF_3$ | H | $OCH(CH_3)C{\equiv}CH$ |
| 1-1686 | F | Br | $CH_3$ | $CF_3$ | H | $OCH(CH_3)CO_2C_2H_5$ |
| 1-1687 | Cl | Cl | H | $CF_3$ | H | H |
| 1-1688 | Cl | Cl | H | $CF_3$ | H | OH |
| 1-1689 | Cl | Cl | H | $CF_3$ | H | $NO_2$ |
| 1-1690 | Cl | Cl | H | $CF_3$ | H | $NH_2$ |
| 1-1691 | Cl | Cl | H | $CF_3$ | H | $NHSO_2CH_3$ |
| 1-1692 | Cl | Cl | H | $CF_3$ | H | $NHSO_2CH_2Cl$ |
| 1-1693 | Cl | Cl | H | $CF_3$ | H | $NHCH_2CO_2CH_3$ |
| 1-1694 | Cl | Cl | H | $CF_3$ | H | $NHCH_2CO_2C_2H_5$ |
| 1-1695 | Cl | Cl | H | $CF_3$ | H | $NHCH_2CO_2{}^iC_3H_7$ |
| 1-1696 | Cl | Cl | H | $CF_3$ | H | $NHCH(CH_3)CO_2CH_3$ |
| 1-1697 | Cl | Cl | H | $CF_3$ | H | $NHCH(CH_3)CO_2C_2H_5$ |
| 1-1698 | Cl | Cl | H | $CF_3$ | H | $NHCH(CH_3)CO_2{}^iC_3H_7$ |

TABLE 1-continued

Compounds of the formula:

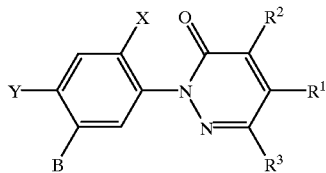

| Compound No. | X | Y | $R^3$ | $R^1$ | $R^2$ | B |
|---|---|---|---|---|---|---|
| 1-1699 | Cl | Cl | H | $CF_3$ | H | $CO_2H$ |
| 1-1700 | Cl | Cl | H | $CF_3$ | H | $CO_2CH_3$ |
| 1-1701 | Cl | Cl | H | $CF_3$ | H | $CO_2C_2H_5$ |
| 1-1702 | Cl | Cl | H | $CF_3$ | H | $CO_2{}^nC_3H_7$ |
| 1-1703 | Cl | Cl | H | $CF_3$ | H | $CO_2{}^nC_4H_9$ |
| 1-1704 | Cl | Cl | H | $CF_3$ | H | $CO_2C_5H_{11}$ |
| 1-1705 | Cl | Cl | H | $CF_3$ | H | $CO_2{}^iC_3H_7$ |
| 1-1706 | Cl | Cl | H | $CF_3$ | H | $CO_2CH_2CH_2Cl$ |
| 1-1707 | Cl | Cl | H | $CF_3$ | H | $CO_2CH_2CH_2Br$ |
| 1-1708 | Cl | Cl | H | $CF_3$ | H | $CON(CH_3)_2$ |
| 1-1709 | Cl | Cl | H | $CF_3$ | H | $CONHCH_3$ |
| 1-1710 | Cl | Cl | H | $CF_3$ | H | $CON(C_2H_5)_2$ |
| 1-1711 | Cl | Cl | H | $CF_3$ | H | $CONHC_2H_5$ |
| 1-1712 | Cl | Cl | H | $CF_3$ | H | $COCH_3$ |
| 1-1713 | Cl | Cl | H | $CF_3$ | H | $COC_2H_5$ |
| 1-1714 | Cl | Cl | H | $CF_3$ | H | $COCH_2Cl$ |
| 1-1715 | Cl | Cl | H | $CF_3$ | H | CHO |
| 1-1716 | Cl | Cl | H | $CF_3$ | H | $CH=CHCO_2CH_3$ |
| 1-1717 | Cl | Cl | H | $CF_3$ | H | $O^iC_3H_7$ |
| 1-1718 | Cl | Cl | H | $CF_3$ | $CH_3$ | H |
| 1-1719 | Cl | Cl | H | $CF_3$ | $CH_3$ | OH |
| 1-1720 | Cl | Cl | H | $CF_3$ | $CH_3$ | $NO_2$ |
| 1-1721 | Cl | Cl | H | $CF_3$ | $CH_3$ | $NH_2$ |
| 1-1722 | Cl | Cl | H | $CF_3$ | $CH_3$ | $NHSO_2CH_3$ |
| 1-1723 | Cl | Cl | H | $CF_3$ | $CH_3$ | $NHSO_2CH_2Cl$ |
| 1-1724 | Cl | Cl | H | $CF_3$ | $CH_3$ | $NHCH_2CO_2CH_3$ |
| 1-1725 | Cl | Cl | H | $CF_3$ | $CH_3$ | $NHCH_2CO_2C_2H_5$ |
| 1-1726 | Cl | Cl | H | $CF_3$ | $CH_3$ | $NHCH_2CO_2{}^iC_3H_7$ |
| 1-1727 | Cl | Cl | H | $CF_3$ | $CH_3$ | $NHCH(CH_3)CO_2CH_3$ |
| 1-1728 | Cl | Cl | H | $CF_3$ | $CH_3$ | $NHCH(CH_3)CO_2C_2H_5$ |
| 1-1729 | Cl | Cl | H | $CF_3$ | $CH_3$ | $NHCH(CH_3)CO_2{}^iC_3H_7$ |
| 1-1730 | Cl | Cl | H | $CF_3$ | $CH_3$ | $CO_2H$ |
| 1-1731 | Cl | Cl | H | $CF_3$ | $CH_3$ | $CO_2CH_3$ |
| 1-1732 | Cl | Cl | H | $CF_3$ | $CH_3$ | $CO_2C_2H_5$ |
| 1-1733 | Cl | Cl | H | $CF_3$ | $CH_3$ | $CO_2{}^nC_3H_7$ |
| 1-1734 | Cl | Cl | H | $CF_3$ | $CH_3$ | $CO_2{}^nC_4H_9$ |
| 1-1735 | Cl | Cl | H | $CF_3$ | $CH_3$ | $CO_2{}^nC_5H_{11}$ |
| 1-1736 | Cl | Cl | H | $CF_3$ | $CH_3$ | $CO_2{}^iC_3H_7$ |
| 1-1737 | Cl | Cl | H | $CF_3$ | $CH_3$ | $CO_2CH_2CH_2Cl$ |
| 1-1738 | Cl | Cl | H | $CF_3$ | $CH_3$ | $CO_2CH_2CH_2Br$ |
| 1-1739 | Cl | Cl | H | $CF_3$ | $CH_3$ | $CON(CH_3)_2$ |
| 1-1740 | Cl | Cl | H | $CF_3$ | $CH_3$ | $CONHCH_3$ |
| 1-1741 | Cl | Cl | H | $CF_3$ | $CH_3$ | $CON(C_2H_5)_2$ |
| 1-1742 | Cl | Cl | H | $CF_3$ | $CH_3$ | $CONHC_2H_5$ |
| 1-1743 | Cl | Cl | H | $CF_3$ | $CH_3$ | $COCH_3$ |
| 1-1744 | Cl | Cl | H | $CF_3$ | $CH_3$ | $COC_2H_5$ |
| 1-1745 | Cl | Cl | H | $CF_3$ | $CH_3$ | $COCH_2Cl$ |
| 1-1746 | Cl | Cl | H | $CF_3$ | $CH_3$ | CHO |
| 1-1747 | Cl | Cl | H | $CF_3$ | $CH_3$ | $CH=CHCO_2CH_3$ |
| 1-1748 | Cl | Cl | H | $CF_3$ | $CH_3$ | $O^iC_3H_7$ |
| 1-1749 | Cl | Cl | $CH_3$ | $CF_3$ | H | H |
| 1-1750 | Cl | Cl | $CH_3$ | $CF_3$ | H | CH |
| 1-1751 | Cl | Cl | $CH_3$ | $CF_3$ | H | $NO_2$ |
| 1-1752 | Cl | Cl | $CH_3$ | $CF_3$ | H | $NH_2$ |
| 1-1753 | Cl | Cl | $CH_3$ | $CF_3$ | H | $NHSO_2CH_3$ |
| 1-1754 | Cl | Cl | $CH_3$ | $CF_3$ | H | $NHSO_2CH_2Cl$ |
| 1-1755 | Cl | Cl | $CH_3$ | $CF_3$ | H | $NHCH_2CO_2CH_3$ |
| 1-1756 | Cl | Cl | $CH_3$ | $CF_3$ | H | $NHCH_2CO_2C_2H_5$ |
| 1-1757 | Cl | Cl | $CH_3$ | $CF_3$ | H | $NHCH_2CO_2{}^iC_3H_7$ |
| 1-1758 | Cl | Cl | $CH_3$ | $CF_3$ | H | $NHCH(CH_3)CO_2CH_3$ |
| 1-1759 | Cl | Cl | $CH_3$ | $CF_3$ | H | $NHCH(CH_3)CO_2C_2H_5$ |
| 1-1760 | Cl | Cl | $CH_3$ | $CF_3$ | H | $NHCH(CH_3)CO_2{}^iC_3H_7$ |
| 1-1761 | Cl | Cl | $CH_3$ | $CF_3$ | H | $CO_2H$ |
| 1-1762 | Cl | Cl | $CH_3$ | $CF_3$ | H | $CO_2CH_3$ |

TABLE 1-continued

Compounds of the formula:

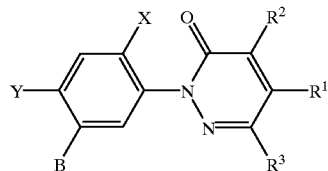

| Compound No. | X | Y | $R^3$ | $R^1$ | $R^2$ | B |
|---|---|---|---|---|---|---|
| 1-1763 | Cl | Cl | $CH_3$ | $CF_3$ | H | $CO_2C_2H_5$ |
| 1-1764 | Cl | Cl | $CH_3$ | $CF_3$ | H | $CO_2{}^nC_3H_7$ |
| 1-1765 | Cl | Cl | $CH_3$ | $CF_3$ | H | $CO_2{}^nC_4H_9$ |
| 1-1766 | Cl | Cl | $CH_3$ | $CF_3$ | H | $CO_2{}^nC_5H_{11}$ |
| 1-1767 | Cl | Cl | $CH_3$ | $CF_3$ | H | $CO_2{}^iC_3H_7$ |
| 1-1768 | Cl | Cl | $CH_3$ | $CF_3$ | H | $CO_2CH_2CH_2Cl$ |
| 1-1769 | Cl | Cl | $CH_3$ | $CF_3$ | H | $CO_2CH_2CH_2Br$ |
| 1-1770 | Cl | Cl | $CH_3$ | $CF_3$ | H | $CON(CH_3)_2$ |
| 1-1771 | Cl | Cl | $CH_3$ | $CF_3$ | H | $CONHCH_3$ |
| 1-1772 | Cl | Cl | $CH_3$ | $CF_3$ | H | $CON(C_2H_5)_2$ |
| 1-1773 | Cl | Cl | $CH_3$ | $CF_3$ | H | $CONHC_2H_5$ |
| 1-1774 | Cl | Cl | $CH_3$ | $CF_3$ | H | $COCH_3$ |
| 1-1775 | Cl | Cl | $CH_3$ | $CF_3$ | H | $COC_2H_5$ |
| 1-1776 | Cl | Cl | $CH_3$ | $CF_3$ | H | $COCH_2Cl$ |
| 1-1777 | Cl | Cl | $CH_3$ | $CF_3$ | H | CHO |
| 1-1778 | Cl | Cl | $CH_3$ | $CF_3$ | H | $CH=CHCO_2CH_3$ |
| 1-1779 | Cl | Cl | $CH_3$ | $CF_3$ | H | $O^iC_3H_7$ |
| 1-1780 | F | Br | H | $CF_3$ | H | $O^iC_3H_7$ |
| 1-1781 | F | Br | H | $CF_3$ | H | $N(SO_2CH_3)_2$ |
| 1-1782 | F | Br | H | $CF_3$ | H | $NHSO_2CH_3$ |
| 1-1783 | F | Br | H | $CF_3$ | $CH_3$ | $O^iC_3H_7$ |
| 1-1784 | F | Br | H | $CF_3$ | $CH_3$ | $N(SO_2CH_3)_2$ |
| 1-1785 | F | Br | H | $CF_3$ | $CH_3$ | $NHSO_2CH_3$ |
| 1-1786 | F | Br | $CH_3$ | $CF_3$ | H | $O^iC_3H_7$ |
| 1-1787 | F | Br | $CH_3$ | $CF_3$ | H | $N(SO_2CH_3)_2$ |
| 1-1788 | F | Br | $CH_3$ | $CF_3$ | H | $NHSO_2CH_3$ |
| 1-1789 | F | Cl | H | $CF_3$ | $CH_3$ | $OCH_2C(CH_3)=CH_2$ |
| 1-1790 | F | Cl | H | $CF_3$ | $CH_3$ | $OCH_2CO_2C_7H_{15}$ |
| 1-1791 | F | Cl | H | $CF_3$ | $CH_3$ | $OCH_2CO_2C_8H_{17}$ |
| 1-1792 | F | Cl | H | $CF_3$ | $CH_3$ | $COOCH_2C_6H_5$ |
| 1-1793 | F | Cl | H | $CF_3$ | $CH_3$ | $C(CH_3)=NOH$ |
| 1-1794 | F | Cl | H | $CF_3$ | $CH_3$ | $C(CH_3)=NOCH_3$ |
| 1-1795 | F | Cl | H | $CF_3$ | $CH_3$ | $C(CH_3)=NOC_2H_5$ |
| 1-1796 | F | Cl | H | $CF_3$ | $CH_3$ | $C(CH_3)=NO^iC_3H_7$ |
| 1-1797 | F | Cl | H | $CF_3$ | $CH_3$ | $C(C_2H_5)=NOH$ |
| 1-1798 | F | Cl | H | $CF_3$ | $CH_3$ | $C(C_2H_5)=NOCH_3$ |
| 1-1799 | F | Cl | H | $CF_3$ | $CH_3$ | $C(C_2H_5)=NOC_2H_5$ |
| 1-1800 | F | Cl | H | $CF_3$ | $CH_3$ | $C(C_2H_5)=NO^iC_3H_7$ |
| 1-1801 | F | Cl | H | $CF_3$ | $CH_3$ | $C(CH_3)=NNH_2$ |
| 1-1802 | F | Cl | H | $CF_3$ | $CH_3$ | $C(CH_3)=NNHCH_3$ |
| 1-1803 | F | Cl | H | $CF_3$ | $CH_3$ | $C(CH_3)=NN(CH_3)_2$ |
| 1-1804 | F | Cl | H | $CF_3$ | $CH_3$ | $C(CH_3)=NNHC_2H_5$ |
| 1-1805 | F | Cl | H | $CF_3$ | $CH_3$ | $C(CH_3)=NN(C_2H_5)_2$ |
| 1-1806 | F | Cl | H | $CF_3$ | $CH_3$ | $C(C_2H_5)=NNH_2$ |
| 1-1807 | F | Cl | H | $CF_3$ | $CH_3$ | $C(C_2H_5)=NNHCH_3$ |
| 1-1808 | F | Cl | H | $CF_3$ | $CH_3$ | $C(C_2H_5)=NN(CH_3)_2$ |
| 1-1809 | F | Cl | H | $CF_3$ | $CH_3$ | $C(C_2H_5)=NNHC_2H_5$ |
| 1-1810 | F | Cl | H | $CF_3$ | $CH_3$ | $C(C_2H_5)=NN(C_2H_5)_2$ |
| 1-1811 | F | Cl | H | $CF_3$ | $CH_3$ | $C(CH_3)(OCH_3)_2$ |
| 1-1812 | F | Cl | H | $CF_3$ | $CH_3$ | $C(CH_3)(OC_2H_5)_2$ |
| 1-1813 | F | Cl | H | $CF_3$ | $CH_3$ | $C(CH_3)(C^iC_3H_7)_2$ |
| 1-1814 | F | Cl | H | $CF_3$ | $CH_3$ | ![dioxolane with CH3] |
| 1-1815 | F | Cl | H | $CF_3$ | $CH_3$ | ![dioxane with CH3] |

TABLE 1-continued

Compounds of the formula:

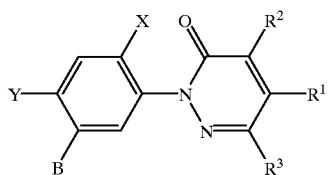

| Compound No. | X | Y | R³ | R¹ | R² | B |
|---|---|---|---|---|---|---|
| 1-1816 | F | Cl | H | $CF_3$ | $CH_3$ | ![dioxolane with $C_2H_5$] |
| 1-1817 | F | Cl | H | $CF_3$ | $CH_3$ | ![dioxane with $C_2H_5$] |
| 1-1818 | F | Cl | H | $CF_3$ | H | $OCH_2C(CH_3)=CH_2$ |
| 1-1819 | F | Cl | H | $CF_3$ | H | $OCH_2CO_2C_7H_{15}$ |
| 1-1820 | F | Cl | H | $CF_3$ | H | $OCH_2CO_2C_8H_{17}$ |
| 1-1821 | F | Cl | H | $CF_3$ | H | $COOCH_2C_6H_5$ |
| 1-1822 | F | Cl | H | $CF_3$ | H | $C(CH_3)=NOH$ |
| 1-1823 | F | Cl | H | $CF_3$ | H | $C(CH_3)=NOCH_3$ |
| 1-1824 | F | Cl | H | $CF_3$ | H | $C(CH_3)=NOC_2H_5$ |
| 1-1825 | F | Cl | H | $CF_3$ | H | $C(CH_3)=NO^iC_3H_7$ |
| 1-1826 | F | Cl | H | $CF_3$ | H | $C(C_2H_5)=NOH$ |
| 1-1827 | F | Cl | H | $CF_3$ | H | $C(C_2H_5)=NOCH_3$ |
| 1-1828 | F | Cl | H | $CF_3$ | H | $C(C_2H_5)=NOC_2H_5$ |
| 1-1829 | F | Cl | H | $CF_3$ | H | $C(C_2H_5)=NO^iC_3H_7$ |
| 1-1830 | F | Cl | H | $CF_3$ | H | $C(CH_3)=NNH_2$ |
| 1-1831 | F | Cl | H | $CF_3$ | H | $C(CH_3)=NNHCH_3$ |
| 1-1832 | F | Cl | H | $CF_3$ | H | $C(CH_3)=NN(CH_3)_2$ |
| 1-1833 | F | Cl | H | $CF_3$ | H | $C(CH_3)=NNHC_2H_5$ |
| 1-1834 | F | Cl | H | $CF_3$ | H | $C(CH_3)=NN(C_2H_5)_2$ |
| 1-1835 | F | Cl | H | $CF_3$ | H | $C(C_2H_5)=NNH_2$ |
| 1-1836 | F | Cl | H | $CF_3$ | H | $C(C_2H_5)=NNHCH_3$ |
| 1-1837 | F | Cl | H | $CF_3$ | H | $C(C_2H_5)=NN(CH_3)_2$ |
| 1-1838 | F | Cl | H | $CF_3$ | H | $C(C_2H_5)=NNHC_2H_5$ |
| 1-1839 | F | Cl | H | $CF_3$ | H | $C(C_2H_5)=NN(C_2H_5)_2$ |
| 1-1840 | F | Cl | H | $CF_3$ | H | $C(CH_3)(OCH_3)_2$ |
| 1-1841 | F | Cl | H | $CF_3$ | H | $C(CH_3)(OC_2H_5)_2$ |
| 1-1842 | F | Cl | H | $CF_3$ | H | $C(CH_3)(O^iC_3H_7)_2$ |
| 1-1843 | F | Cl | H | $CF_3$ | H | ![dioxolane with $CH_3$] |
| 1-1844 | F | Cl | H | $CF_3$ | H | ![dioxane with $CH_3$] |
| 1-1845 | F | Cl | H | $CF_3$ | H | ![dioxolane with $C_2H_5$] |

TABLE 1-continued

Compounds of the formula:

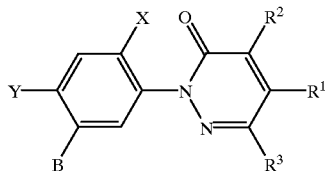

| Compound No. | X | Y | R³ | R¹ | R² | B |
|---|---|---|---|---|---|---|
| 1-1846 | F | Cl | H | CF₃ | H | (1,3-dioxolan-2-yl with C₂H₅) |
| 1-1847 | F | Cl | CH₃ | CF₃ | H | OCH₂C(CH₃)=CH₂ |
| 1-1848 | F | Cl | CH₃ | CF₃ | H | OCH₂CO₂C₇H₁₅ |
| 1-1849 | F | Cl | CH₃ | CF₃ | H | OCH₂CO₂C₈H₁₇ |
| 1-1850 | F | Cl | CH₃ | CF₃ | H | COOCH₂C₆H₅ |
| 1-1851 | F | Cl | CH₃ | CF₃ | H | C(CH₃)=NOH |
| 1-1852 | F | Cl | CH₃ | CF₃ | H | C(CH₃)=NOCH₃ |
| 1-1853 | F | Cl | CH₃ | CF₃ | H | C(CH₃)=NOC₂H₅ |
| 1-1854 | F | Cl | CH₃ | CF₃ | H | C(CH₃)=NOⁱC₃H₇ |
| 1-1855 | F | Cl | CH₃ | CF₃ | H | C(C₂H₅)=NOH |
| 1-1856 | F | Cl | CH₃ | CF₃ | H | C(C₂H₅)=NOCH₃ |
| 1-1857 | F | Cl | CH₃ | CF₃ | H | C(C₂H₅)=NOC₂H₅ |
| 1-1858 | F | Cl | CH₃ | CF₃ | H | C(C₂H₅)=NOⁱC₃H₇ |
| 1-1859 | F | Cl | CH₃ | CF₃ | H | C(CH₃)=NNH₂ |
| 1-1860 | F | Cl | CH₃ | CF₃ | H | C(CH₃)=NNHCH₃ |
| 1-1861 | F | Cl | CH₃ | CF₃ | H | C(CH₃)=NN(CH₃)₂ |
| 1-1862 | F | Cl | CH₃ | CF₃ | H | C(CH₃)=NNHC₂H₅ |
| 1-1863 | F | Cl | CH₃ | CF₃ | H | C(CH₃)=NN(C₂H₅)₂ |
| 1-1864 | F | Cl | CH₃ | CF₃ | H | C(C₂H₅)=NNH₂ |
| 1-1865 | F | Cl | CH₃ | CF₃ | H | C(C₂H₅)=NNHCH₃ |
| 1-1866 | F | Cl | CH₃ | CF₃ | H | C(C₂H₅)=NN(CH₃)₂ |
| 1-1867 | F | Cl | CH₃ | CF₃ | H | C(C₂H₅)=NNHC₂H₅ |
| 1-1868 | F | Cl | CH₃ | CF₃ | H | C(C₂H₅)=NN(C₂H₅)₂ |
| 1-1869 | F | Cl | CH₃ | CF₃ | H | C(CH₃)(OCH₃)₂ |
| 1-1870 | F | Cl | CH₃ | CF₃ | H | C(CH₃)(OC₂H₅)₂ |
| 1-1871 | F | Cl | CH₃ | CF₃ | H | C(CH₃)(CⁱC₃H₇)₂ |
| 1-1872 | F | Cl | CH₃ | CF₃ | H | (1,3-dioxolan-2-yl with CH₃) |
| 1-1873 | F | Cl | CH₃ | CF₃ | H | (1,3-dioxan-2-yl with CH₃) |
| 1-1874 | F | Cl | CH₃ | CF₃ | H | (1,3-dioxolan-2-yl with C₂H₅) |
| 1-1875 | F | Cl | CH₃ | CF₃ | H | (1,3-dioxan-2-yl with C₂H₅) |
| 1-1876 | H | Cl | H | CF₃ | CH₃ | OCH₂C(CH₃)=CH₂ |
| 1-1877 | H | Cl | H | CF₃ | CH₃ | OCH₂CO₂C₇H₁₅ |
| 1-1878 | H | Cl | H | CF₃ | CH₃ | OCH₂CO₂C₈H₁₇ |
| 1-1879 | H | Cl | H | CF₃ | CH₃ | COOCH₂C₆H₅ |
| 1-1880 | H | Cl | H | CF₃ | CH₃ | C(CH₃)=NOH |

TABLE 1-continued

Compounds of the formula:

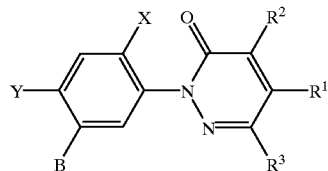

| Compound No. | X | Y | $R^3$ | $R^1$ | $R^2$ | B |
|---|---|---|---|---|---|---|
| 1-1881 | H | Cl | H | $CF_3$ | $CH_3$ | $C(CH_3)=NOCH_3$ |
| 1-1882 | H | Cl | H | $CF_3$ | $CH_3$ | $C(CH_3)=NOC_2H_5$ |
| 1-1883 | H | Cl | H | $CF_3$ | $CH_3$ | $C(CH_3)=NO^iC_3H_7$ |
| 1-1884 | H | Cl | H | $CF_3$ | $CH_3$ | $C(C_2H_5)=NOH$ |
| 1-1885 | H | Cl | H | $CF_3$ | $CH_3$ | $C(C_2H_5)=NOCH_3$ |
| 1-1886 | H | Cl | H | $CF_3$ | $CH_3$ | $C(C_2H_5)=NOC_2H_5$ |
| 1-1887 | H | Cl | H | $CF_3$ | $CH_3$ | $C(C_2H_5)=NO^iC_3H_7$ |
| 1-1888 | H | Cl | H | $CF_3$ | $CH_3$ | $C(CH_3)=NNH_2$ |
| 1-1889 | H | Cl | H | $CF_3$ | $CH_3$ | $C(CH_3)=NNHCH_3$ |
| 1-1890 | H | Cl | H | $CF_3$ | $CH_3$ | $C(CH_3)=NN(CH_3)_2$ |
| 1-1891 | H | Cl | H | $CF_3$ | $CH_3$ | $C(CH_3)=NNHC_2H_5$ |
| 1-1892 | H | Cl | H | $CF_3$ | $CH_3$ | $C(CH_3)=NN(C_2H_5)_2$ |
| 1-1893 | H | Cl | H | $CF_3$ | $CH_3$ | $C(C_2H_5)=NNH_2$ |
| 1-1894 | H | Cl | H | $CF_3$ | $CH_3$ | $C(C_2H_5)=NNHCH_3$ |
| 1-1895 | H | Cl | H | $CF_3$ | $CH_3$ | $C(C_2H_5)=NN(CH_3)_2$ |
| 1-1896 | H | Cl | H | $CF_3$ | $CH_3$ | $C(C_2H_5)=NNHC_2H_5$ |
| 1-1897 | H | Cl | H | $CF_3$ | $CH_3$ | $C(C_2H_5)=NN(C_2H_5)_2$ |
| 1-1898 | H | Cl | H | $CF_3$ | $CH_3$ | $C(CH_3)(OCH_3)_2$ |
| 1-1899 | H | Cl | H | $CF_3$ | $CH_3$ | $C(CH_3)(OC_2H_5)_2$ |
| 1-1900 | H | Cl | H | $CF_3$ | $CH_3$ | $C(CH_3)(C^iC_3H_7)_2$ |
| 1-1901 | H | Cl | H | $CF_3$ | $CH_3$ | 1,3-dioxolan-2-yl with $CH_3$ at C-2 |
| 1-1902 | H | Cl | H | $CF_3$ | $CH_3$ | 1,3-dioxolan-2-yl (isomer) with $CH_3$ |
| 1-1903 | H | Cl | H | $CF_3$ | $CH_3$ | 1,3-dioxolan-2-yl with $C_2H_5$ |
| 1-1904 | H | Cl | H | $CF_3$ | $CH_3$ | 1,3-dioxolan-2-yl (isomer) with $C_2H_5$ |
| 1-1905 | H | Cl | H | $CF_3$ | H | $OCH_2C(CH_3)=CH_2$ |
| 1-1906 | H | Cl | H | $CF_3$ | H | $OCH_2CO_2C_7H_{15}$ |
| 1-1907 | H | Cl | H | $CF_3$ | H | $OCH_2CO_2C_8H_{17}$ |
| 1-1908 | H | Cl | H | $CF_3$ | H | $COOCH_2C_6H_5$ |
| 1-1909 | H | Cl | H | $CF_3$ | H | $C(CH_3)=NOH$ |
| 1-1910 | H | Cl | H | $CF_3$ | H | $C(CH_3)=NOCH_3$ |
| 1-1911 | H | Cl | H | $CF_3$ | H | $C(CH_3)=NOC_2H_5$ |
| 1-1912 | H | Cl | H | $CF_3$ | H | $C(CH_3)=NO^iC_3H_7$ |
| 1-1913 | H | Cl | H | $CF_3$ | H | $C(C_2H_5)=NOH$ |
| 1-1914 | H | Cl | H | $CF_3$ | H | $C(C_2H_5)=NOCH_3$ |
| 1-1915 | H | Cl | H | $CF_3$ | H | $C(C_2H_5)=NOC_2H_5$ |
| 1-1916 | H | Cl | H | $CF_3$ | H | $C(C_2H_5)=NO^iC_3H_7$ |
| 1-1917 | H | Cl | H | $CF_3$ | H | $C(CH_3)=NNH_2$ |
| 1-1918 | H | Cl | H | $CF_3$ | H | $C(CH_3)=NNHCH_3$ |
| 1-1919 | H | Cl | H | $CF_3$ | H | $C(CH_3)=NN(CH_3)_2$ |
| 1-1920 | H | Cl | H | $CF_3$ | H | $C(CH_3)=NNHC_2H_5$ |
| 1-1921 | H | Cl | H | $CF_3$ | H | $C(CH_3)=NN(C_2H_5)_2$ |

TABLE 1-continued

Compounds of the formula:

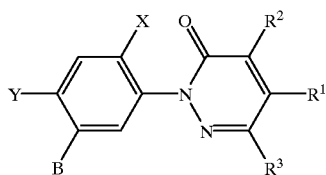

| Compound No. | X | Y | R³ | R¹ | R² | B |
|---|---|---|---|---|---|---|
| 1-1922 | H | Cl | H | CF₃ | H | C(C₂H₅)=NNH₂ |
| 1-1923 | H | Cl | H | CF₃ | H | C(C₂H₅)=NNHCH₃ |
| 1-1924 | H | Cl | H | CF₃ | H | C(C₂H₅)=NN(CH₃)₂ |
| 1-1925 | H | Cl | H | CF₃ | H | C(C₂H₅)=NNHC₂H₅ |
| 1-1926 | H | Cl | H | CF₃ | H | C(C₂H₅)=NN(C₂H₅)₂ |
| 1-1927 | H | Cl | H | CF₃ | H | C(CH₃)(OCH₃)₂ |
| 1-1928 | H | Cl | H | CF₃ | H | C(CH₃)(OC₂H₅)₂ |
| 1-1929 | H | Cl | H | CF₃ | H | C(CH₃)(CⁱC₃H₇)₂ |
| 1-1930 | H | Cl | H | CF₃ | H | [1,3-dioxolan-2-yl with CH₃] |
| 1-1931 | H | Cl | H | CF₃ | H | [1,3-dioxan-2-yl with CH₃] |
| 1-1932 | H | Cl | H | CF₃ | H | [1,3-dioxolan-2-yl with C₂H₅] |
| 1-1933 | H | Cl | H | CF₃ | H | [1,3-dioxan-2-yl with C₂H₅] |
| 1-1934 | H | Cl | CH₃ | CF₃ | H | OCH₂C(CH₃)=CH₂ |
| 1-1935 | H | Cl | CH₃ | CF₃ | H | OCH₂CO₂C₇H₁₅ |
| 1-1936 | H | Cl | CH₃ | CF₃ | H | OCH₂CO₂C₈H₁₇ |
| 1-1937 | H | Cl | CH₃ | CF₃ | H | COOCH₂C₆H₅ |
| 1-1938 | H | Cl | CH₃ | CF₃ | H | C(CH₃)=NOH |
| 1-1939 | H | Cl | CH₃ | CF₃ | H | C(CH₃)=NOCH₃ |
| 1-1940 | H | Cl | CH₃ | CF₃ | H | C(CH₃)=NOC₂H₅ |
| 1-1941 | H | Cl | CH₃ | CF₃ | H | C(CH₃)=NOⁱC₃H₇ |
| 1-1942 | H | Cl | CH₃ | CF₃ | H | C(C₂H₅)=NOH |
| 1-1943 | H | Cl | CH₃ | CF₃ | H | C(C₂H₅)=NOCH₃ |
| 1-1944 | H | Cl | CH₃ | CF₃ | H | C(C₂H₅)=NOC₂H₅ |
| 1-1945 | H | Cl | CH₃ | CF₃ | H | C(C₂H₅)=NOⁱC₃H₇ |
| 1-1946 | H | Cl | CH₃ | CF₃ | H | C(CH₃)=NNH₂ |
| 1-1947 | H | Cl | CH₃ | CF₃ | H | C(CH₃)=NNHCH₃ |
| 1-1948 | H | Cl | CH₃ | CF₃ | H | C(CH₃)=NN(CH₃)₂ |
| 1-1949 | H | Cl | CH₃ | CF₃ | H | C(CH₃)=NNHC₂H₅ |
| 1-1950 | H | Cl | CH₃ | CF₃ | H | C(CH₃)=NN(C₂H₅)₂ |
| 1-1951 | H | Cl | CH₃ | CF₃ | H | C(C₂H₅)=NNH₂ |
| 1-1952 | H | Cl | CH₃ | CF₃ | H | C(C₂H₅)=NNHCH₃ |
| 1-1953 | H | Cl | CH₃ | CF₃ | H | C(C₂H₅)=NN(CH₃)₂ |
| 1-1954 | H | Cl | CH₃ | CF₃ | H | C(C₂H₅)=NNHC₂H₅ |
| 1-1955 | H | Cl | CH₃ | CF₃ | H | C(C₂H₅)=NN(C₂H₅)₂ |
| 1-1956 | H | Cl | CH₃ | CF₃ | H | C(CH₃)(OCH₃)₂ |
| 1-1957 | H | Cl | CH₃ | CF₃ | H | C(CH₃)(OC₂H₅)₂ |
| 1-1958 | H | Cl | CH₃ | CF₃ | H | C(CH₃)(CⁱC₃H₇)₂ |

TABLE 1-continued

Compounds of the formula:

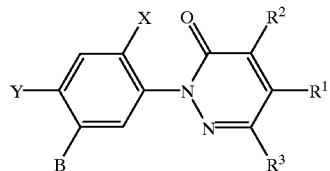

| Compound No. | X | Y | R³ | R¹ | R² | B |
|---|---|---|---|---|---|---|
| 1-1959 | H | Cl | $CH_3$ | $CF_3$ | H | 2-methyl-1,3-dioxolan-2-yl |
| 1-1960 | H | Cl | $CH_3$ | $CF_3$ | H | 2-methyl-1,3-dioxan-2-yl |
| 1-1961 | H | Cl | $CH_3$ | $CF_3$ | H | 2-ethyl-1,3-dioxolan-2-yl |
| 1-1962 | H | Cl | $CH_3$ | $CF_3$ | H | 2-ethyl-1,3-dioxan-2-yl |
| 1-1963 | Cl | Cl | H | $CF_3$ | $CH_3$ | $OCH_2C(CH_3)=CH_2$ |
| 1-1964 | Cl | Cl | H | $CF_3$ | $CH_3$ | $OCH_2CO_2C_7H_{15}$ |
| 1-1965 | Cl | Cl | H | $CF_3$ | $CH_3$ | $OCH_2CO_2C_8H_{17}$ |
| 1-1966 | Cl | Cl | H | $CF_3$ | $CH_3$ | $COCCH_2C_6H_5$ |
| 1-1967 | Cl | Cl | H | $CF_3$ | $CH_3$ | $C(CH_3)=NOH$ |
| 1-1968 | Cl | Cl | H | $CF_3$ | $CH_3$ | $C(CH_3)=NOCH_3$ |
| 1-1969 | Cl | Cl | H | $CF_3$ | $CH_3$ | $C(CH_3)=NOC_2H_5$ |
| 1-1970 | Cl | Cl | H | $CF_3$ | $CH_3$ | $C(CH_3)=NO^iC_3H_7$ |
| 1-1971 | Cl | Cl | H | $CF_3$ | $CH_3$ | $C(C_2H_5)=NOH$ |
| 1-1972 | Cl | Cl | H | $CF_3$ | $CH_3$ | $C(C_2H_5)=NOCH_3$ |
| 1-1973 | Cl | Cl | H | $CF_3$ | $CH_3$ | $C(C_2H_5)=NOC_2H_5$ |
| 1-1974 | Cl | Cl | H | $CF_3$ | $CH_3$ | $C(C_2H_5)=NO^iC_3H_7$ |
| 1-1975 | Cl | Cl | H | $CF_3$ | $CH_3$ | $C(CH_3)=NNH_2$ |
| 1-1976 | Cl | Cl | H | $CF_3$ | $CH_3$ | $C(CH_3)=NNHCH_3$ |
| 1-1977 | Cl | Cl | H | $CF_3$ | $CH_3$ | $C(CH_3)=NN(CH_3)_2$ |
| 1-1978 | Cl | Cl | H | $CF_3$ | $CH_3$ | $C(CH_3)=NNHC_2H_5$ |
| 1-1979 | Cl | Cl | H | $CF_3$ | $CH_3$ | $C(CH_3)=NN(C_2H_5)_2$ |
| 1-1980 | Cl | Cl | H | $CF_3$ | $CH_3$ | $C(C_2H_5)=NNH_2$ |
| 1-1981 | Cl | Cl | H | $CF_3$ | $CH_3$ | $C(C_2H_5)=NNHCH_3$ |
| 1-1982 | Cl | Cl | H | $CF_3$ | $CH_3$ | $C(C_2H_5)=NN(CH_3)_2$ |
| 1-1983 | Cl | Cl | H | $CF_3$ | $CH_3$ | $C(C_2H_5)=NNHC_2H_5$ |
| 1-1984 | Cl | Cl | H | $CF_3$ | $CH_3$ | $C(C_2H_5)=NN(C_2H_5)_2$ |
| 1-1985 | Cl | Cl | H | $CF_3$ | $CH_3$ | $C(CH_3)(OCH_3)_2$ |
| 1-1986 | Cl | Cl | H | $CF_3$ | $CH_3$ | $C(CH_3)(OC_2H_5)_2$ |
| 1-1987 | Cl | Cl | H | $CF_3$ | $CH_3$ | $C(CH_3)(C^iC_3H_7)_2$ |
| 1-1988 | Cl | Cl | H | $CF_3$ | $CH_3$ | 2-methyl-1,3-dioxolan-2-yl |
| 1-1989 | Cl | Cl | H | $CF_3$ | $CH_3$ | 2-methyl-1,3-dioxan-2-yl |

TABLE 1-continued

Compounds of the formula:

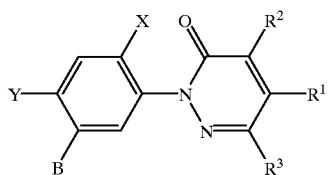

| Compound No. | X | Y | R³ | R¹ | R² | B |
|---|---|---|---|---|---|---|
| 1-1990 | Cl | Cl | H | $CF_3$ | $CH_3$ | ![dioxolane with $C_2H_5$] |
| 1-1991 | Cl | Cl | H | $CF_3$ | $CH_3$ | ![dioxane with $C_2H_5$] |
| 1-1992 | Cl | Cl | H | $CF_3$ | H | $OCH_2C(CH_3)\!=\!CH_2$ |
| 1-1993 | Cl | Cl | H | $CF_3$ | H | $OCH_2CO_2C_7H_{15}$ |
| 1-1994 | Cl | Cl | H | $CF_3$ | H | $OCH_2CO_2C_8H_{17}$ |
| 1-1995 | Cl | Cl | H | $CF_3$ | H | $COOCH_2C_6H_5$ |
| 1-1996 | Cl | Cl | H | $CF_3$ | H | $C(CH_3)\!=\!NOH$ |
| 1-1997 | Cl | Cl | H | $CF_3$ | H | $C(CH_3)\!=\!NOCH_3$ |
| 1-1998 | Cl | Cl | H | $CF_3$ | H | $C(CH_3)\!=\!NOC_2H_5$ |
| 1-1999 | Cl | Cl | H | $CF_3$ | H | $C(CH_3)\!=\!NO^iC_3H_7$ |
| 1-2000 | Cl | Cl | H | $CF_3$ | H | $C(C_2H_5)\!=\!NOH$ |
| 1-2001 | Cl | Cl | H | $CF_3$ | H | $C(C_2H_5)\!=\!NOCH_3$ |
| 1-2002 | Cl | Cl | H | $CF_3$ | H | $C(C_2H_5)\!=\!NOC_2H_5$ |
| 1-2003 | Cl | Cl | H | $CF_3$ | H | $C(C_2H_5)\!=\!NO^iC_3H_7$ |
| 1-2004 | Cl | Cl | H | $CF_3$ | H | $C(CH_3)\!=\!NNH_2$ |
| 1-2005 | Cl | Cl | H | $CF_3$ | H | $C(CH_3)\!=\!NNHCH_3$ |
| 1-2006 | Cl | Cl | H | $CF_3$ | H | $C(CH_3)\!=\!NN(CH_3)_2$ |
| 1-2007 | Cl | Cl | H | $CF_3$ | H | $C(CH_3)\!=\!NNHC_2H_5$ |
| 1-2008 | Cl | Cl | H | $CF_3$ | H | $C(CH_3)\!=\!NN(C_2H_5)_2$ |
| 1-2009 | Cl | Cl | H | $CF_3$ | H | $C(C_2H_5)\!=\!NNH_2$ |
| 1-2010 | Cl | Cl | H | $CF_3$ | H | $C(C_2H_5)\!=\!NNHCH_3$ |
| 1-2011 | Cl | Cl | H | $CF_3$ | H | $C(C_2H_5)\!=\!NN(CH_3)_2$ |
| 1-2012 | Cl | Cl | H | $CF_3$ | H | $C(C_2H_5)\!=\!NNHC_2H_5$ |
| 1-2013 | Cl | Cl | H | $CF_3$ | H | $C(C_2H_5)\!=\!NN(C_2H_5)_2$ |
| 1-2014 | Cl | Cl | H | $CF_3$ | H | $C(CH_3)(OCH_3)_2$ |
| 1-2015 | Cl | Cl | H | $CF_3$ | H | $C(CH_3)(OC_2H_5)_2$ |
| 1-2016 | Cl | cl | H | $CF_3$ | H | $C(CH_3)(C^iC_3H_7)_2$ |
| 1-2017 | Cl | Cl | H | $CF_3$ | H | ![dioxolane with $CH_3$] |
| 1-2018 | Cl | Cl | H | $CF_3$ | H | ![dioxane with $CH_3$] |
| 1-2019 | Cl | Cl | H | $CF_3$ | H | ![dioxolane with $C_2H_5$] |

TABLE 1-continued

Compounds of the formula:

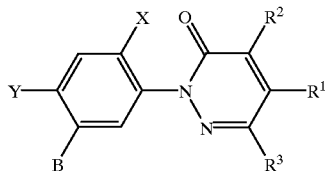

| Compound No. | X | Y | R³ | R¹ | R² | B |
|---|---|---|---|---|---|---|
| 1-2020 | Cl | Cl | H | $CF_3$ | H | ![structure: 2-ethyl-1,3-dioxolane] |
| 1-2021 | Cl | Cl | $CH_3$ | $CF_3$ | H | $OCH_2C(CH_3)=CH_2$ |
| 1-2022 | Cl | Cl | $CH_3$ | $CF_3$ | H | $OCH_2CO_2C_7H_{15}$ |
| 1-2023 | Cl | Cl | $CH_3$ | $CF_3$ | H | $OCH_2CO_2C_8H_{17}$ |
| 1-2024 | Cl | Cl | $CH_3$ | $CF_3$ | H | $COOCH_2C_6H_5$ |
| 1-2025 | Cl | Cl | $CH_3$ | $CF_3$ | H | $C(CH_3)=NOH$ |
| 1-2026 | Cl | Cl | $CH_3$ | $CF_3$ | H | $C(CH_3)=NOCH_3$ |
| 1-2027 | Cl | Cl | $CH_3$ | $CF_3$ | H | $C(CH_3)=NOC_2H_5$ |
| 1-2028 | Cl | Cl | $CH_3$ | $CF_3$ | H | $C(CH_3)=NO^iC_3H_7$ |
| 1-2029 | Cl | Cl | $CH_3$ | $CF_3$ | H | $C(C_2H_5)=NOH$ |
| 1-2030 | Cl | Cl | $CH_3$ | $CF_3$ | H | $C(C_2H_5)=NOCH_3$ |
| 1-2031 | Cl | Cl | $CH_3$ | $CF_3$ | H | $C(C_2H_5)=NOC_2H_5$ |
| 1-2032 | Cl | Cl | $CH_3$ | $CF_3$ | H | $C(C_2H_5)=NO^iC_3H_7$ |
| 1-2033 | Cl | Cl | $CH_3$ | $CF_3$ | H | $C(CH_3)=NNH_2$ |
| 1-2034 | Cl | Cl | $CH_3$ | $CF_3$ | H | $C(CH_3)=NNHCH_3$ |
| 1-2035 | Cl | Cl | $CH_3$ | $CF_3$ | H | $C(CH_3)=NN(CH_3)_2$ |
| 1-2036 | Cl | Cl | $CH_3$ | $CF_3$ | H | $C(CH_3)=NNHC_2H_5$ |
| 1-2037 | Cl | Cl | $CH_3$ | $CF_3$ | H | $C(CH_3)=NN(C_2H_5)_2$ |
| 1-2038 | Cl | Cl | $CH_3$ | $CF_3$ | H | $C(C_2H_5)=NNH_2$ |
| 1-2039 | Cl | Cl | $CH_3$ | $CF_3$ | H | $C(C_2H_5)=NNHCH_3$ |
| 1-2040 | Cl | Cl | $CH_3$ | $CF_3$ | H | $C(C_2H_5)=NN(CH_3)_2$ |
| 1-2041 | Cl | Cl | $CH_3$ | $CF_3$ | H | $C(C_2H_5)=NNHC_2H_5$ |
| 1-2042 | Cl | Cl | $CH_3$ | $CF_3$ | H | $C(C_2H_5)=NN(C_2H_5)_2$ |
| 1-2043 | Cl | Cl | $CH_3$ | $CF_3$ | H | $C(CH_3)(OCH_3)_2$ |
| 1-2044 | Cl | Cl | $CH_3$ | $CF_3$ | H | $C(CH_3)(OC_2H_5)_2$ |
| 1-2045 | Cl | Cl | $CH_3$ | $CF_3$ | H | $C(CH_3)(C^iC_3H_7)_2$ |
| 1-2046 | Cl | Cl | $CH_3$ | $CF_3$ | H | ![structure: 2-methyl-1,3-dioxolane] |
| 1-2047 | Cl | Cl | $CH_3$ | $CF_3$ | H | ![structure: 2-methyl-1,3-dioxane] |
| 1-2048 | Cl | Cl | $CH_3$ | $CF_3$ | H | ![structure: 2-ethyl-1,3-dioxolane] |
| 1-2049 | Cl | Cl | $CH_3$ | $CF_3$ | H | ![structure: 2-ethyl-1,3-dioxane] |
| 1-2050 | F | Cl | H | $CF_3$ | $CH_3$ | $OCH_2COOCH_2COOCH_3$ |
| 1-2051 | F | Cl | H | $CF_3$ | $CH_3$ | $OCH_2COOCH_2COOC_2H_5$ |
| 1-2052 | F | Cl | H | $CF_3$ | $CH_3$ | $OCH_2COOCH_2COO^iC_3H_7$ |
| 1-2053 | F | Cl | H | $CF_3$ | $CH_3$ | $OCH_2COOCH(CH_3)COOCH_3$ |
| 1-2054 | F | Cl | H | $CF_3$ | $CH_3$ | $OCH_2COOCH(CH_3)COOC_2H_5$ |

TABLE 1-continued

Compounds of the formula:

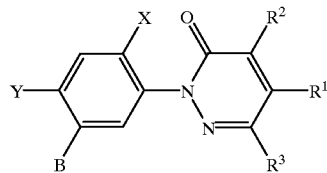

| Compound No. | X | Y | $R^3$ | $R^1$ | $R^2$ | B |
|---|---|---|---|---|---|---|
| 1-2055 | F | Cl | H | $CF_3$ | $CH_3$ | $OCH_2COOCH(CH_3)COO^iC_3H_7$ |
| 1-2056 | F | Cl | H | $CF_3$ | $CH_3$ | $OCH(CH_3)COOCH_2COOCH_3$ |
| 1-2057 | F | Cl | H | $CF_3$ | $CH_3$ | $OCH(CH_3)COOCH_2COOC_2H_5$ |
| 1-2058 | F | Cl | H | $CF_3$ | $CH_3$ | $OCH(CH_3)COOCH_2COO^iC_3H_7$ |
| 1-2059 | F | Cl | H | $CF_3$ | $CH_3$ | $OCH(CH_3)COOCH(CH_3)COOCH_3$ |
| 1-2060 | F | Cl | H | $CF_3$ | $CH_3$ | $OCH(CH_3)COOCH(CH_3)COOC_2H_5$ |
| 1-2061 | F | Cl | H | $CF_3$ | $CH_3$ | $OCH(CH_3)COOCH(CH_3)COO^iC_3H_7$ |
| 1-2062 | F | Cl | H | $CF_3$ | H | $OCH_2COOCH_2COOCH_3$ |
| 1-2063 | F | Cl | H | $CF_3$ | H | $OCH_2COOCH_2COOC_2H_5$ |
| 1-2064 | F | Cl | H | $CF_3$ | H | $OCH_2COOCH_2COO^iC_3H_7$ |
| 1-2065 | F | Cl | H | $CF_3$ | H | $OCH_2COOCH(CH_3)COOCH_3$ |
| 1-2066 | F | Cl | H | $CF_3$ | H | $OCH_2COOCH(CH_3)COOC_2H_5$ |
| 1-2067 | F | Cl | H | $CF_3$ | H | $OCH_2COOCH(CH_3)COO^iC_3H_7$ |
| 1-2068 | F | Cl | H | $CF_3$ | H | $OCH(CH_3)COOCH_2COOCH_3$ |
| 1-2069 | F | Cl | H | $CF_3$ | H | $OCH(CH_3)COOCH_2COOC_2H_5$ |
| 1-2070 | F | Cl | H | $CF_3$ | H | $OCH(CH_3)COOCH_2COO^iC_3H_7$ |
| 1-2071 | F | Cl | H | $CF_3$ | H | $OCH(CH_3)COOCH(CH_3)COOCH_3$ |
| 1-2072 | F | Cl | H | $CF_3$ | H | $OCH(CH_3)COOCH(CH_3)COOC_2H_5$ |
| 1-2073 | F | Cl | H | $CF_3$ | H | $OCH(CH_3)COOCH(CH_3)COO^iC_3H_7$ |
| 1-2074 | F | Cl | $CH_3$ | $CF_3$ | H | $OCH_2COOCH_2COOCH_3$ |
| 1-2075 | F | Cl | $CH_3$ | $CF_3$ | H | $OCH_2COOCH_2COOC_2H_5$ |
| 1-2076 | F | Cl | $CH_3$ | $CF_3$ | H | $OCH_2COOCH_2COO^iC_3H_7$ |
| 1-2077 | F | Cl | $CH_3$ | $CF_3$ | H | $OCH_2COOCH(CH_3)COOCH_3$ |
| 1-2078 | F | Cl | $CH_3$ | $CF_3$ | H | $OCH_2COOCH(CH_3)COOC_2H_5$ |
| 1-2079 | F | Cl | $CH_3$ | $CF_3$ | H | $OCH_2COOCH(CH_3)COO^iC_3H_7$ |
| 1-2080 | F | Cl | $CH_3$ | $CF_3$ | H | $OCH(CH_3)COOCH_2COOCH_3$ |
| 1-2081 | F | Cl | $CH_3$ | $CF_3$ | H | $OCH(CH_3)COOCH_2COOC_2H_5$ |
| 1-2082 | F | Cl | $CH_3$ | $CF_3$ | H | $OCH(CH_3)COOCH_2COO^iC_3H_7$ |
| 1-2083 | F | Cl | $CH_3$ | $CF_3$ | H | $OCH(CH_3)COOCH(CH_3)COOCH_3$ |
| 1-2084 | F | Cl | $CH_3$ | $CF_3$ | H | $OCH(CH_3)COOCH(CH_3)COOC_2H_5$ |
| 1-2085 | F | Cl | $CH_3$ | $CF_3$ | H | $OCH(CH_3)COOCH(CH_3)COO^iC_3H_7$ |
| 1-2086 | H | Cl | H | $CF_3$ | $CH_3$ | $OCH_2COOCH_2COOCH_3$ |
| 1-2087 | H | Cl | H | $CF_3$ | $CH_3$ | $OCH_2COOCH_2COCC_2H_5$ |
| 1-2088 | H | Cl | H | $CF_3$ | $CH_3$ | $OCH_2COOCH_2COO^iC_3H_7$ |
| 1-2089 | H | Cl | H | $CF_3$ | $CH_3$ | $OCH_2COOCH(CH_3)COOCH_3$ |
| 1-2090 | H | Cl | H | $CF_3$ | $CH_3$ | $OCH_2COOCH(CH_3)COOC_2H_5$ |
| 1-2091 | H | Cl | H | $CF_3$ | $CH_3$ | $OCH_2COOCH(CH_3)COO^iC_3H_7$ |
| 1-2092 | H | Cl | H | $CF_3$ | $CH_3$ | $OCH(CH_3)COOCH_2COOCH_3$ |
| 1-2093 | H | Cl | H | $CF_3$ | $CH_3$ | $OCH(CH_3)COOCH_2COOC_2H_5$ |
| 1-2094 | H | Cl | H | $CF_3$ | $CH_3$ | $OCH(CH_3)COOCH_2COC^iC_3H_7$ |
| 1-2095 | H | Cl | H | $CF_3$ | $CH_3$ | $OCH(CH_3)COOCH(CH_3)COOCH_3$ |
| 1-2096 | H | Cl | H | $CF_3$ | $CH_3$ | $OCH(CH_3)COOCH(CH_3)COOC_2H_5$ |
| 1-2097 | H | Cl | H | $CF_3$ | $CH_3$ | $OCH(CH_3)COOCH(CH_3)COO^iC_3H_7$ |
| 1-2098 | H | Cl | H | $CF_3$ | H | $OCH_2COOCH_2COOCH_3$ |
| 1-2099 | H | Cl | H | $CF_3$ | H | $OCH_2COOCH_2COOC_2H_5$ |
| 1-2100 | H | Cl | H | $CF_3$ | H | $OCH_2COOCH_2COO^iC_3H_7$ |
| 1-2101 | H | Cl | H | $CF_3$ | H | $OCH_2COOCH(CH_3)COOCH_3$ |
| 1-2102 | H | Cl | H | $CF_3$ | H | $OCH_2COOCH(CH_3)COOC_2H_5$ |
| 1-2103 | H | Cl | H | $CF_3$ | H | $OCH_2COOCH(CH_3)COO^iC_3H_7$ |
| 1-2104 | H | Cl | H | $CF_3$ | H | $OCH(CH_3)COOCH_2COOCH_3$ |
| 1-2105 | H | Cl | H | $CF_3$ | H | $OCH(CH_3)COOCH_2COOC_2H_5$ |
| 1-2106 | H | Cl | H | $CF_3$ | H | $OCH(CH_3)COOCH_2COO^iC_3H_7$ |
| 1-2107 | H | Cl | H | $CF_3$ | H | $OCH(CH_3)COOCH(CH_3)COOCH_3$ |
| 1-2108 | H | Cl | H | $CF_3$ | H | $OCH(CH_3)COOCH(CH_3)COOC_2H_5$ |
| 1-2109 | H | Cl | H | $CF_3$ | H | $OCH(CH_3)COOCH(CH_3)COOC_3H_7$ |
| 1-2110 | H | Cl | $CH_3$ | $CF_3$ | H | $OCH_2COOCH_2COOCH_3$ |
| 1-2111 | H | Cl | $CH_3$ | $CF_3$ | H | $OCH_2COOCH_2COOC_2H_5$ |
| 1-2112 | H | Cl | $CH_3$ | $CF_3$ | H | $OCH_2COOCH_2COOC_3H_7$ |
| 1-2113 | H | Cl | $CH_3$ | $CF_3$ | H | $OCH_2COOCH(CH_3)COOCH_3$ |
| 1-2114 | H | Cl | $CH_3$ | $CF_3$ | H | $OCH_2COOCH(CH_3)COOC_2H_5$ |
| 1-2115 | H | Cl | $CH_3$ | $CF_3$ | H | $OCH_2COOCH(CH_3)COO^iC_3H_7$ |
| 1-2116 | H | Cl | $CH_3$ | $CF_3$ | H | $OCH(CH_3)COOCH_2COOCH_3$ |
| 1-2117 | H | Cl | $CH_3$ | $CF_3$ | H | $OCH(CH_3)COOCH_2COOC_2H_5$ |
| 1-2118 | H | Cl | $CH_3$ | $CF_3$ | H | $OCH(CH_3)COOCH_2COO^iC_3H_7$ |

TABLE 1-continued

Compounds of the formula:

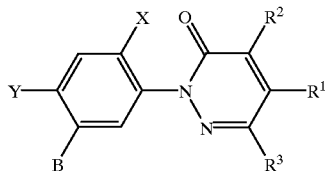

| Compound No. | X | Y | R³ | R¹ | R² | B |
|---|---|---|---|---|---|---|
| 1-2119 | H | Cl | CH₃ | CF₃ | H | OCH(CH₃)COOCH(CH₃)COOCH₃ |
| 1-2120 | H | Cl | CH₃ | CF₃ | H | OCH(CH₃)COOCH(CH₃)COOC₂H₅ |
| 1-2121 | H | Cl | CH₃ | CF₃ | H | OCH(CH₃)COOCH(CH₃)COOⁱC₃H₇ |
| 1-2122 | Cl | Cl | H | CF₃ | CH₃ | OCH₂COOCH₂COOCH₃ |
| 1-2123 | Cl | Cl | H | CF₃ | CH₃ | OCH₂COOCH₂COOC₂H₅ |
| 1-2124 | Cl | Cl | H | CF₃ | CH₃ | OCH₂COOCH₂COOⁱC₃H₇ |
| 1-2125 | Cl | Cl | H | CF₃ | CH₃ | OCH₂COOCH(CH₃)COOCH₃ |
| 1-2126 | Cl | Cl | H | CF₃ | CH₃ | OCH₂COOCH(CH₃)COOC₂H₅ |
| 1-2127 | Cl | Cl | H | CF₃ | CH₃ | OCH₂COOCH(CH₃)COOⁱC₃H₇ |
| 1-2128 | Cl | Cl | H | CF₃ | CH₃ | OCH(CH₃)COOCH₂COOCH₃ |
| 1-2129 | Cl | Cl | H | CF₃ | CH₃ | OCH(CH₃)COOCH₂COOC₂H₅ |
| 1-2130 | Cl | Cl | H | CF₃ | CH₃ | OCH(CH₃)COOCH₂COOⁱC₃H₇ |
| 1-2131 | Cl | Cl | H | CF₃ | CH₃ | OCH(CH₃)COOCH(CH₃)COOCH₃ |
| 1-2132 | Cl | Cl | H | CF₃ | CH₃ | OCH(CH₃)COOCH(CH₃)COOC₂H₅ |
| 1-2133 | Cl | Cl | H | CF₃ | CH₃ | OCH(CH₃)COOCH(CH₃)COOⁱC₃H₇ |
| 1-2134 | Cl | Cl | H | CF₃ | H | OCH₂COOCH₂COOCH₃ |
| 1-2135 | Cl | Cl | H | CF₃ | H | OCH₂COOCH₂COOC₂H₅ |
| 1-2136 | Cl | Cl | H | CF₃ | H | OCH₂COOCH₂COO1C₃H₇ |
| 1-2137 | Cl | Cl | H | CF₃ | H | OCH₂COOCH(CH₃)COOCH₃ |
| 1-2138 | Cl | Cl | H | CF₃ | H | OCH₂COOCH(CH₃)COOC₂H₅ |
| 1-2139 | Cl | Cl | H | CF₃ | H | OCH₂COOCH(CH₃)COOⁱC₃H₇ |
| 1-2140 | Cl | Cl | H | CF₃ | H | OCH(CH₃)COOCH₂COOCH₃ |
| 1-2141 | Cl | Cl | H | CF₃ | H | OCH(CH₃)COOCH₂COOC₂H₅ |
| 1-2142 | Cl | Cl | H | CF₃ | H | OCH(CH₃)COOCH₂COOⁱC₃H₇ |
| 1-2143 | Cl | Cl | H | CF₃ | H | OCH(CH₃)COOCH(CH₃)COOCH₃ |
| 1-2144 | Cl | Cl | H | CF₃ | H | OCH(CH₃)COOCH(CH₃)COOC₂H₅ |
| 1-2145 | Cl | Cl | H | CF₃ | H | OCH(CH₃)COOCH(CH₃)COOⁱC₃H₇ |
| 1-2146 | Cl | Cl | CH₃ | CF₃ | H | OCH₂COOCH₂COOCH₃ |
| 1-2147 | Cl | Cl | CH₃ | CF₃ | H | OCH₂COOCH₂COOC₂H₅ |
| 1-2148 | Cl | Cl | CH₃ | CF₃ | H | OCH₂COOCH₂COOⁱC₃H₇ |
| 1-2149 | Cl | Cl | CH₃ | CF₃ | H | OCH₂COOCH(CH₃)COOCH₃ |
| 1-2150 | Cl | Cl | CH₃ | CF₃ | H | OCH₂COOCH(CH₃)COOC₂H₅ |
| 1-2151 | Cl | Cl | CH₃ | CF₃ | H | OCH₂COOCH(CH₃)COOⁱC₃H₇ |
| 1-2152 | Cl | Cl | CH₃ | CF₃ | H | OCH(CH₃)COOCH₂COOCH₃ |
| 1-2153 | Cl | Cl | CH₃ | CF₃ | H | OCH(CH₃)COOCH₂COOC₂H₅ |
| 1-2154 | Cl | Cl | CH₃ | CF₃ | H | OCH(CH₃)COOCH₂COOⁱC₃H₇ |
| 1-2155 | Cl | Cl | CH₃ | CF₃ | H | OCH(CH₃)COOCH(CH₃)COOCH₃ |
| 1-2156 | Cl | Cl | CH₃ | CF₃ | H | OCH(CH₃)COOCH(CH₃)COOC₂H₅ |
| 1-2157 | Cl | Cl | CH₃ | CF₃ | H | OCH(CH₃)COOCH(CH₃)COOⁱC₃H₇ |

TABLE 2

Compounds of the formula:

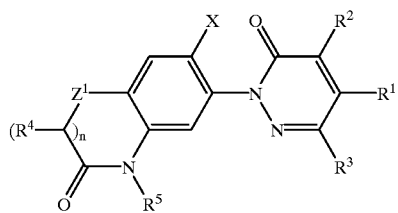

| Compound No. | X | Z¹ | n | R³ | R¹ | R² | R⁴ | R⁵ |
|---|---|---|---|---|---|---|---|---|
| 2-1 | H | O | 1 | H | CF₂Cl | CH₃ | H | H |
| 2-2 | H | O | 1 | H | CF₂Cl | CH₃ | H | CH₃ |
| 2-3 | H | O | 1 | H | CF₂Cl | CH₃ | H | C₂H₅ |
| 2-4 | H | O | 1 | H | CF₂Cl | CH₃ | H | ⁿC₃H₇ |

TABLE 2-continued

Compounds of the formula:

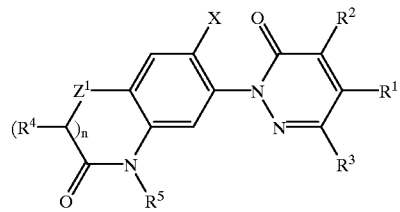

| Compound No. | X | $Z^1$ | n | $R^3$ | $R^1$ | $R^2$ | $R^4$ | $R^5$ |
|---|---|---|---|---|---|---|---|---|
| 2-5 | H | O | 1 | H | $CF_2Cl$ | $CH_3$ | H | $^iC_3H_7$ |
| 2-6 | H | O | 1 | H | $CF_2Cl$ | $CH_3$ | H | $^iC_4H_9$ |
| 2-7 | H | O | 1 | H | $CF_2Cl$ | $CH_3$ | H | $^nC_4H_9$ |
| 2-8 | H | O | 1 | H | $CF_2Cl$ | $CH_3$ | H | $CH_2CH_2Cl$ |
| 2-9 | H | O | 1 | H | $CF_2Cl$ | $CH_3$ | H | $CH_2CH_2Br$ |
| 2-10 | H | O | 1 | H | $CF_2Cl$ | $CH_3$ | H | $CH_2CH=CH_2$ |
| 2-11 | H | O | 1 | H | $CF_2Cl$ | $CH_3$ | H | $CH(CH_3)CH=CH_2$ |
| 2-12 | H | O | 1 | H | $CF_2Cl$ | $CH_3$ | H | $CH_2CCl=CH_2$ |
| 2-13 | H | O | 1 | H | $CF_2Cl$ | $CH_3$ | H | $CH_2C\equiv CH$ |
| 2-14 | H | O | 1 | H | $CF_2Cl$ | $CH_3$ | H | $CH(CH_3)C\equiv CH$ |
| 2-15 | H | O | 1 | H | $CF_2Cl$ | $CH_3$ | H | $CH_2CN$ |
| 2-16 | H | O | 1 | H | $CF_2Cl$ | $CH_3$ | H | $CH_2OCH_3$ |
| 2-17 | H | O | 1 | H | $CF_2Cl$ | $CH_3$ | H | $CH_2OC_2H_5$ |
| 2-18 | H | O | 1 | H | $CF_2Cl$ | $CH_3$ | H | $CH_2COOH$ |
| 2-19 | H | O | 1 | H | $CF_2Cl$ | $CH_3$ | H | $CH_2COOCH_3$ |
| 2-20 | H | O | 1 | H | $CF_2Cl$ | $CH_3$ | H | $CH_2COOC_2H_5$ |
| 2-21 | H | O | 1 | H | $CF_2Cl$ | $CH_3$ | H | $CH_2COO^nC_3H_7$ |
| 2-22 | H | O | 1 | H | $CF_2Cl$ | $CH_3$ | H | $CH_2COO^nC_4H_9$ |
| 2-23 | H | O | 1 | H | $CF_2Cl$ | $CH_3$ | H | $CH_2COO^nC_5H_{11}$ |
| 2-24 | H | O | 1 | H | $CF_2Cl$ | $CH_3$ | H | $CH_2COO^iC_3H_7$ |
| 2-25 | H | O | 1 | H | $CF_2Cl$ | $CH_3$ | H | $CH_2COO^cC_5H_9$ |
| 2-26 | H | O | 1 | H | $CF_2Cl$ | $CH_3$ | H | $CH_2COO^cC_6H_{11}$ |
| 2-27 | H | O | 1 | H | $CF_2Cl$ | $CH_3$ | H | $CH(CH_3)COOH$ |
| 2-28 | H | O | 1 | H | $CF_2Cl$ | $CH_3$ | H | $CH(CH_3)COOCH_3$ |
| 2-29 | H | O | 1 | H | $CF_2Cl$ | $CH_3$ | H | $CH(CH_3)COOC_2H_5$ |
| 2-30 | H | O | 1 | H | $CF_2Cl$ | $CH_3$ | H | $CH(CH_3)COO^nC_3H_7$ |
| 2-31 | H | O | 1 | H | $CF_2Cl$ | $CH_3$ | H | $CH(CH_3)COO^nC_4H_9$ |
| 2-32 | H | O | 1 | H | $CF_2Cl$ | $CH_3$ | H | $CH(CH_3)COO^nC_5H_{11}$ |
| 2-33 | H | O | 1 | H | $CF_2Cl$ | $CH_3$ | H | $CH(CH_3)COO^iC_3H_7$ |
| 2-34 | H | O | 1 | H | $CF_2Cl$ | $CH_3$ | H | $CH(CH_3)COO^cC_5H_9$ |
| 2-35 | H | O | 1 | H | $CF_2Cl$ | $CH_3$ | H | $CH(CH_3)COO^cC_6H_{11}$ |
| 2-36 | H | O | 1 | H | $CF_2Cl$ | $CH_3$ | $CH_3$ | H |
| 2-37 | H | O | 1 | H | $CF_2Cl$ | $CH_3$ | $CH_3$ | $CH_3$ |
| 2-38 | H | O | 1 | H | $CF_2Cl$ | $CH_3$ | $CH_3$ | $C_2H_5$ |
| 2-39 | H | O | 1 | H | $CF_2Cl$ | $CH_3$ | $CH_3$ | $^nC_3H_7$ |
| 2-40 | H | O | 1 | H | $CF_2Cl$ | $CH_3$ | $CH_3$ | $^iC_3H_7$ |
| 2-41 | H | O | 1 | H | $CF_2Cl$ | $CH_3$ | $CH_3$ | $^iC_4H_9$ |
| 2-42 | H | O | 1 | H | $CF_2Cl$ | $CH_3$ | $CH_3$ | $^nC_4H_9$ |
| 2-43 | H | O | 1 | H | $CF_2Cl$ | $CH_3$ | $CH_3$ | $CH_2CH=CH_2$ |
| 2-44 | H | O | 1 | H | $CF_2Cl$ | $CH_3$ | $CH_3$ | $CH(CH_3)CH=CH_2$ |
| 2-45 | H | O | 1 | H | $CF_2Cl$ | $CH_3$ | $CH_3$ | $CH_2C\equiv CH$ |
| 2-46 | H | O | 1 | H | $CF_2Cl$ | $CH_3$ | $CH_3$ | $CH(CH_3)C\equiv CH$ |
| 2-47 | H | O | 1 | H | $CF_2Cl$ | $CH_3$ | $CH_3$ | $CH_2OCH_3$ |
| 2-48 | H | O | 1 | H | $CF_2Cl$ | $CH_3$ | $CH_3$ | $CH_2OC_2H_5$ |
| 2-49 | F | O | 1 | H | $CF_2Cl$ | $CH_3$ | H | H |
| 2-50 | F | O | 1 | H | $CF_2Cl$ | $CH_3$ | H | $CH_3$ |
| 2-51 | F | O | 1 | H | $CF_2Cl$ | $CH_3$ | H | $C_2H_5$ |
| 2-52 | F | O | 1 | H | $CF_2Cl$ | $CH_3$ | H | $^nC_3H_7$ |
| 2-53 | F | O | 1 | H | $CF_2Cl$ | $CH_3$ | H | $^iC_3H_7$ |
| 2-54 | F | O | 1 | H | $CF_2Cl$ | $CH_3$ | H | $^iC_4H_9$ |
| 2-55 | F | O | 1 | H | $CF_2Cl$ | $CH_3$ | H | $^nC_4H_9$ |
| 2-56 | F | O | 1 | H | $CF_2Cl$ | $CH_3$ | H | $CH_2CH_2Cl$ |
| 2-57 | F | O | 1 | H | $CF_2Cl$ | $CH_3$ | H | $CH_2CH_2Br$ |
| 2-58 | F | O | 1 | H | $CF_2Cl$ | $CH_3$ | H | $CH_2CH=CH_2$ |
| 2-59 | F | O | 1 | H | $CF_2Cl$ | $CH_3$ | H | $CH(CH_3)CH=CH_2$ |
| 2-60 | F | O | 1 | H | $CF_2Cl$ | $CH_3$ | H | $CH_2CCl=CH_2$ |
| 2-61 | F | O | 1 | H | $CF_2Cl$ | $CH_3$ | H | $CH_2C\equiv CH$ |
| 2-62 | F | O | 1 | H | $CF_2Cl$ | $CH_3$ | H | $CH(CH_3)C\equiv CH$ |
| 2-63 | F | O | 1 | H | $CF_2Cl$ | $CH_3$ | H | $CH_2CN$ |
| 2-64 | F | O | 1 | H | $CF_2Cl$ | $CH_3$ | H | $CH_2OCH_3$ |
| 2-65 | F | O | 1 | H | $CF_2Cl$ | $CH_3$ | H | $CH_2OC_2H_5$ |
| 2-66 | F | O | 1 | H | $CF_2Cl$ | $CH_3$ | H | $CH_2COOH$ |

TABLE 2-continued

Compounds of the formula:

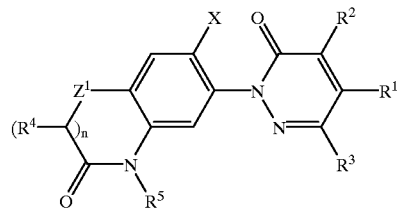

| Compound No. | X | $Z^1$ | n | $R^3$ | $R^1$ | $R^2$ | $R^4$ | $R^5$ |
|---|---|---|---|---|---|---|---|---|
| 2-67 | F | O | 1 | H | $CF_2Cl$ | $CH_3$ | H | $CH_2COOCH_3$ |
| 2-68 | F | O | 1 | H | $CF_2Cl$ | $CH_3$ | H | $CH_2COOC_2H_5$ |
| 2-69 | F | O | 1 | H | $CF_2Cl$ | $CH_3$ | H | $CH_2COO^nC_3H_7$ |
| 2-70 | F | O | 1 | H | $CF_2Cl$ | $CH_3$ | H | $CH_2COO^nC_4H_9$ |
| 2-71 | F | O | 1 | H | $CF_2Cl$ | $CH_3$ | H | $CH_2COO^nC_5H_{11}$ |
| 2-72 | F | O | 1 | H | $CF_2Cl$ | $CH_3$ | H | $CH_2COO^iC_3H_7$ |
| 2-73 | F | O | 1 | H | $CF_2Cl$ | $CH_3$ | H | $CH_2COO^cC_5H_9$ |
| 2-74 | F | O | 1 | H | $CF_2Cl$ | $CH_3$ | H | $CH_2COO^cC_6H_{11}$ |
| 2-75 | F | O | 1 | H | $CF_2Cl$ | $CH_3$ | H | $CH(CH_3)COOH$ |
| 2-76 | F | O | 1 | H | $CF_2Cl$ | $CH_3$ | H | $CH(CH_3)COOCH_3$ |
| 2-77 | F | O | 1 | H | $CF_2Cl$ | $CH_3$ | H | $CH(CH_3)COOC_2H_5$ |
| 2-78 | F | O | 1 | H | $CF_2Cl$ | $CH_3$ | H | $CH(CH_3)COO^nC_3H_7$ |
| 2-79 | F | O | 1 | H | $CF_2Cl$ | $CH_3$ | H | $CH(CH_3)COO^nC_4H_9$ |
| 2-80 | F | O | 1 | H | $CF_2Cl$ | $CH_3$ | H | $CH(CH_3)COO^nC_5H_{11}$ |
| 2-81 | F | O | 1 | H | $CF_2Cl$ | $CH_3$ | H | $CH(CH_3)COO^iC_3H_7$ |
| 2-82 | F | O | 1 | H | $CF_2Cl$ | $CH_3$ | H | $CH(CH_3)COO^cC_5H_9$ |
| 2-83 | F | O | 1 | H | $CF_2Cl$ | $CH_3$ | H | $CH(CH_3)COO^cC_6H_{11}$ |
| 2-84 | F | O | 1 | H | $CF_2Cl$ | $CH_3$ | $CH_3$ | H |
| 2-85 | F | O | 1 | H | $CF_2Cl$ | $CH_3$ | $CH_3$ | $CH_3$ |
| 2-86 | F | O | 1 | H | $CF_2Cl$ | $CH_3$ | $CH_3$ | $C_2H_5$ |
| 2-87 | F | O | 1 | H | $CF_2Cl$ | $CH_3$ | $CH_3$ | $^nC_3H_7$ |
| 2-88 | F | O | 1 | H | $CF_2Cl$ | $CH_3$ | $CH_3$ | $^iC_3H_7$ |
| 2-89 | F | O | 1 | H | $CF_2Cl$ | $CH_3$ | $CH_3$ | $^iC_4H_9$ |
| 2-90 | F | O | 1 | H | $CF_2Cl$ | $CH_3$ | $CH_3$ | $^nC_4H_9$ |
| 2-91 | F | O | 1 | H | $CF_2Cl$ | $CH_3$ | $CH_3$ | $CH_2CH=CH_2$ |
| 2-92 | F | O | 1 | H | $CF_2Cl$ | $CH_3$ | $CH_3$ | $CH(CH_3)CH=CH_2$ |
| 2-93 | F | O | 1 | H | $CF_2Cl$ | $CH_3$ | $CH_3$ | $CH_2C\equiv CH$ |
| 2-94 | F | O | 1 | H | $CF_2Cl$ | $CH_3$ | $CH_3$ | $CH(CH_3)C\equiv CH$ |
| 2-95 | F | O | 1 | H | $CF_2Cl$ | $CH_3$ | $CH_3$ | $CH_2OCH_3$ |
| 2-96 | F | O | 1 | H | $CF_2Cl$ | $CH_3$ | $CH_3$ | $CH_2OC_2H_5$ |
| 2-97 | H | S | 0 | H | $CF_2Cl$ | $CH_3$ | — | H |
| 2-98 | H | S | 0 | H | $CF_2Cl$ | $CH_3$ | — | $CH_3$ |
| 2-99 | H | S | 0 | H | $CF_2Cl$ | $CH_3$ | — | $C_2H_5$ |
| 2-100 | H | S | 0 | H | $CF_2Cl$ | $CH_3$ | — | $^nC_3H_7$ |
| 2-101 | H | S | 0 | H | $CF_2Cl$ | $CH_3$ | — | $^nC_4H_9$ |
| 2-102 | H | S | 0 | H | $CF_2Cl$ | $CH_3$ | — | $^iC_3H_7$ |
| 2-103 | H | S | 0 | H | $CF_2Cl$ | $CH_3$ | — | $^iC_4H_9$ |
| 2-104 | H | S | 0 | H | $CF_2Cl$ | $CH_3$ | — | $CH_2CH_2Cl$ |
| 2-105 | H | S | 0 | H | $CF_2Cl$ | $CH_3$ | — | $CH_2CH_2Br$ |
| 2-106 | H | S | 0 | H | $CF_2Cl$ | $CH_3$ | — | $CH_2CH=CH_2$ |
| 2-107 | H | S | 0 | H | $CF_2Cl$ | $CH_3$ | — | $CH(CH_3)CH=CH_2$ |
| 2-108 | H | S | 0 | H | $CF_2Cl$ | $CH_3$ | — | $CH_2CCl=CH_2$ |
| 2-109 | H | S | 0 | H | $CF_2Cl$ | $CH_3$ | — | $CH_2C\equiv CH$ |
| 2-110 | H | S | 0 | H | $CF_2Cl$ | $CH_3$ | — | $CH(CH_3)C\equiv CH$ |
| 2-111 | H | S | 0 | H | $CF_2Cl$ | $CH_3$ | — | $CH_2CN$ |
| 2-112 | H | S | 0 | H | $CF_2Cl$ | $CH_3$ | — | $CH_2OCH_3$ |
| 2-113 | H | S | 0 | H | $CF_2Cl$ | $CH_3$ | — | $CH_2OC_2H_5$ |
| 2-114 | H | S | 0 | H | $CF_2Cl$ | $CH_3$ | — | $CH_2COOH$ |
| 2-115 | H | S | 0 | H | $CF_2Cl$ | $CH_3$ | — | $CH_2COOCH_3$ |
| 2-116 | H | S | 0 | H | $CF_2Cl$ | $CH_3$ | — | $CH_2COOC_2H_5$ |
| 2-117 | H | S | 0 | H | $CF_2Cl$ | $CH_3$ | — | $CH_2COO^nC_3H_7$ |
| 2-118 | H | S | 0 | H | $CF_2Cl$ | $CH_3$ | — | $CH_2COO^nC_4H_9$ |
| 2-119 | H | S | 0 | H | $CF_2Cl$ | $CH_3$ | — | $CH_2COO^nC_5H_{11}$ |
| 2-120 | H | S | 0 | H | $CF_2Cl$ | $CH_3$ | — | $CH_2COO^iC_3H_7$ |
| 2-121 | H | S | 0 | H | $CF_2Cl$ | $CH_3$ | — | $CH_2COO^cC_5H_9$ |
| 2-122 | H | S | 0 | H | $CF_2Cl$ | $CH_3$ | — | $CH_2COO^cC_6H_{11}$ |
| 2-123 | H | S | 0 | H | $CF_2Cl$ | $CH_3$ | — | $CH(CH_3)COOH$ |
| 2-124 | H | S | 0 | H | $CF_2Cl$ | $CH_3$ | — | $CH(CH_3)COOCH_3$ |
| 2-125 | H | S | 0 | H | $CF_2Cl$ | $CH_3$ | — | $CH(CH_3)COOC_2H_5$ |
| 2-126 | H | S | 0 | H | $CF_2Cl$ | $CH_3$ | — | $CH(CH_3)COO^nC_3H_7$ |
| 2-127 | H | S | 0 | H | $CF_2Cl$ | $CH_3$ | — | $CH(CH_3)COO^nC_4H_9$ |
| 2-128 | H | S | 0 | H | $CF_2Cl$ | $CH_3$ | — | $CH(CH_3)COO^nC_5H_{11}$ |

TABLE 2-continued

Compounds of the formula:

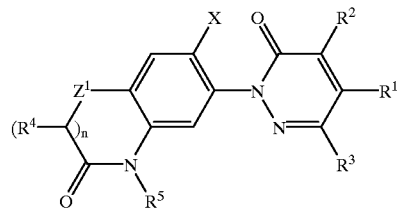

| Compound No. | X | $Z^1$ | n | $R^3$ | $R^1$ | $R^2$ | $R^4$ | $R^5$ |
|---|---|---|---|---|---|---|---|---|
| 2-129 | H | S | 0 | H | $CF_2Cl$ | $CH_3$ | — | $CH(CH_3)COO^iC_3H_7$ |
| 2-130 | H | S | 0 | H | $CF_2Cl$ | $CH_3$ | — | $CH(CH_3)COO^cC_5H_9$ |
| 2-131 | H | S | 0 | H | $CF_2Cl$ | $CH_3$ | — | $CH(CH_3)COO^cC_6H_{11}$ |
| 2-132 | F | S | 0 | H | $CF_2Cl$ | $CH_3$ | — | H |
| 2-133 | F | S | 0 | H | $CF_2Cl$ | $CH_3$ | — | $CH_3$ |
| 2-134 | F | S | 0 | H | $CF_2Cl$ | $CH_3$ | — | $C_2H_5$ |
| 2-135 | F | S | 0 | H | $CF_2Cl$ | $CH_3$ | — | $^nC_3H_7$ |
| 2-136 | F | S | 0 | H | $CF_2Cl$ | $CH_3$ | — | $^nC_4H_9$ |
| 2-137 | F | S | 0 | H | $CF_2Cl$ | $CH_3$ | — | $^iC_3H_7$ |
| 2-138 | F | S | 0 | H | $CF_2Cl$ | $CH_3$ | — | $^iC_4H_9$ |
| 2-139 | F | S | 0 | H | $CF_2Cl$ | $CH_3$ | — | $CH_2CH_2Cl$ |
| 2-140 | F | S | 0 | H | $CF_2Cl$ | $CH_3$ | — | $CH_2CH_2Br$ |
| 2-141 | F | S | 0 | H | $CF_2Cl$ | $CH_3$ | — | $CH_2CH{=}CH_2$ |
| 2-142 | F | S | 0 | H | $CF_2Cl$ | $CH_3$ | — | $CH(CH_3)CH{=}CH_2$ |
| 2-143 | F | S | 0 | H | $CF_2Cl$ | $CH_3$ | — | $CH_2CCl{=}CH_2$ |
| 2-144 | F | S | 0 | H | $CF_2Cl$ | $CH_3$ | — | $CH_2C{\equiv}CH$ |
| 2-145 | F | S | 0 | H | $CF_2Cl$ | $CH_3$ | — | $CH(CH_3)C{\equiv}CH$ |
| 2-146 | F | S | 0 | H | $CF_2Cl$ | $CH_3$ | — | $CH_2CN$ |
| 2-147 | F | S | 0 | H | $CF_2Cl$ | $CH_3$ | — | $CH_2OCH_3$ |
| 2-148 | F | S | 0 | H | $CF_2Cl$ | $CH_3$ | — | $CH_2OC_2H_5$ |
| 2-149 | F | S | 0 | H | $CF_2Cl$ | $CH_3$ | — | $CH_2COOH$ |
| 2-150 | F | S | 0 | H | $CF_2Cl$ | $CH_3$ | — | $CH_2COOCH_3$ |
| 2-151 | F | S | 0 | H | $CF_2Cl$ | $CH_3$ | — | $CH_2COOC_2H_5$ |
| 2-152 | F | S | 0 | H | $CF_2Cl$ | $CH_3$ | — | $CH_2COO^nC_3H_7$ |
| 2-153 | F | S | 0 | H | $CF_2Cl$ | $CH_3$ | — | $CH_2COO^nC_4H_9$ |
| 2-154 | F | S | 0 | H | $CF_2Cl$ | $CH_3$ | — | $CH_2COO^nC_5H_{11}$ |
| 2-155 | F | S | 0 | H | $CF_2Cl$ | $CH_3$ | — | $CH_2COO^iC_3H_7$ |
| 2-156 | F | S | 0 | H | $CF_2Cl$ | $CH_3$ | — | $CH_2COO^cC_5H_9$ |
| 2-157 | F | S | 0 | H | $CF_2Cl$ | $CH_3$ | — | $CH_2COO^cC_6H_{11}$ |
| 2-158 | F | S | 0 | H | $CF_2Cl$ | $CH_3$ | — | $CH(CH_3)COOH$ |
| 2-159 | F | S | 0 | H | $CF_2Cl$ | $CH_3$ | — | $CH(CH_3)COOCH_3$ |
| 2-160 | F | S | 0 | H | $CF_2Cl$ | $CH_3$ | — | $CH(CH_3)COOC_2H_5$ |
| 2-161 | F | S | 0 | H | $CF_2Cl$ | $CH_3$ | — | $CH(CH_3)COO^nC_3H_7$ |
| 2-162 | F | S | 0 | H | $CF_2Cl$ | $CH_3$ | — | $CH(CH_3)COO^nC_4H_9$ |
| 2-163 | F | S | 0 | H | $CF_2Cl$ | $CH_3$ | — | $CH(CH_3)COO^nC_5H_{11}$ |
| 2-164 | F | S | 0 | H | $CF_2Cl$ | $CH_3$ | — | $CH(CH_3)COO^iC_3H_7$ |
| 2-165 | F | S | 0 | H | $CF_2Cl$ | $CH_3$ | — | $CH(CH_3)COO^cC_5H_9$ |
| 2-166 | F | S | 0 | H | $CF_2Cl$ | $CH_3$ | — | $CH(CH_3)COO^cC_6H_{11}$ |
| 2-167 | H | O | 0 | H | $CF_2Cl$ | $CH_3$ | — | H |
| 2-168 | H | O | 0 | H | $CF_2Cl$ | $CH_3$ | — | $CH_3$ |
| 2-169 | H | O | 0 | H | $CF_2Cl$ | $CH_3$ | — | $C_2H_5$ |
| 2-170 | H | O | 0 | H | $CF_2Cl$ | $CH_3$ | — | $^nC_3H_7$ |
| 2-171 | H | O | 0 | H | $CF_2Cl$ | $CH_3$ | — | $^nC_4H_9$ |
| 2-172 | H | O | 0 | H | $CF_2Cl$ | $CH_3$ | — | $^iC_3H_7$ |
| 2-173 | H | O | 0 | H | $CF_2Cl$ | $CH_3$ | — | $^iC_4H_9$ |
| 2-174 | H | O | 0 | H | $CF_2Cl$ | $CH_3$ | — | $CH_2CH{=}CH_2$ |
| 2-175 | H | O | 0 | H | $CF_2Cl$ | $CH_3$ | — | $CH(CH_3)CH{=}CH_2$ |
| 2-176 | H | O | 0 | H | $CF_2Cl$ | $CH_3$ | — | $CH_2C{\equiv}CH$ |
| 2-177 | H | O | 0 | H | $CF_2Cl$ | $CH_3$ | — | $CH(CH_3)C{\equiv}CH$ |
| 2-178 | H | O | 0 | H | $CF_2Cl$ | $CH_3$ | — | $CH_2OCH_3$ |
| 2-179 | H | O | 0 | H | $CF_2Cl$ | $CH_3$ | — | $CH_2OC_2H_5$ |
| 2-180 | F | O | 0 | H | $CF_2Cl$ | $CH_3$ | — | H |
| 2-181 | F | O | 0 | H | $CF_2Cl$ | $CH_3$ | — | $CH_3$ |
| 2-182 | F | O | 0 | H | $CF_2Cl$ | $CH_3$ | — | $C_2H_5$ |
| 2-183 | F | O | 0 | H | $CF_2Cl$ | $CH_3$ | — | $^nC_3H_7$ |
| 2-184 | F | O | 0 | H | $CF_2Cl$ | $CH_3$ | — | $^nC_4H_9$ |
| 2-185 | F | O | 0 | H | $CF_2Cl$ | $CH_3$ | — | $CH_2CH{=}CH_2$ |
| 2-186 | F | O | 0 | H | $CF_2Cl$ | $CH_3$ | — | $CH(CH_3)CH{=}CH_2$ |
| 2-187 | F | O | 0 | H | $CF_2Cl$ | $CH_3$ | — | $CH_2C{\equiv}CH$ |
| 2-188 | F | O | 0 | H | $CF_2Cl$ | $CH_3$ | — | $CH(CH_3)C{\equiv}CH$ |
| 2-189 | F | O | 0 | H | $CF_2Cl$ | $CH_3$ | — | $CH_2OCH_3$ |
| 2-190 | F | O | 0 | H | $CF_2Cl$ | $CH_3$ | — | $CH_2OC_2H_5$ |

TABLE 2-continued

Compounds of the formula:

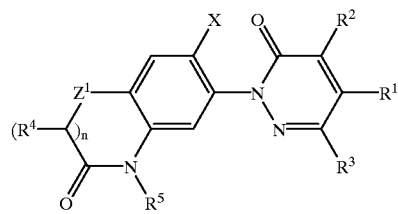

| Compound No. | X | $Z^1$ | n | $R^3$ | $R^1$ | $R^2$ | $R^4$ | $R^5$ |
|---|---|---|---|---|---|---|---|---|
| 2-191 | H | O | 1 | H | $CF_3$ | $CH_3$ | — | H |
| 2-192 | H | O | 1 | H | $CF_3$ | $CH_3$ | H | $CH_3$ |
| 2-193 | H | O | 1 | H | $CF_3$ | $CH_3$ | H | $C_2H_5$ |
| 2-194 | H | O | 1 | H | $CF_3$ | $CH_3$ | H | $^nC_3H_7$ |
| 2-195 | H | O | 1 | H | $CF_3$ | $CH_3$ | H | $^iC_3H_7$ |
| 2-196 | H | O | 1 | H | $CF_3$ | $CH_3$ | H | $^iC_4H_9$ |
| 2-197 | H | O | 1 | H | $CF_3$ | $CH_3$ | H | $^nC_4H_9$ |
| 2-198 | H | O | 1 | H | $CF_3$ | $CH_3$ | H | $CH_2CH_2Cl$ |
| 2-199 | H | O | 1 | H | $CF_3$ | $CH_3$ | H | $CH_2CH_2Br$ |
| 2-200 | H | O | 1 | H | $CF_3$ | $CH_3$ | H | $CH_2CH=CH_2$ |
| 2-201 | H | O | 1 | H | $CF_3$ | $CH_3$ | H | $CH(CH_3)CH=CH_2$ |
| 2-202 | H | O | 1 | H | $CF_3$ | $CH_3$ | H | $CH_2CCl=CH_2$ |
| 2-203 | H | O | 1 | H | $CF_3$ | $CH_3$ | H | $CH_2C\equiv CH$ |
| 2-204 | H | O | 1 | H | $CF_3$ | $CH_3$ | H | $CH(CH_3)C\equiv CH$ |
| 2-205 | H | O | 1 | H | $CF_3$ | $CH_3$ | H | $CH_2CN$ |
| 2-206 | H | O | 1 | H | $CF_3$ | $CH_3$ | H | $CH_2OCH_3$ |
| 2-207 | H | O | 1 | H | $CF_3$ | $CH_3$ | H | $CH_2OC_2H_5$ |
| 2-208 | H | O | 1 | H | $CF_3$ | $CH_3$ | H | $CH_2COOH$ |
| 2-209 | H | O | 1 | H | $CF_3$ | $CH_3$ | H | $CH_2COOCH_3$ |
| 2-210 | H | O | 1 | H | $CF_3$ | $CH_3$ | H | $CH_2COOC_2H_5$ |
| 2-211 | H | O | 1 | H | $CF_3$ | $CH_3$ | H | $CH_2COO^nC_3H_7$ |
| 2-212 | H | O | 1 | H | $CF_3$ | $CH_3$ | H | $CH_2COO^nC_4H_9$ |
| 2-213 | H | O | 1 | H | $CF_3$ | $CH_3$ | H | $CH_2COO^nC_5H_{11}$ |
| 2-214 | H | O | 1 | H | $CF_3$ | $CH_3$ | H | $CH_2COO^iC_3H_7$ |
| 2-215 | H | O | 1 | H | $CF_3$ | $CH_3$ | H | $CH_2COO^cC_5H_9$ |
| 2-216 | H | O | 1 | H | $CF_3$ | $CH_3$ | H | $CH_2COO^cC_6H_{11}$ |
| 2-217 | H | O | 1 | H | $CF_3$ | $CH_3$ | H | $CH(CH_3)COOH$ |
| 2-218 | H | O | 1 | H | $CF_3$ | $CH_3$ | H | $CH(CH_3)COOCH$ |
| 2-219 | H | O | 1 | H | $CF_3$ | $CH_3$ | H | $CH(CH_3)COOC_2H_5$ |
| 2-220 | H | O | 1 | H | $CF_3$ | $CH_3$ | H | $CH(CH_3)COO^nC_3H_7$ |
| 2-221 | H | O | 1 | H | $CF_3$ | $CH_3$ | H | $CH(CH_3)COO^nC_4H_9$ |
| 2-222 | H | O | 1 | H | $CF_3$ | $CH_3$ | H | $CH(CH_3)COO^nC_5H_{11}$ |
| 2-223 | H | O | 1 | H | $CF_3$ | $CH_3$ | H | $CH(CH_3)COO^iC_3H_7$ |
| 2-224 | H | O | 1 | H | $CF_3$ | $CH_3$ | H | $CH(CH_3)COO^cC_5H_9$ |
| 2-225 | H | O | 1 | H | $CF_3$ | $CH_3$ | H | $CH(CH_3)COO^cC_6H_{11}$ |
| 2-226 | H | O | 1 | H | $CF_3$ | $CH_3$ | $CH_3$ | H |
| 2-227 | H | O | 1 | H | $CF_3$ | $CH_3$ | $CH_3$ | $CH_3$ |
| 2-228 | H | O | 1 | H | $CF_3$ | $CH_3$ | $CH_3$ | $C_2H_5$ |
| 2-229 | H | O | 1 | H | $CF_3$ | $CH_3$ | $CH_3$ | $^nC_3H_7$ |
| 2-230 | H | O | 1 | H | $CF_3$ | $CH_3$ | $CH_3$ | $^iC_3H_7$ |
| 2-231 | H | O | 1 | H | $CF_3$ | $CH_3$ | $CH_3$ | $^iC_4H_9$ |
| 2-232 | H | O | 1 | H | $CF_3$ | $CH_3$ | $CH_3$ | $^nC_4H_9$ |
| 2-233 | H | O | 1 | H | $CF_3$ | $CH_3$ | $CH_3$ | $CH_2CH=CH_2$ |
| 2-234 | H | O | 1 | H | $CF_3$ | $CH_3$ | $CH_3$ | $CH(CH_3)CH=CH_2$ |
| 2-235 | H | O | 1 | H | $CF_3$ | $CH_3$ | $CH_3$ | $CH_2C\equiv CH$ |
| 2-236 | H | O | 1 | H | $CF_3$ | $CH_3$ | $CH_3$ | $CH(CH_3)C\equiv CH$ |
| 2-237 | H | O | 1 | H | $CF_3$ | $CH_3$ | $CH_3$ | $CH_2OCH_3$ |
| 2-238 | H | O | 1 | H | $CF_3$ | $CH_3$ | $CH_3$ | $CH_2OC_2H_5$ |
| 2-239 | F | O | 1 | H | $CF_3$ | $CH_3$ | H | H |
| 2-240 | F | O | 1 | H | $CF_3$ | $CH_3$ | H | $CH_3$ |
| 2-241 | F | O | 1 | H | $CF_3$ | $CH_3$ | H | $C_2H_5$ |
| 2-242 | F | O | 1 | H | $CF_3$ | $CH_3$ | H | $^nC_3H_7$ |
| 2-243 | F | O | 1 | H | $CF_3$ | $CH_3$ | H | $^iC_3H_7$ |
| 2-244 | F | O | 1 | H | $CF_3$ | $CH_3$ | H | $^iC_4H_9$ |
| 2-245 | F | O | 1 | H | $CF_3$ | $CH_3$ | H | $^nC_4H_9$ |
| 2-246 | F | O | 1 | H | $CF_3$ | $CH_3$ | H | $CH_2CH_2Cl$ |
| 2-247 | F | O | 1 | H | $CF_3$ | $CH_3$ | H | $CH_2CH_2Br$ |
| 2-248 | F | O | 1 | H | $CF_3$ | $CH_3$ | H | $CH_2CH=CH_2$ |
| 2-249 | F | O | 1 | H | $CF_3$ | $CH_3$ | H | $CH(CH_3)CH=CH_2$ |
| 2-250 | F | O | 1 | H | $CF_3$ | $CH_3$ | H | $CH_2CCl=CH_2$ |
| 2-251 | F | O | 1 | H | $CF_3$ | $CH_3$ | H | $CH_2C\equiv CH$ |
| 2-252 | F | O | 1 | H | $CF_3$ | $CH_3$ | H | $CH(CH_3)C\equiv CH$ |

TABLE 2-continued

Compounds of the formula:

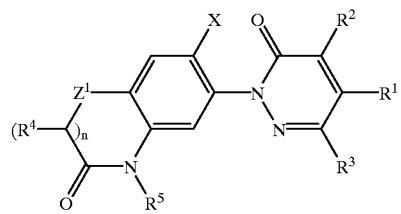

| Compound No. | X | $Z^1$ | n | $R^3$ | $R^1$ | $R^2$ | $R^4$ | $R^5$ |
|---|---|---|---|---|---|---|---|---|
| 2-253 | F | O | 1 | H | $CF_3$ | $CH_3$ | H | $CH_2CN$ |
| 2-254 | F | O | 1 | H | $CF_3$ | $CH_3$ | H | $CH_2OCH_3$ |
| 2-255 | F | O | 1 | H | $CF_3$ | $CH_3$ | H | $CH_2OC_2H_5$ |
| 2-256 | F | O | 1 | H | $CF_3$ | $CH_3$ | H | $CH_2COOH$ |
| 2-257 | F | O | 1 | H | $CF_3$ | $CH_3$ | H | $CH_2COOCH_3$ |
| 2-258 | F | O | 1 | H | $CF_3$ | $CH_3$ | H | $CH_2COOC_2H_5$ |
| 2-259 | F | O | 1 | H | $CF_3$ | $CH_3$ | H | $CH_2COO^nC_3H_7$ |
| 2-260 | F | O | 1 | H | $CF_3$ | $CH_3$ | H | $CH_2COO^nC_4H_9$ |
| 2-261 | F | O | 1 | H | $CF_3$ | $CH_3$ | H | $CH_2COO^nC_5H_{11}$ |
| 2-262 | F | O | 1 | H | $CF_3$ | $CH_3$ | H | $CH_2COO^iC_3H_7$ |
| 2-263 | F | O | 1 | H | $CF_3$ | $CH_3$ | H | $CH_2COO^cC_5H_9$ |
| 2-264 | F | O | 1 | H | $CF_3$ | $CH_3$ | H | $CH_2COO^cC_6H_{11}$ |
| 2-265 | F | O | 1 | H | $CF_3$ | $CH_3$ | H | $CH(CH_3)COOH$ |
| 2-266 | F | O | 1 | H | $CF_3$ | $CH_3$ | H | $CH(CH_3)COOCH$ |
| 2-267 | F | O | 1 | H | $CF_3$ | $CH_3$ | H | $CH(CH_3)COOC_2H_5$ |
| 2-268 | F | O | 1 | H | $CF_3$ | $CH_3$ | H | $CH(CH_3)COO^nC_3H_7$ |
| 2-269 | F | O | 1 | H | $CF_3$ | $CH_3$ | H | $CH(CH_3)COO^nC_4H_9$ |
| 2-270 | F | O | 1 | H | $CF_3$ | $CH_3$ | H | $CH(CH_3)COO^nC_5H_{11}$ |
| 2-271 | F | O | 1 | H | $CF_3$ | $CH_3$ | H | $CH(CH_3)COO^iC_3H_7$ |
| 2-272 | F | O | 1 | H | $CF_3$ | $CH_3$ | H | $CH(CH_3)COO^cC_5H_9$ |
| 2-273 | F | O | 1 | H | $CF_3$ | $CH_3$ | H | $CH(CH_3)COO^cC_6H_{11}$ |
| 2-274 | F | O | 1 | H | $CF_3$ | $CH_3$ | $CH_3$ | H |
| 2-275 | F | O | 1 | H | $CF_3$ | $CH_3$ | $CH_3$ | $CH_3$ |
| 2-276 | F | O | 1 | H | $CF_3$ | $CH_3$ | $CH_3$ | $C_2H_5$ |
| 2-277 | F | O | 1 | H | $CF_3$ | $CH_3$ | $CH_3$ | $^nC_3H_7$ |
| 2-278 | F | O | 1 | H | $CF_3$ | $CH_3$ | $CH_3$ | $^iC_3H_7$ |
| 2-279 | F | O | 1 | H | $CF_3$ | $CH_3$ | $CH_3$ | $^iC_4H_9$ |
| 2-280 | F | O | 1 | H | $CF_3$ | $CH_3$ | $CH_3$ | $^nC_4H_9$ |
| 2-281 | F | O | 1 | H | $CF_3$ | $CH_3$ | $CH_3$ | $CH_2CH=CH_2$ |
| 2-282 | F | O | 1 | H | $CF_3$ | $CH_3$ | $CH_3$ | $CH(CH_3)CH=CH_2$ |
| 2-283 | F | O | 1 | H | $CF_3$ | $CH_3$ | $CH_3$ | $CH_2C\equiv CH$ |
| 2-284 | F | O | 1 | H | $CF_3$ | $CH_3$ | $CH_3$ | $CH(CH_3)C\equiv CH$ |
| 2-285 | F | O | 1 | H | $CF_3$ | $CH_3$ | $CH_3$ | $CH_2OCH_3$ |
| 2-286 | F | O | 1 | H | $CF_3$ | $CH_3$ | $CH_3$ | $CH_2OC_2H_5$ |
| 2-287 | H | S | 0 | H | $CF_3$ | $CH_3$ | — | H |
| 2-288 | H | S | 0 | H | $CF_3$ | $CH_3$ | — | $CH_3$ |
| 2-289 | H | S | 0 | H | $CF_3$ | $CH_3$ | — | $C_2H_5$ |
| 2-290 | H | S | 0 | H | $CF_3$ | $CH_3$ | — | $^nC_3H_7$ |
| 2-291 | H | S | 0 | H | $CF_3$ | $CH_3$ | — | $^nC_4H_9$ |
| 2-292 | H | S | 0 | H | $CF_3$ | $CH_3$ | — | $^iC_3H_7$ |
| 2-293 | H | S | 0 | H | $CF_3$ | $CH_3$ | — | $^iC_4H_9$ |
| 2-294 | H | S | 0 | H | $CF_3$ | $CH_3$ | — | $CH_2CH_2Cl$ |
| 2-295 | H | S | 0 | H | $CF_3$ | $CH_3$ | — | $CH_2CH_2Br$ |
| 2-296 | H | S | 0 | H | $CF_3$ | $CH_3$ | — | $CH_2CH=CH_2$ |
| 2-297 | H | S | 0 | H | $CF_3$ | $CH_3$ | — | $CH(CH_3)CH=CH_2$ |
| 2-298 | H | S | 0 | H | $CF_3$ | $CH_3$ | — | $CH_2CCl=CH_2$ |
| 2-299 | H | S | 0 | H | $CF_3$ | $CH_3$ | — | $CH_2C\equiv CH$ |
| 2-300 | H | S | 0 | H | $CF_3$ | $CH_3$ | — | $CH(CH_3)C\equiv CH$ |
| 2-301 | H | S | 0 | H | $CF_3$ | $CH_3$ | — | $CH_2CN$ |
| 2-302 | H | S | 0 | H | $CF_3$ | $CH_3$ | — | $CH_2OCH_3$ |
| 2-303 | H | S | 0 | H | $CF_3$ | $CH_3$ | — | $CH_2OC_2H_5$ |
| 2-304 | H | S | 0 | H | $CF_3$ | $CH_3$ | — | $CH_2COOH$ |
| 2-305 | H | S | 0 | H | $CF_3$ | $CH_3$ | — | $CH_2COOCH_3$ |
| 2-306 | H | S | 0 | H | $CF_3$ | $CH_3$ | — | $CH_2COOC_2H_5$ |
| 2-307 | H | S | 0 | H | $CF_3$ | $CH_3$ | — | $CH_2COO^nC_3H_7$ |
| 2-308 | H | S | 0 | H | $CF_3$ | $CH_3$ | — | $CH_2COO^nC_4H_9$ |
| 2-309 | H | S | 0 | H | $CF_3$ | $CH_3$ | — | $CH_2COO^nC_5H_{11}$ |
| 2-310 | H | S | 0 | H | $CF_3$ | $CH_3$ | — | $CH_2COO^iC_3H_7$ |
| 2-311 | H | S | 0 | H | $CF_3$ | $CH_3$ | — | $CH_2COO^cC_5H_9$ |
| 2-312 | H | S | 0 | H | $CF_3$ | $CH_3$ | — | $CH_2COO^cC_6H_{11}$ |
| 2-313 | H | S | 0 | H | $CF_3$ | $CH_3$ | — | $CH(CH_3)COOH$ |
| 2-314 | H | S | 0 | H | $CF_3$ | $CH_3$ | — | $CH(CH_3)COOCH$ |

TABLE 2-continued

Compounds of the formula:

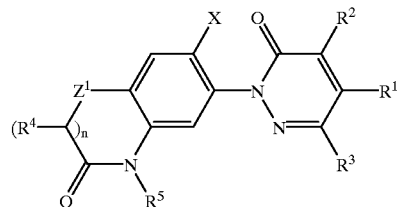

| Compound No. | X | $Z^1$ | n | $R^3$ | $R^1$ | $R^2$ | $R^4$ | $R^5$ |
|---|---|---|---|---|---|---|---|---|
| 2-315 | H | S | 0 | H | $CF_3$ | $CH_3$ | — | $CH(CH_3)COOC_2H_5$ |
| 2-316 | H | S | 0 | H | $CF_3$ | $CH_3$ | — | $CH(CH_3)COO^nC_3H_7$ |
| 2-317 | H | S | 0 | H | $CF_3$ | $CH_3$ | — | $CH(CH_3)COO^nC_4H_9$ |
| 2-318 | H | S | 0 | H | $CF_3$ | $CH_3$ | — | $CH(CH_3)COO^nC_5H_{11}$ |
| 2-319 | H | S | 0 | H | $CF_3$ | $CH_3$ | — | $CH(CH_3)COO^iC_3H_7$ |
| 2-320 | H | S | 0 | H | $CF_3$ | $CH_3$ | — | $CH(CH_3)COO^cC_5H_9$ |
| 2-321 | H | S | 0 | H | $CF_3$ | $CH_3$ | — | $CH(CH_3)COO^cC_6H_{11}$ |
| 2-322 | F | S | 0 | H | $CF_3$ | $CH_3$ | — | H |
| 2-323 | F | S | 0 | H | $CF_3$ | $CH_3$ | — | $CH_3$ |
| 2-324 | F | S | 0 | H | $CF_3$ | $CH_3$ | — | $C_2H_5$ |
| 2-325 | F | S | 0 | H | $CF_3$ | $CH_3$ | — | $^nC_3H_7$ |
| 2-326 | F | S | 0 | H | $CF_3$ | $CH_3$ | — | $^nC_4H_9$ |
| 2-327 | F | S | 0 | H | $CF_3$ | $CH_3$ | — | $^iC_3H_7$ |
| 2-328 | F | S | 0 | H | $CF_3$ | $CH_3$ | — | $^iC_4H_9$ |
| 2-329 | F | S | 0 | H | $CF_3$ | $CH_3$ | — | $CH_2CH_2Cl$ |
| 2-330 | F | S | 0 | H | $CF_3$ | $CH_3$ | — | $CH_2CH_2Br$ |
| 2-331 | F | S | 0 | H | $CF_3$ | $CH_3$ | — | $CH_2CH=CH_2$ |
| 2-332 | F | S | 0 | H | $CF_3$ | $CH_3$ | — | $CH(CH_3)CH=CH_2$ |
| 2-333 | F | S | 0 | H | $CF_3$ | $CH_3$ | — | $CH_2CCl=CH_2$ |
| 2-334 | F | S | 0 | H | $CF_3$ | $CH_3$ | — | $CH_2C\equiv CH$ |
| 2-335 | F | S | 0 | H | $CF_3$ | $CH_3$ | — | $CH(CH_3)C\equiv CH$ |
| 2-336 | F | S | 0 | H | $CF_3$ | $CH_3$ | — | $CH_2CN$ |
| 2-337 | F | S | 0 | H | $CF_3$ | $CH_3$ | — | $CH_2OCH_3$ |
| 2-338 | F | S | 0 | H | $CF_3$ | $CH_3$ | — | $CH_2OC_2H_5$ |
| 2-339 | F | S | 0 | H | $CF_3$ | $CH_3$ | — | $CH_2COOH$ |
| 2-340 | F | S | 0 | H | $CF_3$ | $CH_3$ | — | $CH_2COOCH_3$ |
| 2-341 | F | S | 0 | H | $CF_3$ | $CH_3$ | — | $CH_2COOC_2H_5$ |
| 2-342 | F | S | 0 | H | $CF_3$ | $CH_3$ | — | $CH_2COO^nC_3H_7$ |
| 2-343 | F | S | 0 | H | $CF_3$ | $CH_3$ | — | $CH_2COO^nC_4H_9$ |
| 2-344 | F | S | 0 | H | $CF_3$ | $CH_3$ | — | $CH_2COO^nC_5H_{11}$ |
| 2-345 | F | S | 0 | H | $CF_3$ | $CH_3$ | — | $CH_2COO^iC_3H_7$ |
| 2-346 | F | S | 0 | H | $CF_3$ | $CH_3$ | — | $CH_2COO^cC_5H_9$ |
| 2-347 | F | S | 0 | H | $CF_3$ | $CH_3$ | — | $CH_2COO^cC_6H_{11}$ |
| 2-348 | F | S | 0 | H | $CF_3$ | $CH_3$ | — | $CH(CH_3)COOH$ |
| 2-349 | F | S | 0 | H | $CF_3$ | $CH_3$ | — | $CH(CH_3)COOCH_3$ |
| 2-350 | F | S | 0 | H | $CF_3$ | $CH_3$ | — | $CH(CH_3)COOC_2H_5$ |
| 2-351 | F | S | 0 | H | $CF_3$ | $CH_3$ | — | $CH(CH_3)COO^nC_3H_7$ |
| 2-352 | F | S | 0 | H | $CF_3$ | $CH_3$ | — | $CH(CH_3)COO^nC_4H_9$ |
| 2-353 | F | S | 0 | H | $CF_3$ | $CH_3$ | — | $CH(CH_3)COO^nC_5H_{11}$ |
| 2-354 | F | S | 0 | H | $CF_3$ | $CH_3$ | — | $CH(CH_3)COO^iC_3H_7$ |
| 2-355 | F | S | 0 | H | $CF_3$ | $CH_3$ | — | $CH(CH_3)COO^cC_5H_9$ |
| 2-356 | F | S | 0 | H | $CF_3$ | $CH_3$ | — | $CH(CH_3)COO^cC_6H_{11}$ |
| 2-357 | H | O | 0 | H | $CF_3$ | $CH_3$ | — | H |
| 2-358 | H | O | 0 | H | $CF_3$ | $CH_3$ | — | $CH_3$ |
| 2-359 | H | O | 0 | H | $CF_3$ | $CH_3$ | — | $C_2H_5$ |
| 2-360 | H | O | 0 | H | $CF_3$ | $CH_3$ | — | $^nC_3H_7$ |
| 2-361 | H | O | 0 | H | $CF_3$ | $CH_3$ | — | $^nC_4H_9$ |
| 2-362 | H | O | 0 | H | $CF_3$ | $CH_3$ | — | $^iC_3H_7$ |
| 2-363 | H | O | 0 | H | $CF_3$ | $CH_3$ | — | $^iC_4H_9$ |
| 2-364 | H | O | 0 | H | $CF_3$ | $CH_3$ | — | $CH_2CH=CH_2$ |
| 2-365 | H | O | 0 | H | $CF_3$ | $CH_3$ | — | $CH(CH_3)CH=CH_2$ |
| 2-366 | H | O | 0 | H | $CF_3$ | $CH_3$ | — | $CH_2C\equiv CH$ |
| 2-367 | H | O | 0 | H | $CF_3$ | $CH_3$ | — | $CH(CH_3)C\equiv CH$ |
| 2-368 | H | O | 0 | H | $CF_3$ | $CH_3$ | — | $CH_2OCH_3$ |
| 2-369 | H | O | 0 | H | $CF_3$ | $CH_3$ | — | $CH_2OC_2H_5$ |
| 2-370 | F | O | 0 | H | $CF_3$ | $CH_3$ | — | H |
| 2-371 | F | O | 0 | H | $CF_3$ | $CH_3$ | — | $CH_3$ |
| 2-372 | F | O | 0 | H | $CF_3$ | $CH_3$ | — | $C_2H_5$ |
| 2-373 | F | O | 0 | H | $CF_3$ | $CH_3$ | — | $^nC_3H_7$ |
| 2-374 | F | O | 0 | H | $CF_3$ | $CH_3$ | — | $^nC_4H_9$ |
| 2-375 | F | O | 0 | H | $CF_3$ | $CH_3$ | — | $CH_2CH=CH_2$ |
| 2-376 | F | O | 0 | H | $CF_3$ | $CH_3$ | — | $CH(CH_3)CH=CH_2$ |

TABLE 2-continued

Compounds of the formula:

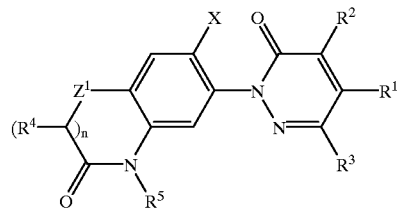

| Compound No. | X | $Z^1$ | n | $R^3$ | $R^1$ | $R^2$ | $R^4$ | $R^5$ |
|---|---|---|---|---|---|---|---|---|
| 2-377 | F | O | 0 | H | $CF_3$ | $CH_3$ | — | $CH_2C{\equiv}CH$ |
| 2-378 | F | O | 0 | H | $CF_3$ | $CH_3$ | — | $CH(CH_3)C{\equiv}CH$ |
| 2-379 | F | O | 0 | H | $CF_3$ | $CH_3$ | — | $CH_2OCH_3$ |
| 2-380 | F | O | 0 | H | $CF_3$ | $CH_3$ | — | $CH_2OC_2H_5$ |
| 2-381 | H | O | 1 | H | $CF_2Cl$ | H | H | H |
| 2-382 | H | O | 1 | H | $CF_2Cl$ | H | H | $CH_3$ |
| 2-383 | H | O | 1 | H | $CF_2Cl$ | H | H | $C_2H_5$ |
| 2-384 | H | O | 1 | H | $CF_2Cl$ | H | H | $^nC_3H_7$ |
| 2-385 | H | O | 1 | H | $CF_2Cl$ | H | H | $^iC_3H_7$ |
| 2-386 | H | O | 1 | H | $CF_2Cl$ | H | H | $^iC_4H_9$ |
| 2-387 | H | O | 1 | H | $CF_2Cl$ | H | H | $^nC_4H_9$ |
| 2-388 | H | O | 1 | H | $CF_2Cl$ | H | H | $CH_2CH_2Cl$ |
| 2-389 | H | O | 1 | H | $CF_2Cl$ | H | H | $CH_2CH_2Br$ |
| 2-390 | H | O | 1 | H | $CF_2Cl$ | H | H | $CH_2CH{=}CH_2$ |
| 2-391 | H | O | 1 | H | $CF_2Cl$ | H | H | $CH(CH_3)CH{=}CH_2$ |
| 2-392 | H | O | 1 | H | $CF_2Cl$ | H | H | $CH_2CCl{=}CH_2$ |
| 2-393 | H | O | 1 | H | $CF_2Cl$ | H | H | $CH_2C{\equiv}CH$ |
| 2-394 | H | O | 1 | H | $CF_2Cl$ | H | H | $CH(CH_3)C{\equiv}CH$ |
| 2-395 | H | O | 1 | H | $CF_2Cl$ | H | H | $CH_2CN$ |
| 2-396 | H | O | 1 | H | $CF_2Cl$ | H | H | $CH_2OCH_3$ |
| 2-397 | H | O | 1 | H | $CF_2Cl$ | H | H | $CH_2OC_2H_5$ |
| 2-398 | H | O | 1 | H | $CF_2Cl$ | H | H | $CH_2COOH$ |
| 2-399 | H | O | 1 | H | $CF_2Cl$ | H | H | $CH_2COOCH_3$ |
| 2-400 | H | O | 1 | H | $CF_2Cl$ | H | H | $CH_2COOC_2H_5$ |
| 2-401 | H | O | 1 | H | $CF_2Cl$ | H | H | $CH_2COO^nC_3H_7$ |
| 2-402 | H | O | 1 | H | $CF_2Cl$ | H | H | $CH_2COO^nC_4H_9$ |
| 2-403 | H | O | 1 | H | $CF_2Cl$ | H | H | $CH_2COO^nC_5H_{11}$ |
| 2-404 | H | O | 1 | H | $CF_2Cl$ | H | H | $CH_2COO^iC_3H_7$ |
| 2-405 | H | O | 1 | H | $CF_2Cl$ | H | H | $CH_2COO^cC_5H_9$ |
| 2-406 | H | O | 1 | H | $CF_2Cl$ | H | H | $CH_2COO^cC_6H_{11}$ |
| 2-407 | H | O | 1 | H | $CF_2Cl$ | H | H | $CH(CH_3)COOH$ |
| 2-408 | H | O | 1 | H | $CF_2Cl$ | H | H | $CH(CH_3)COOCH_3$ |
| 2-409 | H | O | 1 | H | $CF_2Cl$ | H | H | $CH(CH_3)COOC_2H_5$ |
| 2-410 | H | O | 1 | H | $CF_2Cl$ | H | H | $CH(CH_3)COO^nC_3H_7$ |
| 2-411 | H | O | 1 | H | $CF_2Cl$ | H | H | $CH(CH_3)COO^nC_4H_9$ |
| 2-412 | H | O | 1 | H | $CF_2Cl$ | H | H | $CH(CH_3)COO^nC_5H_{11}$ |
| 2-413 | H | O | 1 | H | $CF_2Cl$ | H | H | $CH(CH_3)COO^iC_3H_7$ |
| 2-414 | H | O | 1 | H | $CF_2Cl$ | H | H | $CH(CH_3)COO^cC_5H_9$ |
| 2-415 | H | O | 1 | H | $CF_2Cl$ | H | H | $CH(CH_3)COO^cC_6H_{11}$ |
| 2-416 | H | O | 1 | H | $CF_2Cl$ | H | $CH_3$ | H |
| 2-417 | H | O | 1 | H | $CF_2Cl$ | H | $CH_3$ | $CH_3$ |
| 2-418 | H | O | 1 | H | $CF_2Cl$ | H | $CH_3$ | $C_2H_5$ |
| 2-419 | H | O | 1 | H | $CF_2Cl$ | H | $CH_3$ | $^nC_3H_7$ |
| 2-420 | H | O | 1 | H | $CF_2Cl$ | H | $CH_3$ | $^iC_3H_7$ |
| 2-421 | H | O | 1 | H | $CF_2Cl$ | H | $CH_3$ | $^iC_4H_9$ |
| 2-422 | H | O | 1 | H | $CF_2Cl$ | H | $CH_3$ | $^nC_4H_9$ |
| 2-423 | H | O | 1 | H | $CF_2Cl$ | H | $CH_3$ | $CH_2CH{=}CH_2$ |
| 2-424 | H | O | 1 | H | $CF_2Cl$ | H | $CH_3$ | $CH(CH_3)CH{=}CH_2$ |
| 2-425 | H | O | 1 | H | $CF_2Cl$ | H | $CH_3$ | $CH_2C{\equiv}CH$ |
| 2-426 | H | O | 1 | H | $CF_2Cl$ | H | $CH_3$ | $CH(CH_3)C{\equiv}CH$ |
| 2-427 | H | O | 1 | H | $CF_2Cl$ | H | $CH_3$ | $CH_2OCH_3$ |
| 2-428 | H | O | 1 | H | $CF_2Cl$ | H | $CH_3$ | $CH_2OC_2H_5$ |
| 2-429 | F | O | 1 | H | $CF_2Cl$ | H | H | H |
| 2-430 | F | O | 1 | H | $CF_2Cl$ | H | H | $CH_3$ |
| 2-431 | F | O | 1 | H | $CF_2Cl$ | H | H | $C_2H_5$ |
| 2-432 | F | O | 1 | H | $CF_2Cl$ | H | H | $^nC_3H_7$ |
| 2-433 | F | O | 1 | H | $CF_2Cl$ | H | H | $^iC_3H_7$ |
| 2-434 | F | O | 1 | H | $CF_2Cl$ | H | H | $^iC_4H_9$ |
| 2-435 | F | O | 1 | H | $CF_2Cl$ | H | H | $^nC_4H_9$ |
| 2-436 | F | O | 1 | H | $CF_2Cl$ | H | H | $CH_2CH_2Cl$ |
| 2-437 | F | O | 1 | H | $CF_2Cl$ | H | H | $CH_2CH_2Br$ |
| 2-438 | F | O | 1 | H | $CF_2Cl$ | H | H | $CH_2CH{=}CH_2$ |

TABLE 2-continued

Compounds of the formula:

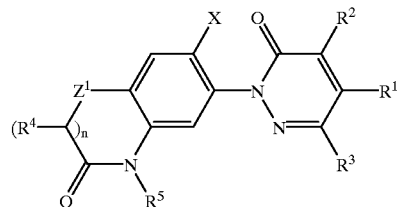

| Compound No. | X | $Z^1$ | n | $R^3$ | $R^1$ | $R^2$ | $R^4$ | $R^5$ |
|---|---|---|---|---|---|---|---|---|
| 2-439 | F | O | 1 | H | $CF_2Cl$ | H | H | $CH(CH_3)CH=CH_2$ |
| 2-440 | F | O | 1 | H | $CF_2Cl$ | H | H | $CH_2CCl=CH_2$ |
| 2-441 | F | O | 1 | H | $CF_2Cl$ | H | H | $CH_2C\equiv CH$ |
| 2-442 | F | O | 1 | H | $CF_2Cl$ | H | H | $CH(CH_3)C\equiv CH$ |
| 2-443 | F | O | 1 | H | $CF_2Cl$ | H | H | $CH_2CN$ |
| 2-444 | F | O | 1 | H | $CF_2Cl$ | H | H | $CH_2OCH_3$ |
| 2-445 | F | O | 1 | H | $CF_2Cl$ | H | H | $CH_2OC_2H_5$ |
| 2-446 | F | O | 1 | H | $CF_2Cl$ | H | H | $CH_2COOH$ |
| 2-447 | F | O | 1 | H | $CF_2Cl$ | H | H | $CH_2COOCH_3$ |
| 2-448 | F | O | 1 | H | $CF_2Cl$ | H | H | $CH_2COOC_2H_5$ |
| 2-449 | F | O | 1 | H | $CF_2Cl$ | H | H | $CH_2COO^nC_3H_7$ |
| 2-450 | F | O | 1 | H | $CF_2Cl$ | H | H | $CH_2COO^nC_4H_9$ |
| 2-451 | F | O | 1 | H | $CF_2Cl$ | H | H | $CH_2COO^nC_5H_{11}$ |
| 2-452 | F | O | 1 | H | $CF_2Cl$ | H | H | $CH_2COO^iC_3H_7$ |
| 2-453 | F | O | 1 | H | $CF_2Cl$ | H | H | $CH_2COO^cC_5H_9$ |
| 2-454 | F | O | 1 | H | $CF_2Cl$ | H | H | $CH_2COO^cC_6H_{11}$ |
| 2-455 | F | O | 1 | H | $CF_2Cl$ | H | H | $CH(CH_3)COOH$ |
| 2-456 | F | O | 1 | H | $CF_2Cl$ | H | H | $CH(CH_3)COOCH_3$ |
| 2-457 | F | O | 1 | H | $CF_2Cl$ | H | H | $CH(CH_3)COOC_2H_5$ |
| 2-458 | F | O | 1 | H | $CF_2Cl$ | H | H | $CH(CH_3)COO^nC_3H_7$ |
| 2-459 | F | O | 1 | H | $CF_2Cl$ | H | H | $CH(CH_3)COO^nC_4H_9$ |
| 2-460 | F | O | 1 | H | $CF_2Cl$ | H | H | $CH(CH_3)COO^nC_5H_{11}$ |
| 2-461 | F | O | 1 | H | $CF_2Cl$ | H | H | $CH(CH_3)COO^iC_3H_7$ |
| 2-462 | F | O | 1 | H | $CF_2Cl$ | H | H | $CH(CH_3)COO^cC_5H_9$ |
| 2-463 | F | O | 1 | H | $CF_2Cl$ | H | H | $CH(CH_3)COO^cC_6H_{11}$ |
| 2-464 | F | O | 1 | H | $CF_2Cl$ | H | $CH_3$ | H |
| 2-465 | F | O | 1 | H | $CF_2Cl$ | H | $CH_3$ | $CH_3$ |
| 2-466 | F | O | 1 | H | $CF_2Cl$ | H | $CH_3$ | $C_2H_5$ |
| 2-467 | F | O | 1 | H | $CF_2Cl$ | H | $CH_3$ | $^nC_3H_7$ |
| 2-468 | F | O | 1 | H | $CF_2Cl$ | H | $CH_3$ | $^iC_3H_7$ |
| 2-469 | F | O | 1 | H | $CF_2Cl$ | H | $CH_3$ | $^iC_4H_9$ |
| 2-470 | F | O | 1 | H | $CF_2Cl$ | H | $CH_3$ | $^nC_4H_9$ |
| 2-471 | F | O | 1 | H | $CF_2Cl$ | H | $CH_3$ | $CH_2CH=CH_2$ |
| 2-472 | F | O | 1 | H | $CF_2Cl$ | H | $CH_3$ | $CH(CH_3)CH=CH_2$ |
| 2-473 | F | O | 1 | H | $CF_2Cl$ | H | $CH_3$ | $CH_2C\equiv CH$ |
| 2-474 | F | O | 1 | H | $CF_2Cl$ | H | $CH_3$ | $CH(CH_3)C\equiv CH$ |
| 2-475 | F | O | 1 | H | $CF_2Cl$ | H | $CH_3$ | $CH_2OCH_3$ |
| 2-476 | F | O | 1 | H | $CF_2Cl$ | H | $CH_3$ | $CH_2OC_2H_5$ |
| 2-477 | H | S | 0 | H | $CF_2Cl$ | H | — | H |
| 2-478 | H | S | 0 | H | $CF_2Cl$ | H | — | $CH_3$ |
| 2-479 | H | S | 0 | H | $CF_2Cl$ | H | — | $C_2H_5$ |
| 2-480 | H | S | 0 | H | $CF_2Cl$ | H | — | $^nC_3H_7$ |
| 2-481 | H | S | 0 | H | $CF_2Cl$ | H | — | $^nC_4H_9$ |
| 2-482 | H | S | 0 | H | $CF_2Cl$ | H | — | $^iC_3H_7$ |
| 2-483 | H | S | 0 | H | $CF_2Cl$ | H | — | $^iC_4H_9$ |
| 2-484 | H | S | 0 | H | $CF_2Cl$ | H | — | $CH_2CH_2Cl$ |
| 2-485 | H | S | 0 | H | $CF_2Cl$ | H | — | $CH_2CH_2Br$ |
| 2-486 | H | S | 0 | H | $CF_2Cl$ | H | — | $CH_2CH=CH_2$ |
| 2-487 | H | S | 0 | H | $CF_2Cl$ | H | — | $CH(CH_3)CH=CH_2$ |
| 2-488 | H | S | 0 | H | $CF_2Cl$ | H | — | $CH_2CCl=CH_2$ |
| 2-489 | H | S | 0 | H | $CF_2Cl$ | H | — | $CH_2C\equiv CH$ |
| 2-490 | H | S | 0 | H | $CF_2Cl$ | H | — | $CH(CH_3)C\equiv CH$ |
| 2-491 | H | S | 0 | H | $CF_2Cl$ | H | — | $CH_2CN$ |
| 2-492 | H | S | 0 | H | $CF_2Cl$ | H | — | $CH_2OCH_3$ |
| 2-493 | H | S | 0 | H | $CF_2Cl$ | H | — | $CH_2OC_2H_5$ |
| 2-494 | H | S | 0 | H | $CF_2Cl$ | H | — | $CH_2COOH$ |
| 2-495 | H | S | 0 | H | $CF_2Cl$ | H | — | $CH_2COOCH_3$ |
| 2-496 | H | S | 0 | H | $CF_2Cl$ | H | — | $CH_2COOC_2H_5$ |
| 2-497 | H | S | 0 | H | $CF_2Cl$ | H | — | $CH_2COO^nC_3H_7$ |
| 2-498 | H | S | 0 | H | $CF_2Cl$ | H | — | $CH_2COO^nC_4H_9$ |
| 2-499 | H | S | 0 | H | $CF_2Cl$ | H | — | $CH_2COO^nC_5H_{11}$ |
| 2-500 | H | S | 0 | H | $CF_2Cl$ | H | — | $CH_2COO^iC_3H_7$ |

TABLE 2-continued

Compounds of the formula:

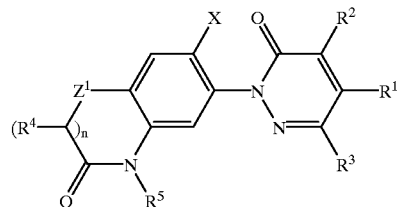

| Compound No. | X | $Z^1$ | n | $R^3$ | $R^1$ | $R^2$ | $R^4$ | $R^5$ |
|---|---|---|---|---|---|---|---|---|
| 2-501 | H | S | 0 | H | $CF_2Cl$ | H | — | $CH_2COO^cC_5H_9$ |
| 2-502 | H | S | 0 | H | $CF_2Cl$ | H | — | $CH_2COO^cC_6H_{11}$ |
| 2-503 | H | S | 0 | H | $CF_2Cl$ | H | — | $CH(CH_3)COOH$ |
| 2-504 | H | S | 0 | H | $CF_2Cl$ | H | — | $CH(CH_3)COOCH_3$ |
| 2-505 | H | S | 0 | H | $CF_2Cl$ | H | — | $CH(CH_3)COOC_2H_5$ |
| 2-506 | H | S | 0 | H | $CF_2Cl$ | H | — | $CH(CH_3)COO^nC_3H_7$ |
| 2-507 | H | S | 0 | H | $CF_2Cl$ | H | — | $CH(CH_3)COO^nC_4H_9$ |
| 2-508 | H | S | 0 | H | $CF_2Cl$ | H | — | $CH(CH_3)COO^nC_5H_{11}$ |
| 2-509 | H | S | 0 | H | $CF_2Cl$ | H | — | $CH(CH_3)COO^iC_3H_7$ |
| 2-510 | H | S | 0 | H | $CF_2Cl$ | H | — | $CH(CH_3)COO^cC_5H_9$ |
| 2-511 | H | S | 0 | H | $CF_2Cl$ | H | — | $CH(CH_3)COO^cC_6H_{11}$ |
| 2-512 | F | S | 0 | H | $CF_2Cl$ | H | — | H |
| 2-513 | F | S | 0 | H | $CF_2Cl$ | H | — | $CH_3$ |
| 2-514 | F | S | 0 | H | $CF_2Cl$ | H | — | $C_2H_5$ |
| 2-515 | F | S | 0 | H | $CF_2Cl$ | H | — | $^nC_3H_7$ |
| 2-516 | F | S | 0 | H | $CF_2Cl$ | H | — | $^nC_4H_9$ |
| 2-517 | F | S | 0 | H | $CF_2Cl$ | H | — | $^iC_3H_7$ |
| 2-518 | F | S | 0 | H | $CF_2Cl$ | H | — | $^iC_4H_9$ |
| 2-519 | F | S | 0 | H | $CF_2Cl$ | H | — | $CH_2CH_2Cl$ |
| 2-520 | F | S | 0 | H | $CF_2Cl$ | H | — | $CH_2CH_2Br$ |
| 2-521 | F | S | 0 | H | $CF_2Cl$ | H | — | $CH_2CH=CH_2$ |
| 2-522 | F | S | 0 | H | $CF_2Cl$ | H | — | $CH(CH_3)CH=CH_2$ |
| 2-523 | F | S | 0 | H | $CF_2Cl$ | H | — | $CH_2CCl=CH_2$ |
| 2-524 | F | S | 0 | H | $CF_2Cl$ | H | — | $CH_2C\equiv CH$ |
| 2-525 | F | S | 0 | H | $CF_2Cl$ | H | — | $CH(CH_3)C\equiv CH$ |
| 2-526 | F | S | 0 | H | $CF_2Cl$ | H | — | $CH_2CN$ |
| 2-527 | F | S | 0 | H | $CF_2Cl$ | H | — | $CH_2OCH_3$ |
| 2-528 | F | S | 0 | H | $CF_2Cl$ | H | — | $CH_2OC_2H_5$ |
| 2-529 | F | S | 0 | H | $CF_2Cl$ | H | — | $CH_2COOH$ |
| 2-530 | F | S | 0 | H | $CF_2Cl$ | H | — | $CH_2COOCH_3$ |
| 2-531 | F | S | 0 | H | $CF_2Cl$ | H | — | $CH_2COOC_2H_5$ |
| 2-532 | F | S | 0 | H | $CF_2Cl$ | H | — | $CH_2COO^nC_3H_7$ |
| 2-533 | F | S | 0 | H | $CF_2Cl$ | H | — | $CH_2COO^nC_4H_9$ |
| 2-534 | F | S | 0 | H | $CF_2Cl$ | H | — | $CH_2COO^nC_5H_{11}$ |
| 2-535 | F | S | 0 | H | $CF_2Cl$ | H | — | $CH_2COO^iC_3H_7$ |
| 2-536 | F | S | 0 | H | $CF_2Cl$ | H | — | $CH_2COO^cC_5H_9$ |
| 2-537 | F | S | 0 | H | $CF_2Cl$ | H | — | $CH_2COO^cC_6H_{11}$ |
| 2-538 | F | S | 0 | H | $CF_2Cl$ | H | — | $CH(CH_3)COOH$ |
| 2-539 | F | S | 0 | H | $CF_2Cl$ | H | — | $CH(CH_3)COOCH_3$ |
| 2-540 | F | S | 0 | H | $CF_2Cl$ | H | — | $CH(CH_3)COOC_2H_5$ |
| 2-541 | F | S | 0 | H | $CF_2Cl$ | H | — | $CH(CH_3)COO^nC_3H_7$ |
| 2-542 | F | S | 0 | H | $CF_2Cl$ | H | — | $CH(CH_3)COO^nC_4H_9$ |
| 2-543 | F | S | 0 | H | $CF_2Cl$ | H | — | $CH(CH_3)COO^nC_5H_{11}$ |
| 2-544 | F | S | 0 | H | $CF_2Cl$ | H | — | $CH(CH_3)COO^iC_3H_7$ |
| 2-545 | F | S | 0 | H | $CF_2Cl$ | H | — | $CH(CH_3)COO^cC_5H_9$ |
| 2-546 | F | S | 0 | H | $CF_2Cl$ | H | — | $CH(CH_3)COO^cC_6H_{11}$ |
| 2-547 | H | O | 0 | H | $CF_2Cl$ | H | — | H |
| 2-548 | H | O | 0 | H | $CF_2Cl$ | H | — | $CH_3$ |
| 2-549 | H | O | 0 | H | $CF_2Cl$ | H | — | $C_2H_5$ |
| 2-550 | H | O | 0 | H | $CF_2Cl$ | H | — | $^nC_3H_7$ |
| 2-551 | H | O | 0 | H | $CF_2Cl$ | H | — | $^nC_4H_9$ |
| 2-552 | H | O | 0 | H | $CF_2Cl$ | H | — | $^iC_3H_7$ |
| 2-553 | H | O | 0 | H | $CF_2Cl$ | H | — | $^iC_4H_9$ |
| 2-554 | H | O | 0 | H | $CF_2Cl$ | H | — | $CH_2CH=CH_2$ |
| 2-555 | H | O | 0 | H | $CF_2Cl$ | H | — | $CH(CH_3)CH=CH_2$ |
| 2-556 | H | O | 0 | H | $CF_2Cl$ | H | — | $CH_2C\equiv CH$ |
| 2-557 | H | O | 0 | H | $CF_2Cl$ | H | — | $CH(CH_3)C\equiv CH$ |
| 2-558 | H | O | 0 | H | $CF_2Cl$ | H | — | $CH_2OCH_3$ |
| 2-559 | H | O | 0 | H | $CF_2Cl$ | H | — | $CH_2OC_2H_5$ |
| 2-560 | F | O | 0 | H | $CF_2Cl$ | H | — | H |
| 2-561 | F | O | 0 | H | $CF_2Cl$ | H | — | $CH_3$ |
| 2-562 | F | O | 0 | H | $CF_2Cl$ | H | — | $C_2H_5$ |

TABLE 2-continued

Compounds of the formula:

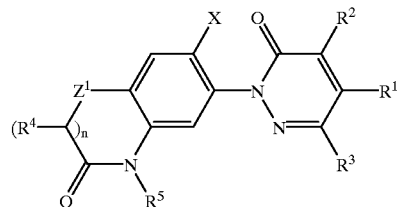

| Compound No. | X | $Z^1$ | n | $R^3$ | $R^1$ | $R^2$ | $R^4$ | $R^5$ |
|---|---|---|---|---|---|---|---|---|
| 2-563 | F | O | 0 | H | $CF_2Cl$ | H | — | $^nC_3H_7$ |
| 2-564 | F | O | 0 | H | $CF_2Cl$ | H | — | $^nC_4H_9$ |
| 2-565 | F | O | 0 | H | $CF_2Cl$ | H | — | $CH_2CH=CH_2$ |
| 2-566 | F | O | 0 | H | $CF_2Cl$ | H | — | $CH(CH_3)CH=CH_2$ |
| 2-567 | F | O | 0 | H | $CF_2Cl$ | H | — | $CH_2C\equiv CH$ |
| 2-568 | F | O | 0 | H | $CF_2Cl$ | H | — | $CH(CH_3)C\equiv CH$ |
| 2-569 | F | O | 0 | H | $CF_2Cl$ | H | — | $CH_2OCH_3$ |
| 2-570 | F | O | 0 | H | $CF_2Cl$ | H | — | $CH_2OC_2H_5$ |
| 2-571 | H | O | 1 | H | $CF_3$ | H | H | H |
| 2-572 | H | O | 1 | H | $CF_3$ | H | H | $CH_3$ |
| 2-573 | H | O | 1 | H | $CF_3$ | H | H | $C_2H_5$ |
| 2-574 | H | O | 1 | H | $CF_3$ | H | H | $^nC_3H_7$ |
| 2-575 | H | O | 1 | H | $CF_3$ | H | H | $^iC_3H_7$ |
| 2-576 | H | O | 1 | H | $CF_3$ | H | H | $^iC_4H_9$ |
| 2-577 | H | O | 1 | H | $CF_3$ | H | H | $^nC_4H_9$ |
| 2-578 | H | O | 1 | H | $CF_3$ | H | H | $CH_2CH_2Cl$ |
| 2-579 | H | O | 1 | H | $CF_3$ | H | H | $CH_2CH_2Br$ |
| 2-580 | H | O | 1 | H | $CF_3$ | H | H | $CH_2CH=CH_2$ |
| 2-581 | H | O | 1 | H | $CF_3$ | H | H | $CH(CH_3)CH=CH_2$ |
| 2-582 | H | O | 1 | H | $CF_3$ | H | H | $CH_2CCl=CH_2$ |
| 2-583 | H | O | 1 | H | $CF_3$ | H | H | $CH_2C\equiv CH$ |
| 2-584 | H | O | 1 | H | $CF_3$ | H | H | $CH(CH_3)C\equiv CH$ |
| 2-585 | H | O | 1 | H | $CF_3$ | H | H | $CH_2CN$ |
| 2-586 | H | O | 1 | H | $CF_3$ | H | H | $CH_2OCH_3$ |
| 2-587 | H | O | 1 | H | $CF_3$ | H | H | $CH_2OC_2H_5$ |
| 2-588 | H | O | 1 | H | $CF_3$ | H | H | $CH_2COOH$ |
| 2-589 | H | O | 1 | H | $CF_3$ | H | H | $CH_2COOCH_3$ |
| 2-590 | H | O | 1 | H | $CF_3$ | H | H | $CH_2COOC_2H_5$ |
| 2-591 | H | O | 1 | H | $CF_3$ | H | H | $CH_2COO^nC_3H_7$ |
| 2-592 | H | O | 1 | H | $CF_3$ | H | H | $CH_2COO^nC_4H_9$ |
| 2-593 | H | O | 1 | H | $CF_3$ | H | H | $CH_2COO^nC_5H_{11}$ |
| 2-594 | H | O | 1 | H | $CF_3$ | H | H | $CH_2COO^iC_3H_7$ |
| 2-595 | H | O | 1 | H | $CF_3$ | H | H | $CH_2COO^cC_5H_9$ |
| 2-596 | H | O | 1 | H | $CF_3$ | H | H | $CH_2COO^cC_6H_{11}$ |
| 2-597 | H | O | 1 | H | $CF_3$ | H | H | $CH(CH_3)COOH$ |
| 2-598 | H | O | 1 | H | $CF_3$ | H | H | $CH(CH_3)COOCH$ |
| 2-599 | H | O | 1 | H | $CF_3$ | H | H | $CH(CH_3)COOC_2H_5$ |
| 2-600 | H | O | 1 | H | $CF_3$ | H | H | $CH(CH_3)COO^nC_3H_7$ |
| 2-601 | H | O | 1 | H | $CF_3$ | H | H | $CH(CH_3)COO^nC_4H_9$ |
| 2-602 | H | O | 1 | H | $CF_3$ | H | H | $CH(CH_3)COO^nC_5H_{11}$ |
| 2-603 | H | O | 1 | H | $CF_3$ | H | H | $CH(CH_3)COO^iC_3H_7$ |
| 2-604 | H | O | 1 | H | $CF_3$ | H | H | $CH(CH_3)COO^cC_5H_9$ |
| 2-605 | H | O | 1 | H | $CF_3$ | H | H | $CH(CH_3)COO^cC_6H_{11}$ |
| 2-606 | H | O | 1 | H | $CF_3$ | H | $CH_3$ | H |
| 2-607 | H | O | 1 | H | $CF_3$ | H | $CH_3$ | $CH_3$ |
| 2-608 | H | O | 1 | H | $CF_3$ | H | $CH_3$ | $C_2H_5$ |
| 2-609 | H | O | 1 | H | $CF_3$ | H | $CH_3$ | $^nC_3H_7$ |
| 2-610 | H | O | 1 | H | $CF_3$ | H | $CH_3$ | $^iC_3H_7$ |
| 2-611 | H | O | 1 | H | $CF_3$ | H | $CH_3$ | $^iC_4H_9$ |
| 2-612 | H | O | 1 | H | $CF_3$ | H | $CH_3$ | $^nC_4H_9$ |
| 2-613 | H | O | 1 | H | $CF_3$ | H | $CH_3$ | $CH_2CH=CH_2$ |
| 2-614 | H | O | 1 | H | $CF_3$ | H | $CH_3$ | $CH(CH_3)CH=CH_2$ |
| 2-615 | H | O | 1 | H | $CF_3$ | H | $CH_3$ | $CH_2C\equiv CH$ |
| 2-616 | H | O | 1 | H | $CF_3$ | H | $CH_3$ | $CH(CH_3)C\equiv CH$ |
| 2-617 | H | O | 1 | H | $CF_3$ | H | $CH_3$ | $CH_2OCH_3$ |
| 2-618 | H | O | 1 | H | $CF_3$ | H | $CH_3$ | $CH_2OC_2H_5$ |
| 2-619 | F | O | 1 | H | $CF_3$ | H | H | H |
| 2-620 | F | O | 1 | H | $CF_3$ | H | H | $CH_3$ |
| 2-621 | F | O | 1 | H | $CF_3$ | H | H | $C_2H_5$ |
| 2-622 | F | O | 1 | H | $CF_3$ | H | H | $^nC_3H_7$ |
| 2-623 | F | O | 1 | H | $CF_3$ | H | H | $^iC_3H_7$ |
| 2-624 | F | O | 1 | H | $CF_3$ | H | H | $^iC_4H_9$ |

TABLE 2-continued

Compounds of the formula:

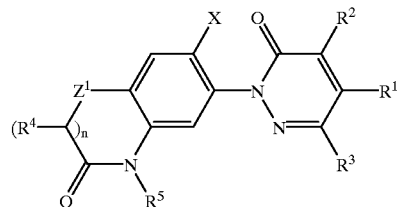

| Compound No. | X | $Z^1$ | n | $R^3$ | $R^1$ | $R^2$ | $R^4$ | $R^5$ |
|---|---|---|---|---|---|---|---|---|
| 2-625 | F | O | 1 | H | $CF_3$ | H | H | $^nC_4H_9$ |
| 2-626 | F | O | 1 | H | $CF_3$ | H | H | $CH_2CH_2Cl$ |
| 2-627 | F | O | 1 | H | $CF_3$ | H | H | $CH_2CH_2Br$ |
| 2-628 | F | O | 1 | H | $CF_3$ | H | H | $CH_2CH=CH_2$ |
| 2-629 | F | O | 1 | H | $CF_3$ | H | H | $CH(CH_3)CH=CH_2$ |
| 2-630 | F | O | 1 | H | $CF_3$ | H | H | $CH_2CCl=CH_2$ |
| 2-631 | F | O | 1 | H | $CF_3$ | H | H | $CH_2C\equiv CH$ |
| 2-632 | F | O | 1 | H | $CF_3$ | H | H | $CH(CH_3)C\equiv CH$ |
| 2-633 | F | O | 1 | H | $CF_3$ | H | H | $CH_2CN$ |
| 2-634 | F | O | 1 | H | $CF_3$ | H | H | $CH_2OCH_3$ |
| 2-635 | F | O | 1 | H | $CF_3$ | H | H | $CH_2OC_2H_5$ |
| 2-636 | F | O | 1 | H | $CF_3$ | H | H | $CH_2COOH$ |
| 2-637 | F | O | 1 | H | $CF_3$ | H | H | $CH_2COOCH_3$ |
| 2-638 | F | O | 1 | H | $CF_3$ | H | H | $CH_2COOC_2H_5$ |
| 2-639 | F | O | 1 | H | $CF_3$ | H | H | $CH_2COO^nC_3H_7$ |
| 2-640 | F | O | 1 | H | $CF_3$ | H | H | $CH_2COO^nC_4H_9$ |
| 2-641 | F | O | 1 | H | $CF_3$ | H | H | $CH_2COO^nC_5H_{11}$ |
| 2-642 | F | O | 1 | H | $CF_3$ | H | H | $CH_2COO^iC_3H_7$ |
| 2-643 | F | O | 1 | H | $CF_3$ | H | H | $CH_2COO^cC_5H_9$ |
| 2-644 | F | O | 1 | H | $CF_3$ | H | H | $CH_2COO^cC_6H_{11}$ |
| 2-645 | F | O | 1 | H | $CF_3$ | H | H | $CH(CH_3)COOH$ |
| 2-646 | F | O | 1 | H | $CF_3$ | H | H | $CH(CH_3)COOCH$ |
| 2-647 | F | O | 1 | H | $CF_3$ | H | H | $CH(CH_3)COOC_2H_5$ |
| 2-648 | F | O | 1 | H | $CF_3$ | H | H | $CH(CH_3)COO^nC_3H_7$ |
| 2-649 | F | O | 1 | H | $CF_3$ | H | H | $CH(CH_3)COO^nC_4H_9$ |
| 2-650 | F | O | 1 | H | $CF_3$ | H | H | $CH(CH_3)COO^nC_5H_{11}$ |
| 2-651 | F | O | 1 | H | $CF_3$ | H | H | $CH(CH_3)COO^iC_3H_7$ |
| 2-652 | F | O | 1 | H | $CF_3$ | H | H | $CH(CH_3)COO^cC_5H_9$ |
| 2-653 | F | O | 1 | H | $CF_3$ | H | H | $CH(CH_3)COO^cC_6H_{11}$ |
| 2-654 | F | O | 1 | H | $CF_3$ | H | $CH_3$ | H |
| 2-655 | F | O | 1 | H | $CF_3$ | H | $CH_3$ | $CH_3$ |
| 2-656 | F | O | 1 | H | $CF_3$ | H | $CH_3$ | $C_2H_5$ |
| 2-657 | F | O | 1 | H | $CF_3$ | H | $CH_3$ | $^nC_3H_7$ |
| 2-658 | F | O | 1 | H | $CF_3$ | H | $CH_3$ | $^iC_3H_7$ |
| 2-659 | F | O | 1 | H | $CF_3$ | H | $CH_3$ | $^iC_4H_9$ |
| 2-660 | F | O | 1 | H | $CF_3$ | H | $CH_3$ | $^nC_4H_9$ |
| 2-661 | F | O | 1 | H | $CF_3$ | H | $CH_3$ | $CH_2CH=CH_2$ |
| 2-662 | F | O | 1 | H | $CF_3$ | H | $CH_3$ | $CH(CH_3)CH=CH_2$ |
| 2-663 | F | O | 1 | H | $CF_3$ | H | $CH_3$ | $CH_2C\equiv CH$ |
| 2-664 | F | O | 1 | H | $CF_3$ | H | $CH_3$ | $CH(CH_3)C\equiv CH$ |
| 2-665 | F | O | 1 | H | $CF_3$ | H | $CH_3$ | $CH_2OCH_3$ |
| 2-666 | F | O | 1 | H | $CF_3$ | H | $CH_3$ | $CH_2OC_2H_5$ |
| 2-667 | H | S | 0 | H | $CF_3$ | H | — | H |
| 2-668 | H | S | 0 | H | $CF_3$ | H | — | $CH_3$ |
| 2-669 | H | S | 0 | H | $CF_3$ | H | — | $C_2H_5$ |
| 2-670 | H | S | 0 | H | $CF_3$ | H | — | $^nC_3H_7$ |
| 2-671 | H | S | 0 | H | $CF_3$ | H | — | $^nC_4H_9$ |
| 2-672 | H | S | 0 | H | $CF_3$ | H | — | $^iC_3H_7$ |
| 2-673 | H | S | 0 | H | $CF_3$ | H | — | $^iC_4H_9$ |
| 2-674 | H | S | 0 | H | $CF_3$ | H | — | $CH_2CH_2Cl$ |
| 2-675 | H | S | 0 | H | $CF_3$ | H | — | $CH_2CH_2Br$ |
| 2-676 | H | S | 0 | H | $CF_3$ | H | — | $CH_2CH=CH_2$ |
| 2-677 | H | S | 0 | H | $CF_3$ | H | — | $CH(CH_3)CH=CH_2$ |
| 2-678 | H | S | 0 | H | $CF_3$ | H | — | $CH_2CCl=CH_2$ |
| 2-679 | H | S | 0 | H | $CF_3$ | H | — | $CH_2C\equiv CH$ |
| 2-680 | H | S | 0 | H | $CF_3$ | H | — | $CH(CH_3)C\equiv CH$ |
| 2-681 | H | S | 0 | H | $CF_3$ | H | — | $CH_2CN$ |
| 2-682 | H | S | 0 | H | $CF_3$ | H | — | $CH_2OCH_3$ |
| 2-683 | H | S | 0 | H | $CF_3$ | H | — | $CH_2OC_2H_5$ |
| 2-684 | H | S | 0 | H | $CF_3$ | H | — | $CH_2COOH$ |
| 2-685 | H | S | 0 | H | $CF_3$ | H | — | $CH_2COOCH_3$ |
| 2-686 | H | S | 0 | H | $CF_3$ | H | — | $CH_2COOC_2H_5$ |

TABLE 2-continued

Compounds of the formula:

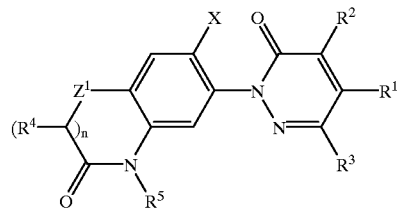

| Compound No. | X | $Z^1$ | n | $R^3$ | $R^1$ | $R^2$ | $R^4$ | $R^5$ |
|---|---|---|---|---|---|---|---|---|
| 2-687 | H | S | 0 | H | $CF_3$ | H | — | $CH_2COO^nC_3H_7$ |
| 2-688 | H | S | 0 | H | $CF_3$ | H | — | $CH_2COO^nC_4H_9$ |
| 2-689 | H | S | 0 | H | $CF_3$ | H | — | $CH_2COO^nC_5H_{11}$ |
| 2-690 | H | S | 0 | H | $CF_3$ | H | — | $CH_2COO^iC_3H_7$ |
| 2-691 | H | S | 0 | H | $CF_3$ | H | — | $CH_2COO^cC_5H_9$ |
| 2-692 | H | S | 0 | H | $CF_3$ | H | — | $CH_2COO^cC_6H_{11}$ |
| 2-693 | H | S | 0 | H | $CF_3$ | H | — | $CH(CH_3)COOH$ |
| 2-694 | H | S | 0 | H | $CF_3$ | H | — | $CH(CH_3)COOCH$ |
| 2-695 | H | S | 0 | H | $CF_3$ | H | — | $CH(CH_3)COOC_2H_5$ |
| 2-696 | H | S | 0 | H | $CF_3$ | H | — | $CH(CH_3)COO^nC_3H_7$ |
| 2-697 | H | S | 0 | H | $CF_3$ | H | — | $CH(CH_3)COO^nC_4H_9$ |
| 2-698 | H | S | 0 | H | $CF_3$ | H | — | $CH(CH_3)COO^nC_5H_{11}$ |
| 2-699 | H | S | 0 | H | $CF_3$ | H | — | $CH(CH_3)COO^iC_3H_7$ |
| 2-700 | H | S | 0 | H | $CF_3$ | H | — | $CH(CH_3)COO^cC_5H_9$ |
| 2-701 | H | S | 0 | H | $CF_3$ | H | — | $CH(CH_3)COO^cC_6H_{11}$ |
| 2-702 | F | S | 0 | H | $CF_3$ | H | — | H |
| 2-703 | F | S | 0 | H | $CF_3$ | H | — | $CH_3$ |
| 2-704 | F | S | 0 | H | $CF_3$ | H | — | $C_2H_5$ |
| 2-705 | F | S | 0 | H | $CF_3$ | H | — | $^nC_3H_7$ |
| 2-706 | F | S | 0 | H | $CF_3$ | H | — | $^nC_4H_9$ |
| 2-707 | F | S | 0 | H | $CF_3$ | H | — | $^iC_3H_7$ |
| 2-708 | F | S | 0 | H | $CF_3$ | H | — | $^iC_4H_9$ |
| 2-709 | F | S | 0 | H | $CF_3$ | H | — | $CH_2CH_2Cl$ |
| 2-710 | F | S | 0 | H | $CF_3$ | H | — | $CH_2CH_2Br$ |
| 2-711 | F | S | 0 | H | $CF_3$ | H | — | $CH_2CH=CH_2$ |
| 2-712 | F | S | 0 | H | $CF_3$ | H | — | $CH(CH_3)CH=CH_2$ |
| 2-713 | F | S | 0 | H | $CF_3$ | H | — | $CH_2CCl=CH_2$ |
| 2-714 | F | S | 0 | H | $CF_3$ | H | — | $CH_2C\equiv CH$ |
| 2-715 | F | S | 0 | H | $CF_3$ | H | — | $CH(CH_3)C\equiv CH$ |
| 2-716 | F | S | 0 | H | $CF_3$ | H | — | $CH_2CN$ |
| 2-717 | F | S | 0 | H | $CF_3$ | H | — | $CH_2OCH_3$ |
| 2-718 | F | S | 0 | H | $CF_3$ | H | — | $CH_2OC_2H_5$ |
| 2-719 | F | S | 0 | H | $CF_3$ | H | — | $CH_2COOH$ |
| 2-720 | F | S | 0 | H | $CF_3$ | H | — | $CH_2COOCH_3$ |
| 2-721 | F | S | 0 | H | $CF_3$ | H | — | $CH_2COOC_2H_5$ |
| 2-722 | F | S | 0 | H | $CF_3$ | H | — | $CH_2COO^nC_3H_7$ |
| 2-723 | F | S | 0 | H | $CF_3$ | H | — | $CH_2COO^nC_4H_9$ |
| 2-724 | F | S | 0 | H | $CF_3$ | H | — | $CH_2COO^nC_5H_{11}$ |
| 2-725 | F | S | 0 | H | $CF_3$ | H | — | $CH_2COO^iC_3H_7$ |
| 2-726 | F | S | 0 | H | $CF_3$ | H | — | $CH_2COO^cC_5H_9$ |
| 2-727 | F | S | 0 | H | $CF_3$ | H | — | $CH_2COO^cC_6H_{11}$ |
| 2-728 | F | S | 0 | H | $CF_3$ | H | — | $CH(CH_3)COOH$ |
| 2-729 | F | S | 0 | H | $CF_3$ | H | — | $CH(CH_3)COOCH_3$ |
| 2-730 | F | S | 0 | H | $CF_3$ | H | — | $CH(CH_3)COOC_2H_5$ |
| 2-731 | F | S | 0 | H | $CF_3$ | H | — | $CH(CH_3)COO^nC_3H_7$ |
| 2-732 | F | S | 0 | H | $CF_3$ | H | — | $CH(CH_3)COO^nC_4H_9$ |
| 2-733 | F | S | 0 | H | $CF_3$ | H | — | $CH(CH_3)COO^nC_5H_{11}$ |
| 2-734 | F | S | 0 | H | $CF_3$ | H | — | $CH(CH_3)COO^iC_3H_7$ |
| 2-735 | F | S | 0 | H | $CF_3$ | H | — | $CH(CH_3)COO^cC_5H_9$ |
| 2-736 | F | S | 0 | H | $CF_3$ | H | — | $CH(CH_3)COO^cC_6H_{11}$ |
| 2-737 | H | O | 0 | H | $CF_3$ | H | — | H |
| 2-738 | H | O | 0 | H | $CF_3$ | H | — | $CH_3$ |
| 2-739 | H | O | 0 | H | $CF_3$ | H | — | $C_2H_5$ |
| 2-740 | H | O | 0 | H | $CF_3$ | H | — | $^nC_3H_7$ |
| 2-741 | H | O | 0 | H | $CF_3$ | H | — | $^nC_4H_9$ |
| 2-742 | H | O | 0 | H | $CF_3$ | H | — | $^iC_3H_7$ |
| 2-743 | H | O | 0 | H | $CF_3$ | H | — | $^iC_4H_9$ |
| 2-744 | H | O | 0 | H | $CF_3$ | H | — | $CH_2CH=CH_2$ |
| 2-745 | H | O | 0 | H | $CF_3$ | H | — | $CH(CH_3)CH=CH_2$ |
| 2-746 | H | O | 0 | H | $CF_3$ | H | — | $CH_2C\equiv CH$ |
| 2-747 | H | O | 0 | H | $CF_3$ | H | — | $CH(CH_3)C\equiv CH$ |
| 2-748 | H | O | 0 | H | $CF_3$ | H | — | $CH_2OCH_3$ |

TABLE 2-continued

Compounds of the formula:

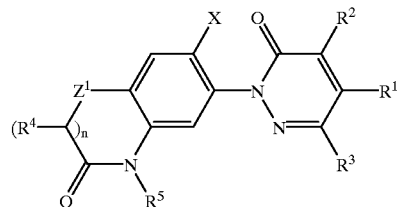

| Compound No. | X | $Z^1$ | n | $R^3$ | $R^1$ | $R^2$ | $R^4$ | $R^5$ |
|---|---|---|---|---|---|---|---|---|
| 2-749 | H | O | 0 | H | $CF_3$ | H | — | $CH_2OC_2H_5$ |
| 2-750 | F | O | 0 | H | $CF_3$ | H | — | H |
| 2-751 | F | O | 0 | H | $CF_3$ | H | — | $CH_3$ |
| 2-752 | F | O | 0 | H | $CF_3$ | H | — | $C_2H_5$ |
| 2-753 | F | O | 0 | H | $CF_3$ | H | — | $^nC_3H_7$ |
| 2-754 | F | O | 0 | H | $CF_3$ | H | — | $^nC_4H_9$ |
| 2-755 | F | O | 0 | H | $CF_3$ | H | — | $CH_2CH=CH_2$ |
| 2-756 | F | O | 0 | H | $CF_3$ | H | — | $CH(CH_3)CH=CH_2$ |
| 2-757 | F | O | 0 | H | $CF_3$ | H | — | $CH_2C\equiv CH$ |
| 2-758 | F | O | 0 | H | $CF_3$ | H | — | $CH(CH_3)C\equiv CH$ |
| 2-759 | F | O | 0 | H | $CF_3$ | H | — | $CH_2OCH_3$ |
| 2-760 | F | O | 0 | H | $CF_3$ | H | — | $CH_2OC_2H_5$ |
| 2-761 | H | O | 1 | $CH_3$ | $CF_3$ | H | H | H |
| 2-762 | H | O | 1 | $CH_3$ | $CF_3$ | H | H | $CH_3$ |
| 2-763 | H | O | 1 | $CH_3$ | $CF_3$ | H | H | $C_2H_5$ |
| 2-764 | H | O | 1 | $CH_3$ | $CF_3$ | H | H | $^nC_3H_7$ |
| 2-765 | H | O | 1 | $CH_3$ | $CF_3$ | H | H | $^iC_3H_7$ |
| 2-766 | H | O | 1 | $CH_3$ | $CF_3$ | H | H | $^iC_4H_9$ |
| 2-767 | H | O | 1 | $CH_3$ | $CF_3$ | H | H | $^nC_4H_9$ |
| 2-768 | H | O | 1 | $CH_3$ | $CF_3$ | H | H | $CH_2CH_2Cl$ |
| 2-769 | H | O | 1 | $CH_3$ | $CF_3$ | H | H | $CH_2CH_2Br$ |
| 2-770 | H | O | 1 | $CH_3$ | $CF_3$ | H | H | $CH_2CH=CH_2$ |
| 2-771 | H | O | 1 | $CH_3$ | $CF_3$ | H | H | $CH(CH_3)CH=CH_2$ |
| 2-772 | H | O | 1 | $CH_3$ | $CF_3$ | H | H | $CH_2CCl=CH_2$ |
| 2-773 | H | O | 1 | $CH_3$ | $CF_3$ | H | H | $CH_2C\equiv CH$ |
| 2-774 | H | O | 1 | $CH_3$ | $CF_3$ | H | H | $CH(CH_3)C\equiv CH$ |
| 2-775 | H | O | 1 | $CH_3$ | $CF_3$ | H | H | $CH_2CN$ |
| 2-776 | H | O | 1 | $CH_3$ | $CF_3$ | H | H | $CH_2OCH_3$ |
| 2-777 | H | O | 1 | $CH_3$ | $CF_3$ | H | H | $CH_2OC_2H_5$ |
| 2-778 | H | O | 1 | $CH_3$ | $CF_3$ | H | H | $CH_2COOH$ |
| 2-779 | H | O | 1 | $CH_3$ | $CF_3$ | H | H | $CH_2COOCH_3$ |
| 2-780 | H | O | 1 | $CH_3$ | $CF_3$ | H | H | $CH_2COOC_2H_5$ |
| 2-781 | H | O | 1 | $CH_3$ | $CF_3$ | H | H | $CH_2COO^nC_3H_7$ |
| 2-782 | H | O | 1 | $CH_3$ | $CF_3$ | H | H | $CH_2COO^nC_4H_9$ |
| 2-783 | H | O | 1 | $CH_3$ | $CF_3$ | H | H | $CH_2COO^nC_5H_{11}$ |
| 2-784 | H | O | 1 | $CH_3$ | $CF_3$ | H | H | $CH_2COO^iC_3H_7$ |
| 2-785 | H | O | 1 | $CH_3$ | $CF_3$ | H | H | $CH_2COO^cC_5H_9$ |
| 2-786 | H | O | 1 | $CH_3$ | $CF_3$ | H | H | $CH_2COO^cC_6H_{11}$ |
| 2-787 | H | O | 1 | $CH_3$ | $CF_3$ | H | H | $CH(CH_3)COOH$ |
| 2-788 | H | O | 1 | $CH_3$ | $CF_3$ | H | H | $CH(CH_3)COOCH_3$ |
| 2-789 | H | O | 1 | $CH_3$ | $CF_3$ | H | H | $CH(CH_3)COOC_2H_5$ |
| 2-790 | H | O | 1 | $CH_3$ | $CF_3$ | H | H | $CH(CH_3)COO^nC_3H_7$ |
| 2-791 | H | O | 1 | $CH_3$ | $CF_3$ | H | H | $CH(CH_3)COO^nC_4H_9$ |
| 2-792 | H | O | 1 | $CH_3$ | $CF_3$ | H | H | $CH(CH_3)COO^nC_5H_{11}$ |
| 2-793 | H | O | 1 | $CH_3$ | $CF_3$ | H | H | $CH(CH_3)COO^iC_3H_7$ |
| 2-794 | H | O | 1 | $CH_3$ | $CF_3$ | H | H | $CH(CH_3)COO^cC_5H_9$ |
| 2-795 | H | O | 1 | $CH_3$ | $CF_3$ | H | H | $CH(CH_3)COO^cC_6H_{11}$ |
| 2-796 | H | O | 1 | $CH_3$ | $CF_3$ | H | $CH_3$ | H |
| 2-797 | H | O | 1 | $CH_3$ | $CF_3$ | H | $CH_3$ | $CH_3$ |
| 2-798 | H | O | 1 | $CH_3$ | $CF_3$ | H | $CH_3$ | $C_2H_5$ |
| 2-799 | H | O | 1 | $CH_3$ | $CF_3$ | H | $CH_3$ | $^nC_3H_7$ |
| 2-800 | H | O | 1 | $CH_3$ | $CF_3$ | H | $CH_3$ | $^iC_3H_7$ |
| 2-801 | H | O | 1 | $CH_3$ | $CF_3$ | H | $CH_3$ | $^iC_4H_9$ |
| 2-802 | H | O | 1 | $CH_3$ | $CF_3$ | H | $CH_3$ | $^nC_4H_9$ |
| 2-803 | H | O | 1 | $CH_3$ | $CF_3$ | H | $CH_3$ | $CH_2CH=CH_2$ |
| 2-804 | H | O | 1 | $CH_3$ | $CF_3$ | H | $CH_3$ | $CH(CH_3)CH=CH_2$ |
| 2-805 | H | O | 1 | $CH_3$ | $CF_3$ | H | $CH_3$ | $CH_2C\equiv CH$ |
| 2-806 | H | O | 1 | $CH_3$ | $CF_3$ | H | $CH_3$ | $CH(CH_3)C\equiv CH$ |
| 2-807 | H | O | 1 | $CH_3$ | $CF_3$ | H | $CH_3$ | $CH_2OCH_3$ |
| 2-808 | H | O | 1 | $CH_3$ | $CF_3$ | H | $CH_3$ | $CH_2OC_2H_5$ |
| 2-809 | F | O | 1 | $CH_3$ | $CF_3$ | H | H | H |
| 2-810 | F | O | 1 | $CH_3$ | $CF_3$ | H | H | $CH_3$ |

TABLE 2-continued

Compounds of the formula:

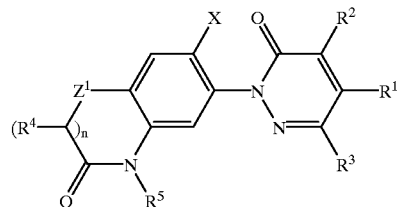

| Compound No. | X | $Z^1$ | n | $R^3$ | $R^1$ | $R^2$ | $R^4$ | $R^5$ |
|---|---|---|---|---|---|---|---|---|
| 2-811 | F | O | 1 | $CH_3$ | $CF_3$ | H | H | $C_2H_5$ |
| 2-812 | F | O | 1 | $CH_3$ | $CF_3$ | H | H | $^nC_3H_7$ |
| 2-813 | F | O | 1 | $CH_3$ | $CF_3$ | H | H | $^iC_3H_7$ |
| 2-814 | F | O | 1 | $CH_3$ | $CF_3$ | H | H | $^iC_4H_9$ |
| 2-815 | F | O | 1 | $CH_3$ | $CF_3$ | H | H | $^nC_4H_9$ |
| 2-816 | F | O | 1 | $CH_3$ | $CF_3$ | H | H | $CH_2CH_2Cl$ |
| 2-817 | F | O | 1 | $CH_3$ | $CF_3$ | H | H | $CH_2CH_2Br$ |
| 2-818 | F | O | 1 | $CH_3$ | $CF_3$ | H | H | $CH_2CH=CH_2$ |
| 2-819 | F | O | 1 | $CH_3$ | $CF_3$ | H | H | $CH(CH_3)CH=CH_2$ |
| 2-820 | F | O | 1 | $CH_3$ | $CF_3$ | H | H | $CH_2CCl=CH_2$ |
| 2-821 | F | O | 1 | $CH_3$ | $CF_3$ | H | H | $CH_2C\equiv CH$ |
| 2-822 | F | O | 1 | $CH_3$ | $CF_3$ | H | H | $CH(CH_3)C\equiv CH$ |
| 2-823 | F | O | 1 | $CH_3$ | $CF_3$ | H | H | $CH_2CN$ |
| 2-824 | F | O | 1 | $CH_3$ | $CF_3$ | H | H | $CH_2OCH_3$ |
| 2-825 | F | O | 1 | $CH_3$ | $CF_3$ | H | H | $CH_2OC_2H_5$ |
| 2-826 | F | O | 1 | $CH_3$ | $CF_3$ | H | H | $CH_2COOH$ |
| 2-827 | F | O | 1 | $CH_3$ | $CF_3$ | H | H | $CH_2COOCH_3$ |
| 2-828 | F | O | 1 | $CH_3$ | $CF_3$ | H | H | $CH_2COOC_2H_5$ |
| 2-829 | F | O | 1 | $CH_3$ | $CF_3$ | H | H | $CH_2COO^nC_3H_7$ |
| 2-830 | F | O | 1 | $CH_3$ | $CF_3$ | H | H | $CH_2COO^nC_4H_9$ |
| 2-831 | F | O | 1 | $CH_3$ | $CF_3$ | H | H | $CH_2COO^nC_5H_{11}$ |
| 2-832 | F | O | 1 | $CH_3$ | $CF_3$ | H | H | $CH_2COO^iC_3H_7$ |
| 2-833 | F | O | 1 | $CH_3$ | $CF_3$ | H | H | $CH_2COO^cC_5H_9$ |
| 2-834 | F | O | 1 | $CH_3$ | $CF_3$ | H | H | $CH_2COO^cC_6H_{11}$ |
| 2-835 | F | O | 1 | $CH_3$ | $CF_3$ | H | H | $CH(CH_3)COOH$ |
| 2-836 | F | O | 1 | $CH_3$ | $CF_3$ | H | H | $CH(CH_3)COOCH_3$ |
| 2-837 | F | O | 1 | $CH_3$ | $CF_3$ | H | H | $CH(CH_3)COOC_2H_5$ |
| 2-838 | F | O | 1 | $CH_3$ | $CF_3$ | H | H | $CH(CH_3)COO^nC_3H_7$ |
| 2-839 | F | O | 1 | $CH_3$ | $CF_3$ | H | H | $CH(CH_3)COO^nC_4H_9$ |
| 2-840 | F | O | 1 | $CH_3$ | $CF_3$ | H | H | $CH(CH_3)COO^nC_5H_{11}$ |
| 2-841 | F | O | 1 | $CH_3$ | $CF_3$ | H | H | $CH(CH_3)COO^iC_3H_7$ |
| 2-842 | F | O | 1 | $CH_3$ | $CF_3$ | H | H | $CH(CH_3)COO^cC_5H_9$ |
| 2-843 | F | O | 1 | $CH_3$ | $CF_3$ | H | H | $CH(CH_3)COO^cC_6H_{11}$ |
| 2-843 | F | O | 1 | $CH_3$ | $CF_3$ | H | $CH_3$ | H |
| 2-845 | F | O | 1 | $CH_3$ | $CF_3$ | H | $CH_3$ | $CH_3$ |
| 2-846 | F | O | 1 | $CH_3$ | $CF_3$ | H | $CH_3$ | $C_2H_5$ |
| 2-847 | F | O | 1 | $CH_3$ | $CF_3$ | H | $CH_3$ | $^nC_3H_7$ |
| 2-848 | F | O | 1 | $CH_3$ | $CF_3$ | H | $CH_3$ | $^iC_3H_7$ |
| 2-849 | F | O | 1 | $CH_3$ | $CF_3$ | H | $CH_3$ | $^iC_4H_9$ |
| 2-850 | F | O | 1 | $CH_3$ | $CF_3$ | H | $CH_3$ | $^nC_4H_9$ |
| 2-851 | F | O | 1 | $CH_3$ | $CF_3$ | H | $CH_3$ | $CH_2CH=CH_2$ |
| 2-852 | F | O | 1 | $CH_3$ | $CF_3$ | H | $CH_3$ | $CH(CH_3)CH=CH_2$ |
| 2-853 | F | O | 1 | $CH_3$ | $CF_3$ | H | $CH_3$ | $CH_2C\equiv CH$ |
| 2-854 | F | O | 1 | $CH_3$ | $CF_3$ | H | $CH_3$ | $CH(CH_3)C\equiv CH$ |
| 2-855 | F | O | 1 | $CH_3$ | $CF_3$ | H | $CH_3$ | $CH_2OCH_3$ |
| 2-856 | F | O | 1 | $CH_3$ | $CF_3$ | H | $CH_3$ | $CH_2OC_2H_5$ |
| 2-857 | H | S | 0 | $CH_3$ | $CF_3$ | H | — | H |
| 2-858 | H | S | 0 | $CH_3$ | $CF_3$ | H | — | $CH_3$ |
| 2-859 | H | S | 0 | $CH_3$ | $CF_3$ | H | — | $C_2H_5$ |
| 2-860 | H | S | 0 | $CH_3$ | $CF_3$ | H | — | $^nC_3H_7$ |
| 2-861 | H | S | 0 | $CH_3$ | $CF_3$ | H | — | $^nC_4H_9$ |
| 2-862 | H | S | 0 | $CH_3$ | $CF_3$ | H | — | $^iC_3H_7$ |
| 2-863 | H | S | 0 | $CH_3$ | $CF_3$ | H | — | $^iC_4H_9$ |
| 2-864 | H | S | 0 | $CH_3$ | $CF_3$ | H | — | $CH_2CH_2Cl$ |
| 2-865 | H | S | 0 | $CH_3$ | $CF_3$ | H | — | $CH_2CH_2Br$ |
| 2-866 | H | S | 0 | $CH_3$ | $CF_3$ | H | — | $CH_2CH=CH_2$ |
| 2-867 | H | S | 0 | $CH_3$ | $CF_3$ | H | — | $CH(CH_3)CH=CH_2$ |
| 2-868 | H | S | 0 | $CH_3$ | $CF_3$ | H | — | $CH_2CCl=CH_2$ |
| 2-869 | H | S | 0 | $CH_3$ | $CF_3$ | H | — | $CH_2C\equiv CH$ |
| 2-870 | H | S | 0 | $CH_3$ | $CF_3$ | H | — | $CH(CH_3)C\equiv CH$ |
| 2-871 | H | S | 0 | $CH_3$ | $CF_3$ | H | — | $CH_2CN$ |
| 2-872 | H | S | 0 | $CH_3$ | $CF_3$ | H | — | $CH_2OCH_3$ |

TABLE 2-continued

Compounds of the formula:

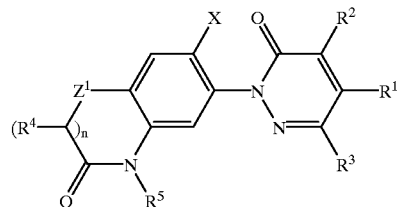

| Compound No. | X | $Z^1$ | n | $R^3$ | $R^1$ | $R^2$ | $R^4$ | $R^5$ |
|---|---|---|---|---|---|---|---|---|
| 2-873 | H | S | 0 | $CH_3$ | $CF_3$ | H | — | $CH_2OC_2H_5$ |
| 2-874 | H | S | 0 | $CH_3$ | $CF_3$ | H | — | $CH_2COOH$ |
| 2-875 | H | S | 0 | $CH_3$ | $CF_3$ | H | — | $CH_2COOCH_3$ |
| 2-876 | H | S | 0 | $CH_3$ | $CF_3$ | H | — | $CH_2COOC_2H_5$ |
| 2-877 | H | S | 0 | $CH_3$ | $CF_3$ | H | — | $CH_2COO^nC_3H_7$ |
| 2-878 | H | S | 0 | $CH_3$ | $CF_3$ | H | — | $CH_2COO^nC_4H_9$ |
| 2-879 | H | S | 0 | $CH_3$ | $CF_3$ | H | — | $CH_2COO^nC_5H_{11}$ |
| 2-880 | H | S | 0 | $CH_3$ | $CF_3$ | H | — | $CH_2COO^iC_3H_7$ |
| 2-881 | H | S | 0 | $CH_3$ | $CF_3$ | H | — | $CH_2COO^cC_5H_9$ |
| 2-882 | H | S | 0 | $CH_3$ | $CF_3$ | H | — | $CH_2COO^cC_6H_{11}$ |
| 2-883 | H | S | 0 | $CH_3$ | $CF_3$ | H | — | $CH(CH_3)COOH$ |
| 2-884 | H | S | 0 | $CH_3$ | $CF_3$ | H | — | $CH(CH_3)COOCH_3$ |
| 2-885 | H | S | 0 | $CH_3$ | $CF_3$ | H | — | $CH(CH_3)COOC_2H_5$ |
| 2-886 | H | S | 0 | $CH_3$ | $CF_3$ | H | — | $CH(CH_3)COO^nC_3H_7$ |
| 2-887 | H | S | 0 | $CH_3$ | $CF_3$ | H | — | $CH(CH_3)COO^nC_4H_9$ |
| 2-888 | H | S | 0 | $CH_3$ | $CF_3$ | H | — | $CH(CH_3)COO^nC_5H_{11}$ |
| 2-889 | H | S | 0 | $CH_3$ | $CF_3$ | H | — | $CH(CH_3)COO^iC_3H_7$ |
| 2-890 | H | S | 0 | $CH_3$ | $CF_3$ | H | — | $CH(CH_3)COO^cC_5H_9$ |
| 2-891 | H | S | 0 | $CH_3$ | $CF_3$ | H | — | $CH(CH_3)COO^cC_6H_{11}$ |
| 2-892 | F | S | 0 | $CH_3$ | $CF_3$ | H | — | H |
| 2-893 | F | S | 0 | $CH_3$ | $CF_3$ | H | — | $CH_3$ |
| 2-894 | F | S | 0 | $CH_3$ | $CF_3$ | H | — | $C_2H_5$ |
| 2-895 | F | S | 0 | $CH_3$ | $CF_3$ | H | — | $^nC_3H_7$ |
| 2-896 | F | S | 0 | $CH_3$ | $CF_3$ | H | — | $^nC_4H_9$ |
| 2-897 | F | S | 0 | $CH_3$ | $CF_3$ | H | — | $^iC_3H_7$ |
| 2-898 | F | S | 0 | $CH_3$ | $CF_3$ | H | — | $^iC_4H_9$ |
| 2-899 | F | S | 0 | $CH_3$ | $CF_3$ | H | — | $CH_2CH_2Cl$ |
| 2-900 | F | S | 0 | $CH_3$ | $CF_3$ | H | — | $CH_2CH_2Br$ |
| 2-901 | F | S | 0 | $CH_3$ | $CF_3$ | H | — | $CH_2CH=CH_2$ |
| 2-902 | F | S | 0 | $CH_3$ | $CF_3$ | H | — | $CH(CH_3)CH=CH_2$ |
| 2-903 | F | S | 0 | $CH_3$ | $CF_3$ | H | — | $CH_2CCl=CH_2$ |
| 2-904 | F | S | 0 | $CH_3$ | $CF_3$ | H | — | $CH_2C\equiv CH$ |
| 2-905 | F | S | 0 | $CH_3$ | $CF_3$ | H | — | $CH(CH_3)C\equiv CH$ |
| 2-906 | F | S | 0 | $CH_3$ | $CF_3$ | H | — | $CH_2CN$ |
| 2-907 | F | S | 0 | $CH_3$ | $CF_3$ | H | — | $CH_2OCH_3$ |
| 2-908 | F | S | 0 | $CH_3$ | $CF_3$ | H | — | $CH_2OC_2H_5$ |
| 2-909 | F | S | 0 | $CH_3$ | $CF_3$ | H | — | $CH_2COOH$ |
| 2-910 | F | S | 0 | $CH_3$ | $CF_3$ | H | — | $CH_2COOCH_3$ |
| 2-911 | F | S | 0 | $CH_3$ | $CF_3$ | H | — | $CH_2COOC_2H_5$ |
| 2-912 | F | S | 0 | $CH_3$ | $CF_3$ | H | — | $CH_2COO^nC_3H_7$ |
| 2-913 | F | S | 0 | $CH_3$ | $CF_3$ | H | — | $CH_2COO^nC_4H_9$ |
| 2-914 | F | S | 0 | $CH_3$ | $CF_3$ | H | — | $CH_2COO^nC_5H_{11}$ |
| 2-915 | F | S | 0 | $CH_3$ | $CF_3$ | H | — | $CH_2COO^iC_3H_7$ |
| 2-916 | F | S | 0 | $CH_3$ | $CF_3$ | H | — | $CH_2COO^cC_5H_9$ |
| 2-917 | F | S | 0 | $CH_3$ | $CF_3$ | H | — | $CH_2COO^cC_6H_{11}$ |
| 2-918 | F | S | 0 | $CH_3$ | $CF_3$ | H | — | $CH(CH_3)COOH$ |
| 2-919 | F | S | 0 | $CH_3$ | $CF_3$ | H | — | $CH(CH_3)COOCH_3$ |
| 2-920 | F | S | 0 | $CH_3$ | $CF_3$ | H | — | $CH(CH_3)COOC_2H_5$ |
| 2-921 | F | S | 0 | $CH_3$ | $CF_3$ | H | — | $CH(CH_3)COO^nC_3H_7$ |
| 2-922 | F | S | 0 | $CH_3$ | $CF_3$ | H | — | $CH(CH_3)COO^nC_4H_9$ |
| 2-923 | F | S | 0 | $CH_3$ | $CF_3$ | H | — | $CH(CH_3)COO^nC_5H_{11}$ |
| 2-924 | F | S | 0 | $CH_3$ | $CF_3$ | H | — | $CH(CH_3)COO^iC_3H_7$ |
| 2-925 | F | S | 0 | $CH_3$ | $CF_3$ | H | — | $CH(CH_3)COO^cC_5H_9$ |
| 2-926 | F | S | 0 | $CH_3$ | $CF_3$ | H | — | $CH(CH_3)COO^cC_6H_{11}$ |
| 2-927 | H | O | 0 | $CH_3$ | $CF_3$ | H | — | H |
| 2-928 | H | O | 0 | $CH_3$ | $CF_3$ | H | — | $CH_3$ |
| 2-929 | H | O | 0 | $CH_3$ | $CF_3$ | H | — | $C_2H_5$ |
| 2-930 | H | O | 0 | $CH_3$ | $CF_3$ | H | — | $^nC_3H_7$ |
| 2-931 | H | O | 0 | $CH_3$ | $CF_3$ | H | — | $^nC_4H_9$ |
| 2-932 | H | O | 0 | $CH_3$ | $CF_3$ | H | — | $^iC_3H_7$ |
| 2-933 | H | O | 0 | $CH_3$ | $CF_3$ | H | — | $^iC_4H_9$ |
| 2-934 | H | O | 0 | $CH_3$ | $CF_3$ | H | — | $CH_2CH=CH_2$ |

TABLE 2-continued

Compounds of the formula:

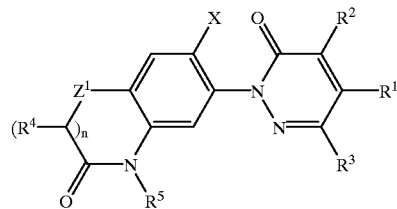

| Compound No. | X | $Z^1$ | n | $R^3$ | $R^1$ | $R^2$ | $R^4$ | $R^5$ |
|---|---|---|---|---|---|---|---|---|
| 2-935 | H | O | 0 | $CH_3$ | $CF_3$ | H | — | $CH(CH_3)CH=CH_2$ |
| 2-936 | H | O | 0 | $CH_3$ | $CF_3$ | H | — | $CH_2C\equiv CH$ |
| 2-937 | H | O | 0 | $CH_3$ | $CF_3$ | H | — | $CH(CH_3)C\equiv CH$ |
| 2-938 | H | O | 0 | $CH_3$ | $CF_3$ | H | — | $CH_2OCH_3$ |
| 2-939 | H | O | 0 | $CH_3$ | $CF_3$ | H | — | $CH_2OC_2H_5$ |
| 2-940 | F | O | 0 | $CH_3$ | $CF_3$ | H | — | H |
| 2-941 | F | O | 0 | $CH_3$ | $CF_3$ | H | — | $CH_3$ |
| 2-942 | F | O | 0 | $CH_3$ | $CF_3$ | H | — | $C_2H_5$ |
| 2-943 | F | O | 0 | $CH_3$ | $CF_3$ | H | — | $^nC_3H_7$ |
| 2-944 | F | O | 0 | $CH_3$ | $CF_3$ | H | — | $^nC_4H_9$ |
| 2-945 | F | O | 0 | $CH_3$ | $CF_3$ | H | — | $CH_2CH=CH_2$ |
| 2-946 | F | O | 0 | $CH_3$ | $CF_3$ | H | — | $CH(CH_3)CH=CH_2$ |
| 2-947 | F | O | 0 | $CH_3$ | $CF_3$ | H | — | $CH_2C\equiv CH$ |
| 2-948 | F | O | 0 | $CH_3$ | $CF_3$ | H | — | $CH(CH_3)C\equiv CH$ |
| 2-949 | F | O | 0 | $CH_3$ | $CF_3$ | H | — | $CH_2OCH_3$ |
| 2-950 | F | O | 0 | $CH_3$ | $CF_3$ | H | — | $CH_2OC_2H_5$ |

TABLE 3

Compounds of the formula:

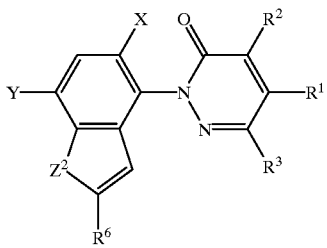

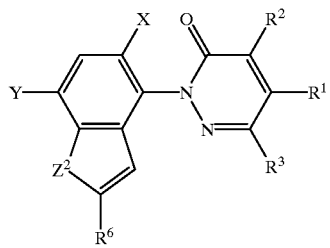

| Compound No. | X | Y | $Z^2$ | $R^3$ | $R^1$ | $R^2$ | $R^6$ |
|---|---|---|---|---|---|---|---|
| 3-1 | H | F | O | H | $CF_2Cl$ | H | $CH_3$ |
| 3-2 | H | Cl | O | H | $CF_2Cl$ | H | $CH_3$ |
| 3-3 | H | Br | O | H | $CF_2Cl$ | H | $CH_3$ |
| 3-4 | F | F | O | H | $CF_2Cl$ | H | $CH_3$ |
| 3-5 | F | Cl | O | H | $CF_2Cl$ | H | $CH_3$ |
| 3-6 | F | Br | O | H | $CF_2Cl$ | H | $CH_3$ |
| 3-7 | H | F | O | H | $CF_2Cl$ | $CH_3$ | $CH_3$ |
| 3-8 | H | Cl | O | H | $CF_2Cl$ | $CH_3$ | $CH_3$ |
| 3-9 | H | Br | O | H | $CF_2Cl$ | $CH_3$ | $CH_3$ |
| 3-10 | F | F | O | H | $CF_2Cl$ | $CH_3$ | $CH_3$ |
| 3-11 | F | Cl | O | H | $CF_2Cl$ | $CH_3$ | $CH_3$ |
| 3-12 | F | Br | O | H | $CF_2Cl$ | $CH_3$ | $CH_3$ |
| 3-13 | H | F | O | H | $CF_2Cl$ | H | $C_2H_5$ |
| 3-14 | H | Cl | O | H | $CF_2Cl$ | H | $C_2H_5$ |
| 3-15 | H | Br | O | H | $CF_2Cl$ | H | $C_2H_5$ |
| 3-16 | F | F | O | H | $CF_2Cl$ | H | $C_2H_5$ |
| 3-17 | F | Cl | O | H | $CF_2Cl$ | H | $C_2H_5$ |
| 3-18 | F | Br | O | H | $CF_2Cl$ | H | $C_2H_5$ |
| 3-19 | H | F | O | H | $CF_2Cl$ | $CH_3$ | $C_2H_5$ |
| 3-20 | H | Cl | O | H | $CF_2Cl$ | $CH_3$ | $C_2H_5$ |
| 3-21 | H | Br | O | H | $CF_2Cl$ | $CH_3$ | $C_2H_5$ |
| 3-22 | F | F | O | H | $CF_2Cl$ | $CH_3$ | $C_2H_5$ |
| 3-23 | F | Cl | O | H | $CF_2Cl$ | $CH_3$ | $C_2H_5$ |
| 3-24 | F | Br | O | H | $CF_2Cl$ | $CH_3$ | $C_2H_5$ |
| 3-25 | H | F | O | H | $CF_2Cl$ | $CH_3$ | $CH_2Br$ |
| 3-26 | H | F | O | H | $CF_2Cl$ | $CH_3$ | $CHBr_2$ |
| 3-27 | H | F | O | H | $CF_2Cl$ | $CH_3$ | $CBr_3$ |
| 3-28 | H | F | O | H | $CF_2Cl$ | $CH_3$ | $CHO$ |
| 3-29 | H | F | O | H | $CF_2Cl$ | $CH_3$ | $CN$ |
| 3-30 | H | F | O | H | $CF_2Cl$ | $CH_3$ | $COOH$ |
| 3-31 | H | F | O | H | $CF_2Cl$ | $CH_3$ | $CH_2OH$ |
| 3-32 | H | F | O | H | $CF_2Cl$ | $CH_3$ | $CH_2OCH_3$ |
| 3-33 | H | F | O | H | $CF_2Cl$ | $CH_3$ | $CH_2OC_2H_5$ |
| 3-34 | H | F | O | H | $CF_2Cl$ | $CH_3$ | $CH_2O^iC_3H_7$ |
| 3-35 | H | F | O | H | $CF_2Cl$ | $CH_3$ | $CH_2OCH_2OCH_3$ |
| 3-36 | H | F | O | H | $CF_2Cl$ | $CH_3$ | $CH_2OCH_2OC_2H_5$ |
| 3-37 | H | F | O | H | $CF_2Cl$ | $CH_3$ | $CH_2OCOCH_3$ |
| 3-38 | H | F | O | H | $CF_2Cl$ | $CH_3$ | $CH_2OCOC_2H_5$ |
| 3-39 | H | F | O | H | $CF_2Cl$ | $CH_3$ | $CH_2OCO^iC_3H_7$ |
| 3-40 | H | F | O | H | $CF_2Cl$ | $CH_3$ | $CH_2OCOCH_2Cl$ |
| 3-41 | H | F | O | H | $CF_2Cl$ | $CH_3$ | $CH_2OCOCCl_3$ |
| 3-42 | H | F | O | H | $CF_2Cl$ | $CH_3$ | $CH_2OCOCF_3$ |
| 3-43 | H | F | O | H | $CF_2Cl$ | $CH_3$ | $COOCH_3$ |
| 3-44 | H | F | O | H | $CF_2Cl$ | $CH_3$ | $COOC_2H_5$ |

TABLE 3-continued

Compounds of the formula:

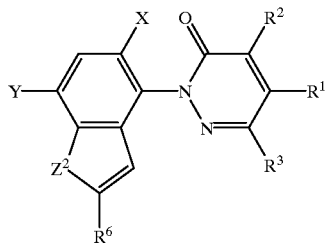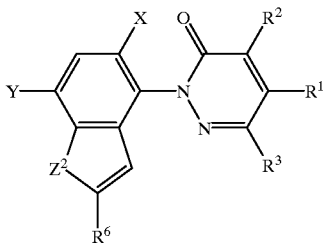

| Compound No. | X | Y | $Z^2$ | $R^3$ | $R^1$ | $R^2$ | $R^6$ |
|---|---|---|---|---|---|---|---|
| 3-45 | H | F | O | H | $CF_2Cl$ | $CH_3$ | $COO^nC_3H_7$ |
| 3-46 | H | F | O | H | $CF_2Cl$ | $CH_3$ | $COO^nC_4H_9$ |
| 3-47 | H | F | O | H | $CF_2Cl$ | $CH_3$ | $COO^nC_5H_{11}$ |
| 3-48 | H | F | O | H | $CF_2Cl$ | $CH_3$ | $COO^iC_3H_7$ |
| 3-49 | H | F | O | H | $CF_2Cl$ | $CH_3$ | $COCH_3$ |
| 3-50 | H | F | O | H | $CF_2Cl$ | $CH_3$ | $COC_2H_5$ |
| 3-51 | H | Cl | O | H | $CF_2Cl$ | $CH_3$ | $CH_2Br$ |
| 3-52 | H | Cl | O | H | $CF_2Cl$ | $CH_3$ | $CHBr_2$ |
| 3-53 | H | Cl | O | H | $CF_2Cl$ | $CH_3$ | $CBr_3$ |
| 3-54 | H | Cl | O | H | $CF_2Cl$ | $CH_3$ | CHO |
| 3-55 | H | Cl | O | H | $CF_2Cl$ | $CH_3$ | CN |
| 3-56 | H | Cl | O | H | $CF_2Cl$ | $CH_3$ | COOH |
| 3-57 | H | Cl | O | H | $CF_2Cl$ | $CH_3$ | $CH_2OH$ |
| 3-58 | H | Cl | O | H | $CF_2Cl$ | $CH_3$ | $CH_2OCH_3$ |
| 3-59 | H | Cl | O | H | $CF_2Cl$ | $CH_3$ | $CH_2OC_2H_5$ |
| 3-60 | H | Cl | O | H | $CF_2Cl$ | $CH_3$ | $CH_2O^iC_3H_7$ |
| 3-61 | H | Cl | O | H | $CF_2Cl$ | $CH_3$ | $CH_2OCH_2OCH_3$ |
| 3-62 | H | Cl | O | H | $CF_2Cl$ | $CH_3$ | $CH_2OCH_2OC_2H_5$ |
| 3-63 | H | Cl | O | H | $CF_2Cl$ | $CH_3$ | $CH_2OCOCH_3$ |
| 3-64 | H | Cl | O | H | $CF_2Cl$ | $CH_3$ | $CH_2OCOC_2H_5$ |
| 3-65 | H | Cl | O | H | $CF_2Cl$ | $CH_3$ | $CH_2OCO^iC_3H_7$ |
| 3-66 | H | Cl | O | H | $CF_2Cl$ | $CH_3$ | $CH_2OCOCH_2Cl$ |
| 3-67 | H | Cl | O | H | $CF_2Cl$ | $CH_3$ | $CH_2OCOCCl_3$ |
| 3-67 | H | Cl | O | H | $CF_2Cl$ | $CH_3$ | $CH_2OCOCF_3$ |
| 3-69 | H | Cl | O | H | $CF_2Cl$ | $CH_3$ | $COOCH_3$ |
| 3-70 | H | Cl | O | H | $CF_2Cl$ | $CH_3$ | $COOC_2H_5$ |
| 3-71 | H | Cl | O | H | $CF_2Cl$ | $CH_3$ | $COO^nC_3H_7$ |
| 3-72 | H | Cl | O | H | $CF_2Cl$ | $CH_3$ | $COO^nC_4H_9$ |
| 3-73 | H | Cl | O | H | $CF_2Cl$ | $CH_3$ | $COO^nC_5H_{11}$ |
| 3-74 | H | Cl | O | H | $CF_2Cl$ | $CH_3$ | $COO^iC_3H_7$ |
| 3-75 | H | Cl | O | H | $CF_2Cl$ | $CH_3$ | $COCH_3$ |
| 3-76 | H | Cl | O | H | $CF_2Cl$ | $CH_3$ | $COC_2H_5$ |
| 3-77 | F | F | O | H | $CF_2Cl$ | $CH_3$ | $CH_2Br$ |
| 3-78 | F | F | O | H | $CF_2Cl$ | $CH_3$ | $CHBr_2$ |
| 3-79 | F | F | O | H | $CF_2Cl$ | $CH_3$ | $CBr_3$ |
| 3-80 | F | F | O | H | $CF_2Cl$ | $CH_3$ | CHO |
| 3-81 | F | F | O | H | $CF_2Cl$ | $CH_3$ | CN |
| 3-82 | F | F | O | H | $CF_2Cl$ | $CH_3$ | COOH |
| 3-83 | F | F | O | H | $CF_2Cl$ | $CH_3$ | $CH_2OH$ |
| 3-84 | F | F | O | H | $CF_2Cl$ | $CH_3$ | $CH_2OCH_3$ |
| 3-85 | F | F | O | H | $CF_2Cl$ | $CH_3$ | $CH_2OC_2H_5$ |
| 3-86 | F | F | O | H | $CF_2Cl$ | $CH_3$ | $CH_2O^iC_3H_7$ |
| 3-87 | F | F | O | H | $CF_2Cl$ | $CH_3$ | $CH_2OCH_2OCH_3$ |
| 3-88 | F | F | O | H | $CF_2Cl$ | $CH_3$ | $CH_2OCH_2OC_2H_5$ |
| 3-89 | F | F | O | H | $CF_2Cl$ | $CH_3$ | $CH_2OCOCH_3$ |
| 3-90 | F | F | O | H | $CF_2Cl$ | $CH_3$ | $CH_2OCOC_2H_5$ |
| 3-91 | F | F | O | H | $CF_2Cl$ | $CH_3$ | $CH_2OCO^iC_3H_7$ |
| 3-92 | F | F | O | H | $CF_2Cl$ | $CH_3$ | $CH_2OCOCH_2Cl$ |
| 3-93 | F | F | O | H | $CF_2Cl$ | $CH_3$ | $CH_2OCOCCl_3$ |
| 3-94 | F | F | O | H | $CF_2Cl$ | $CH_3$ | $CH_2OCOCF_3$ |
| 3-95 | F | F | O | H | $CF_2Cl$ | $CH_3$ | $COOCH_3$ |
| 3-96 | F | F | O | H | $CF_2Cl$ | $CH_3$ | $COOC_2H_5$ |
| 3-97 | F | F | O | H | $CF_2Cl$ | $CH_3$ | $COO^nC_3H_7$ |
| 3-98 | F | F | O | H | $CF_2Cl$ | $CH_3$ | $COO^nC_4H_9$ |
| 3-99 | F | F | O | H | $CF_2Cl$ | $CH_3$ | $COO^nC_5H_{11}$ |
| 3-100 | F | F | O | H | $CF_2Cl$ | $CH_3$ | $COO^iC_3H_7$ |
| 3-101 | F | F | O | H | $CF_2Cl$ | $CH_3$ | $COCH_3$ |
| 3-102 | F | F | O | H | $CF_2Cl$ | $CH_3$ | $COC_2H_5$ |
| 3-103 | F | Cl | O | H | $CF_2Cl$ | $CH_3$ | $CH_2Br$ |
| 3-104 | F | Cl | O | H | $CF_2Cl$ | $CH_3$ | $CHBr_2$ |
| 3-105 | F | Cl | O | H | $CF_2Cl$ | $CH_3$ | $CBr_3$ |
| 3-106 | F | Cl | O | H | $CF_2Cl$ | $CH_3$ | CHO |
| 3-107 | F | Cl | O | H | $CF_2Cl$ | $CH_3$ | CN |
| 3-108 | F | Cl | O | H | $CF_2Cl$ | $CH_3$ | COOH |
| 3-109 | F | Cl | O | H | $CF_2Cl$ | $CH_3$ | $CH_2OH$ |
| 3-110 | F | Cl | O | H | $CF_2Cl$ | $CH_3$ | $CH_2OCH_3$ |
| 3-111 | F | Cl | O | H | $CF_2Cl$ | $CH_3$ | $CH_2OC_2H_5$ |
| 3-112 | F | Cl | O | H | $CF_2Cl$ | $CH_3$ | $CH_2O^iC_3H_7$ |
| 3-113 | F | Cl | O | H | $CF_2Cl$ | $CH_3$ | $CH_2OCH_2OCH_3$ |
| 3-114 | F | Cl | O | H | $CF_2Cl$ | $CH_3$ | $CH_2OCH_2OC_2H_5$ |
| 3-115 | F | Cl | O | H | $CF_2Cl$ | $CH_3$ | $CH_2OCOCH_3$ |
| 3-116 | F | Cl | O | H | $CF_2Cl$ | $CH_3$ | $CH_2OCOC_2H_5$ |
| 3-117 | F | Cl | O | H | $CF_2Cl$ | $CH_3$ | $CH_2OCO^iC_3H_7$ |
| 3-118 | F | Cl | O | H | $CF_2Cl$ | $CH_3$ | $CH_2OCOCH_2Cl$ |
| 3-119 | F | Cl | O | H | $CF_2Cl$ | $CH_3$ | $CH_2OCOCCl_3$ |
| 3-120 | F | Cl | O | H | $CF_2Cl$ | $CH_3$ | $CH_2OCOCF_3$ |
| 3-121 | F | Cl | O | H | $CF_2Cl$ | $CH_3$ | $COOCH_3$ |
| 3-122 | F | Cl | O | H | $CF_2Cl$ | $CH_3$ | $COOC_2H_5$ |
| 3-123 | F | Cl | O | H | $CF_2Cl$ | $CH_3$ | $COO^nC_3H_7$ |
| 3-124 | F | Cl | O | H | $CF_2Cl$ | $CH_3$ | $COO^nC_4H_9$ |
| 3-125 | F | Cl | O | H | $CF_2Cl$ | $CH_3$ | $COO^nC_5H_{11}$ |
| 3-126 | F | Cl | O | H | $CF_2Cl$ | $CH_3$ | $COO^iC_3H_7$ |
| 3-127 | F | Cl | O | H | $CF_2Cl$ | $CH_3$ | $COCH_3$ |
| 3-128 | F | Cl | O | H | $CF_2Cl$ | $CH_3$ | $COC_2H_5$ |
| 3-129 | H | F | O | H | $CF_3$ | H | $CH_3$ |
| 3-130 | H | Cl | O | H | $CF_3$ | H | $CH_3$ |
| 3-131 | H | Br | O | H | $CF_3$ | H | $CH_3$ |
| 3-132 | F | F | O | H | $CF_3$ | H | $CH_3$ |
| 3-133 | F | Cl | O | H | $CF_3$ | H | $CH_3$ |
| 3-134 | F | Br | O | H | $CF_3$ | H | $CH_3$ |
| 3-135 | H | F | O | H | $CF_3$ | $CH_3$ | $CH_3$ |
| 3-136 | H | Cl | O | H | $CF_3$ | $CH_3$ | $CH_3$ |
| 3-137 | H | Br | O | H | $CF_3$ | $CH_3$ | $CH_3$ |
| 3-138 | F | F | O | H | $CF_3$ | $CH_3$ | $CH_3$ |
| 3-139 | F | Cl | O | H | $CF_3$ | $CH_3$ | $CH_3$ |
| 3-140 | F | Br | O | H | $CF_3$ | $CH_3$ | $CH_3$ |
| 3-141 | H | F | O | H | $CF_3$ | H | $C_2H_5$ |
| 3-142 | H | Cl | O | H | $CF_3$ | H | $C_2H_5$ |
| 3-143 | H | Br | O | H | $CF_3$ | H | $C_2H_5$ |
| 3-144 | F | F | O | H | $CF_3$ | H | $C_2H_5$ |
| 3-145 | F | Cl | O | H | $CF_3$ | H | $C_2H_5$ |
| 3-146 | F | Br | O | H | $CF_3$ | H | $C_2H_5$ |
| 3-147 | H | F | O | H | $CF_3$ | $CH_3$ | $C_2H_5$ |
| 3-148 | H | Cl | O | H | $CF_3$ | $CH_3$ | $C_2H_5$ |
| 3-149 | H | Br | O | H | $CF_3$ | $CH_3$ | $C_2H_5$ |
| 3-150 | F | F | O | H | $CF_3$ | $CH_3$ | $C_2H_5$ |
| 3-151 | F | Cl | O | H | $CF_3$ | $CH_3$ | $C_2H_5$ |
| 3-152 | F | Br | O | H | $CF_3$ | $CH_3$ | $C_2H_5$ |
| 3-153 | H | F | O | H | $CF_3$ | $CH_3$ | $CH_2Br$ |
| 3-154 | H | F | O | H | $CF_3$ | $CH_3$ | $CHBr_2$ |
| 3-155 | H | F | O | H | $CF_3$ | $CH_3$ | $CBr_3$ |
| 3-156 | H | F | O | H | $CF_3$ | $CH_3$ | CHO |
| 3-157 | H | F | O | H | $CF_3$ | $CH_3$ | CN |
| 3-158 | H | F | O | H | $CF_3$ | $CH_3$ | COOH |
| 3-159 | H | F | O | H | $CF_3$ | $CH_3$ | $CH_2OH$ |
| 3-160 | H | F | O | H | $CF_3$ | $CH_3$ | $CH_2OCH_3$ |
| 3-161 | H | F | O | H | $CF_3$ | $CH_3$ | $CH_2OC_2H_5$ |
| 3-162 | H | F | O | H | $CF_3$ | $CH_3$ | $CH_2O^iC_3H_7$ |
| 3-163 | H | F | O | H | $CF_3$ | $CH_3$ | $CH_2OCH_2OCH_3$ |
| 3-164 | H | F | O | H | $CF_3$ | $CH_3$ | $CH_2OCH_2OC_2H_5$ |
| 3-165 | H | F | O | H | $CF_3$ | $CH_3$ | $CH_2OCOCH_3$ |
| 3-166 | H | F | O | H | $CF_3$ | $CH_3$ | $CH_2OCOC_2H_5$ |

TABLE 3-continued

Compounds of the formula:

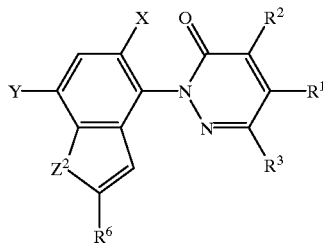 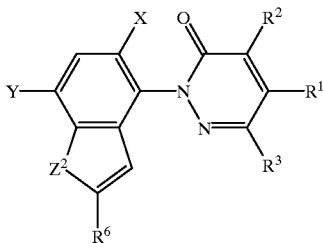

| Compound No. | X | Y | $Z^2$ | $R^3$ | $R^1$ | $R^2$ | $R^6$ |
|---|---|---|---|---|---|---|---|
| 3-167 | H | F | O | H | $CF_3$ | $CH_3$ | $CH_2OCO^iC_3H_7$ |
| 3-168 | H | F | O | H | $CF_3$ | $CH_3$ | $CH_2OCOCH_2Cl$ |
| 3-169 | H | F | O | H | $CF_3$ | $CH_3$ | $CH_2OCOCCl_3$ |
| 3-170 | H | F | O | H | $CF_3$ | $CH_3$ | $CH_2OCOCF_3$ |
| 3-171 | H | F | O | H | $CF_3$ | $CH_3$ | $COOCH_3$ |
| 3-172 | H | F | O | H | $CF_3$ | $CH_3$ | $COOC_2H_5$ |
| 3-173 | H | F | O | H | $CF_3$ | $CH_3$ | $COO^nC_3H_7$ |
| 3-174 | H | F | O | H | $CF_3$ | $CH_3$ | $COO^nC_4H_9$ |
| 3-175 | H | F | O | H | $CF_3$ | $CH_3$ | $COO^nC_5H_{11}$ |
| 3-176 | H | F | O | H | $CF_3$ | $CH_3$ | $COO^iC_3H_7$ |
| 3-177 | H | F | O | H | $CF_3$ | $CH_3$ | $COCH_3$ |
| 3-178 | H | F | O | H | $CF_3$ | $CH_3$ | $COC_2H_5$ |
| 3-179 | H | Cl | O | H | $CF_3$ | $CH_3$ | $CH_2Br$ |
| 3-180 | H | Cl | O | H | $CF_3$ | $CH_3$ | $CHBr_2$ |
| 3-181 | H | Cl | O | H | $CF_3$ | $CH_3$ | $CBr_3$ |
| 3-182 | H | Cl | O | H | $CF_3$ | $CH_3$ | CHO |
| 3-183 | H | Cl | O | H | $CF_3$ | $CH_3$ | CN |
| 3-184 | H | Cl | O | H | $CF_3$ | $CH_3$ | COOH |
| 3-185 | H | Cl | O | H | $CF_3$ | $CH_3$ | $CH_2OH$ |
| 3-186 | H | Cl | O | H | $CF_3$ | $CH_3$ | $CH_2OCH_3$ |
| 3-187 | H | Cl | O | H | $CF_3$ | $CH_3$ | $CH_2OC_2H_5$ |
| 3-188 | H | Cl | O | H | $CF_3$ | $CH_3$ | $CH_2O^iC_3H_7$ |
| 3-189 | H | Cl | O | H | $CF_3$ | $CH_3$ | $CH_2OCH_2OCH_3$ |
| 3-190 | H | Cl | O | H | $CF_3$ | $CH_3$ | $CH_2OCH_2OC_2H_5$ |
| 3-191 | H | Cl | O | H | $CF_3$ | $CH_3$ | $CH_2OCOCH_3$ |
| 3-192 | H | Cl | O | H | $CF_3$ | $CH_3$ | $CH_2OCOC_2H_5$ |
| 3-193 | H | Cl | O | H | $CF_3$ | $CH_3$ | $CH_2OCO^iC_3H_7$ |
| 3-194 | H | Cl | O | H | $CF_3$ | $CH_3$ | $CH_2OCOCH_2Cl$ |
| 3-195 | H | Cl | O | H | $CF_3$ | $CH_3$ | $CH_2OCOCCl_3$ |
| 3-196 | H | Cl | O | H | $CF_3$ | $CH_3$ | $CH_2OCOCF_3$ |
| 3-197 | H | Cl | O | H | $CF_3$ | $CH_3$ | $COOCH_3$ |
| 3-198 | H | Cl | O | H | $CF_3$ | $CH_3$ | $COOC_2H_5$ |
| 3-199 | H | Cl | O | H | $CF_3$ | $CH_3$ | $COO^nC_3H_7$ |
| 3-200 | H | Cl | O | H | $CF_3$ | $CH_3$ | $COO^nC_4H_9$ |
| 3-201 | H | Cl | O | H | $CF_3$ | $CH_3$ | $COO^nC_5H_{11}$ |
| 3-202 | H | Cl | O | H | $CF_3$ | $CH_3$ | $COO^iC_3H_7$ |
| 3-203 | H | Cl | O | H | $CF_3$ | $CH_3$ | $COCH_3$ |
| 3-204 | H | Cl | O | H | $CF_3$ | $CH_3$ | $COC_2H_5$ |
| 3-205 | F | F | O | H | $CF_3$ | $CH_3$ | $CH_2Br$ |
| 3-206 | F | F | O | H | $CF_3$ | $CH_3$ | $CHBr_2$ |
| 3-207 | F | F | O | H | $CF_3$ | $CH_3$ | $CBr_3$ |
| 3-208 | F | F | O | H | $CF_3$ | $CH_3$ | CHO |
| 3-209 | F | F | O | H | $CF_3$ | $CH_3$ | CN |
| 3-210 | F | F | O | H | $CF_3$ | $CH_3$ | COOH |
| 3-211 | F | F | O | H | $CF_3$ | $CH_3$ | $CH_2OH$ |
| 3-212 | F | F | O | H | $CF_3$ | $CH_3$ | $CH_2OCH_3$ |
| 3-213 | F | F | O | H | $CF_3$ | $CH_3$ | $CH_2OC_2H_5$ |
| 3-214 | F | F | O | H | $CF_3$ | $CH_3$ | $CH_2O^iC_3H_7$ |
| 3-215 | F | F | O | H | $CF_3$ | $CH_3$ | $CH_2OCH_2OCH_3$ |
| 3-216 | F | F | O | H | $CF_3$ | $CH_3$ | $CH_2OCH_2OC_2H_5$ |
| 3-217 | F | F | O | H | $CF_3$ | $CH_3$ | $CH_2OCOCH_3$ |
| 3-218 | F | F | O | H | $CF_3$ | $CH_3$ | $CH_2OCOC_2H_5$ |
| 3-219 | F | F | O | H | $CF_3$ | $CH_3$ | $CH_2OCO^iC_3H_7$ |
| 3-220 | F | F | O | H | $CF_3$ | $CH_3$ | $CH_2OCOCH_2Cl$ |
| 3-221 | F | F | O | H | $CF_3$ | $CH_3$ | $CH_2OCOCCl_3$ |
| 3-222 | F | F | O | H | $CF_3$ | $CH_3$ | $CH_2OCOCF_3$ |
| 3-223 | F | F | O | H | $CF_3$ | $CH_3$ | $COOCH_3$ |
| 3-224 | F | F | O | H | $CF_3$ | $CH_3$ | $COOC_2H_5$ |
| 3-225 | F | F | O | H | $CF_3$ | $CH_3$ | $COO^nC_3H_7$ |
| 3-226 | F | F | O | H | $CF_3$ | $CH_3$ | $COO^nC_4H_9$ |
| 3-227 | F | F | O | H | $CF_3$ | $CH_3$ | $COO^nC_5H_{11}$ |
| 3-228 | F | F | O | H | $CF_3$ | $CH_3$ | $COO^iC_3H_7$ |
| 3-229 | F | F | O | H | $CF_3$ | $CH_3$ | $COCH_3$ |
| 3-230 | F | F | O | H | $CF_3$ | $CH_3$ | $COC_2H_5$ |
| 3-231 | F | Cl | O | H | $CF_3$ | $CH_3$ | $CH_2Br$ |
| 3-232 | F | Cl | O | H | $CF_3$ | $CH_3$ | $CHBr_2$ |
| 3-233 | F | Cl | O | H | $CF_3$ | $CH_3$ | $CBr_3$ |
| 3-234 | F | Cl | O | H | $CF_3$ | $CH_3$ | CHO |
| 3-235 | F | Cl | O | H | $CF_3$ | $CH_3$ | CN |
| 3-236 | F | Cl | O | H | $CF_3$ | $CH_3$ | COOH |
| 3-237 | F | Cl | O | H | $CF_3$ | $CH_3$ | $CH_2OH$ |
| 3-238 | F | Cl | O | H | $CF_3$ | $CH_3$ | $CH_2OCH_3$ |
| 3-239 | F | Cl | O | H | $CF_3$ | $CH_3$ | $CH_2OC_2H_5$ |
| 3-240 | F | Cl | O | H | $CF_3$ | $CH_3$ | $CH_2O^iC_3H_7$ |
| 3-241 | F | Cl | O | H | $CF_3$ | $CH_3$ | $CH_2OCH_2OCH_3$ |
| 3-242 | F | Cl | O | H | $CF_3$ | $CH_3$ | $CH_2OCH_2OC_2H_5$ |
| 3-243 | F | Cl | O | H | $CF_3$ | $CH_3$ | $CH_2OCOCH_3$ |
| 3-244 | F | Cl | O | H | $CF_3$ | $CH_3$ | $CH_2OCOC_2H_5$ |
| 3-245 | F | Cl | O | H | $CF_3$ | $CH_3$ | $CH_2OCO^iC_3H_7$ |
| 3-246 | F | Cl | O | H | $CF_3$ | $CH_3$ | $CH_2OCOCH_2Cl$ |
| 3-247 | F | Cl | O | H | $CF_3$ | $CH_3$ | $CH_2OCOCCl_3$ |
| 3-248 | F | Cl | O | H | $CF_3$ | $CH_3$ | $CH_2OCOCF_3$ |
| 3-249 | F | Cl | O | H | $CF_3$ | $CH_3$ | $COOCH_3$ |
| 3-250 | F | Cl | O | H | $CF_3$ | $CH_3$ | $COOC_2H_5$ |
| 3-251 | F | Cl | O | H | $CF_3$ | $CH_3$ | $COO^nC_3H_7$ |
| 3-252 | F | Cl | O | H | $CF_3$ | $CH_3$ | $COO^nC_4H_9$ |
| 3-253 | F | Cl | O | H | $CF_3$ | $CH_3$ | $COO^nC_5H_{11}$ |
| 3-254 | F | Cl | O | H | $CF_3$ | $CH_3$ | $COO^iC_3H_7$ |
| 3-255 | F | Cl | O | H | $CF_3$ | $CH_3$ | $COCH_3$ |
| 3-256 | F | Cl | O | H | $CF_3$ | $CH_3$ | $COC_2H_5$ |
| 3-257 | H | F | O | H | $CF_2Cl$ | H | $CH_2Br$ |
| 3-258 | H | F | O | H | $CF_2Cl$ | H | $CHBr_2$ |
| 3-259 | H | F | O | H | $CF_2Cl$ | H | $CBr_3$ |
| 3-260 | H | F | O | H | $CF_2Cl$ | H | CHO |
| 3-261 | H | F | O | H | $CF_2Cl$ | H | CN |
| 3-262 | H | F | O | H | $CF_2Cl$ | H | COOH |
| 3-263 | H | F | O | H | $CF_2Cl$ | H | $CH_2OH$ |
| 3-264 | H | F | O | H | $CF_2Cl$ | H | $CH_2OCH_3$ |
| 3-265 | H | F | O | H | $CF_2Cl$ | H | $CH_2OC_2H_5$ |
| 3-266 | H | F | O | H | $CF_2Cl$ | H | $CH_2O^iC_3H_7$ |
| 3-267 | H | F | O | H | $CF_2Cl$ | H | $CH_2OCH_2OCH_3$ |
| 3-268 | H | F | O | H | $CF_2Cl$ | H | $CH_2OCH_2OC_2H_5$ |
| 3-269 | H | F | O | H | $CF_2Cl$ | H | $CH_2OCOCH_3$ |
| 3-270 | H | F | O | H | $CF_2Cl$ | H | $CH_2OCOC_2H_5$ |
| 3-271 | H | F | O | H | $CF_2Cl$ | H | $CH_2OCO^iC_3H_7$ |
| 3-272 | H | F | O | H | $CF_2Cl$ | H | $CH_2OCOCH_2Cl$ |
| 3-273 | H | F | O | H | $CF_2Cl$ | H | $CH_2OCOCCl_3$ |
| 3-274 | H | F | O | H | $CF_2Cl$ | H | $CH_2OCOCF_3$ |
| 3-275 | H | F | O | H | $CF_2Cl$ | H | $COOCH_3$ |
| 3-276 | H | F | O | H | $CF_2Cl$ | H | $COOC_2H_5$ |
| 3-277 | H | F | O | H | $CF_2Cl$ | H | $COO^nC_3H_7$ |
| 3-278 | H | F | O | H | $CF_2Cl$ | H | $COO^nC_4H_9$ |
| 3-279 | H | F | O | H | $CF_2Cl$ | H | $COO^nC_5H_{11}$ |
| 3-280 | H | F | O | H | $CF_2Cl$ | H | $COO^iC_3H_7$ |
| 3-281 | H | F | O | H | $CF_2Cl$ | H | $COCH_3$ |
| 3-282 | H | F | O | H | $CF_2Cl$ | H | $COC_2H_5$ |
| 3-283 | H | Cl | O | H | $CF_2Cl$ | H | $CH_2Br$ |
| 3-284 | H | Cl | O | H | $CF_2Cl$ | H | $CHBr_2$ |
| 3-285 | H | Cl | O | H | $CF_2Cl$ | H | $CBr_3$ |
| 3-286 | H | Cl | O | H | $CF_2Cl$ | H | CHO |
| 3-287 | H | Cl | O | H | $CF_2Cl$ | H | CN |
| 3-288 | H | Cl | O | H | $CF_2Cl$ | H | COOH |

TABLE 3-continued

Compounds of the formula:

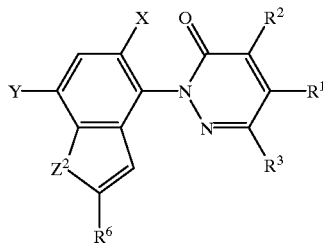

| Compound No. | X | Y | $Z^2$ | $R^3$ | $R^1$ | $R^2$ | $R^6$ |
|---|---|---|---|---|---|---|---|
| 3-289 | H | Cl | O | H | $CF_2Cl$ | H | $CH_2OH$ |
| 3-290 | H | Cl | O | H | $CF_2Cl$ | H | $CH_2OCH_3$ |
| 3-291 | H | Cl | O | H | $CF_2Cl$ | H | $CH_2OC_2H_5$ |
| 3-292 | H | Cl | O | H | $CF_2Cl$ | H | $CH_2O^iC_3H_7$ |
| 3-293 | H | Cl | O | H | $CF_2Cl$ | H | $CH_2OCH_2OCH_3$ |
| 3-294 | H | Cl | O | H | $CF_2Cl$ | H | $CH_2OCH_2OC_2H_5$ |
| 3-295 | H | Cl | O | H | $CF_2Cl$ | H | $CH_2OCOCH_3$ |
| 3-296 | H | Cl | O | H | $CF_2Cl$ | H | $CH_2OCOC_2H_5$ |
| 3-297 | H | Cl | O | H | $CF_2Cl$ | H | $CH_2OCO^iC_3H_7$ |
| 3-298 | H | Cl | O | H | $CF_2Cl$ | H | $CH_2OCOCH_2Cl$ |
| 3-299 | H | Cl | O | H | $CF_2Cl$ | H | $CH_2OCOCCl_3$ |
| 3-300 | H | Cl | O | H | $CF_2Cl$ | H | $CH_2OCOCF_3$ |
| 3-301 | H | Cl | O | H | $CF_2Cl$ | H | $COOCH_3$ |
| 3-302 | H | Cl | O | H | $CF_2Cl$ | H | $COOC_2H_5$ |
| 3-303 | H | Cl | O | H | $CF_2Cl$ | H | $COO^nC_3H_7$ |
| 3-304 | H | Cl | O | H | $CF_2Cl$ | H | $COO^nC_4H_9$ |
| 3-305 | H | Cl | O | H | $CF_2Cl$ | H | $COO^nC_5H_{11}$ |
| 3-306 | H | Cl | O | H | $CF_2Cl$ | H | $COO^iC_3H_7$ |
| 3-307 | H | Cl | O | H | $CF_2Cl$ | H | $COCH_3$ |
| 3-308 | H | Cl | O | H | $CF_2Cl$ | H | $COC_2H_5$ |
| 3-309 | F | F | O | H | $CF_2Cl$ | H | $CH_2Br$ |
| 3-310 | F | F | O | H | $CF_2Cl$ | H | $CHBr_2$ |
| 3-311 | F | F | O | H | $CF_2Cl$ | H | $CBr_3$ |
| 3-312 | F | F | O | H | $CF_2Cl$ | H | CHO |
| 3-313 | F | F | O | H | $CF_2Cl$ | H | CN |
| 3-314 | F | F | O | H | $CF_2Cl$ | H | COOH |
| 3-315 | F | F | O | H | $CF_2Cl$ | H | $CH_2OH$ |
| 3-316 | F | F | O | H | $CF_2Cl$ | H | $CH_2OCH_3$ |
| 3-317 | F | F | O | H | $CF_2Cl$ | H | $CH_2OC_2H_5$ |
| 3-318 | F | F | O | H | $CF_2Cl$ | H | $CH_2O^iC_3H_7$ |
| 3-319 | F | F | O | H | $CF_2Cl$ | H | $CH_2OCH_2OCH_3$ |
| 3-320 | F | F | O | H | $CF_2Cl$ | H | $CH_2OCH_2OC_2H_5$ |
| 3-321 | F | F | O | H | $CF_2Cl$ | H | $CH_2OCOCH_3$ |
| 3-322 | F | F | O | H | $CF_2Cl$ | H | $CH_2OCOC_2H_5$ |
| 3-323 | F | F | O | H | $CF_2Cl$ | H | $CH_2OCO^iC_3H_7$ |
| 3-324 | F | F | O | H | $CF_2Cl$ | H | $CH_2OCOCH_2Cl$ |
| 3-325 | F | F | O | H | $CF_2Cl$ | H | $CH_2OCOCCl_3$ |
| 3-326 | F | F | O | H | $CF_2Cl$ | H | $CH_2OCOCF_3$ |
| 3-327 | F | F | O | H | $CF_2Cl$ | H | $COOCH_3$ |
| 3-328 | F | F | O | H | $CF_2Cl$ | H | $COOC_2H_5$ |
| 3-329 | F | F | O | H | $CF_2Cl$ | H | $COO^nC_3H_7$ |
| 3-330 | F | F | O | H | $CF_2Cl$ | H | $COO^nC_4H_9$ |
| 3-331 | F | F | O | H | $CF_2Cl$ | H | $COO^nC_5H_{11}$ |
| 3-332 | F | F | O | H | $CF_2Cl$ | H | $COO^iC_3H_7$ |
| 3-333 | F | F | O | H | $CF_2Cl$ | H | $COCH_3$ |
| 3-334 | F | F | O | H | $CF_2Cl$ | H | $COC_2H_5$ |
| 3-335 | F | Cl | O | H | $CF_2Cl$ | H | $CH_2Br$ |
| 3-336 | F | Cl | O | H | $CF_2Cl$ | H | $CHBr_2$ |
| 3-337 | F | Cl | O | H | $CF_2Cl$ | H | $CBr_3$ |
| 3-338 | F | Cl | O | H | $CF_2Cl$ | H | CHO |
| 3-339 | F | Cl | O | H | $CF_2Cl$ | H | CN |
| 3-340 | F | Cl | O | H | $CF_2Cl$ | H | COOH |
| 3-341 | F | Cl | O | H | $CF_2Cl$ | H | $CH_2OH$ |
| 3-342 | F | Cl | O | H | $CF_2Cl$ | H | $CH_2OCH_3$ |
| 3-343 | F | Cl | O | H | $CF_2Cl$ | H | $CH_2OC_2H_5$ |
| 3-344 | F | Cl | O | H | $CF_2Cl$ | H | $CH_2O^iC_3H_7$ |
| 3-345 | F | Cl | O | H | $CF_2Cl$ | H | $CH_2OCH_2OCH_3$ |
| 3-346 | F | Cl | O | H | $CF_2Cl$ | H | $CH_2OCH_2OC_2H_5$ |
| 3-347 | F | Cl | O | H | $CF_2Cl$ | H | $CH_2OCOCH_3$ |
| 3-348 | F | Cl | O | H | $CF_2Cl$ | H | $CH_2OCOC_2H_5$ |
| 3-349 | F | Cl | O | H | $CF_2Cl$ | H | $CH_2OCO^iC_3H_7$ |
| 3-350 | F | Cl | O | H | $CF_2Cl$ | H | $CH_2OCOCH_2Cl$ |
| 3-351 | F | Cl | O | H | $CF_2Cl$ | H | $CH_2OCOCCl_3$ |
| 3-352 | F | Cl | O | H | $CF_2Cl$ | H | $CH_2OCOCF_3$ |
| 3-353 | F | Cl | O | H | $CF_2Cl$ | H | $COOCH_3$ |
| 3-354 | F | Cl | O | H | $CF_2Cl$ | H | $COOC_2H_5$ |
| 3-355 | F | Cl | O | H | $CF_2Cl$ | H | $COO^nC_3H_7$ |
| 3-356 | F | Cl | O | H | $CF_2Cl$ | H | $COO^nC_4H_9$ |
| 3-357 | F | Cl | O | H | $CF_2Cl$ | H | $COO^nC_5H_{11}$ |
| 3-358 | F | Cl | O | H | $CF_2Cl$ | H | $COO^iC_3H_7$ |
| 3-359 | F | Cl | O | H | $CF_2Cl$ | H | $COCH_3$ |
| 3-360 | F | Cl | O | H | $CF_2Cl$ | H | $COC_2H_5$ |
| 3-361 | F | Br | O | H | $CF_3$ | H | $C_2H_5$ |
| 3-362 | H | F | O | H | $CF_3$ | H | $CH_2Br$ |
| 3-363 | H | F | O | H | $CF_3$ | H | $CHBr_2$ |
| 3-364 | H | F | O | H | $CF_3$ | H | $CBr_3$ |
| 3-365 | H | F | O | H | $CF_3$ | H | CHO |
| 3-366 | H | F | O | H | $CF_3$ | H | CN |
| 3-367 | H | F | O | H | $CF_3$ | H | COOH |
| 3-368 | H | F | O | H | $CF_3$ | H | $CH_2OH$ |
| 3-369 | H | F | O | H | $CF_3$ | H | $CH_2OCH_3$ |
| 3-370 | H | F | O | H | $CF_3$ | H | $CH_2OC_2H_5$ |
| 3-371 | H | F | O | H | $CF_3$ | H | $CH_2O^iC_3H_7$ |
| 3-372 | H | F | O | H | $CF_3$ | H | $CH_2OCH_2OCH_3$ |
| 3-373 | H | F | O | H | $CF_3$ | H | $CH_2OCH_2OC_2H_5$ |
| 3-374 | H | F | O | H | $CF_3$ | H | $CH_2OCOCH_3$ |
| 3-375 | H | F | O | H | $CF_3$ | H | $CH_2OCOC_2H_5$ |
| 3-376 | H | F | O | H | $CF_3$ | H | $CH_2OCO^iC_3H_7$ |
| 3-377 | H | F | O | H | $CF_3$ | H | $CH_2OCOCH_2Cl$ |
| 3-378 | H | F | O | H | $CF_3$ | H | $CH_2OCOCCl_3$ |
| 3-379 | H | F | O | H | $CF_3$ | H | $CH_2OCOCF_3$ |
| 3-380 | H | F | O | H | $CF_3$ | H | $COOCH_3$ |
| 3-381 | H | F | O | H | $CF_3$ | H | $COOC_2H_5$ |
| 3-382 | H | F | O | H | $CF_3$ | H | $COO^nC_3H_7$ |
| 3-383 | H | F | O | H | $CF_3$ | H | $COO^nC_4H_9$ |
| 3-384 | H | F | O | H | $CF_3$ | H | $COO^nC_5H_{11}$ |
| 3-385 | H | F | O | H | $CF_3$ | H | $COO^iC_3H_7$ |
| 3-386 | H | F | O | H | $CF_3$ | H | $COCH_3$ |
| 3-387 | H | F | O | H | $CF_3$ | H | $COC_2H_5$ |
| 3-388 | H | Cl | O | H | $CF_3$ | H | $CH_2Br$ |
| 3-389 | H | Cl | O | H | $CF_3$ | H | $CHBr_2$ |
| 3-390 | H | Cl | O | H | $CF_3$ | H | $CBr_3$ |
| 3-391 | H | Cl | O | H | $CF_3$ | H | CHO |
| 3-392 | H | Cl | O | H | $CF_3$ | H | CN |
| 3-393 | H | Cl | O | H | $CF_3$ | H | COOH |
| 3-394 | H | Cl | O | H | $CF_3$ | H | $CH_2OH$ |
| 3-395 | H | Cl | O | H | $CF_3$ | H | $CH_2OCH_3$ |
| 3-396 | H | Cl | O | H | $CF_3$ | H | $CH_2OC_2H_5$ |
| 3-397 | H | Cl | O | H | $CF_3$ | H | $CH_2O^iC_3H_7$ |
| 3-398 | H | Cl | O | H | $CF_3$ | H | $CH_2OCH_2OCH_3$ |
| 3-399 | H | Cl | O | H | $CF_3$ | H | $CH_2OCH_2OC_2H_5$ |
| 3-400 | H | Cl | O | H | $CF_3$ | H | $CH_2OCOCH_3$ |
| 3-401 | H | Cl | O | H | $CF_3$ | H | $CH_2OCOC_2H_5$ |
| 3-402 | H | Cl | O | H | $CF_3$ | H | $CH_2OCO^iC_3H_7$ |
| 3-403 | H | Cl | O | H | $CF_3$ | H | $CH_2OCOCH_2Cl$ |
| 3-404 | H | Cl | O | H | $CF_3$ | H | $CH_2OCOCCl_3$ |
| 3-405 | H | Cl | O | H | $CF_3$ | H | $CH_2OCOCF_3$ |
| 3-406 | H | Cl | O | H | $CF_3$ | H | $COOCH_3$ |
| 3-407 | H | Cl | O | H | $CF_3$ | H | $COOC_2H_5$ |
| 3-408 | H | Cl | O | H | $CF_3$ | H | $COO^nC_3H_7$ |
| 3-409 | H | Cl | O | H | $CF_3$ | H | $COO^nC_4H_9$ |
| 3-410 | H | Cl | O | H | $CF_3$ | H | $COO^nC_5H_{11}$ |

TABLE 3-continued

Compounds of the formula:

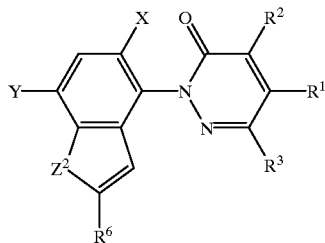 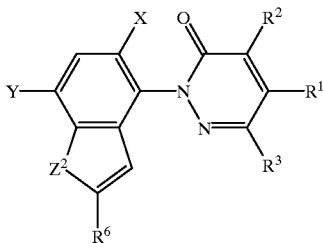

| Compound No. | X | Y | Z² | R³ | R¹ | R² | R⁶ |
|---|---|---|---|---|---|---|---|
| 3-411 | H | Cl | O | H | CF₃ | H | COOⁱC₃H₇ |
| 3-412 | H | Cl | O | H | CF₃ | H | COCH₃ |
| 3-413 | H | Cl | O | H | CF₃ | H | COC₂H₅ |
| 3-414 | F | F | O | H | CF₃ | H | CH₂Br |
| 3-415 | F | F | O | H | CF₃ | H | CHBr₂ |
| 3-416 | F | F | O | H | CF₃ | H | CBr₃ |
| 3-417 | F | F | O | H | CF₃ | H | CHO |
| 3-418 | F | F | O | H | CF₃ | H | CN |
| 3-419 | F | F | O | H | CF₃ | H | COOH |
| 3-420 | F | F | O | H | CF₃ | H | CH₂OH |
| 3-421 | F | F | O | H | CF₃ | H | CH₂OCH₃ |
| 3-422 | F | F | O | H | CF₃ | H | CH₂OC₂H₅ |
| 3-423 | F | F | O | H | CF₃ | H | CH₂OⁱC₃H₇ |
| 3-424 | F | F | O | H | CF₃ | H | CH₂OCH₂OCH₃ |
| 3-425 | F | F | O | H | CF₃ | H | CH₂OCH₂OC₂H₅ |
| 3-426 | F | F | O | H | CF₃ | H | CH₂OCOCH₃ |
| 3-427 | F | F | O | H | CF₃ | H | CH₂OCOC₂H₅ |
| 3-428 | F | F | O | H | CF₃ | H | CH₂OCOⁱC₃H₇ |
| 3-429 | F | F | O | H | CF₃ | H | CH₂OCOCH₂Cl |
| 3-430 | F | F | O | H | CF₃ | H | CH₂OCOCCl₃ |
| 3-431 | F | F | O | H | CF₃ | H | CH₂OCOCF₃ |
| 3-432 | F | F | O | H | CF₃ | H | COOCH₃ |
| 3-433 | F | F | O | H | CF₃ | H | COOC₂H₅ |
| 3-434 | F | F | O | H | CF₃ | H | COOⁿC₃H₇ |
| 3-435 | F | F | O | H | CF₃ | H | COOⁿC₄H₉ |
| 3-436 | F | F | O | H | CF₃ | H | COOⁿC₅H₁₁ |
| 3-437 | F | F | O | H | CF₃ | H | COOⁱC₃H₇ |
| 3-438 | F | F | O | H | CF₃ | H | COCH₃ |
| 3-439 | F | F | O | H | CF₃ | H | COC₂H₅ |
| 3-440 | F | Cl | O | H | CF₃ | H | CH₂Br |
| 3-441 | F | Cl | O | H | CF₃ | H | CHBr₂ |
| 3-442 | F | Cl | O | H | CF₃ | H | CBr₃ |
| 3-443 | F | Cl | O | H | CF₃ | H | CHO |
| 3-444 | F | Cl | O | H | CF₃ | H | CN |
| 3-445 | F | Cl | O | H | CF₃ | H | COOH |
| 3-446 | F | Cl | O | H | CF₃ | H | CH₂OH |
| 3-447 | F | Cl | O | H | CF₃ | H | CH₂OCH₃ |
| 3-448 | F | Cl | O | H | CF₃ | H | CH₂OC₂H₅ |
| 3-449 | F | Cl | O | H | CF₃ | H | CH₂OⁱC₃H₇ |
| 3-450 | F | Cl | O | H | CF₃ | H | CH₂OCH₂OCH₃ |
| 3-451 | F | Cl | O | H | CF₃ | H | CH₂OCH₂OC₂H₅ |
| 3-452 | F | Cl | O | H | CF₃ | H | CH₂OCOCH₃ |
| 3-453 | F | Cl | O | H | CF₃ | H | CH₂OCOC₂H₅ |
| 3-454 | F | Cl | O | H | CF₃ | H | CH₂OCOⁱC₃H₇ |
| 3-455 | F | Cl | O | H | CF₃ | H | CH₂OCOCH₂Cl |
| 3-456 | F | Cl | O | H | CF₃ | H | CH₂OCOCCl₃ |
| 3-457 | F | Cl | O | H | CF₃ | H | CH₂OCOCF₃ |
| 3-458 | F | Cl | O | H | CF₃ | H | COOCH₃ |
| 3-459 | F | Cl | O | H | CF₃ | H | COOC₂H₅ |
| 3-460 | F | Cl | O | H | CF₃ | H | COOⁿC₃H₇ |
| 3-461 | F | Cl | O | H | CF₃ | H | COOⁿC₄H₉ |
| 3-462 | F | Cl | O | H | CF₃ | H | COOⁿC₅H₁₁ |
| 3-463 | F | Cl | O | H | CF₃ | H | COOⁱC₃H₇ |
| 3-464 | F | Cl | O | H | CF₃ | H | COCH₃ |
| 3-465 | F | Cl | O | H | CF₃ | H | COC₂H₅ |
| 3-466 | H | F | O | CH₃ | CF₃ | H | CH₃ |
| 3-467 | H | Cl | O | CH₃ | CF₃ | H | CH₃ |
| 3-468 | H | Br | O | CH₃ | CF₃ | H | CH₃ |
| 3-469 | F | F | O | CH₃ | CF₃ | H | CH₃ |
| 3-470 | F | Cl | O | CH₃ | CF₃ | H | CH₃ |
| 3-471 | F | Br | O | CH₃ | CF₃ | H | CH₃ |
| 3-472 | H | F | O | CH₃ | CF₃ | H | C₂H₅ |
| 3-473 | H | Cl | O | CH₃ | CF₃ | H | C₂H₅ |
| 3-474 | H | Br | O | CH₃ | CF₃ | H | C₂H₅ |
| 3-475 | F | F | O | CH₃ | CF₃ | H | C₂H₅ |
| 3-476 | F | Cl | O | CH₃ | CF₃ | H | C₂H₅ |
| 3-477 | F | Br | O | CH₃ | CF₃ | H | C₂H₅ |
| 3-478 | F | Br | O | CH₃ | CF₃ | H | C₂H₅ |
| 3-479 | H | F | O | CH₃ | CF₃ | H | CH₂Br |
| 3-480 | H | F | O | CH₃ | CF₃ | H | CHBr₂ |
| 3-481 | H | F | O | CH₃ | CF₃ | H | CBr₃ |
| 3-482 | H | F | O | CH₃ | CF₃ | H | CHO |
| 3-483 | H | F | O | CH₃ | CF₃ | H | CN |
| 3-484 | H | F | O | CH₃ | CF₃ | H | COOH |
| 3-485 | H | F | O | CH₃ | CF₃ | H | CH₂OH |
| 3-486 | H | F | O | CH₃ | CF₃ | H | CH₂OCH₃ |
| 3-487 | H | F | O | CH₃ | CF₃ | H | CH₂OC₂H₅ |
| 3-488 | H | F | O | CH₃ | CF₃ | H | CH₂OⁱC₃H₇ |
| 3-489 | H | F | O | CH₃ | CF₃ | H | CH₂OCH₂OCH₃ |
| 3-490 | H | F | O | CH₃ | CF₃ | H | CH₂OCH₂OC₂H₅ |
| 3-491 | H | F | O | CH₃ | CF₃ | H | CH₂OCOCH₃ |
| 3-492 | H | F | O | CH₃ | CF₃ | H | CH₂OCOC₂H₅ |
| 3-493 | H | F | O | CH₃ | CF₃ | H | CH₂OCOⁱC₃H₇ |
| 3-494 | H | F | O | CH₃ | CF₃ | H | CH₂OCOCH₂Cl |
| 3-495 | H | F | O | CH₃ | CF₃ | H | CH₂OCOCCl₃ |
| 3-496 | H | F | O | CH₃ | CF₃ | H | CH₂OCOCF₃ |
| 3-497 | H | F | O | CH₃ | CF₃ | H | COOCH₃ |
| 3-498 | H | F | O | CH₃ | CF₃ | H | COOC₂H₅ |
| 3-499 | H | F | O | CH₃ | CF₃ | H | COOⁿC₃H₇ |
| 3-500 | H | F | O | CH₃ | CF₃ | H | COOⁿC₄H₉ |
| 3-501 | H | F | O | CH₃ | CF₃ | H | COOⁿC₅H₁₁ |
| 3-502 | H | F | O | CH₃ | CF₃ | H | COOⁱC₃H₇ |
| 3-503 | H | F | O | CH₃ | CF₃ | H | COCH₃ |
| 3-504 | H | F | O | CH₃ | CF₃ | H | COC₂H₅ |
| 3-505 | H | Cl | O | CH₃ | CF₃ | H | CH₂Br |
| 3-506 | H | Cl | O | CH₃ | CF₃ | H | CHBr₂ |
| 3-507 | H | Cl | O | CH₃ | CF₃ | H | CBr₃ |
| 3-508 | H | Cl | O | CH₃ | CF₃ | H | CHO |
| 3-509 | H | Cl | O | CH₃ | CF₃ | H | CN |
| 3-510 | H | Cl | O | CH₃ | CF₃ | H | COOH |
| 3-511 | H | Cl | O | CH₃ | CF₃ | H | CH₂OH |
| 3-512 | H | Cl | O | CH₃ | CF₃ | H | CH₂OCH₃ |
| 3-513 | H | Cl | O | CH₃ | CF₃ | H | CH₂OC₂H₅ |
| 3-514 | H | Cl | O | CH₃ | CF₃ | H | CH₂OⁱC₃H₇ |
| 3-515 | H | Cl | O | CH₃ | CF₃ | H | CH₂OCH₂OCH₃ |
| 3-516 | H | Cl | O | CH₃ | CF₃ | H | CH₂OCH₂OC₂H₅ |
| 3-517 | H | Cl | O | CH₃ | CF₃ | H | CH₂OCOCH₃ |
| 3-518 | H | Cl | O | CH₃ | CF₃ | H | CH₂OCOC₂H₅ |
| 3-519 | H | Cl | O | CH₃ | CF₃ | H | CH₂OCOⁱC₃H₇ |
| 3-520 | H | Cl | O | CH₃ | CF₃ | H | CH₂OCOCH₂Cl |
| 3-521 | H | Cl | O | CH₃ | CF₃ | H | CH₂OCOCCl₃ |
| 3-522 | H | Cl | O | CH₃ | CF₃ | H | CH₂OCOCF₃ |
| 3-523 | H | Cl | O | CH₃ | CF₃ | H | COOCH₃ |
| 3-524 | H | Cl | O | CH₃ | CF₃ | H | COOC₂H₅ |
| 3-525 | H | Cl | O | CH₃ | CF₃ | H | COOⁿC₃H₇ |
| 3-526 | H | Cl | O | CH₃ | CF₃ | H | COOⁿC₄H₉ |
| 3-527 | H | Cl | O | CH₃ | CF₃ | H | COOⁿC₅H₁₁ |
| 3-528 | H | Cl | O | CH₃ | CF₃ | H | COOⁱC₃H₇ |
| 3-529 | H | Cl | O | CH₃ | CF₃ | H | COCH₃ |
| 3-530 | H | Cl | O | CH₃ | CF₃ | H | COC₂H₅ |
| 3-531 | F | F | O | CH₃ | CF₃ | H | CH₂Br |
| 3-532 | F | F | O | CH₃ | CF₃ | H | CHBr₂ |

TABLE 3-continued

Compounds of the formula:

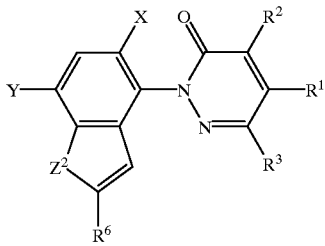

| Compound No. | X | Y | Z² | R³ | R¹ | R² | R⁶ |
|---|---|---|---|---|---|---|---|
| 3-533 | F | F | O | $CH_3$ | $CF_3$ | H | $CBr_3$ |
| 3-534 | F | F | O | $CH_3$ | $CF_3$ | H | CHO |
| 3-535 | F | F | O | $CH_3$ | $CF_3$ | H | CN |
| 3-536 | F | F | O | $CH_3$ | $CF_3$ | H | COOH |
| 3-537 | F | F | O | $CH_3$ | $CF_3$ | H | $CH_2OH$ |
| 3-538 | F | F | O | $CH_3$ | $CF_3$ | H | $CH_2OCH_3$ |
| 3-539 | F | F | O | $CH_3$ | $CF_3$ | H | $CH_2OC_2H_5$ |
| 3-540 | F | F | O | $CH_3$ | $CF_3$ | H | $CH_2O^iC_3H_7$ |
| 3-541 | F | F | O | $CH_3$ | $CF_3$ | H | $CH_2OCH_2OCH_3$ |
| 3-542 | F | F | O | $CH_3$ | $CF_3$ | H | $CH_2OCH_2OC_2H_5$ |
| 3-543 | F | F | O | $CH_3$ | $CF_3$ | H | $CH_2OCOCH_3$ |
| 3-544 | F | F | O | $CH_3$ | $CF_3$ | H | $CH_2OCOC_2H_5$ |
| 3-545 | F | F | O | $CH_3$ | $CF_3$ | H | $CH_2OCO^iC_3H_7$ |
| 3-546 | F | F | O | $CH_3$ | $CF_3$ | H | $CH_2OCOCH_2Cl$ |
| 3-547 | F | F | O | $CH_3$ | $CF_3$ | H | $CH_2OCOCCl_3$ |
| 3-548 | F | F | O | $CH_3$ | $CF_3$ | H | $CH_2OCOCF_3$ |
| 3-549 | F | F | O | $CH_3$ | $CF_3$ | H | $COOCH_3$ |
| 3-550 | F | F | O | $CH_3$ | $CF_3$ | H | $COOC_2H_5$ |
| 3-551 | F | F | O | $CH_3$ | $CF_3$ | H | $COO^nC_3H_7$ |
| 3-552 | F | F | O | $CH_3$ | $CF_3$ | H | $COO^nC_4H_9$ |
| 3-553 | F | F | O | $CH_3$ | $CF_3$ | H | $COO^nC_5H_{11}$ |
| 3-554 | F | F | O | $CH_3$ | $CF_3$ | H | $COO^iC_3H_7$ |
| 3-555 | F | F | O | $CH_3$ | $CF_3$ | H | $COCH_3$ |
| 3-556 | F | F | O | $CH_3$ | $CF_3$ | H | $COC_2H_5$ |
| 3-557 | F | Cl | O | $CH_3$ | $CF_3$ | H | $CH_2Br$ |
| 3-558 | F | Cl | O | $CH_3$ | $CF_3$ | H | $CHBr_2$ |
| 3-559 | F | Cl | O | $CH_3$ | $CF_3$ | H | $CBr_3$ |
| 3-560 | F | Cl | O | $CH_3$ | $CF_3$ | H | CHO |
| 3-561 | F | Cl | O | $CH_3$ | $CF_3$ | H | CN |
| 3-562 | F | Cl | O | $CH_3$ | $CF_3$ | H | COOH |
| 3-563 | F | Cl | O | $CH_3$ | $CF_3$ | H | $CH_2OH$ |
| 3-564 | F | Cl | O | $CH_3$ | $CF_3$ | H | $CH_2OCH_3$ |
| 3-565 | F | Cl | O | $CH_3$ | $CF_3$ | H | $CH_2OC_2H_5$ |
| 3-566 | F | Cl | O | $CH_3$ | $CF_3$ | H | $CH_2O^iC_3H_7$ |
| 3-567 | F | Cl | O | $CH_3$ | $CF_3$ | H | $CH_2OCH_2OCH_3$ |
| 3-568 | F | Cl | O | $CH_3$ | $CF_3$ | H | $CH_2OCH_2OC_2H_5$ |
| 3-569 | F | Cl | O | $CH_3$ | $CF_3$ | H | $CH_2OCOCH_3$ |
| 3-570 | F | Cl | O | $CH_3$ | $CF_3$ | H | $CH_2OCOC_2H_5$ |
| 3-571 | F | Cl | O | $CH_3$ | $CF_3$ | H | $CH_2OCO^iC_3H_7$ |
| 3-572 | F | Cl | O | $CH_3$ | $CF_3$ | H | $CH_2OCOCH_2Cl$ |
| 3-573 | F | Cl | O | $CH_3$ | $CF_3$ | H | $CH_2OCOCCl_3$ |
| 3-574 | F | Cl | O | $CH_3$ | $CF_3$ | H | $CH_2OCOCF_3$ |
| 3-575 | F | Cl | O | $CH_3$ | $CF_3$ | H | $COOCH_3$ |
| 3-576 | F | Cl | O | $CH_3$ | $CF_3$ | H | $COOC_2H_5$ |
| 3-577 | F | Cl | O | $CH_3$ | $CF_3$ | H | $COO^nC_3H_7$ |
| 3-578 | F | Cl | O | $CH_3$ | $CF_3$ | H | $COO^nC_4H_9$ |
| 3-579 | F | Cl | O | $CH_3$ | $CF_3$ | H | $COO^nC_5H_{11}$ |
| 3-580 | F | Cl | O | $CH_3$ | $CF_3$ | H | $COO^iC_3H_7$ |
| 3-581 | F | Cl | O | $CH_3$ | $CF_3$ | H | $COCH_3$ |
| 3-582 | F | Cl | O | $CH_3$ | $CF_3$ | H | $COC_2H_5$ |

TABLE 4

Compounds of the formula:

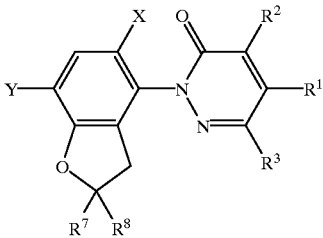

| Compound No. | X | Y | R³ | R¹ | R² | R⁷ | R⁸ |
|---|---|---|---|---|---|---|---|
| 4-1 | H | Cl | H | $CF_2Cl$ | $CH_3$ | H | $CH_2Cl$ |
| 4-2 | H | Cl | H | $CF_2Cl$ | $CH_3$ | H | $CH_2Br$ |
| 4-3 | H | Cl | H | $CF_2Cl$ | $CH_3$ | H | $CH_2OCH_3$ |
| 4-4 | H | Cl | H | $CF_2Cl$ | $CH_3$ | H | $CH_2OC_2H_5$ |
| 4-5 | H | Cl | H | $CF_2Cl$ | $CH_3$ | H | $CH_2OCH_2OCH_3$ |
| 4-6 | H | Cl | H | $CF_2Cl$ | $CH_3$ | H | $CH_2OCH_2OC_2H_5$ |
| 4-7 | H | Cl | H | $CF_2Cl$ | $CH_3$ | H | $CH_2OCOCH_3$ |
| 4-8 | H | Cl | H | $CF_2Cl$ | $CH_3$ | H | $CH_2OCOC_2H_5$ |
| 4-9 | H | Cl | H | $CF_2Cl$ | $CH_3$ | H | $CH_2OCO^iC_3H_7$ |
| 4-10 | H | Cl | H | $CF_2Cl$ | $CH_3$ | H | $CH_2OCOCH_2Cl$ |
| 4-11 | H | Cl | H | $CF_2Cl$ | $CH_3$ | H | $CH_2OCOCCl_3$ |
| 4-12 | H | Cl | H | $CF_2Cl$ | $CH_3$ | H | $CH_2OCOCF_3$ |
| 4-13 | H | Cl | H | $CF_2Cl$ | $CH_3$ | H | COOH |
| 4-14 | H | Cl | H | $CF_2Cl$ | $CH_3$ | H | $COOCH_3$ |
| 4-15 | H | Cl | H | $CF_2Cl$ | $CH_3$ | H | $COOC_2H_5$ |
| 4-16 | H | Cl | H | $CF_2Cl$ | $CH_3$ | H | $COO^nC_3H_7$ |
| 4-17 | H | Cl | H | $CF_2Cl$ | $CH_3$ | H | $COO^nC_4H_9$ |
| 4-18 | H | Cl | H | $CF_2Cl$ | $CH_3$ | H | $COO^nC_5H_{11}$ |
| 4-19 | H | Cl | H | $CF_2Cl$ | $CH_3$ | H | $COO^iC_3H_7$ |
| 4-20 | H | Cl | H | $CF_2Cl$ | $CH_3$ | H | $COO^cC_5H_9$ |
| 4-21 | H | Cl | H | $CF_2Cl$ | $CH_3$ | H | $COO^cC_6H_{11}$ |
| 4-22 | H | Cl | H | $CF_2Cl$ | $CH_3$ | H | $COOCH_2CH=CH_2$ |
| 4-23 | H | Cl | H | $CF_2Cl$ | $CH_3$ | H | $COOCH_2C\equiv CH$ |
| 4-24 | H | Cl | H | $CF_2Cl$ | $CH_3$ | H | $CONH_2$ |
| 4-25 | H | Cl | H | $CF_2Cl$ | $CH_3$ | H | $CONHCH_3$ |
| 4-26 | H | Cl | H | $CF_2Cl$ | $CH_3$ | H | $CONHC_2H_5$ |
| 4-27 | H | Cl | H | $CF_2Cl$ | $CH_3$ | H | $CON(CH_3)_2$ |
| 4-28 | H | Cl | H | $CF_2Cl$ | $CH_3$ | H | $CON(C_2H_5)_2$ |
| 4-29 | F | Cl | H | $CF_2Cl$ | $CH_3$ | H | $CH_2Cl$ |
| 4-30 | F | Cl | H | $CF_2Cl$ | $CH_3$ | H | $CH_2Br$ |
| 4-31 | F | Cl | H | $CF_2Cl$ | $CH_3$ | H | $CH_2OCH_3$ |
| 4-32 | F | Cl | H | $CF_2Cl$ | $CH_3$ | H | $CH_2OC_2H_5$ |
| 4-33 | F | Cl | H | $CF_2Cl$ | $CH_3$ | H | $CH_2OCH_2OCH_3$ |
| 4-34 | F | Cl | H | $CF_2Cl$ | $CH_3$ | H | $CH_2OCH_2OC_2H_5$ |
| 4-35 | F | Cl | H | $CF_2Cl$ | $CH_3$ | H | $CH_2OCOCH_3$ |
| 4-36 | F | Cl | H | $CF_2Cl$ | $CH_3$ | H | $CH_2OCOC_2H_5$ |
| 4-37 | F | Cl | H | $CF_2Cl$ | $CH_3$ | H | $CH_2OCO^iC_3H_7$ |
| 4-38 | F | Cl | H | $CF_2Cl$ | $CH_3$ | H | $CH_2OCOCH_2Cl$ |
| 4-39 | F | Cl | H | $CF_2Cl$ | $CH_3$ | H | $CH_2OCOCCl_3$ |
| 4-40 | F | Cl | H | $CF_2Cl$ | $CH_3$ | H | $CH_2OCOCF_3$ |
| 4-41 | F | Cl | H | $CF_2Cl$ | $CH_3$ | H | COOH |
| 4-42 | F | Cl | H | $CF_2Cl$ | $CH_3$ | H | $COOCH_3$ |
| 4-43 | F | Cl | H | $CF_2Cl$ | $CH_3$ | H | $COOC_2H_5$ |
| 4-44 | F | Cl | H | $CF_2Cl$ | $CH_3$ | H | $COO^nC_3H_7$ |
| 4-45 | F | Cl | H | $CF_2Cl$ | $CH_3$ | H | $COO^nC_4H_9$ |
| 4-46 | F | Cl | H | $CF_2Cl$ | $CH_3$ | H | $COO^nC_5H_{11}$ |
| 4-47 | F | Cl | H | $CF_2Cl$ | $CH_3$ | H | $COO^iC_3H_7$ |
| 4-48 | F | Cl | H | $CF_2Cl$ | $CH_3$ | H | $COO^cC_5H_9$ |
| 4-49 | F | Cl | H | $CF_2Cl$ | $CH_3$ | H | $COO^cC_6H_{11}$ |
| 4-50 | F | Cl | H | $CF_2Cl$ | $CH_3$ | H | $COOCH_2CH=CH_2$ |
| 4-51 | F | Cl | H | $CF_2Cl$ | $CH_3$ | H | $COOCH_2C\equiv CH$ |
| 4-52 | F | Cl | H | $CF_2Cl$ | $CH_3$ | H | $CONH_2$ |
| 4-53 | F | Cl | H | $CF_2Cl$ | $CH_3$ | H | $CONHCH_3$ |
| 4-54 | F | Cl | H | $CF_2Cl$ | $CH_3$ | H | $CONHC_2H_5$ |
| 4-55 | F | Cl | H | $CF_2Cl$ | $CH_3$ | H | $CON(CH_3)_2$ |
| 4-56 | F | Cl | H | $CF_2Cl$ | $CH_3$ | H | $CON(C_2H_5)_2$ |
| 4-57 | H | Cl | H | $CF_2Cl$ | $CH_3$ | $CH_3$ | $CH_2Cl$ |
| 4-58 | H | Cl | H | $CF_2Cl$ | $CH_3$ | $CH_3$ | $CH_2Br$ |
| 4-59 | H | Cl | H | $CF_2Cl$ | $CH_3$ | $CH_3$ | $CH_2OCH_3$ |
| 4-60 | H | Cl | H | $CF_2Cl$ | $CH_3$ | $CH_3$ | $CH_2OC_2H_5$ |
| 4-61 | H | Cl | H | $CF_2Cl$ | $CH_3$ | $CH_3$ | $CH_2OCH_2OCH_3$ |

TABLE 4-continued

Compounds of the formula:

[Structure: a benzofuran fused bicyclic with X, Y substituents, connected via N to a pyridazinone ring bearing R¹, R², R³; the furan carbon bears R⁷, R⁸]

| Compound No. | X | Y | R³ | R¹ | R² | R⁷ | R⁸ |
|---|---|---|---|---|---|---|---|
| 4-62 | H | Cl | H | $CF_2Cl$ | $CH_3$ | $CH_3$ | $CH_2OCH_2OC_2H_5$ |
| 4-63 | H | Cl | H | $CF_2Cl$ | $CH_3$ | $CH_3$ | $CH_2OCOCH_3$ |
| 4-64 | H | Cl | H | $CF_2Cl$ | $CH_3$ | $CH_3$ | $CH_2OCOC_2H_5$ |
| 4-65 | H | Cl | H | $CF_2Cl$ | $CH_3$ | $CH_3$ | $CH_2OCO^iC_3H_7$ |
| 4-66 | H | Cl | H | $CF_2Cl$ | $CH_3$ | $CH_3$ | $CH_2OCOCH_2Cl$ |
| 4-67 | H | Cl | H | $CF_2Cl$ | $CH_3$ | $CH_3$ | $CH_2OCOCCl_3$ |
| 4-68 | H | Cl | H | $CF_2Cl$ | $CH_3$ | $CH_3$ | $CH_2OCOCF_3$ |
| 4-69 | H | Cl | H | $CF_2Cl$ | $CH_3$ | $CH_3$ | COOH |
| 4-70 | H | Cl | H | $CF_2Cl$ | $CH_3$ | $CH_3$ | $COOCH_3$ |
| 4-71 | H | Cl | H | $CF_2Cl$ | $CH_3$ | $CH_3$ | $COOC_2H_5$ |
| 4-72 | H | Cl | H | $CF_2Cl$ | $CH_3$ | $CH_3$ | $COO^nC_3H_7$ |
| 4-73 | H | Cl | H | $CF_2Cl$ | $CH_3$ | $CH_3$ | $COO^nC_4H_9$ |
| 4-74 | H | Cl | H | $CF_2Cl$ | $CH_3$ | $CH_3$ | $COO^nC_5H_{11}$ |
| 4-75 | H | Cl | H | $CF_2Cl$ | $CH_3$ | $CH_3$ | $COO^iC_3H_7$ |
| 4-76 | H | Cl | H | $CF_2Cl$ | $CH_3$ | $CH_3$ | $COO^cC_5H_9$ |
| 4-77 | H | Cl | H | $CF_2Cl$ | $CH_3$ | $CH_3$ | $COO^cC_6H_{11}$ |
| 4-78 | H | Cl | H | $CF_2Cl$ | $CH_3$ | $CH_3$ | $COOCH_2CH=CH_2$ |
| 4-79 | H | Cl | H | $CF_2Cl$ | $CH_3$ | $CH_3$ | $COOCH_2C\equiv CH$ |
| 4-80 | H | Cl | H | $CF_2Cl$ | $CH_3$ | $CH_3$ | $CONH_2$ |
| 4-81 | H | Cl | H | $CF_2Cl$ | $CH_3$ | $CH_3$ | $CONHCH_3$ |
| 4-82 | H | Cl | H | $CF_2Cl$ | $CH_3$ | $CH_3$ | $CONHC_2H_5$ |
| 4-83 | H | Cl | H | $CF_2Cl$ | $CH_3$ | $CH_3$ | $CON(CH_3)_2$ |
| 4-84 | H | Cl | H | $CF_2Cl$ | $CH_3$ | $CH_3$ | $CON(C_2H_5)_2$ |
| 4-85 | F | Cl | H | $CF_2Cl$ | $CH_3$ | $CH_3$ | $CH_2Cl$ |
| 4-86 | F | Cl | H | $CF_2Cl$ | $CH_3$ | $CH_3$ | $CH_2Br$ |
| 4-87 | F | Cl | H | $CF_2Cl$ | $CH_3$ | $CH_3$ | $CH_2OCH_3$ |
| 4-88 | F | Cl | H | $CF_2Cl$ | $CH_3$ | $CH_3$ | $CH_2OC_2H_5$ |
| 4-89 | F | Cl | H | $CF_2Cl$ | $CH_3$ | $CH_3$ | $CH_2OCH_2OCH_3$ |
| 4-90 | F | Cl | H | $CF_2Cl$ | $CH_3$ | $CH_3$ | $CH_2OCH_2OC_2H_5$ |
| 4-91 | F | Cl | H | $CF_2Cl$ | $CH_3$ | $CH_3$ | $CH_2OCOCH_3$ |
| 4-92 | F | Cl | H | $CF_2Cl$ | $CH_3$ | $CH_3$ | $CH_2OCOC_2H_5$ |
| 4-93 | F | Cl | H | $CF_2Cl$ | $CH_3$ | $CH_3$ | $CH_2OCO^iC_3H_7$ |
| 4-94 | F | Cl | H | $CF_2Cl$ | $CH_3$ | $CH_3$ | $CH_2OCOCH_2Cl$ |
| 4-95 | F | Cl | H | $CF_2Cl$ | $CH_3$ | $CH_3$ | $CH_2OCOCCl_3$ |
| 4-96 | F | Cl | H | $CF_2Cl$ | $CH_3$ | $CH_3$ | $CH_2OCOCF_3$ |
| 4-97 | F | Cl | H | $CF_2Cl$ | $CH_3$ | $CH_3$ | COOH |
| 4-98 | F | Cl | H | $CF_2Cl$ | $CH_3$ | $CH_3$ | $COOCH_3$ |
| 4-99 | F | Cl | H | $CF_2Cl$ | $CH_3$ | $CH_3$ | $COOC_2H_5$ |
| 4-100 | F | Cl | H | $CF_2Cl$ | $CH_3$ | $CH_3$ | $COO^nC_3H_7$ |
| 4-101 | F | Cl | H | $CF_2Cl$ | $CH_3$ | $CH_3$ | $COO^nC_4H_9$ |
| 4-102 | F | Cl | H | $CF_2Cl$ | $CH_3$ | $CH_3$ | $COO^nC_5H_{11}$ |
| 4-103 | F | Cl | H | $CF_2Cl$ | $CH_3$ | $CH_3$ | $COO^iC_3H_7$ |
| 4-104 | F | Cl | H | $CF_2Cl$ | $CH_3$ | $CH_3$ | $COO^cC_5H_9$ |
| 4-105 | F | Cl | H | $CF_2Cl$ | $CH_3$ | $CH_3$ | $COO^cC_6H_{11}$ |
| 4-106 | F | Cl | H | $CF_2Cl$ | $CH_3$ | $CH_3$ | $COOCH_2CH=CH_2$ |
| 4-107 | F | Cl | H | $CF_2Cl$ | $CH_3$ | $CH_3$ | $COOCH_2C\equiv CH$ |
| 4-108 | F | Cl | H | $CF_2Cl$ | $CH_3$ | $CH_3$ | $CONH_2$ |
| 4-109 | F | Cl | H | $CF_2Cl$ | $CH_3$ | $CH_3$ | $CONHCH_3$ |
| 4-110 | F | Cl | H | $CF_2Cl$ | $CH_3$ | $CH_3$ | $CONHC_2H_5$ |
| 4-111 | F | Cl | H | $CF_2Cl$ | $CH_3$ | $CH_3$ | $CON(CH_3)_2$ |
| 4-112 | F | Cl | H | $CF_2Cl$ | $CH_3$ | $CH_3$ | $CON(C_2H_5)_2$ |
| 4-113 | H | Cl | H | $CF_3$ | $CH_3$ | H | $CH_2Cl$ |
| 4-114 | H | Cl | H | $CF_3$ | $CH_3$ | H | $CH_2Br$ |
| 4-115 | H | Cl | H | $CF_3$ | $CH_3$ | H | $CH_2OCH_3$ |
| 4-116 | H | Cl | H | $CF_3$ | $CH_3$ | H | $CH_2OC_2H_5$ |
| 4-117 | H | Cl | H | $CF_3$ | $CH_3$ | H | $CH_2OCH_2OCH_3$ |
| 4-118 | H | Cl | H | $CF_3$ | $CH_3$ | H | $CH_2OCH_2OC_2H_5$ |
| 4-119 | H | Cl | H | $CF_3$ | $CH_3$ | H | $CH_2OCOCH_3$ |
| 4-120 | H | Cl | H | $CF_3$ | $CH_3$ | H | $CH_2OCOC_2H_5$ |
| 4-121 | H | Cl | H | $CF_3$ | $CH_3$ | H | $CH_2OCO^iC_3H_7$ |
| 4-122 | H | Cl | H | $CF_3$ | $CH_3$ | H | $CH_2OCOCH_2Cl$ |
| 4-123 | H | Cl | H | $CF_3$ | $CH_3$ | H | $CH_2OCOCCl_3$ |
| 4-124 | H | Cl | H | $CF_3$ | $CH_3$ | H | $CH_2OCOCF_3$ |
| 4-125 | H | Cl | H | $CF_3$ | $CH_3$ | H | COOH |
| 4-126 | H | Cl | H | $CF_3$ | $CH_3$ | H | $COOCH_3$ |
| 4-127 | H | Cl | H | $CF_3$ | $CH_3$ | H | $COOC_2H_5$ |
| 4-128 | H | Cl | H | $CF_3$ | $CH_3$ | H | $COO^nC_3H_7$ |
| 4-129 | H | Cl | H | $CF_3$ | $CH_3$ | H | $COO^nC_4H_9$ |
| 4-130 | H | Cl | H | $CF_3$ | $CH_3$ | H | $COO^nC_5H_{11}$ |
| 4-131 | H | Cl | H | $CF_3$ | $CH_3$ | H | $COO^iC_3H_7$ |
| 4-132 | H | Cl | H | $CF_3$ | $CH_3$ | H | $COO^cC_5H_9$ |
| 4-133 | H | Cl | H | $CF_3$ | $CH_3$ | H | $COO^cC_6H_{11}$ |
| 4-134 | H | Cl | H | $CF_3$ | $CH_3$ | H | $COOCH_2CH=CH_2$ |
| 4-135 | H | Cl | H | $CF_3$ | $CH_3$ | H | $COOCH_2C\equiv CH$ |
| 4-136 | H | Cl | H | $CF_3$ | $CH_3$ | H | $CONH_2$ |
| 4-137 | H | Cl | H | $CF_3$ | $CH_3$ | H | $CONHCH_3$ |
| 4-138 | H | Cl | H | $CF_3$ | $CH_3$ | H | $CONHC_2H_5$ |
| 4-139 | H | Cl | H | $CF_3$ | $CH_3$ | H | $CON(CH_3)_2$ |
| 4-140 | H | Cl | H | $CF_3$ | $CH_3$ | H | $CON(C_2H_5)_2$ |
| 4-141 | F | Cl | H | $CF_3$ | $CH_3$ | H | $CH_2Cl$ |
| 4-142 | F | Cl | H | $CF_3$ | $CH_3$ | H | $CH_2Br$ |
| 4-143 | F | Cl | H | $CF_3$ | $CH_3$ | H | $CH_2OCH_3$ |
| 4-144 | F | Cl | H | $CF_3$ | $CH_3$ | H | $CH_2OC_2H_5$ |
| 4-145 | F | Cl | H | $CF_3$ | $CH_3$ | H | $CH_2OCH_2OCH_3$ |
| 4-146 | F | Cl | H | $CF_3$ | $CH_3$ | H | $CH_2OCH_2OC_2H_5$ |
| 4-147 | F | Cl | H | $CF_3$ | $CH_3$ | H | $CH_2OCOCH_3$ |
| 4-148 | F | Cl | H | $CF_3$ | $CH_3$ | H | $CH_2OCOC_2H_5$ |
| 4-149 | F | Cl | H | $CF_3$ | $CH_3$ | H | $CH_2OCO^iC_3H_7$ |
| 4-150 | F | Cl | H | $CF_3$ | $CH_3$ | H | $CH_2OCOCH_2Cl$ |
| 4-151 | F | Cl | H | $CF_3$ | $CH_3$ | H | $CH_2OCOCCl_3$ |
| 4-152 | F | Cl | H | $CF_3$ | $CH_3$ | H | $CH_2OCOCF_3$ |
| 4-153 | F | Cl | H | $CF_3$ | $CH_3$ | H | COOH |
| 4-154 | F | Cl | H | $CF_3$ | $CH_3$ | H | $COOCH_3$ |
| 4-155 | F | Cl | H | $CF_3$ | $CH_3$ | H | $COOC_2H_5$ |
| 4-156 | F | Cl | H | $CF_3$ | $CH_3$ | H | $COO^nC_3H_7$ |
| 4-157 | F | Cl | H | $CF_3$ | $CH_3$ | H | $COO^nC_4H_9$ |
| 4-158 | F | Cl | H | $CF_3$ | $CH_3$ | H | $COO^nC_5H_{11}$ |
| 4-159 | F | Cl | H | $CF_3$ | $CH_3$ | H | $COO^iC_3H_7$ |
| 4-160 | F | Cl | H | $CF_3$ | $CH_3$ | H | $COO^cC_5H_9$ |
| 4-161 | F | Cl | H | $CF_3$ | $CH_3$ | H | $COO^cC_6H_{11}$ |
| 4-162 | F | Cl | H | $CF_3$ | $CH_3$ | H | $COOCH_2CH=CH_2$ |
| 4-163 | F | Cl | H | $CF_3$ | $CH_3$ | H | $COOCH_2C\equiv CH$ |
| 4-164 | F | Cl | H | $CF_3$ | $CH_3$ | H | $CONH_2$ |
| 4-165 | F | Cl | H | $CF_3$ | $CH_3$ | H | $CONHCH_3$ |
| 4-166 | F | Cl | H | $CF_3$ | $CH_3$ | H | $CONHC_2H_5$ |
| 4-167 | F | Cl | H | $CF_3$ | $CH_3$ | H | $CON(CH_3)_2$ |
| 4-168 | F | Cl | H | $CF_3$ | $CH_3$ | H | $CON(C_2H_5)_2$ |
| 4-169 | H | Cl | H | $CF_3$ | $CH_3$ | $CH_3$ | $CH_2Cl$ |
| 4-170 | H | Cl | H | $CF_3$ | $CH_3$ | $CH_3$ | $CH_2Br$ |
| 4-171 | H | Cl | H | $CF_3$ | $CH_3$ | $CH_3$ | $CH_2OCH_3$ |
| 4-172 | H | Cl | H | $CF_3$ | $CH_3$ | $CH_3$ | $CH_2OC_2H_5$ |
| 4-173 | H | Cl | H | $CF_3$ | $CH_3$ | $CH_3$ | $CH_2OCH_2OCH_3$ |
| 4-174 | H | Cl | H | $CF_3$ | $CH_3$ | $CH_3$ | $CH_2OCH_2OC_2H_5$ |
| 4-175 | H | Cl | H | $CF_3$ | $CH_3$ | $CH_3$ | $CH_2OCOCH_3$ |
| 4-176 | H | Cl | H | $CF_3$ | $CH_3$ | $CH_3$ | $CH_2OCOC_2H_5$ |
| 4-177 | H | Cl | H | $CF_3$ | $CH_3$ | $CH_3$ | $CH_2OCO^iC_3H_7$ |
| 4-178 | H | Cl | H | $CF_3$ | $CH_3$ | $CH_3$ | $CH_2OCOCH_2Cl$ |
| 4-179 | H | Cl | H | $CF_3$ | $CH_3$ | $CH_3$ | $CH_2OCOCCl_3$ |
| 4-180 | H | Cl | H | $CF_3$ | $CH_3$ | $CH_3$ | $CH_2OCOCF_3$ |
| 4-181 | H | Cl | H | $CF_3$ | $CH_3$ | $CH_3$ | COOH |
| 4-182 | H | Cl | H | $CF_3$ | $CH_3$ | $CH_3$ | $COOCH_3$ |
| 4-183 | H | Cl | H | $CF_3$ | $CH_3$ | $CH_3$ | $COOC_2H_5$ |

TABLE 4-continued

Compounds of the formula:

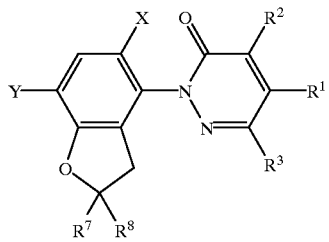

| Compound No. | X | Y | R³ | R¹ | R² | R⁷ | R⁸ |
|---|---|---|---|---|---|---|---|
| 4-184 | H | Cl | H | CF₃ | CH₃ | CH₃ | COO$^n$C₃H₇ |
| 4-185 | H | Cl | H | CF₃ | CH₃ | CH₃ | COO$^n$C₄H₉ |
| 4-186 | H | Cl | H | CF₃ | CH₃ | CH₃ | COO$^n$C₅H₁₁ |
| 4-187 | H | Cl | H | CF₃ | CH₃ | CH₃ | COO$^i$C₃H₇ |
| 4-188 | H | Cl | H | CF₃ | CH₃ | CH₃ | COO$^c$C₅H₉ |
| 4-189 | H | Cl | H | CF₃ | CH₃ | CH₃ | COO$^c$C₆H₁₁ |
| 4-190 | H | Cl | H | CF₃ | CH₃ | CH₃ | COOCH₂CH=CH₂ |
| 4-191 | H | Cl | H | CF₃ | CH₃ | CH₃ | COOCH₂C≡CH |
| 4-192 | H | Cl | H | CF₃ | CH₃ | CH₃ | CONH₂ |
| 4-193 | H | Cl | H | CF₃ | CH₃ | CH₃ | CONHCH₃ |
| 4-194 | H | Cl | H | CF₃ | CH₃ | CH₃ | CONHC₂H₅ |
| 4-195 | H | Cl | H | CF₃ | CH₃ | CH₃ | CON(CH₃)₂ |
| 4-196 | H | Cl | H | CF₃ | CH₃ | CH₃ | CON(C₂H₅)₂ |
| 4-197 | F | Cl | H | CF₃ | CH₃ | CH₃ | CH₂Cl |
| 4-198 | F | Cl | H | CF₃ | CH₃ | CH₃ | CH₂Br |
| 4-199 | F | Cl | H | CF₃ | CH₃ | CH₃ | CH₂OCH₃ |
| 4-200 | F | Cl | H | CF₃ | CH₃ | CH₃ | CH₂OC₂H₅ |
| 4-201 | F | Cl | H | CF₃ | CH₃ | CH₃ | CH₂OCH₂OCH₃ |
| 4-202 | F | Cl | H | CF₃ | CH₃ | CH₃ | CH₂OCH₂OC₂H₅ |
| 4-203 | F | Cl | H | CF₃ | CH₃ | CH₃ | CH₂OCOCH₃ |
| 4-204 | F | Cl | H | CF₃ | CH₃ | CH₃ | CH₂OCOC₂H₅ |
| 4-205 | F | Cl | H | CF₃ | CH₃ | CH₃ | CH₂OCO$^i$C₃H₇ |
| 4-206 | F | Cl | H | CF₃ | CH₃ | CH₃ | CH₂OCOCH₂Cl |
| 4-207 | F | Cl | H | CF₃ | CH₃ | CH₃ | CH₂OCOCCl₃ |
| 4-208 | F | Cl | H | CF₃ | CH₃ | CH₃ | CH₂OCOCF₃ |
| 4-209 | F | Cl | H | CF₃ | CH₃ | CH₃ | COOH |
| 4-210 | F | Cl | H | CF₃ | CH₃ | CH₃ | COOCH₃ |
| 4-211 | F | Cl | H | CF₃ | CH₃ | CH₃ | COOC₂H₅ |
| 4-212 | F | Cl | H | CF₃ | CH₃ | CH₃ | COO$^n$C₃H₇ |
| 4-213 | F | Cl | H | CF₃ | CH₃ | CH₃ | COO$^n$C₄H₉ |
| 4-214 | F | Cl | H | CF₃ | CH₃ | CH₃ | COO$^n$C₅H₁₁ |
| 4-215 | F | Cl | H | CF₃ | CH₃ | CH₃ | COO$^i$C₃H₇ |
| 4-216 | F | Cl | H | CF₃ | CH₃ | CH₃ | COO$^c$C₅H₉ |
| 4-217 | F | Cl | H | CF₃ | CH₃ | CH₃ | COO$^c$C₆H₁₁ |
| 4-218 | F | Cl | H | CF₃ | CH₃ | CH₃ | COOCH₂CH=CH₂ |
| 4-219 | F | Cl | H | CF₃ | CH₃ | CH₃ | COOCH₂C≡CH |
| 4-220 | F | Cl | H | CF₃ | CH₃ | CH₃ | CONH₂ |
| 4-221 | F | Cl | H | CF₃ | CH₃ | CH₃ | CONHCH₃ |
| 4-222 | F | Cl | H | CF₃ | CH₃ | CH₃ | CONHC₂H₅ |
| 4-223 | F | Cl | H | CF₃ | CH₃ | CH₃ | CON(CH₃)₂ |
| 4-224 | F | Cl | H | CF₃ | CH₃ | CH₃ | CON(C₂H₅)₂ |
| 4-225 | H | Cl | H | CF₂Cl | CH₃ | H | CH₂Cl |
| 4-226 | H | Cl | H | CF₂Cl | CH₃ | H | CH₂Br |
| 4-227 | H | Cl | H | CF₂Cl | CH₃ | H | CH₂OCH₃ |
| 4-228 | H | Cl | H | CF₂Cl | CH₃ | H | CH₂OC₂H₅ |
| 4-229 | H | Cl | H | CF₂Cl | CH₃ | H | CH₂OCH₂OCH₃ |
| 4-230 | H | Cl | H | CF₂Cl | CH₃ | H | CH₂OCH₂OC₂H₅ |
| 4-231 | H | Cl | H | CF₂Cl | CH₃ | H | CH₂OCOCH₃ |
| 4-232 | H | Cl | H | CF₂Cl | CH₃ | H | CH₂OCOC₂H₅ |
| 4-233 | H | Cl | H | CF₂Cl | CH₃ | H | CH₂OCO$^i$C₃H₇ |
| 4-234 | H | Cl | H | CF₂Cl | CH₃ | H | CH₂OCOCH₂Cl |
| 4-235 | H | Cl | H | CF₂Cl | CH₃ | H | CH₂OCOCCl₃ |
| 4-236 | H | Cl | H | CF₂Cl | CH₃ | H | CH₂OCOCF₃ |
| 4-237 | H | Cl | H | CF₂Cl | CH₃ | H | COOH |
| 4-238 | H | Cl | H | CF₂Cl | CH₃ | H | COOCH₃ |
| 4-239 | H | Cl | H | CF₂Cl | CH₃ | H | COOC₂H₅ |
| 4-240 | H | Cl | H | CF₂Cl | CH₃ | H | COO$^n$C₃H₇ |
| 4-241 | H | Cl | H | CF₂Cl | CH₃ | H | COO$^n$C₄H₉ |
| 4-242 | H | Cl | H | CF₂Cl | CH₃ | H | COO$^n$C₅H₁₁ |
| 4-243 | H | Cl | H | CF₂Cl | CH₃ | H | COO$^i$C₃H₇ |
| 4-244 | H | Cl | H | CF₂Cl | CH₃ | H | COO$^c$C₅H₉ |
| 4-245 | H | Cl | H | CF₂Cl | CH₃ | H | COO$^c$C₆H₁₁ |
| 4-246 | H | Cl | H | CF₂Cl | CH₃ | H | COOCH₂CH=CH₂ |
| 4-247 | H | Cl | H | CF₂Cl | CH₃ | H | COOCH₂C≡CH |
| 4-248 | H | Cl | H | CF₂Cl | CH₃ | H | CONH₂ |
| 4-249 | H | Cl | H | CF₂Cl | CH₃ | H | CONHCH₃ |
| 4-250 | H | Cl | H | CF₂Cl | CH₃ | H | CONHC₂H₅ |
| 4-251 | H | Cl | H | CF₂Cl | CH₃ | H | CON(CH₃)₂ |
| 4-252 | H | Cl | H | CF₂Cl | CH₃ | H | CON(C₂H₅)₂ |
| 4-253 | F | Cl | H | CF₂Cl | CH₃ | H | CH₂Cl |
| 4-254 | F | Cl | H | CF₂Cl | CH₃ | H | CH₂Br |
| 4-255 | F | Cl | H | CF₂Cl | CH₃ | H | CH₂OCH₃ |
| 4-256 | F | Cl | H | CF₂Cl | CH₃ | H | CH₂OC₂H₅ |
| 4-257 | F | Cl | H | CF₂Cl | CH₃ | H | CH₂OCH₂OCH₃ |
| 4-258 | F | Cl | H | CF₂Cl | CH₃ | H | CH₂OCH₂OC₂H₅ |
| 4-259 | F | Cl | H | CF₂Cl | CH₃ | H | CH₂OCOCH₃ |
| 4-260 | F | Cl | H | CF₂Cl | CH₃ | H | CH₂OCOC₂H₅ |
| 4-261 | F | Cl | H | CF₂Cl | CH₃ | H | CH₂OCO$^i$C₃H₇ |
| 4-262 | F | Cl | H | CF₂Cl | CH₃ | H | CH₂OCOCH₂Cl |
| 4-263 | F | Cl | H | CF₂Cl | CH₃ | H | CH₂OCOCCl₃ |
| 4-264 | F | Cl | H | CF₂Cl | CH₃ | H | CH₂OCOCF₃ |
| 4-265 | F | Cl | H | CF₂Cl | CH₃ | H | COOH |
| 4-266 | F | Cl | H | CF₂Cl | CH₃ | H | COOCH₃ |
| 4-267 | F | Cl | H | CF₂Cl | CH₃ | H | COOC₂H₅ |
| 4-268 | F | Cl | H | CF₂Cl | CH₃ | H | COO$^n$C₃H₇ |
| 4-269 | F | Cl | H | CF₂Cl | CH₃ | H | COO$^n$C₄H₉ |
| 4-270 | F | Cl | H | CF₂Cl | CH₃ | H | COO$^n$C₅H₁₁ |
| 4-271 | F | Cl | H | CF₂Cl | CH₃ | H | COO$^i$C₃H₇ |
| 4-272 | F | Cl | H | CF₂Cl | CH₃ | H | COO$^c$C₅H₉ |
| 4-273 | F | Cl | H | CF₂Cl | CH₃ | H | COO$^c$C₆H₁₁ |
| 4-274 | F | Cl | H | CF₂Cl | CH₃ | H | COOCH₂CH=CH₂ |
| 4-275 | F | Cl | H | CF₂Cl | CH₃ | H | COOCH₂C≡CH |
| 4-276 | F | Cl | H | CF₂Cl | CH₃ | H | CONH₂ |
| 4-277 | F | Cl | H | CF₂Cl | CH₃ | H | CONHCH₃ |
| 4-278 | F | Cl | H | CF₂Cl | CH₃ | H | CONHC₂H₅ |
| 4-279 | F | Cl | H | CF₂Cl | CH₃ | H | CON(CH₃)₂ |
| 4-280 | F | Cl | H | CF₂Cl | CH₃ | H | CON(C₂H₅)₂ |
| 4-281 | H | Cl | H | CF₂Cl | CH₃ | CH₃ | CH₂Cl |
| 4-282 | H | Cl | H | CF₂Cl | CH₃ | CH₃ | CH₂Br |
| 4-283 | H | Cl | H | CF₂Cl | CH₃ | CH₃ | CH₂OCH₃ |
| 4-284 | H | Cl | H | CF₂Cl | CH₃ | CH₃ | CH₂OC₂H₅ |
| 4-285 | H | Cl | H | CF₂Cl | CH₃ | CH₃ | CH₂OCH₂OCH₃ |
| 4-286 | H | Cl | H | CF₂Cl | CH₃ | CH₃ | CH₂OCH₂OC₂H₅ |
| 4-287 | H | Cl | H | CF₂Cl | CH₃ | CH₃ | CH₂OCOCH₃ |
| 4-288 | H | Cl | H | CF₂Cl | CH₃ | CH₃ | CH₂OCOC₂H₅ |
| 4-289 | H | Cl | H | CF₂Cl | CH₃ | CH₃ | CH₂OCO$^i$C₃H₇ |
| 4-290 | H | Cl | H | CF₂Cl | CH₃ | CH₃ | CH₂OCOCH₂Cl |
| 4-291 | H | Cl | H | CF₂Cl | CH₃ | CH₃ | CH₂OCOCCl₃ |
| 4-292 | H | Cl | H | CF₂Cl | CH₃ | CH₃ | CH₂OCOCF₃ |
| 4-293 | H | Cl | H | CF₂Cl | CH₃ | CH₃ | COOH |
| 4-294 | H | Cl | H | CF₂Cl | CH₃ | CH₃ | COOCH₃ |
| 4-295 | H | Cl | H | CF₂Cl | CH₃ | CH₃ | COOC₂H₅ |
| 4-296 | H | Cl | H | CF₂Cl | CH₃ | CH₃ | COO$^n$C₃H₇ |
| 4-297 | H | Cl | H | CF₂Cl | CH₃ | CH₃ | COO$^n$C₄H₉ |
| 4-298 | H | Cl | H | CF₂Cl | CH₃ | CH₃ | COO$^n$C₅H₁₁ |
| 4-299 | H | Cl | H | CF₂Cl | CH₃ | CH₃ | COO$^i$C₃H₇ |
| 4-300 | H | Cl | H | CF₂Cl | CH₃ | CH₃ | COO$^c$C₅H₉ |
| 4-301 | H | Cl | H | CF₂Cl | CH₃ | CH₃ | COO$^c$C₆H₁₁ |
| 4-302 | H | Cl | H | CF₂Cl | CH₃ | CH₃ | COOCH₂CH=CH₂ |
| 4-303 | H | Cl | H | CF₂Cl | CH₃ | CH₃ | COOCH₂C≡CH |
| 4-304 | H | Cl | H | CF₂Cl | CH₃ | CH₃ | CONH₂ |
| 4-305 | H | Cl | H | CF₂Cl | CH₃ | CH₃ | CONHCH₃ |

TABLE 4-continued

Compounds of the formula:

[Structure: pyridazinone linked to dihydrobenzofuran with substituents X, Y, R¹, R², R³, R⁷, R⁸]

| Compound No. | X | Y | $R^3$ | $R^1$ | $R^2$ | $R^7$ | $R^8$ |
|---|---|---|---|---|---|---|---|
| 4-306 | H | Cl | H | $CF_2Cl$ | $CH_3$ | $CH_3$ | $CONHC_2H_5$ |
| 4-307 | H | Cl | H | $CF_2Cl$ | $CH_3$ | $CH_3$ | $CON(CH_3)_2$ |
| 4-308 | H | Cl | H | $CF_2Cl$ | $CH_3$ | $CH_3$ | $CON(C_2H_5)_2$ |
| 4-309 | F | Cl | H | $CF_2Cl$ | $CH_3$ | $CH_3$ | $CH_2Cl$ |
| 4-310 | F | Cl | H | $CF_2Cl$ | $CH_3$ | $CH_3$ | $CH_2Br$ |
| 4-311 | F | Cl | H | $CF_2Cl$ | $CH_3$ | $CH_3$ | $CH_2OCH_3$ |
| 4-312 | F | Cl | H | $CF_2Cl$ | $CH_3$ | $CH_3$ | $CH_2OC_2H_5$ |
| 4-313 | F | Cl | H | $CF_2Cl$ | $CH_3$ | $CH_3$ | $CH_2OCH_2OCH_3$ |
| 4-314 | F | Cl | H | $CF_2Cl$ | $CH_3$ | $CH_3$ | $CH_2OCH_2OC_2H_5$ |
| 4-315 | F | Cl | H | $CF_2Cl$ | $CH_3$ | $CH_3$ | $CH_2OCOCH_3$ |
| 4-316 | F | Cl | H | $CF_2Cl$ | $CH_3$ | $CH_3$ | $CH_2OCOC_2H_5$ |
| 4-317 | F | Cl | H | $CF_2Cl$ | $CH_3$ | $CH_3$ | $CH_2OCO^iC_3H_7$ |
| 4-318 | F | Cl | H | $CF_2Cl$ | $CH_3$ | $CH_3$ | $CH_2OCOCH_2Cl$ |
| 4-319 | F | Cl | H | $CF_2Cl$ | $CH_3$ | $CH_3$ | $CH_2OCOCCl_3$ |
| 4-320 | F | Cl | H | $CF_2Cl$ | $CH_3$ | $CH_3$ | $CH_2OCOCF_3$ |
| 4-321 | F | Cl | H | $CF_2Cl$ | $CH_3$ | $CH_3$ | COOH |
| 4-322 | F | Cl | H | $CF_2Cl$ | $CH_3$ | $CH_3$ | $COOCH_3$ |
| 4-323 | F | Cl | H | $CF_2Cl$ | $CH_3$ | $CH_3$ | $COOC_2H_5$ |
| 4-324 | F | Cl | H | $CF_2Cl$ | $CH_3$ | $CH_3$ | $COO^nC_3H_7$ |
| 4-325 | F | Cl | H | $CF_2Cl$ | $CH_3$ | $CH_3$ | $COO^nC_4H_9$ |
| 4-326 | F | Cl | H | $CF_2Cl$ | $CH_3$ | $CH_3$ | $COO^nC_5H_{11}$ |
| 4-327 | F | Cl | H | $CF_2Cl$ | $CH_3$ | $CH_3$ | $COO^iC_3H_7$ |
| 4-328 | F | Cl | H | $CF_2Cl$ | $CH_3$ | $CH_3$ | $COO^cC_5H_9$ |
| 4-329 | F | Cl | H | $CF_2Cl$ | $CH_3$ | $CH_3$ | $COO^cC_6H_{11}$ |
| 4-330 | F | Cl | H | $CF_2Cl$ | $CH_3$ | $CH_3$ | $COOCH_2CH=CH_2$ |
| 4-331 | F | Cl | H | $CF_2Cl$ | $CH_3$ | $CH_3$ | $COOCH_2C\equiv CH$ |
| 4-332 | F | Cl | H | $CF_2Cl$ | $CH_3$ | $CH_3$ | $CONH_2$ |
| 4-333 | F | Cl | H | $CF_2Cl$ | $CH_3$ | $CH_3$ | $CONHCH_3$ |
| 4-334 | F | Cl | H | $CF_2Cl$ | $CH_3$ | $CH_3$ | $CONHC_2H_5$ |
| 4-335 | F | Cl | H | $CF_2Cl$ | $CH_3$ | $CH_3$ | $CON(CH_3)_2$ |
| 4-336 | F | Cl | H | $CF_2Cl$ | $CH_3$ | $CH_3$ | $CON(C_2H_5)_2$ |
| 4-337 | H | Cl | H | $CF_3$ | $CH_3$ | H | $CH_2Cl$ |
| 4-338 | H | Cl | H | $CF_3$ | $CH_3$ | H | $CH_2Br$ |
| 4-339 | H | Cl | H | $CF_3$ | $CH_3$ | H | $CH_2OCH_3$ |
| 4-340 | H | Cl | H | $CF_3$ | $CH_3$ | H | $CH_2OC_2H_5$ |
| 4-341 | H | Cl | H | $CF_3$ | $CH_3$ | H | $CH_2OCH_2OCH_3$ |
| 4-342 | H | Cl | H | $CF_3$ | $CH_3$ | H | $CH_2OCH_2OC_2H_5$ |
| 4-343 | H | Cl | H | $CF_3$ | $CH_3$ | H | $CH_2OCOCH_3$ |
| 4-344 | H | Cl | H | $CF_3$ | $CH_3$ | H | $CH_2OCOC_2H_5$ |
| 4-345 | H | Cl | H | $CF_3$ | $CH_3$ | H | $CH_2OCO^iC_3H_7$ |
| 4-346 | H | Cl | H | $CF_3$ | $CH_3$ | H | $CH_2OCOCH_2Cl$ |
| 4-347 | H | Cl | H | $CF_3$ | $CH_3$ | H | $CH_2OCOCCl_3$ |
| 4-348 | H | Cl | H | $CF_3$ | $CH_3$ | H | $CH_2OCOCF_3$ |
| 4-349 | H | Cl | H | $CF_3$ | $CH_3$ | H | COOH |
| 4-350 | H | Cl | H | $CF_3$ | $CH_3$ | H | $COOCH_3$ |
| 4-351 | H | Cl | H | $CF_3$ | $CH_3$ | H | $COOC_2H_5$ |
| 4-352 | H | Cl | H | $CF_3$ | $CH_3$ | H | $COO^nC_3H_7$ |
| 4-353 | H | Cl | H | $CF_3$ | $CH_3$ | H | $COO^nC_4H_9$ |
| 4-354 | H | Cl | H | $CF_3$ | $CH_3$ | H | $COO^nC_5H_{11}$ |
| 4-355 | H | Cl | H | $CF_3$ | $CH_3$ | H | $COO^iC_3H_7$ |
| 4-356 | H | Cl | H | $CF_3$ | $CH_3$ | H | $COO^cC_5H_9$ |
| 4-357 | H | Cl | H | $CF_3$ | $CH_3$ | H | $COO^cC_6H_{11}$ |
| 4-358 | H | Cl | H | $CF_3$ | $CH_3$ | H | $COOCH_2CH=CH_2$ |
| 4-359 | H | Cl | H | $CF_3$ | $CH_3$ | H | $COOCH_2C\equiv CH$ |
| 4-360 | H | Cl | H | $CF_3$ | $CH_3$ | H | $CONH_2$ |
| 4-361 | H | Cl | H | $CF_3$ | $CH_3$ | H | $CONHCH_3$ |
| 4-362 | H | Cl | H | $CF_3$ | $CH_3$ | H | $CONHC_2H_5$ |
| 4-363 | H | Cl | H | $CF_3$ | $CH_3$ | H | $CON(CH_3)_2$ |
| 4-364 | H | Cl | H | $CF_3$ | $CH_3$ | H | $CON(C_2H_5)_2$ |
| 4-365 | F | Cl | H | $CF_3$ | $CH_3$ | H | $CH_2Cl$ |
| 4-366 | F | Cl | H | $CF_3$ | $CH_3$ | H | $CH_2Br$ |
| 4-367 | F | Cl | H | $CF_3$ | $CH_3$ | H | $CH_2OCH_3$ |
| 4-368 | F | Cl | H | $CF_3$ | $CH_3$ | H | $CH_2OC_2H_5$ |
| 4-369 | F | Cl | H | $CF_3$ | $CH_3$ | H | $CH_2OCH_2OCH_3$ |
| 4-370 | F | Cl | H | $CF_3$ | $CH_3$ | H | $CH_2OCH_2OC_2H_5$ |
| 4-371 | F | Cl | H | $CF_3$ | $CH_3$ | H | $CH_2OCOCH_3$ |
| 4-372 | F | Cl | H | $CF_3$ | $CH_3$ | H | $CH_2OCOC_2H_5$ |
| 4-373 | F | Cl | H | $CF_3$ | $CH_3$ | H | $CH_2OCO^iC_3H_7$ |
| 4-374 | F | Cl | H | $CF_3$ | $CH_3$ | H | $CH_2OCOCH_2Cl$ |
| 4-375 | F | Cl | H | $CF_3$ | $CH_3$ | H | $CH_2OCOCCl_3$ |
| 4-376 | F | Cl | H | $CF_3$ | $CH_3$ | H | $CH_2OCOCF_3$ |
| 4-377 | F | Cl | H | $CF_3$ | $CH_3$ | H | COOH |
| 4-378 | F | Cl | H | $CF_3$ | $CH_3$ | H | $COOCH_3$ |
| 4-379 | F | Cl | H | $CF_3$ | $CH_3$ | H | $COOC_2H_5$ |
| 4-380 | F | Cl | H | $CF_3$ | $CH_3$ | H | $COO^nC_3H_7$ |
| 4-381 | F | Cl | H | $CF_3$ | $CH_3$ | H | $COO^nC_4H_9$ |
| 4-382 | F | Cl | H | $CF_3$ | $CH_3$ | H | $COO^nC_5H_{11}$ |
| 4-383 | F | Cl | H | $CF_3$ | $CH_3$ | H | $COO^iC_3H_7$ |
| 4-384 | F | Cl | H | $CF_3$ | $CH_3$ | H | $COO^cC_5H_9$ |
| 4-385 | F | Cl | H | $CF_3$ | $CH_3$ | H | $COO^cC_6H_{11}$ |
| 4-386 | F | Cl | H | $CF_3$ | $CH_3$ | H | $COOCH_2CH=CH_2$ |
| 4-387 | F | Cl | H | $CF_3$ | $CH_3$ | H | $COOCH_2C\equiv CH$ |
| 4-388 | F | Cl | H | $CF_3$ | $CH_3$ | H | $CONH_2$ |
| 4-389 | F | Cl | H | $CF_3$ | $CH_3$ | H | $CONHCH_3$ |
| 4-390 | F | Cl | H | $CF_3$ | $CH_3$ | H | $CONHC_2H_5$ |
| 4-391 | F | Cl | H | $CF_3$ | $CH_3$ | H | $CON(CH_3)_2$ |
| 4-392 | F | Cl | H | $CF_3$ | $CH_3$ | H | $CON(C_2H_5)_2$ |
| 4-393 | H | Cl | H | $CF_3$ | $CH_3$ | $CH_3$ | $CH_2Cl$ |
| 4-394 | H | Cl | H | $CF_3$ | $CH_3$ | $CH_3$ | $CH_2Br$ |
| 4-395 | H | Cl | H | $CF_3$ | $CH_3$ | $CH_3$ | $CH_2OCH_3$ |
| 4-396 | H | Cl | H | $CF_3$ | $CH_3$ | $CH_3$ | $CH_2OC_2H_5$ |
| 4-397 | H | Cl | H | $CF_3$ | $CH_3$ | $CH_3$ | $CH_2OCH_2OCH_3$ |
| 4-398 | H | Cl | H | $CF_3$ | $CH_3$ | $CH_3$ | $CH_2OCH_2OC_2H_5$ |
| 4-399 | H | Cl | H | $CF_3$ | $CH_3$ | $CH_3$ | $CH_2OCOCH_3$ |
| 4-400 | H | Cl | H | $CF_3$ | $CH_3$ | $CH_3$ | $CH_2OCOC_2H_5$ |
| 4-401 | H | Cl | H | $CF_3$ | $CH_3$ | $CH_3$ | $CH_2OCO^iC_3H_7$ |
| 4-402 | H | Cl | H | $CF_3$ | $CH_3$ | $CH_3$ | $CH_2OCOCH_2Cl$ |
| 4-403 | H | Cl | H | $CF_3$ | $CH_3$ | $CH_3$ | $CH_2OCOCCl_3$ |
| 4-404 | H | Cl | H | $CF_3$ | $CH_3$ | $CH_3$ | $CH_2OCOCF_3$ |
| 4-405 | H | Cl | H | $CF_3$ | $CH_3$ | $CH_3$ | COOH |
| 4-406 | H | Cl | H | $CF_3$ | $CH_3$ | $CH_3$ | $COOCH_3$ |
| 4-407 | H | Cl | H | $CF_3$ | $CH_3$ | $CH_3$ | $COOC_2H_5$ |
| 4-408 | H | Cl | H | $CF_3$ | $CH_3$ | $CH_3$ | $COO^nC_3H_7$ |
| 4-409 | H | Cl | H | $CF_3$ | $CH_3$ | $CH_3$ | $COO^nC_4H_9$ |
| 4-410 | H | Cl | H | $CF_3$ | $CH_3$ | $CH_3$ | $COO^nC_5H_{11}$ |
| 4-411 | H | Cl | H | $CF_3$ | $CH_3$ | $CH_3$ | $COO^iC_3H_7$ |
| 4-412 | H | Cl | H | $CF_3$ | $CH_3$ | $CH_3$ | $COO^cC_5H_9$ |
| 4-413 | H | Cl | H | $CF_3$ | $CH_3$ | $CH_3$ | $COO^cC_6H_{11}$ |
| 4-414 | H | Cl | H | $CF_3$ | $CH_3$ | $CH_3$ | $COOCH_2CH=CH_2$ |
| 4-415 | H | Cl | H | $CF_3$ | $CH_3$ | $CH_3$ | $COOCH_2C\equiv CH$ |
| 4-416 | H | Cl | H | $CF_3$ | $CH_3$ | $CH_3$ | $CONH_2$ |
| 4-417 | H | Cl | H | $CF_3$ | $CH_3$ | $CH_3$ | $CONHCH_3$ |
| 4-418 | H | Cl | H | $CF_3$ | $CH_3$ | $CH_3$ | $CONHC_2H_5$ |
| 4-419 | H | Cl | H | $CF_3$ | $CH_3$ | $CH_3$ | $CON(CH_3)_2$ |
| 4-420 | H | Cl | H | $CF_3$ | $CH_3$ | $CH_3$ | $CON(C_2H_5)_2$ |
| 4-421 | F | Cl | H | $CF_3$ | $CH_3$ | $CH_3$ | $CH_2Cl$ |
| 4-422 | F | Cl | H | $CF_3$ | $CH_3$ | $CH_3$ | $CH_2Br$ |
| 4-423 | F | Cl | H | $CF_3$ | $CH_3$ | $CH_3$ | $CH_2OCH_3$ |
| 4-424 | F | Cl | H | $CF_3$ | $CH_3$ | $CH_3$ | $CH_2OC_2H_5$ |
| 4-425 | F | Cl | H | $CF_3$ | $CH_3$ | $CH_3$ | $CH_2OCH_2OCH_3$ |
| 4-426 | F | Cl | H | $CF_3$ | $CH_3$ | $CH_3$ | $CH_2OCH_2OC_2H_5$ |
| 4-427 | F | Cl | H | $CF_3$ | $CH_3$ | $CH_3$ | $CH_2OCOCH_3$ |

TABLE 4-continued

Compounds of the formula:

(structure shown with X, Y, O, R², R¹, R³, R⁷, R⁸ substituents on a dihydrobenzofuran-pyridazinone)

| Compound No. | X | Y | $R^3$ | $R^1$ | $R^2$ | $R^7$ | $R^8$ |
|---|---|---|---|---|---|---|---|
| 4-428 | F | Cl | H | $CF_3$ | $CH_3$ | $CH_3$ | $CH_2OCOC_2H_5$ |
| 4-429 | F | Cl | H | $CF_3$ | $CH_3$ | $CH_3$ | $CH_2OCO^iC_3H_7$ |
| 4-430 | F | Cl | H | $CF_3$ | $CH_3$ | $CH_3$ | $CH_2OCOCH_2Cl$ |
| 4-431 | F | Cl | H | $CF_3$ | $CH_3$ | $CH_3$ | $CH_2OCOCCl_3$ |
| 4-432 | F | Cl | H | $CF_3$ | $CH_3$ | $CH_3$ | $CH_2OCOCF_3$ |
| 4-433 | F | Cl | H | $CF_3$ | $CH_3$ | $CH_3$ | COOH |
| 4-434 | F | Cl | H | $CF_3$ | $CH_3$ | $CH_3$ | $COOCH_3$ |
| 4-435 | F | Cl | H | $CF_3$ | $CH_3$ | $CH_3$ | $COOC_2H_5$ |
| 4-436 | F | Cl | H | $CF_3$ | $CH_3$ | $CH_3$ | $COO^nC_3H_7$ |
| 4-437 | F | Cl | H | $CF_3$ | $CH_3$ | $CH_3$ | $COO^nC_4H_9$ |
| 4-438 | F | Cl | H | $CF_3$ | $CH_3$ | $CH_3$ | $COO^nC_5H_{11}$ |
| 4-439 | F | Cl | H | $CF_3$ | $CH_3$ | $CH_3$ | $COO^iC_3H_7$ |
| 4-440 | F | Cl | H | $CF_3$ | $CH_3$ | $CH_3$ | $COO^cC_5H_9$ |
| 4-441 | F | Cl | H | $CF_3$ | $CH_3$ | $CH_3$ | $COO^cC_6H_{11}$ |
| 4-442 | F | Cl | H | $CF_3$ | $CH_3$ | $CH_3$ | $COOCH_2CH=CH_2$ |
| 4-443 | F | Cl | H | $CF_3$ | $CH_3$ | $CH_3$ | $COOCH_2C\equiv CH$ |
| 4-444 | F | Cl | H | $CF_3$ | $CH_3$ | $CH_3$ | $CONH_2$ |
| 4-445 | F | Cl | H | $CF_3$ | $CH_3$ | $CH_3$ | $CONHCH_3$ |
| 4-446 | F | Cl | H | $CF_3$ | $CH_3$ | $CH_3$ | $CONHC_2H_5$ |
| 4-447 | F | Cl | H | $CF_3$ | $CH_3$ | $CH_3$ | $CON(CH_3)_2$ |
| 4-448 | F | Cl | H | $CF_3$ | $CH_3$ | $CH_3$ | $CON(C_2H_5)_2$ |
| 4-449 | F | Cl | H | $CF_3$ | $CH_3$ | H | $CH_3$ |
| 4-450 | F | Cl | H | $CF_3$ | $CH_3$ | H | $CH_2OH$ |
| 4-451 | F | Cl | H | $CF_3$ | $CH_3$ | $CH_3$ | $CH_3$ |
| 4-452 | F | Cl | H | $CF_3$ | $CH_3$ | $CH_3$ | $CH_2OH$ |
| 4-453 | F | Cl | H | $CF_3$ | H | H | $CH_3$ |
| 4-454 | F | Cl | H | $CF_3$ | H | H | $CH_2OH$ |
| 4-455 | F | Cl | H | $CF_3$ | H | $CH_3$ | $CH_3$ |
| 4-456 | F | Cl | H | $CF_3$ | H | $CH_3$ | $CH_2OH$ |
| 4-457 | H | Cl | H | $CF_3$ | $CH_3$ | H | $CH_3$ |
| 4-458 | H | Cl | H | $CF_3$ | $CH_3$ | H | $CH_2OH$ |
| 4-459 | H | Cl | H | $CF_3$ | $CH_3$ | $CH_3$ | $CH_3$ |
| 4-460 | H | Cl | H | $CF_3$ | $CH_3$ | $CH_3$ | $CH_2OH$ |
| 4-461 | H | Cl | H | $CF_3$ | H | H | $CH_3$ |
| 4-462 | H | Cl | H | $CF_3$ | H | H | $CH_2OH$ |
| 4-463 | H | Cl | H | $CF_3$ | H | $CH_3$ | $CH_3$ |
| 4-464 | H | Cl | H | $CF_3$ | H | $CH_3$ | $CH_2OH$ |
| 4-465 | F | Cl | H | $CF_2Cl$ | $CH_3$ | H | $CH_3$ |
| 4-466 | F | Cl | H | $CF_2Cl$ | $CH_3$ | H | $CH_2OH$ |
| 4-467 | F | Cl | H | $CF_2Cl$ | $CH_3$ | $CH_3$ | $CH_3$ |
| 4-468 | F | Cl | H | $CF_2Cl$ | $CH_3$ | $CH_3$ | $CH_2OH$ |
| 4-469 | F | Cl | H | $CF_2Cl$ | H | H | $CH_3$ |
| 4-470 | F | Cl | H | $CF_2Cl$ | H | H | $CH_2OH$ |
| 4-471 | F | Cl | H | $CF_2Cl$ | H | $CH_3$ | $CH_3$ |
| 4-472 | F | Cl | H | $CF_2Cl$ | H | $CH_3$ | $CH_2OH$ |
| 4-473 | H | Cl | H | $CF_2Cl$ | $CH_3$ | H | $CH_3$ |
| 4-474 | H | Cl | H | $CF_2Cl$ | $CH_3$ | H | $CH_2OH$ |
| 4-475 | H | Cl | H | $CF_2Cl$ | $CH_3$ | $CH_3$ | $CH_3$ |
| 4-476 | H | Cl | H | $CF_2Cl$ | $CH_3$ | $CH_3$ | $CH_2OH$ |
| 4-477 | H | Cl | H | $CF_2Cl$ | H | H | $CH_3$ |
| 4-478 | H | Cl | H | $CF_2Cl$ | H | H | $CH_2OH$ |
| 4-479 | H | Cl | H | $CF_2Cl$ | H | $CH_3$ | $CH_3$ |
| 4-480 | H | Cl | H | $CF_2Cl$ | H | $CH_3$ | $CH_2OH$ |
| 4-481 | H | Cl | H | $CF_3$ | H | H | $CH_2Cl$ |
| 4-482 | H | Cl | H | $CF_3$ | H | H | $CH_2Br$ |
| 4-483 | H | Cl | H | $CF_3$ | H | H | $CH_2OCH_3$ |
| 4-484 | H | Cl | H | $CF_3$ | H | H | $CH_2OC_2H_5$ |
| 4-485 | H | Cl | H | $CF_3$ | H | H | $CH_2OCH_2OCH_3$ |
| 4-486 | H | Cl | H | $CF_3$ | H | H | $CH_2OCH_2OC_2H_5$ |
| 4-487 | H | Cl | H | $CF_3$ | H | H | $CH_2OCOCH_3$ |
| 4-488 | H | Cl | H | $CF_3$ | H | H | $CH_2OCOC_2H_5$ |
| 4-489 | H | Cl | H | $CF_3$ | H | H | $CH_2OCO^iC_3H_7$ |
| 4-490 | H | Cl | H | $CF_3$ | H | H | $CH_2OCOCH_2Cl$ |
| 4-491 | H | Cl | H | $CF_3$ | H | H | $CH_2OCOCCl_3$ |
| 4-492 | H | Cl | H | $CF_3$ | H | H | $CH_2OCOCF_3$ |
| 4-493 | H | Cl | H | $CF_3$ | H | H | COOH |
| 4-494 | H | Cl | H | $CF_3$ | H | H | $COOCH_3$ |
| 4-495 | H | Cl | H | $CF_3$ | H | H | $COOC_2H_5$ |
| 4-496 | H | Cl | H | $CF_3$ | H | H | $COO^nC_3H_7$ |
| 4-497 | H | Cl | H | $CF_3$ | H | H | $COO^nC_4H_9$ |
| 4-498 | H | Cl | H | $CF_3$ | H | H | $COO^nC_5H_{11}$ |
| 4-499 | H | Cl | H | $CF_3$ | H | H | $COO^iC_3H_7$ |
| 4-500 | H | Cl | H | $CF_3$ | H | H | $COO^cC_5H_9$ |
| 4-501 | H | Cl | H | $CF_3$ | H | H | $COO^cC_6H_{11}$ |
| 4-502 | H | Cl | H | $CF_3$ | H | H | $COOCH_2CH=CH_2$ |
| 4-503 | H | Cl | H | $CF_3$ | H | H | $COOCH_2C\equiv CH$ |
| 4-504 | H | Cl | H | $CF_3$ | H | H | $CONH_2$ |
| 4-505 | H | Cl | H | $CF_3$ | H | H | $CONHCH_3$ |
| 4-506 | H | Cl | H | $CF_3$ | H | H | $CONHC_2H_5$ |
| 4-507 | H | Cl | H | $CF_3$ | H | H | $CON(CH_3)_2$ |
| 4-508 | H | Cl | H | $CF_3$ | H | H | $CON(C_2H_5)_2$ |
| 4-509 | F | Cl | H | $CF_3$ | H | H | $CH_2Cl$ |
| 4-510 | F | Cl | H | $CF_3$ | H | H | $CH_2Br$ |
| 4-511 | F | Cl | H | $CF_3$ | H | H | $CH_2OCH_3$ |
| 4-512 | F | Cl | H | $CF_3$ | H | H | $CH_2OC_2H_5$ |
| 4-513 | F | Cl | H | $CF_3$ | H | H | $CH_2OCH_2OCH_3$ |
| 4-514 | F | Cl | H | $CF_3$ | H | H | $CH_2OCH_2OC_2H_5$ |
| 4-515 | F | Cl | H | $CF_3$ | H | H | $CH_2OCOCH_3$ |
| 4-516 | F | Cl | H | $CF_3$ | H | H | $CH_2OCOC_2H_5$ |
| 4-517 | F | Cl | H | $CF_3$ | H | H | $CH_2OCO^iC_3H_7$ |
| 4-518 | F | Cl | H | $CF_3$ | H | H | $CH_2OCOCH_2Cl$ |
| 4-519 | F | Cl | H | $CF_3$ | H | H | $CH_2OCOCCl_3$ |
| 4-520 | F | Cl | H | $CF_3$ | H | H | $CH_2OCOCF_3$ |
| 4-521 | F | Cl | H | $CF_3$ | H | H | COOH |
| 4-522 | F | Cl | H | $CF_3$ | H | H | $COOCH_3$ |
| 4-523 | F | Cl | H | $CF_3$ | H | H | $COOC_2H_5$ |
| 4-524 | F | Cl | H | $CF_3$ | H | H | $COO^nC_3H_7$ |
| 4-525 | F | Cl | H | $CF_3$ | H | H | $COO^nC_4H_9$ |
| 4-526 | F | Cl | H | $CF_3$ | H | H | $COO^nC_5H_{11}$ |
| 4-527 | F | Cl | H | $CF_3$ | H | H | $COO^iC_3H_7$ |
| 4-528 | F | Cl | H | $CF_3$ | H | H | $COO^cC_5H_9$ |
| 4-529 | F | Cl | H | $CF_3$ | H | H | $COO^cC_6H_{11}$ |
| 4-530 | F | Cl | H | $CF_3$ | H | H | $COOCH_2CH=CH_2$ |
| 4-531 | F | Cl | H | $CF_3$ | H | H | $COOCH_2C\equiv CH$ |
| 4-532 | F | Cl | H | $CF_3$ | H | H | $CONH_2$ |
| 4-533 | F | Cl | H | $CF_3$ | H | H | $CONHCH_3$ |
| 4-534 | F | Cl | H | $CF_3$ | H | H | $CONHC_2H_5$ |
| 4-535 | F | Cl | H | $CF_3$ | H | H | $CON(CH_3)_2$ |
| 4-536 | F | Cl | H | $CF_3$ | H | H | $CON(C_2H_5)_2$ |
| 4-537 | H | Cl | H | $CF_3$ | H | $CH_3$ | $CH_2Cl$ |
| 4-538 | H | Cl | H | $CF_3$ | H | $CH_3$ | $CH_2Br$ |
| 4-539 | H | Cl | H | $CF_3$ | H | $CH_3$ | $CH_2OCH_3$ |
| 4-540 | H | Cl | H | $CF_3$ | H | $CH_3$ | $CH_2OC_2H_5$ |
| 4-541 | H | Cl | H | $CF_3$ | H | $CH_3$ | $CH_2OCH_2OCH_3$ |
| 4-542 | H | Cl | H | $CF_3$ | H | $CH_3$ | $CH_2OCH_2OC_2H_5$ |
| 4-543 | H | Cl | H | $CF_3$ | H | $CH_3$ | $CH_2OCOCH_3$ |
| 4-544 | H | Cl | H | $CF_3$ | H | $CH_3$ | $CH_2OCOC_2H_5$ |
| 4-545 | H | Cl | H | $CF_3$ | H | $CH_3$ | $CH_2OCO^iC_3H_7$ |
| 4-546 | H | Cl | H | $CF_3$ | H | $CH_3$ | $CH_2OCOCH_2Cl$ |
| 4-547 | H | Cl | H | $CF_3$ | H | $CH_3$ | $CH_2OCOCCl_3$ |
| 4-548 | H | Cl | H | $CF_3$ | H | $CH_3$ | $CH_2OCOCF_3$ |
| 4-549 | H | Cl | H | $CF_3$ | H | $CH_3$ | COOH |

TABLE 4-continued

Compounds of the formula:

[Structure: pyridazinone linked to dihydrobenzofuran with substituents X, Y, R¹, R², R³, R⁷, R⁸]

| Compound No. | X | Y | $R^3$ | $R^1$ | $R^2$ | $R^7$ | $R^8$ |
|---|---|---|---|---|---|---|---|
| 4-550 | H | Cl | H | $CF_3$ | H | $CH_3$ | $COOCH_3$ |
| 4-551 | H | Cl | H | $CF_3$ | H | $CH_3$ | $COOC_2H_5$ |
| 4-552 | H | Cl | H | $CF_3$ | H | $CH_3$ | $COO^nC_3H_7$ |
| 4-553 | H | Cl | H | $CF_3$ | H | $CH_3$ | $COO^nC_4H_9$ |
| 4-554 | H | Cl | H | $CF_3$ | H | $CH_3$ | $COO^nC_5H_{11}$ |
| 4-555 | H | Cl | H | $CF_3$ | H | $CH_3$ | $COO^iC_3H_7$ |
| 4-556 | H | Cl | H | $CF_3$ | H | $CH_3$ | $COO^cC_5H_9$ |
| 4-557 | H | Cl | H | $CF_3$ | H | $CH_3$ | $COO^cC_6H_{11}$ |
| 4-558 | H | Cl | H | $CF_3$ | H | $CH_3$ | $COOCH_2CH=CH_2$ |
| 4-559 | H | Cl | H | $CF_3$ | H | $CH_3$ | $COOCH_2C\equiv CH$ |
| 4-560 | H | Cl | H | $CF_3$ | H | $CH_3$ | $CONH_2$ |
| 4-561 | H | Cl | H | $CF_3$ | H | $CH_3$ | $CONHCH_3$ |
| 4-562 | H | Cl | H | $CF_3$ | H | $CH_3$ | $CONHC_2H_5$ |
| 4-563 | H | Cl | H | $CF_3$ | H | $CH_3$ | $CON(CH_3)_2$ |
| 4-564 | H | Cl | H | $CF_3$ | H | $CH_3$ | $CON(C_2H_5)_2$ |
| 4-565 | F | Cl | H | $CF_3$ | H | $CH_3$ | $CH_2Cl$ |
| 4-566 | F | Cl | H | $CF_3$ | H | $CH_3$ | $CH_2Br$ |
| 4-567 | F | Cl | H | $CF_3$ | H | $CH_3$ | $CH_2OCH_3$ |
| 4-568 | F | Cl | H | $CF_3$ | H | $CH_3$ | $CH_2OC_2H_5$ |
| 4-569 | F | Cl | H | $CF_3$ | H | $CH_3$ | $CH_2OCH_2OCH_3$ |
| 4-570 | F | Cl | H | $CF_3$ | H | $CH_3$ | $CH_2OCH_2OC_2H_5$ |
| 4-571 | F | Cl | H | $CF_3$ | H | $CH_3$ | $CH_2OCOCH_3$ |
| 4-572 | F | Cl | H | $CF_3$ | H | $CH_3$ | $CH_2OCOC_2H_5$ |
| 4-573 | F | Cl | H | $CF_3$ | H | $CH_3$ | $CH_2OCO^iC_3H_7$ |
| 4-574 | F | Cl | H | $CF_3$ | H | $CH_3$ | $CH_2OCOCH_2Cl$ |
| 4-575 | F | Cl | H | $CF_3$ | H | $CH_3$ | $CH_2OCOCCl_3$ |
| 4-576 | F | Cl | H | $CF_3$ | H | $CH_3$ | $CH_2OCOCF_3$ |
| 4-577 | F | Cl | H | $CF_3$ | H | $CH_3$ | $COOH$ |
| 4-578 | F | Cl | H | $CF_3$ | H | $CH_3$ | $COOCH_3$ |
| 4-579 | F | Cl | H | $CF_3$ | H | $CH_3$ | $COOC_2H_5$ |
| 4-580 | F | Cl | H | $CF_3$ | H | $CH_3$ | $COO^nC_3H_7$ |
| 4-581 | F | Cl | H | $CF_3$ | H | $CH_3$ | $COO^nC_4H_9$ |
| 4-582 | F | Cl | H | $CF_3$ | H | $CH_3$ | $COO^nC_5H_{11}$ |
| 4-583 | F | Cl | H | $CF_3$ | H | $CH_3$ | $COO^iC_3H_7$ |
| 4-584 | F | Cl | H | $CF_3$ | H | $CH_3$ | $COO^cC_5H_9$ |
| 4-585 | F | Cl | H | $CF_3$ | H | $CH_3$ | $COO^cC_6H_{11}$ |
| 4-586 | F | Cl | H | $CF_3$ | H | $CH_3$ | $COOCH_2CH=CH_2$ |
| 4-587 | F | Cl | H | $CF_3$ | H | $CH_3$ | $COOCH_2C\equiv CH$ |
| 4-588 | F | Cl | H | $CF_3$ | H | $CH_3$ | $CONH_2$ |
| 4-589 | F | Cl | H | $CF_3$ | H | $CH_3$ | $CONHCH_3$ |
| 4-590 | F | Cl | H | $CF_3$ | H | $CH_3$ | $CONHC_2H_5$ |
| 4-591 | F | Cl | H | $CF_3$ | H | $CH_3$ | $CON(CH_3)_2$ |
| 4-592 | F | Cl | H | $CF_3$ | H | $CH_3$ | $CON(C_2H_5)_2$ |
| 4-593 | H | Cl | H | $CF_3$ | H | H | $CH_2Cl$ |
| 4-594 | H | Cl | H | $CF_3$ | H | H | $CH_2Br$ |
| 4-595 | H | Cl | H | $CF_3$ | H | H | $CH_2OCH_3$ |
| 4-596 | H | Cl | H | $CF_3$ | H | H | $CH_2OC_2H_5$ |
| 4-597 | H | Cl | H | $CF_3$ | H | H | $CH_2OCH_2OCH_3$ |
| 4-598 | H | Cl | H | $CF_3$ | H | H | $CH_2OCH_2OC_2H_5$ |
| 4-599 | H | Cl | H | $CF_3$ | H | H | $CH_2OCOCH_3$ |
| 4-600 | H | Cl | H | $CF_3$ | H | H | $CH_2OCOC_2H_5$ |
| 4-601 | H | Cl | H | $CF_3$ | H | H | $CH_2OCO^iC_3H_7$ |
| 4-602 | H | Cl | H | $CF_3$ | H | H | $CH_2OCOCH_2Cl$ |
| 4-603 | H | Cl | H | $CF_3$ | H | H | $CH_2OCOCCl_3$ |
| 4-604 | H | Cl | H | $CF_3$ | H | H | $CH_2OCOCF_3$ |
| 4-605 | H | Cl | H | $CF_3$ | H | H | $COOH$ |
| 4-606 | H | Cl | H | $CF_3$ | H | H | $COOCH_3$ |
| 4-607 | H | Cl | H | $CF_3$ | H | H | $COOC_2H_5$ |
| 4-608 | H | Cl | H | $CF_3$ | H | H | $COO^nC_3H_7$ |
| 4-609 | H | Cl | H | $CF_3$ | H | H | $COO^nC_4H_9$ |
| 4-610 | H | Cl | H | $CF_3$ | H | H | $COO^nC_5H_{11}$ |
| 4-611 | H | Cl | H | $CF_3$ | H | H | $COO^iC_3H_7$ |
| 4-612 | H | Cl | H | $CF_3$ | H | H | $COO^cC_5H_9$ |
| 4-613 | H | Cl | H | $CF_3$ | H | H | $COO^cC_6H_{11}$ |
| 4-614 | H | Cl | H | $CF_3$ | H | H | $COOCH_2CH=CH_2$ |
| 4-615 | H | Cl | H | $CF_3$ | H | H | $COOCH_2C\equiv CH$ |
| 4-616 | H | Cl | H | $CF_3$ | H | H | $CONH_2$ |
| 4-617 | H | Cl | H | $CF_3$ | H | H | $CONHCH_3$ |
| 4-618 | H | Cl | H | $CF_3$ | H | H | $CONHC_2H_5$ |
| 4-619 | H | Cl | H | $CF_3$ | H | H | $CON(CH_3)_2$ |
| 4-620 | H | Cl | H | $CF_3$ | H | H | $CON(C_2H_5)_2$ |
| 4-621 | F | Cl | H | $CF_3$ | H | H | $CH_2Cl$ |
| 4-622 | F | Cl | H | $CF_3$ | H | H | $CH_2Br$ |
| 4-623 | F | Cl | H | $CF_3$ | H | H | $CH_2OCH_3$ |
| 4-624 | F | Cl | H | $CF_3$ | H | H | $CH_2OC_2H_5$ |
| 4-625 | F | Cl | H | $CF_3$ | H | H | $CH_2OCH_2OCH_3$ |
| 4-626 | F | Cl | H | $CF_3$ | H | H | $CH_2OCH_2OC_2H_5$ |
| 4-627 | F | Cl | H | $CF_3$ | H | H | $CH_2OCOCH_3$ |
| 4-628 | F | Cl | H | $CF_3$ | H | H | $CH_2OCOC_2H_5$ |
| 4-629 | F | Cl | H | $CF_3$ | H | H | $CH_2OCO^iC_3H_7$ |
| 4-630 | F | Cl | H | $CF_3$ | H | H | $CH_2OCOCH_2Cl$ |
| 4-631 | F | Cl | H | $CF_3$ | H | H | $CH_2OCOCCl_3$ |
| 4-632 | F | Cl | H | $CF_3$ | H | H | $CH_2OCOCF_3$ |
| 4-633 | F | Cl | H | $CF_3$ | H | H | $COOH$ |
| 4-634 | F | Cl | H | $CF_3$ | H | H | $COOCH_3$ |
| 4-635 | F | Cl | H | $CF_3$ | H | H | $COOC_2H_5$ |
| 4-636 | F | Cl | H | $CF_3$ | H | H | $COO^nC_3H_7$ |
| 4-637 | F | Cl | H | $CF_3$ | H | H | $COO^nC_4H_9$ |
| 4-638 | F | Cl | H | $CF_3$ | H | H | $COO^nC_5H_{11}$ |
| 4-639 | F | Cl | H | $CF_3$ | H | H | $COO^iC_3H_7$ |
| 4-640 | F | Cl | H | $CF_3$ | H | H | $COO^cC_5H_9$ |
| 4-641 | F | Cl | H | $CF_3$ | H | H | $COO^cC_6H_{11}$ |
| 4-642 | F | Cl | H | $CF_3$ | H | H | $COOCH_2CH=CH_2$ |
| 4-643 | F | Cl | H | $CF_3$ | H | H | $COOCH_2C\equiv CH$ |
| 4-644 | F | Cl | H | $CF_3$ | H | H | $CONH_2$ |
| 4-645 | F | Cl | H | $CF_3$ | H | H | $CONHCH_3$ |
| 4-646 | F | Cl | H | $CF_3$ | H | H | $CONHC_2H_5$ |
| 4-647 | F | Cl | H | $CF_3$ | H | H | $CON(CH_3)_2$ |
| 4-648 | F | Cl | H | $CF_3$ | H | H | $CON(C_2H_5)_2$ |
| 4-649 | H | Cl | H | $CF_3$ | H | $CH_3$ | $CH_2Cl$ |
| 4-650 | H | Cl | H | $CF_3$ | H | $CH_3$ | $CH_2Br$ |
| 4-651 | H | Cl | H | $CF_3$ | H | $CH_3$ | $CH_2OCH_3$ |
| 4-652 | H | Cl | H | $CF_3$ | H | $CH_3$ | $CH_2OC_2H_5$ |
| 4-653 | H | Cl | H | $CF_3$ | H | $CH_3$ | $CH_2OCH_2OCH_3$ |
| 4-654 | H | Cl | H | $CF_3$ | H | $CH_3$ | $CH_2OCH_2OC_2H_5$ |
| 4-655 | H | Cl | H | $CF_3$ | H | $CH_3$ | $CH_2OCOCH_3$ |
| 4-656 | H | Cl | H | $CF_3$ | H | $CH_3$ | $CH_2OCOC_2H_5$ |
| 4-657 | H | Cl | H | $CF_3$ | H | $CH_3$ | $CH_2OCO^iC_3H_7$ |
| 4-658 | H | Cl | H | $CF_3$ | H | $CH_3$ | $CH_2OCOCH_2Cl$ |
| 4-659 | H | Cl | H | $CF_3$ | H | $CH_3$ | $CH_2OCOCCl_3$ |
| 4-660 | H | Cl | H | $CF_3$ | H | $CH_3$ | $CH_2OCOCF_3$ |
| 4-661 | H | Cl | H | $CF_3$ | H | $CH_3$ | $COOH$ |
| 4-662 | H | Cl | H | $CF_3$ | H | $CH_3$ | $COOCH_3$ |
| 4-663 | H | Cl | H | $CF_3$ | H | $CH_3$ | $COOC_2H_5$ |
| 4-664 | H | Cl | H | $CF_3$ | H | $CH_3$ | $COO^nC_3H_7$ |
| 4-665 | H | Cl | H | $CF_3$ | H | $CH_3$ | $COO^nC_4H_9$ |
| 4-666 | H | Cl | H | $CF_3$ | H | $CH_3$ | $COO^nC_5H_{11}$ |
| 4-667 | H | Cl | H | $CF_3$ | H | $CH_3$ | $COO^iC_3H_7$ |
| 4-668 | H | Cl | H | $CF_3$ | H | $CH_3$ | $COO^cC_5H_9$ |
| 4-669 | H | Cl | H | $CF_3$ | H | $CH_3$ | $COO^cC_6H_{11}$ |
| 4-670 | H | Cl | H | $CF_3$ | H | $CH_3$ | $COOCH_2CH=CH_2$ |
| 4-671 | H | Cl | H | $CF_3$ | H | $CH_3$ | $COOCH_2C\equiv CH$ |

TABLE 4-continued

Compounds of the formula:

[Structure: benzofuran-pyridazinone with substituents X, Y, R¹, R², R³, R⁷, R⁸]

| Compound No. | X | Y | R³ | R¹ | R² | R⁷ | R⁸ |
|---|---|---|---|---|---|---|---|
| 4-672 | H | Cl | H | $CF_3$ | H | $CH_3$ | $CONH_2$ |
| 4-673 | H | Cl | H | $CF_3$ | H | $CH_3$ | $CONHCH_3$ |
| 4-674 | H | Cl | H | $CF_3$ | H | $CH_3$ | $CONHC_2H_5$ |
| 4-675 | H | Cl | H | $CF_3$ | H | $CH_3$ | $CON(CH_3)_2$ |
| 4-676 | H | Cl | H | $CF_3$ | H | $CH_3$ | $CON(C_2H_5)_2$ |
| 4-677 | F | Cl | H | $CF_3$ | H | $CH_3$ | $CH_2Cl$ |
| 4-678 | F | Cl | H | $CF_3$ | H | $CH_3$ | $CH_2Br$ |
| 4-679 | F | Cl | H | $CF_3$ | H | $CH_3$ | $CH_2OCH_3$ |
| 4-680 | F | Cl | H | $CF_3$ | H | $CH_3$ | $CH_2OC_2H_5$ |
| 4-681 | F | Cl | H | $CF_3$ | H | $CH_3$ | $CH_2OCH_2OCH_3$ |
| 4-682 | F | Cl | H | $CF_3$ | H | $CH_3$ | $CH_2OCH_2OC_2H_5$ |
| 4-683 | F | Cl | H | $CF_3$ | H | $CH_3$ | $CH_2OCOCH_3$ |
| 4-684 | F | Cl | H | $CF_3$ | H | $CH_3$ | $CH_2OCOC_2H_5$ |
| 4-685 | F | Cl | H | $CF_3$ | H | $CH_3$ | $CH_2OCO^iC_3H_7$ |
| 4-686 | F | Cl | H | $CF_3$ | H | $CH_3$ | $CH_2OCOCH_2Cl$ |
| 4-687 | F | Cl | H | $CF_3$ | H | $CH_3$ | $CH_2OCOCCl_3$ |
| 4-688 | F | Cl | H | $CF_3$ | H | $CH_3$ | $CH_2OCOCF_3$ |
| 4-689 | F | Cl | H | $CF_3$ | H | $CH_3$ | $COOH$ |
| 4-690 | F | Cl | H | $CF_3$ | H | $CH_3$ | $COOCH_3$ |
| 4-691 | F | Cl | H | $CF_3$ | H | $CH_3$ | $COOC_2H_5$ |
| 4-692 | F | Cl | H | $CF_3$ | H | $CH_3$ | $COO^nC_3H_7$ |
| 4-693 | F | Cl | H | $CF_3$ | H | $CH_3$ | $COO^nC_4H_9$ |
| 4-694 | F | Cl | H | $CF_3$ | H | $CH_3$ | $COO^nC_5H_{11}$ |
| 4-695 | F | Cl | H | $CF_3$ | H | $CH_3$ | $COO^iC_3H_7$ |
| 4-696 | F | Cl | H | $CF_3$ | H | $CH_3$ | $COO^cC_5H_9$ |
| 4-697 | F | Cl | H | $CF_3$ | H | $CH_3$ | $COO^cC_6H_{11}$ |
| 4-698 | F | Cl | H | $CF_3$ | H | $CH_3$ | $COOCH_2CH=CH_2$ |
| 4-699 | F | Cl | H | $CF_3$ | H | $CH_3$ | $COOCH_2C\equiv CH$ |
| 4-700 | F | Cl | H | $CF_3$ | H | $CH_3$ | $CONH_2$ |
| 4-701 | F | Cl | H | $CF_3$ | H | $CH_3$ | $CONHCH_3$ |
| 4-702 | F | Cl | H | $CF_3$ | H | $CH_3$ | $CONHC_2H_5$ |
| 4-703 | F | Cl | H | $CF_3$ | H | $CH_3$ | $CON(CH_3)_2$ |
| 4-704 | F | Cl | H | $CF_3$ | H | $CH_3$ | $CON(C_2H_5)_2$ |
| 4-705 | H | Cl | $CH_3$ | $CF_3$ | H | H | $CH_2Cl$ |
| 4-706 | H | Cl | $CH_3$ | $CF_3$ | H | H | $CH_2Br$ |
| 4-707 | H | Cl | $CH_3$ | $CF_3$ | H | H | $CH_2OCH_3$ |
| 4-708 | H | Cl | $CH_3$ | $CF_3$ | H | H | $CH_2OC_2H_5$ |
| 4-709 | H | Cl | $CH_3$ | $CF_3$ | H | H | $CH_2OCH_2OCH_3$ |
| 4-710 | H | Cl | $CH_3$ | $CF_3$ | H | H | $CH_2OCH_2OC_2H_5$ |
| 4-711 | H | Cl | $CH_3$ | $CF_3$ | H | H | $CH_2OCOCH_3$ |
| 4-712 | H | Cl | $CH_3$ | $CF_3$ | H | H | $CH_2OCOC_2H_5$ |
| 4-713 | H | Cl | $CH_3$ | $CF_3$ | H | H | $CH_2OCO^iC_3H_7$ |
| 4-714 | H | Cl | $CH_3$ | $CF_3$ | H | H | $CH_2OCOCH_2Cl$ |
| 4-715 | H | Cl | $CH_3$ | $CF_3$ | H | H | $CH_2OCOCCl_3$ |
| 4-716 | H | Cl | $CH_3$ | $CF_3$ | H | H | $CH_2OCOCF_3$ |
| 4-717 | H | Cl | $CH_3$ | $CF_3$ | H | H | $COOH$ |
| 4-718 | H | Cl | $CH_3$ | $CF_3$ | H | H | $COOCH_3$ |
| 4-719 | H | Cl | $CH_3$ | $CF_3$ | H | H | $COOC_2H_5$ |
| 4-720 | H | Cl | $CH_3$ | $CF_3$ | H | H | $COO^nC_3H_7$ |
| 4-721 | H | Cl | $CH_3$ | $CF_3$ | H | H | $COO^nC_4H_9$ |
| 4-722 | H | Cl | $CH_3$ | $CF_3$ | H | H | $COO^nC_5H_{11}$ |
| 4-723 | H | Cl | $CH_3$ | $CF_3$ | H | H | $COO^iC_3H_7$ |
| 4-724 | H | Cl | $CH_3$ | $CF_3$ | H | H | $COO^cC_5H_9$ |
| 4-725 | H | Cl | $CH_3$ | $CF_3$ | H | H | $COO^cC_6H_{11}$ |
| 4-726 | H | Cl | $CH_3$ | $CF_3$ | H | H | $COOCH_2CH=CH_2$ |
| 4-727 | H | Cl | $CH_3$ | $CF_3$ | H | H | $COOCH_2C\equiv CH$ |
| 4-728 | H | Cl | $CH_3$ | $CF_3$ | H | H | $CONH_2$ |
| 4-729 | H | Cl | $CH_3$ | $CF_3$ | H | H | $CONHCH_3$ |
| 4-730 | H | Cl | $CH_3$ | $CF_3$ | H | H | $CONHC_2H_5$ |
| 4-731 | H | Cl | $CH_3$ | $CF_3$ | H | H | $CON(CH_3)_2$ |
| 4-732 | H | Cl | $CH_3$ | $CF_3$ | H | H | $CON(C_2H_5)_2$ |
| 4-733 | F | Cl | $CH_3$ | $CF_3$ | H | H | $CH_2Cl$ |
| 4-734 | F | Cl | $CH_3$ | $CF_3$ | H | H | $CH_2Br$ |
| 4-735 | F | Cl | $CH_3$ | $CF_3$ | H | H | $CH_2OCH_3$ |
| 4-736 | F | Cl | $CH_3$ | $CF_3$ | H | H | $CH_2OC_2H_5$ |
| 4-737 | F | Cl | $CH_3$ | $CF_3$ | H | H | $CH_2OCH_2OCH_3$ |
| 4-738 | F | Cl | $CH_3$ | $CF_3$ | H | H | $CH_2OCH_2OC_2H_5$ |
| 4-739 | F | Cl | $CH_3$ | $CF_3$ | H | H | $CH_2OCOCH_3$ |
| 4-740 | F | Cl | $CH_3$ | $CF_3$ | H | H | $CH_2OCOC_2H_5$ |
| 4-741 | F | Cl | $CH_3$ | $CF_3$ | H | H | $CH_2OCO^iC_3H_7$ |
| 4-742 | F | Cl | $CH_3$ | $CF_3$ | H | H | $CH_2OCOCH_2Cl$ |
| 4-743 | F | Cl | $CH_3$ | $CF_3$ | H | H | $CH_2OCOCCl_3$ |
| 4-744 | F | Cl | $CH_3$ | $CF_3$ | H | H | $CH_2OCOCF_3$ |
| 4-745 | F | Cl | $CH_3$ | $CF_3$ | H | H | $COOH$ |
| 4-746 | F | Cl | $CH_3$ | $CF_3$ | H | H | $COOCH_3$ |
| 4-747 | F | Cl | $CH_3$ | $CF_3$ | H | H | $COOC_2H_5$ |
| 4-748 | F | Cl | $CH_3$ | $CF_3$ | H | H | $COO^nC_3H_7$ |
| 4-749 | F | Cl | $CH_3$ | $CF_3$ | H | H | $COO^nC_4H_9$ |
| 4-750 | F | Cl | $CH_3$ | $CF_3$ | H | H | $COO^nC_5H_{11}$ |
| 4-751 | F | Cl | $CH_3$ | $CF_3$ | H | H | $COO^iC_3H_7$ |
| 4-752 | F | Cl | $CH_3$ | $CF_3$ | H | H | $COO^cC_5H_9$ |
| 4-753 | F | Cl | $CH_3$ | $CF_3$ | H | H | $COO^cC_6H_{11}$ |
| 4-754 | F | Cl | $CH_3$ | $CF_3$ | H | H | $COOCH_2CH=CH_2$ |
| 4-755 | F | Cl | $CH_3$ | $CF_3$ | H | H | $COOCH_2C\equiv CH$ |
| 4-756 | F | Cl | $CH_3$ | $CF_3$ | H | H | $CONH_2$ |
| 4-757 | F | Cl | $CH_3$ | $CF_3$ | H | H | $CONHCH_3$ |
| 4-758 | F | Cl | $CH_3$ | $CF_3$ | H | H | $CONHC_2H_5$ |
| 4-759 | F | Cl | $CH_3$ | $CF_3$ | H | H | $CON(CH_3)_2$ |
| 4-760 | F | Cl | $CH_3$ | $CF_3$ | H | H | $CON(C_2H_5)_2$ |
| 4-761 | H | Cl | $CH_3$ | $CF_3$ | H | $CH_3$ | $CH_2Cl$ |
| 4-762 | H | Cl | $CH_3$ | $CF_3$ | H | $CH_3$ | $CH_2Br$ |
| 4-763 | H | Cl | $CH_3$ | $CF_3$ | H | $CH_3$ | $CH_2OCH_3$ |
| 4-764 | H | Cl | $CH_3$ | $CF_3$ | H | $CH_3$ | $CH_2OC_2H_5$ |
| 4-765 | H | Cl | $CH_3$ | $CF_3$ | H | $CH_3$ | $CH_2OCH_2OCH_3$ |
| 4-766 | H | Cl | $CH_3$ | $CF_3$ | H | $CH_3$ | $CH_2OCH_2OC_2H_5$ |
| 4-767 | H | Cl | $CH_3$ | $CF_3$ | H | $CH_3$ | $CH_2OCOCH_3$ |
| 4-768 | H | Cl | $CH_3$ | $CF_3$ | H | $CH_3$ | $CH_2OCOC_2H_5$ |
| 4-769 | H | Cl | $CH_3$ | $CF_3$ | H | $CH_3$ | $CH_2OCO^iC_3H_7$ |
| 4-770 | H | Cl | $CH_3$ | $CF_3$ | H | $CH_3$ | $CH_2OCOCH_2Cl$ |
| 4-771 | H | Cl | $CH_3$ | $CF_3$ | H | $CH_3$ | $CH_2OCOCCl_3$ |
| 4-772 | H | Cl | $CH_3$ | $CF_3$ | H | $CH_3$ | $CH_2OCOCF_3$ |
| 4-773 | H | Cl | $CH_3$ | $CF_3$ | H | $CH_3$ | $COOH$ |
| 4-774 | H | Cl | $CH_3$ | $CF_3$ | H | $CH_3$ | $COOCH_3$ |
| 4-775 | H | Cl | $CH_3$ | $CF_3$ | H | $CH_3$ | $COOC_2H_5$ |
| 4-776 | H | Cl | $CH_3$ | $CF_3$ | H | $CH_3$ | $COO^nC_3H_7$ |
| 4-777 | H | Cl | $CH_3$ | $CF_3$ | H | $CH_3$ | $COO^nC_4H_9$ |
| 4-778 | H | Cl | $CH_3$ | $CF_3$ | H | $CH_3$ | $COO^nC_5H_{11}$ |
| 4-779 | H | Cl | $CH_3$ | $CF_3$ | H | $CH_3$ | $COO^iC_3H_7$ |
| 4-780 | H | Cl | $CH_3$ | $CF_3$ | H | $CH_3$ | $COO^cC_5H_9$ |
| 4-781 | H | Cl | $CH_3$ | $CF_3$ | H | $CH_3$ | $COO^cC_6H_{11}$ |
| 4-782 | H | Cl | $CH_3$ | $CF_3$ | H | $CH_3$ | $COOCH_2CH=CH_2$ |
| 4-783 | H | Cl | $CH_3$ | $CF_3$ | H | $CH_3$ | $COOCH_2C\equiv CH$ |
| 4-784 | H | Cl | $CH_3$ | $CF_3$ | H | $CH_3$ | $CONH_2$ |
| 4-785 | H | Cl | $CH_3$ | $CF_3$ | H | $CH_3$ | $CONHCH_3$ |
| 4-786 | H | Cl | $CH_3$ | $CF_3$ | H | $CH_3$ | $CONHC_2H_5$ |
| 4-787 | H | Cl | $CH_3$ | $CF_3$ | H | $CH_3$ | $CON(CH_3)_2$ |
| 4-788 | H | Cl | $CH_3$ | $CF_3$ | H | $CH_3$ | $CON(C_2H_5)_2$ |
| 4-789 | F | Cl | $CH_3$ | $CF_3$ | H | $CH_3$ | $CH_2Cl$ |
| 4-790 | F | Cl | $CH_3$ | $CF_3$ | H | $CH_3$ | $CH_2Br$ |
| 4-791 | F | Cl | $CH_3$ | $CF_3$ | H | $CH_3$ | $CH_2OCH_3$ |
| 4-792 | F | Cl | $CH_3$ | $CF_3$ | H | $CH_3$ | $CH_2OC_2H_5$ |
| 4-793 | F | Cl | $CH_3$ | $CF_3$ | H | $CH_3$ | $CH_2OCH_2OCH_3$ |

TABLE 4-continued

Compounds of the formula:

| Compound No. | X | Y | $R^3$ | $R^1$ | $R^2$ | $R^7$ | $R^8$ |
|---|---|---|---|---|---|---|---|
| 4-794 | F | Cl | $CH_3$ | $CF_3$ | H | $CH_3$ | $CH_2OCH_2OC_2H_5$ |
| 4-795 | F | Cl | $CH_3$ | $CF_3$ | H | $CH_3$ | $CH_2OCOCH_3$ |
| 4-796 | F | Cl | $CH_3$ | $CF_3$ | H | $CH_3$ | $CH_2OCOC_2H_5$ |
| 4-797 | F | Cl | $CH_3$ | $CF_3$ | H | $CH_3$ | $CH_2OCO^iC_3H_7$ |
| 4-798 | F | Cl | $CH_3$ | $CF_3$ | H | $CH_3$ | $CH_2OCOCH_2Cl$ |
| 4-799 | F | Cl | $CH_3$ | $CF_3$ | H | $CH_3$ | $CH_2OCOCCl_3$ |
| 4-800 | F | Cl | $CH_3$ | $CF_3$ | H | $CH_3$ | $CH_2OCOCF_3$ |
| 4-801 | F | Cl | $CH_3$ | $CF_3$ | H | $CH_3$ | COOH |
| 4-802 | F | Cl | $CH_3$ | $CF_3$ | H | $CH_3$ | $COOCH_3$ |
| 4-803 | F | Cl | $CH_3$ | $CF_3$ | H | $CH_3$ | $COOC_2H_5$ |
| 4-804 | F | Cl | $CH_3$ | $CF_3$ | H | $CH_3$ | $COO^nC_3H_7$ |
| 4-805 | F | Cl | $CH_3$ | $CF_3$ | H | $CH_3$ | $COO^nC_4H_9$ |
| 4-806 | F | Cl | $CH_3$ | $CF_3$ | H | $CH_3$ | $COO^nC_5H_{11}$ |
| 4-807 | F | Cl | $CH_3$ | $CF_3$ | H | $CH_3$ | $COO^iC_3H_7$ |
| 4-808 | F | Cl | $CH_3$ | $CF_3$ | H | $CH_3$ | $COO^cC_5H_9$ |
| 4-809 | F | Cl | $CH_3$ | $CF_3$ | H | $CH_3$ | $COO^cC_6H_{11}$ |
| 4-810 | F | Cl | $CH_3$ | $CF_3$ | H | $CH_3$ | $COOCH_2CH=CH_2$ |
| 4-811 | F | Cl | $CH_3$ | $CF_3$ | H | $CH_3$ | $COOCH_2C\equiv CH$ |
| 4-812 | F | Cl | $CH_3$ | $CF_3$ | H | $CH_3$ | $CONH_2$ |
| 4-813 | F | Cl | $CH_3$ | $CF_3$ | H | $CH_3$ | $CONHCH_3$ |
| 4-814 | F | Cl | $CH_3$ | $CF_3$ | H | $CH_3$ | $CONHC_2H_5$ |
| 4-815 | F | Cl | $CH_3$ | $CF_3$ | H | $CH_3$ | $CON(CH_3)_2$ |
| 4-816 | F | Cl | $CH_3$ | $CF_3$ | H | $CH_3$ | $CON(C_2H_5)_2$ |
| 4-817 | H | Cl | $CH_3$ | $CF_3$ | H | H | $CH_2Cl$ |
| 4-818 | H | Cl | $CH_3$ | $CF_3$ | H | H | $CH_2Br$ |
| 4-819 | H | Cl | $CH_3$ | $CF_3$ | H | H | $CH_2OCH_3$ |
| 4-820 | H | Cl | $CH_3$ | $CF_3$ | H | H | $CH_2OC_2H_5$ |
| 4-821 | H | Cl | $CH_3$ | $CF_3$ | H | H | $CH_2OCH_2OCH_3$ |
| 4-822 | H | Cl | $CH_3$ | $CF_3$ | H | H | $CH_2OCH_2OC_2H_5$ |
| 4-823 | H | Cl | $CH_3$ | $CF_3$ | H | H | $CH_2OCOCH_3$ |
| 4-824 | H | Cl | $CH_3$ | $CF_3$ | H | H | $CH_2OCOC_2H_5$ |
| 4-825 | H | Cl | $CH_3$ | $CF_3$ | H | H | $CH_2OCO^iC_3H_7$ |
| 4-826 | H | Cl | $CH_3$ | $CF_3$ | H | H | $CH_2OCOCH_2Cl$ |
| 4-827 | H | Cl | $CH_3$ | $CF_3$ | H | H | $CH_2OCOCCl_3$ |
| 4-828 | H | Cl | $CH_3$ | $CF_3$ | H | H | $CH_2OCOCF_3$ |
| 4-829 | H | Cl | $CH_3$ | $CF_3$ | H | H | COOH |
| 4-830 | H | Cl | $CH_3$ | $CF_3$ | H | H | $COOCH_3$ |
| 4-831 | H | Cl | $CH_3$ | $CF_3$ | H | H | $COOC_2H_5$ |
| 4-832 | H | Cl | $CH_3$ | $CF_3$ | H | H | $COO^nC_3H_7$ |
| 4-833 | H | Cl | $CH_3$ | $CF_3$ | H | H | $COO^nC_4H_9$ |
| 4-834 | H | Cl | $CH_3$ | $CF_3$ | H | H | $COO^nC_5H_{11}$ |
| 4-835 | H | Cl | $CH_3$ | $CF_3$ | H | H | $COO^iC_3H_7$ |
| 4-836 | H | Cl | $CH_3$ | $CF_3$ | H | H | $COO^cC_5H_9$ |
| 4-837 | H | Cl | $CH_3$ | $CF_3$ | H | H | $COO^cC_6H_{11}$ |
| 4-838 | H | Cl | $CH_3$ | $CF_3$ | H | H | $COOCH_2CH=CH_2$ |
| 4-839 | H | Cl | $CH_3$ | $CF_3$ | H | H | $COOCH_2C\equiv CH$ |
| 4-840 | H | Cl | $CH_3$ | $CF_3$ | H | H | $CONH_2$ |
| 4-841 | H | Cl | $CH_3$ | $CF_3$ | H | H | $CONHCH_3$ |
| 4-842 | H | Cl | $CH_3$ | $CF_3$ | H | H | $CONHC_2H_5$ |
| 4-843 | H | Cl | $CH_3$ | $CF_3$ | H | H | $CON(CH_3)_2$ |
| 4-844 | H | Cl | $CH_3$ | $CF_3$ | H | H | $CON(C_2H_5)_2$ |
| 4-845 | F | Cl | $CH_3$ | $CF_3$ | H | H | $CH_2Cl$ |
| 4-846 | F | Cl | $CH_3$ | $CF_3$ | H | H | $CH_2Br$ |
| 4-847 | F | Cl | $CH_3$ | $CF_3$ | H | H | $CH_2OCH_3$ |
| 4-848 | F | Cl | $CH_3$ | $CF_3$ | H | H | $CH_2OC_2H_5$ |
| 4-849 | F | Cl | $CH_3$ | $CF_3$ | H | H | $CH_2OCH_2OCH_3$ |
| 4-850 | F | Cl | $CH_3$ | $CF_3$ | H | H | $CH_2OCH_2OC_2H_5$ |
| 4-851 | F | Cl | $CH_3$ | $CF_3$ | H | H | $CH_2OCOCH_3$ |
| 4-852 | F | Cl | $CH_3$ | $CF_3$ | H | H | $CH_2OCOC_2H_5$ |
| 4-853 | F | Cl | $CH_3$ | $CF_3$ | H | H | $CH_2OCO^iC_3H_7$ |
| 4-854 | F | Cl | $CH_3$ | $CF_3$ | H | H | $CH_2OCOCH_2Cl$ |
| 4-855 | F | Cl | $CH_3$ | $CF_3$ | H | H | $CH_2OCOCCl_3$ |
| 4-856 | F | Cl | $CH_3$ | $CF_3$ | H | H | $CH_2OCOCF_3$ |
| 4-857 | F | Cl | $CH_3$ | $CF_3$ | H | H | COOH |
| 4-858 | F | Cl | $CH_3$ | $CF_3$ | H | H | $COOCH_3$ |
| 4-859 | F | Cl | $CH_3$ | $CF_3$ | H | H | $COOC_2H_5$ |
| 4-860 | F | Cl | $CH_3$ | $CF_3$ | H | H | $COO^nC_3H_7$ |
| 4-861 | F | Cl | $CH_3$ | $CF_3$ | H | H | $COO^nC_4H_9$ |
| 4-862 | F | Cl | $CH_3$ | $CF_3$ | H | H | $COO^nC_5H_{11}$ |
| 4-863 | F | Cl | $CH_3$ | $CF_3$ | H | H | $COO^iC_3H_7$ |
| 4-864 | F | Cl | $CH_3$ | $CF_3$ | H | H | $COO^cC_5H_9$ |
| 4-865 | F | Cl | $CH_3$ | $CF_3$ | H | H | $COO^cC_6H_{11}$ |
| 4-866 | F | Cl | $CH_3$ | $CF_3$ | H | H | $COOCH_2CH=CH_2$ |
| 4-867 | F | Cl | $CH_3$ | $CF_3$ | H | H | $COOCH_2C\equiv CH$ |
| 4-868 | F | Cl | $CH_3$ | $CF_3$ | H | H | $CONH_2$ |
| 4-869 | F | Cl | $CH_3$ | $CF_3$ | H | H | $CONHCH_3$ |
| 4-870 | F | Cl | $CH_3$ | $CF_3$ | H | H | $CONHC_2H_5$ |
| 4-871 | F | Cl | $CH_3$ | $CF_3$ | H | H | $CON(CH_3)_2$ |
| 4-872 | F | Cl | $CH_3$ | $CF_3$ | H | H | $CON(C_2H_5)_2$ |
| 4-873 | H | Cl | $CH_3$ | $CF_3$ | H | $CH_3$ | $CH_2Cl$ |
| 4-874 | H | Cl | $CH_3$ | $CF_3$ | H | $CH_3$ | $CH_2Br$ |
| 4-875 | H | Cl | $CH_3$ | $CF_3$ | H | $CH_3$ | $CH_2OCH_3$ |
| 4-876 | H | Cl | $CH_3$ | $CF_3$ | H | $CH_3$ | $CH_2OC_2H_5$ |
| 4-877 | H | Cl | $CH_3$ | $CF_3$ | H | $CH_3$ | $CH_2OCH_2OCH_3$ |
| 4-878 | H | Cl | $CH_3$ | $CF_3$ | H | $CH_3$ | $CH_2OCH_2OC_2H_5$ |
| 4-879 | H | Cl | $CH_3$ | $CF_3$ | H | $CH_3$ | $CH_2OCOCH_3$ |
| 4-880 | H | Cl | $CH_3$ | $CF_3$ | H | $CH_3$ | $CH_2OCOC_2H_5$ |
| 4-881 | H | Cl | $CH_3$ | $CF_3$ | H | $CH_3$ | $CH_2OCO^iC_3H_7$ |
| 4-882 | H | Cl | $CH_3$ | $CF_3$ | H | $CH_3$ | $CH_2OCOCH_2Cl$ |
| 4-883 | H | Cl | $CH_3$ | $CF_3$ | H | $CH_3$ | $CH_2OCOCCl_3$ |
| 4-884 | H | Cl | $CH_3$ | $CF_3$ | H | $CH_3$ | $CH_2OCOCF_3$ |
| 4-885 | H | Cl | $CH_3$ | $CF_3$ | H | $CH_3$ | COOH |
| 4-886 | H | Cl | $CH_3$ | $CF_3$ | H | $CH_3$ | $COOCH_3$ |
| 4-887 | H | Cl | $CH_3$ | $CF_3$ | H | $CH_3$ | $COOC_2H_5$ |
| 4-888 | H | Cl | $CH_3$ | $CF_3$ | H | $CH_3$ | $COO^nC_3H_7$ |
| 4-889 | H | Cl | $CH_3$ | $CF_3$ | H | $CH_3$ | $COO^nC_4H_9$ |
| 4-890 | H | Cl | $CH_3$ | $CF_3$ | H | $CH_3$ | $COO^nC_5H_{11}$ |
| 4-891 | H | Cl | $CH_3$ | $CF_3$ | H | $CH_3$ | $COO^iC_3H_7$ |
| 4-892 | H | Cl | $CH_3$ | $CF_3$ | H | $CH_3$ | $COO^cC_5H_9$ |
| 4-893 | H | Cl | $CH_3$ | $CF_3$ | H | $CH_3$ | $COO^cC_6H_{11}$ |
| 4-894 | H | Cl | $CH_3$ | $CF_3$ | H | $CH_3$ | $COOCH_2CH=CH_2$ |
| 4-895 | H | Cl | $CH_3$ | $CF_3$ | H | $CH_3$ | $COOCH_2C\equiv CH$ |
| 4-896 | H | Cl | $CH_3$ | $CF_3$ | H | $CH_3$ | $CONH_2$ |
| 4-897 | H | Cl | $CH_3$ | $CF_3$ | H | $CH_3$ | $CONHCH_3$ |
| 4-898 | H | Cl | $CH_3$ | $CF_3$ | H | $CH_3$ | $CONHC_2H_5$ |
| 4-899 | H | Cl | $CH_3$ | $CF_3$ | H | $CH_3$ | $CON(CH_3)_2$ |
| 4-900 | H | Cl | $CH_3$ | $CF_3$ | H | $CH_3$ | $CON(C_2H_5)_2$ |
| 4-901 | F | Cl | $CH_3$ | $CF_3$ | H | $CH_3$ | $CH_2Cl$ |
| 4-902 | F | Cl | $CH_3$ | $CF_3$ | H | $CH_3$ | $CH_2Br$ |
| 4-903 | F | Cl | $CH_3$ | $CF_3$ | H | $CH_3$ | $CH_2OCH_3$ |
| 4-904 | F | Cl | $CH_3$ | $CF_3$ | H | $CH_3$ | $CH_2OC_2H_5$ |
| 4-905 | F | Cl | $CH_3$ | $CF_3$ | H | $CH_3$ | $CH_2OCH_2OCH_3$ |
| 4-906 | F | Cl | $CH_3$ | $CF_3$ | H | $CH_3$ | $CH_2OCH_2OC_2H_5$ |
| 4-907 | F | Cl | $CH_3$ | $CF_3$ | H | $CH_3$ | $CH_2OCOCH_3$ |
| 4-908 | F | Cl | $CH_3$ | $CF_3$ | H | $CH_3$ | $CH_2OCOC_2H_5$ |
| 4-909 | F | Cl | $CH_3$ | $CF_3$ | H | $CH_3$ | $CH_2OCO^iC_3H_7$ |
| 4-910 | F | Cl | $CH_3$ | $CF_3$ | H | $CH_3$ | $CH_2OCOCH_2Cl$ |
| 4-911 | F | Cl | $CH_3$ | $CF_3$ | H | $CH_3$ | $CH_2OCOCCl_3$ |
| 4-912 | F | Cl | $CH_3$ | $CF_3$ | H | $CH_3$ | $CH_2OCOCF_3$ |
| 4-913 | F | Cl | $CH_3$ | $CF_3$ | H | $CH_3$ | COOH |
| 4-914 | F | Cl | $CH_3$ | $CF_3$ | H | $CH_3$ | $COOCH_3$ |
| 4-915 | F | Cl | $CH_3$ | $CF_3$ | H | $CH_3$ | $COOC_2H_5$ |

TABLE 4-continued

Compounds of the formula:

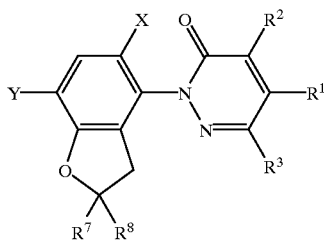

| Compound No. | X | Y | R³ | R¹ | R² | R⁷ | R⁸ |
|---|---|---|---|---|---|---|---|
| 4-916 | F | Cl | $CH_3$ | $CF_3$ | H | $CH_3$ | $COO^nC_3H_7$ |
| 4-917 | F | Cl | $CH_3$ | $CF_3$ | H | $CH_3$ | $COO^nC_4H_9$ |
| 4-918 | F | Cl | $CH_3$ | $CF_3$ | H | $CH_3$ | $COO^nC_5H_{11}$ |
| 4-919 | F | Cl | $CH_3$ | $CF_3$ | H | $CH_3$ | $COO^iC_3H_7$ |
| 4-920 | F | Cl | $CH_3$ | $CF_3$ | H | $CH_3$ | $COO^cC_5H_9$ |
| 4-921 | F | Cl | $CH_3$ | $CF_3$ | H | $CH_3$ | $COO^cC_6H_{11}$ |
| 4-922 | F | Cl | $CH_3$ | $CF_3$ | H | $CH_3$ | $COOCH_2CH=CH_2$ |
| 4-923 | F | Cl | $CH_3$ | $CF_3$ | H | $CH_3$ | $COOCH_2C\equiv CH$ |
| 4-924 | F | Cl | $CH_3$ | $CF_3$ | H | $CH_3$ | $CONH_2$ |
| 4-925 | F | Cl | $CH_3$ | $CF_3$ | H | $CH_3$ | $CONHCH_3$ |
| 4-926 | F | Cl | $CH_3$ | $CF_3$ | H | $CH_3$ | $CONHC_2H_5$ |
| 4-927 | F | Cl | $CH_3$ | $CF_3$ | H | $CH_3$ | $CON(CH_3)_2$ |
| 4-928 | F | Cl | $CH_3$ | $CF_3$ | H | $CH_3$ | $CON(C_2H_5)_2$ |
| 4-929 | F | Cl | $CH_3$ | $CF_3$ | H | H | $CH_3$ |
| 4-930 | F | Cl | $CH_3$ | $CF_3$ | H | H | $CH_2OH$ |
| 4-931 | F | Cl | $CH_3$ | $CF_3$ | H | $CH_3$ | $CH_3$ |
| 4-932 | F | Cl | $CH_3$ | $CF_3$ | H | $CH_3$ | $CH_2OH$ |
| 4-933 | H | Cl | $CH_3$ | $CF_3$ | H | H | $CH_3$ |
| 4-934 | H | Cl | $CH_3$ | $CF_3$ | H | H | $CH_2OH$ |
| 4-935 | H | Cl | $CH_3$ | $CF_3$ | H | $CH_3$ | $CH_3$ |
| 4-936 | H | Cl | $CH_3$ | $CF_3$ | H | $CH_3$ | $CH_2OH$ |

TABLE 5

Compounds of the formula:

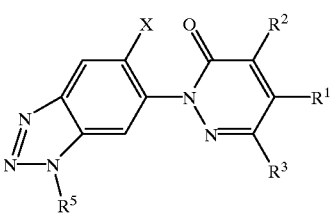

| Compound No. | X | R³ | R¹ | R² | R⁵ |
|---|---|---|---|---|---|
| 5-1 | H | H | $CF_2Cl$ | $CH_3$ | $CH_3$ |
| 5-2 | H | H | $CF_2Cl$ | $CH_3$ | $C_2H_5$ |
| 5-3 | H | H | $CF_2Cl$ | $CH_3$ | $^iC_3H_7$ |
| 5-4 | H | H | $CF_2Cl$ | $CH_3$ | $^nC_3H_7$ |
| 5-5 | H | H | $CF_2Cl$ | $CH_3$ | $^iC_4H_9$ |
| 5-6 | H | H | $CF_2Cl$ | $CH_3$ | $CH_2CH=CH_2$ |
| 5-7 | H | H | $CF_2Cl$ | $CH_3$ | $CH(CH_3)CH=CH_2$ |
| 5-8 | H | H | $CF_2Cl$ | $CH_3$ | $CH_2C\equiv CH$ |
| 5-9 | H | H | $CF_2Cl$ | $CH_3$ | $CH(CH_3)C\equiv CH$ |
| 5-10 | F | H | $CF_2Cl$ | $CH_3$ | $CH_3$ |
| 5-11 | F | H | $CF_2Cl$ | $CH_3$ | $C_2H_5$ |
| 5-12 | F | H | $CF_2Cl$ | $CH_3$ | $^iC_3H_7$ |
| 5-13 | F | H | $CF_2Cl$ | $CH_3$ | $^nC_3H_7$ |
| 5-14 | F | H | $CF_2Cl$ | $CH_3$ | $^iC_4H_9$ |
| 5-15 | F | H | $CF_2Cl$ | $CH_3$ | $CH_2CH=CH_2$ |
| 5-16 | F | H | $CF_2Cl$ | $CH_3$ | $CH(CH_3)CH=CH_2$ |
| 5-17 | F | H | $CF_2Cl$ | $CH_3$ | $CH_2C\equiv CH$ |
| 5-18 | F | H | $CF_2Cl$ | $CH_3$ | $CH(CH_3)C\equiv CH$ |
| 5-19 | H | H | $CF_3$ | $CH_3$ | $CH_3$ |

TABLE 5-continued

Compounds of the formula:

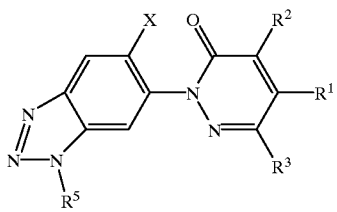

| Compound No. | X | R³ | R¹ | R² | R⁵ |
|---|---|---|---|---|---|
| 5-20 | H | H | $CF_3$ | $CH_3$ | $C_2H_5$ |
| 5-21 | H | H | $CF_3$ | $CH_3$ | $^iC_3H_7$ |
| 5-22 | H | H | $CF_3$ | $CH_3$ | $^nC_3H_7$ |
| 5-23 | H | H | $CF_3$ | $CH_3$ | $^iC_4H_9$ |
| 5-24 | H | H | $CF_3$ | $CH_3$ | $CH_2CH=CH_2$ |
| 5-25 | H | H | $CF_3$ | $CH_3$ | $CH(CH_3)CH=CH_2$ |
| 5-26 | H | H | $CF_3$ | $CH_3$ | $CH_2C\equiv CH$ |
| 5-27 | H | H | $CF_3$ | $CH_3$ | $CH(CH_3)C\equiv CH$ |
| 5-28 | F | H | $CF_3$ | $CH_3$ | $CH_3$ |
| 5-29 | F | H | $CF_3$ | $CH_3$ | $C_2H_5$ |
| 5-30 | F | H | $CF_3$ | $CH_3$ | $^iC_3H_7$ |
| 5-31 | F | H | $CF_3$ | $CH_3$ | $^iC_4H_9$ |
| 5-32 | F | H | $CF_3$ | $CH_3$ | $CH_2CH=CH_2$ |
| 5-33 | F | H | $CF_3$ | $CH_3$ | $CH(CH_3)CH=CH_2$ |
| 5-34 | F | H | $CF_3$ | $CH_3$ | $CH_2C\equiv CH$ |
| 5-35 | F | H | $CF_3$ | $CH_3$ | $CH(CH_3)C\equiv CH$ |
| 5-36 | H | H | $CF_2Cl$ | H | $CH_3$ |
| 5-37 | H | H | $CF_2Cl$ | H | $C_2H_5$ |
| 5-38 | H | H | $CF_2Cl$ | H | $^iC_3H_7$ |
| 5-39 | H | H | $CF_2Cl$ | H | $^nC_3H_7$ |
| 5-40 | H | H | $CF_2Cl$ | H | $^iC_4H_9$ |
| 5-41 | H | H | $CF_2Cl$ | H | $CH_2CH=CH_2$ |
| 5-42 | H | H | $CF_2Cl$ | H | $CH(CH_3)CH=CH_2$ |
| 5-43 | H | H | $CF_2Cl$ | H | $CH_2C\equiv CH$ |
| 5-44 | H | H | $CF_2Cl$ | H | $CH(CH_3)C\equiv CH$ |
| 5-45 | F | H | $CF_2Cl$ | H | $CH_3$ |
| 5-46 | F | H | $CF_2Cl$ | H | $C_2H_5$ |
| 5-47 | F | H | $CF_2Cl$ | H | $^iC_3H_7$ |
| 5-48 | F | H | $CF_2Cl$ | H | $^nC_3H_7$ |
| 5-49 | F | H | $CF_2Cl$ | H | $^iC_4H_9$ |
| 5-50 | F | H | $CF_2Cl$ | H | $CH_2CH=CH_2$ |
| 5-51 | F | H | $CF_2Cl$ | H | $CH(CH_3)CH=CH_2$ |
| 5-52 | F | H | $CF_2Cl$ | H | $CH_2C\equiv CH$ |
| 5-53 | F | H | $CF_2Cl$ | H | $CH(CH_3)C\equiv CH$ |
| 5-54 | H | H | $CF_3$ | H | $CH_3$ |
| 5-55 | H | H | $CF_3$ | H | $C_2H_5$ |
| 5-56 | H | H | $CF_3$ | H | $^iC_3H_7$ |
| 5-57 | H | H | $CF_3$ | H | $^nC_3H_7$ |
| 5-58 | H | H | $CF_3$ | H | $^iC_4H_9$ |
| 5-59 | H | H | $CF_3$ | H | $CH_2CH=CH_2$ |
| 5-60 | H | H | $CF_3$ | H | $CH(CH_3)CH=CH_2$ |
| 5-61 | H | H | $CF_3$ | H | $CH_2C\equiv CH$ |
| 5-62 | H | H | $CF_3$ | H | $CH(CH_3)C\equiv CH$ |
| 5-63 | F | H | $CF_3$ | H | $CH_3$ |
| 5-64 | F | H | $CF_3$ | H | $C_2H_5$ |
| 5-65 | F | H | $CF_3$ | H | $^iC_3H_7$ |
| 5-66 | F | H | $CF_3$ | H | $^iC_4H_9$ |
| 5-67 | F | H | $CF_3$ | H | $CH_2CH=CH_2$ |
| 5-68 | F | H | $CF_3$ | H | $CH(CH_3)CH=CH_2$ |
| 5-69 | F | H | $CF_3$ | H | $CH_2C\equiv CH$ |
| 5-70 | F | H | $CF_3$ | H | $CH(CH_3)C\equiv CH$ |
| 5-71 | H | $CH_3$ | $CF_3$ | H | $CH_3$ |
| 5-72 | H | $CH_3$ | $CF_3$ | H | $C_2H_5$ |
| 5-73 | H | $CH_3$ | $CF_3$ | H | $^iC_3H_7$ |
| 5-74 | H | $CH_3$ | $CF_3$ | H | $^nC_3H_7$ |
| 5-75 | H | $CH_3$ | $CF_3$ | H | $^iC_4H_9$ |
| 5-76 | H | $CH_3$ | $CF_3$ | H | $CH_2CH=CH_2$ |
| 5-77 | H | $CH_3$ | $CF_3$ | H | $CH(CH_3)CH=CH_2$ |
| 5-78 | H | $CH_3$ | $CF_3$ | H | $CH_2C\equiv CH$ |
| 5-79 | H | $CH_3$ | $CF_3$ | H | $CH(CH_3)C\equiv CH$ |
| 5-80 | F | $CH_3$ | $CF_3$ | H | $CH_3$ |
| 5-81 | F | $CH_3$ | $CF_3$ | H | $C_2H_5$ |

TABLE 5-continued

Compounds of the formula:

[Chemical structure diagram]

| Compound No. | X | R³ | R¹ | R² | R⁵ |
|---|---|---|---|---|---|
| 5-82 | F | CH₃ | CF₃ | H | $^iC_3H_7$ |
| 5-83 | F | CH₃ | CF₃ | H | $^iC_4H_9$ |
| 5-84 | F | CH₃ | CF₃ | H | CH₂CH=CH₂ |
| 5-85 | F | CH₃ | CF₃ | H | CH(CH₃)CH=CH₂ |
| 5-86 | F | CH₃ | CF₃ | H | CH₂C≡CH |
| 5-87 | F | CH₃ | CF₃ | H | CH(CH₃)C≡CH |

The physical properties (melting point, m.p.) or ¹H-NMR (250 or 300 MHz, CDCl₃, TMS, δ(ppm)) data for some of the present compounds are shown below.

Compound 1-332, m.p. 97.0° C.

Compound 1-335, m.p. 80.8° C.

Compound 1-337, m.p. 91.5° C.

Compound 1-338, m.p. 86.1° C.

Compound 1-344, m.p. 94.2° C.

Compound 1-347, m.p. 80.7° C.

Compound 1-350, 2.41 (3H, q, J=1.8 Hz), 4.05–4.35 (2H, b), 6.87–6.94 (1H, m), 7.03 (1H, d, J=2.4 Hz), 7.33 (1H, d, J=8.5 Hz), 7.98 (1H, s)

Compound 1-353, m.p. 124.0° C.

Compound 1-367, 2.44 (3H, q, J=1.9 Hz), 3.04 (3H, s), 6.88 (1H, s), 7.37 (1H, d, J=9.0Hz), 7.79 (1H, d, J=7.0 Hz), 8.01 (1H, s)

Compound 1-369, 2.44 (3H, q, J=2.0 Hz), 4.57 (2H, s), 7.06 (1H, s), 7.38 (1H, d, J=9.0Hz), 7.83 (1H, d, J=6.9 Hz), 8.01 (1H, s)

Compound 1-391, m.p. 177.6° C.

Compound 1-392, m.p. 172.56° C.

Compound 1-398, m.p. 133.1° C.

Compound 1-420, 1.25 (3H, t, J=7.5 Hz), 1.51 (3H, d, J=7.0 Hz), 2.42 (3H, q, J=1.8 Hz), 4.0–4.18 (3H, m), 4.82 (1H, d, J=7.9 Hz), 6.59 (1H, d, J=6.3 Hz), 7.23 (1H, d, J=9.3 Hz), 7.97 (1H, s)

Compound 1-429, 1.40 (6H, d, J=6.3 Hz), 2.43 (3H, q, J=2.4 Hz), 4.52–4.63 (1H, m), 7.14 (0.5H, d, J=2.4 Hz), 7.17 (0.5H, d, J=2.4 Hz), 7.24 (1H, d, J=3.6 Hz), 7.29 (1H, s), 7.46 (1H, d, J=8.4 Hz)

Compound 1-439, m.p. 110.6° C.

Compound 1-449, 1.29 (3H, t, J=7.5 Hz), 2.42 (3H, q, J=2.4 Hz), 4.28 (2H, q, J=7.5 Hz), 4.73 (2H, s), 7.20–7.32 (2H, m), 7.49 (1H, d, J=10.4 Hz), 8.00 (1H, s)

Compound 1-456, 1.70 (3H, d, J=6.9 Hz), 2.41 (3H, q, J=2.1 Hz), 3.77 (3H, s), 4.81 (1H, q, J=6.9 Hz), 7.21–7.28 (2H, m), 7.47 (1H, d, J=8.7 Hz), 7.99 (1H, s)

Compound 1-474, m.p. 110.6° C.

Compound 1-475, 1.46 (3H, t, J=5.8 Hz), 2.44 (3H, q, J=1.5 Hz), 4.07 (2H, q, J=5.8 Hz), 6.94 (1H, d, J=5.0 Hz), 7.29 (1H, d, J=7.5 Hz), 8.01 (1H, s)

Compound 1-476, 1.38 (6H, d, J=6.3 Hz), 2.43 (3H, q, J=2.0 Hz), 4.47 (1H, m), 6.99 (1H, d, J=5.0Hz), 7.29 (1H, d, J=9.5 Hz), 8.00 (1H, s)

Compound 1-482, m.p. 79.8° C.

Compound 1-483, m.p. 132.7° C.

Compound 1-486, m.p. 140.7° C. (decomp.)

Compound 1-487, m.p. 114.1° C.

Compound 1-491, m.p. 82.9° C.

Compound 1-495, m.p. 80.4° C.

Compound 1-496, m.p. 102.0° C.

Compound 1-497, m.p. 82.9° C.

Compound 1-498, m.p. 75.6° C.

Compound 1-499, 0.88 (3H, t, J=7 Hz), 1.2–1.4 (4H, m), 1.55–1.70 (2H, m), 2.43 (3H, q, J=2 Hz), 4.19 (2H, t, J=7 Hz), 4.68 (2H, s), 6.98 (1H, d, J=7 Hz), 7.33 (1H, d, J=8 Hz), 7.99 (1H, s)

Compound 1-500, 1.26 (6H, d, J=6.3 Hz), 2.43 (3H, q, J=2 Hz), 4.65 (2H, s), 5.05–5.18 (1H, m), 6.98 (1H, d, J=7 Hz), 7.33 (1H, d, J=8 Hz), 7.98 (1H, s)

Compound 1-501, 1.5–1.9 (8H, m), 2.43 (3H, q, J=2 Hz), 4.65 (2H, s), 5.2–5.4 (1H, m), 6.97 (1H, d, J=7 Hz), 7.33 (1H, d, J=8 Hz), 7.98 (1H, s)

Compound 1-503, 1.68 (3H, d, J=7 Hz), 2.43 (3H, q, J=2 Hz), 3.76 (3H, s), 4.73 (1H, q, J=7 Hz), 6.98 (1H, d, J=7 Hz), 7.32 (1H, d, J=8 Hz), 7.99 (1H, s)

Compound 1-504, 1.25 (3H, t, J=7.3 Hz), 1.68 (3H, d, J=6.8 Hz), 2.42 (3H, q, J=2.0 Hz), 4.21 (2H, q, J=7.3 Hz), 4.70 (1H, q, J=6.8 Hz), 6.99 (1H, d, J=6.8 Hz), 7.32 (1H, d, J=9.3 Hz), 7.98 (1H, s)

Compound 1-511, m.p. 110.7° C.

Compound 1-518, m.p. 131.2° C. (decomp.)

Compound 1-576, 2.43 (3H, q, J=1.8 Hz), 3.67 (2H, s), 3.72 (3H, s), 7.32 (1H, d, J=8.5 Hz), 7.59 (1H, d, J=7.1 Hz), 8.2 (1H, s)

Compound 1-577, 1.15 (3H, t, J=7.5 Hz), 2.36 (3H, q, J=1.8 Hz), 3.58 (2H, s), 4.09 (2H, q, J=7.5 Hz), 7.28 (1H, d, J=8.6 Hz), 7.52 (1H, d, J=7.1 Hz), 7.93 (1H, s)

Compound 1-579, m.p. 71.6° C.

Compound 1-581, m.p. 97.5° C.

Compound 1-584, 1.53 (3H, d, J=7.2 Hz), 2.43 (3H, q, J=1.8 Hz), 3.66 (3H, s), 3.88 (1H, q, J=7.2 Hz), 7.38 (1H, d, J=9.6 Hz), 7.66 (1H, d, J=7.5 Hz), 7.99 (1H, s)

Compound 1-585, 1.17 (3H, t, J=6.9 Hz), 1.53 (3H, d, J=7.2 Hz), 2.43 (3H, q, J=1.8 Hz), 3.89 (1H, q, J=7.2 Hz), 4.11 (2H, q, J=6.9 Hz), 7.37 (1H, d, J=9.6 Hz), 7.67 (1H, d, J=9.0 Hz), 7.99 (11H, s)

Compound 1-586, 0.85 (3H, t, J=6.8 Hz), 1.51–1.62 (5H, m), 2.43 (3H, q, J=1.8 Hz), 3.89 (1H, q, J=7.2 Hz), 4.02 (2H, t, J=6.8 Hz), 7.33 (1H, d, J=9.5 Hz), 7.66 (1H, d, J=7.5 Hz), 7.98 (1H, s)

Compound 1-587, 0.88 (3H, t, J=7.2Hz), 1.30–1.40 (2H, m), 1.47–1.55 (5H, m), 2.43 (3H, q, J=1.8 Hz), 3.89 (1H, q, J=7.1 Hz), 4.02–4.08 (2H, m), 7.36 (1H, d, J=9.4 Hz), 7.66 (1H, d, J=7.5 Hz), 7.99 (1H, s)

Compound 1-619, 2.45 (3H, q, J=1.6 Hz), 7.60 (1H, d, J=8.6 Hz), 7.80–7.86 (1H, m), 8.04 (1H, s), 8.36 (1H, d, J=2.5 Hz)

Compound 1-621, 1.40 (3H, t, J=7.1 Hz), 2.43 (3H, q, J=1.8 Hz), 4.41 (2H, q, J=7.1 Hz), 7.56 (1H, d, J=8.6 Hz), 7.72–7.78 (1H, m), 8.02 (1H, s), 8.16 (1H, d, J=2.7 Hz)

Compound 1-625, 1.39 (6H, d, J=6.2 Hz), 2.43 (3H, q, J=1.6 Hz), 5.23–5.28 (1H, m), 7.54 (1H, d, J=8.7 Hz), 7.70–7.76 (1H, m), 8.02 (1H, s), 8.10 (1H, d, J=2.6 Hz)

Compound 1-632, m.p. 76.1° C.

Compound 1-637, m.p. 102.8° C.

Compound 1-641, 2.43 (3H, q, J=2.0 Hz), 3.92 (3H, s), 7.39 (1H, d, J=9.5 Hz), 8.02 (1H, s), 8.07 (1H, d, J=7.7 Hz)

Compound 1-642, 1.39 (3H, t, J=7.2 Hz), 2.44 (3H, q, J=1.9 Hz), 4.40 (2H, q, J=7.2 Hz), 7.38 (1H, d, J=9.5 Hz), 8.00–8.06 (2H, m)

Compound 1-981, m.p. 87.1° C.

Compound 1-987, 4.0–4.4 (2H, b), 6.8–6.9 (1H, m), 7.04 (1H, d, J=2.4 Hz), 7.28 (1H, q, J=1.2 Hz), 7.35 (1H, d, l =8.6 Hz), 8.02 (1H, d, J=2.2 Hz)

Compound 1-1025, 5.92 (1H, s), 7.16 (0.5H, d, J=2.4 Hz), 7.19 (0.5H, d, J=2.4 Hz), 7.30 (1H, q, J=1.1 Hz), 7.34 (1H, d, J=5.7 Hz), 7.43 (1H, d, J=9.0 Hz), 8.04 (1H, q, J=3.0 Hz)

Compound 1-1028, m.p. 180.2° C., 5.65–5.9 (1H, br), 7.09 (1H, d, J=7 Hz), 7.27–7.30 (2H, m), 8.10 (1H, q, J=2.2 Hz)

Compound 1-1029, 7.09 (1H, d, J=6.4 Hz), 7.31 (1H, q, J=1.1 Hz), 7.42 (1H, d, J=8.8 Hz), 8.04 (1H, q, J=2.2 Hz)

Compound 1-1035, m.p. 61.1° C.

Compound 1-1057, m.p. 158° C.

Compound 1-1066, m.p. 89.1° C.

Compound 1-1076, m.p. 113.5° C.

Compound 1-1086, m.p. 83.9° C.

Compound 1-1093, m.p. 83.1° C.

Compound 1-1113, m.p. 68.6° C.

Compound 1-1123, m.p. 147.4° C.

Compound 1-1124, m.p. 117.2° C.

Compound 1-1133, m.p. 149.2° C. (decomp.)

Compound 1-1140, m.p. 99.1° C.

Compound 1-1141, m.p. 80.2° C.

Compound 1-1213, m.p. 85.8° C.

Compound 1-1214, m.p. 65.1° C.

Compound 1-1221, 1.54 (3H, d, J=7.2 Hz), 3.66 (3H, s), 3.90 (1H, q, J=7.2 Hz), 7.31 (1H, s), 7.39 (1H, d, J=9.0 Hz), 7.67 (1H, d, J=8.7 Hz), 8.04 (1H, d, J=3.6 Hz)

Compound 1-1222, 1.16 (3H, t, J=5.1 Hz), 1.53 (3H, d, J=7.2 Hz), 3.89 (1H, q, J=7.2 Hz), 4.10 (2H, q, J=5.1 Hz), 7.30 (1H, q, J=1.1 Hz), 7.38 (1H, d, J=9.0 Hz), 7.68 (1H, d, J=7.5 Hz), 8.04 (1H, q, J=2.2 Hz)

Compound 1-1226, 1.12 (3H, d, J=6.0 Hz), 1.21 (3H, d, J=6.0 Hz), 1.52 (3H, d, J=3.0 Hz), 3.88 (1H, q, J=3.0 Hz), 4.85–5.03 (1H, m), 7.30 (1H, q, J =1.8 Hz), 7.37 (1H, d, J=9.0 Hz), 7.67 (1H, d, J=7.5 Hz), 8.02 (1H, q, J=2.1 Hz)

Compound 1-1256, 7.35 (1H, q, J=1.1 Hz), 7.62 (1H, d, J=8.7 Hz), 7.82–7.88 (1H, m), 8.09 (1H, d, J=2.2 Hz), 8.35 (1H, d, J=2.6 Hz)

Compound 1-1258, 1.41 (3H, t, J=7.1 Hz), 4.42 (2H, q, J=7.1 Hz), 7.31 (1H, s), 7.57 (1H, d, J=8.7 Hz), 7.74–7.79 (1H, m), 8.07 (1H, q, J=2.1 Hz), 8.16 (1H, d, J=2.6Hz)

Compound 1-1269, m.p. 89.7° C.

Compound 1-1274, m.p. 154.2° C.

Compound 1-1278, m.p. 128.6° C.

Compound 1-1279, 1.40 (3H, t, J=7.1 Hz), 4.40 (2H, q, J=7.1 Hz), 7.33 (1H, q, J=1.1 Hz), 7.39 (1H, d, J=9.4 Hz), 8.05 (1H, d, J=8.3 Hz), 8.07 (1H, s)

Compound 1-1346, 2.48 (3H, s), 5.66 (1H, s), 7.08 (1H, d, J=7.8 Hz), 7.28 (1H, d, J=9.0 Hz), 7.32 (1H, s)

Compound 1-1431, m.p. 74.5° C.

Compound 1-1441, m.p. 128.2° C.

Compound 1-1442, 1.73 (3H, d, J=6.6 Hz), 2.49 (3H, q, J=1.3 Hz), 2.54 (1H, d, J=2.0 Hz), 4.84 (1H, m), 7.22 (1H, d, J=6.5 Hz), 7.28–7.34 (2H, m)

Compound 1-1451, 1.29 (3H, t, J=7.0 Hz), 2.47 (3H, q, J=1.4 Hz), 4.27 (2H, q, J=7.0 Hz), 4.68 (2H, s), 6.99 (1H, d, J=7.1 Hz), 7.32 (1H, s), 7.34 (1H, d, J=7.2Hz)

Compound 1-1458, 1.69 (3H, d, J=6.8 Hz), 2.48 (3H, q, J=1.3 Hz), 3.76 (3H, s), 4.74 (1H, q, J=6.8 Hz), 7.01 (1H, d, J=6.5 Hz), 7.29–7.34 (2H, m)

Compound 1-1540, 1.17 (3H, t, J=7.0 Hz), 1.54 (3H, d, J=7.3 Hz), 2.48 (3H, q, J=1.4 Hz), 3.89 (1H, q, J=7.3 Hz), 4.11 (2H, q, J=7.0 Hz), 7.31 (1H, s), 7.37 (1H, d, J=9.5 Hz), 7.67 (1H, d, J=7.5 Hz)

Compound 1-1617, m.p. 105.7° C.

Compound 1-1622, 1.27 (3H, t, =7.0 Hz), 2.42 (3H, q, J=2.0 Hz), 3.26 (0.3H, d, J=7.6 Hz), 3.32 (0.7H, d, J=7.6 Hz), 3.49 (0.7H, d, J=7.6 Hz), 3.54 (0.3H, d, J=7.6 Hz), 4.23 (2H, q, J=7.0 Hz), 4.54 (0.5H, d, J=7.6 Hz), 4.57 (0.5 H, d, J=7.6 Hz), 7.34 (1H, d, J=9.3 Hz), 7.40 (1H, d, J=7.5 Hz), 8.00 (1H, s)

Compound 1-1627, m.p. 182.2° C.

Compound 1-1638, 3.66 (2H, s), 7.31 (1H, s), 7.34 (1H, d, J=9.3 Hz), 7.62 (1H, d, J=7.2 Hz), 8.08 (1H, s)

Compound 1-1639, m.p. 158.9° C. (decomp.)

Compound 1-1641, 1.55 (3H, d, J=7.2 Hz), 3.88 (1H, q, J=7.2 Hz), 7.32 (1H, s), 7.37 (1H, d, J=9.2 Hz), 7.69 (1H, d, J=7.1 Hz), 8.03 (1H, s)

Compound 1-1650, 1.11 (3H, t, J=7.5 Hz), 2.03–2.12 (2H, m), 2.43 (3H, q, J=1.8 Hz), 3.75 (3H, s), 4.58 (1H, t, J=7.5 Hz), 6.92 (1H, d, J=8.2 Hz), 7.32 (1H, d, J=9.3 Hz), 8.00 (1H, s)

Compound 1-1655, m.p. 119.7° C., 1.29 (3H, t, J=7.1 Hz), 2.43 (3H, q, J=1.8 Hz), 4.26 (2H, q, J=7.1 Hz), 4.68 (2H, s), 6.91 (1H, s), 7.60 (1H, s), 7.99 (1H, s)

Compound 1-1663, m.p. 136.2° C., 2.44 (3H, q, J=1.8 Hz), 2.58 (1H, t, J=2.3 Hz), 4.78 (2H, d, J=2.3 Hz), 7.12 (1H, s), 7.59 (1H, s), 8.01 (1H, s)

Compound 1-1665, 1.23 (3H, t, J=6.9 Hz), 1.68 (3H, d, J=6.8 Hz), 2.42 (3H, q, J=1.8 Hz), 4.1–4.3 (2H, m), 4.72 (1H, q, J=6.8 Hz), 6.90 (1H, s), 7.58 (1H, s), 7.97 (1H, s)

Compound 1-1670, m.p. 118.1° C.

Compound 1-1673, m.p. 107.2° C.

Compound 1-1678, m.p. 164.7° C.

Compound 1-1679, 1.73 (3H, d, J=6.9 Hz), 2.54 (1H, d, J=2.1 Hz), 4.73–4.90 (1H, m), 7.20 (1H, d, J=6.3 Hz), 7.30 (1H, s), 7.49 (1H, d, J=8.7 Hz), 8.00 (1H, s)

Compound 1-1680, m.p. 90.1° C.

Compound 1-1681, m.p. 148.1° C.

Compound 1-1682, m.p. 107.0° C.

Compound 1-1683, 1.25 (3H, t, J=7.2 Hz), 1.68 (3H, d, J=6.8 Hz), 2.42 (3H, q, J=1.5 Hz), 4.13–4.26 (2H, m), 4.70 (1H, q, J=6.8 Hz), 6.96 (1H, d, J=6.3 Hz), 7.48 (1H, d, J=9.0 Hz), 7.97 (1H, s)

Compound 1-1687, m.p. 200.1° C.

Compound 1-1689, m.p. 76.3° C.

Compound 1-1690, m.p. 196.1° C.

Compound 1-1691, 3.06 (3H, s), 7.10–7.30 (1H, b), 7.30 (1H, s), 7.64 (1H, s), 7.74 (1H, s), 8.06 (1H, q, J=2.1 Hz)

Compound 1-1701, 1.39 (3H, t, J=7.1 Hz), 4.40 (2H, q, J=7.1 Hz), 7.33 (1H, q, J=1.1 Hz), 7.69 (1H, s), 7.97 (1H, s), 8.06 (1H, q, J=2.2 Hz)

Compound 1-1718, m.p. 63.9° C.

Compound 1-1719, m.p. 189.5° C.

Compound 1-1720, m.p. 117.3° C.

Compound 1-1721, m.p. 156.1° C.

Compound 1-1722, 2.47 (3H, q, J=1.8 Hz), 3.05 (3H, s), 7.15–7.30 (1H, b), 7.66 (1H, s), 7.78 (1H, s), 8.03 (1H, s)

Compound 1-1732, 1.38 (3H, t, J=7.1 Hz), 2.44 (3H, q, J=1.8 Hz), 4.39 (2H, q, J=7.1 Hz), 7.68 (1H, s), 7.96 (1H, s), 8.02 (1H, s)

Compound 1-1748, 1.38 (6H, d, J=6.0 Hz), 2.44 (3H, q, J=1.9 Hz), 4.40–4.59 (1H, m), 6.95 (1H, s), 7.55 (1H, s), 8.00 (1H, s)

Compound 1-1780, m.p. 76.4° C.

Compound 1-1781, 3.51 (3H, s), 3.51 (3H, s), 7.30 (1H, q, J=1.2 Hz), 7.59 (1H, d, J=6.7 Hz), 7.65 (1H, d, J=9.0 Hz), 8.06 (1H, d, J=2.1 Hz)

Compound 1-1782, 3.03 (3H, s), 7.09 (1H, s), 7.32 (1H, q, J=1.0 Hz), 7.53 (1H, d, J=8.7 Hz), 7.77 (1H, d, J=6.8 Hz), 8.07 (1H, q, J=2.2 Hz)

Compound 1-1783, 1.38 (6H, d, J=6.1 Hz), 2.43 (3H, q, J=1.7 Hz), 4.4–4.6 (1H, m), 6.95 (1H, d, J=6.4 Hz), 7.47 (1H, d, J=8.9 Hz), 8.00 (1H, s)

Compound 1-1785, 2.43 (3H, q, J=1.9 Hz), 3.03 (3H, s), 7.03 (1H, s), 7.52 (1H, d, J=8.8 Hz), 7.76 (1H, d, J=6.9 Hz), 8.02 (1H, s)

Compound 1-1789, m.p. 78.3° C.

Compound 1-1790, m.p. 63.2° C.

Compound 1-1879, 2.42 (3H, q, J=1.8 Hz), 5.38 (2H, s), 7.28–7.47 (5H, m), 7.56 (1H, d, J=8.7 Hz), 7.72–7.79 (1H, m), 8.00 (1H, s), 8.18 (1H, d, J=2.5 Hz)

Compound 1-1881, 2.20 (0.75H, s), 2.24 (2.25H, s), 2.42 (3H, q, J=1.9 Hz), 3.82 (0.75H, s), 3.98 (2.25H, s), 7.47–7.68 (3H, m), 8.00 (1H, s)

Compound 1-1901, m.p. 99.2° C.

Compound 1-1908, m.p. 77.6° C.

Compound 1-1910, m.p. 75.3° C.

Compound 1-1930, m.p. 139.7° C.

Compound 1-2051, 1.25 (3H, t, J=7.2 Hz), 2.42 (3H, q, J=1.9 Hz), 4.17 (2H, q, J=7.2 Hz), 4.71 (2H, s), 4.82 (21H, s), 7.10 (1H, d, J=6.3 Hz), 7.33 (1H, d, J=9.1 Hz), 7.99 (1H, s)

Compound 1-2054, 1.24 (3H, t, J=7.1 Hz), 1.51 (3H, d, J=7.2 Hz), 2.42 (3H, q, J=1.8 Hz), 4.15 (2H, q, J=7.1 Hz), 4.78 (2H, s), 5.19 (1H, q, J=7.2 Hz), 7.08 (1H, d, J=6.3 Hz), 7.32 (1H, d, J=9.1 Hz), 7.98 (1H, s)

Compound 2-203, 2.3–2.4 (1H, m), 2.35 (3H, q, J=1.9 Hz), 4.5–4.7 (4H, m), 7.00 (1H, d, J=6.5 Hz), 7.19 (1H, m), 7.39 (1H, d, J=2.5 Hz), 7.95 (1H, s)

Compound 2-251, m.p. 168.3° C.

Compound 2-328, 0.90 (3H, t, J=7.3 Hz), 1.54 (3H, d, J=7.0 Hz), 1.70–1.90 (2H, m), 2.46 (3H, m), 4.50 (1H, m), 7.18 (1H, d, J=5.75 Hz), 7.35 (1H, d, J=8.8 Hz), 8.04 (1H, s)

Compound 2-583, m.p. 149.1° C.

Compound 2-631, m.p. 168.3° C.

Compound 2-708, 0.90 (3H, t, J=7.3 Hz), 1.55 (3H, d, J=7.0 Hz), 1.75–1.95 (2H, m), 4.50 (1H, m), 7.22 (1H, d, J=5.8 Hz), 7.30-7.40 (2H, m), 8.08 (1H, q, J=2.2 Hz)

Compound 2-821, m.p. 162.7° C.

Compound 3-139, m.p. 88.2° C.

Compound 4-434, 1.67 (3H, s), 2.35 (3H, q, J=1.7 Hz), 3.0–3.2 (1H, m), 3.4–3.7 (1H, m), 3.71 (3H, s), 7.03 (1H, d, J=5.0 Hz), 7.97 (1H, q, J=3.3 Hz)

Compound 4-451, 1.53 (6H, s), 2.43 (3H, q, J=1.9 Hz), 2.96 (1H, d, J=16.2 Hz), 3.08 (1H, d, J=16.2 Hz), 7.07 (1H, d, J=9.9 Hz), 7.99 (1H, s)

Compound 4-452, 1.4–1.5 (3H, m), 2.43 (3H, q, J=2.0 Hz), 2.7–3.0 (1H, m), 3.1–3.5 (1H, m), 3.5–3.8 (2H, m), 7.07 (1H, d, J=10.0 Hz), 8.00 (1H, q, J=2.5 Hz)

The following will describe formulation examples, in which the present compounds are designated by their compound numbers shown in Tables 1 to 5 and parts are by weight.

FORMULATION EXAMPLE 1

Fifty parts of each of compounds 1-1 to 1-2157, 2-1 to 2-950, 3-1 to 3-582, 4-1 to 4-936, and 5-1 to 5-87, 3 parts of calcium ligninsulfonate, 2 parts of sodium laurylsulfate, and 45 parts of synthetic hydrated silicon oxide are well pulverized and mixed to give a wettable powder for each compound.

FORMULATION EXAMPLE 2

Ten parts of each of compounds 1-1 to 1-2157, 2-1 to 2-950, 3-1 to 3-582, 4-1 to 4-936, and 5-1 to 5-87, 14 parts of polyoxyethylene styryl phenyl ether, 6 parts of calcium dodecylbenzenesulfonate, 35 parts of xylene, and 35 parts of cyclohexanone are well mixed to give an emulsifiable concentrate for each compound.

FORMULATION EXAMPLE 3

Two parts of each of compounds 1-1 to 1-2157, 2-1 to 2-950, 3-1 to 3-582, 4-1 to 4-936, and 5-1 to 5-87, 2 parts of synthetic hydrated silicon oxide, 2 parts of calcium ligninsulfonate, 30 parts of bentonite, and 64 parts of kaoline clay are well pulverized and mixed, to which water is added, and the mixture is well kneaded, granulated, and dried to give a granule for each compound.

FORMULATION EXAMPLE 4

Twenty-five parts of each of compounds 1-1 to 1-2157, 2-1 to 2-950, 3-1 to 3-582, 4-1 to 4-936, and 5-1 to 5-87, 50 parts of 10% aqueous polyvinyl alcohol solution, and 25 parts of water are mixed, and the mixture is pulverized until the average particle size becomes 5 $\mu$m or less to give a flowable for each compound.

FORMULATION EXAMPLE 5

Five parts of compound 1-1650 is added to 40 parts of 10% aqueous polyvinyl alcohol solution and dispersed by emulsion with a homogenizer until the mean particle size becomes 10 $\mu$m or less, to which 55 parts of water is added to give a concentrated emulsion.

The following test examples will demonstrate that the present compounds are useful as active ingredients of herbicides. The present compounds are designated by their compound numbers shown in Tables 1 to 5.

The herbicidal activity and phytotoxicity were evaluated at 6 levels with indices of 0 to 5, i.e., designated by the numeral "0", "1", "2", "3", "4" or "5", wherein "0" means that there was no or little difference in the degree of germination or growth between the treated and the untreated test plants at the time of examination, and "5" means that the test plants died complete or their germination or growth was completely inhibited. The herbicidal activity is excellent when rated at "4" or "5" but insufficient when rated at "3" or lower. The phytotoxicity is no problematic on practical use when rated at "0" or "1" but not allowed when rated at "2" or higher.

TEST EXAMPLE 1

Foliar Treatment on Upland Fields

Cylindrical plastic pots of 10 cm in diameter and 10 cm in depth were filled with soil, in which the seeds of entireleaf morningglory (*Ipomoea hederacea* var. *integriuscula*) and velvetleaf (*Abutilon theophrasti*) were sowed, and the test plants were grown in a greenhouse for 19 days. Each of the test compounds listed below was formulated into an emulsifiable concentrate according to Formulation Example 2, which was diluted with water containing a spreading agent to a prescribed concentration. The dilution was uniformly sprayed over the foliage of the test plants with a sprayer at a volume of 1000 liters per hectare. After the application, the test plants were grown in the greenhouse for 19 days, and the herbicidal activity was examined. The results are shown in Table 6.

TABLE 6

| Test compound | Application amount of active ingredient (g/ha) | Herbicidal activity Entireleaf morningglory | Velvetleaf |
|---|---|---|---|
| 1-332 | 500 | 5 | 5 |
| 1-335 | 500 | 5 | 5 |
| 1-338 | 500 | 5 | 5 |
| 1-347 | 500 | 5 | 5 |
| 1-350 | 500 | 5 | 5 |
| 1-353 | 500 | 5 | 5 |
| 1-367 | 500 | 5 | 5 |
| 1-369 | 500 | 5 | 5 |
| 1-391 | 500 | 5 | 5 |
| 1-392 | 500 | 5 | 5 |
| 1-398 | 500 | 5 | 5 |
| 1-420 | 500 | 5 | 5 |
| 1-429 | 500 | 5 | 5 |
| 1-439 | 500 | 5 | 5 |
| 1-449 | 500 | 5 | 5 |
| 1-456 | 500 | 5 | 5 |
| 1-474 | 500 | 5 | 5 |
| 1-475 | 500 | 5 | 5 |
| 1-476 | 500 | 5 | 5 |
| 1-482 | 500 | 5 | 5 |
| 1-483 | 500 | 5 | 5 |
| 1-486 | 500 | 5 | 5 |
| 1-487 | 500 | 5 | 5 |
| 1-491 | 500 | 5 | 5 |
| 1-495 | 500 | 5 | 5 |
| 1-496 | 500 | 5 | 5 |
| 1-497 | 500 | 5 | 5 |
| 1-498 | 500 | 5 | 5 |
| 1-499 | 500 | 5 | 5 |
| 1-500 | 500 | 5 | 5 |
| 1-501 | 500 | 5 | 5 |
| 1-503 | 500 | 5 | 5 |
| 1-504 | 500 | 5 | 5 |
| 1-511 | 500 | 5 | 5 |
| 1-576 | 500 | 5 | 5 |
| 1-577 | 500 | 5 | 5 |
| 1-579 | 500 | 5 | 5 |
| 1-581 | 500 | 5 | 5 |
| 1-584 | 500 | 5 | 5 |
| 1-585 | 500 | 5 | 5 |
| 1-586 | 500 | 5 | 5 |
| 1-587 | 500 | 5 | 5 |
| 1-619 | 500 | 5 | 5 |
| 1-621 | 500 | 5 | 5 |
| 1-625 | 500 | 5 | 5 |
| 1-637 | 500 | 5 | 5 |
| 1-641 | 500 | 5 | 5 |
| 1-642 | 500 | 5 | 5 |
| 1-987 | 500 | 5 | 5 |
| 1-1025 | 500 | 5 | 5 |
| 1-1028 | 500 | 5 | 5 |
| 1-1029 | 500 | 5 | 5 |
| 1-1035 | 500 | 5 | 5 |
| 1-1057 | 500 | 5 | 5 |
| 1-1066 | 500 | 5 | 5 |
| 1-1076 | 500 | 5 | 5 |
| 1-1086 | 500 | 5 | 5 |
| 1-1093 | 500 | 5 | 5 |
| 1-1113 | 500 | 5 | 5 |
| 1-1123 | 500 | 5 | 5 |
| 1-1124 | 500 | 5 | 5 |
| 1-1133 | 500 | 5 | 5 |
| 1-1140 | 500 | 5 | 5 |
| 1-1141 | 500 | 5 | 5 |
| 1-1213 | 500 | 5 | 5 |
| 1-1214 | 500 | 5 | 5 |
| 1-1221 | 500 | 5 | 5 |
| 1-1222 | 500 | 5 | 5 |
| 1-1226 | 500 | 5 | 5 |
| 1-1274 | 500 | 5 | 5 |
| 1-1278 | 500 | 5 | 5 |
| 1-1279 | 500 | 5 | 5 |
| 1-1422 | 500 | 5 | 5 |
| 1-1431 | 500 | 5 | 5 |
| 1-1441 | 500 | 5 | 5 |
| 1-1451 | 500 | 5 | 5 |
| 1-1458 | 500 | 5 | 5 |
| 1-1540 | 500 | 5 | 5 |
| 1-1617 | 500 | 5 | 5 |
| 1-1622 | 500 | 5 | 5 |
| 1-1627 | 500 | 5 | 5 |
| 1-1638 | 500 | 5 | 5 |
| 1-1639 | 500 | 5 | 5 |
| 1-1641 | 500 | 5 | 5 |
| 1-1650 | 500 | 5 | 5 |
| 1-1655 | 500 | 5 | 5 |
| 1-1663 | 500 | 5 | 5 |
| 1-1665 | 500 | 5 | 5 |
| 1-1670 | 500 | 5 | 5 |
| 1-1673 | 500 | 5 | 5 |
| 1-1678 | 500 | 5 | 5 |
| 1-1679 | 500 | 5 | 5 |
| 1-1680 | 500 | 5 | 5 |
| 1-1681 | 500 | 5 | 5 |
| 1-1682 | 500 | 5 | 5 |
| 1-1683 | 500 | 5 | 5 |
| 1-1691 | 500 | 5 | 5 |
| 1-1701 | 500 | 5 | 5 |
| 1-1718 | 500 | 5 | 5 |
| 1-1719 | 500 | 5 | 5 |
| 1-1722 | 500 | 5 | 5 |
| 1-1732 | 500 | 5 | 5 |
| 1-1748 | 500 | 5 | 5 |
| 1-1780 | 500 | 5 | 5 |
| 1-1781 | 500 | 5 | 5 |
| 1-1782 | 500 | 5 | 5 |
| 1-1783 | 500 | 5 | 5 |
| 1-1785 | 500 | 5 | 5 |
| 2-203 | 500 | 5 | 5 |
| 2-251 | 500 | 5 | 5 |
| 2-328 | 500 | 5 | 5 |
| 2-583 | 500 | 5 | 5 |
| 2-631 | 500 | 5 | 5 |
| 2-708 | 500 | 5 | 5 |
| 2-821 | 500 | 5 | 5 |
| 3-139 | 500 | 5 | 5 |
| 4-434 | 500 | 5 | 5 |
| 4-451 | 500 | 5 | 5 |
| 1-344 | 2000 | 5 | 5 |
| 1-981 | 2000 | 5 | 5 |
| 1-1689 | 2000 | 5 | 5 |
| 1-1720 | 2000 | 5 | 5 |
| 1-1721 | 2000 | 5 | 5 |

TEST EXAMPLE 2

Foliar Treatment on Upland Fields

Cylindrical plastic pots of 10 cm in diameter and 10 cm in depth were filled with soil, in which the seeds of barnyardgrass (*Echinochloa crus-galli*), entireleaf morningglory (*Ipomoea hederacea* var. *integriuscula*), and velvetleaf (*Abutilon theophrasti*) were sowed, and the test plants were grown in a greenhouse for 19 days. Each of the test compounds listed below was formulated into an emulsifiable concentrate according to Formulation Example 2, which was diluted with water containing a spreading agent to a prescribed concentration. The dilution was uniformly sprayed over the foliage of the test plants with a sprayer at a volume of 1000 liters per hectare. After the application, the test plants were grown in the greenhouse for 19 days, and the herbicidal activity was examined. The results are shown in Table 7.

TABLE 7

| Test compound | Application amount of active ingredient (g/ha) | Herbicidal activity | | |
|---|---|---|---|---|
| | | Barnyard-grass | Entireleaf morningglory | Velvetleaf |
| 1-369 | 32 | 5 | 5 | 5 |
| 1-420 | 32 | 5 | 5 | 5 |
| 1-439 | 32 | 4 | 5 | 5 |
| 1-482 | 32 | 5 | 5 | 5 |
| 1-486 | 32 | 4 | 5 | 5 |
| 1-487 | 32 | 5 | 5 | 5 |
| 1-491 | 32 | 5 | 5 | 5 |
| 1-495 | 32 | 5 | 5 | 5 |
| 1-496 | 32 | 5 | 5 | 5 |
| 1-499 | 32 | 5 | 5 | 5 |
| 1-503 | 32 | 5 | 5 | 5 |
| 1-576 | 32 | 5 | 5 | 5 |
| 1-577 | 32 | 5 | 5 | 5 |
| 1-579 | 32 | 5 | 5 | 5 |
| 1-581 | 32 | 5 | 5 | 5 |
| 1-584 | 32 | 5 | 5 | 5 |
| 1-585 | 32 | 5 | 5 | 5 |
| 1-625 | 32 | 5 | 5 | 5 |
| 1-641 | 32 | 5 | 5 | 5 |
| 1-642 | 32 | 5 | 5 | 5 |
| 1-1057 | 32 | 5 | 5 | 5 |
| 1-1076 | 32 | 4 | 5 | 5 |
| 1-1123 | 32 | 4 | 5 | 5 |
| 1-1124 | 32 | 5 | 5 | 5 |
| 1-1140 | 32 | 5 | 5 | 5 |
| 1-1141 | 32 | 4 | 5 | 5 |
| 1-1213 | 32 | 5 | 5 | 5 |
| 1-1214 | 32 | 5 | 5 | 5 |
| 1-1221 | 32 | 5 | 5 | 5 |
| 1-1222 | 32 | 5 | 5 | 5 |
| 1-1226 | 32 | 5 | 5 | 5 |
| 1-1279 | 32 | 5 | 5 | 5 |
| 1-1422 | 32 | 5 | 5 | 5 |
| 1-1431 | 32 | 5 | 5 | 5 |
| 1-1441 | 32 | 5 | 5 | 5 |
| 1-1458 | 32 | 5 | 5 | 5 |
| 1-1540 | 32 | 5 | 5 | 5 |
| 1-1665 | 32 | 5 | 5 | 5 |
| 1-1670 | 32 | 5 | 5 | 5 |
| 1-1673 | 32 | 5 | 5 | 5 |
| 1-1678 | 32 | 5 | 5 | 5 |
| 1-1679 | 32 | 5 | 5 | 5 |
| 1-1680 | 32 | 5 | 5 | 5 |
| 1-1681 | 32 | 5 | 5 | 5 |
| 1-1682 | 32 | 5 | 5 | 5 |
| 1-1683 | 32 | 5 | 5 | 5 |
| 1-1701 | 32 | 5 | 5 | 5 |
| 1-1732 | 32 | 5 | 5 | 5 |
| 1-1780 | 32 | 5 | 5 | 5 |
| 1-1783 | 32 | 5 | 5 | 5 |
| 2-203 | 32 | 4 | 5 | 5 |
| 2-251 | 32 | 5 | 5 | 5 |

TABLE 7-continued

| Test compound | Application amount of active ingredient (g/ha) | Herbicidal activity | | |
|---|---|---|---|---|
| | | Barnyard-grass | Entireleaf morningglory | Velvetleaf |
| 2-583 | 32 | 4 | 5 | 5 |
| 2-631 | 32 | 5 | 5 | 5 |
| 2-821 | 32 | 5 | 5 | 5 |
| 4-434 | 32 | 5 | 5 | 5 |

TEST EXAMPLE 3

Soil Surface Treatment on Upland Fields

Cylindrical plastic pots of 10 cm in diameter and 10 cm in depth were filled with soil, in which the seeds of entireleaf morningglory (*Ipomoea hederacea* var. *integriuscula*) and velvetleaf (*Abutilon theophrasti*) were sowed. Each of the test compounds listed below was formulated into an emulsifiable concentrate according to Formulation Example 2, which was diluted with water to a prescribed concentration. The dilution was uniformly sprayed over the soil surface in the pots with a sprayer at a volume of 1000 liters per hectare. After the application, the test plants were grown in a greenhouse for 19 days, and the herbicidal activity was examined. The results are shown in Table 8.

TABLE 8

| Test compound | Application amount of active ingredient (g/ha) | Herbicidal activity | |
|---|---|---|---|
| | | Entireleaf morningglory | Velvetleaf |
| 1-347 | 500 | 5 | 5 |
| 1-332 | 500 | 5 | 5 |
| 1-335 | 500 | 5 | 5 |
| 1-338 | 500 | 5 | 5 |
| 1-353 | 500 | 5 | 5 |
| 1-367 | 500 | 5 | 5 |
| 1-369 | 500 | 5 | 5 |
| 1-391 | 500 | 5 | 5 |
| 1-392 | 500 | 5 | 5 |
| 1-398 | 500 | 5 | 5 |
| 1-420 | 500 | 5 | 5 |
| 1-439 | 500 | 5 | 5 |
| 1-449 | 500 | 5 | 5 |
| 1-456 | 500 | 5 | 5 |
| 1-474 | 500 | 5 | 5 |
| 1-475 | 500 | 5 | 5 |
| 1-476 | 500 | 5 | 5 |
| 1-482 | 500 | 5 | 5 |
| 1-486 | 500 | 5 | 5 |
| 1-487 | 500 | 5 | 5 |
| 1-491 | 500 | 5 | 5 |
| 1-495 | 500 | 5 | 5 |
| 1-496 | 500 | 5 | 5 |
| 1-497 | 500 | 5 | 5 |
| 1-498 | 500 | 5 | 5 |
| 1-499 | 500 | 5 | 5 |
| 1-500 | 500 | 5 | 5 |
| 1-501 | 500 | 5 | 5 |
| 1-503 | 500 | 5 | 5 |
| 1-504 | 500 | 5 | 5 |
| 1-511 | 500 | 5 | 5 |
| 1-576 | 500 | 5 | 5 |
| 1-577 | 500 | 5 | 5 |
| 1-579 | 500 | 5 | 5 |
| 1-581 | 500 | 5 | 5 |
| 1-584 | 500 | 5 | 5 |
| 1-585 | 500 | 5 | 5 |
| 1-587 | 500 | 5 | 5 |
| 1-621 | 500 | 5 | 5 |
| 1-625 | 500 | 5 | 5 |
| 1-641 | 500 | 5 | 5 |

TABLE 8-continued

| Test compound | Application amount of active ingredient (g/ha) | Herbicidal activity Entireleaf morningglory | Velvetleaf |
|---|---|---|---|
| 1-642 | 500 | 5 | 5 |
| 1-1028 | 500 | 5 | 5 |
| 1-1029 | 500 | 5 | 5 |
| 1-1035 | 500 | 5 | 5 |
| 1-1057 | 500 | 5 | 5 |
| 1-1066 | 500 | 5 | 5 |
| 1-1076 | 500 | 5 | 5 |
| 1-1093 | 500 | 5 | 5 |
| 1-1113 | 500 | 5 | 5 |
| 1-1123 | 500 | 5 | 5 |
| 1-1124 | 500 | 5 | 5 |
| 1-1133 | 500 | 5 | 5 |
| 1-1140 | 500 | 5 | 5 |
| 1-1141 | 500 | 5 | 5 |
| 1-1213 | 500 | 5 | 5 |
| 1-1214 | 500 | 5 | 5 |
| 1-1221 | 500 | 5 | 5 |
| 1-1222 | 500 | 5 | 5 |
| 1-1226 | 500 | 5 | 5 |
| 1-1279 | 500 | 5 | 5 |
| 1-1422 | 500 | 5 | 5 |
| 1-1431 | 500 | 5 | 5 |
| 1-1441 | 500 | 5 | 5 |
| 1-1451 | 500 | 5 | 5 |
| 1-1458 | 500 | 5 | 5 |
| 1-1540 | 500 | 5 | 5 |
| 1-1617 | 500 | 5 | 5 |
| 1-1622 | 500 | 5 | 5 |
| 1-1627 | 500 | 5 | 5 |
| 1-1638 | 500 | 5 | 5 |
| 1-1639 | 500 | 5 | 5 |
| 1-1641 | 500 | 5 | 5 |
| 1-1650 | 500 | 5 | 5 |
| 1-1655 | 500 | 5 | 5 |
| 1-1663 | 500 | 5 | 5 |
| 1-1665 | 500 | 5 | 5 |
| 1-1670 | 500 | 5 | 5 |
| 1-1673 | 500 | 5 | 5 |
| 1-1678 | 500 | 5 | 5 |
| 1-1679 | 500 | 5 | 5 |
| 1-1680 | 500 | 5 | 5 |
| 1-1681 | 500 | 5 | 5 |
| 1-1682 | 500 | 5 | 5 |
| 1-1683 | 500 | 5 | 5 |
| 1-1691 | 500 | 5 | 5 |
| 1-1780 | 500 | 5 | 5 |
| 1-1781 | 500 | 5 | 5 |
| 1-1782 | 500 | 5 | 5 |
| 1-1783 | 500 | 5 | 5 |
| 1-1785 | 500 | 5 | 5 |
| 2-203 | 500 | 5 | 5 |
| 2-251 | 500 | 5 | 5 |
| 2-328 | 500 | 5 | 5 |
| 2-583 | 500 | 5 | 5 |
| 2-631 | 500 | 5 | 5 |
| 2-708 | 500 | 5 | 5 |
| 2-821 | 500 | 5 | 5 |
| 4-434 | 500 | 5 | 5 |

TEST EXAMPLE 4

Flooding Treatment on Paddy Fields

Cylindrical plastic pots of 9 cm in diameter and 11 cm in depth were filled with soil, in which the seeds of barnyardgrass (*Echinochloa oryzicola*) were sowed. These pots were flooded to form a paddy field, and the test plants were grown in a greenhouse for 7 days. Each of the test compounds listed below was formulated into an emulsifiable concentrate according to Formulation Example 2, which was diluted with water to a prescribed concentration. The dilution was applied to the water surface in the pots at a volume of 50 liters per hectare. After the application, the test plants were grown in the greenhouse for 19 days, and the herbicidal activity was examined. The results are shown in Table 9.

TABLE 9

| Test compound | Application amount of active ingredient (g/ha) | Herbicidal activity Barnyardgrass |
|---|---|---|
| 1-332 | 250 | 5 |
| 1-335 | 250 | 5 |
| 1-338 | 250 | 5 |
| 1-347 | 250 | 5 |
| 1-353 | 250 | 5 |
| 1-367 | 250 | 5 |
| 1-369 | 250 | 5 |
| 1-391 | 250 | 5 |
| 1-392 | 250 | 5 |
| 1-398 | 250 | 5 |
| 1-420 | 250 | 5 |
| 1-439 | 250 | 5 |
| 1-449 | 250 | 5 |
| 1-456 | 250 | 5 |
| 1-474 | 250 | 5 |
| 1-475 | 250 | 5 |
| 1-476 | 250 | 5 |
| 1-482 | 250 | 5 |
| 1-483 | 250 | 5 |
| 1-486 | 250 | 5 |
| 1-487 | 250 | 5 |
| 1-491 | 250 | 5 |
| 1-495 | 250 | 5 |
| 1-496 | 250 | 5 |
| 1-497 | 250 | 5 |
| 1-498 | 250 | 5 |
| 1-499 | 250 | 5 |
| 1-500 | 250 | 5 |
| 1-501 | 250 | 5 |
| 1-503 | 250 | 5 |
| 1-504 | 250 | 5 |
| 1-511 | 250 | 5 |
| 1-576 | 250 | 5 |
| 1-577 | 250 | 5 |
| 1-579 | 250 | 5 |
| 1-581 | 250 | 5 |
| 1-584 | 250 | 5 |
| 1-585 | 250 | 5 |
| 1-586 | 250 | 5 |
| 1-587 | 250 | 5 |
| 1-621 | 250 | 5 |
| 1-625 | 250 | 5 |
| 1-641 | 250 | 5 |
| 1-642 | 250 | 5 |
| 1-1025 | 250 | 5 |
| 1-1028 | 250 | 5 |
| 1-1029 | 250 | 5 |
| 1-1035 | 250 | 5 |
| 1-1057 | 250 | 5 |
| 1-1066 | 250 | 5 |
| 1-1076 | 250 | 5 |
| 1-1086 | 250 | 5 |
| 1-1093 | 250 | 5 |
| 1-1113 | 250 | 5 |
| 1-1123 | 250 | 5 |
| 1-1124 | 250 | 5 |
| 1-1133 | 250 | 5 |
| 1-1140 | 250 | 5 |
| 1-1141 | 250 | 5 |
| 1-1213 | 250 | 5 |
| 1-1214 | 250 | 5 |
| 1-1221 | 250 | 5 |
| 1-1222 | 250 | 5 |
| 1-1226 | 250 | 5 |
| 1-1274 | 250 | 5 |
| 1-1278 | 250 | 5 |
| 1-1279 | 250 | 5 |
| 1-1422 | 250 | 5 |
| 1-1431 | 250 | 5 |
| 1-1441 | 250 | 5 |

TABLE 9-continued

| Test compound | Application amount of active ingredient (g/ha) | Herbicidal activity Barnyardgrass |
|---|---|---|
| 1-1451 | 250 | 5 |
| 1-1458 | 250 | 5 |
| 1-1540 | 250 | 5 |
| 1-1617 | 250 | 5 |
| 1-1622 | 250 | 5 |
| 1-1627 | 250 | 5 |
| 1-1638 | 250 | 5 |
| 1-1639 | 250 | 5 |
| 1-1641 | 250 | 5 |
| 1-1650 | 250 | 5 |
| 1-1655 | 250 | 5 |
| 1-1663 | 250 | 5 |
| 1-1665 | 250 | 5 |
| 1-1670 | 250 | 5 |
| 1-1673 | 250 | 5 |
| 1-1678 | 250 | 5 |
| 1-1679 | 250 | 5 |
| 1-1680 | 250 | 5 |
| 1-1681 | 250 | 5 |
| 1-1682 | 250 | 5 |
| 1-1683 | 250 | 5 |
| 1-1687 | 250 | 5 |
| 1-1691 | 250 | 5 |
| 1-1701 | 250 | 5 |
| 1-1718 | 250 | 5 |
| 1-1719 | 250 | 5 |
| 1-1722 | 250 | 5 |
| 1-1732 | 250 | 5 |
| 1-1748 | 250 | 5 |
| 1-1780 | 250 | 5 |
| 1-1781 | 250 | 5 |
| 1-1782 | 250 | 5 |
| 1-1783 | 250 | 5 |
| 1-1785 | 250 | 5 |
| 2-203 | 250 | 5 |

TABLE 9-continued

| Test compound | Application amount of active ingredient (g/ha) | Herbicidal activity Barnyardgrass |
|---|---|---|
| 2-251 | 250 | 5 |
| 2-328 | 250 | 5 |
| 2-583 | 250 | 5 |
| 2-631 | 250 | 5 |
| 2-708 | 250 | 5 |
| 2-821 | 250 | 5 |
| 3-139 | 250 | 5 |
| 4-434 | 250 | 5 |
| 4-451 | 250 | 5 |
| 1-344 | 500 | 5 |
| 1-1690 | 500 | 5 |

TABLE 9-continued

| Test compound | Application amount of active ingredient (g/ha) | Herbicidal activity Barnyardgrass |
|---|---|---|
| 1-1720 | 500 | 5 |
| 1-1721 | 500 | 5 |

TEST EXAMPLE 5

Foliar Treatment on Upland Fields

Plastic pots of 25×18 cm in area and 7 cm in depth were filled with soil, in which the seeds of soybean (*Glycine max*), corn (*Zea mays*), entireleaf morningglory (*Ipomoea hederacea* var. *integrinuscula*), common cocklebur (*Xanthium pensylvanicum*), common ragweed (*Ambrosia artemisiifolia*), and common lambsquarters (*Chenopodium album*) were sowed, and the test plants were grown for 16 days. Each of the test compounds listed below was formulated into an emulsifiable concentrate according to Formulation Example 2, which was diluted with water to a prescribed concentration. The dilution was uniformly sprayed over the foliage of the test plants with a sprayer at a volume of 1000 liters per hectare. At this time, the unfavorable weeds and crop plants, although their growth state was different depending upon the weed species, were at the 1- to 4-leaf stage, and the plant height was 5 to 20 cm. After 18 days from the application, the herbicidal activity and phytotoxicity were examined. The results are shown in Table 10. This test was made in a greenhouse over the entire period.

TABLE 10

| Test compound | Application amount of active ingredient (g/ha) | Herbicidal activity and phytotoxicity | | | | | |
|---|---|---|---|---|---|---|---|
| | | Corn | Soybean | Common cocklebur | Entireleaf morningglory | Common ragweed | Common lambsquarters |
| 1-495 | 63 | 1 | 1 | 5 | 5 | 5 | 5 |
| 1-496 | 63 | 1 | 1 | 5 | 5 | 5 | 5 |
| 1-499 | 63 | 1 | 1 | 5 | 5 | 5 | 4 |
| 1-503 | 63 | 1 | 2 | 5 | 5 | 5 | 5 |
| 1-577 | 63 | 1 | 2 | 5 | 5 | 5 | 5 |

TEST EXAMPLE 6

Foliar Treatment on Upland Fields

Plastic pots of 16×11 cm² in are and 7 cm in depth were filled with soil, in which the seeds of wheat (*Triticum aestivum*), pale smartweed (*Polygonum lapathifolium*), catchweed bedstraw (*Galium aparine*), and common chickweed (*Stellaria media*) were sowed, and the test plants were grown for 29 days. Each of the test compounds listed below was formulated into an emulsifiable concentrate according to Formulation Example 2, which was diluted with water to a prescribed concentration. The dilution was uniformly sprayed over the foliage of the test plants with a sprayer at a volume of 1000 liters per hectare. At this time, the unfavorable weeds and crop plants, although their growth state was different depending upon the weed species, were at the 1- to 4-leaf stage, and the plant height was 5 to 15 cm. After 25 days from the application, the herbicidal activity and phytotoxicity were examined. The results are shown in Table 11. This test was made in a greenhouse over the entire period.

TABLE 11

| Test compound | Application amount of active ingredient (g/ha) | Herbicidal activity and phytotoxicity | | | |
|---|---|---|---|---|---|
| | | Wheat | Pale smartweed | Catchweed bedstraw | Common chickweed |
| 1-439 | 63 | 1 | 5 | 5 | 5 |
| 1-482 | 63 | 1 | 5 | 5 | 5 |
| 1-486 | 63 | 1 | 5 | 5 | 5 |
| 1-496 | 63 | 0 | 4 | 5 | 4 |
| 1-1076 | 63 | 1 | 5 | 5 | 5 |
| 1-1123 | 63 | 1 | 5 | 5 | 5 |
| 1-1441 | 63 | 1 | 5 | 5 | 5 |

TEST EXAMPLE 7

Soil Surface Treatment on Upland Fields

Plastic pots of 25×18 cm² in area and 7 cm in depth were filled with soil, in which the seeds of soybean (*Glycine max*), corn (*Zea mays*), common lambsquarters (*Chenopodium album*), slender amaranth (*Amaranthus gracilis*), and pale smartweed (*Polygonum lapathifolium*) were sowed. Each of the test compounds listed below was formulated into an emulsifiable concentrate according to Formulation Example 2, which was diluted with water to a prescribed concentration. The dilution was uniformly sprayed over the soil surface in the pots with a sprayer at a volume of 1000 liters per hectare. After the application, the test plants were grown in a greenhouse for 19 days, and the herbicidal activity and phytotoxicity were examined. The results are shown in Table 12.

TABLE 12

| Test compound | Application amount of active ingredient (g/ha) | Herbicidal activity and phytotoxicity | | | | |
|---|---|---|---|---|---|---|
| | | Soybean | Corn | Common lambsquarters | Slender amaranth | Pale smartweed |
| 1-511 | 63 | 1 | 0 | 5 | 5 | 5 |
| 1-642 | 63 | 1 | 0 | 5 | 5 | 5 |
| 1-1279 | 63 | 0 | 1 | 5 | 5 | 5 |
| 1-1691 | 63 | 0 | 1 | 5 | 5 | 5 |
| 2-203 | 63 | 2 | 2 | 5 | 5 | 5 |
| 2-631 | 63 | 1 | 3 | 5 | 5 | 5 |

We claim:

1. A compound of the formula:

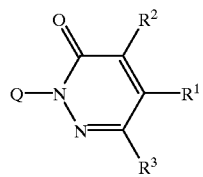

(1)

wherein $R^1$ is $C_1-C_3$ haloalkyl; $R^2$ and $R^3$ are the same or different and are hydrogen, $C_1-C_3$ alkyl, $C_1-C_3$ haloalkyl, or $C_1-C_3$ alkoxy $C_1-C_3$ alkyl; and Q is (Q-1) of the formula:

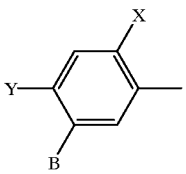

(Q-1)

wherein X is hydrogen or halogen;

Y is halogen, nitro, cyano, or trifluoromethyl;

B is hydrogen, halogen, nitro, cyano, chlorosulfonyl, $OR^{10}$, $SR^{10}$, $SO_2-OR^{10}$, $N(R^{11})R^{12}$, $SO_2N(R^{11})R^{12}$, $NR^{11}(COR^{13})$, $NR^{11}(SO_2R^{14})$, $N(SO_2R^{14})(SO_2R^{15})$, $N(SO_2R^{14})(COR^{13})$, $NHCOOR^{13}$, $COOR^{10}$, $CON(R^{11})R^{12}$, $CSN(R^{11})R^{12}$, $COR^{16}$, $CR^{17}=CR^{18}COR^{16}$, $CR^{17}=CR^{18}COOR^{13}$, $CR^{17}=CR^{18}CON(R^{11})R^{12}$, $CH_2CH-WCOOR^{13}$, $CH_2CHWCON(R^{11})R^{12}$, $CR^{17}=NOR^{33}$, $CR^{17}=NN(R^{11})R^{12}$, $CR^{17}(Z^2-R^{34})_2$, $OCO_2R^{19}$, or $OCOR^{19}$;

wherein $R^{10}$ is hydrogen, $C_1-C_6$ alkyl, $C_1-C_6$ haloalkyl, $C_3-C_8$ cycloalkyl, benzyl, $C_3-C_6$ alkenyl, $C_3-C_6$ haloalkenyl, $C_3-C_6$ alkynyl, $C_3-C_6$ haloalkynyl, cyano $C_1-C_6$ alkyl, $C_2-C_8$ alkoxyalkyl, $C_2-C_8$ alkylthioalkyl, carboxy $C_1-C_6$ alkyl, $(C_1-C_8$ alkoxy)carbonyl $C_1-C_6$ alkyl, $(C_1-C_6$ haloalkoxy)carbonyl $C_1-C_6$ alkyl, {$(C_1-C_4$ alkoxy) $C_1-C_4$ alkoxy}carbonyl $C_1-C_6$ alkyl, $(C_3-C_8$ cycloalkoxy)carbonyl $C_1-C_6$ alkyl, $(C_1-C_6$ alkyl)carbonyl $C_1-C_6$ alkyl, $(C_1-C_6$haloalkyl)carbonyl $C_1-C_6$ alkyl, {$(C_1-C_4$ alkoxy) $C_1-C_4$ alkyl}carbonyl $C_1-C_6$ alkyl, $(C_3-C_8$ cycloalkyl)carbonyl $C_1-C_6$ alkyl, $CH_2CON-(R^{11})R^{12}$, $CH_2COON(R^{11})R^{12}$, $CH(C_1-C_4$ alkyl) $CON(R^{11})R^{12}$, $CH(-C_1-C_4$ alkyl)-$COON(R^{11})R^{12}$, {$(C_1-C_6$ alkoxy)carbonyl $C_1-C_6$ alkyl}oxycarbonyl $C_1-C_6$ alkyl, or hydroxy $C_1-C_6$ alkyl;

$R^{11}$ and $R^{12}$ are independently hydrogen, $C_1-C_6$ alkyl, $C_1-C_6$ haloalkyl, $C_3-C_6$ alkenyl, $C_3-C_6$ alkynyl, cyano $C_1-C_6$ alkyl, $C_2-C_8$ alkoxyalkyl, $C_2-C_8$ alkylthioalkyl, carboxy $C_1-C_6$ alkyl, $(C_1-C_6$ alkoxy)carbonyl $C_1-C_6$ alkyl, $(C_3-C_8$ cycloalkoxy)carbonyl $C_1-C_6$ alkyl, {$(C_1-C_4$ alkoxy) $C_1-C_4$ alkoxy}carbonyl $C_1-C_6$ alkyl, or $R^{11}$ and $R^{12}$ are combined together to form tetramethylene, pentamethylene, or ethyleneoxyethylene;

$R^{13}$ is hydrogen, $C_1-C_6$ alkyl, $C_1-C_6$ haloalkyl, $C_3-C_8$ cycloalkyl, or $C_3-C_6$ alkenyl;

$R^{14}$ and $R^{15}$ are independently $C_1-C_6$ alkyl, $C_1-C_6$ haloalkyl, or phenyl optionally substituted with methyl or nitro;

$R^{16}$ is hydrogen, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_2-C_8$ alkoxyalkyl, or hydroxy $C_1-C_6$ alkyl;

$R^{17}$ and $R^{18}$ are independently hydrogen or $C_1-C_6$ alkyl;

$R^{19}$ is $C_1-C_6$ alkyl;

$R^{33}$ is hydrogen, $C_1-C_6$ alkyl, $C_1-C_6$ haloalkyl, $C_3-C_8$ cycloalkyl, $C_3-C_6$ alkenyl, $C_3-C_6$ haloalkenyl, $C_3-C_6$ alkynyl, $C_3-C_6$ haloalkynyl, cyano $C_1-C_6$ alkyl, or $(C_1-C_6$ alkoxy)carbonyl $C_1-C_6$ alkyl;

$R^{34}$ is $C_1-C_6$ alkyl, or two $R^{34}$'s are combined together to form $(CH_2)_2$ or $(CH_2)_3$;

W is hydrogen, chlorine, or bromine; and $Z^2$ is oxygen or sulfur.

2. A compound according to claim 1, wherein $R^1$ is trifluoromethyl.

3. A compound according to claim 1, wherein $R^2$ is hydrogen or $C_1$–$C_3$ alkyl, and $R^3$ is hydrogen or $C_1$–$C_3$ alkyl.

4. A compound according to claim 1, wherein $R^1$ is trifluoromethyl, $R^2$ is hydrogen or $C_1$–$C_3$ alkyl, and $R^3$ is hydrogen or $C_1$–$C_3$ alkyl.

5. A compound according to claim 1, 2, 3 or 4, wherein B is $OR^{10}$.

6. A compound according to claim 1, 2, 3, or 4, wherein B is $SR^{10}$.

7. A compound according to claim 1, 2, 3, or 4, wherein B is $N(R^{11})R^{12}$.

8. A compound according to claim 1, 2, 3, or 4, wherein B is $NR^{11}(SO_2R^{14})$.

9. A compound according to claim 1, 2, 3, or 4, wherein B is $COOR^{10}$.

10. A compound according to claim 1, 2, 3, or 4, wherein X is fluorine and Y is chlorine.

11. A compound according to claim 1, 2, 3, or 4, wherein X is fluorine, Y is chlorine, and B is $OR^{10}$.

12. A compound according to claim 1, which is 2-(4-chloro-2-fluoro-5-isopropoxyphenyl)-4-methyl-5-trifluoromethylpyridazin-3-one (compound 1-476).

13. A compound according to claim 1, which is 2-(4-chloro-2-fluoro-5-methoxyphenyl)-4-methyl-5-trifluoromethylpyridazin-3-one (compound 1-474).

14. A compound according to claim 1, which is 2-(4-chloro-2-fluoro-5-ethoxyphenyl)-4-methyl-5-trifluoromethylpyridazin-3-one (compound 1-475).

15. A compound according to claim 1, which is 2-(4-chloro-2-fluoro-5-propargyloxyphenyl)-4-methyl-5-trifluoromethylpyridazin-3-one (compound 1-486).

16. A compound according to claim 1, which is methyl 2-chloro-4-fluoro-5-(4-methyl-5-trifluoromethyl-3-pyridazinon-2-yl)phenoxyacetate (compound 1-495).

17. A compound according to claim 1, which is ethyl 2-chloro-4-fluoro-5-(4-methyl-5-trifluoromethyl-3-pyridazinon-2-yl)phenoxyacetate (compound 1-496).

18. A compound according to claim 1, which is propyl 2-chloro-4-fluoro-5-(4-methyl-5-trifluoromethyl-3-pyridazinon-2-yl)phenoxyacetate (compound 1-497).

19. A compound according to claim 1, which is isopropyl 2-chloro-4-fluoro-5-(4-methyl-5-trifluoromethyl-3-pyridazinon-2-yl)phenoxyacetate (compound 1-500).

20. A compound according to claim 1, which is butyl 2-chloro-4-fluoro-5-(4-methyl-5-trifluoromethyl-3-pyridazinon-2-yl)phenoxyacetate (compound 1-498).

21. A compound according to claim 1, which is pentyl 2-chloro-4-fluoro-5-(4-methyl-5-trifluoromethyl-3-pyridazinon-2-yl)phenoxyacetate (compound 1-499).

22. A compound according to claim 1, which is cyclopentyl 2-chloro-4-fluoro-5-(4-methyl-5-trifluoromethyl-3-pyridazinon-2-yl)phenoxyacetate (compound 1-501).

23. A compound according to claim 1, which is ethyl 2-{2-chloro-4-fluoro-5-(4-methyl-5-trifluoromethyl-3-pyridazinon-2-yl)phenoxy}propionate (compound 1-504).

24. A compound according to claim 1, which is methyl 2-{2-chloro-4-fluoro-5-(4-methyl-5-trifluoromethyl-3-pyridazinon-2-yl)phenoxy}propionate (compound 1-503).

25. A compound according to claim 1, which is ethyl 2-chloro-4-fluoro-5-(4-methyl-5-trifluoromethyl-3-pyridazinon-2-yl)phenylthioacetate (compound 1-577).

26. A compound according to claim 1, which is methyl 2-chloro-4-fluoro-5-(4-methyl-5-trifluoromethyl-3-pyridazinon-2-yl)phenylthioacetate (compound 1-576).

27. A compound according to claim 1, which is ethyl 2-{2-chloro-4-fluoro-5-(4-methyl-5-trifluoromethyl-3-pyridazinon-2-yl)phenylthio}propionate (compound 1-585).

28. A compound according to claim 1, which is methyl 2-{2-chloro-4-fluoro-5-(4-methyl-5-trifluoromethyl-3-pyridazinon-2 -yl)phenylthio}propionate (compound 1-584).

29. A compound according to claim 1, which is methyl 2-{2-chloro-4-fluoro-5-(5-trifluoromethyl-3-pyridazinon-2-yl)phenoxy}propionate (compound 1-1140).

30. A compound according to claim 1, which is ethyl 2-{2-chloro-4-fluoro-5-(5-trifluoromethyl-3-pyridazinon-2-yl)phenoxy}propionate (compound 1-1141).

31. A compound according to claim 1, which is ethyl 2-chloro-4-fluoro-5-(5-trifluoromethyl-3-pyridazinon-2-yl)phenylthioacetate (compound 1-1214).

32. A compound according to claim 1, which is methyl 2-chloro-4-fluoro-5-(5-trifluoromethyl-3-pyridazinon-2-yl)phenylthioacetate (compound 1-1213).

33. A compound according to claim 1, which is ethyl 2-{2-chloro-4-fluoro-5-(5-trifluoromethyl-3-pyridazinon-2-yl)phenylthio}propionate (compound 1-1222).

34. A compound according to claim 1, which is methyl 2-{2-chloro-4-fluoro-5-(5-trifluoromethyl-3-pyridazinon-2-yl)phenylthio}propionate (compound 1-1221).

35. A compound according to claim 1, which is isopropyl 2-{2-chloro-4-fluoro-5-(5-trifluoromethyl-3-pyridazinon-2-yl)phenylthio}propionate (compound 1-1226).

36. A compound according to claim 1, which is ethyl 2-{2-chloro-4-fluoro-5-(4-methyl-5-trifluoromethyl-3-pyridazinon-2-yl)phenylamino}propionate (compound 1-420).

37. A compound according to claim 1, which is ethyl 2-{2-chloro-4-fluoro-5-(5-trifluoromethyl-3-pyridazinon-2-yl)phenylamino}propionate (compound 1-1057).

38. A compound according to claim 1, which is N-{2-chloro-4-fluoro-5-(4-methyl-5-trifluoromethyl-3-pyridazinon-2-yl)phenyl}methanesulfonamide (compound 1-367).

39. A compound according to claim 1, which is N-{2-chloro-4-fluoro-5-(4-methyl-5-trifluoromethyl-3-pyridazinon-2-yl)phenyl}chloromethanesulfonamide (compound 1-369).

40. A compound according to claim 1, which is N-{2-chloro-5-(4-methyl-5-trifluoromethyl-3-pyridazinon-2-yl)phenyl}methanesulfonamide (compound 1-398).

41. A compound according to claim 1, which is methyl 2-chloro-4-fluoro-5-(4-methyl-5-trifluoromethyl-3-pyridazinon-2-yl)benzoate (compound 1-641).

42. A compound according to claim 1, which is ethyl 2-chloro-4-fluoro-5-(4-methyl-5-trifluoromethyl-3-pyridazinon-2-yl)benzoate (compound 1-642).

43. A compound according to claim 1, which is ethyl 2-chloro-5-(4-methyl-5-trifluoromethyl-3-pyridazinon-2-yl)benzoate (compound 1-621).

44. A compound according to claim 1, which is isopropyl 2-chloro-5-(4-methyl-5-trifluoromethyl-3-pyridazinon-2-yl)benzoate (compound 1-625).

45. A compound according to claim 1, which is 2-(4-chloro-2-fluoro-5-propargyloxyphenyl)-6-methyl-5-trifluoromethylpyridazin-3-one (compound 1-1441).

46. A compound according to claim 1, wherein X is hydrogen.

47. A compound according to claim 1, wherein B is hydrogen.

48. A compound according to claim 1, wherein B is $OR^{10}$ or $SR^{10}$ and $R^{10}$ is ($C_1$–$C_6$ alkyl)carbonyl $C_1$–$C_6$ alkyl, ($C_1$–$C_6$ haloalkyl)carbonyl $C_1$–$C_6$ alkyl, {($C_1$–$C_4$ alkoxy) $C_1$–$C_4$ alkyl}carbonyl $C_1$–$C_6$ alkyl, ($C_3$–$C_8$ cycloalkyl) carbonyl $C_1$–$C_6$ alkyl, $CH_2CON(R^{11})R^{12}$, $CH_2COON(R^{11})R^{12}$, $CH(C_1$–$C_4$ alkyl)$CON(R^{11})R^{12}$, $CH(C_1$–$C_4$ alkyl) $COON(R^{11})R^{12}$ or {($C_1$–$C_6$ alkoxy)carbonyl $C_1$–$C_6$ alkyl}oxycarbonyl $C_1$–$C_6$ alkyl.

49. A compound according to claim 1, wherein B is $SO_2OR^{10}$, and $R^{10}$ is cyano $C_1$–$C_6$ alkyl, $C_2$–$C_8$ alkylthioalkyl, carboxy $C_1$–$C_6$ alkyl, ($C_1$–$C_8$ alkoxy) carbonyl $C_1$–$C_6$ alkyl, ($C_1$–$C_6$ haloalkoxy)carbonyl $C_1$–$C_6$ alkyl, {($C_1$–$C_4$ alkoxy)$C_1$–$C_4$ alkoxy}carbonyl $C_1$–$C_6$ alkyl, ($C_3$–$C_8$ cycloalkoxy)carbonyl $C_1$–$C_6$ alkyl, ($C_1$–$C_6$ alkyl) carbonyl $C_1$–$C_6$ alkyl, ($C_1$–$C_6$ haloalkyl)carbonyl $C_1$–$C_6$ alkyl, {($C_1$–$C_4$ alkoxy)$C_1$–$C_4$ alkyl}carbonyl $C_1$–$C_6$ alkyl, ($C_3$–$C_8$ cycloalkyl)carbonyl $C_1$–C6 alkyl, $CH_2CON(R^{11})R^{12}$, $CH_2COON(R^{11})R^{12}$, $CH(C_1$–$C_4$ alkyl)$CON(R^{11})R^{12}$, $CH(C_1$–$C_4$ alkyl)$COON(R^{11})R^{12}$, {($C_1$–$C_6$ alkoxy)carbonyl $C_1$–$C_6$ alkyl}oxycarbonyl $C_1$–$C_6$ alkyl, or hydroxy $C_1$–$C_6$ alkyl.

50. A compound according to claim 1, wherein B is $N(R^{11})R^{12}$, and $R^{11}$ and $R^{12}$ are independently {($C_1$–$C_4$ alkoxy)$C_1$–$C_4$ alkoxy}carbonyl $C_1$–$C_6$ alkyl, or $R^{11}$ and $R^{12}$ are combined together to form ethyleneoxyethlene.

51. A compound according to claim 1, wherein B is $SO_2N(R^{11})R^{12}$, and $R^{11}$ and $R^{12}$ are independently cyano $C_1$–$C_6$ alkyl, $C_2$–$C_8$ alkylthioalkyl, carboxy $C_1$–$C_6$ alkyl, ($C_1$–$C_6$ alkoxy)carbonyl $C_1$–$C_6$ alkyl, ($C_3$–$C_8$ cycloalkoxy) carbonyl $C_1$–$C_6$ alkyl, {($C_1$–$C_4$ alkoxy)$C_1$–$C_4$ alkoxy}carbonyl $C_1$–$C_6$ alkyl, or $R^{11}$ and $R^{12}$ are combined together to form ethyleneoxyethlene.

52. A compound according to claim 1, wherein B is $NR^{11}(COR^{13})$ and $R^{11}$ is $C_1$–$C_6$ haloalkyl, $C_3$–$C_6$ alkenyl, $C_3$–$C_6$ alkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy) carbonyl $C_1$–$C_6$ alkyl, ($C_3$–$C_8$ cycloalkoxy)carbonyl $C_1$–$C_6$ alkyl, or {($C_1$–$C_4$ alkoxy)$C_1$–$C_4$ alkoxy}carbonyl $C_1$–$C_6$ alkyl.

53. A compound according to claim 1, wherein B is $NR^{11}(SO_2R^{14})$, and $R^{11}$ is $C_1$–$C_6$ haloalkyl, $C_3$–$C_6$ alkenyl, $C_3$–$C_6$ alkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy) carbonyl $C_1$–$C_6$ alkyl, ($C_3$–$C_8$ cycloalkoxy)carbonyl $C_1$–$C_6$ alkyl, or {($C_1$–$C_4$ alkoxy)$C_1$–$C_4$ alkoxy}carbonyl $C_1$–$C_6$ alkyl.

54. A compound according to claim 1, wherein B is $N(SO_2R^{14})(SO_2R^{15})$, and both of $R^{14}$ and $R^{15}$ are $C_1$–$C_6$ haloalkyl.

55. A compound according to claim 1, wherein B is $N(SO_2R^{14})(COR^{13})$, and $R^{14}$ is $C_1$–$C_6$ haloalkyl.

56. A compound according to claim 1, wherein B is $COOR^{10}$, and $R^{10}$ is cyano $C_1$–$C_6$ alkyl, $C_2$–$C_8$ alkylthioalkyl, carboxy $C_1$–$C_6$ alkyl, ($C_1$–$C_8$ alkoxy) carbonyl $C_1$–$C_6$ alkyl, ($C_1$–$C_6$ haloalkoxy)carbonyl $C_1$–$C_6$ alkyl, {($C_1$–$C_4$ alkoxy)$C_1$–$C_4$ alkoxy}carbonyl $C_1$–$C_6$ alkyl, ($C_3$–$C_8$ cycloalkoxy)carbonyl $C_1$–$C_6$ alkyl, ($C_1$–$C_6$ alkyl) carbonyl $C_1$–$C_6$ alkyl, ($C_1$–$C_6$ haloalkyl)carbonyl $C_1$–$C_6$ alkyl, {($C_1$–$C_4$ alkoxy)$C_1$–$C_4$ alkyl}carbonyl $C_1$–$C_6$ alkyl, ($C_3$–$C_8$ cycloalkyl)carbonyl $C_1$–$C_6$ alkyl, $CH_2CON(R^{11})R^{12}$, $CH_2COON(R^{11})R^{12}$, $CH(C_1$–$C_4$ alkyl)$CON(R^{11})R^{12}$, $CH(C_1$–$C_4$ alkyl)$COON(R^{11})R^{12}$, {($C_1$–$C_6$ alkoxy)carbonyl $C_1$–$C_6$ alkyl}oxycarbonyl $C_1$–$C_6$ alkyl, or hydroxy $C_1$–$C_6$ alkyl.

57. A compound according to claim 1, wherein B is $CON(R^{11})R^{12}$, and $R^{11}$ and $R^{12}$ are independently cyano $C_1$–$C_6$ alkyl, $C_2$–$C_8$ alkylthioalkyl, carboxy $C_1$–$C_6$ alkyl, ($C_1$–$C_6$ alkoxy)carbonyl $C_1$–$C_6$ alkyl, ($C_3$–$C_8$ cycloalkoxy) carbonyl $C_1$–$C_6$ alkyl, {($C_1$–$C_4$ alkoxy) $C_1$–$C_4$ alkoxy}carbonyl $C_1$–$C_6$ alkyl, or $R^{11}$ and $R^{12}$ are combined together to form ethyleneoxyethlene.

58. A compound according to claim 1, wherein B is $CSN(R^{11})R^{12}$.

59. A compound according to claim 1, wherein B is $CR^{17}$=$CR^{18}CON(R^{11})R^{12}$, and $R^{11}$ and $R^{12}$ are independently cyano $C_1$–$C_6$ alkyl, $C_2$–$C_8$ alkylthioalkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl, {($C_1$–$C_4$ alkoxy) $C_1$–$C_4$ alkoxy}carbonyl $C_1$–$C_6$ alkyl, or $R^{11}$ and $R^{12}$ are combined together to form ethyleneoxyethlene.

60. A compound according to claim 1, wherein B is $CH_2CHWCON(R^{11})R^{12}$, and $R^{11}$ and $R^{12}$ are independently cyano $C_1$–$C_6$ alkyl, $C_2$–$C_8$ alkylthioalkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl, {($C_1C_4$ alkoxy) $C_1$–$C_4$ alkoxy}carbonyl $C_1$–$C_6$ alkyl, or $R^{11}$ and $R^{12}$ are combined together to form ethyleneoxyethlene.

61. A compound according to claim 1, wherein B is $CR^{17}$=$NOR^{33}$, and $R^{33}$ is cyano $C_1$–$C_6$ alkyl or ($C_1$–$C_6$ alkoxy)carbonyl $C_1$–$C_6$ alkyl.

62. A compound according to claim 1, wherein B is $CR^{17}$=$NN(R^{11})R^{12}$, and $R^{11}$ and $R^{12}$ are independently cyano $C_1$–$C_6$ alkyl, $C_2$–$C_8$ alkylthioalkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl, {($C_1$–$C_4$ alkoxy) $C_1$–$C_4$ alkoxy}carbonyl $C_1$–$C_6$ alkyl, or $R^{11}$ and $R^{12}$ are combined together to form ethyleneoxyethlene.

63. A compound according to claim 1, wherein X is fluorine, Y is chlorine, $R^1$ is trifluoromethyl, $R^2$ is methyl, and $R^3$ is hydrogen.

64. A compound according to claim 63, wherein B is $OR^{10}$, and $R^{10}$ is hydrogen, $C_1$–$C_6$ alkyl, $C_3$–$C_6$ alkenyl, $C_3$–$C_6$ alkynyl, or ($C_1$–$C_8$ alkoxy)carbonyl $C_1$–$C_6$ alkyl.

65. A compound according to claim 63, wherein B is $OR^{10}$, and $R^{10}$ is ($C_1$–$C_8$ alkoxy)carbonyl $C_1$–$C_6$ alkyl.

66. A compound according to claim 63, wherein B is $OR^{10}$, and $R^{10}$ is $C_3$–$C_6$ alkynyl.

67. A compound according to claim 1, which is 2-{4-chloro-2-fluoro-5-(1-methyl-2-propynyloxy)phenyl}-4-methyl-5-trifluoromethylpyridazin-3-one (compound 1-487).

68. A herbicidal composition comprising a herbicidally effective amount of the compound according to claim 1, and an inert carrier or diluent.

69. A method for controlling weeds, which comprises applying a herbicidally effective amount of the compound according to claim 1 to an area where the weeds grow or will grow.

70. A method according to claim 69, wherein the compound is one wherein X is fluorine, Y is chlorine, $R^1$ is trifluoromethyl, $R^2$ is methyl, $R^3$ is hydrogen, B is $OR^{10}$, and $R^{10}$ is ($C_1$–$C_8$ alkoxy)carbonyl $C_1$–$C_6$ alkyl.

71. A method according to claim 69, wherein the compound is ethyl 2-chloro-4-fluoro-5-(4-methyl-5-trifluoromethyl-3-pyridazinon-2-yl)phenoxyacetate (compound 1-496).

72. A method according to claim 70 or 71, wherein said compound is applied by post-emergence treatment.

73. A method according to claim 70 or 71, wherein the area is a corn field.

74. A method according to claim 72 wherein the area is a corn field.

75. A method according to claim 70 or 71, wherein the area is a barley or wheat field.

76. A method according to claim 72, wherein the area is a barley or wheat field.

77. A method according to claim 70 or 71, wherein the area is a soybean field.

78. A method according to claim 72, wherein the area is a soybean field.

79. A method according to any one of claims 70–71, wherein the weed is velvetleaf.

80. A method according to claim 72, wherein the weed is velvetleaf.

81. A method according to claim 73, wherein the weed is velvetleaf.

82. A method according to claim 75, wherein the weed is velvetleaf.

83. A method according to claim 77, wherein the weed is velvetleaf.

84. A method according to claim 78, wherein the weed is velvetleaf.

85. A method according to any one of claims 70–71, wherein the weed is entireleaf morningglory.

86. A method according to claim 72, wherein the weed is entireleaf morningglory.

87. A method according to claim 73, wherein the weed is entireleaf morningglory.

88. A method according to claim 75, wherein the weed is entireleaf morningglory.

89. A method according to claim 77, wherein the weed is entireleaf morningglory.

90. A method according to claim 78, wherein the weed is entireleaf morningglory.

91. A method according to any one of claims 70–71, wherein the weed is redroot pigweed.

92. A method according to claim 72, wherein the weed is redroot pigweed.

93. A method according to claim 73, wherein the weed is redroot pigweed.

94. A method according to claim 75, wherein the weed is redroot pigweed.

95. A method according to claim 77, wherein the weed is redroot pigweed.

96. A method according to claim 78, wherein the weed is redroot pigweed.

97. A method according to any one of claims 70–71, wherein the weed is hemp sesbania.

98. A method according to claim 72, wherein the weed is hemp sesbania.

99. A method according to claim 73, wherein the weed is hemp sesbania.

100. A method according to claim 75, wherein the weed is hemp sesbania.

101. A method according to any one of claims 70–71, wherein the weed is jimsonweed.

102. A method according to claim 72, wherein the weed is jimsonweed.

103. A method according to claim 73, wherein the weed is jimsonweed.

104. A method according to claim 75, wherein the weed is jimsonweed.

105. A method according to any one of claims 70–71, wherein the weed is black nightshade.

106. A method according to claim 72, wherein the weed is black nightshade.

107. A method according to claim 73, wherein the weed is black nightshade.

108. A method according to claim 75, wherein the weed is black nightshade.

109. A method according to claim 77, wherein the weed is black nightshade.

110. A method according to claim 78, wherein the week is black nightshade.

111. A method according to claim 69, wherein the compound is one wherein X is fluorine, Y is chlorine, $R^1$ is trifluoromethyl, $R^2$ is methyl, $R^3$ is hydrogen, B is $OR^{10}$, and $R^{10}$ is $C_3$–$C_6$ alkynyl.

112. A method according to claim 111, wherein said compound is applied by post-emergence treatment.

113. A method according to claim 111 or 112, wherein the area is a barley or wheat field.

114. A method according to any one of claims 111 or 112, wherein the weed is common chickweed.

115. A method according to claim 113, wherein the weed is common chickweed.

116. A method according to claim 115, wherein the weed is common chickweed.

117. A method according to any one of claims 111 or 112, wherein the weed is wild mustard.

118. A method according to claim 113, wherein the weed is wild mustard.

119. A method according to any of claims 111–112, wherein the weed is field pansy.

120. A method according to claim 113, wherein the weed is field pansy.

121. A method according to any one of claims 111 or 112, wherein the weed is wild pansy.

122. A method according to claim 113, wherein the weed is wild pansy.

123. A method according to any one of claims 111 or 112, wherein the weed is catchweed bedstraw.

124. A method according to claim 113, wherein the weed is catchweed bedstraw.

125. A method according to any one of claims 111 or 112, wherein the weed is red deadnettle.

126. A method according to claim 113, wherein the weed is red deadnettle.

127. A method according to any one of claims 111 or 112, wherein the weed is birdseye speedwell.

128. A method according to claim 113, wherein the weed is birdseye speedwell.

129. A process for producing a compound of a formula (3):

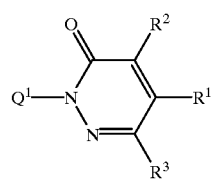

(3)

wherein $R^1$, $R^2$, and $R^3$ are defined as in claim 1, and $Q^1$ is of the formula:

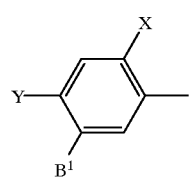

wherein X and Y are as defined in claim 1, $B^1$ is hydrogen, halogen, nitro, cyano, $OR^{27}$, $SR^{27}$, $SO_2OR^{27}$, $NR^{11}(R^{12})$, $SO_2NR^{11}(R^{12})$, $NR^{11}(COR^{13})$, $NR^{11}(SO_2R^{14})$, $N(SO_2R^{14})(SO_2R^{15})$, $N(SO_2R^{14})(COR^{13})$, $NHCOOR^{13}$, $COOR^{27}$, $CONR^{11}(R^{12})$, $CSNR^{11}(R^{12})$, $CR^{17}=CR^{18}COOR^{13}$, $CR^{17}=CR^{18}CONR^{11}(R^{12})$, $CH_2CHWCOOR^{13}$, $CH_2CHWCONR^{11}(R^{12})$, $CR^{17}=NOR^{33}$, $CR^{17}=NNR^{11}(R^{12})$, $CR^{17}(Z^2R^{34})_2$, $OCO_2R^{19}$, or $OCOR^{19}$, $R^{27}$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy)$C_1$–$C_4$ alkoxy}carbonyl $C_1$–$C_6$ alkyl, ($C_3$–$C_8$ cycloalkoxy)carbonyl $C_1$–$C_6$ alkyl, $CH_2CON(R^{11})R^{12}$, $CH_2COON(R^{11})R^{12}$, $CH(C_1$–$C_4$ alkyl)$CON(R^{11})R^{12}$, $CH(C_1$–$C_4$ alkyl)$COON(R^{11})R^{12}$, {($C_1$–$C_6$ alkoxy)carbonyl $C_1$–$C_6$ alkyl}oxycarbonyl $C_1$–$C_6$ alkyl, or hydroxy $C_1$–$C_6$ alkyl, and $R^{11}$ $R^{12}$, $R^{13}$, $R^{14}$, $R^{15}$, $R^{17}$, $R^{18}$, $R^{19}$, $R^{33}$, $R^{34}$ and $Z^2$ are as defined in claim 1 which comprises reacting a hydrazone derivative of formula (4):

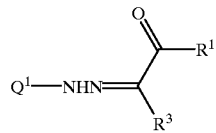

(4)

wherein $R^1$, $R^3$, and $Q^1$ are defined above, with a compound of the formula (5):

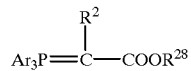

(5)

wherein $R^2$ is as defined above; $R^{28}$ is $C_1$–$C_6$ alkyl; and Ar is an optionally substituted phenyl.

* * * * *

UNITED STATES PATENT AND TRADEMARK OFFICE
CERTIFICATE OF CORRECTION

PATENT NO.    : 6,090,753
DATED         : July 18, 2000
INVENTOR(S)   : Tadashi Katayama, Shinichi Kawamura, Yuzuru Sanemitsu and Yoko Mine It is certified that error appears in the above-identified patent and that said Letters Patent is hereby corrected as shown below:

<u>Column 235,</u>
Line 17, after "alkyl," insert -- W is hydrogen, chloride, or bromine, --.

Signed and Sealed this

Third Day of December, 2002

JAMES E. ROGAN
*Director of the United States Patent and Trademark Office*